(12) United States Patent
Chartier-Courtaud et al.

(10) Patent No.: US 12,343,380 B2
(45) Date of Patent: Jul. 1, 2025

(54) EXPANSION OF TILs UTILIZING AKT PATHWAYS INHIBITORS

(71) Applicant: Iovance Biotherapeutics, Inc., San Carlos, CA (US)

(72) Inventors: Cecile Chartier-Courtaud, Palo Alto, CA (US); Maria Fardis, San Carlos, CA (US)

(73) Assignee: Iovance Biotherapeutics, Inc.

( * ) Notice: Subject to any disclaimer, the term of this patent is extended or adjusted under 35 U.S.C. 154(b) by 1093 days.

(21) Appl. No.: 17/290,639

(22) PCT Filed: Nov. 4, 2019

(86) PCT No.: PCT/US2019/059598
§ 371 (c)(1),
(2) Date: Apr. 30, 2021

(87) PCT Pub. No.: WO2020/096927
PCT Pub. Date: May 14, 2020

(65) Prior Publication Data
US 2022/0033775 A1    Feb. 3, 2022

Related U.S. Application Data

(60) Provisional application No. 62/756,031, filed on Nov. 5, 2018.

(51) Int. Cl.
| | | |
|---|---|---|
| A61K 35/17 | (2025.01) | |
| A61K 38/20 | (2006.01) | |
| A61K 39/395 | (2006.01) | |
| A61K 40/11 | (2025.01) | |
| A61K 40/42 | (2025.01) | |
| C12N 5/0783 | (2010.01) | |

(52) U.S. Cl.
CPC ...... *A61K 38/2013* (2013.01); *A61K 39/3955* (2013.01); *A61K 40/11* (2025.01); *A61K 40/42* (2025.01); *C12N 5/0638* (2013.01); *C12N 2501/2302* (2013.01); *C12N 2501/2315* (2013.01); *C12N 2501/2321* (2013.01); *C12N 2501/515* (2013.01); *C12N 2501/727* (2013.01); *C12N 2501/999* (2013.01); *C12N 2502/11* (2013.01)

(58) Field of Classification Search
None
See application file for complete search history.

(56) References Cited

U.S. PATENT DOCUMENTS

| | | | | |
|---|---|---|---|---|
| 2012/0244133 | A1* | 9/2012 | Rosenberg | A61K 39/4611 435/372 |
| 2018/0362927 | A1* | 12/2018 | Blazar | C12N 5/0636 |

FOREIGN PATENT DOCUMENTS

| | | |
|---|---|---|
| WO | 2017070042 A1 | 4/2017 |
| WO | 2017070395 A1 | 4/2017 |
| WO | 2017219150 A1 | 12/2017 |
| WO | WO2018/182817 | 10/2018 |

OTHER PUBLICATIONS

International Preliminary Report on Patentability for PCT/US2019/059598; dated May 11, 2021; 6 pages.
Written Opinion for PCT/US2019/059598; dated Apr. 7, 2020; 8 pages.
Crompton, et al.; "Akt Inhibition Enhances Expansion of Potent Tumor-Specific Lymphocytes with Memory Cell Characteristics"; Cancer Research, vol. 75, No. 2; Nov. 28, 2014; pp. 296-305.

* cited by examiner

*Primary Examiner* — Michael D Pak
(74) *Attorney, Agent, or Firm* — Morgan, Lewis & Bockius LLP

(57) ABSTRACT

In some embodiments, methods of expanding tumor infiltrating lymphocytes using AKT pathway inhibitors and methods of using the expanded tumor infiltrating lymphocytes in the treatment of human diseases, including cancers, are disclosed.

28 Claims, 54 Drawing Sheets
Specification includes a Sequence Listing.

Figure 1

Process 2A: about 22 days from initiation of First Expansion – Step E

1. STEP A

Obtain Patient Tumor Sample

2. STEP B

Fragmentation

Optional Cryopreservation of Tumor Tissue Fragments

First Expansion 3 days to 14 days

3. STEP C

First Expansion to Second Expansion Transition

No Storage and Closed System

4. STEP D

Second Expansion

IL-2, OKT-3, and antigen-presenting feeder cells

Closed System

5. STEP E

Harvest TILS from Step D

Closed System

6. STEP F

Final Formulation and/or Transfer to Infusion Bag (optionally cryopreserve)

Figure 5

| Process 1C<br>43 – 55 Days for Steps A – E | Process 2A<br>About 22 Days from initiation of preREP to Step E |
|---|---|
| 1. Step A<br>Obtain Patient Tumor Sample | 1. Step A<br>Obtain Patient Tumor Sample |
| 2. Step B<br>Fragmentation and First Expansion<br>11 days to 21 days | 2. Step B<br>Fragmentation, optional cryopreservation of tumor fragments, and then First Expansion<br>11 days to 21 days<br>(beginning from start of first expansion culture) |
| 3. Step C<br>First Expansion to Second Expansion Transition<br>Optional Storage until Selection | 3. Step C<br>First Expansion to Second Expansion Transition<br>No Storage and Closed System |
| 4. Step D<br>Second Expansion<br>IL-2, OKT-3, antigen-presenting feeder cells<br>Optionally repeat one or more times | 4. Step D<br>Second Expansion<br>IL-2, OKT-3, antigen-presenting feeder cells<br>Closed System |
| 5. Step E<br>Harvest TILs from Step D | 5. Step E<br>Harvest TILs from Step D<br>Closed System |
| 6. Step F<br>Final Formulation and/or Transfer to Infusion Bag | 6. Step F<br>Final Formulation and/or Transfer to Infusion Bag<br>Optional cryopreservation |

Figure 6

| Process Step | Process 1C Embodiment | Process 2A Embodiment | Advantages |
|---|---|---|---|
| Pre-REP | • 4 fragments per 10 GREX-10 flasks<br>• 11-21 day duration | • 40 fragments per 1 GREX-100M flask<br>• 11 day duration | • Increased tumor fragments per flask<br>• Shortened culture time<br>• Reduced number of steps<br>• Amenable to closed system |
| Pre-REP to REP Transition | • Pre-REP TIL are frozen until phenotyped for selection then thawed to proceed to the REP (~day 30)<br>• REP requires >40×10$^6$ TIL | • Pre-REP TIL directly move to REP on day 11<br>• REP requires 25-200×10$^6$ TIL | • Shortened pre-REP-to-REP process<br>• Reduced number of steps<br>• Eliminated phenotyping selection<br>• Amenable to closed system |
| REP | • 6 GREX-100M flasks on REP day 0<br>• 5×10$^6$ TIL and 5×10$^8$ PBMC feeders per flask on REP day 0<br>• Split to 18-36 flasks on REP day 7<br>• 14 day duration | • 1 GREX-500M flask on day 11<br>• 25-200×10$^6$ TIL and 5x10$^9$ PBMC feeders on day 11<br>• Split to ≤ 6 GREX-500M flasks on day 16<br>• 11 day duration | • Reduced number of steps<br>• Shorter REP duration<br>• Closed system transfer of TIL between flasks<br>• Closed system media exchanges |
| Harvest | • TIL harvested via centrifugation | • TIL harvested via LOVO automated cell washing system | • Reduced number of steps<br>• Automated cell washing<br>• Closed system<br>• Reduced loss of product during wash |
| Final Formulation | • Fresh product in Hypothermosol<br>• Single infusion bag<br>• Limited shipping stability | • Cyropreserved product in PlasmaLyte-A + 1% HSA and CS10 stored in LN$_2$<br>• Multiple aliquots<br>• Longer shipping stability | • Shipping flexibility<br>• Flexible patient scheduling<br>• More timely release testing |
| Overall Estimated Process Time | • 43-55 days | • 22 days | • Faster turnaround to patient |

*Figure 8A*

| Process 2A: about 22 days from Steps A - E | Process GEN 3: about 14-18 days from Steps A - E |
|---|---|
| STEP A<br>Obtain Patient Tumor Sample<br>(optionally can be frozen before Step B) | STEP A<br>Obtain Patient Tumor Sample<br>(optionally can be frozen before Step B) |
| STEP B<br>First Expansion<br>(physical fragmentation to at least 40 fragments per container grown for about 3 days to 14 days with media comprising IL-2) | STEP B<br>Priming First Expansion<br>(physical fragmentation of up to 60 fragments per container grown for about 1 days to 7 days with media comprising IL-2, OKT-3, and antigen-presenting feeder cells) |
| STEP C<br>First Expansion to Second Expansion Transition<br>(Step B TILs directly move to Step D, optionally on Step B day 11) | STEP C<br>Priming First Expansion to Rapid Second Expansion Transition<br>(Step B TILs directly move to Step D on day 7) |
| STEP D<br>Second Expansion<br>(TILs grown in growth media medium comprising IL-2, OKT-3, and antigen-presenting feeder cells in a closed container) | STEP D<br>Rapid Second Expansion<br>(TILs grown in growth media medium comprising IL-2, OKT-3, and 2X antigen-presenting feeder cells; Days 10-11 scale up and add additional IL-2) |
| STEP E<br>Harvest TILS from Step D<br>(TILs harvested via closed system) | STEP E<br>Harvest TILS from Step D |
| STEP F<br>Final Formulation and/or Transfer to Infusion Bag<br>(optionally cryopreserve) | STEP F<br>Final Formulation and/or Transfer to Infusion Bag<br>(optionally cryopreserve) |

*Figure 8B*

Process GEN 3: about 14-18 days from Steps A - E

STEP A
Obtain Patient Tumor Sample
(optionally can be frozen before Step B)

STEP B
Priming First Expansion
(physical fragmentation of up to 60 fragments per container grown for about 1 days to 7 days with media comprising IL-2, OKT-3, and antigen-presenting feeder cells)

STEP C
Priming First Expansion to Rapid Second Expansion Transition
(Step B TILs directly move to Step D on day 7)

STEP D
Rapid Second Expansion
(TILs grown in growth media medium comprising IL-2, OKT-3, and 2X antigen-presenting feeder cells; Days 10-11 scale up and add additional IL-2)

STEP E
Harvest TILS from Step D

STEP F
Final Formulation and/or Transfer to Infusion Bag
(optionally cryopreserve)

*Figure 17*
A
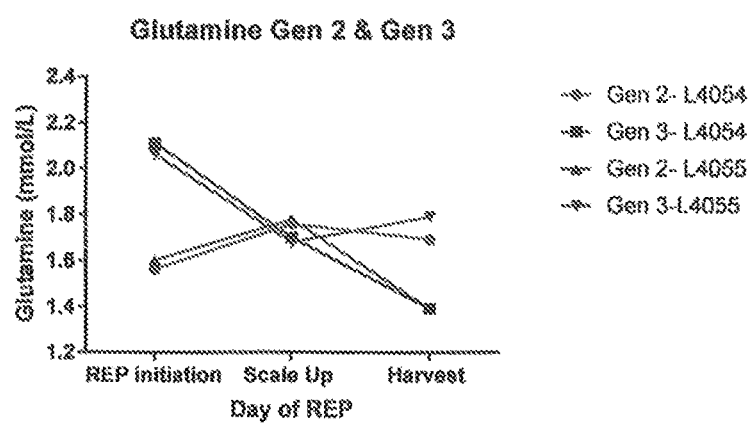
B
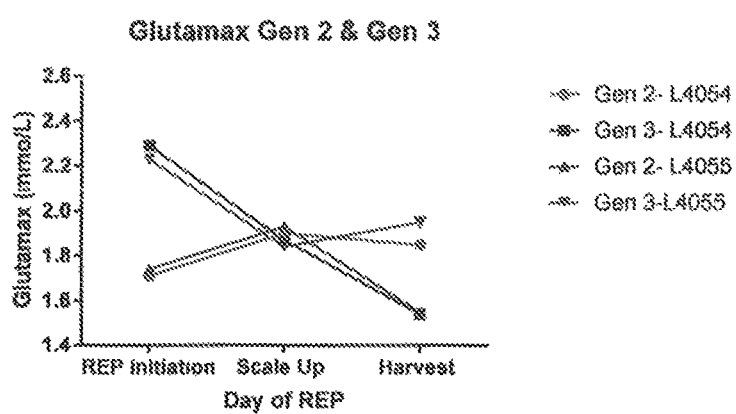

C

- 199 sequences are shared between Gen 3 and Gen 2 final product, corresponding to 97.07% of top 80% of unique CDR3 sequences from Gen 2 shared with Gen 3 final product.

*Figure 23*

| Volume (mL) | | Count 1 (cells/mL) | Count 2 (cells/mL) | Count 3 (cells/mL) | Average (cells/mL) | Total Cells Average*Volume |
|---|---|---|---|---|---|---|
| 188 | Total | 2.46E+05 | 2.28E+05 | 2.31E+05 | 2.35E+05 | 4.42E+07 |
| | Live | 2.37E+05 | 2.27E+05 | 2.26E+05 | 2.30E+05 | 4.32E+07 |
| | Dead | 9.26E+03 | 7.03E+02 | 4.63E+03 | 4.86E+03 | 9.14E+05 |
| | % Viability | 96.20% | 99.70% | 98.00% | 97.97% | |
| 188 | Total | 8.26E+04 | 8.00E+04 | 7.66E+04 | 7.97E+04 | 1.50E+07 |
| | Live | 7.60E+04 | 7.54E+04 | 6.89E+04 | 7.34E+04 | 1.38E+07 |
| | Dead | 6.61E+03 | 4.63E+03 | 7.73E+03 | 6.32E+03 | 1.19E+06 |
| | % Viability | 92.00% | 94.20% | 89.90% | 92.03% | |
| 200 | Total | 2.44E+04 | 4.20E+04 | 1.05E+04 | 2.56E+04 | 5.13E+06 |
| | Live | 1.74E+04 | 2.80E+04 | 7.03E+03 | 1.75E+04 | 3.50E+06 |
| | Dead | 7.03E+03 | 1.40E+04 | 3.48E+03 | 8.17E+03 | 1.63E+06 |
| | % Viability | 71.20% | 66.70% | 66.90% | 68.27% | |

*Figure 24*

| ID | Volume (mL) | | Count 1 (cells/mL) | Count 3 (cells/mL) | Count 2 (cells/mL) | Average (cells/mL) | Total Cells Average*Volume |
|---|---|---|---|---|---|---|---|
| Gen 3 #L4054 First Round | 1000 | Total | 9.11E+05 | 1.01E+06 | 1.08E+06 | 1.00E+06 | 1.00E+09 |
| | | Live | 8.60E+05 | 9.34E+05 | 1.01E+06 | 9.35E+05 | 9.35E+08 |
| | | Dead | 5.09E+04 | 7.49E+04 | 6.74E+04 | 6.44E+04 | 6.44E+07 |
| | | % Viability | 94.40% | 92.60% | 93.70% | 93.57% | |
| Gen 3 #L4055 Second Round | 1000 | Total | 8.56E+05 | 9.04E+05 | 8.81E+05 | 8.80E+05 | 8.80E+08 |
| | | Live | 8.24E+05 | 8.67E+05 | 8.42E+05 | 8.44E+05 | 8.44E+08 |
| | | Dead | 3.17E+04 | 3.70E+04 | 3.87E+04 | 3.58E+04 | 3.58E+07 |
| | | % Viability | 96.30% | 95.90% | 95.60% | 95.93% | |
| Gen 3 #M1085T | 200 | Total | 2.32E+06 | 2.25E+06 | | 2.29E+06 | 4.57E+08 |
| | | Live | 1.68E+06 | 1.57E+06 | | 1.63E+06 | 3.25E+08 |
| | | Dead | 6.41E+05 | 6.79E+05 | | 6.60E+05 | 1.32E+08 |
| | | % Viability | 72.40% | 69.90% | | 71.15% | |
| Gen 2 #L4054 First Round | 142 | Total | 1.08E+06 | 9.84E+05 | | | |
| | | Live | | 9.71E+05 | 9.79E+05 | | |
| | | Dead | | 1.26E+04 | 2.12E+04 | | |
| | | % Viability | 98.10% | 98.70% | 97.90% | 98.23% | |
| Gen 2 #L4055 Second Round | 96 | Total | 2.93E+05 | 3.05E+05 | 2.64E+05 | 2.87E+05 | 2.76E+07 |
| | | Live | 2.88E+05 | 2.96E+05 | 2.55E+05 | 2.80E+05 | 2.68E+07 |
| | | Dead | 4.72E+03 | 9.14E+03 | 8.26E+03 | 7.37E+03 | 7.08E+05 |
| | | % Viability | 98.40% | 97.00% | 96.90% | 97.43% | |
| Gen 2 #M1085T | 200 | Total | 9.10E+04 | 5.60E+04 | | 7.35E+04 | 1.47E+07 |
| | | Live | 8.05E+04 | 4.21E+04 | | 6.13E+04 | 1.23E+07 |
| | | Dead | 1.04E+04 | 1.39E+04 | | 1.22E+04 | 2.43E+06 |
| | | % Viability | 88.50% | 75.20% | | 81.85% | |

*Figure 25*

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 3 #L4054 First Round -pre LOVO | 1243.1 | Total | 1.40E+07 | 1.46E+07 | | 1.43E+07 | 1.78E+10 |
| | | Live | 1.32E+07 | 1.35E+07 | | 1.34E+07 | 1.66E+10 |
| | | Dead | | 1.12E+06 | | | |
| | | % Viability | 94.00% | 92.40% | | 93.20% | |
| Gen 3 #L4054 First Round -post LOVO | 330 | Total | 6.35E+07 | 6.07E+07 | | 6.21E+07 | 2.05E+10 |
| | | Live | 5.72E+07 | 5.44E+07 | | 5.58E+07 | 1.84E+10 |
| | | Dead | 6.35E+06 | 6.27E+06 | | 6.31E+06 | 2.08E+09 |
| | | % Viability | 90.00% | 89.70% | | 89.85% | |

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 3 #L4055 Second Round -pre LOVO | 1032.6 | Total | 9.49E+06 | 1.05E+07 | | 1.00E+07 | 1.03E+10 |
| | | Live | 8.90E+06 | 9.79E+06 | | 9.35E+06 | 9.65E+09 |
| | | Dead | 5.85E+05 | 6.75E+05 | | 6.30E+05 | 6.51E+08 |
| | | % Viability | 93.80% | 93.60% | | 93.70% | |
| Gen 3 #L4055 Second Round -post LOVO | 330 | Total | 3.31E+07 | 2.82E+07 | 3.18E+07 | 3.07E+07 | 1.01E+10 |
| | | Live | 2.85E+07 | 2.46E+07 | 2.77E+07 | 2.66E+07 | 8.78E+09 |
| | | Dead | 4.56E+06 | 3.61E+06 | 4.12E+06 | 4.09E+06 | 1.35E+09 |
| | | % Viability | 86.20% | 87.20% | 87.10% | 86.70% | |

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 3 #M1085T pre-LOVO | 5000 | Total | 2.26E+06 | 2.64E+06 | | 2.45E+06 | 1.23E+10 |
| | | Live | 1.97E+06 | 2.31E+06 | | 2.14E+06 | 1.07E+10 |
| | | Dead | 2.85E+05 | 3.30E+05 | | 3.08E+05 | 1.54E+09 |
| | | % Viability | 87.40% | 87.50% | | 87.45% | |
| Gen 3 #M1085T - post LOVO pre CS10 addition | 150 | Total | 6.27E+07 | 5.44E+07 | | 5.86E+07 | 8.78E+09 |
| | | Live | 5.50E+07 | 4.74E+07 | | 5.12E+07 | 7.68E+09 |
| | | Dead | 7.70E+06 | 6.96E+06 | | 7.33E+06 | 1.10E+09 |
| | | % Viability | 87.70% | 87.20% | | 87.45% | |

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 2 #L4054 First Round | 913 | Total | 3.83E+06 | 4.30E+06 | | 3.92E+06 | 3.57E+09 |
| | | Live | 3.35E+06 | 4.00E+06 | | 3.68E+06 | 3.36E+09 |
| | | Dead | 1.75E+05 | 3.03E+05 | | 2.39E+05 | 2.18E+08 |
| | | % Viability | 95.00% | 93.00% | | 94.00% | |
| Gen 2 #L4055 Second Round | 292 | Total | 1.29E+07 | 1.36E+07 | | 1.33E+07 | 3.87E+09 |
| | | Live | 1.16E+07 | 1.23E+07 | | 1.20E+07 | 3.49E+09 |
| | | Dead | 1.27E+06 | 1.23E+06 | | 1.25E+06 | 3.65E+08 |
| | | % Viability | 90.10% | 90.90% | | 90.50% | |
| Gen 2 #M1085T | 369 | Total | 6.75E+06 | 6.98E+06 | | 6.87E+06 | 2.53E+09 |
| | | Live | 5.22E+06 | 5.58E+06 | | 5.40E+06 | 1.99E+09 |
| | | Dead | 1.54E+06 | 1.40E+06 | | 1.47E+06 | 5.42E+08 |
| | | % Viability | 77.20% | 79.90% | | 78.55% | |

*Figure 26*

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 2 #L4054 First Round -pre LOVO | 1385.7 | Total | 3.55E+07 | 4.12E+07 | 4.03E+07 | 3.90E+07 | 5.40E+10 |
| | | Live | 3.26E+07 | 3.73E+07 | 3.67E+07 | 3.55E+07 | 4.92E+10 |
| | | Dead | 2.93E+06 | 3.87E+06 | 3.59E+06 | 3.46E+06 | 4.80E+09 |
| | | % Viability | 91.70% | 90.60% | 91.10% | 91.13% | |
| Gen 2 #L4054 First Round -post LOVO | 330 | Total | 1.70E+08 | 1.79E+08 | 1.68E+08 | 1.72E+08 | 5.69E+10 |
| | | Live | 1.49E+08 | 1.58E+08 | 1.48E+08 | 1.52E+08 | 5.01E+10 |
| | | Dead | 2.16E+07 | 2.04E+07 | 2.00E+07 | 2.07E+07 | 6.82E+09 |
| | | % Viability | 87.30% | 88.60% | 88.10% | 87.95% | |

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 2 #L4055 First Round -pre LOVO | 1968.2 | Total | 3.15E+07 | 2.51E+07 | 2.97E+07 | 2.88E+07 | 5.66E+10 |
| | | Live | 2.89E+07 | 2.25E+07 | 2.72E+07 | 2.62E+07 | 5.16E+10 |
| | | Dead | 2.57E+06 | 2.61E+06 | 2.52E+06 | 2.57E+06 | 5.05E+09 |
| | | % Viability | 91.80% | 89.60% | 91.50% | 90.97% | |
| Gen 2 #L4055 First Round -post LOVO | 330 | Total | 2.33E+08 | 1.89E+08 | 1.53E+08 | 1.92E+08 | 6.33E+10 |
| | | Live | 2.03E+08 | 1.66E+08 | 1.33E+08 | 1.67E+08 | 5.52E+10 |
| | | Dead | 3.00E+07 | 2.24E+07 | 1.94E+07 | 2.39E+07 | 7.90E+09 |
| | | % Viability | 87.10% | 88.10% | 87.30% | 87.50% | |

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 2 #M1085T-pre LOVO | N/A | Total | | | | #DIV/0! | #DIV/0! |
| | | Live | | | | #DIV/0! | #DIV/0! |
| | | Dead | | | | #DIV/0! | #DIV/0! |
| | | % Viability | | | | #DIV/0! | |
| Gen 2 #M1085T - post LOVO pre CS10 addition | 150 | Total | 8.51E+07 | 9.05E+07 | 8.75E+07 | 8.78E+07 | 1.32E+10 |
| | | Live | 7.33E+07 | 7.79E+07 | 7.56E+07 | 7.56E+07 | 1.13E+10 |
| | | Dead | 1.18E+07 | 1.26E+07 | 1.22E+07 | 1.22E+07 | 1.83E+09 |
| | | % Viability | 86.10% | 86.10% | | 86.10% | |

For L4054 Gen 2, post LOVO count was extrapolated to 4 flasks, because was the total number of the study. 1 flask was contaminated, and the extrapolation was done for total = 6.67E+10

| Sample number # | Description | Sucrose (g/L) | Lactate (g/L) | Ammonia (mmol/L) | Glutamine (mmol/L) | Glutamax (mmol/L) | Glutamax-Glutamine (mmol/L) |
|---|---|---|---|---|---|---|---|
| 1 | Gen 2 Rep Initiation First Round #L4055 | 1.78 | 0.14 | 2.16 | 1.82 | 1.73 | 0.16 |
| 2 | Gen 2 Scale Up First Round #L4055 | 1.36 | 0.28 | 1.40 | 1.78 | 1.90 | 0.15 |
| 3 | Gen 2 Harvest First Round #L4054 | 0.83 | 1.68 | 2.46 | 1.69 | 1.86 | 0.17 |
| 4 | Gen 3-REP Initiation First Round #L4054 | 1.68 | 0.29 | 1.78 | 2.11 | 2.29 | 0.18 |
| 5 | Gen 3-Scale Up First Round #L4054 | 1.28 | 0.54 | 1.64 | 1.70 | 1.87 | 0.16 |
| 6 | Gen 3-Harvest First Round #L4054 | 1.07 | 1.92 | 2.22 | 1.39 | 1.54 | 0.18 |
| 7 | Gen 2 Rep Initiation Second Round #L4055 | 1.81 | 0.08 | 2.29 | 1.60 | 1.78 | 0.18 |
| 8 | Gen 2-Scale Up Second Round #L4055 | 1.82 | 0.77 | 1.49 | 1.78 | 1.93 | 0.15 |
| 9 | Gen 2-Harvest Second Round #L4055 | 0.85 | 1.88 | 2.46 | 1.85 | 1.98 | 0.16 |
| 10 | Gen 3-REP Initiation Second Round #L4055 | 1.77 | 0.18 | 1.74 | 2.06 | 2.23 | 0.17 |
| 11 | Gen 3-Scale up Second Round #L4055 | 1.80 | 0.73 | 1.54 | 1.68 | 1.84 | 0.15 |
| 12 | Gen 3-Harvest Second Round #L4055 | 1.44 | 1.32 | 2.07 | 1.78 | 1.95 | 0.18 |

Figure 35

| | $FIL | S/L/1301 \| Geometr | S/L/Pt \| Geometric Mean (FL03-A |
|---|---|---|---|
| A1 gen2L4054 ne | A1 gen2L4054 neg.fcs | 34.5 | 3.2 |
| A2 gen2L4054 ne | A2 gen2L4054 neg.fcs | 34 | 3.1 |
| A3 gen2L4054 po | A3 gen2L4054 pos.fcs | 1834 | 70 |
| A4 gen2L4054 po | A4 gen2L4054 pos.fcs | 1872 | 70 |
| A5 gen2L4055 ne | A5 gen2L4055 neg.fcs | 31.9 | 4.2 |
| A6 gen2L4055 ne | A6 gen2L4055 neg.fcs | 32.4 | 4.8 |
| A7 gen2L4055 po | A7 gen2L4055 pos.fcs | 1941 | 88 |
| A8 gen2L4055 po | A8 gen2L4055 pos.fcs | 1933 | 91 |
| B1 gen3L4054 ne | B1 gen3L4054 neg.fcs | 31.2 | 3.4 |
| B2 gen3L4054 ne | B2 gen3L4054 neg.fcs | 31.9 | 3.3 |
| B3 gen3L4054 po | B3 gen3L4054 pos.fcs | 2016 | 61 |
| B4 gen3L4054 po | B4 gen3L4054 pos.fcs | 2014 | 76 |
| B5 gen3L4055 ne | B5 gen3L4055 neg.fcs | 33.7 | 6.7 |
| B6 gen3L4055 ne | B6 gen3L4055 neg.fcs | 35.4 | 6 |
| B7 gen3L4055 po | B7 gen3L4055 pos.fcs | 2158 | 99 |
| B8 gen3L4055 po | B8 gen3L4055 pos.fcs | 1938 | 99 |
| Mean | - | 998 | 43 |
| SD | - | 999 | 41 |

*Figure 36*

| Study | Sample | Sample id | Species | Chain | Reads | CDR3 | Unique CDR3 | D50 |
|---|---|---|---|---|---|---|---|---|
| 20180511_Study1_FCA | Gen2-L4054 | 59990 | TRB | h | 1181732 | 1181732 | 9915 | 0 |
| 20180511_Study1_FCA | Gen3-L4054 | 59991 | TRB | h | 1145697 | 1145697 | 18130 | 0 |
| 20180511_Study1_FCA | Gen2-L4055 | 59987 | TRB | h | 1166465 | 1166465 | 12996 | 0.1 |
| 20180511_Study1_FCA | Gen3-L4055 | 59982 | TRB | h | 1059985 | 1059985 | 27246 | 0.9 |

| Process Day | Conditions | Gen 3.1 |
|---|---|---|
| Day 0 pre REP Initiation | Media CM1 | 500 mL |
| | IL-2 (6000 IU/mL) | + |
| | OKT3 (30ng/mL) | + |
| | Feeders (250 E+06) | + |

| Process Day | Conditions | Gen 3.1 |
|---|---|---|
| Day 7 REP Initiation | Media CM2 | 500 mL |
| | IL-2 (6000 IU/mL) | + |
| | OKT3 (30ng/mL) added on Day 7 | + |
| | Feeders Added on Day 7 | 500 E06 |
| | Total Feeders at Day | 750 E+06 |

| Process Day | Conditions | Gen 3.1 |
|---|---|---|
| Day 9-11 – Scale Up | From G-REX 100MCS transfer TIL suspension to 1 G-REX 500MCS (up to 3 GREX 500MCS) | Yes |
| Day 16- Harvest | LOVO- automated cell washer | Yes |

Figure 40

| Process Comparison | Key Process Changes | Benefit |
|---|---|---|
| Gen 2 : Gen 2.1 | • Initiate process with two flasks instead of one flask<br>• Divide REP initiation feeder layer between 2 G-Rex500MCS Flasks<br>• Pre-formulate media and warm prior to use | • Potential doubling of final cell count (dose) with increased TIL repertoire.<br>• Process redundancy throughout process |
| Gen 2.1 : Gen 3.1 | • Fresh or Frozen tumor<br>• 14-16 day process (from 22 day)<br>• Reduce total feeder layer on process<br>• Feeder layer and OKT3 present at Day 0<br>• REP initiated with fragments<br>• 100MCS scales to 500MCS<br>• Scales to multiple pre-REP flasks<br>• Standard Media and Defined Media (Serum Free) | • Increased potency<br>• Improved phenotype<br>• Decreased process time<br>• Reduced reagent testing<br>• Decreased process variability<br>• Defined reagents<br>• Increased repertoire<br>• Reduce impurities (feeder)<br>• Comparable or Higher Dose. |

*Figure 41*

| Process Comparison | Key Process Changes | Desired Improvement | Criteria for Success | Outcome |
|---|---|---|---|---|
| Gen 2 : Gen 3.0 | • 14-16 days<br>• Initiate REP with fragments up to 4 flask<br>• 100MCS scales to 500MCS | • Increased potency<br>• Improved phenotype<br>• Decreased process time | • Increase potency as measured by INF-g ✓<br>• Comparable phenotype ✓<br>• Comparable Dose ✓<br>• Comparable purity ✓ (feeder cell)<br>• Maintain clonal diversity ✓ | • Potency increased over Gen2<br>• Improved expression of CD28 on CD8 cells<br>• Maximum capacity of flask reached by day 16 on Gen 3.1<br>• Reduced feeder cell usage<br>• Increased diversity |

*Figure 42*

| Process | Gen 2 | Gen 3 |
|---|---|---|
| L4054 | Standard Media | Standard Media |
| L4055 | Standard Media | Standard Media |
| M1085T | Standard Media | Standard Media |

| Process | Gen 3 | Gen 3.1 control | Gen 3.1 |
|---|---|---|---|
| L4063 | Standard Media | Standard Media | Standard Media |
| L4064 | Defined Media | Defined Media | Defined Media |

Standard Media:
Pre REP: CM1
REP initiation : CM2
Split or Scale up : CM4

Defined Media:
CTS Optimizer (Serum Free Media) in each day of the process

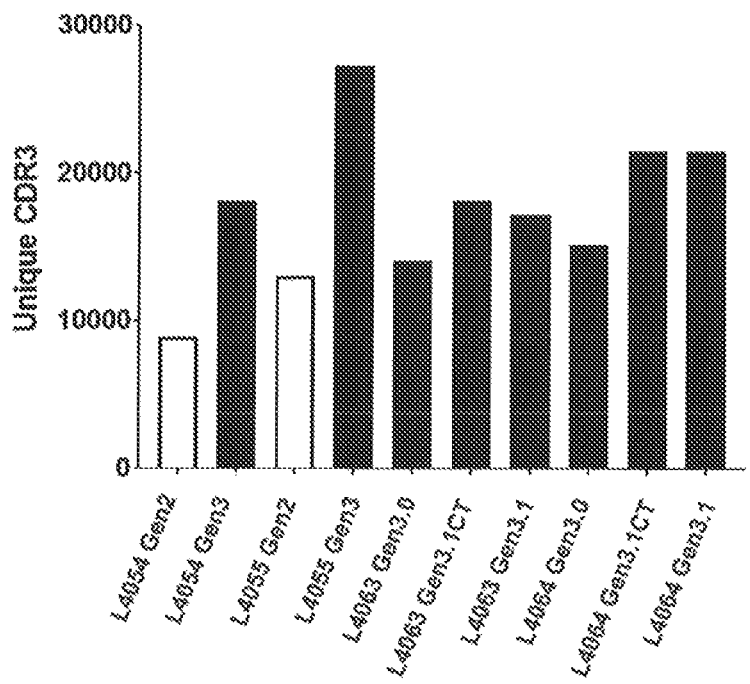
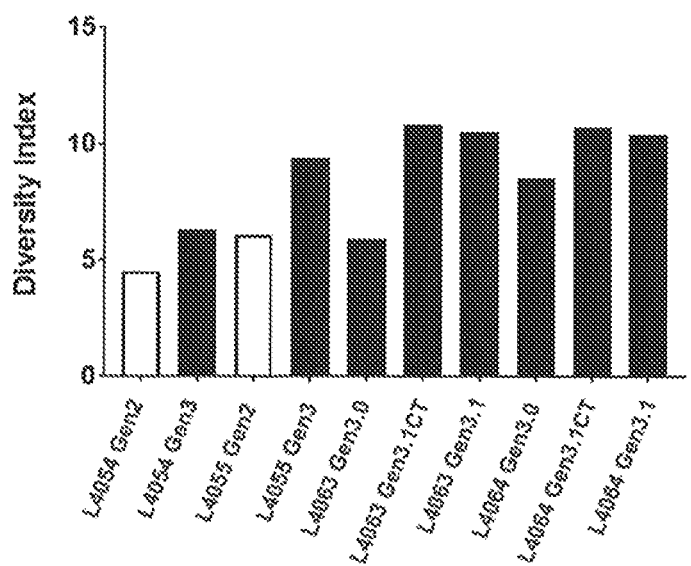
Figure 45

EXPANSION OF TILs UTILIZING AKT PATHWAYS INHIBITORS

CROSS-REFERENCE TO RELATED APPLICATIONS

This application is a National Stage Application of International PCT application PCT/US2019/059598 filed Nov. 4, 2019 which claims priority to U.S. Provisional Application No. 62/756,031, filed on Nov. 5, 2018, each of which is herein incorporated by reference in its entirety.

FIELD OF THE INVENTION

The invention described herein relates generally to the expansion of lymphocytes and more particularly, but not exclusively, to expansion of lymphocytes using inhibitors of kinases in the AKT signaling pathway.

BACKGROUND OF THE INVENTION

Treatment of refractory cancers using adoptive transfer of tumor infiltrating lymphocytes (TILs) represents a potentially powerful approach to treat patients with poor prognoses. Gattinoni, et al., *Nat. Rev. Immunol.* 2006, 6, 383-393. Successful immunotherapy requires a large number of TILs; therefore, a robust and reliable process is needed for manufacturing and commercialization. This scaling for commercialization has been a profound challenge because of the legion technical, logistical, and regulatory issues with cell expansion. IL-2-based TIL expansion followed by a "rapid expansion process" (REP) has become a preferred method for TIL expansion because of its efficiency. Dudley, et al., *Science* 2002, 298, 850-54; Dudley, et al., *J. Clin. Oncol.* 2005, 23, 2346-57; Dudley, et al., *J. Clin. Oncol.* 2008, 26, 5233-39; Riddell, et al., *Science* 1992, 257, 238-41; Dudley, et al., *J. Immunother.* 2003, 26, 332-42. A REP can result in a 1,000-fold expansion of TILs over a 14-day period, although it requires a large excess (e.g., 200-fold) of irradiated allogeneic peripheral blood mononuclear cells (PBMCs, also known as mononuclear cells (MNCs)), often from multiple donors, as feeder cells, as well as anti-CD3 antibody (OKT3) and high doses of IL-2. Dudley, et al., *J. Immunother.* 2003, 26, 332-42. TILs that have undergone a REP procedure have produced successful adoptive cell therapy following host immunosuppression in some melanoma patients.

Current TIL manufacturing processes are limited by duration, cost, sterility concerns, and other factors described herein. Among the many limitations of the current processes is the variability of the phenotypes of the expanded lymphocytes. Methods of expansion that enrich the expanded lymphocyte population with therapeutically useful phenotypes would greatly progress the art; such methods are disclosed herein.

SUMMARY OF THE INVENTION

In an embodiment, the invention provides a method of treating a cancer in a patient suffering therefrom with a population of tumor infiltrating lymphocytes (TILs) comprising the steps of:
(a) resecting a tumor from the patient;
(b) obtaining a first population of TILs from the tumor;
(c) performing an initial expansion of the first population of TILs in a first cell culture medium to obtain a second population of TILs, wherein the second population of TILs is at least 5-fold greater in number than the first population of TILs, wherein the first cell culture medium comprises IL-2, a tumor necrosis factor receptor superfamily (TNFRSF) agonist, and at least one AKT pathway inhibitor (AKTi), and wherein the initial expansion is performed over a period of 21 days or less;
(d) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3 antibody), peripheral blood mononuclear cells (PBMCs), and optionally the TNFRSF agonist and at least one AKT pathway inhibitor (AKTi), and wherein the rapid expansion is performed over a period of 14 days or less;
(e) harvesting the third population of TILs; and
(f) administering a therapeutically effective portion of the third population of TILs to the patient.

A method of treating a cancer in a patient suffering therefrom with a population of tumor infiltrating lymphocytes (TILs) comprising the steps of:
(a) resecting a tumor from the patient;
(b) obtaining a first population of TILs from the tumor;
(c) performing an initial expansion of the first population of TILs in a first cell culture medium to obtain a second population of TILs, wherein the second population of TILs is at least 5-fold greater in number than the first population of TILs, wherein the first cell culture medium comprises IL-2 and an AKT pathway inhibitor (AKTi), and wherein the initial expansion is performed over a period of 21 days or less;
(d) performing a rapid expansion of the second population of TILs in a second cell culture medium to obtain a third population of TILs, wherein the third population of TILs is at least 50-fold greater in number than the second population of TILs after 7 days from the start of the rapid expansion; wherein the second cell culture medium comprises IL-2, OKT-3 (anti-CD3) antibody, peripheral blood mononuclear cells (PBMCs), and optionally the AKT pathway inhibitor and a second AKT pathway inhibitor (AKTi), and wherein the rapid expansion is performed over a period of 14 days or less;
(e) harvesting the third population of TILs; and
(f) administering a therapeutically effective portion of the third population of TILs to the patient.

In an embodiment, the invention provides a method for expanding tumor infiltrating lymphocytes (TILs).

The present invention provides a method for expanding tumor infiltrating lymphocytes (TILs) comprising:
(a) obtaining a tumor sample from a patient, wherein said tumor sample comprises a first population of TILs;
(b) processing said tumor sample into multiple tumor fragments;
(c) adding said tumor fragments into a closed container;
(d) performing an initial expansion of said first population of TILs in a first cell culture medium to obtain a second population of TILs, wherein said first cell culture medium comprises IL-2 and at least one AKT pathway inhibitor (AKTi), wherein said initial expansion is performed in said closed container providing at least 100 cm$^2$ of gas-permeable surface area, wherein said initial expansion is performed within a first period of about 7-14 days to obtain a second population of TILs, wherein said second population of TILs is at least 50-fold greater in number than said first population of TILs, and wherein the transition from step (c) to step (d) occurs without opening the system;

(e) expanding said second population of TILs in a second cell culture medium, wherein said second cell culture medium comprises IL-2, OKT-3, and at least one AKT pathway inhibitor (AKTi), and peripheral blood mononuclear cells (PBMCs, also known as mononuclear cells (MNCs)), wherein said expansion is performed within a second period of about 7-14 days to obtain a third population of TILs, wherein said third population of TILs exhibits an increased subpopulation of effector T cells and/or central memory T cells relative to the second population of TILs, wherein said expansion is performed in a closed container providing at least 500 cm$^2$ of gas-permeable surface area, and wherein the transition from step (d) to step (e) occurs without opening the system;

(f) harvesting said third population of TILs obtained from step (e), wherein the transition from step (e) to step (f) occurs without opening the system; and (g) transferring said harvested TIL population from step (f) to an infusion bag, wherein said transfer from step (f) to (g) occurs without opening the system.

In some embodiments, the method is an in vitro or an ex vivo method.

In some embodiments, the method further comprises harvesting in step (f) via a cell processing system, such as the LOVO system manufactured by Fresenius Kabi. The term "LOVO cell processing system" also refers to any instrument or device manufactured by any vendor that can pump a solution comprising cells through a membrane or filter such as a spinning membrane or spinning filter in a sterile and/or closed system environment, allowing for continuous flow and cell processing to remove supernatant or cell culture media without pelletization. In some cases, the cell processing system can perform cell separation, washing, fluid-exchange, concentration, and/or other cell processing steps in a closed, sterile system.

In some embodiments, the closed container is selected from the group consisting of a G-container and a Xuri cellbag.

In some embodiments, the infusion bag in step (g) is a HypoThermosol-containing infusion bag.

In some embodiments, the first period in step (d) and said second period in step (e) are each individually performed within a period of 10 days, 11 days, or 12 days.

In some embodiments, the first period in step (d) and said second period in step (e) are each individually performed within a period of 11 days.

In some embodiments, steps (a) through (g) are performed within a period of about 25 days to about 30 days.

In some embodiments, steps (a) through (g) are performed within a period of about 20 days to about 25 days.

In some embodiments, steps (a) through (g) are performed within a period of about 20 days to about 22 days.

In some embodiments, steps (a) through (g) are performed in 22 days or less.

In some embodiments, steps (c) through (f) are performed in a single container, wherein performing steps (c) through (f) in a single container results in an increase in TIL yield per resected tumor as compared to performing steps (c) through (f) in more than one container.

In some embodiments, the PBMCs are added to the TILs during the second period in step
(e) without opening the system.

In some embodiments, the effector T cells and/or central memory T cells obtained from said third population of TILs exhibit one or more characteristics selected from the group consisting of expressing CD27$^+$, expressing CD28$^+$, longer telomeres, increased CD57 expression, and decreased CD56 expression relative to effector T cells and/or central memory T cells obtained from said second population of cells.

In some embodiments, the effector T cells and/or central memory T cells obtained from said third population of TILs exhibit increased CD57 expression and decreased CD56 expression relative to effector T cells and/or central memory T cells obtained from said second population of cells.

In some embodiments, the risk of microbial contamination is reduced as compared to an open system.

In some embodiments, the TILs from step (g) are infused into a patient. In some embodiments, the TILs from step (g) are infused into a patient in combination with an AKT pathway inhibitor. In some embodiments, the AKT pathway inhibitor is an AKT inhibitor. In some embodiments, the AKT inhibitor is afuresertib, or pharmaceutically acceptable salts, solvates, hydrates, cocrystals, or prodrugs thereof, and combinations thereof. In some embodiments, the AKT pathway inhibitor (AKTi) is selected from the group consisting of afuresertib, uprosertib, ipatasertib, AT7867, AT13148, MK-2206, LY294002, or pharmaceutically acceptable salts, solvates, hydrates, cocrystals, or prodrugs thereof, and combinations thereof.

The present invention also provides a method of treating cancer in a patient with a population of tumor infiltrating lymphocytes (TILs) comprising the steps of:

(a) obtaining a tumor sample from the patient, wherein said tumor sample comprises a first population of TILs;

(b) processing said tumor sample into multiple tumor fragments;

(c) adding said tumor fragments into a in a first closed container in a closed system;

(d) performing an initial expansion of said first population of TILs in a first cell culture medium to obtain a second population of TILs, wherein said first cell culture medium comprises IL-2 and at least one AKT pathway inhibitor (AKTi), wherein said initial expansion is performed in said closed container providing at least 100 cm$^2$ of gas-permeable surface area, wherein said initial expansion is performed within a first period of about 7-14 days to obtain a second population of TILs, wherein said second population of TILs is at least 50-fold greater in number than said first population of TILs, and wherein the transition from step (c) to step (d) occurs without opening the system;

(e) performing a second expansion of said second population of TILs in a second cell culture medium, wherein said second cell culture medium comprises IL-2, OKT-3, and at least one AKT pathway inhibitor (AKTi), and peripheral blood mononuclear cells (PBMCs), wherein said second expansion is performed within a second period of about 7-14 days to obtain a third population of TILs, wherein said third population of TILs exhibits an increased subpopulation of effector T cells and/or central memory T cells relative to the second population of TILs, wherein said second expansion is performed in the closed system in a second closed container providing at least 500 cm$^2$ of gas-permeable surface area, and wherein the transition from step (d) to step (e) occurs without opening the system;

(f) harvesting said third population of TILs obtained from step (e), wherein the transition from step (e) to step (f) occurs without opening the system;

(g) transferring said harvested TIL population from step (f) to an infusion bag, wherein said transfer from step (f) to (g) occurs without opening the system; and (h) administering a therapeutically effective amount of TIL cells from said infusion bag in step (g) to said patient.

In some embodiments, the a therapeutically effective amount of TIL cells from said infusion bag from step (h) are administered to the patient in combination with an AKT pathway inhibitor. In some embodiments, the at least one AKT pathway inhibitor is afuresertib, or pharmaceutically acceptable salts, solvates, hydrates, cocrystals, or prodrugs thereof, and combinations thereof. In some embodiments, the at least one AKT pathway inhibitor is selected from the group consisting of afuresertib, uprosertib, ipatasertib, AT7867, AT13148, MK-2206, LY294002, or pharmaceutically acceptable salts, solvates, hydrates, cocrystals, or prodrugs thereof, and combinations thereof.

In some embodiments, the method further comprises a culture medium of step (d) comprising one or more AKT pathway inhibitors. In some embodiments, the one or more AKT pathway inhibitors target different protein kinases in the AKT signaling pathway.

In some embodiments, the method further comprises a culture medium of step (e) comprising one or more AKT pathway inhibitors. In some embodiments, the one or more AKT pathway inhibitors target different kinases in the AKT signaling pathway.

In some embodiments, one or more AKT pathway inhibitors are added only to a first culture medium. In some embodiments, one or more AKT pathway inhibitors are added only to a second culture medium.

In some embodiments, the one or more AKT pathway inhibitors targeting different kinases in the AKT signaling pathway comprise an AKT inhibitor and an mTOR inhibitor. In some embodiments, the one or more AKT pathway inhibitors targeting different kinases in the AKT signaling pathway comprise an AKT inhibitor and a PI3K inhibitor. In some embodiments, the one or more AKT pathway inhibitors targeting different kinases in the AKT signaling pathway comprise an AKT inhibitor and a FOXO inhibitor. In some embodiments, the one or more AKT pathway inhibitors targeting different kinases in the AKT signaling pathway comprise an AKT inhibitor and a PDK1 inhibitor. In some embodiments, the one or more AKT pathway inhibitors targeting different kinases in the AKT signaling pathway comprise an AKT inhibitor and a CHK1 inhibitor. In some embodiments, the one or more AKT pathway inhibitors targeting different kinases in the AKT signaling pathway comprise an AKT inhibitor and a RAF1 inhibitor. In some embodiments, the one or more AKT pathway inhibitors targeting different kinases in the AKT signaling pathway comprise an AKT inhibitor and an AMPK inhibitor. In some embodiments, the one or more AKT pathway inhibitors targeting different kinases in the AKT signaling pathway comprise an AKT inhibitor and a PIKfyve inhibitor.

In some embodiments, the cancer is selected from cervical cancer, head and neck cancer (including, for example, head and neck squamous cell carcinoma (HNSCC) glioblastoma, ovarian cancer, sarcoma, pancreatic cancer, bladder cancer, breast cancer, triple negative breast cancer, melanoma, refractory melanoma, metastatic melanoma, and non-small cell lung carcinoma. The tissue structure of solid tumors includes interdependent tissue compartments including the parenchyma (cancer cells) and the supporting stromal cells in which the cancer cells are dispersed and which may provide a supporting microenvironment.

Other embodiments include combinations and variations of these compositions and methods.

BRIEF DESCRIPTION OF THE DRAWINGS

The foregoing summary, as well as the following detailed description of the invention, will be better understood when read in conjunction with the appended drawings.

FIG. 1: Depicts the major steps of an embodiment of the 2A process, including the optional cryopreservation of fresh tumor tissue after fragmentation in Step B. The total time from the initiation of the first expansion culture to the end of Step E is about 22 days.

FIG. 5: Generally compares an embodiment of Process 1C to an exemplary embodiment of Process 2A. Process 2A contemplates initiation of pre-REP cultures from either fresh tumor tissue fragments or thawed cryopreserved tumor tissue fragments.

FIG. 6: Further compares embodiments of Process 1C to embodiments of Process 2A.

FIG. 8: FIG. 8A shows a comparison between the 2A process (approximately 22-day process) and an embodiment of the Gen 3 process for TIL manufacturing (approximately 14-days to 16-days process). FIG. 8B depicts an Exemplary Process Gen3 chart providing an overview of Steps A through F (approximately 14-days to 16-days process).

FIG. 10A shows L4054—Phenotypic characterization on TIL product on Gen 2 and Gen 3 process. FIG. 10B shows L4055-Phenotypic characterization on TIL product on Gen 2 and Gen 3 process. FIG. 10C shows M1085T-Phenotypic characterization on TIL product on Gen 2 and Gen 3 process.

FIG. 11A L4054—Memory markers analysis on TIL product from the Gen 2 and Gen 3 processes. FIG. 11B L4055—Memory markers analysis on TIL product from the Gen 2 and Gen 3 processes. FIG. 11C M1085T—Memory markers analysis on TIL product from the Gen 2 and Gen 3 processes.

FIG. 23: Raw data for cell counts Day 7-Gen 3 REP initiation presented in Table 22 (see Example 6 below).

FIG. 24: Raw data for cell counts Day 11-Gen 2 REP initiation and Gen 3 Scale Up presented in Table 38 (see Example 6 below).

FIG. 25: Raw data for cell counts Day 16-Gen 2 Scale Up and Gen 3 Harvest (e.g., day 16) presented in Table 39 (see Example 6 below).

FIG. 26: Raw data for cell counts Day 22-Gen 2 Harvest (e.g., day 22) presented in Table 39 (see Example 5 below). For L4054 Gen 2, post LOVO count was extrapolated to 4 flasks, because was the total number of the study. 1 flask was contaminated, and the extrapolation was done for total=6.67E+10.

Figure 28:
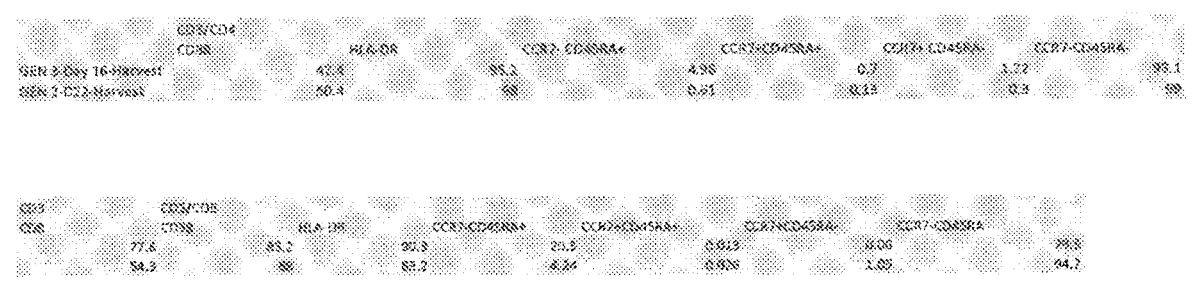

FIG. 28: Raw data for flow cytometry results depicted in FIGS. 10C and 11C.

Figure 29:
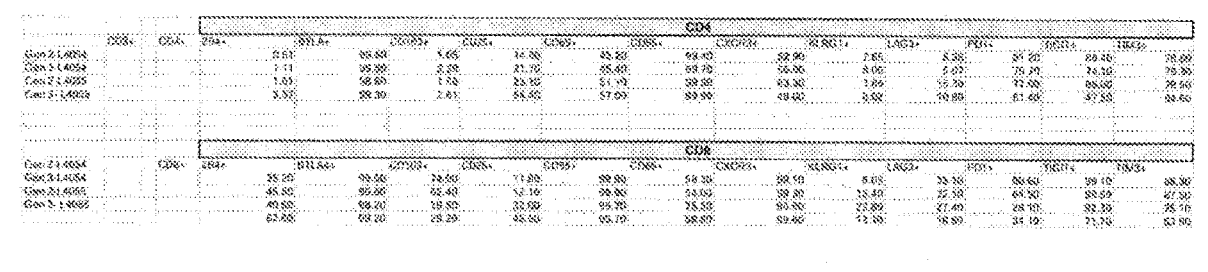

FIG. 29: Raw data for flow cytometry results depicted in FIGS. 12 and 13.

Figure 31:
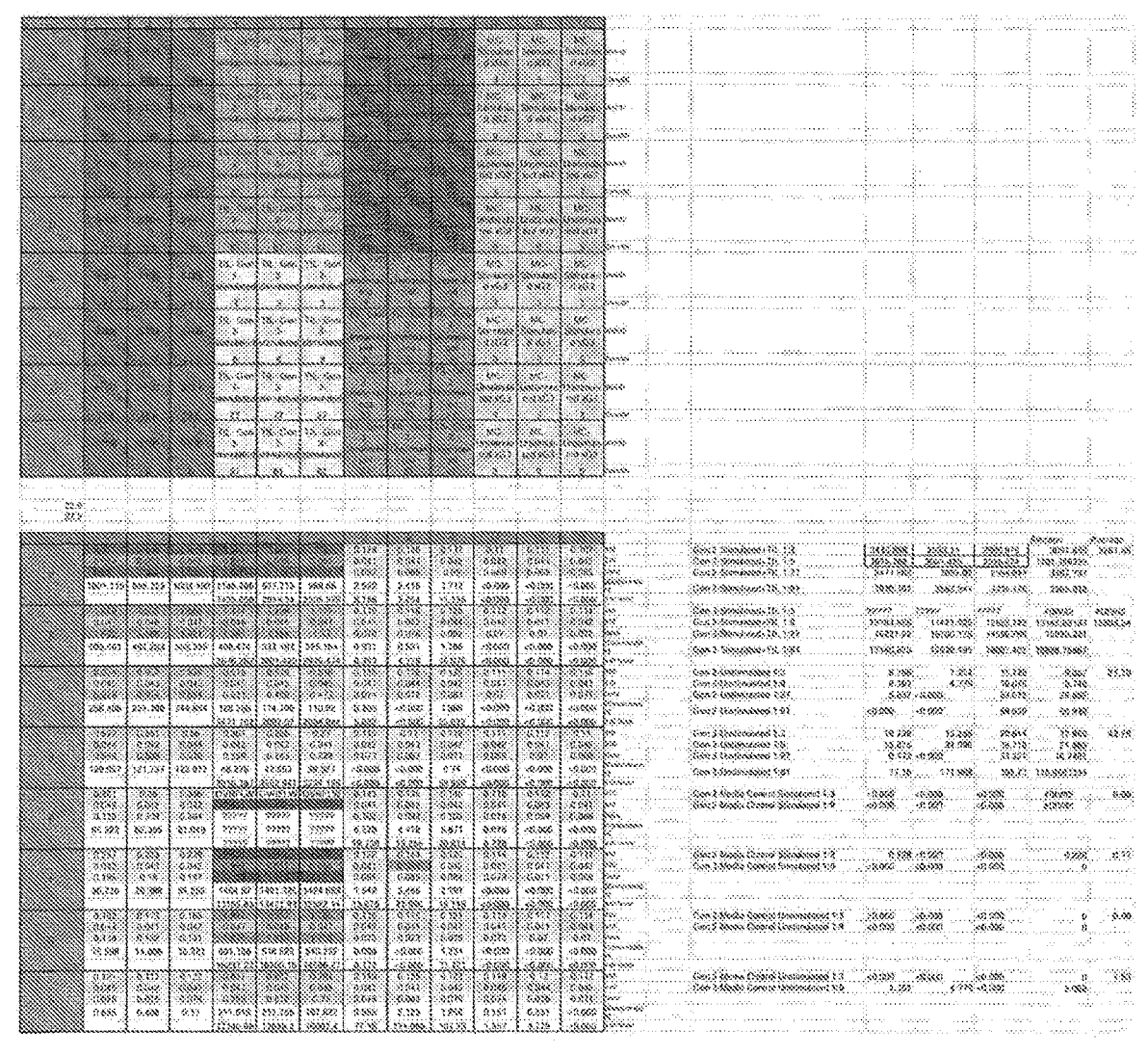

FIG. 31: Raw data for IFNγ production assay results for L4055 samples depicted in FIG. 7.

Figure 33:
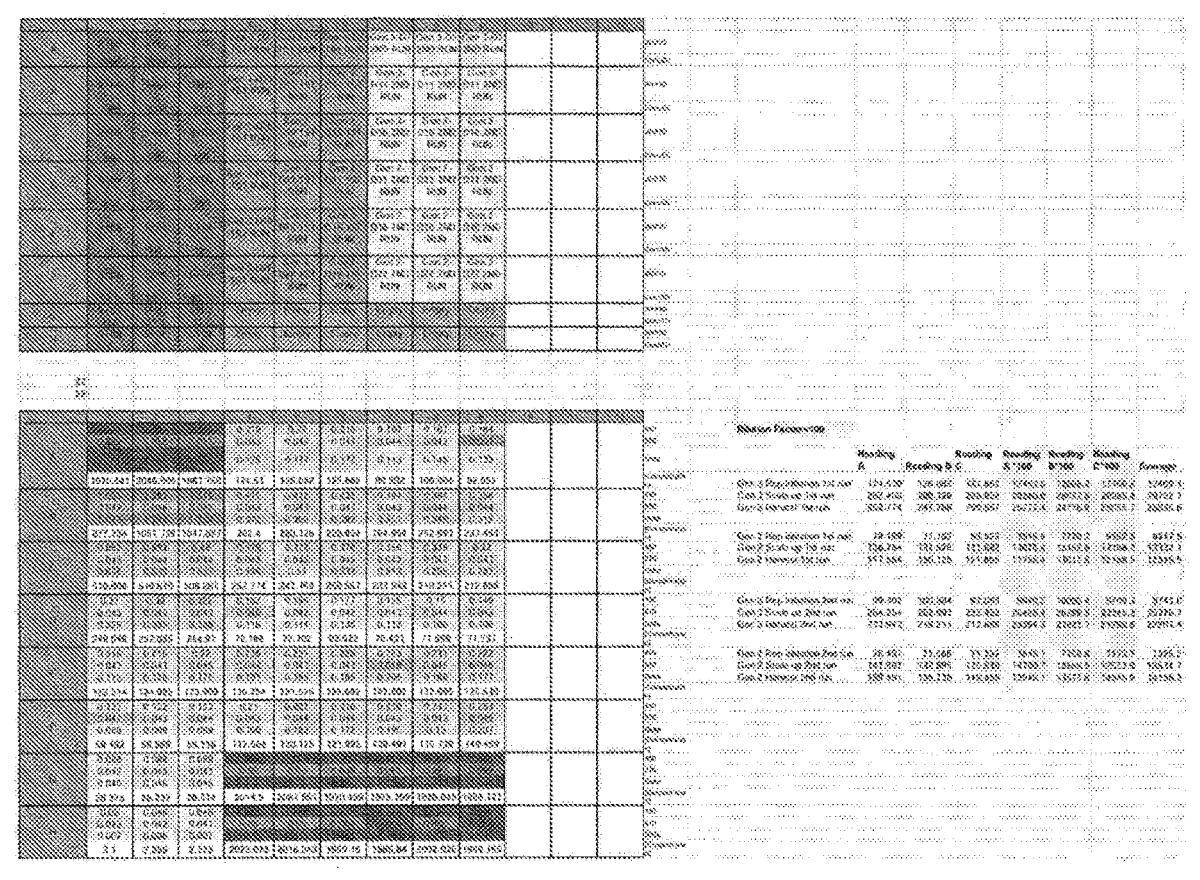

FIG. 33: Raw data for IL-2 ELISA assay results depicted in FIG. 23.

FIG. 34: Raw data for the metabolic substrate and metabolic analysis results presented in FIGS. 16 and 17.

FIG. 35: Raw data for the relative telomere length analysis results presented in FIG. 18.

FIG. 36: Raw data for the unique CD3 sequence and clonal diversity analyses results presented in FIGS. 19 and 22.

FIG. 38: Table describing various features of embodiments of the Gen 2, Gen 2.1 and Gen 3.0 process.

FIG. 39: Overview of the media conditions for an embodiment of the Gen 3 process, referred to as Gen 3.1.

FIG. 40: Table describing various features of embodiments of the Gen 2, Gen 2.1 and Gen 3.0 process.

FIG. 41: Table comparing various features of embodiments of the Gen 2 and Gen 3.0 processes.

FIG. 42: Table providing media uses in the various embodiments of the described expansion processes.

FIG. 45: Top: Unique CDR3 sequence analysis for TIL final product: Columns show the number of unique TCR B clonotypes identified from 1×10$^6$ cells collected on Gen 2 (e.g., day 22) and Gen 3 process (e.g., day 14-16). Gen 3 shows higher clonal diversity compared to Gen 2 based on the number of unique peptide CDRs within the sample. Bottom: Diversity Index for TIL final product: Shanon entropy diversity index is a more reliable a common metric for comparison. Gen 3 showed a slightly higher diversity than Gen 2.

BRIEF DESCRIPTION OF THE SEQUENCE LISTING

Figure 2A:
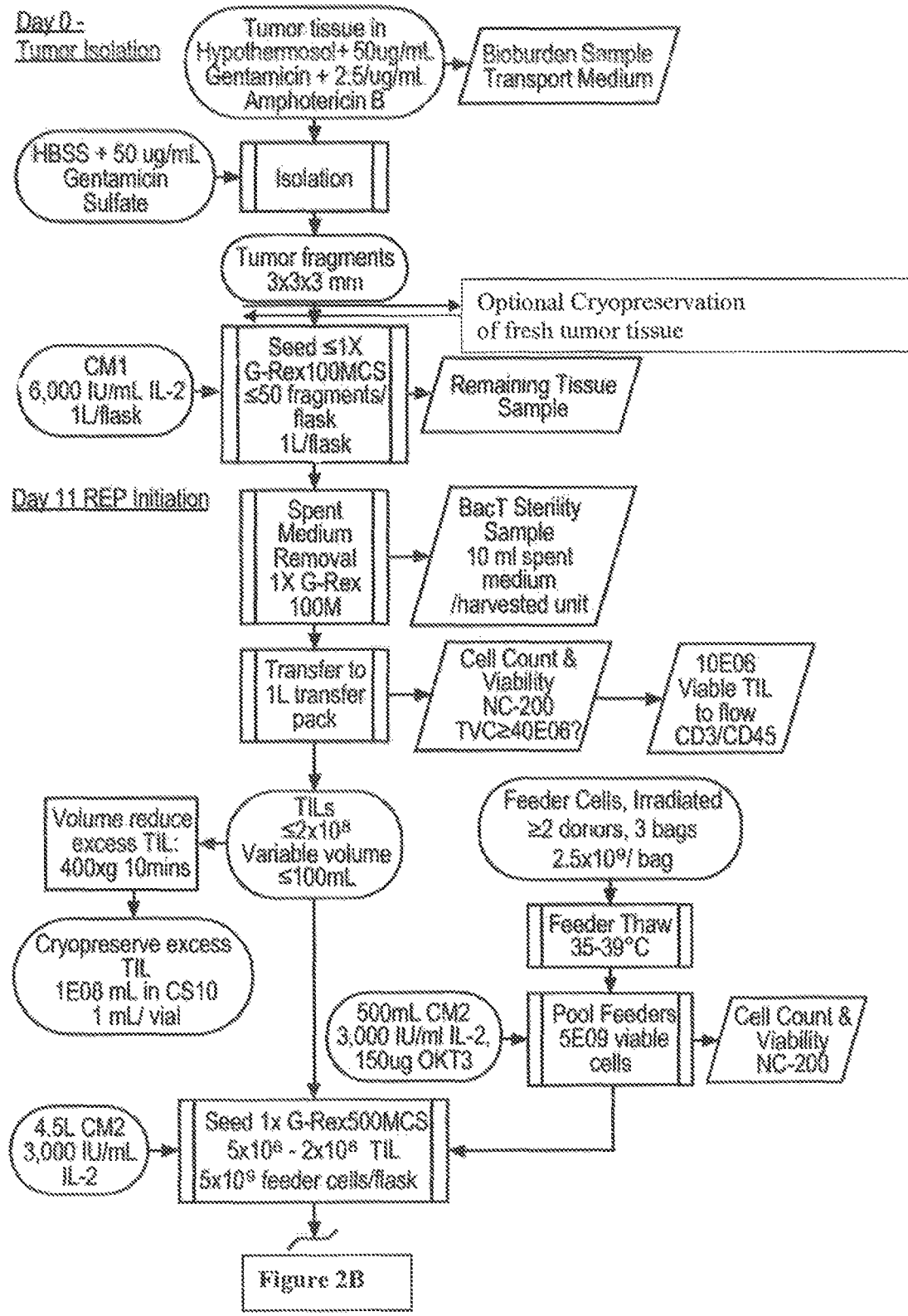
FIG. 2: Panels A through C depict the various steps of an embodiment of the TIL manufacturing process, including cryopreservation of fresh tumor fragments allowing later initiation of preREP culture.
Figure 2B:
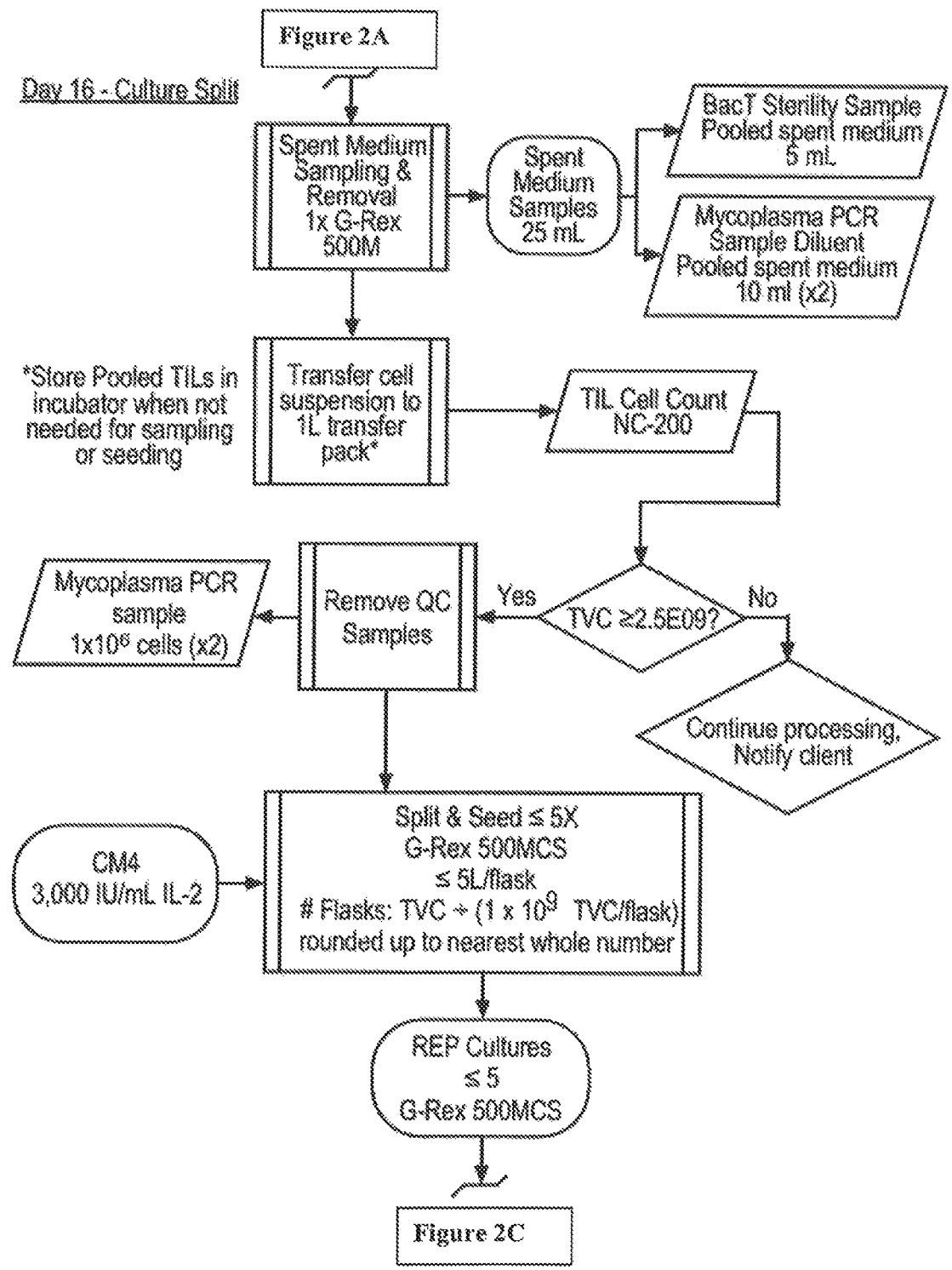
Figure 2C:
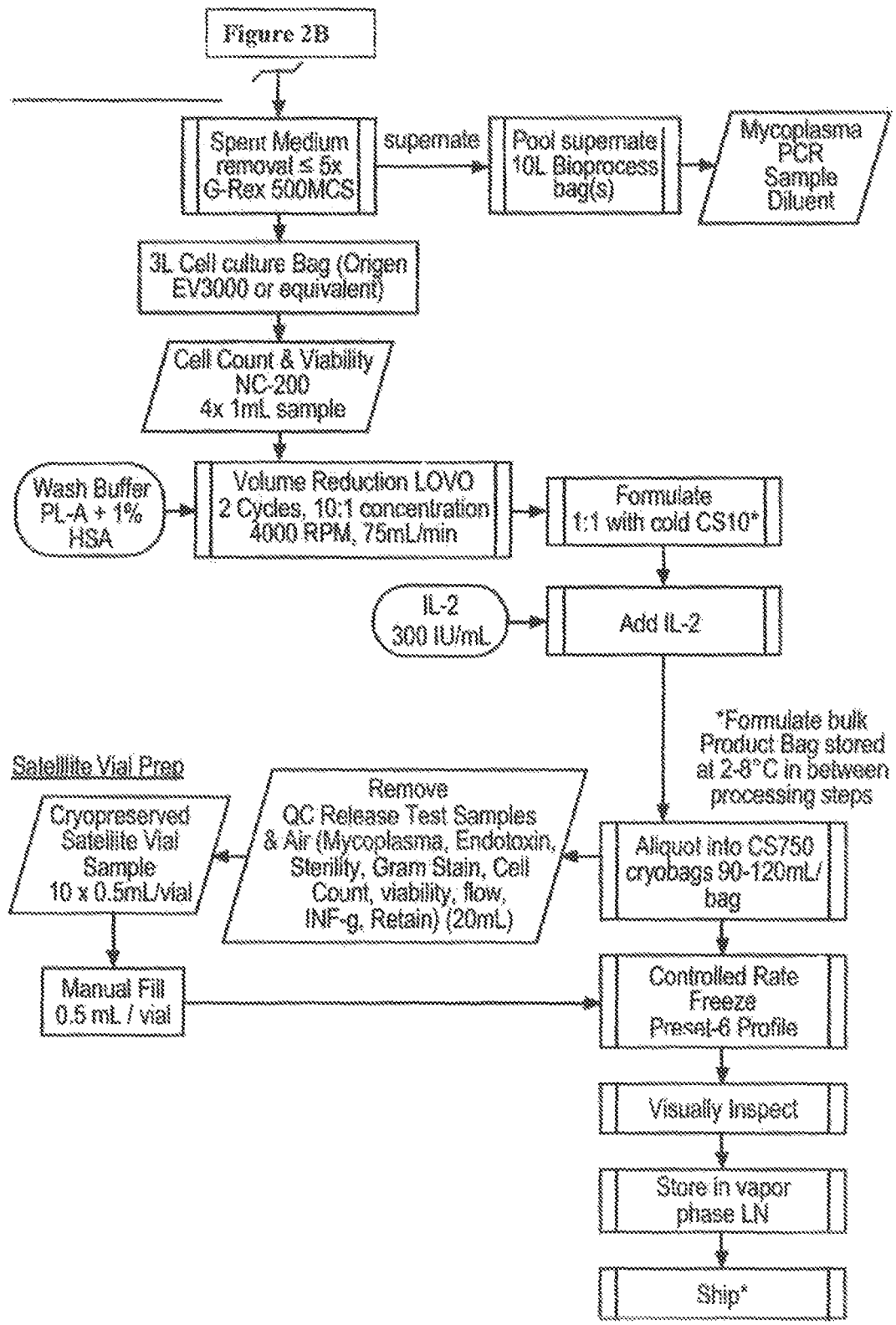
Figure 3:
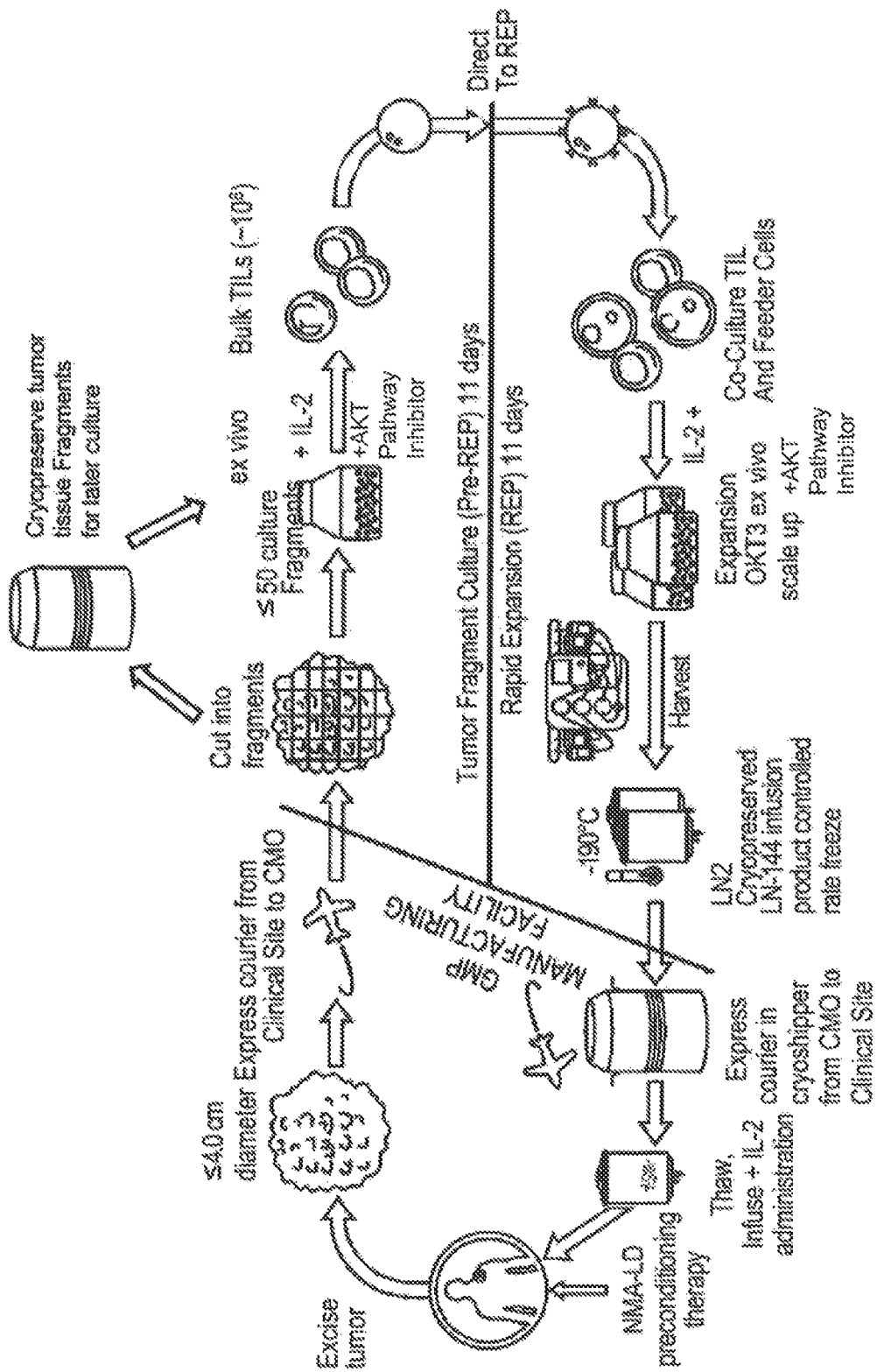
FIG. 3: Depicts an embodiment of TIL manufacturing, including the cryopreservation of fresh tumor fragments that are then later used to initiate a preREP culture indicating points in the procedure where AKT pathway inhibitors are added to the culture medium.

SEQ ID NO:1 is the amino acid sequence of the heavy chain of muromonab.
SEQ ID NO:2 is the amino acid sequence of the light chain of muromonab.
SEQ ID NO:3 is the amino acid sequence of a recombinant human IL-2 protein.
SEQ ID NO:4 is the amino acid sequence of aldesleukin.
SEQ ID NO:5 is the amino acid sequence of a recombinant human IL-4 protein.
SEQ ID NO:6 is the amino acid sequence of a recombinant human IL-7 protein.
SEQ ID NO:7 is the amino acid sequence of a recombinant human IL-15 protein.
SEQ ID NO:8 is the amino acid sequence of a recombinant human IL-21 protein.
SEQ ID NO:9 is the amino acid sequence of human 4-1BB.
SEQ ID NO:10 is the amino acid sequence of murine 4-1BB.
SEQ ID NO:11 is the heavy chain for the 4-1BB agonist monoclonal antibody utomilumab (PF-05082566).
SEQ ID NO:12 is the light chain for the 4-1BB agonist monoclonal antibody utomilumab (PF-05082566).
SEQ ID NO:13 is the heavy chain variable region ($V_H$) for the 4-1BB agonist monoclonal antibody utomilumab (PF-05082566).
SEQ ID NO:14 is the light chain variable region ($V_L$) for the 4-1BB agonist monoclonal antibody utomilumab (PF-05082566).
SEQ ID NO:15 is the heavy chain CDR1 for the 4-1BB agonist monoclonal antibody utomilumab (PF-05082566).
SEQ ID NO:16 is the heavy chain CDR2 for the 4-1BB agonist monoclonal antibody utomilumab (PF-05082566).
SEQ ID NO:17 is the heavy chain CDR3 for the 4-1BB agonist monoclonal antibody utomilumab (PF-05082566).
SEQ ID NO:18 is the light chain CDR1 for the 4-1BB agonist monoclonal antibody utomilumab (PF-05082566).
SEQ ID NO:19 is the light chain CDR2 for the 4-1BB agonist monoclonal antibody utomilumab (PF-05082566).
SEQ ID NO:20 is the light chain CDR3 for the 4-1BB agonist monoclonal antibody utomilumab (PF-05082566).
SEQ ID NO:21 is the heavy chain for the 4-1BB agonist monoclonal antibody urelumab (BMS-663513).
SEQ ID NO:22 is the light chain for the 4-1BB agonist monoclonal antibody urelumab (BMS-663513).
SEQ ID NO:23 is the heavy chain variable region ($V_H$) for the 4-1BB agonist monoclonal antibody urelumab (BMS-663513).
SEQ ID NO:24 is the light chain variable region ($V_L$) for the 4-1BB agonist monoclonal antibody urelumab (BMS-663513).
SEQ ID NO:25 is the heavy chain CDR1 for the 4-1BB agonist monoclonal antibody urelumab (BMS-663513).
SEQ ID NO:26 is the heavy chain CDR2 for the 4-1BB agonist monoclonal antibody urelumab (BMS-663513).
SEQ ID NO:27 is the heavy chain CDR3 for the 4-1BB agonist monoclonal antibody urelumab (BMS-663513).
SEQ ID NO:28 is the light chain CDR1 for the 4-1BB agonist monoclonal antibody urelumab (BMS-663513).
SEQ ID NO:29 is the light chain CDR2 for the 4-1BB agonist monoclonal antibody urelumab (BMS-663513).
SEQ ID NO:30 is the light chain CDR3 for the 4-1BB agonist monoclonal antibody urelumab (BMS-663513).
SEQ ID NO:31 is an Fc domain for a TNFRSF agonist fusion protein.
SEQ ID NO:32 is a linker for a TNFRSF agonist fusion protein.
SEQ ID NO:33 is a linker for a TNFRSF agonist fusion protein.
SEQ ID NO:34 is a linker for a TNFRSF agonist fusion protein.
SEQ ID NO:35 is a linker for a TNFRSF agonist fusion protein.
SEQ ID NO:36 is a linker for a TNFRSF agonist fusion protein.
SEQ ID NO:37 is a linker for a TNFRSF agonist fusion protein.
SEQ ID NO:38 is a linker for a TNFRSF agonist fusion protein.
SEQ ID NO:39 is a linker for a TNFRSF agonist fusion protein.
SEQ ID NO:40 is a linker for a TNFRSF agonist fusion protein.
SEQ ID NO:41 is a linker for a TNFRSF agonist fusion protein.
SEQ ID NO:42 is an Fc domain for a TNFRSF agonist fusion protein.
SEQ ID NO:43 is a linker for a TNFRSF agonist fusion protein.
SEQ ID NO:44 is a linker for a TNFRSF agonist fusion protein.
SEQ ID NO:45 is a linker for a TNFRSF agonist fusion protein.
SEQ ID NO:46 is a 4-1BB ligand (4-1BBL) amino acid sequence.
SEQ ID NO:47 is a soluble portion of 4-1BBL polypeptide.
SEQ ID NO:48 is a heavy chain variable region ($V_H$) for the 4-1BB agonist antibody 4B4-1-1 version 1.
SEQ ID NO:49 is a light chain variable region ($V_L$) for the 4-1BB agonist antibody 4B4-1-1 version 1.
SEQ ID NO:50 is a heavy chain variable region ($V_H$) for the 4-1BB agonist antibody 4B4-1-1 version 2.
SEQ ID NO:51 is a light chain variable region ($V_L$) for the 4-1BB agonist antibody 4B4-1-1 version 2.
SEQ ID NO:52 is a heavy chain variable region ($V_H$) for the 4-1BB agonist antibody H39E3-2.
SEQ ID NO:53 is a light chain variable region ($V_L$) for the 4-1BB agonist antibody H39E3-2.
SEQ ID NO:54 is the amino acid sequence of human OX40.
SEQ ID NO:55 is the amino acid sequence of murine OX40.
SEQ ID NO:56 is the heavy chain for the OX40 agonist monoclonal antibody tavolixizumab (MEDI-0562).
SEQ ID NO:57 is the light chain for the OX40 agonist monoclonal antibody tavolixizumab (MEDI-0562).
SEQ ID NO:58 is the heavy chain variable region ($V_H$) for the OX40 agonist monoclonal antibody tavolixizumab (MEDI-0562).
SEQ ID NO:59 is the light chain variable region ($V_L$) for the OX40 agonist monoclonal antibody tavolixizumab (MEDI-0562).

SEQ ID NO:60 is the heavy chain CDR1 for the OX40 agonist monoclonal antibody tavolixizumab (MEDI-0562).

SEQ ID NO:61 is the heavy chain CDR2 for the OX40 agonist monoclonal antibody tavolixizumab (MEDI-0562).

SEQ ID NO:62 is the heavy chain CDR3 for the OX40 agonist monoclonal antibody tavolixizumab (MEDI-0562).

SEQ ID NO:63 is the light chain CDR1 for the OX40 agonist monoclonal antibody tavolixizumab (MEDI-0562).

SEQ ID NO:64 is the light chain CDR2 for the OX40 agonist monoclonal antibody tavolixizumab (MEDI-0562).

SEQ ID NO:65 is the light chain CDR3 for the OX40 agonist monoclonal antibody tavolixizumab (MEDI-0562).

SEQ ID NO:66 is the heavy chain for the OX40 agonist monoclonal antibody 11D4.

SEQ ID NO:67 is the light chain for the OX40 agonist monoclonal antibody 11D4.

SEQ ID NO:68 is the heavy chain variable region ($V_H$) for the OX40 agonist monoclonal antibody 11D4.

SEQ ID NO:69 is the light chain variable region ($V_L$) for the OX40 agonist monoclonal antibody 11D4.

SEQ ID NO:70 is the heavy chain CDR1 for the OX40 agonist monoclonal antibody 11D4.

SEQ ID NO:71 is the heavy chain CDR2 for the OX40 agonist monoclonal antibody 11D4.

SEQ ID NO:72 is the heavy chain CDR3 for the OX40 agonist monoclonal antibody 11D4.

SEQ ID NO:73 is the light chain CDR1 for the OX40 agonist monoclonal antibody 11D4.

SEQ ID NO:74 is the light chain CDR2 for the OX40 agonist monoclonal antibody 11D4.

SEQ ID NO:75 is the light chain CDR3 for the OX40 agonist monoclonal antibody 11D4.

SEQ ID NO:76 is the heavy chain for the OX40 agonist monoclonal antibody 18D8.

SEQ ID NO:77 is the light chain for the OX40 agonist monoclonal antibody 18D8.

SEQ ID NO:78 is the heavy chain variable region ($V_H$) for the OX40 agonist monoclonal antibody 18D8.

SEQ ID NO:79 is the light chain variable region ($V_L$) for the OX40 agonist monoclonal antibody 18D8.

SEQ ID NO:80 is the heavy chain CDR1 for the OX40 agonist monoclonal antibody 18D8.

SEQ ID NO:81 is the heavy chain CDR2 for the OX40 agonist monoclonal antibody 18D8.

SEQ ID NO:82 is the heavy chain CDR3 for the OX40 agonist monoclonal antibody 18D8.

SEQ ID NO:83 is the light chain CDR1 for the OX40 agonist monoclonal antibody 18D8.

SEQ ID NO:84 is the light chain CDR2 for the OX40 agonist monoclonal antibody 18D8.

SEQ ID NO:85 is the light chain CDR3 for the OX40 agonist monoclonal antibody 18D8.

SEQ ID NO:86 is the heavy chain variable region ($V_H$) for the OX40 agonist monoclonal antibody Hu119-122.

SEQ ID NO:87 is the light chain variable region ($V_L$) for the OX40 agonist monoclonal antibody Hu119-122.

SEQ ID NO:88 is the heavy chain CDR1 for the OX40 agonist monoclonal antibody Hu119-122.

SEQ ID NO:89 is the heavy chain CDR2 for the OX40 agonist monoclonal antibody Hu119-122.

SEQ ID NO:90 is the heavy chain CDR3 for the OX40 agonist monoclonal antibody Hu119-122.

SEQ ID NO:91 is the light chain CDR1 for the OX40 agonist monoclonal antibody Hu119-122.

SEQ ID NO:92 is the light chain CDR2 for the OX40 agonist monoclonal antibody Hu119-122.

SEQ ID NO:93 is the light chain CDR3 for the OX40 agonist monoclonal antibody Hu119-122.

SEQ ID NO:94 is the heavy chain variable region ($V_H$) for the OX40 agonist monoclonal antibody Hu106-222.

SEQ ID NO:95 is the light chain variable region ($V_L$) for the OX40 agonist monoclonal antibody Hu106-222.

SEQ ID NO:96 is the heavy chain CDR1 for the OX40 agonist monoclonal antibody Hu106-222.

SEQ ID NO:97 is the heavy chain CDR2 for the OX40 agonist monoclonal antibody Hu106-222.

SEQ ID NO:98 is the heavy chain CDR3 for the OX40 agonist monoclonal antibody Hu106-222.

SEQ ID NO:99 is the light chain CDR1 for the OX40 agonist monoclonal antibody Hu106-222.

SEQ ID NO:100 is the light chain CDR2 for the OX40 agonist monoclonal antibody Hu106-222.

SEQ ID NO:101 is the light chain CDR3 for the OX40 agonist monoclonal antibody Hu106-222.

SEQ ID NO:102 is an OX40 ligand (OX40L) amino acid sequence.

SEQ ID NO:103 is a soluble portion of OX40L polypeptide.

SEQ ID NO:104 is an alternative soluble portion of OX40L polypeptide.

SEQ ID NO:105 is the heavy chain variable region ($V_H$) for the OX40 agonist monoclonal antibody 008.

SEQ ID NO:106 is the light chain variable region ($V_L$) for the OX40 agonist monoclonal antibody 008.

SEQ ID NO:107 is the heavy chain variable region ($V_H$) for the OX40 agonist monoclonal antibody 011.

SEQ ID NO:108 is the light chain variable region ($V_L$) for the OX40 agonist monoclonal antibody 011.

SEQ ID NO:109 is the heavy chain variable region ($V_H$) for the OX40 agonist monoclonal antibody 021.

SEQ ID NO:110 is the light chain variable region ($V_L$) for the OX40 agonist monoclonal antibody 021.

SEQ ID NO:111 is the heavy chain variable region ($V_H$) for the OX40 agonist monoclonal antibody 023.

SEQ ID NO:112 is the light chain variable region ($V_L$) for the OX40 agonist monoclonal antibody 023.

SEQ ID NO:113 is the heavy chain variable region ($V_H$) for an OX40 agonist monoclonal antibody.

SEQ ID NO:114 is the light chain variable region ($V_L$) for an OX40 agonist monoclonal antibody.

SEQ ID NO:115 is the heavy chain variable region ($V_H$) for an OX40 agonist monoclonal antibody.

SEQ ID NO:116 is the light chain variable region ($V_L$) for an OX40 agonist monoclonal antibody.

SEQ ID NO:117 is the heavy chain variable region ($V_H$) for a humanized OX40 agonist monoclonal antibody.

SEQ ID NO:118 is the heavy chain variable region ($V_H$) for a humanized OX40 agonist monoclonal antibody.

SEQ ID NO:119 is the light chain variable region ($V_L$) for a humanized OX40 agonist monoclonal antibody.

SEQ ID NO:120 is the light chain variable region ($V_L$) for a humanized OX40 agonist monoclonal antibody.

SEQ ID NO:121 is the heavy chain variable region ($V_H$) for a humanized OX40 agonist monoclonal antibody.

SEQ ID NO:122 is the heavy chain variable region ($V_H$) for a humanized OX40 agonist monoclonal antibody.

SEQ ID NO:123 is the light chain variable region ($V_L$) for a humanized OX40 agonist monoclonal antibody.

SEQ ID NO:124 is the light chain variable region ($V_L$) for a humanized OX40 agonist monoclonal antibody.

SEQ ID NO:125 is the heavy chain variable region ($V_H$) for an OX40 agonist monoclonal antibody.

SEQ ID NO:126 is the light chain variable region (V$_L$) for an OX40 agonist monoclonal antibody.

SEQ ID NO:127 is the heavy chain amino acid sequence of the PD-1 inhibitor nivolumab.

SEQ ID NO:128 is the light chain amino acid sequence of the PD-1 inhibitor nivolumab.

SEQ ID NO:129 is the heavy chain variable region (V$_H$) amino acid sequence of the PD-1 inhibitor nivolumab.

SEQ ID NO:130 is the light chain variable region (V$_L$) amino acid sequence of the PD-1 inhibitor nivolumab.

SEQ ID NO:131 is the heavy chain CDR1 amino acid sequence of the PD-1 inhibitor nivolumab.

SEQ ID NO:132 is the heavy chain CDR2 amino acid sequence of the PD-1 inhibitor nivolumab.

SEQ ID NO:133 is the heavy chain CDR3 amino acid sequence of the PD-1 inhibitor nivolumab.

SEQ ID NO:134 is the light chain CDR1 amino acid sequence of the PD-1 inhibitor nivolumab.

SEQ ID NO:135 is the light chain CDR2 amino acid sequence of the PD-1 inhibitor nivolumab.

SEQ ID NO:136 is the light chain CDR3 amino acid sequence of the PD-1 inhibitor nivolumab.

SEQ ID NO:137 is the heavy chain amino acid sequence of the PD-1 inhibitor pembrolizumab.

SEQ ID NO:138 is the light chain amino acid sequence of the PD-1 inhibitor pembrolizumab.

SEQ ID NO:139 is the heavy chain variable region (V$_H$) amino acid sequence of the PD-1 inhibitor pembrolizumab.

SEQ ID NO:140 is the light chain variable region (V$_L$) amino acid sequence of the PD-1 inhibitor pembrolizumab.

SEQ ID NO:141 is the heavy chain CDR1 amino acid sequence of the PD-1 inhibitor pembrolizumab.

SEQ ID NO:142 is the heavy chain CDR2 amino acid sequence of the PD-1 inhibitor pembrolizumab.

SEQ ID NO:143 is the heavy chain CDR3 amino acid sequence of the PD-1 inhibitor pembrolizumab.

SEQ ID NO:144 is the light chain CDR1 amino acid sequence of the PD-1 inhibitor pembrolizumab.

SEQ ID NO:145 is the light chain CDR2 amino acid sequence of the PD-1 inhibitor pembrolizumab.

SEQ ID NO:146 is the light chain CDR3 amino acid sequence of the PD-1 inhibitor pembrolizumab.

SEQ ID NO:147 is the heavy chain amino acid sequence of the PD-L1 inhibitor durvalumab.

SEQ ID NO:148 is the light chain amino acid sequence of the PD-L1 inhibitor durvalumab.

SEQ ID NO:149 is the heavy chain variable region (V$_H$) amino acid sequence of the PD-L1 inhibitor durvalumab.

SEQ ID NO:150 is the light chain variable region (V$_L$) amino acid sequence of the PD-L1 inhibitor durvalumab.

SEQ ID NO:151 is the heavy chain CDR1 amino acid sequence of the PD-L1 inhibitor durvalumab.

SEQ ID NO:152 is the heavy chain CDR2 amino acid sequence of the PD-L1 inhibitor durvalumab.

SEQ ID NO:153 is the heavy chain CDR3 amino acid sequence of the PD-L1 inhibitor durvalumab.

SEQ ID NO:154 is the light chain CDR1 amino acid sequence of the PD-L1 inhibitor durvalumab.

SEQ ID NO:155 is the light chain CDR2 amino acid sequence of the PD-L1 inhibitor durvalumab.

SEQ ID NO:156 is the light chain CDR3 amino acid sequence of the PD-L1 inhibitor durvalumab.

SEQ ID NO:157 is the heavy chain amino acid sequence of the PD-L1 inhibitor avelumab.

SEQ ID NO:158 is the light chain amino acid sequence of the PD-L1 inhibitor avelumab.

SEQ ID NO:159 is the heavy chain variable region (V$_H$) amino acid sequence of the PD-L1 inhibitor avelumab.

SEQ ID NO:160 is the light chain variable region (V$_L$) amino acid sequence of the PD-L1 inhibitor avelumab.

SEQ ID NO:161 is the heavy chain CDR1 amino acid sequence of the PD-L1 inhibitor avelumab.

SEQ ID NO:162 is the heavy chain CDR2 amino acid sequence of the PD-L1 inhibitor avelumab.

SEQ ID NO:163 is the heavy chain CDR3 amino acid sequence of the PD-L1 inhibitor avelumab.

SEQ ID NO:164 is the light chain CDR1 amino acid sequence of the PD-L1 inhibitor avelumab.

SEQ ID NO:165 is the light chain CDR2 amino acid sequence of the PD-L1 inhibitor avelumab.

SEQ ID NO:166 is the light chain CDR3 amino acid sequence of the PD-L1 inhibitor avelumab.

SEQ ID NO:167 is the heavy chain amino acid sequence of the PD-L1 inhibitor atezolizumab.

SEQ ID NO:168 is the light chain amino acid sequence of the PD-L1 inhibitor atezolizumab.

SEQ ID NO:169 is the heavy chain variable region (V$_H$) amino acid sequence of the PD-L1 inhibitor atezolizumab.

SEQ ID NO:170 is the light chain variable region (V$_L$) amino acid sequence of the PD-L1 inhibitor atezolizumab.

SEQ ID NO:171 is the heavy chain CDR1 amino acid sequence of the PD-L1 inhibitor atezolizumab.

SEQ ID NO:172 is the heavy chain CDR2 amino acid sequence of the PD-L1 inhibitor atezolizumab.

SEQ ID NO:173 is the heavy chain CDR3 amino acid sequence of the PD-L1 inhibitor atezolizumab.

SEQ ID NO:174 is the light chain CDR1 amino acid sequence of the PD-L1 inhibitor atezolizumab.

SEQ ID NO:175 is the light chain CDR2 amino acid sequence of the PD-L1 inhibitor atezolizumab.

SEQ ID NO:176 is the light chain CDR3 amino acid sequence of the PD-L1 inhibitor atezolizumab.

DETAILED DESCRIPTION OF THE INVENTION

Unless defined otherwise, all technical and scientific terms used herein have the same meaning as is commonly understood by one of skill in the art to which this invention belongs. All patents and publications referred to herein are incorporated by reference in their entireties.

Definitions

The term "AKT pathway inhibitor" refers to inhibitors of the kinases and phosphatases that constitute the AKT signaling network. The AKT signaling network comprises PI3K, AKT, PDK1, mTORC2, GSK3, FOXO (including FOXO1, FOXO3A, and FOXO4), mTORC1, PTEN, BAD, ASK1, MERIT40, MDM2, CHK1, IKKα, p21CIP1, p27KIP1, RAF1, PFKFB2, PDE3B, AMPK, ACLY, PIKfyve, eNOS, and WNK1.

The term "LOVO cell processing system" and "LOVO" refers to the cell processing system manufactured by Fresenius Kabi USA, LLC. These two terms also refer to any instrument or device manufactured by any vendor that can pump a solution comprising cells through a membrane or filter such as a spinning membrane or spinning filter in a sterile and/or closed system environment, allowing for continuous flow and cell processing to remove supernatant or cell culture media without pelletization. In some embodiments, such a cell harvester and/or cell processing system can perform cell separation, washing, fluid-exchange, concentration, and/or other cell processing steps in a closed, sterile system.

The term "fungin" refers to the antifungal reagent Fungin™ sold by InvitroGen, San Diego, CA, USA, (catalog numbers ant-fn-1 and ant-fn-2). Fungin is a soluble formulation of pimaricin, CAS 7681-93-8. As used herein, "fungin" encompasses any commercial formulation of pimaricin or natamycin.

The term "fungizone" is a trademark of E. R. Squibb and Sons, LLC, and refers to the antimycotic amphotericin B, CAS 1397-89-3. Amphotericin B is commercially available, for example from SIGMA-Aldrich, St. Louis, MO, USA, (catalog number A2942, as a 250 μg/mL solution in deionized water). As used herein, "fungizone" encompasses any commercial formulation of amphotericin B.

The term "physiologically buffered isotonic saline solution" means any one of the many such salt solutions known to the skilled artisan wherein the solution is made to a physiological pH and isotonic salt concentration. In the art, these are commonly referred to as balanced salt solutions. Without limitation such physiologically buffered isotonic saline solution may comprise Hank's Balanced Salt Solution ("HBSS"), Tris-buffered saline ("TBS"), Phosphate buffered Saline ("PBS"), or Dulbecco's Phosphate Buffered Saline ("DPBS" or "dPBS").

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "ex vivo" refers to an event which involves treating or performing a procedure on a cell, tissue and/or organ which has been removed from a subject's body. Aptly, the cell, tissue and/or organ may be returned to the subject's body in a method of surgery or treatment.

The term "rapid expansion" means an increase in the number of antigen-specific TILs of at least about 3-fold (or 4-, 5-, 6-, 7-, 8-, or 9-fold) over a period of a week, more preferably at least about 10-fold (or 20-, 30-, 40-, 50-, 60-, 70-, 80-, or 90-fold) over a period of a week, or most preferably at least about 100-fold over a period of a week. A number of rapid expansion protocols are outlined below.

By "tumor infiltrating lymphocytes" or "TILs" herein is meant a population of cells originally obtained as white blood cells that have left the bloodstream of a subject and migrated into a tumor. TILs include, but are not limited to, $CD8^+$ cytotoxic T cells (lymphocytes), Th1 and Th17 $CD4^+$ T cells, natural killer cells, dendritic cells and M1 macrophages. TILs include both primary and secondary TILs. "Primary TILs" are those that are obtained from patient tissue samples as outlined herein (sometimes referred to as "freshly harvested"), and "secondary TILs" are any TIL cell populations that have been expanded or proliferated as discussed herein, including, but not limited to bulk TILs and expanded TILs ("REP TILs" or "post-REP TILs"). TIL cell populations can include genetically modified TILs.

By "population of cells" (including TILs) herein is meant a number of cells that share common traits. In general, populations generally range from $1\times10^6$ to $1\times10^{10}$ in number, with different TIL populations comprising different numbers. For example, initial growth of primary TILs in the presence of IL-2 results in a population of bulk TILs of roughly $1\times10^8$ cells. REP expansion is generally done to provide populations of $1.5\times10^9$ to $1.5\times10^{10}$ cells for infusion.

By "cryopreserved TILs" herein is meant that TILs, either primary, bulk, or expanded (REP TILs), are treated and stored at a temperature in the range of about −150° C. to −60° C. General methods for cryopreservation are also described elsewhere herein, including in the Examples. For clarity and the avoidance of doubt, "cryopreserved TILs" are distinguishable from frozen tissue samples which may be used as a source of primary TILs.

By "thawed cryopreserved TILs" herein is meant a population of TILs that was previously cryopreserved and then treated to return to room temperature or higher, including but not limited to cell culture temperatures or temperatures wherein TILs may be administered to a patient.

TILs can generally be defined either biochemically, using cell surface markers, or functionally, by their ability to infiltrate tumors and effect treatment. TILs can be generally categorized by expressing one or more of the following biomarkers: CD4, CD8, TCR αβ, CD27, CD28, CD56, CCR7, CD45Ra, CD95, PD-1, and CD25. Additionally, and alternatively, TILs can be functionally defined by their ability to infiltrate solid tumors upon reintroduction into a patient.

The term "cryopreservation media" or "cryopreservation medium" refers to any medium that can be used for cryopreservation of cells. Such media can include media comprising 5% v/v DMSO to 10% v/v DMSO; such media can also include media comprising 7% v/v DMSO to 10% v/v DMSO. Exemplary media include CryoStor CS10, Hyperthermasol, as well as combinations thereof. The term "CS10" refers to a cryopreservation medium which is obtained from Stemcell Technologies or from Biolife Solutions. The CS10 medium may be referred to by the trade name "CryoStor® CS10". The CS10 medium is a serum-free, animal component-free medium which comprises DMSO.

The term "central memory T cell" refers to a subset of T cells that in the human are CD45R0+ and constitutively express CCR7 ($CCR7^{hi}$) and CD62L ($CD62^{hi}$). The surface phenotype of central memory T cells also includes TCR, CD3, CD127 (IL-7R), and IL-15R. Transcription factors for central memory T cells include BCL-6, BCL-6B, MBD2, and BMI1. Central memory T cells primarily secret IL-2 and CD40L as effector molecules after TCR triggering. Central memory T cells are predominant in the CD4 compartment in blood, and in the human are proportionally enriched in lymph nodes and tonsils.

The term "effector memory T cell" refers to a subset of human or mammalian T cells that, like central memory T cells, are $CD45R0^+$, but have lost the constitutive expression of CCR7 ($CCR7^{lo}$) and are heterogeneous or low for CD62L expression ($CD62L^{lo}$). The surface phenotype of central memory T cells also includes TCR, CD3, CD127 (IL-7R), and IL-15R. Transcription factors for central memory T cells include BLIMP1. Effector memory T cells rapidly secret high levels of inflammatory cytokines following antigenic stimulation, including interferon-γ, IL-4, and IL-5. Effector memory T cells are predominant in the CD8 compartment in blood, and in the human are proportionally enriched in the lung, liver, and gut. $CD8^m$ effector memory T cells carry large amounts of perforin.

The term "closed system" refers to a system that is closed to the outside environment. Any closed system appropriate for cell culture methods can be employed with the methods of the present invention. Closed systems include, for example, but are not limited to closed G-containers. Once a tumor fragment is added to the closed system, the system is not opened to the outside environment until the TILs are ready to be administered to the patient.

The terms "fragmenting," "fragment," and "fragmented," as used herein to describe processes for disrupting a tumor, includes mechanical fragmentation methods such as crushing, slicing, dividing, and morcellating tumor tissue as well as any other method for disrupting the physical structure of tumor tissue.

The terms "peripheral blood mononuclear cells" and "PBMCs" refers to a peripheral blood cell having a round nucleus, including lymphocytes (T cells, B cells, NK cells) and monocytes. Preferably, the peripheral blood mononuclear cells are irradiated allogeneic peripheral blood mononuclear cells. PBMCs are a type of antigen-presenting cell.

The term "anti-CD3 antibody" refers to an antibody or variant thereof, e.g., a monoclonal antibody and including human, humanized, chimeric or murine antibodies which are directed against the CD3 receptor in the T cell antigen receptor of mature T cells. Anti-CD3 antibodies include OKT-3, also known as muromonab. Anti-CD3 antibodies also include the UHCT1 clone, also known as T3 and CD3ε. Other anti-CD3 antibodies include, for example, otelixizumab, teplizumab, and visilizumab.

The term "OKT-3" (also referred to herein as "OKT3") refers to a monoclonal antibody or biosimilar or variant thereof, including human, humanized, chimeric, or murine antibodies, directed against the CD3 receptor in the T cell antigen receptor of mature T cells, and includes commercially-available forms such as OKT-3 (30 ng/mL, MACS GMP CD3 pure, Miltenyi Biotech, Inc., San Diego, CA, USA) and muromonab or variants, conservative amino acid substitutions, glycoforms, or biosimilars thereof. The amino acid sequences of the heavy and light chains of muromonab are given in Table 1 (SEQ ID NO:1 and SEQ ID NO:2). A hybridoma capable of producing OKT-3 is deposited with the American Type Culture Collection and assigned the ATCC accession number CRL 8001. A hybridoma capable of producing OKT-3 is also deposited with European Collection of Authenticated Cell Cultures (ECACC) and assigned Catalogue No. 86022706.

TABLE 1

Amino acid sequences of muromonab.

| Identifier | Sequence (One-Letter Amino Acid Symbols) | |
|---|---|---|
| SEQ ID NO: 1 Muromonab heavy chain | QVQLQQSGAE LARPGASVKM SCKASGYTFT RYTMHWVKQR PGQGLEWIGY INPSRGYTNY | 60 |
| | NQKFKDKATL TTDKSSSTAY MQLSSLTSED SAVYYCARYY DDHYCLDYWG QGTTLTVSSA | 120 |
| | KTTAPSVYPL APVCGGTTGS SVTLGCLVKG YFPEPVTLTW NSGSLSSGVH TFPAVLQSDL | 180 |
| | YTLSSSVTVT SSTWPSQSIT CNVAHPASST KVDKKIEPRP KSCDKTHTCP PCPAPELLGG | 240 |
| | PSVFLFPPKP KDTLMISRTP EVTCVVVDVS HEDPEVKFNW YVDGVEVHNA KTKPREEQYN | 300 |
| | STYRVVSVLT VLHQDWLNGK EYKCKVSNKA LPAPIEKTIS KAKGQPREPQ VYTLPPSRDE | 360 |
| | LTKNQVSLTC LVKGFYPSDI AVEWESNGQP ENNYKTTPPV LDSDGSFFLY SKLTVDKSRW | 420 |
| | QQGNVFSCSV MHEALHNHYT QKSLSLSPGK | 450 |
| SEQ ID NO: 2 Muromonab light chain | QIVLTQSPAI MSASPGEKVT MTCSASSSVS YMNWYQQKSG TSPKRWIYDT SKLASGVPAH | 60 |
| | FRGSGSGTSY SLTISGMEAE DAATYYCQQW SSNPFTFGSG TKLEINRADT APTVSIFPPS | 120 |
| | SEQLTSGGAS VVCFLNNFYP KDINVKWKID GSERQNGVLN SWTDQDSKDS TYSMSSTLTL | 180 |
| | TKDEYERHNS YTCEATHKTS TSPIVKSFNR NEC | 213 |

TABLE 2

Amino acid sequences of interleukins.

| Identifier | Sequence (One-Letter Amino Acid Symbols) | |
|---|---|---|
| SEQ ID NO: 3 recombinant human IL-2 (rhIL-2) | MAPTSSSTKK TQLQLEHLLL DLQMILNGIN NYKNPKLTRM LTFKFYMPKK ATELKHLQCL | 60 |
| | EEELKPLEEV LNLAQSKNFH LRPRDLISNI NVIVLELKGS ETTFMCEYAD ETATIVEFLN | 120 |
| | RWITFCQSII STLT | 134 |
| SEQ ID NO: 4 Aldesleukin | PTSSSTKKTQ LQLEHLLLDL QMILNGINNY KNPKLTRMLT FKFYMPKKAT ELKHLQCLEE | 60 |
| | ELKPLEEVLN LAQSKNFHLR PRDLISNINV IVLELKGSET TFMCEYADET ATIVEFLNRW | 120 |
| | ITFSQSIIST LT | 132 |
| SEQ ID NO: 5 recombinant human IL-4 (rhIL-4) | MHKCDITLQE IIKTLNSLTE QKTLCTELTV TDIFAASKNT TEKETFCRAA TVLRQFYSHH | 60 |
| | EKDTRCLGAT AQQFHRHKQL IRFLKRLDRN LWGLAGLNSC PVKEANQSTL ENFLERLKTI | 120 |
| | MREKYSKCSS | 130 |
| SEQ ID NO: 6 recombinant human IL-7 | MDCDIEGKDG KQYESVLMVS IDQLLDSMKE IGSNCLNNEF NFFKRHICDA NKEGMFLFRA | 60 |
| | ARKLRQFLKM NSTGDFDLHL LKVSEGTTIL LNCTGQVKGR KPAALGEAQP TKSLEENKSL | 120 |
| | KEQKKLNDLC FLKRLLQEIK TCWNKILMGT KEH | 153 |
| SEQ ID NO: 7 recombinant human IL-15 (rhIL-15) | MNWVNVISDL KKIEDLIQSM HIDATLYTES DVHPSCKVTA MKCFLLELQV ISLESGDASI | 60 |
| | HDTVENLIIL ANNSLSSNGN VTESGCKECE ELEEKNIKEF LQSFVHIVQM FINTS | 115 |

TABLE 2-continued

Amino acid sequences of interleukins.

| Identifier | Sequence (One-Letter Amino Acid Symbols) | |
|---|---|---|
| SEQ ID NO: 8 recombinant human IL-21 (rhIL-21) | MQDRHMIRMR QLIDIVDQLK NYVNDLVPEF LPAPEDVETN CEWSAFSCFQ KAQLKSANTG<br>NNERIINVSI KKLKRKPPST NAGRRQKHRL TCPSCDSYEK KPPKEFLERF KSLLQKMIHQ<br>HLSSRTHGSE DS | 60<br>120<br>132 |

The term "IL-2" (also referred to herein as "IL2") refers to the T cell growth factor known as interleukin-2, and includes all forms of IL-2 including human and mammalian forms, conservative amino acid substitutions, glycoforms, biosimilars, and variants thereof. IL-2 is described, e.g., in Nelson, *J. Immunol.* 2004, 172, 3983-88 and Malek, *Annu. Rev. Immunol.* 2008, 26, 453-79, the disclosures of which are incorporated by reference herein. The amino acid sequence of recombinant human IL-2 suitable for use in the invention is given in Table 2 (SEQ ID NO:3). For example, the term IL-2 encompasses human, recombinant forms of IL-2 such as aldesleukin (PROLEUKIN, available commercially from multiple suppliers in 22 million IU per single use vials), as well as the form of recombinant IL-2 commercially supplied by CellGenix, Inc., Portsmouth, NH, USA (CELLGRO GMP) or ProSpec-Tany TechnoGene Ltd., East Brunswick, NJ, USA (Cat. No. CYT-209-b) and other commercial equivalents from other vendors. Aldesleukin (des-alanyl-1, serine-125 human IL-2) is a nonglycosylated human recombinant form of IL-2 with a molecular weight of approximately 15 kDa. The amino acid sequence of aldesleukin suitable for use in the invention is given in Table 2 (SEQ ID NO:4). The term IL-2 also encompasses pegylated forms of IL-2, as described herein, including the pegylated IL2 prodrug NKTR-214, available from Nektar Therapeutics, South San Francisco, CA, USA. NKTR-214 and pegylated IL-2 suitable for use in the invention is described in U.S. Patent Application Publication No. US 2014/0328791 A1 and International Patent Application Publication No. WO 2012/065086 A1, the disclosures of which are incorporated by reference herein. Alternative forms of conjugated IL-2 suitable for use in the invention are described in U.S. Pat. Nos. 4,766,106, 5,206,344, 5,089,261 and 4,902,502, the disclosures of which are incorporated by reference herein. Formulations of IL-2 suitable for use in the invention are described in U.S. Pat. No. 6,706,289, the disclosure of which is incorporated by reference herein.

The term "IL-4" (also referred to herein as "IL4") refers to the cytokine known as interleukin 4, which is produced by Th2 T cells and by eosinophils, basophils, and mast cells. IL-4 regulates the differentiation of naïve helper T cells (Th0 cells) to Th2 T cells. Steinke and Borish, *Respir. Res.* 2001, 2, 66-70. Upon activation by IL-4, Th2 T cells subsequently produce additional IL-4 in a positive feedback loop. IL-4 also stimulates B cell proliferation and class II MHC expression, and induces class switching to IgE and IgG1 expression from B cells. Recombinant human IL-4 suitable for use in the invention is commercially available from multiple suppliers, including ProSpec-Tany TechnoGene Ltd., East Brunswick, NJ, USA (Cat. No. CYT-211) and ThermoFisher Scientific, Inc., Waltham, MA, USA (human IL-15 recombinant protein, Cat. No. Gibco CTP0043). The amino acid sequence of recombinant human IL-4 suitable for use in the invention is given in Table 2 (SEQ ID NO:5).

The term "IL-7" (also referred to herein as "IL7") refers to a glycosylated tissue-derived cytokine known as interleukin 7, which may be obtained from stromal and epithelial cells, as well as from dendritic cells. Fry and Mackall, *Blood* 2002, 99, 3892-904. IL-7 can stimulate the development of T cells. IL-7 binds to the IL-7 receptor, a heterodimer consisting of IL-7 receptor alpha and common gamma chain receptor, which in a series of signals important for T cell development within the thymus and survival within the periphery. Recombinant human IL-7 suitable for use in the invention is commercially available from multiple suppliers, including ProSpec-Tany TechnoGene Ltd., East Brunswick, NJ, USA (Cat. No. CYT-254) and ThermoFisher Scientific, Inc., Waltham, MA, USA (human IL-15 recombinant protein, Cat. No. Gibco PHC0071). The amino acid sequence of recombinant human IL-7 suitable for use in the invention is given in Table 2 (SEQ ID NO:6).

The term "IL-15" (also referred to herein as "IL15") refers to the T cell growth factor known as interleukin-15, and includes all forms of IL-2 including human and mammalian forms, conservative amino acid substitutions, glycoforms, biosimilars, and variants thereof. IL-15 is described, e.g., in Fehniger and Caligiuri, Blood 2001, 97, 14-32, the disclosure of which is incorporated by reference herein. IL-15 shares β and γ signaling receptor subunits with IL-2. Recombinant human IL-15 is a single, non-glycosylated polypeptide chain containing 114 amino acids (and an N-terminal methionine) with a molecular mass of 12.8 kDa. Recombinant human IL-15 is commercially available from multiple suppliers, including ProSpec-Tany TechnoGene Ltd., East Brunswick, NJ, USA (Cat. No. CYT-230-b) and ThermoFisher Scientific, Inc., Waltham, MA, USA (human IL-15 recombinant protein, Cat. No. 34-8159-82). The amino acid sequence of recombinant human IL-15 suitable for use in the invention is given in Table 2 (SEQ ID NO:7).

The term "IL-21" (also referred to herein as "IL21") refers to the pleiotropic cytokine protein known as interleukin-21, and includes all forms of IL-21 including human and mammalian forms, conservative amino acid substitutions, glycoforms, biosimilars, and variants thereof. IL-21 is described, e.g., in Spolski and Leonard, *Nat. Rev. Drug. Disc.,* 13:379-95 (2014), the disclosure of which is incorporated by reference herein. IL-21 is primarily produced by natural killer T cells and activated human CD4$^+$ T cells. Recombinant human IL-21 is a single, non-glycosylated polypeptide chain containing 132 amino acids with a molecular mass of 15.4 kDa. Recombinant human IL-21 is commercially available from multiple suppliers, including ProSpec-Tany TechnoGene Ltd., East Brunswick, NJ, USA (Cat. No. CYT-408-b) and ThermoFisher Scientific, Inc., Waltham, MA, USA (human IL-21 recombinant protein, Cat. No. 14-8219-80). The amino acid sequence of recombinant human IL-21 suitable for use in the invention is given in Table 2 (SEQ ID NO:8).

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro, in vivo, and ex vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

"Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, preferably from 0% to 10%, more preferably from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

Compounds of the invention also include antibodies. The terms "antibody" and its plural form "antibodies" refer to whole immunoglobulins and any antigen-binding fragment ("antigen-binding portion") or single chains thereof. An "antibody" further refers to a glycoprotein comprising at least two heavy (H) chains and two light (L) chains interconnected by disulfide bonds, or an antigen-binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions of an antibody may be further subdivided into regions of hypervariability, which are referred to as complementarity determining regions (CDR) or hypervariable regions (HVR), and which can be interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen epitope or epitopes. The constant regions of the antibodies may mediate the binding of the immunoglobulin to host tissues or factors, including various cells of the immune system (e.g., effector cells) and the first component (C1q) of the classical complement system.

The terms "antigen-binding portion" or "antigen-binding fragment" of an antibody (or simply "antibody portion"), as used herein, refers to one or more fragments of an antibody that retain the ability to specifically bind to an antigen (e.g., IL-33, ST2, CD20, PD-1, PD-L1, or PD-L2). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and CH1 domains; (ii) a F(ab')2 fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a domain antibody (dAb) fragment (Ward et al., Nature, 1989, 341, 544-546), which may consist of a $V_H$ or a $V_L$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv); see, e.g., Bird et al., Science 1988, 242, 423-426; and Huston et al., Proc. Natl. Acad. Sci. USA 1988, 85, 5879-5883). Such scFv antibodies are also intended to be encompassed within the terms "antigen-binding portion" or "antigen-binding fragment" of an antibody. These antibody fragments are obtained using conventional techniques known to those with skill in the art, and the fragments are screened for utility in the same manner as are intact antibodies.

The term "human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). The term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes. In mammals, there are five antibody isotypes: IgA, IgD, IgG, IgM and IgE. In humans, there are four subclasses of the IgG isotype: IgG1, IgG2, IgG3 and IgG4, and two subclasses of the IgA isotype: IgA1 and IgA2.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another active pharmaceutical ingredient or antibody. The terms "conjugate," "antibody-drug conjugate", "ADC," or "immunoconjugate" refers to an antibody, or a fragment thereof, conjugated to a therapeutic moiety, such as a bacterial toxin, a cytotoxic drug or a radionuclide-containing toxin. Toxic moieties can be conjugated to antibodies of the invention using methods available in the art.

The terms "humanized antibody," "humanized antibodies," and "humanized" are intended to refer to antibodies in which CDR sequences derived from the germline of another mammalian species, such as a mouse, have been grafted onto human framework sequences. Additional framework region modifications may be made within the human framework sequences. Humanized forms of non-human (for example, murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a 15 hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 1986, 321, 522-525; Riechmann et al., Nature 1988, 332, 323-329; and Presta, Curr. Op. Struct. Biol. 1992, 2, 593-596.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

A "diabody" is a small antibody fragment with two antigen-binding sites. The fragments comprises a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., European Patent No. EP 404,097, International Patent Publication No. WO 93/11161; and Bolliger et al., Proc. Natl. Acad. Sci. USA 1993, 90, 6444-6448.

The term "glycosylation" refers to a modified derivative of an antibody. An aglycoslated antibody lacks glycosylation. Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Aglycosylation may increase the affinity of the antibody for antigen, as described in U.S. Pat. Nos. 5,714,350 and 6,350,861. Additionally, or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see e.g. U.S. Patent Publication No. 2004/0110704 or Yamane-Ohnuki, et al. *Biotechnol. Bioeng.*, 2004, 87, 614-622). As another example, European Patent No. EP 1,176,195 describes a cell line with a functionally disrupted FUT8 gene, which encodes a fucosyl transferase, such that antibodies expressed in such a cell line exhibit hypofucosylation by reducing or eliminating the alpha 1,6 bond-related enzyme, and also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). International Patent Publication WO 03/035835 describes a variant CHO cell line, Lec 13 cells, with reduced ability to attach fucose to Asn(297)-linked carbohydrates, also resulting in hypofucosylation of antibodies expressed in that host cell (see also Shields, et al., *J. Biol. Chem.* 2002, 277, 26733-26740. International Patent Publication WO 99/54342 describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana, et al., *Nat. Biotech.* 1999, 17, 176-180). Alternatively, the fucose residues of the antibody may be cleaved off using a fucosidase enzyme. For example, the fucosidase alpha-L-fucosidase removes fucosyl residues from antibodies as described in Tarentino, et al., *Biochem.* 1975, 14, 5516-5523.

"Pegylation" refers to a modified antibody, or a fragment thereof, that typically is reacted with polyethylene glycol (PEG), such as a reactive ester or aldehyde derivative of PEG, under conditions in which one or more PEG groups become attached to the antibody or antibody fragment. Pegylation may, for example, increase the biological (e.g., serum) half life of the antibody. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. The antibody to be pegylated may be an aglycosylated antibody. Methods for pegylation are known in the art and can be applied to the antibodies of the invention, as described for example in European Patent Nos. EP 0154316 and EP 0401384.

The term "biosimilar" means a biological product that is highly similar to a U.S. licensed reference biological product notwithstanding minor differences in clinically inactive components, and for which there are no clinically meaningful differences between the biological product and the reference product in terms of the safety, purity, and potency of the product. Furthermore, a similar biological or "biosimilar" medicine is a biological medicine that is similar to another biological medicine that has already been authorized for use by the European Medicines Agency. The term "biosimilar" is also used synonymously by other national and regional regulatory agencies. Biological products or biological medicines are medicines that are made by or derived from a biological source, such as a bacterium or yeast. They can consist of relatively small molecules such as human insulin or erythropoietin, or complex molecules such as monoclonal antibodies. For example, if the reference anti-CD20 monoclonal antibody is rituximab, an anti-CD20 biosimilar monoclonal antibody approved by drug regulatory authorities with reference to rituximab is a "biosimilar to" rituximab or is a "biosimilar thereof" of rituximab. In Europe, a similar biological or "biosimilar" medicine is a biological medicine that is similar to another biological medicine that has already been authorized for use by the European Medicines Agency (EMA). The relevant legal basis for similar biological applications in Europe is Article 6 of Regulation (EC) No 726/2004 and Article 10(4) of Directive 2001/83/EC, as amended and therefore in Europe, the biosimilar may be authorised, approved for authorisation or subject of an application for authorisation under Article 6 of Regulation (EC) No 726/2004 and Article 10(4) of Directive 2001/83/EC. The already authorized original biological medicinal product may be referred to as a "reference medicinal product" in Europe. Some of the requirements for a product to be considered a biosimilar are outlined in the CHMP Guideline on Similar Biological Medicinal Products. In addition, product specific guidelines, including guidelines relating to monoclonal antibody biosimilars, are provided on a product-by-product basis by the EMA and published on its website. A biosimilar as described herein may be similar to the reference medicinal product by way of quality characteristics, biological activity, mechanism of action, safety profiles and/or efficacy. In addition, the biosimilar may be used or be intended for use to treat the same conditions as the reference medicinal product. Thus, a biosimilar as described herein may be deemed to have similar or highly similar quality characteristics to a reference medicinal product. Alternatively, or in addition, a biosimilar as described herein may be deemed to have similar or highly similar biological activity to a reference medicinal product. Alternatively, or in addition, a biosimilar as described herein may be deemed to have a similar or highly similar safety profile to a reference medicinal product. Alternatively, or in addition, a biosimilar as described herein may be deemed to have similar or highly similar efficacy to a reference medicinal product. As described herein, a biosimilar in Europe is compared to a reference medicinal product which has been authorised by the EMA. However, in some instances, the biosimilar may be compared to a biological medicinal product which has been authorised outside the European Economic Area (a non-EEA authorised "comparator") in certain studies. Such studies include for example certain clinical and in vivo non-clinical studies. As used herein, the term "biosimilar" also relates to a biological medicinal product which has been or may be compared to a non-EEA authorised comparator. Certain biosimilars are proteins such as antibodies, antibody fragments (for example, antigen binding portions) and fusion proteins. A protein biosimilar may have an amino acid sequence that has minor modifications in the amino acid structure (including for example deletions, additions, and/or substitutions of amino acids) which do not significantly affect the function of the polypeptide. The biosimilar may comprise an amino acid sequence having a sequence identity of 97% or greater to the amino acid sequence of its reference medicinal product, e.g., 97%, 98%, 99% or 100%. The biosimilar may comprise one or more post-translational modifications, for example, although not limited to, glycosylation, oxidation, deamidation, and/or truncation which is/are different to the post-translational modifications of the reference medicinal product, provided that the differences do not result in a change in safety and/or efficacy of the medicinal product. The biosimilar may have an identical or different glycosylation pattern to the reference medicinal product. Particularly, although not exclusively, the biosimilar may have a different glycosylation pattern if the differences address or are intended to address safety concerns associated with the reference medicinal product. Additionally, the biosimilar may deviate from the reference medicinal product in for example its strength, pharmaceutical form, formulation, excipients and/or presentation, providing safety and efficacy of the medicinal product is not compromised. The biosimilar may comprise differences in for example pharmacokinetic (PK) and/or pharmacodynamic (PD) profiles as compared to the reference medicinal product but is still deemed sufficiently similar to the reference medicinal product as to be authorised or considered suitable for authorisation. In certain circumstances, the biosimilar exhibits different binding characteristics as compared to the reference medicinal product, wherein the different binding characteristics are considered by a Regulatory Authority such as the EMA not to be a barrier for authorisation as a similar biological product. The term "biosimilar" is also used synonymously by other national and regional regulatory agencies.

The term "hematological malignancy" refers to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, ALL, CLL, SLL, acute myelogenous leukemia (AML), chronic myelogenous leukemia (CML), acute monocytic leukemia (AMoL), Hodgkin's lymphoma, and non-Hodgkin's lymphomas. The term "B cell hematological malignancy" refers to hematological malignancies that affect B cells.

The term "solid tumor" refers to an abnormal mass of tissue that usually does not contain cysts or liquid areas. Solid tumors may be benign or malignant. The term "solid tumor cancer" refers to malignant, neoplastic, or cancerous solid tumors. Solid tumor cancers include, but are not limited to, sarcomas, carcinomas, and lymphomas, such as cancers of the lung, breast, prostate, colon, rectum, and bladder. The tissue structure of solid tumors includes interdependent tissue compartments including the parenchyma (cancer cells) and the supporting stromal cells in which the cancer cells are dispersed and which may provide a supporting microenvironment.

The term "liquid tumor" refers to an abnormal mass of cells that is fluid in nature. Liquid tumor cancers include, but are not limited to, leukemias, myelomas, and lymphomas, as well as other hematological malignancies. TILs obtained from liquid tumors may also be referred to herein as marrow infiltrating lymphocytes (MILs).

The term "microenvironment," as used herein, may refer to the solid or hematological tumor microenvironment as a whole or to an individual subset of cells within the microenvironment. The tumor microenvironment, as used herein, refers to a complex mixture of "cells, soluble factors, signaling molecules, extracellular matrices, and mechanical cues that promote neoplastic transformation, support tumor growth and invasion, protect the tumor from host immunity, foster therapeutic resistance, and provide niches for dominant metastases to thrive," as described in Swartz, et al., *Cancer Res.*, 2012, 72, 2473. Although tumors express antigens that should be recognized by T cells, tumor clearance by the immune system is rare because of immune suppression by the microenvironment.

In an embodiment, the invention includes a method of treating a cancer with a population of TILs, wherein a patient is pre-treated with non-myeloablative chemotherapy prior to an infusion of TILs according to the invention. In some embodiments, the population of TILs may be provided wherein a patient is pre-treated with nonmyeloablative chemotherapy prior to an infusion of TILs according to the present invention. In an embodiment, the non-myeloablative chemotherapy is cyclophosphamide 60 mg/kg/d for 2 days (days 27 and 26 prior to TIL infusion) and fludarabine 25 mg/m2/d for 5 days (days 27 to 23 prior to TIL infusion). In an embodiment, after non-myeloablative chemotherapy and TIL infusion (at day 0) according to the invention, the patient receives an intravenous infusion of IL-2 intravenously at 720,000 IU/kg every 8 hours to physiologic tolerance.

Experimental findings indicate that lymphodepletion prior to adoptive transfer of tumor-specific T lymphocytes plays a key role in enhancing treatment efficacy by eliminating regulatory T cells and competing elements of the immune system ("cytokine sinks"). Accordingly, some embodiments of the invention utilize a lymphodepletion step (sometimes also referred to as "immunosuppressive conditioning") on the patient prior to the introduction of the rTILs of the invention The terms "sequence identity," "percent identity," and "sequence percent identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. Suitable programs to determine percent sequence identity include for example the BLAST suite of programs available from the U.S. Government's National Center for Biotechnology Information BLAST web site. Comparisons between two sequences can be carried using either the BLASTN or BLASTP algorithm. BLASTN is used to compare nucleic acid sequences, while BLASTP is used to compare amino acid sequences. ALIGN, ALIGN-2 (Genentech, South San Francisco, CA) or MegAlign, available from DNASTAR, are additional publicly available software programs that can be used to align sequences. One skilled in the art can determine appropriate parameters for maximal alignment by particular alignment software. In certain embodiments, the default parameters of the alignment software are used.

Certain embodiments of the present invention comprise a variant of an antibody, e.g., an anti-IL-33 or anti-ST2 antibody and/or an anti-CD20 antibody and/or an anti-PD-1 antibody, anti-PD-L1 and/or an anti-PD-L2 antibody. As used herein, the term "variant" encompasses but is not limited to antibodies which comprise an amino acid sequence which differs from the amino acid sequence of a reference antibody by way of one or more substitutions, deletions and/or additions at certain positions within or adjacent to the amino acid sequence of the reference antibody. The variant may comprise one or more conservative substitutions in its amino acid sequence as compared to the amino acid sequence of a reference antibody. Conservative substitutions may involve, e.g., the substitution of similarly charged or uncharged amino acids. The variant retains the ability to specifically bind to the antigen of the reference antibody.

For the avoidance of doubt, it is intended herein that particular features (for example integers, characteristics, values, uses, diseases, formulae, compounds or groups) described in conjunction with a particular aspect, embodiment or example of the invention are to be understood as applicable to any other aspect, embodiment or example described herein unless incompatible therewith. Thus such features may be used where appropriate in conjunction with any of the definition, claims or embodiments defined herein. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any disclosed embodiments. The invention extends to any novel one, or novel combination, of the features disclosed in this specification (including any accompanying claims, abstract and drawings), or to any novel one, or any novel combination, of the steps of any method or process so disclosed.

AKT Pathway Inhibitors

The serine/threonine kinase Akt family contains several members, including Akt1 (also designated PKB or RacPK), Akt2 (also designated PKBβ or RacPK-β) and Akt 3 (also designated PKBγ or thyoma viral proto-oncogene 3). Akt1 and Akt2 are activated by PDGF stimulation. AKT kinases are tethered to the membrane via their plextrin homology domain through interactions with PIP3 lipids. Manning and Toker summarize the past 25 years of research on this complex signaling pathway in "AKT/PKB Signaling: Navigating the Network," *Cell* 169: 381-405 (2017).

Afuresertib

In an embodiment, the AKT pathway inhibitor is Afuresertib. Afuresertib is also known as CAS 1047644-62-1, GSK2110183, ZINC43197674, and CHEMBL2219422, among other names. Afuresertib is an orally bioavailable inhibitor of the serine/threonine protein kinase Akt (protein kinase B). In an embodiment, the AKT pathway inhibitor is N-[(2S)-1-amino-3-(3-fluorophenyl)propan-2-yl]-5-chloro-4-(4-chloro-2-methylpyrazol-3-yl)thiophene-2-carboxamide.

In an embodiment the AKT pathway inhibitor is a compound of the formula:

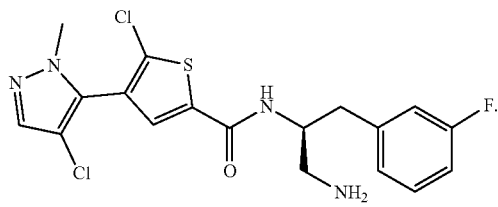 [SMILES: Cn1ncc(Cl)c1-c1cc(C(=O)N[C@H](CN)Cc2cccc(F)c2)sc1Cl]

Methods of synthesis are disclosed, for example, in Lin et al., "Discovery of 2-pyrimidyl-5-amidothiophenes as potent inhibitors for AKT: Synthesis and SAR studies", Bioorg. Med. Chem. Let. 16:4163-4168 (2006) and published U.S. Patent Application US20100041726A1, Seefeld et al., both of which are incorporated by reference in their entirety, and particularly for methods of synthesis detailed, for example, in Schemes 1 to 3 and methods of identification and analysis of such compounds.

Uprosertib

In an embodiment, the AKT pathway inhibitor is Uprosertib. In an embodiment, the AKT pathway inhibitor is N-[(2S)-1-amino-3-(3,4-difluorophenyl)propan-2-yl]-5-chloro-4-(4-chloro-2-methylpyrazol-3-yl)furan-2-carboxamide. In an embodiment, the AKT pathway inhibitor is a compound of the formula:

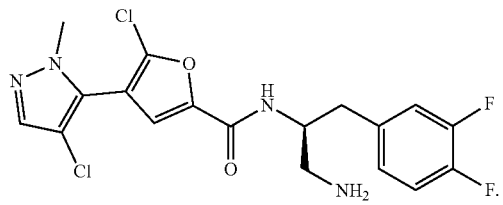 [SMILES: Cn1ncc(Cl)c1-c1cc(C(=O)N[C@H](CN)Cc2ccc(F)c(F)c2)oc1Cl]

Methods of synthesis are disclosed, for example, in published U.S. Patent Application US20100041726A1, Seefeld et al.

Ipatasertib

In an embodiment, the AKT pathway inhibitor is Ipatasertib. In an embodiment, the AKT pathway inhibitor is 2-(4-chlorophenyl)-1-(4-(7-hydroxy-5-methyl-6,7-dihydro-5H-cyclopenta(d)pyrimidin-4-yl)piperazin-1-yl)-3-(isopropylamino)propan-1-one. In an embodiment, the AKT pathway inhibitor is a compound of the formula:

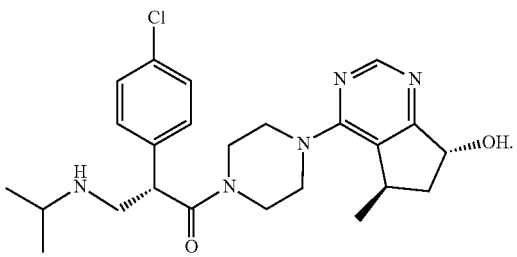 [SMILES: CC(C)NC[C@@H](C(=O)N1CCN(c2ncnc3c2[C@H](C)C[C@H]3O)CC1)c1ccc(Cl)cc1]

Methods of synthesis are disclosed, for example, in U.S. Pat. No. 8,063,050, which is incorporated by reference in its entirety with particular attention drawn to Formula I, and Schemes A-J.

AT7867

In an embodiment, the AKT pathway inhibitor is AT7867. In an embodiment, the AKT pathway inhibitor is 4-(4-chlorophenyl)-4-(4-(1h-pyrazol-4-yl)phenyl)piperidine. In an embodiment, the AKT pathway inhibitor is a compound of the formula:

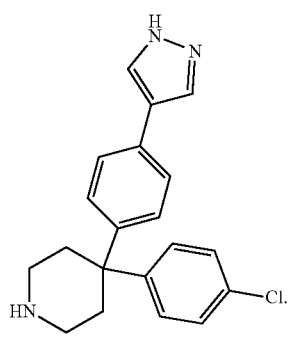 [SMILES: Clc1ccc(C2(c3ccc(-c4cn[nH]c4)cc3)CCNCC2)cc1]

Method of synthesis are disclosed, for example, in U.S. Pat. No. 8,247,576, which is incorporated by reference in its entirety with particular attention drawn to Example 57 and Examples 63 to 68.

AT13148

In an embodiment, the AKT pathway inhibitor is AT13148, also known as CS-3136 and ZINC95920747. In an embodiment, the AKT pathway inhibitor is (S)-1-(4-(1H-Pyrazol-4-yl)phenyl)-2-amino-1-(4-chlorophenyl)ethanol. In an embodiment, the AKT pathway inhibitor is a compound of the formula:

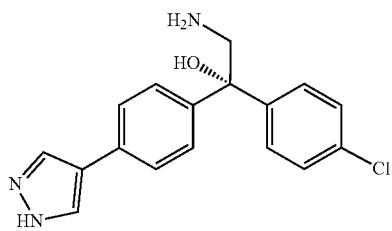 [SMILES: NC[C@@](O)(c1ccc(Cl)cc1)c1ccc(-c2cn[nH]c2)cc1]

Method of synthesis are disclosed, for example, in U.S. Pat. No. 8,247,576, which is incorporated by reference in its entirety.

MK-2206

In an embodiment, the AKT pathway inhibitor is MK-2206, also known as 1032349-93-1. In an embodiment, the AKT pathway inhibitor is 8-[4-(1-aminocyclobutyl)phenyl]-9-phenyl-2H-[1,2,4]triazolo[3,4-f][1,6]naphthyridin-3-one. In an embodiment, the AKT pathway inhibitor is a compound of the formula:

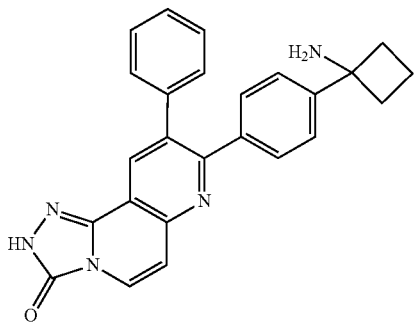 [SMILES: NC1(c2ccc(-c3nc4ccn5c(=O)[nH]nc5c4cc3-c3ccccc3)cc2)CCC1]

Method of synthesis are disclosed, for example, in U.S. Pat. No. 8,609,688 which is incorporated by reference in its entirety with particular attention drawn to General Procedure A.

Therapeutic methods of use are disclosed by Yap et al., "First-in-man clinical trial of the oral pan-AKT inhibitor MK-2206 in patients with advanced solid tumors", *J Clin Oncol.* 29: 4688-95 (2011).

LY294002

In an embodiment, the AKT pathway inhibitor is LY294002, also known as CAS 154447-36-6. In an embodiment, the AKT pathway inhibitor is 2-(4-morpholinyl)-8-phenyl-4H-1-benzopyran-4-one. In an embodiment, the AKT pathway inhibitor is a compound of the formula:

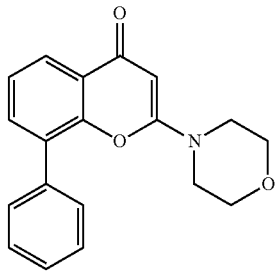 [SMILES: O=c1cc(N2CCOCC2)oc2c(-c3ccccc3)cccc12]

Method of synthesis are disclosed, for example, in U.S. Pat. Nos. 6,800,620 and 7,511,041, which are incorporated by reference in their entirety. Attention is particularly drawn to the methods of synthesis taught in the General Procedures disclosed in U.S. Pat. No. 6,800,620. LY294002 is a PI3K kinase inhibitor, which is a component kinase in the AKT pathway.

AZD8055

In an embodiment, the AKT pathway inhibitor is AZD8055, also known as CAS 1009298-09-2. In an embodiment, the AKT pathway inhibitor is [5-[2,4-bis[(3S)-3-methylmorpholin-4-yl]pyrido[2,3-d]pyrimidin-7-yl]-2-methoxyphenyl]methanol. In an embodiment, the AKT pathway inhibitor is a compound of the formula:

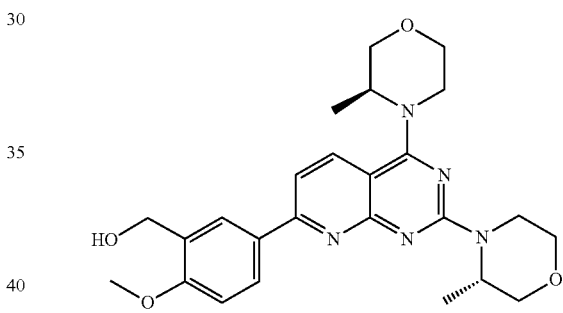

AZD8055 is an mTOR kinase inhibitor, which is a component kinase in the AKT pathway. Method of synthesis are disclosed, for example, in U.S. Pat. No. 7,902,189 which is incorporated by reference in its entirety with particular attention drawn to Examples 1 through 3. Other mTOR kinase inhibitors are taught, e.g. by Barlaam et al. in U.S. Pat. No. 9,657,008, which is incorporated by reference in its entirety.

Identifying Functionally Useful AKT Pathway Inhibitors

Small molecules that inhibit kinases are generally known to one skilled in the art, for example, Bhullar et al., summarize approaches to identifying useful inhibitors of the 538 known protein kinases in "Kinase-targeted cancer therapies: progress, challenges and future directions," *Mol. Cancer* 17:48 (2018). Bhullar highlights that kinase inhibitors may target the ATP binding site and be ATP-competitive compounds (Type I inhibitor), target an inactive conformation of a kinase (Type II inhibitor), act through allosteric inhibition (Type III inhibitor), target a substrate binding site (Type IV inhibitor) or covalently react with the kinase (Type V inhibitor). Because of the several means of interacting with a kinase, there is limited predictability from structure to binding mode and inhibitory mechanism.

As described above, the AKT signally pathway is comprised of many separate protein kinases that interact through a complex network to effect metabolic, transcriptional, and translational changes in a cell as the result of extracellular signals transduced through the receptor-linked network. See e.g., Manning and Toker, "AKT/PKB Signaling: Navigating the Network," Cell 169: 381-405 (2017).

Useful inhibitors of AKT pathway protein kinases are identified by functional screening described herein. Example 6 describes such a functional screen for AKT pathway protein kinase inhibitors that when used in lymphocyte culture, enhance the population of memory T-cell phenotype lymphocytes and increase the population of lymphocytes with the young TIL phenotypic properties. Among other features, the target phenotype comprises increased representation within the population of expanded or cultured lymphocytes expressing memory T-Cell cell surface markers, e.g. CD27, CD 28, IL7R, CCR9, SELL (L-selectin or CD62L), FCER1G, SATB1, LEF1, and KLF2; and decreased representation within the population of expanded or cultured lymphocytes expressing T-Cell effector surface markers, e.g. IFNG, XCL1, ACL2, CD300A, and KLRG1. CD62L (L-selectin) is known to be a key marker for memory T-cells that preferentially respond to antigen. Hengel et al., "Cutting Edge: L-Selectin (CD62L) Expression Distinguishes Small Resting Memory CD4+ T Cells That Preferentially Respond to Recall Antigen", J. Immunol. 170:28-32 (2003). A less useful population comprises cells not expressing CD62L and expressing CD45RO, e.g. CD8+ CD62L− CD45RO+ lymphocytes. See e.g., Booth et al., "Different Proliferative Potential and Migratory Characteristics of Human CD4+ Regulatory T Cells That Express either CD45RA or CD45RO", J. Immunol. 184:4317-4326 (2010).

Without being limited to any particular theory, it is believed that the use of Akt inhibitors according to the methods of the invention allows the preparation of TILs that retain a "younger" phenotype, and as such the preparations of TILs of the invention are expected to exhibit greater cytotoxicity against cancer cells than TILs prepared by other methods. In particular, it is believed that the inhibition of the Akt pathway during the initial expansion of TILs obtained from tumor inhibits or attenuates the maturation of TILs in the initial expansion culture, and that the exposure TILs to OKT-3, IL-2 and antigen-presenting cells (APCs) in the second expansion activates the TILs while inhibiting or attenuating the maturation of TILs, yielding a population of TILs with a less mature phenotype, which TILs are less exhausted by expansion in culture and exhibit greater cytotoxicity against cancer cells.

In some embodiments, the invention provides methods using Akt inhibitors during the initial expansion of TILs and during the second expansion of TILs.

In other embodiments, the invention provides methods using a priming initial expansion comprising exposing TILs to Akt inhibitor, OKT-3 and IL-2 in culture to achieve an initial activation of TILs and a second rapid expansion comprising exposing TILs to additional OKT-3, IL-2 and APCs in culture to boost the initial activation of TILs.

In other embodiments, the invention provides methods using a priming initial expansion comprising exposing TILs to Akt inhibitor, OKT-3, IL-2 and APCs in culture to achieve an initial activation of TILs and a second rapid expansion comprising exposing TILs to additional OKT-3, IL-2 and APCs in culture to boost the initial activation of TILs.

In other embodiments, the invention provides methods using a priming initial expansion comprising exposing TILs to Akt inhibitor, OKT-3 and IL-2 in culture to achieve an initial activation of TILs and a second rapid expansion comprising exposing TILs to additional Akt inhibitor, OKT-3, IL-2 and APCs in culture to boost the initial activation of TILs.

In other embodiments, the invention provides methods using a priming initial expansion comprising exposing TILs to Akt inhibitor, OKT-3, IL-2 and APCs in culture to achieve an initial activation of TILs and a second rapid expansion comprising exposing TILs to additional Akt inhibitor, OKT-3, IL-2 and APCs in culture to boost the initial activation of TILs.

In other embodiments, the invention provides methods using a priming initial expansion comprising exposing TILs to OKT-3 and IL-2 in culture to achieve an initial activation of TILs and a second rapid expansion comprising exposing TILs to additional Akt inhibitor, OKT-3, IL-2 and APCs in culture to boost the initial activation of TILs.

In other embodiments, the invention provides methods using a priming initial expansion comprising exposing TILs to OKT-3, IL-2 and APCs in culture to achieve an initial activation of TILs and a second rapid expansion comprising exposing TILs to additional Akt inhibitor, OKT-3, IL-2 and APCs in culture to boost the initial activation of TILs.

TIL Manufacturing Processes—Process 2A

There are various methods to expand TILs known to one skilled in the art. For example, Jin et al., J. Immunother. 35(3): 283-292 (2012), "Simplified Method of the Growth of Human Tumor Infiltrating Lymphocytes in Gas-permeable Flasks to Numbers Needed for Patient Treatment," the disclosure of which is incorporated by reference herein, teaches simplified methods of producing TILs for clinical use. Jin et al. teaches a first TIL culture followed by a rapid expansion (REP) protocol, which combined, enables one skilled in the art to produce clinically useful quantities of TILs. In some embodiments, the invention provides a method of manufacturing TILs comprising the step of cryopreserving a tumor, thawing a tumor, and performing the process described in Jin et al. Briefly, this process involves the following process. TILs may initially be cultured from enzymatic tumor digests and tumor fragments (about 1 to 8 mm$^3$) produced by sharp dissection. Tumor digests are produced by incubation in enzyme media (RPMI 1640, 2 mM GlutaMAX, 10 mg/mL gentamicin, 30 U/mL DNase, and 1.0 mg/mL collagenase) followed by mechanical dissociation (GentleMACS, Miltenyi Biotec, Auburn, CA). Immediately after placing the tumor in enzyme media, it is mechanically dissociated for approximately 1 minute. The material was then incubated for 30 minutes at 37° C. in 5% $CO_2$ and is then mechanically disrupted again for approximately 1 minute and incubated again for 30 minutes at 37° C. in 5% $CO_2$. The tumor is then mechanically disrupted a third time for approximately 1 minute. If after the third mechanical disruption, large pieces of tissue were present, 1 or 2 additional mechanical dissociations may be applied to the sample, with or without 30 additional minutes of incubation at 37° C. in 5% $CO_2$. At the end of the final incubation, if the cell suspension contained a large number of red blood cells or dead cells, a density gradient separation using Ficoll may be performed to remove these cells. When TIL cultures are initiated in 24-well plates (Costar 24-well cell culture cluster, flat bottom; Corning Incorporated, Corning, NY), each well is seeded with $1 \times 10^6$ tumor digest cells or one tumor fragment approximately about 1 to 8 mm$^3$ in size in 2 mL of complete medium (CM) with IL-2 (6000 IU/mL; Chiron Corp., Emeryville, CA). CM comprised RPMI 1640 with GlutaMAX, supplemented with 10% human AB serum, 25 mM Hepes, and about 10 µg/mL gentamicin. When cultures were initiated in gas-permeable flasks with a 40 mL capacity and a 10 cm$^2$ gas-permeable silicon bottom (G-Rex10; Wilson Wolf Manufacturing, New Brighton, MN), each flask is loaded with 10 to 40×10$^6$ viable tumor digest cells or 5 to 30 tumor fragments in 10 to 40 mL of CM with IL-2. Both the G-Rex10 and 24-well plates are incubated in a humidified incubator at 37° C. in 5% CO2 and 5 days after culture initiation, half the media is removed and replaced with fresh CM and IL-2 and after day 5, half the media is changed every 2-3 days. REP of TIL is performed using T-175 flasks and gas-permeable bags or gas-permeable G-Rex flasks. For TIL REP in T-175 flasks, 1×10$^6$ TILs suspended in 150 mL of media was added to each T-175 flask. The TIL were cultured with irradiated (50 Gy) allogeneic PBMC as "feeder" cells at a ratio of 1 to 100 and the cells are cultured in a 1 to 1 mixture of CM and AIM-V medium (50/50 medium), supplemented with 3000 IU/mL of IL-2 and 30 ng/mL of anti-CD3. The T-175 flasks are incubated at 37° C. in 5% CO$_2$. Half the media is changed on day 5 using 50/50 medium with 3000 IU/mL of IL-2. On day 7, cells from 2 T-175 flasks are combined in a 3 L bag and 300 mL of AIM-V with 5% human AB serum and 3000 IU/mL of IL-2 is added to the 300 mL of TIL suspension. The number of cells in each bag was counted every day or 2 and fresh media was added to keep the cell count between 0.5 and 2.0×10$^6$ cells/mL. For TIL REP in 500 mL capacity flasks with 100 cm$^2$ gas-permeable silicon bottoms (G-Rex100, Wilson Wolf), 5×10$^6$ to 10×10$^6$ TIL are cultured with irradiated allogeneic PBMC at a ratio of 1 to 100 in 400 mL of 50/50 medium, supplemented with 3000 IU/mL of IL-2 and 30 ng/mL of anti-CD3. G-Rex100 flasks are incubated at 37° C. in 5% CO$_2$. On day 5, 250 mL of supernatant is removed and placed into centrifuge bottles and centrifuged at 1500 rpm (491 g) for 10 minutes. TIL pellets are resuspended with 150 mL of fresh 50/50 medium with 3000 IU/mL of IL-2 and added back to the original G-Rex100 flasks. When TIL are expanded serially in G-Rex100 flasks, on day 7 the TIL in each G-Rex100 were suspended in the 300 mL of media present in each flask and the cell suspension was divided into three 100 mL aliquots that were used to seed 3 G-Rex100 flasks. 150 mL of AIM-V with 5% human AB serum and 3000 IU/mL of IL-2 is added to each flask. The G-Rex100 flasks are incubated at 37° C. in 5% CO$_2$ and after 4 days 150 mL of AIM-V with 3000 IU/mL of IL-2 was added to each G-Rex100 flask. The cells are harvested on day 14 of culture.

In some embodiments, the invention provides a method of manufacturing TILs comprising the step of cryopreserving a tumor, thawing a tumor, and performing the following process. TTLs can be produced by rapid expansion using stimulation of peripheral blood mononuclear cells (PBMC) in vitro with an antigen (one or more, including antigenic portions thereof, such as epitope(s), or a cell) of the cancer, which can be optionally expressed from a vector, such as an HLA-A2 binding peptide, e.g., 0.3 µM MART-1:26-35 (27 L) or gp100:209-217 (210M), in the presence of a T-cell growth factor, such as 300 IU/mL IL-2 or IL-15, with IL-2 being preferred. The in vitro-induced TILs are rapidly expanded by re-stimulation with the same antigen(s) of the cancer pulsed onto HLA-A2-expressing antigen-presenting cells. Alternatively, the TILs can be re-stimulated with irradiated, autologous lymphocytes or with irradiated HLA-A2$^+$ allogeneic lymphocytes and IL-2, for example. TILs can be selected for highly avid recognition of any of the unique antigens produced as a result of the estimated 10,000 genetic mutations encoded by each tumor cell genome. The antigen, however, need not be unique. T-cells can be selected for highly avid recognition of one or more antigens of a cancer, including an antigenic portion of one or more antigens, such as an epitope, or a cell of the cancer. An "antigen of a cancer" and an "antigen of the cancer" are intended to encompass all of the aforementioned antigens. If the cancer is melanoma, such as metastatic melanoma, preferably the TILs are selected for highly avid recognition of MART-1 (such as MART-1:26-35 (27 L)), gp100 (such as gp100:209-217 (210M)), or a "unique" or patient-specific antigen derived from a tumor encoded mutation. Other suitable melanoma antigens for which highly avid recognition by TILs can be selected include, but are not limited to, tyrosinase, tyrosinase related protein (TRP)1, TRP2, and MAGE. Antigens, such as NY-ESO-1, telomerase, p53, HER2/neu, carcinoembryonic antigen, or prostate-specific antigen, can be used to select for highly avid recognition by TTLs for treatment of lung carcinoma, breast cancer, colon cancer, prostate cancer, and the like TILs can be selected include, but are not limited to, tyrosinase, tyrosinase related protein.

IL-2-based TIL expansion followed by a "rapid expansion process" (REP) has become a preferred method for TIL expansion because of its speed and efficiency. Dudley, et al., *Science* 2002, 298, 850-54; Dudley, et al., *J. Clin. Oncol.* 2005, 23, 2346-57; Dudley, et al., *J. Clin. Oncol.* 2008, 26, 5233-39; Riddell, et al., *Science* 1992, 257, 238-41; Dudley, et al., *J. Immunother.* 2003, 26, 332-42. REP can result in a 1,000-fold expansion of TTLs over a 14-day period, although it requires a large excess (e.g., 200-fold) of irradiated allogeneic peripheral blood mononuclear cells (PBMCs), often from multiple donors, as feeder cells, as well as anti-CD3 antibody (OKT3) and high doses of IL-2. Dudley, et al., *J. Immunother.* 2003, 26, 332-42. The cryopreserved tumor fragments are suitable starting points for initial or first cultures to manufacture TTLs for therapeutic or other purposes.

An exemplary TIL process known as process 2A containing some of these features is depicted in FIG. 1. Another exemplary TIL process, known as process 1C, is described and compared to process 2A in FIGS. 5 and 6. An embodiment of process 2A is shown FIG. 1.

As discussed herein, the present invention can include a step relating to the restimulation of cryopreserved TTLs to increase their metabolic activity and thus relative health prior to transplant into a patient, and methods of testing said metabolic health. As generally outlined herein, TILs are generally taken from a patient sample and manipulated to expand their number prior to transplant into a patient. In some embodiments, the TILs may be optionally genetically manipulated as discussed below.

In some embodiments, the TILs may be cryopreserved and thawed for administration to a patient. Once thawed, they may also be restimulated to increase their metabolism prior to infusion into a patient.

In some embodiments, the first expansion (including processes referred to as the preREP as well as processes shown in FIG. 1 as Step A) is shortened to 3 to 14 days and the second expansion (including processes referred to as the REP as well as processes shown in FIG. 1 as Step B) is shorted to 7 to 14 days, as discussed in detail below as well as in the examples and figures. In some embodiments, the first expansion (for example, an expansion described as Step B in FIG. 1) is shortened to 11 days and the second expansion (for example, an expansion as described in Step D in FIG. 1) is shortened to 11 days. In some embodiments, the combination of the first expansion and second expansion (for example, expansions described as Step B and Step D in FIG. 1) is shortened to 22 days, as discussed in detail below and in the examples and figures.

The "Step" Designations A, B, C, etc., below are in reference to FIG. 1 and in reference to certain embodiments described herein. The ordering of the Steps below and in FIG. 1 is exemplary and any combination or order of steps, as well as additional steps, repetition of steps, and/or omission of steps is contemplated by the present application and the methods disclosed herein.

Step A. Obtain Patient Tumor Sample

In general, TILs are initially obtained from a patient tumor sample ("primary TILs") and then expanded into a larger population for further manipulation as described herein, optionally cryopreserved, restimulated as outlined herein and optionally evaluated for phenotype and metabolic parameters as an indication of TIL health.

A patient tumor sample may be obtained using methods known in the art, generally via surgical resection, needle biopsy or other means for obtaining a sample that contains a mixture of tumor and TIL cells. In general, the tumor sample may be from any solid tumor, including primary tumors, invasive tumors or metastatic tumors. The tumor sample may also be a liquid tumor, such as a tumor obtained from a hematological malignancy. The solid tumor may be of any cancer type, including, but not limited to, breast, pancreatic, prostate, colorectal, lung, brain, renal, stomach, and skin (including but not limited to squamous cell carcinoma, basal cell carcinoma, and melanoma). In some embodiments, useful TILs are obtained from malignant melanoma tumors, as these have been reported to have particularly high levels of TILs.

The term "solid tumor" refers to an abnormal mass of tissue that usually does not contain cysts or liquid areas. Solid tumors may be benign or malignant. The term "solid tumor cancer" refers to malignant, neoplastic, or cancerous solid tumors. Solid tumor cancers include, but are not limited to, sarcomas, carcinomas, and lymphomas, such as cancers of the lung, breast, triple negative breast cancer, prostate, colon, rectum, and bladder. In some embodiments, the cancer is selected from cervical cancer, head and neck cancer (including, for example, head and neck squamous cell carcinoma (HNSCC) glioblastoma, ovarian cancer, sarcoma, pancreatic cancer, bladder cancer, breast cancer, triple negative breast cancer, and non-small cell lung carcinoma. The tissue structure of solid tumors includes interdependent tissue compartments including the parenchyma (cancer cells) and the supporting stromal cells in which the cancer cells are dispersed and which may provide a supporting microenvironment.

The term "hematological malignancy" refers to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, acute lymphoblastic leukemia (ALL), chronic lymphocytic lymphoma (CLL), small lymphocytic lymphoma (SLL), acute myelogenous leukemia (AML), chronic myelogenous leukemia (CML), acute monocytic leukemia (AMoL), Hodgkin's lymphoma, and non-Hodgkin's lymphomas. The term "B cell hematological malignancy" refers to hematological malignancies that affect B cells.

Once obtained, the tumor sample is generally fragmented using sharp dissection into small pieces of between 1 to about 8 mm3, with from about 2-3 mm$^3$ being particularly useful. The TILs are cultured from these fragments using enzymatic tumor digests. Such tumor digests may be produced by incubation in enzymatic media (e.g., Roswell Park Memorial Institute (RPMI) 1640 buffer, 2 mM glutamate, 10 mcg/mL gentamicine, 30 units/mL of DNase and 1.0 mg/mL of collagenase) followed by mechanical dissociation (e.g., using a tissue dissociator). Tumor digests may be produced by placing the tumor in enzymatic media and mechanically dissociating the tumor for approximately 1 minute, followed by incubation for 30 minutes at 37° C. in 5% $CO_2$, followed by repeated cycles of mechanical dissociation and incubation under the foregoing conditions until only small tissue pieces are present. At the end of this process, if the cell suspension contains a large number of red blood cells or dead cells, a density gradient separation using FICOLL branched hydrophilic polysaccharide may be performed to remove these cells. Alternative methods known in the art may be used, such as those described in U.S. Patent Application Publication No. 2012/0244133 A1, the disclosure of which is incorporated by reference herein. Any of the foregoing methods may be used in any of the embodiments described herein for methods of expanding TILs or methods treating a cancer.

In general, the harvested cell suspension is called a "primary cell population" or a "freshly harvested" cell population.

In some embodiments, fragmentation includes physical fragmentation, including for example, dissection as well as digestion. In some embodiments, the fragmentation is physical fragmentation. In some embodiments, the fragmentation is dissection. In some embodiments, the fragmentation is by digestion. In some embodiments, TILs can be initially cultured from enzymatic tumor digests and tumor fragments obtained from patients. In an embodiment, TILs can be initially cultured from enzymatic tumor digests and tumor fragments obtained from patients.

In some embodiments, where the tumor is a solid tumor, the tumor undergoes physical fragmentation after the tumor sample is obtained in, for example, Step A (as provided in FIG. 1). In some embodiments, the fragmentation occurs before cryopreservation. In some embodiments, the fragmentation occurs after cryopreservation. In some embodiments, the fragmentation occurs after obtaining the tumor and in the absence of any cryopreservation. In some embodiments, the tumor is fragmented and 10, 20, 30, 40 or more fragments or pieces are placed in each container for the first expansion. In some embodiments, the tumor is fragmented and 30 or 40 fragments or pieces are placed in each container for the first expansion. In some embodiments, the tumor is fragmented and 40 fragments or pieces are placed in each container for the first expansion. In some embodiments, the multiple fragments comprise about 4 to about 50 fragments, wherein each fragment has a volume of about 27 mm$^3$. In some embodiments, the multiple fragments comprise about 30 to about 60 fragments with a total volume of about 1300 mm$^3$ to about 1500 mm$^3$. In some embodiments, the multiple fragments comprise about 50 fragments with a total volume of about 1350 mm$^3$. In some embodiments, the multiple fragments comprise about 50 fragments with a total mass of about 1 gram to about 1.5 grams. In some embodiments, the multiple fragments comprise about 4 fragments.

In some embodiments, the TILs are obtained from tumor fragments. In some embodiments, the tumor fragment is obtained by sharp dissection. In some embodiments, the tumor fragment is between about 1 mm$^3$ and 10 mm$^3$. In some embodiments, the tumor fragment is between about 1 mm$^3$ and 8 mm$^3$. In some embodiments, the tumor fragment is about 1 mm$^3$. In some embodiments, the tumor fragment is about 2 mm$^3$. In some embodiments, the tumor fragment is about 3 mm³. In some embodiments, the tumor fragment is about 4 mm³. In some embodiments, the tumor fragment is about 5 mm³. In some embodiments, the tumor fragment is about 6 mm³. In some embodiments, the tumor fragment is about 7 mm³. In some embodiments, the tumor fragment is about 8 mm³. In some embodiments, the tumor fragment is about 9 mm³. In some embodiments, the tumor fragment is about 10 mm³. In some embodiments, the tumors are 1-4 mm×1-4 mm×1-4 mm. In some embodiments, the tumors are 1 mm×1 mm×1 mm. In some embodiments, the tumors are 2 mm×2 mm×2 mm. In some embodiments, the tumors are 3 mm×3 mm×3 mm. In some embodiments, the tumors are 4 mm×4 mm×4 mm. In embodiments wherein the tumor tissue is first frozen before initiating a culture, tumors are about 6 mm×6 mm×6 mm.

In some embodiments, the tumors are resected in order to minimize the amount of hemorrhagic, necrotic, and/or fatty tissues on each piece. In some embodiments, the tumors are resected in order to minimize the amount of hemorrhagic tissue on each piece. In some embodiments, the tumors are resected in order to minimize the amount of necrotic tissue on each piece. In some embodiments, the tumors are resected in order to minimize the amount of fatty tissue on each piece.

In some embodiments, the tumor fragmentation is performed in order to maintain the tumor internal structure. In some embodiments, the tumor fragmentation is performed without preforming a sawing motion with a scalpel. In some embodiments, the TILs are obtained from tumor digests. In some embodiments, tumor digests were generated by incubation in enzyme media, for example but not limited to RPMI 1640, 2 mM GlutaMAX, 10 μg/mL gentamicin, 30 U/mL DNase, and 1.0 mg/mL collagenase, followed by mechanical dissociation (GentleMACS, Miltenyi Biotec, Auburn, CA). After placing the tumor in enzyme media, the tumor can be mechanically dissociated for approximately 1 minute. The solution can then be incubated for 30 minutes at 37° C. in 5% $CO_2$ and it then mechanically disrupted again for approximately 1 minute. After being incubated again for 30 minutes at 37° C. in 5% $CO_2$, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% $CO_2$. In some embodiments, at the end of the final incubation if the cell suspension contained a large number of red blood cells or dead cells, a density gradient separation using Ficoll can be performed to remove these cells.

In some embodiments, the harvested cell suspension prior to the first expansion step is called a "primary cell population" or a "freshly harvested" cell population.

In some embodiments, cells can be optionally frozen after sample harvest and stored frozen prior to entry into the expansion described in Step B, which is described in further detail below, as well as exemplified in FIG. 1.

Step B: First Expansion

In some embodiments, the present methods provide for obtaining young TILs, which are capable of increased replication cycles upon administration to a subject/patient and as such may provide additional therapeutic benefits over older TILs (for example "older TILs" have further undergone more rounds of ex vivo replication prior to administration to a subject/patient). Features of young TILs have been described in the literature, for example Donia, et al., Scandinavian Journal of Immunology, 75:157-167 (2012); Dudley et al., *Clin Cancer Res,* 16:6122-6131 (2010); Huang et al., *J Immunother,* 28(3):258-267 (2005); Besser et al., *Clin Cancer Res,* 19(17):OF1-OF9 (2013); Besser et al., *J Immunother,* 32:415-423 (2009); Robbins, et al., *J Immunol,* 2004; 173:7125-7130; Shen et al., *J Immunother,* 30:123-129 (2007); Zhou, et al., *J Immunother,* 28:53-62 (2005); and Tran, et al., *J Immunother,* 31:742-751 (2008), all of which are incorporated herein by reference in their entireties.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained by the present method exhibit an increase in the T-cell repertoire diversity as compared to freshly harvested TILs and/or TILs prepared using other methods than those provide herein including for example, methods other than those embodied in FIG. 1. In some embodiments, the TILs obtained by the present method exhibit an increase in the T-cell repertoire diversity as compared to freshly harvested TILs and/or TILs prepared using methods referred to as process 1C, as exemplified in FIG. 5 and/or FIG. 6. In some embodiments, the TILs obtained in the first expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β).

After dissection or digestion of tumor fragments, for example such as described in Step A of FIG. 1, the resulting cells are cultured in serum containing IL-2 under conditions that favor the growth of TILs over tumor and other cells. In some embodiments, the tumor digests are incubated in 2 mL wells in media comprising inactivated human AB serum with 6000 IU/mL of IL-2. This primary cell population is cultured for a period of days, generally from 3 to 14 days, resulting in a bulk TIL population, generally about 1×10⁸ bulk TIL cells. In some embodiments, this primary cell population is cultured for a period of 7 to 14 days, resulting in a bulk TIL population, generally about 1×10⁸ bulk TIL cells. In some embodiments, this primary cell population is cultured for a period of 10 to 14 days, resulting in a bulk TIL population, generally about 1×10⁸ bulk TIL cells. In some embodiments, this primary cell population is cultured for a period of about 11 days, resulting in a bulk TIL population, generally about 1×10⁸ bulk TIL cells.

In a preferred embodiment, expansion of TILs may be performed using an initial bulk TIL expansion step (for example such as those described in Step B of FIG. 1, which can include processes referred to as pre-REP) as described below and herein, followed by a second expansion (Step D, including processes referred to as rapid expansion protocol (REP) steps) as described below under Step D and herein, followed by optional cryopreservation, and followed by a second Step D (including processes referred to as restimulation REP steps) as described below and herein. The TILs obtained from this process may be optionally characterized for phenotypic characteristics and metabolic parameters as described herein.

In embodiments where TIL cultures are initiated in 24-well plates, for example, using Costar 24-well cell culture cluster, flat bottom (Corning Incorporated, Corning, NY, each well can be seeded with $1 \times 10^6$ tumor digest cells or one tumor fragment in 2 mL of complete medium (CM) with IL-2 (6000 IU/mL; Chiron Corp., Emeryville, CA). In some embodiments, the tumor fragment is between about 1 mm$^3$ and 10 mm$^3$.

In some embodiments, the first expansion culture medium is referred to as "CM", an abbreviation for culture media. In some embodiments, CM for Step B consists of RPMI 1640 with GlutaMAX, supplemented with 10% human AB serum, 25 mM Hepes, and 10 μg/mL gentamicin. In embodiments where cultures are initiated in gas-permeable flasks with a 40 mL capacity and a 10 cm$^2$ gas-permeable silicon bottom (for example, G-Rex10; Wilson Wolf Manufacturing, New Brighton, MN) (FIG. 1), each flask was loaded with $10 \times 10^6$ to $40 \times 10^6$ viable tumor digest cells or 5 to 30 tumor fragments in 10 to 40 mL of CM with IL-2. Both the G-Rex10 and 24-well plates were incubated in a humidified incubator at 37° C. in 5% $CO_2$ and 5 days after culture initiation, half the media was removed and replaced with fresh CM and IL-2 and after day 5, half the media was changed every 2 to 3 days.

After preparation of the tumor fragments, the resulting cells (i.e., fragments) are cultured in serum containing IL-2 under conditions that favor the growth of TILs over tumor and other cells. In some embodiments, the tumor digests are incubated in 2 mL wells in media comprising inactivated human AB serum (or, in some cases, as outlined herein, in the presence of aAPC cell population) with 6000 IU/mL of IL-2. This primary cell population is cultured for a period of days, generally from 10 to 14 days, resulting in a bulk TIL population, generally about $1 \times 10^8$ bulk TIL cells. In some embodiments, the growth media during the first expansion comprises IL-2 or a variant thereof. In some embodiments, the IL is recombinant human IL-2 (rhIL-2). In some embodiments the IL-2 stock solution has a specific activity of $20-30 \times 10^6$ IU/mg for a 1 mg vial. In some embodiments the IL-2 stock solution has a specific activity of $20 \times 10^6$ IU/mg for a 1 mg vial. In some embodiments the IL-2 stock solution has a specific activity of $25 \times 10^6$ IU/mg for a 1 mg vial. In some embodiments the IL-2 stock solution has a specific activity of $30 \times 10^6$ IU/mg for a 1 mg vial. In some embodiments, the IL-2 stock solution has a final concentration of $4-8 \times 10^6$ IU/mg of IL-2. In some embodiments, the IL-2 stock solution has a final concentration of $5-7 \times 10^6$ IU/mg of IL-2. In some embodiments, the IL-2 stock solution has a final concentration of $6 \times 10^6$ IU/mg of IL-2. In some embodiments, the IL-2 stock solution is prepare as described in Example E. In some embodiments, the first expansion culture media comprises about 10,000 IU/mL of IL-2, about 9,000 IU/mL of IL-2, about 8,000 IU/mL of IL-2, about 7,000 IU/mL of IL-2, about 6000 IU/mL of IL-2 or about 5,000 IU/mL of IL-2. In some embodiments, the first expansion culture media comprises about 9,000 IU/mL of IL-2 to about 5,000 IU/mL of IL-2. In some embodiments, the first expansion culture media comprises about 8,000 IU/mL of IL-2 to about 6,000 IU/mL of IL-2. In some embodiments, the first expansion culture media comprises about 7,000 IU/mL of IL-2 to about 6,000 IU/mL of IL-2. In some embodiments, the first expansion culture media comprises about 6,000 IU/mL of IL-2. In an embodiment, the cell culture medium further comprises IL-2. In some embodiments, the cell culture medium comprises about 3000 IU/mL of IL-2. In an embodiment, the cell culture medium further comprises IL-2. In a preferred embodiment, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or about 8000 IU/mL of IL-2.

In some embodiments, first expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the first expansion culture media comprises about 500 IU/mL of IL-15 to about 100 IU/mL of IL-15. In some embodiments, the first expansion culture media comprises about 400 IU/mL of IL-15 to about 100 IU/mL of IL-15. In some embodiments, the first expansion culture media comprises about 300 IU/mL of IL-15 to about 100 IU/mL of IL-15. In some embodiments, the first expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, first expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the first expansion culture media comprises about 20 IU/mL of IL-21 to about 0.5 IU/mL of IL-21. In some embodiments, the first expansion culture media comprises about 15 IU/mL of IL-21 to about 0.5 IU/mL of IL-21. In some embodiments, the first expansion culture media comprises about 12 IU/mL of IL-21 to about 0.5 IU/mL of IL-21. In some embodiments, the first expansion culture media comprises about 10 IU/mL of IL-21 to about 0.5 IU/mL of IL-21. In some embodiments, the first expansion culture media comprises about 5 IU/mL of IL-21 to about 1 IU/mL of IL-21. In some embodiments, the first expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In an embodiment, the cell culture medium comprises OKT-3 antibody. In some embodiments, the cell culture medium comprises about 30 ng/mL of OKT-3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 µg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In some embodiments, the cell culture medium does not comprise OKT-3 antibody. In some embodiments, the OKT-3 antibody is muromonab.

In some embodiments, the cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 µg/mL and 100 µg/mL. In some embodiments, the TNFRSF agonist is added at a concentration sufficient to achieve a concentration in the cell culture medium of between 20 µg/mL and 40 µg/mL.

In some embodiments, in addition to one or more TNFRSF agonists, the cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist.

In some embodiments, the first expansion culture medium is referred to as "CM", an abbreviation for culture media. In some embodiments, it is referred to as CM1 (culture medium 1). In some embodiments, CM consists of RPMI 1640 with GlutaMAX, supplemented with 10% human AB serum, 25 mM Hepes, and 10 mg/mL gentamicin. In embodiments where cultures are initiated in gas-permeable flasks with a 40 mL capacity and a 10 cm$^2$ gas-permeable silicon bottom (for example, G-Rex10; Wilson Wolf Manufacturing, New Brighton, MN) (FIG. 1), each flask was loaded with 10×10$^6$ to 40×10$^6$ viable tumor digest cells or 5-30 tumor fragments in 10 to 40 mL of CM with IL-2. Both the G-Rex10 and 24-well plates were incubated in a humidified incubator at 37° C. in 5% CO$_2$ and 5 days after culture initiation, half the media was removed and replaced with fresh CM and IL-2 and after day 5, half the media was changed every 2 to 3 days. In some embodiments, the CM is the CM1 described in the Examples, see, Example 1. In some embodiments, the first expansion occurs in an initial cell culture medium or a first cell culture medium. In some embodiments, the initial cell culture medium or the first cell culture medium comprises IL-2.

Figure 4:
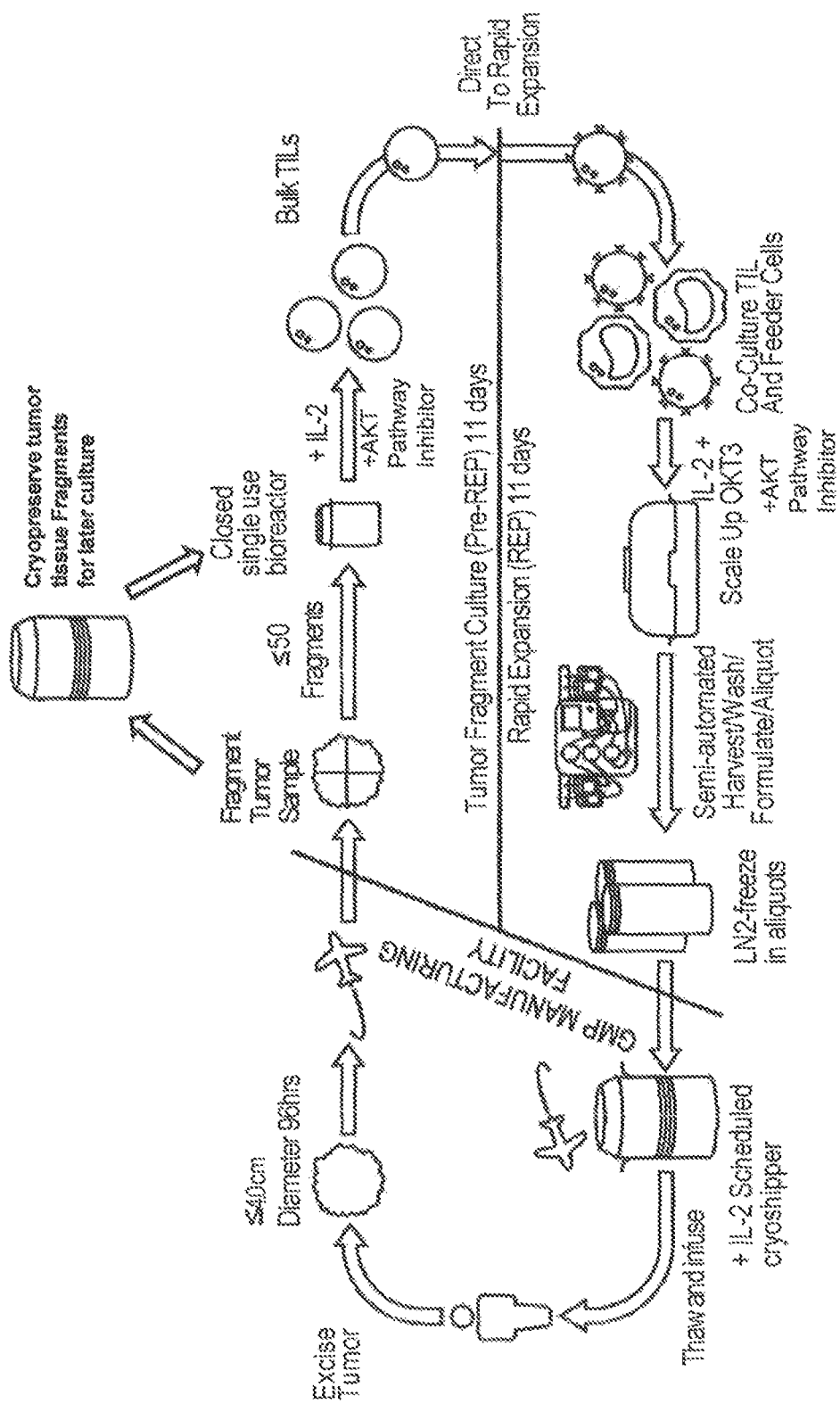
FIG. 4: Depicts an embodiment of TIL manufacturing, including the cryopreservation of fresh tumor fragments that are then later used to initiate a pre-REP culture.
Figure 7:
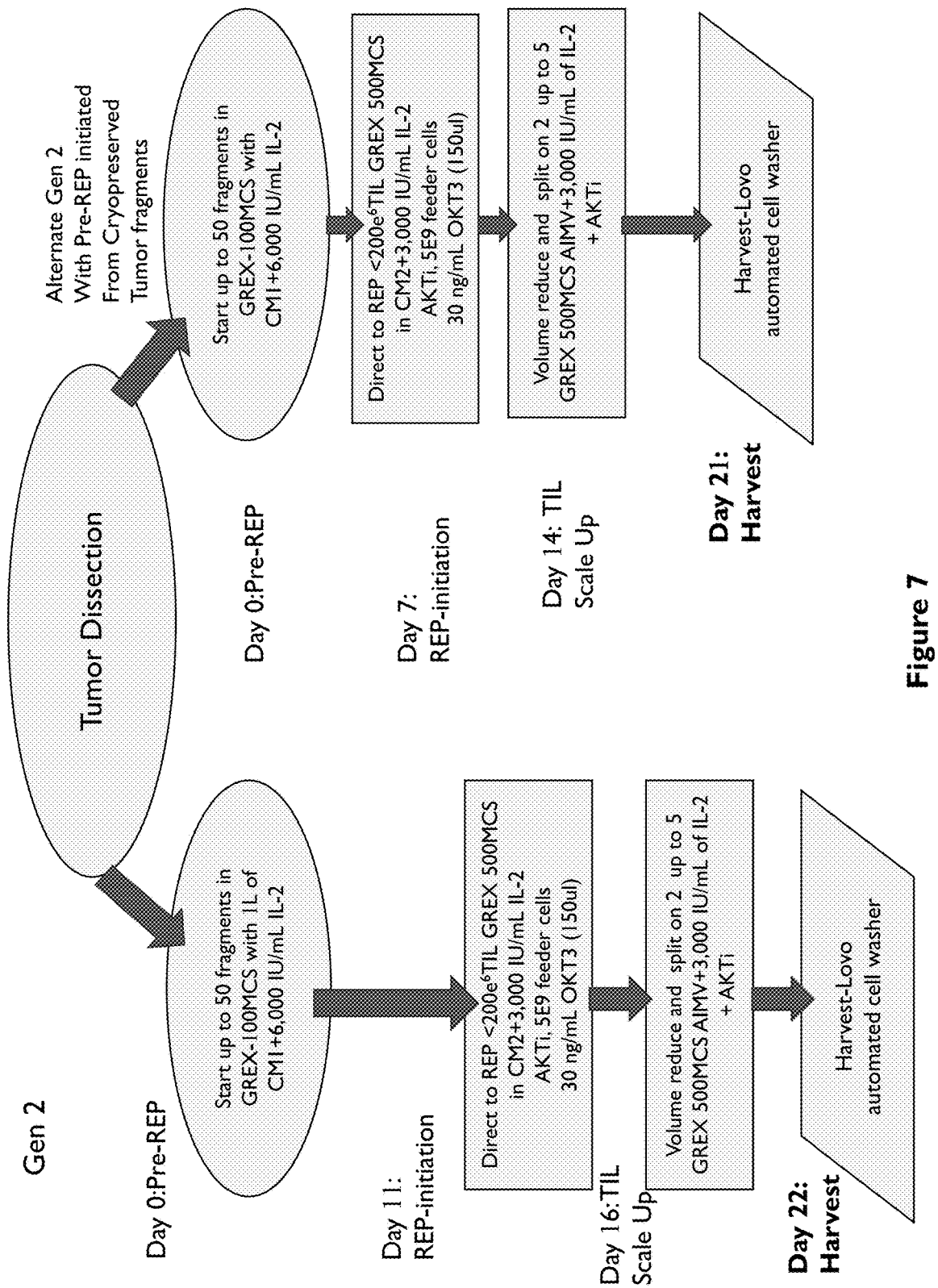
FIG. 7: Depicts an embodiment of the 2A process wherein the REP is initiated "early."
Figure 9:
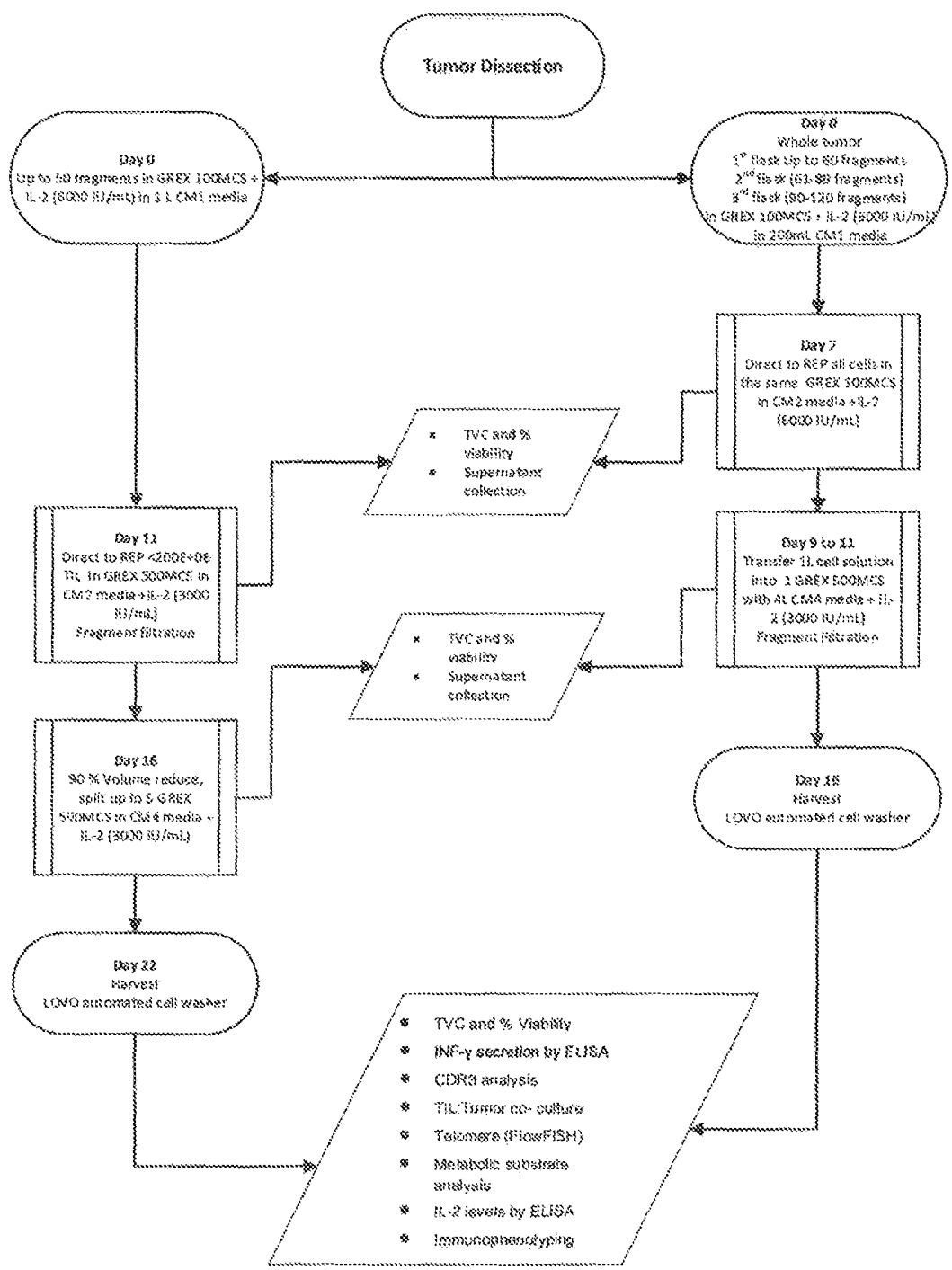
FIG. 9: Provides an experimental flow chart for comparability between GEN 2 (process 2A) versus GEN 3.

In some embodiments, the first expansion (including processes such as for example those described in Step B of FIG. 1, which can include those sometimes referred to as the pre-REP) process is shortened to 3 to 14 days, as discussed in the examples and figures. In some embodiments, the first expansion (including processes such as for example those described in Step B of FIG. 1, which can include those sometimes referred to as the pre-REP) is shortened to 7 to 14 days, as discussed in the Examples and shown in FIGS. 4 and 5, as well as including for example, an expansion as described in Step B of FIG. 1. In some embodiments, the first expansion of Step B is shortened to 10-14 days. In some embodiments, the first expansion is shortened to 11 days, as discussed in, for example, an expansion as described in Step B of FIG. 1.

In some embodiments, the first TIL expansion can proceed for 1 day, 2 days, 3 days, 4 days, 5 days, 6 days, 7 days, 8 days, 9 days, 10 days, 11 days, 12 days, 13 days, or 14 days. In some embodiments, the first TIL expansion can proceed for 1 day to 14 days. In some embodiments, the first TIL expansion can proceed for 2 days to 14 days. In some embodiments, the first TIL expansion can proceed for 3 days to 14 days. In some embodiments, the first TIL expansion can proceed for 4 days to 14 days. In some embodiments, the first TIL expansion can proceed for 5 days to 14 days. In some embodiments, the first TIL expansion can proceed for 6 days to 14 days. In some embodiments, the first TIL expansion can proceed for 7 days to 14 days. In some embodiments, the first TIL expansion can proceed for 8 days to 14 days. In some embodiments, the first TIL expansion can proceed for 9 days to 14 days. In some embodiments, the first TIL expansion can proceed for 10 days to 14 days. In some embodiments, the first TIL expansion can proceed for 11 days to 14 days. In some embodiments, the first TIL expansion can proceed for 12 days to 14 days. In some embodiments, the first TIL expansion can proceed for 13 days to 14 days. In some embodiments, the first TIL expansion can proceed for 14 days. In some embodiments, the first TIL expansion can proceed for 1 day to 11 days. In some embodiments, the first TIL expansion can proceed for 2 days to 11 days. In some embodiments, the first TIL expansion can proceed for 3 days to 11 days. In some embodiments, the first TIL expansion can proceed for 4 days to 11 days. In some embodiments, the first TIL expansion can proceed for 5 days to 11 days. In some embodiments, the first TIL expansion can proceed for 6 days to 11 days. In some embodiments, the first TIL expansion can proceed for 7 days to 11 days. In some embodiments, the first TIL expansion can proceed for 8 days to 11 days. In some embodiments, the first TIL expansion can proceed for 9 days to 11 days. In some embodiments, the first TIL expansion can proceed for 10 days to 11 days. In some embodiments, the first TIL expansion can proceed for 11 days.

In some embodiments, a combination of IL-2, IL-7, IL-15, and/or IL-21 are employed as a combination during the first expansion. In some embodiments, IL-2, IL-7, IL-15, and/or IL-21 as well as any combinations thereof can be included during the first expansion, including for example during a Step B processes according to FIG. 1, as well as described herein. In some embodiments, a combination of IL-2, IL-15, and IL-21 are employed as a combination during the first expansion. In some embodiments, IL-2, IL-15, and IL-21 as well as any combinations thereof can be included during Step B processes according to FIG. 1 and as described herein.

In some embodiments, the first expansion (including processes referred to as the pre-REP; for example, Step B according to FIG. 1) process is shortened to 3 to 14 days, as discussed in the examples and figures. In some embodiments, the first expansion of Step B is shortened to 7 to 14 days. In some embodiments, the first expansion of Step B is shortened to 10 to 14 days. In some embodiments, the first expansion is shortened to 11 days.

In some embodiments, the first expansion, for example, Step B according to FIG. 1, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

Step C: First Expansion to Second Expansion Transition

In some cases, the bulk TIL population obtained from the first expansion, including for example the TIL population obtained from for example, Step B as indicated in FIG. 1, can be cryopreserved immediately, using the protocols discussed herein below. Alternatively, the TIL population obtained from the first expansion, referred to as the second TIL population, can be subjected to a second expansion (which can include expansions sometimes referred to as REP) and then cryopreserved as discussed below. Similarly, in the case where genetically modified TILs will be used in therapy, the first TIL population (sometimes referred to as the bulk TIL population) or the second TIL population (which can in some embodiments include populations referred to as the REP TIL populations) can be subjected to genetic modifications for suitable treatments prior to expansion or after the first expansion and prior to the second expansion.

In some embodiments, the TILs obtained from the first expansion (for example, from Step B as indicated in FIG. 1) are stored until phenotyped for selection. In some embodiments, the TILs obtained from the first expansion (for example, from Step B as indicated in FIG. 1) are not stored and proceed directly to the second expansion. In some embodiments, the TILs obtained from the first expansion are not cryopreserved after the first expansion and prior to the second expansion. In some embodiments, the transition from the first expansion to the second expansion occurs at about 3 days, 4, days, 5 days, 6 days, 7 days, 8 days, 9 days, 10 days, 11 days, 12 days, 13 days, or 14 days from when fragmentation occurs. In some embodiments, the transition from the first expansion to the second expansion occurs at about 3 days to 14 days from when fragmentation occurs. In some embodiments, the transition from the first expansion to the second expansion occurs at about 4 days to 14 days from when fragmentation occurs. In some embodiments, the transition from the first expansion to the second expansion occurs at about 4 days to 10 days from when fragmentation occurs. In some embodiments, the transition from the first expansion to the second expansion occurs at about 7 days to 14 days from when fragmentation occurs. In some embodiments, the transition from the first expansion to the second expansion occurs at about 14 days from when fragmentation occurs.

In some embodiments, the transition from the first expansion to the second expansion occurs at 1 day, 2 days, 3 days, 4 days, 5 days, 6 days, 7 days, 8 days, 9 days, 10 days, 11 days, 12 days, 13 days, or 14 days from when fragmentation occurs. In some embodiments, the transition from the first expansion to the second expansion occurs 1 day to 14 days from when fragmentation occurs. In some embodiments, the first TIL expansion can proceed for 2 days to 14 days. In some embodiments, the transition from the first expansion to the second expansion occurs 3 days to 14 days from when fragmentation occurs. In some embodiments, the transition from the first expansion to the second expansion occurs 4 days to 14 days from when fragmentation occurs. In some embodiments, the transition from the first expansion to the second expansion occurs 5 days to 14 days from when fragmentation occurs. In some embodiments, the transition from the first expansion to the second expansion occurs 6 days to 14 days from when fragmentation occurs. In some embodiments, the transition from the first expansion to the second expansion occurs 7 days to 14 days from when fragmentation occurs. In some embodiments, the transition from the first expansion to the second expansion occurs 8 days to 14 days from when fragmentation occurs. In some embodiments, the transition from the first expansion to the second expansion occurs 9 days to 14 days from when fragmentation occurs. In some embodiments, the transition from the first expansion to the second expansion occurs 10 days to 14 days from when fragmentation occurs. In some embodiments, the transition from the first expansion to the second expansion occurs 11 days to 14 days from when fragmentation occurs. In some embodiments, the transition from the first expansion to the second expansion occurs 12 days to 14 days from when fragmentation occurs. In some embodiments, the transition from the first expansion to the second expansion occurs 13 days to 14 days from when fragmentation occurs. In some embodiments, the transition from the first expansion to the second expansion occurs 14 days from when fragmentation occurs. In some embodiments, the transition from the first expansion to the second expansion occurs 1 day to 11 days from when fragmentation occurs. In some embodiments, the transition from the first expansion to the second expansion occurs 2 days to 11 days from when fragmentation occurs. In some embodiments, the transition from the first expansion to the second expansion occurs 3 days to 11 days from when fragmentation occurs. In some embodiments, the transition from the first expansion to the second expansion occurs 4 days to 11 days from when fragmentation occurs. In some embodiments, the transition from the first expansion to the second expansion occurs 5 days to 11 days from when fragmentation occurs. In some embodiments, the transition from the first expansion to the second expansion occurs 6 days to 11 days from when fragmentation occurs. In some embodiments, the transition from the first expansion to the second expansion occurs 7 days to 11 days from when fragmentation occurs. In some embodiments, the transition from the first expansion to the second expansion occurs 8 days to 11 days from when fragmentation occurs. In some embodiments, the transition from the first expansion to the second expansion occurs 9 days to 11 days from when fragmentation occurs. In some embodiments, the transition from the first expansion to the second expansion occurs 10 days to 11 days from when fragmentation occurs. In some embodiments, the transition from the first expansion to the second expansion occurs 11 days from when fragmentation occurs.

In some embodiments, the TILs are not stored after the first expansion and prior to the second expansion, and the TILs proceed directly to the second expansion (for example, in some embodiments, there is no storage during the transition from Step B to Step D as shown in FIG. 1). In some embodiments, the transition occurs in closed system, as described herein. In some embodiments, the TILs from the first expansion, the second population of TILs, proceeds directly into the second expansion with no transition period.

In some embodiments, the transition from the first expansion to the second expansion, for example, Step C according to FIG. 1, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

Cytokines

The expansion methods described herein generally use culture media with high doses of a cytokine, in particular IL-2, as is known in the art.

Alternatively, using combinations of cytokines for the rapid expansion and or second expansion of TILs is additionally possible, with combinations of two or more of IL-2, IL-15 and IL-21 as is generally outlined in International Publication No. WO 2015/189356 and W International Publication No. WO 2015/189357, hereby expressly incorporated by reference in their entirety. Thus, possible combinations include IL-2 and IL-15, IL-2 and IL-21, IL-15 and IL-21 and IL-2, IL-15 and IL-21, with the latter finding particular use in many embodiments. The use of combinations of cytokines specifically favors the generation of lymphocytes, and in particular T-cells as described therein.

Step D: Second Expansion

In some embodiments, the TIL cell population is expanded in number after harvest and initial bulk processing for example, after Step A and Step B, and the transition referred to as Step C, as indicated in FIG. 1). This further expansion is referred to herein as the second expansion, which can include expansion processes generally referred to in the art as a rapid expansion process (REP; as well as processes as indicated in Step D of FIG. 1). The second expansion is generally accomplished using a culture media comprising a number of components, including feeder cells, a cytokine source, and an anti-CD3 antibody, in a gas-permeable container.

In some embodiments, the second expansion or second TIL expansion (which can include expansions sometimes referred to as REP; as well as processes as indicated in Step D of FIG. 1) of TIL can be performed using any TIL flasks or containers known by those of skill in the art. In some embodiments, the second TIL expansion can proceed for 7 days, 8 days, 9 days, 10 days, 11 days, 12 days, 13 days, or 14 days. In some embodiments, the second TIL expansion can proceed for about 7 days to about 14 days. In some embodiments, the second TIL expansion can proceed for about 8 days to about 14 days. In some embodiments, the second TIL expansion can proceed for about 9 days to about 14 days. In some embodiments, the second TIL expansion can proceed for about 10 days to about 14 days. In some embodiments, the second TIL expansion can proceed for about 11 days to about 14 days. In some embodiments, the second TIL expansion can proceed for about 12 days to about 14 days. In some embodiments, the second TIL expansion can proceed for about 13 days to about 14 days. In some embodiments, the second TIL expansion can proceed for about 14 days.

In an embodiment, the second expansion can be performed in a gas permeable container using the methods of the present disclosure (including for example, expansions referred to as REP; as well as processes as indicated in Step D of FIG. 1). For example, TILs can be rapidly expanded using non-specific T-cell receptor stimulation in the presence of interleukin-2 (IL-2) or interleukin-15 (IL-15). The non-specific T-cell receptor stimulus can include, for example, an anti-CD3 antibody, such as about 30 ng/ml of OKT3, a mouse monoclonal anti-CD3 antibody (commercially available from Ortho-McNeil, Raritan, NJ or Miltenyi Biotech, Auburn, CA) or UHCT-1 (commercially available from BioLegend, San Diego, CA, USA). TILs can be expanded to induce further stimulation of the TILs in vitro by including one or more antigens during the second expansion, including antigenic portions thereof, such as epitope(s), of the cancer, which can be optionally expressed from a vector, such as a human leukocyte antigen A2 (HLA-A2) binding peptide, e.g., 0.3 µM MART-1:26-35 (27 L) or gpl 00:209-217 (210M), optionally in the presence of a T-cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. TIL may also be rapidly expanded by re-stimulation with the same antigen(s) of the cancer pulsed onto HLA-A2-expressing antigen-presenting cells. Alternatively, the TILs can be further re-stimulated with, e.g., example, irradiated, autologous lymphocytes or with irradiated HLA-A2$^+$ allogeneic lymphocytes and IL-2. In some embodiments, the re-stimulation occurs as part of the second expansion. In some embodiments, the second expansion occurs in the presence of irradiated, autologous lymphocytes or with irradiated HLA-A2$^+$ allogeneic lymphocytes and IL-2.

In an embodiment, the cell culture medium further comprises IL-2. In some embodiments, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In an embodiment, the cell culture medium comprises OKT-3 antibody. In some embodiments, the cell culture medium comprises about 30 ng/mL of OKT-3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 µg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In some embodiments, the cell culture medium does not comprise OKT-3 antibody. In some embodiments, the OKT-3 antibody is muromonab.

In some embodiments, the cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 µg/mL and 100 µg/mL. In some embodiments, the TNFRSF agonist is added at a concentration sufficient to achieve a concentration in the cell culture medium of between 20 µg/mL and 40 µg/mL.

In some embodiments, in addition to one or more TNFRSF agonists, the cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist.

In some embodiments, a combination of IL-2, IL-7, IL-15, and/or IL-21 are employed as a combination during the second expansion. In some embodiments, IL-2, IL-7, IL-15, and/or IL-21 as well as any combinations thereof can be included during the second expansion, including for example during a Step D processes according to FIG. 1, as well as described herein. In some embodiments, a combination of IL-2, IL-15, and IL-21 are employed as a combination during the second expansion. In some embodiments, IL-2, IL-15, and IL-21 as well as any combinations thereof can be included during Step D processes according to FIG. 1 and as described herein.

In some embodiments, the second expansion can be conducted in a supplemented cell culture medium comprising IL-2, OKT-3, antigen-presenting feeder cells, and optionally a TNFRSF agonist. In some embodiments, the second expansion occurs in a supplemented cell culture medium. In some embodiments, the supplemented cell culture medium comprises IL-2, OKT-3, and antigen-presenting feeder cells. In some embodiments, the second cell culture medium comprises IL-2, OKT-3, and antigen-presenting cells (APCs; also referred to as antigen-presenting feeder cells). In some embodiments, the second expansion occurs in a cell culture medium comprising IL-2, OKT-3, and antigen-presenting feeder cells (i.e., antigen presenting cells).

In some embodiments, the second expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the second expansion culture media comprises about 500 IU/mL of IL-15 to about 100 IU/mL of IL-15. In some embodiments, the second expansion culture media comprises about 400 IU/mL of IL-15 to about 100 IU/mL of IL-15. In some embodiments, the second expansion culture media comprises about 300 IU/mL of IL-15 to about 100 IU/mL of IL-15. In some embodiments, the second expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, the second expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the second expansion culture media comprises about 20 IU/mL of IL-21 to about 0.5 IU/mL of IL-21. In some embodiments, the second expansion culture media comprises about 15 IU/mL of IL-21 to about 0.5 IU/mL of IL-21. In some embodiments, the second expansion culture media comprises about 12 IU/mL of IL-21 to about 0.5 IU/mL of IL-21. In some embodiments, the second expansion culture media comprises about 10 IU/mL of IL-21 to about 0.5 IU/mL of IL-21. In some embodiments, the second expansion culture media comprises about 5 IU/mL of IL-21 to about 1 IU/mL of IL-21. In some embodiments, the second expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In some embodiments the antigen-presenting feeder cells (APCs) are PBMCs. In an embodiment, the ratio of TILs to PBMCs and/or antigen-presenting cells in the rapid expansion and/or the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to PBMCs in the rapid expansion and/or the second expansion is between 1 to 50 and 1 to 300. In an embodiment, the ratio of TILs to PBMCs in the rapid expansion and/or the second expansion is between 1 to 100 and 1 to 200.

In an embodiment, REP and/or the second expansion is performed in flasks with the bulk TILs being mixed with a 100- or 200-fold excess of inactivated feeder cells, 30 mg/mL OKT3 anti-CD3 antibody and 3000 IU/mL IL-2 in 150 ml media. Media replacement is done (generally ⅔ media replacement via respiration with fresh media) until the cells are transferred to an alternative growth chamber. Alternative growth chambers include G-REX flasks and gas permeable containers as more fully discussed below.

In some embodiments, the second expansion (which can include processes referred to as the REP process) is shortened to 7-14 days, as discussed in the examples and figures. In some embodiments, the second expansion is shortened to 11 days.

In an embodiment, REP and/or the second expansion may be performed using T-175 flasks and gas permeable bags as previously described (Tran, et al., *J. Immunother,* 2008, 31, 742-51; Dudley, et al., *J. Immunother,* 2003, 26, 332-42) or gas permeable cultureware (G-Rex flasks). In some embodiments, the second expansion (including expansions referred to as rapid expansions) is performed in T-175 flasks, and about $1 \times 10^6$ TILs suspended in 150 mL of media may be added to each T-175 flask. The TILs may be cultured in a 1 to 1 mixture of CM and AIM-V medium, supplemented with 3000 IU per mL of IL-2 and 30 ng per ml of anti-CD3. The T-175 flasks may be incubated at 37° C. in 5% $CO_2$. Half the media may be exchanged on day 5 using 50/50 medium with 3000 IU per mL of IL-2. In some embodiments, on day 7 cells from two T-175 flasks may be combined in a 3 L bag and 300 mL of AIM V with 5% human AB serum and 3000 IU per mL of IL-2 was added to the 300 ml of TIL suspension. The number of cells in each bag was counted every day or two and fresh media was added to keep the cell count between 0.5 and $2.0 \times 10^6$ cells/mL.

In an embodiment, the second expansion (which can include expansions referred to as REP, as well as those referred to in Step D of FIG. 1) may be performed in 500 mL capacity gas permeable flasks with 100 cm gas-permeable silicon bottoms (G-Rex 100, commercially available from Wilson Wolf Manufacturing Corporation, New Brighton, MN, USA), $5 \times 10^6$ or $10 \times 10^6$ TIL may be cultured with PBMCs in 400 mL of 50/50 medium, supplemented with 5% human AB serum, 3000 IU per mL of IL-2 and 30 ng per ml of anti-CD3 (OKT3). The G-Rex 100 flasks may be incubated at 37° C. in 5% $CO_2$. On day 5, 250 mL of supernatant may be removed and placed into centrifuge bottles and centrifuged at 1500 rpm (491×g) for 10 minutes. The TIL pellets may be re-suspended with 150 mL of fresh medium with 5% human AB serum, 3000 IU per mL of IL-2, and added back to the original G-Rex 100 flasks. When TIL are expanded serially in G-Rex 100 flasks, on day 7 the TIL in each G-Rex 100 may be suspended in the 300 mL of media present in each flask and the cell suspension may be divided into 3 100 mL aliquots that may be used to seed 3 G-Rex 100 flasks. Then 150 mL of AIM-V with 5% human AB serum and 3000 IU per mL of IL-2 may be added to each flask. The G-Rex 100 flasks may be incubated at 37° C. in 5% $CO_2$ and after 4 days 150 mL of AIM-V with 3000 IU per mL of IL-2 may be added to each G-REX 100 flask. The cells may be harvested on day 14 of culture.

In an embodiment, the second expansion (including expansions referred to as REP) is performed in flasks with the bulk TILs being mixed with a 100- or 200-fold excess of inactivated feeder cells, 30 mg/mL OKT3 anti-CD3 antibody and 3000 IU/mL IL-2 in 150 ml media. In some embodiments, media replacement is done until the cells are transferred to an alternative growth chamber. In some embodiments, ⅔ of the media is replaced by respiration with fresh media. In some embodiments, alternative growth chambers include G-REX flasks and gas permeable containers as more fully discussed below.

In an embodiment, the second expansion (including expansions referred to as REP) is performed and further comprises a step wherein TILs are selected for superior tumor reactivity. Any selection method known in the art may be used. For example, the methods described in U.S. Patent Application Publication No. 2016/0010058 A1, the disclosures of which are incorporated herein by reference, may be used for selection of TILs for superior tumor reactivity.

Optionally, a cell viability assay can be performed after the second expansion (including expansions referred to as the REP expansion), using standard assays known in the art. For example, a trypan blue exclusion assay can be done on a sample of the bulk TILs, which selectively labels dead cells and allows a viability assessment. In some embodiments, TIL samples can be counted and viability determined using a Cellometer K2 automated cell counter (Nexcelom Bioscience, Lawrence, MA). In some embodiments, viability is determined according to the standard Cellometer K2 Image Cytometer Automatic Cell Counter protocol.

In some embodiments, the second expansion (including expansions referred to as REP) of TIL can be performed using T-175 flasks and gas-permeable bags as previously described (Tran K Q, Zhou J, Durflinger K H, et al., 2008, *J Immunother.*, 31:742-751, and Dudley M E, Wunderlich J R, Shelton T E, et al. 2003, *J Immunother.*, 26:332-342) or gas-permeable G-Rex flasks. In some embodiments, the second expansion is performed using flasks. In some embodiments, the second expansion is performed using gas-permeable G-Rex flasks. In some embodiments, the second expansion is performed in T-175 flasks, and about $1×10^6$ TIL are suspended in about 150 mL of media and this is added to each T-175 flask. The TIL are cultured with irradiated (50 Gy) allogeneic PBMC as "feeder" cells at a ratio of 1 to 100 and the cells were cultured in a 1 to 1 mixture of CM and AIM-V medium (50/50 medium), supplemented with 3000 IU/mL of IL-2 and 30 ng/mL of anti-CD3. The T-175 flasks are incubated at 37° C. in 5% $CO_2$. In some embodiments, half the media is changed on day 5 using 50/50 medium with 3000 IU/mL of IL-2. In some embodiments, on day 7, cells from 2 T-175 flasks are combined in a 3 L bag and 300 mL of AIM-V with 5% human AB serum and 3000 IU/mL of IL-2 is added to the 300 mL of TIL suspension. The number of cells in each bag can be counted every day or two and fresh media can be added to keep the cell count between about 0.5 and about $2.0×10^6$ cells/mL.

In some embodiments, the second expansion (including expansions referred to as REP) are performed in 500 mL capacity flasks with 100 cm² gas-permeable silicon bottoms (G-Rex 100, Wilson Wolf) (FIG. 1), about $5×10^6$ or $10×10^6$ TIL are cultured with irradiated allogeneic PBMC at a ratio of 1 to 100 in 400 mL of 50/50 medium, supplemented with 3000 IU/mL of IL-2 and 30 ng/mL of anti-CD3. The G-Rex 100 flasks are incubated at 37° C. in 5% $CO_2$. In some embodiments, on day 5, 250 mL of supernatant is removed and placed into centrifuge bottles and centrifuged at 1500 rpm (491 g) for 10 minutes. The TIL pellets can then be resuspended with 150 mL of fresh 50/50 medium with 3000 IU/mL of IL-2 and added back to the original G-Rex 100 flasks. In embodiments where TILs are expanded serially in G-Rex 100 flasks, on day 7 the TIL in each G-Rex 100 are suspended in the 300 mL of media present in each flask and the cell suspension was divided into three 100 mL aliquots that are used to seed 3 G-Rex 100 flasks. Then 150 mL of AIM-V with 5% human AB serum and 3000 IU/mL of IL-2 is added to each flask. The G-Rex 100 flasks are incubated at 37° C. in 5% $CO_2$ and after 4 days 150 mL of AIM-V with 3000 IU/mL of IL-2 is added to each G-Rex 100 flask. The cells are harvested on day 14 of culture.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained in the second expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β).

In some embodiments, the second expansion culture medium (e.g., sometimes referred to as CM2 or the second cell culture medium), comprises IL-2, OKT-3, as well as the antigen-presenting feeder cells (APCs), as discussed in more detail below.

In some embodiments, the second expansion, for example, Step D according to FIG. 1, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

Feeder Cells and Antigen Presenting Cells

In an embodiment, the second expansion procedures described herein (for example including expansion such as those described in Step D from FIG. 1, as well as those referred to as REP) require an excess of feeder cells during REP TIL expansion and/or during the second expansion. In many embodiments, the feeder cells are peripheral blood mononuclear cells (PBMCs) obtained from standard whole blood units from healthy allogeneic blood donors. The PBMCs are obtained using standard methods such as Ficoll-Paque gradient separation, see, e.g. "Isolation of mononuclear cells: Methodology and Application", GE Life Sciences technical publication 18-1152-69-AE, available at https://us.vwr.com/assetsvc/asset/en_US/id/16286835/contents.

In general, the allogenic PBMCs are inactivated, either via irradiation or heat treatment, and used in the REP procedures, as described in the examples, which provides an exemplary protocol for evaluating the replication incompetence of irradiate allogeneic PBMCs.

In some embodiments, PBMCs are considered replication incompetent and accepted for use in the TIL expansion procedures described herein if the total number of viable cells on day 14 is less than the initial viable cell number put into culture on day 0 of the REP and/or day 0 of the second expansion (i.e., the start day of the second expansion).

In some embodiments, PBMCs are considered replication incompetent and accepted for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 30 ng/ml OKT3 antibody and 3000 IU/ml IL-2.

In some embodiments, PBMCs are considered replication incompetent and acceptable for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 5 to 60 ng/ml OKT3 antibody and 1000-6000 IU/ml IL-2. In some embodiments, the PBMCs are cultured in the presence of 10 to 50 ng/ml OKT3 antibody and 2000-5000 IU/ml IL-2. In some embodiments, the PBMCs are cultured in the presence of 20 to 40 ng/ml OKT3 antibody and 2000-4000 IU/ml IL-2. In some embodiments, the PBMCs are cultured in the presence of 25 to 35 ng/ml OKT3 antibody and 2500-3500 IU/ml IL-2.

In some embodiments, the antigen-presenting feeder cells are PBMCs. In some embodiments, the antigen-presenting feeder cells are artificial antigen-presenting feeder cells. In an embodiment, the ratio of TILs to antigen-presenting feeder cells in the second expansion is about 1 to 10, about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to antigen-presenting feeder cells in the second expansion is between 1 to 50 and 1 to 300. In an embodiment, the ratio of TILs to antigen-presenting feeder cells in the second expansion is between 1 to 100 and 1 to 200.

In an embodiment, the second expansion procedures described herein require a ratio of about $2.5 \times 10^9$ feeder cells to about $100 \times 10^6$ TILs. In another embodiment, the second expansion procedures described herein require a ratio of about $2.5 \times 10^9$ feeder cells to about $50 \times 10^6$ TILs. In yet another embodiment, the second expansion procedures described herein require about $2.5 \times 10^9$ feeder cells to about $25 \times 10^6$ TILs.

In an embodiment, the second expansion procedures described herein require an excess of feeder cells during the second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation. In an embodiment, artificial antigen-presenting (aAPC) cells are used in place of PBMCs.

In general, the allogenic PBMCs are inactivated, either via irradiation or heat treatment, and used in the TIL expansion procedures described herein, including the exemplary procedures described in the figures and examples.

In an embodiment, artificial antigen presenting cells are used in the second expansion as a replacement for, or in combination with, PBMCs.

Cytokines

The TIL expansion methods described herein generally use culture media with high doses of a cytokine, in particular IL-2, as is known in the art.

Alternatively, using combinations of cytokines for the rapid expansion and or second expansion of TILs is additionally possible, with combinations of two or more of IL-2, IL-15 and IL-21 as is generally outlined in International Publication No. WO 2015/189356 and W International Publication No. WO 2015/189357, hereby expressly incorporated by reference in their entirety. Thus, possible combinations include IL-2 and IL-15, IL-2 and IL-21, IL-15 and IL-21 and IL-2, IL-15 and IL-21, with the latter finding particular use in many embodiments. The use of combinations of cytokines specifically favors the generation of lymphocytes, and in particular T-cells as described therein.

Step E: Harvest TILs

After the second expansion step, cells can be harvested. In some embodiments the TILs are harvested after one, two, three, four or more expansion steps, for example as provided in FIG. 1. In some embodiments the TILs are harvested after two expansion steps, for example as provided in FIG. 1.

TILs can be harvested in any appropriate and sterile manner, including for example by centrifugation. Methods for TIL harvesting are well known in the art and any such know methods can be employed with the present process. In some embodiments, TILS are harvest using an automated system.

Cell harvesters and/or cell processing systems are commercially available from a variety of sources, including, for example, Fresenius Kabi, Tomtec Life Science, Perkin Elmer, and Inotech Biosystems International, Inc. Any cell based harvester can be employed with the present methods. In some embodiments, the cell harvester and/or cell processing systems is a membrane-based cell harvester. In some embodiments, cell harvesting is via a cell processing system, such as the LOVO system (manufactured by Fresenius Kabi). The term "LOVO cell processing system" also refers to any instrument or device manufactured by any vendor that can pump a solution comprising cells through a membrane or filter such as a spinning membrane or spinning filter in a sterile and/or closed system environment, allowing for continuous flow and cell processing to remove supernatant or cell culture media without pelletization. In some embodiments, the cell harvester and/or cell processing system can perform cell separation, washing, fluid-exchange, concentration, and/or other cell processing steps in a closed, sterile system.

In some embodiments, the harvest, for example, Step E according to FIG. 1, is performed from a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

In some embodiments, Step E according to FIG. 1, is performed according to the processes described in Example 7. In some embodiments, the closed system is accessed via syringes under sterile conditions in order to maintain the sterility and closed nature of the system. In some embodiments, a closed system, as described in Example 7, is employed.

In some embodiments, TILs are harvested according to the methods described in Example 7. In some embodiments, TTLs between days 1 and 11 are harvested using the methods as described herein (referred to as the Day 11 TIL harvest in Example 7). In some embodiments, TTLs between days 12 and 22 are harvested using the methods as described herein (referred to as the Day 22 TIL harvest in Example 7).

Step F: Final Formulation Transfer to Infusion Bag

After Steps A through E as provided in an exemplary order in FIG. 1 and as outlined in detailed above and herein are complete, cells are transferred to a container for use in administration to a patient. In some embodiments, once a therapeutically sufficient number of TILs are obtained using the expansion methods described above, they are transferred to a container for use in administration to a patient.

In an embodiment, TILs expanded using APCs of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic.

Anti-CD3 Antibodies as Optional Media Components

In some embodiments, the culture media used in expansion methods described herein (including those referred to as REP, see for example, FIG. 1) also includes an anti-CD3 antibody. An anti-CD3 antibody in combination with IL-2 induces T cell activation and cell division in the TIL population. This effect can be seen with full length antibodies as well as Fab and F(ab')2 fragments, with the former being generally preferred; see, e.g., Tsoukas et al., *J. Immunol.*, 1985, 135, 1719, hereby incorporated by reference in its entirety.

As will be appreciated by those in the art, there are a number of suitable anti-human CD3 antibodies that find use in the invention, including anti-human CD3 polyclonal and monoclonal antibodies from various mammals, including, but not limited to, murine, human, primate, rat, and canine antibodies. In particular embodiments, the OKT3 anti-CD3 antibody muromonab (including the embodiments shown in Table 1) is used (commercially available from Ortho-Mc-Neil, Raritan, NJ or Miltenyi Biotech, Auburn, CA). Anti-CD3 antibodies also include the UHCT1 clone, also known as T3 and CD3ε. Other anti-CD3 antibodies include, for example, otelixizumab, teplizumab, and visilizumab.

4-1BB (CD137) Agonists as Optional Media Components

In an embodiment, the TNFRSF agonist is a 4-1BB (CD137) agonist. The 4-1BB agonist may be any 4-1BB binding molecule known in the art. The 4-1BB binding molecule may be a monoclonal antibody or fusion protein capable of binding to human or mammalian 4-1BB. The 4-1BB agonists or 4-1BB binding molecules may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. The 4-1BB agonist or 4-1BB binding molecule may have both a heavy and a light chain. As used herein, the term binding molecule also includes antibodies (including full length antibodies), monoclonal antibodies (including full length monoclonal antibodies), polyclonal antibodies, multispecific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to 4-1BB. In an embodiment, the 4-1BB agonist is an antigen binding protein that is a fully human antibody. In an embodiment, the 4-1BB agonist is an antigen binding protein that is a humanized antibody. In some embodiments, 4-1BB agonists for use in the presently disclosed methods and compositions include anti-4-1BB antibodies, human anti-4-1BB antibodies, mouse anti-4-1BB antibodies, mammalian anti-4-1BB antibodies, monoclonal anti-4-1BB antibodies, polyclonal anti-4-1BB antibodies, chimeric anti-4-1BB antibodies, anti-4-1BB adnectins, anti-4-1BB domain antibodies, single chain anti-4-1BB fragments, heavy chain anti-4-1BB fragments, light chain anti-4-1BB fragments, anti-4-1BB fusion proteins, and fragments, derivatives, conjugates, variants, or biosimilars thereof. Agonistic anti-4-1BB antibodies are known to induce strong immune responses. Lee, et al., *PLOS One*, 2013, 8:e69677. In a preferred embodiment, the 4-1BB agonist is an agonistic, anti-4-1BB humanized or fully human monoclonal antibody (i.e., an antibody derived from a single cell line). In an embodiment, the 4-1BB agonist is EU-101 (Eutilex Co. Ltd.), utomilumab, or urelumab, or a fragment, derivative, conjugate, variant, or biosimilar thereof. In a preferred embodiment, the 4-1BB agonist is utomilumab or urelumab, or a fragment, derivative, conjugate, variant, or biosimilar thereof.

In a preferred embodiment, the 4-1BB agonist or 4-1BB binding molecule may also be a fusion protein. In a preferred embodiment, a multimeric 4-1BB agonist, such as a trimeric or hexameric 4-1BB agonist (with three or six ligand binding domains), may induce superior receptor (4-1BBL) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG1-Fc and optionally further linking two or more of these fusion proteins are described, for example, in Gieffers, et al., *Mol. Cancer Therapeutics*, 2013, 12:2735-47.

Agonistic 4-1BB antibodies and fusion proteins are known to induce strong immune responses. In a preferred embodiment, the 4-1BB agonist is a monoclonal antibody or fusion protein that binds specifically to 4-1BB antigen in a manner sufficient to reduce toxicity. In some embodiments, the 4-1BB agonist is an agonistic 4-1BB monoclonal antibody or fusion protein that abrogates antibody-dependent cellular toxicity (ADCC), for example NK cell cytotoxicity. In some embodiments, the 4-1BB agonist is an agonistic 4-1BB monoclonal antibody or fusion protein that abrogates antibody-dependent cell phagocytosis (ADCP). In some embodiments, the 4-1BB agonist is an agonistic 4-1BB monoclonal antibody or fusion protein that abrogates complement-dependent cytotoxicity (CDC). In some embodiments, the 4-1BB agonist is an agonistic 4-1BB monoclonal antibody or fusion protein which abrogates Fc region functionality.

In some embodiments, the 4-1BB agonists are characterized by binding to human 4-1BB (SEQ ID NO:9) with high affinity and agonistic activity. In an embodiment, the 4-1BB agonist is a binding molecule that binds to human 4-1BB (SEQ ID NO:9). In an embodiment, the 4-1BB agonist is a binding molecule that binds to murine 4-1BB (SEQ ID NO:10). The amino acid sequences of 4-1BB antigen to which a 4-1BB agonist or binding molecule binds are summarized in Table 3.

In some embodiments, the compositions, processes and methods described include a 4-1BB agonist that binds to human or murine 4-1BB with a $k_{dissoc}$ of about $2 \times 10^{-5}$ 1/s or slower, binds to human or murine 4-1BB with a $k_{dissoc}$ of about $2.1 \times 10^{-5}$ 1/s or slower, binds to human or murine 4-1BB with a $k_{dissoc}$ of about $2.2 \times 10^{-5}$ 1/s or slower, binds to human or murine 4-1BB with a $k_{dissoc}$ of about $2.3 \times 10^{-5}$ 1/s or slower, binds to human or murine 4-1BB with a $k_{dissoc}$ of about $2.4 \times 10^{-5}$ 1/s or slower, binds to human or murine 4-1BB with a $k_{dissoc}$ of about $2.5 \times 10^{-5}$ 1/s or slower, binds to human or murine 4-1BB with a $k_{dissoc}$ of about $2.6 \times 10^{-5}$ 1/s or slower or binds to human or murine 4-1BB with a $k_{dissoc}$ of about $2.7 \times 10^{-5}$ 1/s or slower, binds to human or murine 4-1BB with a $k_{dissoc}$ of about $2.8 \times 10^{-5}$ 1/s or slower, binds to human or murine 4-1BB with a $k_{dissoc}$ of about $2.9 \times 10^{-5}$ 1/s or slower, or binds to human or murine 4-1BB with a $k_{dissoc}$ of about $3 \times 10^{-5}$ 1/s or slower.

In some embodiments, the compositions, processes and methods described include a 4-1BB agonist that binds to human or murine 4-1BB with an $IC_{50}$ of about 10 nM or lower, binds to human or murine 4-1BB with an $IC_{50}$ of about 9 nM or lower, binds to human or murine 4-1BB with an $IC_{50}$ of about 8 nM or lower, binds to human or murine

TABLE 3

Amino acid sequences of 4-1BB antigens.

| Identifier | Sequence (One-Letter Amino Acid Symbols) | | | | | |
|---|---|---|---|---|---|---|
| SEQ ID NO: 9 human 4-1BB, Tumor necrosis factor receptor superfamily, member 9 (*Homo sapiens*) | MGNSCYNIVA TCDICRQCKG CFGTFNDQKR PGHSPQIISF CSCRFPEEEE | TLLLVLNFER VFRTRKECSS GICRPWTNCS FLALTSTALL GGCEL | TRSLQDPCSN TSNAECDCTP LDGKSVLVNG FLLFFLTLRF | CPAGTFCDNN GFHCLGAGCS TKERDVVCGP SVVKRGRKKL | RNQICSPCPP MCEQDCKQGQ SPADLSPGAS LYIFKQPFMR | NSFSSAGGQR ELTKKGCKDC SVTPPAPARE PVQTTQEEDG | 60 120 180 240 255 |
| SEQ ID NO: 10 murine 4-1BB, Tumor necrosis factor receptor superfamily, member 9 (*Mus musculus*) | MGNNCYNVVV CNICRVCAGY LGTFNDQNGT GHSLQVLTLF CRCPQEEEGG | IVLLLVGCEK FRFKKFCSST GVCRPWTNCS LALTSALLLA GGGYEL | VGAVQNSCDN HNAECECIEG LDGRSVLKTG LIFITLLFSV | CQPGTFCRKY FHCLGPQCTR TTEKDVVCGP LKWIRKKFPH | NPVCKSCPPS CEKDCRPGQE PVVSFSPSTT IFKQPFKKTT | TFSSIGGQPN LTKQGCKTCS ISVTPEGGPG GAAQEEDACS | 60 120 180 240 256 |

In some embodiments, the compositions, processes and methods described include a 4-1BB agonist that binds human or murine 4-1BB with a $K_D$ of about 100 pM or lower, binds human or murine 4-1BB with a $K_D$ of about 90 pM or lower, binds human or murine 4-1BB with a $K_D$ of about 80 pM or lower, binds human or murine 4-1BB with a $K_D$ of about 70 pM or lower, binds human or murine 4-1BB with a $K_D$ of about 60 pM or lower, binds human or murine 4-1BB with a $K_D$ of about 50 pM or lower, binds human or murine 4-1BB with a $K_D$ of about 40 pM or lower, or binds human or murine 4-1BB with a $K_D$ of about 30 pM or lower.

In some embodiments, the compositions, processes and methods described include a 4-1BB agonist that binds to human or murine 4-1BB with a $k_{assoc}$ of about $7.5 \times 10^5$ 1/M·s or faster, binds to human or murine 4-1BB with a $k_{assoc}$ of about $7.5 \times 10^5$ 1/M·s or faster, binds to human or murine 4-1BB with a $k_{assoc}$ of about $8 \times 10^5$ 1/M·s or faster, binds to human or murine 4-1BB with a $k_{assoc}$ of about $8.5 \times 10^5$ 1/M·s or faster, binds to human or murine 4-1BB with a $k_{assoc}$ of about $9 \times 10^5$ 1/M·s or faster, binds to human or murine 4-1BB with a $k_{assoc}$ of about $9.5 \times 10^5$ 1/M·s or faster, or binds to human or murine 4-1BB with a $k_{assoc}$ of about $1 \times 10^6$ 1/M·s or faster.

4-1BB with an $IC_{50}$ of about 7 nM or lower, binds to human or murine 4-1 in with an $IC_{50}$ of about 6 nM or lower, binds to human or murine 4-1 in with an $IC_{50}$ of about 5 nM or lower, binds to human or murine 4-1 in with an $IC_{50}$ of about 4 nM or lower, binds to human or murine 4-1BB with an $IC_{50}$ of about 3 nM or lower, binds to human or murine 4-1BB with an $IC_{50}$ of about 2 nM or lower, or binds to human or murine 4-1BB with an $IC_{50}$ of about 1 nM or lower.

In a preferred embodiment, the 4-1 in agonist is utomilumab, also known as PF-05082566 or MOR-7480, or a fragment, derivative, variant, or biosimilar thereof. Utomilumab is available from Pfizer, Inc. Utomilumab is an immunoglobulin G2-lambda, anti-[*Homo sapiens* TNFRSF9 (tumor necrosis factor receptor (TNFR) superfamily member 9, 4-1 in, T cell antigen ILA, CD137)], *Homo sapiens* (fully human) monoclonal antibody. The amino acid sequences of utomilumab are set forth in Table 4. Utomilumab comprises glycosylation sites at Asn59 and Asn292; heavy chain intrachain disulfide bridges at positions 22-96 ($V_H$-$V_L$), 143-199 ($C_H$1-$C_L$), 256-316 ($C_H$2) and 362-420 ($C_H$3); light chain intrachain disulfide bridges at positions 22'-87' ($V_H$-$V_L$) and 136'-195' ($C_H$1-$C_L$); interchain heavy chain-heavy chain disulfide bridges at IgG2A isoform positions 218-218, 219-219, 222-222, and 225-225, at IgG2A/B isoform positions 218-130, 219-219, 222-222, and 225-225, and at IgG2n isoform positions 219-130 (2), 222-222, and 225-225; and interchain heavy chain-light chain disulfide bridges at IgG2A isoform positions 130-213' (2), IgG2A/B isoform positions 218-213' and 130-213', and at IgG2n isoform positions 218-213' (2). The preparation and properties of utomilumab and its variants and fragments are described in U.S. Pat. Nos. 8,821,867; 8,337,850; and 9,468,678, and International Patent Application Publication No. WO 2012/032433 A1, the disclosures of each of which are incorporated by reference herein. Preclinical characteristics of utomilumab are described in Fisher, et al., *Cancer Immunolog. & Immunother.*, 2012, 61:1721-33. Current clinical trials of utomilumab in a variety of hematological and solid tumor indications include U.S. National Institutes of Health clinicaltrials.gov identifiers NCT02444793, NCT01307267, NCT02315066, and NCT02554812.

In an embodiment, a 4-1BB agonist comprises a heavy chain given by SEQ ID NO:11 and a light chain given by SEQ ID NO:12. In an embodiment, a 4-1BB agonist comprises heavy and light chains having the sequences shown in SEQ ID NO:11 and SEQ ID NO:12, respectively, or antigen binding fragments, Fab fragments, single-chain variable fragments (scFv), variants, or conjugates thereof. In an embodiment, a 4-1BB agonist comprises heavy and light chains that are each at least 99% identical to the sequences shown in SEQ ID NO:11 and SEQ ID NO:12, respectively. In an embodiment, a 4-1BB agonist comprises heavy and light chains that are each at least 98% identical to the sequences shown in SEQ ID NO:11 and SEQ ID NO:12, respectively. In an embodiment, a 4-1BB agonist comprises heavy and light chains that are each at least 97% identical to the sequences shown in SEQ ID NO:11 and SEQ ID NO:12, respectively. In an embodiment, a 4-1BB agonist comprises heavy and light chains that are each at least 96% identical to the sequences shown in SEQ ID NO:11 and SEQ ID NO:12, respectively. In an embodiment, a 4-1BB agonist comprises heavy and light chains that are each at least 95% identical to the sequences shown in SEQ ID NO:11 and SEQ ID NO:12, respectively.

In an embodiment, the 4-1 in agonist comprises the heavy and light chain CDRs or variable regions (VRs) of utomilumab. In an embodiment, the 4-1BB agonist heavy chain variable region ($V_H$) comprises the sequence shown in SEQ ID NO:13, and the 4-1BB agonist light chain variable region ($V_L$) comprises the sequence shown in SEQ ID NO:14, and conservative amino acid substitutions thereof. In an embodiment, a 4-1BB agonist comprises $V_H$ and $V_L$ regions that are each at least 99% identical to the sequences shown in SEQ ID NO:13 and SEQ ID NO:14, respectively. In an embodiment, a 4-1BB agonist comprises $V_H$ and $V_L$ regions that are each at least 98% identical to the sequences shown in SEQ ID NO:13 and SEQ ID NO:14, respectively. In an embodiment, a 4-1BB agonist comprises $V_H$ and $V_L$ regions that are each at least 97% identical to the sequences shown in SEQ ID NO:13 and SEQ ID NO:14, respectively. In an embodiment, a 4-1BB agonist comprises $V_H$ and $V_L$ regions that are each at least 96% identical to the sequences shown in SEQ ID NO:13 and SEQ ID NO:14, respectively. In an embodiment, a 4-1BB agonist comprises $V_H$ and $V_L$ regions that are each at least 95% identical to the sequences shown in SEQ ID NO:13 and SEQ ID NO:14, respectively. In an embodiment, a 4-1BB agonist comprises an scFv antibody comprising $V_H$ and $V_L$ regions that are each at least 99% identical to the sequences shown in SEQ ID NO:13 and SEQ ID NO:14.

In an embodiment, a 4-1BB agonist comprises heavy chain CDR1, CDR2 and CDR3 domains having the sequences set forth in SEQ ID NO:15, SEQ ID NO:16, and SEQ ID NO:17, respectively, and conservative amino acid substitutions thereof, and light chain CDR1, CDR2 and CDR3 domains having the sequences set forth in SEQ ID NO:18, SEQ ID NO:19, and SEQ ID NO:20, respectively, and conservative amino acid substitutions thereof.

In an embodiment, the 4-1BB agonist is a 4-1BB agonist biosimilar monoclonal antibody approved by drug regulatory authorities with reference to utomilumab. In an embodiment, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is utomilumab. In some embodiments, the one or more post-translational modifications are selected from one or more of: glycosylation, oxidation, deamidation, and truncation. In some embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is utomilumab. The 4-1BB agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab.

TABLE 4

Amino acid sequences for 4-1BB agonist antibodies related to utomilumab.

| Identifier | Sequence (One-Letter Amino Acid Symbols) | | | | | |
|---|---|---|---|---|---|---|
| SEQ ID NO: 11 heavy chain for utomilumab | EVQLVQSGAE | VKKPGESLRI | SCKGSGYSFS | TYWISWVRQM | PGKGLEWMGK | IYPGDSYTNY | 60 |
| | SPSFQGQVTI | SADKSISTAY | LQWSSLKASD | TAMYYCARGY | GIFDYWGQGT | LVTVSSASTK | 120 |
| | GPSVFPLAPC | SRSTSESTAA | LGCLVKDYFP | EPVTVSWNSG | ALTSGVHTFP | AVLQSSGLYS | 180 |
| | LSSVVTVPSS | NFGTQTYTCN | VDHKPSNTKV | DKTVERKCCV | ECPPCPAPPV | AGPSVFLFPP | 240 |
| | KPKDTLMISR | TPEVTCVVVD | VSHEDPEVQF | NWYVDGVEVH | NAKTKPREEQ | FNSTFRVVSV | 300 |

TABLE 4-continued

Amino acid sequences for 4-1BB agonist antibodies related to utomilumab.

| Identifier | Sequence (One-Letter Amino Acid Symbols) | |
|---|---|---|
| | LTVVHQDWLN GKEYKCKVSN KGLPAPIEKT ISKTKGQPRE PQVYTLPPSR EEMTKNQVSL | 360 |
| | TCLVKGFYPS DIAVEWESNG QPENNYKTTP PMLDSDGSFF LYSKLTVDKS RWQQGNVFSC | 420 |
| | SVMHEALHNH YTQKSLSLSP G | 441 |
| SEQ ID NO: 12 light chain for utomilumab | SYELTQPPSV SVSPGQTASI TCSGDNIGDQ YAHWYQQKPG QSPVLVIYQD KNRPSGIPER | 60 |
| | FSGSNSGNTA TLTISGTQAM DEADYYCATY TGFGSLAVFG GGTKLTVLGQ PKAAPSVTLF | 120 |
| | PPSSEELQAN KATLVCLISD FYPGAVTVAW KADSSPVKAG VETTTPSKQS NNKYAASSYL | 180 |
| | SLTPEQWKSH RSYSCQVTHE GSTVEKTVAP TECS | 214 |
| SEQ ID NO: 13 heavy chain variable region for utomilumab | EVQLVQSGAE VKKPGESLRI SCKGSGYSFS TYWISWVRQM PGKGLEWMG KIYPGDSYTN | 60 |
| | YSPSFQGQVT ISADKSISTA YLQWSSLKAS DTAMYYCARG YGIFDYWGQ GTLVTVSS | 118 |
| SEQ ID NO: 14 light chain variable region for utomilumab | SYELTQPPSV SVSPGQTASI TCSGDNIGDQ YAHWYQQKPG QSPVLVIYQD KNRPSGIPER | 60 |
| | FSGSNSGNTA TLTISGTQAM DEADYYCATY TGFGSLAVFG GGTKLTVL | 108 |
| SEQ ID NO: 15 heavy chain CDR1 for utomilumab | STYWIS | 6 |
| SEQ ID NO: 16 heavy chain CDR2 for utomilumab | KIYPGDSYTN YSPSFQG | 17 |
| SEQ ID NO: 17 heavy chain CDR3 for utomilumab | RGYGIFDY | 8 |
| SEQ ID NO: 18 light chain CDR1 for utomilumab | SGDNIGDQYA H | 11 |
| SEQ ID NO: 19 light chain CDR2 for utomilumab | QDKNRPS | 7 |
| SEQ ID NO: 20 light chain CDR3 for utomilumab | ATYTGFGSLA V | 11 |

In a preferred embodiment, the 4-1BB agonist is the monoclonal antibody urelumab, also known as BMS-663513 and 20H4.9.h4a, or a fragment, derivative, variant, or biosimilar thereof. Urelumab is available from Bristol-Myers Squibb, Inc., and Creative Biolabs, Inc. Urelumab is an immunoglobulin G4-kappa, anti-[*Homo sapiens* TNFRSF9 (tumor necrosis factor receptor superfamily member 9, 4-1BB, T cell antigen ILA, CD137)], *Homo sapiens* (fully human) monoclonal antibody. The amino acid sequences of urelumab are set forth in Table 5. Urelumab comprises N-glycosylation sites at positions 298 (and 298″); heavy chain intrachain disulfide bridges at positions 22-95 ($V_H$-$V_L$), 148-204 ($C_H$1-$C_L$), 262-322 ($C_H$2) and 368-426 ($C_H$3) (and at positions 22″-95″, 148″-204″, 262″-322″, and 368″-426″); light chain intrachain disulfide bridges at positions 23′-88′ $V_H$-$V_L$) and 136′-196′ ($C_H$1-$C_L$) (and at positions 23′″-88′″ and 136′″-196′″); interchain heavy chain-heavy chain disulfide bridges at positions 227-227″ and 230-230″; and interchain heavy chain-light chain disulfide bridges at 135-216′ and 135″-216′″. The preparation and properties of urelumab and its variants and fragments are described in U.S. Pat. Nos. 7,288,638 and 8,962,804, the disclosures of which are incorporated by reference herein. The preclinical and clinical characteristics of urelumab are described in Segal, et al., *Clin. Cancer Res.*, 2016, available at http://dx.doi.org/10.1158/1078-0432.CCR-16-1272. Current clinical trials of urelumab in a variety of hematological and solid tumor indications include U.S. National Institutes of Health clinicaltrials.gov identifiers NCT01775631, NCT02110082, NCT02253992, and NCT01471210.

In an embodiment, a 4-1BB agonist comprises a heavy chain given by SEQ ID NO:21 and a light chain given by SEQ ID NO:22. In an embodiment, a 4-1BB agonist comprises heavy and light chains having the sequences shown in SEQ ID NO:21 and SEQ ID NO:22, respectively, or antigen binding fragments, Fab fragments, single-chain variable fragments (scFv), variants, or conjugates thereof. In an embodiment, a 4-1BB agonist comprises heavy and light chains that are each at least 99% identical to the sequences shown in SEQ ID NO:21 and SEQ ID NO:22, respectively. In an embodiment, a 4-1BB agonist comprises heavy and light chains that are each at least 98% identical to the sequences shown in SEQ ID NO:21 and SEQ ID NO:22, respectively. In an embodiment, a 4-1BB agonist comprises heavy and light chains that are each at least 97% identical to the sequences shown in SEQ ID NO:21 and SEQ ID NO:22, respectively. In an embodiment, a 4-1BB agonist comprises heavy and light chains that are each at least 96% identical to the sequences shown in SEQ ID NO:21 and SEQ ID NO:22, respectively. In an embodiment, a 4-1BB agonist comprises heavy and light chains that are each at least 95% identical to the sequences shown in SEQ ID NO:21 and SEQ ID NO:22, respectively.

In an embodiment, the 4-1BB agonist comprises the heavy and light chain CDRs or variable regions (VRs) of urelumab. In an embodiment, the 4-1BB agonist heavy chain variable region ($V_H$) comprises the sequence shown in SEQ ID NO:23, and the 4-1BB agonist light chain variable region ($V_L$) comprises the sequence shown in SEQ ID NO:24, and conservative amino acid substitutions thereof. In an embodiment, a 4-1 in agonist comprises $V_H$ and $V_L$ regions that are each at least 99% identical to the sequences shown in SEQ ID NO:23 and SEQ ID NO:24, respectively. In an embodiment, a 4-1BB agonist comprises $V_H$ and $V_L$ regions that are each at least 98% identical to the sequences shown in SEQ ID NO:23 and SEQ ID NO:24, respectively. In an embodiment, a 4-1BB agonist comprises $V_H$ and $V_L$ regions that are each at least 97% identical to the sequences shown in SEQ ID NO:23 and SEQ ID NO:24, respectively. In an embodiment, a 4-1BB agonist comprises $V_H$ and $V_L$ regions that are each at least 96% identical to the sequences shown in SEQ ID NO:23 and SEQ ID NO:24, respectively. In an embodiment, a 4-1BB agonist comprises $V_H$ and $V_L$ regions that are each at least 95% identical to the sequences shown in SEQ ID NO:23 and SEQ ID NO:24, respectively. In an embodiment, a 4-1BB agonist comprises an scFv antibody comprising $V_H$ and $V_L$ regions that are each at least 99% identical to the sequences shown in SEQ ID NO:23 and SEQ ID NO:24.

In an embodiment, a 4-1 in agonist comprises heavy chain CDR1, CDR2 and CDR3 domains having the sequences set forth in SEQ ID NO:25, SEQ ID NO:26, and SEQ ID NO:27, respectively, and conservative amino acid substitutions thereof, and light chain CDR1, CDR2 and CDR3 domains having the sequences set forth in SEQ ID NO:28, SEQ ID NO:29, and SEQ ID NO:30, respectively, and conservative amino acid substitutions thereof.

In an embodiment, the 4-1 in agonist is a 4-1 in agonist biosimilar monoclonal antibody approved by drug regulatory authorities with reference to urelumab. In an embodiment, the biosimilar monoclonal antibody comprises an 4-1 in antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is urelumab. In some embodiments, the one or more post-translational modifications are selected from one or more of: glycosylation, oxidation, deamidation, and truncation. In some embodiments, the biosimilar is a 4-1 in agonist antibody authorized or submitted for authorization, wherein the 4-1 in agonist antibody is provided in a formulation which differs from the formulations of a reference medicinal product or reference biological product, wherein the reference medicinal product or reference biological product is urelumab. The 4-1 in agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab.

TABLE 5

Amino acid sequences for 4-1BB agonist antibodies related to urelumab.

| Identifier | Sequence (One-Letter Amino Acid Symbols) | | | | | |
|---|---|---|---|---|---|---|
| SEQ ID NO: 21 heavy chain for urelumab | QVQLQQWGAG | LLKPSETLSL | TCAVYGGSFS | GYYWSWIRQS | PEKGLEWIGE | INHGGYVTYN | 60 |
| | PSLESRVTIS | VDTSKNQFSL | KLSSVTAADT | AVYYCARDYG | PGNYDWYFDL | WGRGTLVTVS | 120 |
| | SASTKGPSVF | PLAPCSRSTS | ESTAALGCLV | KDYFPEPVTV | SWNSGALTSG | VHTFPAVLQS | 180 |
| | SGLYSLSSVV | TVPSSSLGTK | TYTCNVDHKP | SNTKVDKRVE | SKYGPPCPPC | PAPEFLGGPS | 240 |
| | VFLFPPKPKD | TLMISRTPEV | TCVVVDVSQE | DPEVQFNWYV | DGVEVHNAKT | KPREEQFNST | 300 |
| | YRVVSVLTVL | HQDWLNGKEY | KCKVSNKGLP | SSIEKTISKA | KGQPREPQVY | TLPPSQEEMT | 360 |
| | KNQVSLTCLV | KGFYPSDIAV | EWESNGQPEN | NYKTTPPVLD | SDGSFFLYSR | LTVDKSRWQE | 420 |
| | GNVFSCSVMH | EALHNHYTQK | SLSLSLGK | | | | 448 |
| SEQ ID NO: 22 light chain for urelumab | EIVLTQSPAT | LSLSPGERAT | LSCRASQSVS | SYLAWYQQKP | GQAPRLLIYD | ASNRATGIPA | 60 |
| | RFSGSGSGTD | FTLTISSLEP | EDFAVYYCQQ | RSNWPPALTF | CGGTKVEIKR | TVAAPSVFIF | 120 |
| | PPSDEQLKSG | TASVVCLLNN | FYPREAKVQW | KVDNALQSGN | SQESVTEQDS | KDSTYSLSST | 180 |
| | LTLSKADYEK | HKVYACEVTH | QGLSSPVTKS | FNRGEC | | | 216 |
| SEQ ID NO: 23 variable heavy chain for urelumab | MKHLWFFLLL | VAAPRWVLSQ | VQLQQWGAGL | LKPSETLSLT | CAVYGGSFSG | YYWSWIRQSP | 60 |
| | EKGLEWIGEI | NHGGYVTYNP | SLESRVTISV | DTSKNQFSLK | LSSVTAADTA | VYYCARDYGP | 120 |
| SEQ ID NO: 24 variable light chain for urelumab | MEAPAQLLFL | LLLWLPDTTG | EIVLTQSPAT | LSLSPGERAT | LSCRASQSVS | SYLAWYQQKP | 60 |
| | GQAPRLLIYD | ASNRATGIPA | RFSGSGSGTD | FTLTISSLEP | EDFAVYYCQQ | | 110 |

TABLE 5-continued

Amino acid sequences for 4-1BB agonist antibodies related to urelumab.

| Identifier | Sequence (One-Letter Amino Acid Symbols) | |
|---|---|---|
| SEQ ID NO: 25<br>heavy chain CDR1<br>for urelumab | GYYWS | 5 |
| SEQ ID NO: 26<br>heavy chain CDR2<br>for urelumab | EINHGGYVTY NPSLES | 16 |
| SEQ ID NO: 27<br>heavy chain CDR3<br>for urelumab | DYGPGNYDWY FDL | 13 |
| SEQ ID NO: 28<br>light chain CDR1<br>for urelumab | RASQSVSSYL A | 11 |
| SEQ ID NO: 29<br>light chain CDR2<br>for urelumab | DASNRAT | 7 |
| SEQ ID NO: 30<br>light chain CDR3<br>for urelumab | QQRSDWPPAL T | 11 |

In an embodiment, the 4-1BB agonist is selected from the group consisting of 1D8, 3Elor, 4B4 (BioLegend 309809), H4-1BB-M127 (BD Pharmingen 552532), BBK2 (Thermo Fisher MS621PABX), 145501 (Leinco Technologies B591), the antibody produced by cell line deposited as ATCC No. HB-11248 and disclosed in U.S. Pat. No. 6,974,863, 5F4 (BioLegend 31 1503), C65-485 (BD Pharmingen 559446), antibodies disclosed in U.S. Patent Application Publication No. US 2005/0095244, antibodies disclosed in U.S. Pat. No. 7,288,638 (such as 20H4.9-IgGl (BMS-663031)), antibodies disclosed in U.S. Pat. No. 6,887,673 (such as 4E9 or BMS-554271), antibodies disclosed in U.S. Pat. No. 7,214,493, antibodies disclosed in U.S. Pat. No. 6,303,121, antibodies disclosed in U.S. Pat. No. 6,569,997, antibodies disclosed in U.S. Pat. No. 6,905,685 (such as 4E9 or BMS-554271), antibodies disclosed in U.S. Pat. No. 6,362,325 (such as 1D8 or BMS-469492; 3H3 or BMS-469497; or 3E1), antibodies disclosed in U.S. Pat. No. 6,974,863 (such as 53A2); antibodies disclosed in U.S. Pat. No. 6,210,669 (such as 1D8, 3B8, or 3E1), antibodies described in U.S. Pat. No. 5,928,893, antibodies disclosed in U.S. Pat. No. 6,303,121, antibodies disclosed in U.S. Pat. No. 6,569,997, antibodies disclosed in International Patent Application Publication Nos. WO 2012/177788, WO 2015/119923, and WO 2010/042433, and fragments, derivatives, conjugates, variants, or biosimilars thereof, wherein the disclosure of each of the foregoing patents or patent application publications is incorporated by reference here.

In an embodiment, the 4-1BB agonist is a 4-1BB agonistic fusion protein described in International Patent Application Publication Nos. WO 2008/025516 A1, WO 2009/007120 A1, WO 2010/003766 A1, WO 2010/010051 A1, and WO 2010/078966 A1; U.S. Patent Application Publication Nos. US 2011/0027218 A1, US 2015/0126709 A1, US 2011/0111494 A1, US 2015/0110734 A1, and US 2015/0126710 A1; and U.S. Pat. Nos. 9,359,420, 9,340,599, 8,921,519, and 8,450,460, the disclosures of which are incorporated by reference herein.

Figure 50:
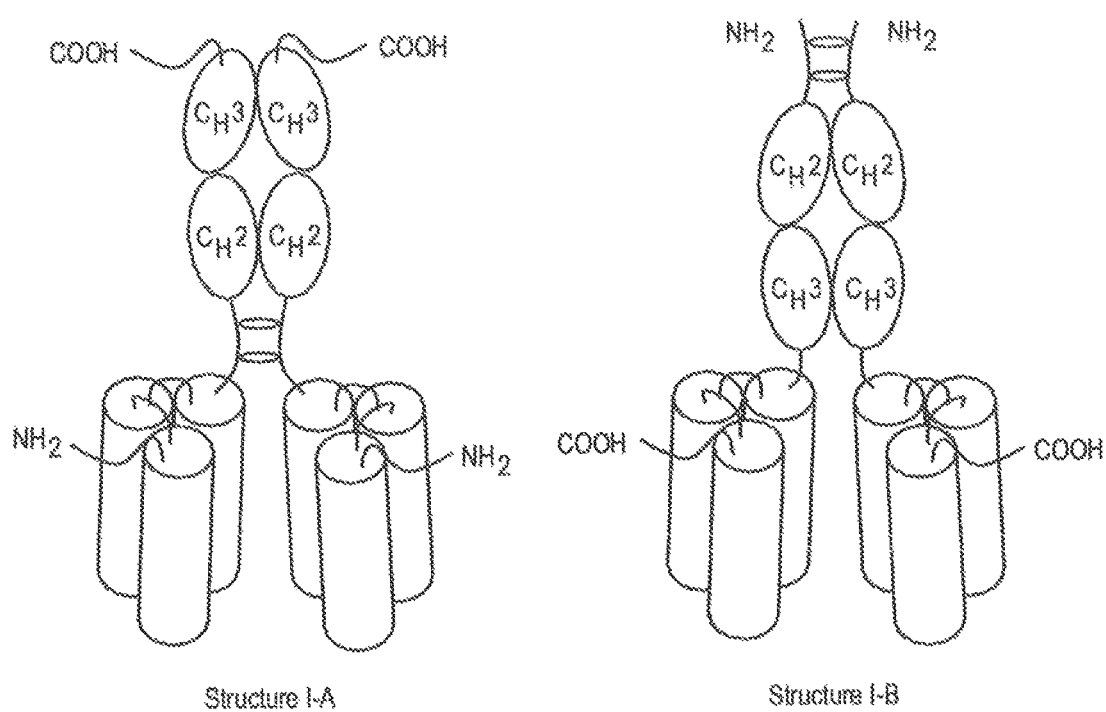
FIG. 50: Schematic illustrates the structures I-A and I-B, the cylinders refer to individual polypeptide binding domains. Structures I-A and I-B comprise three linearly-linked TNFRSF binding domains derived from e.g., 4-1BBL or an antibody that binds 4-1BB, which fold to form a trivalent protein, which is then linked to a second trivalent protein through IgG1-Fc (including $C_H3$ and $C_H2$ domains) is then used to link two of the trivalent proteins together through disulfide bonds (small elongated ovals), stabilizing the structure and providing an agonists capable of bringing together the intracellular signaling domains of the six receptors and signaling proteins to form a signaling complex. The TNFRSF binding domains denoted as cylinders may be scFv domains comprising, e.g., a $V_H$ and a $V_L$ chain connected by a linker that may comprise hydrophilic residues and Gly and Ser sequences for flexibility, as well as Glu and Lys for solubility.

In an embodiment, the 4-1BB agonist is a 4-1BB agonistic fusion protein as depicted in Structure I-A (C-terminal Fc-antibody fragment fusion protein) or Structure I-B (N-terminal Fc-antibody fragment fusion protein) of FIG. 50, or a fragment, derivative, conjugate, variant, or biosimilar thereof. In structures I-A and I-B, the cylinders refer to individual polypeptide binding domains. Structures I-A and I-B comprise three linearly-linked TNFRSF binding domains derived from e.g., 4-1BBL or an antibody that binds 4-1BB, which fold to form a trivalent protein, which is then linked to a second trivalent protein through IgG1-Fc (including $C_H3$ and $C_H2$ domains) is then used to link two of the trivalent proteins together through disulfide bonds (small elongated ovals), stabilizing the structure and providing an agonists capable of bringing together the intracellular signaling domains of the six receptors and signaling proteins to form a signaling complex. The TNFRSF binding domains denoted as cylinders may be scFv domains comprising, e.g., a $V_H$ and a $V_L$ chain connected by a linker that may comprise hydrophilic residues and Gly and Ser sequences for flexibility, as well as Glu and Lys for solubility. Any scFv domain design may be used, such as those described in de Marco, *Microbial Cell Factories*, 2011, 10, 44; Ahmad, et al., *Clin. & Dev. Immunol.*, 2012, 980250; Monnier, et al., *Antibodies*, 2013, 2, 193-208; or in references incorporated elsewhere herein. Fusion protein structures of this form are described in U.S. Pat. Nos. 9,359,420, 9,340,599, 8,921,519, and 8,450,460, the disclosures of which are incorporated by reference herein.

Amino acid sequences for the other polypeptide domains of structure I-A are given in Table 6. The Fc domain preferably comprises a complete constant domain (amino acids 17-230 of SEQ ID NO:31) the complete hinge domain (amino acids 1-16 of SEQ ID NO:31) or a portion of the hinge domain (e.g., amino acids 4-16 of SEQ ID NO:31). Preferred linkers for connecting a C-terminal Fc-antibody may be selected from the embodiments given in SEQ ID NO:32 to SEQ ID NO:41, including linkers suitable for fusion of additional polypeptides.

TABLE 6

Amino acid sequences for TNFRSF fusion proteins, including 4-1BB fusion proteins, with C-terminal Fc-antibody fragment fusion protein design (structure I-A).

| Identifier | Sequence (One-Letter Amino Acid Symbols) | |
|---|---|---|
| SEQ ID NO: 31 Fc domain | KSCDKTHTCP PCPAPELLGG PSVFLFPPKP KDTLMISRTP EVTCVVVDVS HEDPEVKFNW | 60 |
| | YVDGVEVHNA KTKPREEQYN STYRVVSVLT VLHQDWLNGK EYKCKVSNKA LPAPIEKTIS | 120 |
| | KAKGQPREPQ VYTLPPSREE MTKNQVSLTC LVKGFYPSDI AVEWESNGQP ENNYKTTPPV | 180 |
| | LDSDGSFFLY SKLTVDKSRW QQGNVFSCSV MHEALHNHYT QKSLSLSPGK | 230 |
| SEQ ID NO: 32 linker | GGPGSSKSCD KTHTCPPCPA PE | 22 |
| SEQ ID NO: 33 linker | GGSGSSKSCD KTHTCPPCPA PE | 22 |
| SEQ ID NO: 34 linker | GGPGSSSSSS SKSCDKTHTC PPCPAPE | 27 |
| SEQ ID NO: 35 linker | GGSGSSSSSS SKSCDKTHTC PPCPAPE | 27 |
| SEQ ID NO: 36 linker | GGPGSSSSSS SSSKSCDKTH TCPPCPAPE | 29 |
| SEQ ID NO: 37 linker | GGSGSSSSSS SSSKSCDKTH TCPPCPAPE | 29 |
| SEQ ID NO: 38 linker | GGPGSSGSGS SDKTHTCPPC PAPE | 24 |
| SEQ ID NO: 39 linker | GGPGSSGSGS DKTHTCPPCP APE | 23 |
| SEQ ID NO: 40 linker | GGPSSSGSDK THTCPPCPAP E | 21 |
| SEQ ID NO: 41 linker | GGSSSSSSSS GSDKTHTCPP CPAPE | 25 |

Amino acid sequences for the other polypeptide domains of structure I-B are given in Table 7. If an Fc antibody fragment is fused to the N-terminus of an TNRFSF fusion protein as in structure I-B, the sequence of the Fc module is preferably that shown in SEQ ID NO:42, and the linker sequences are preferably selected from those embodiments set forth in SED ID NO:43 to SEQ ID NO:45.

TABLE 7

Amino acid sequences for TNFRSF fusion proteins, including 4-1BB fusion proteins, with N-terminal Fc-antibody fragment fusion protein design (structure I-B).

| Identifier | Sequence (One-Letter Amino Acid Symbols) | |
|---|---|---|
| SEQ ID NO: 42 Fc domain | METDTLLLWV LLLWVPAGNG DKTHTCPPCP APELLGGPSV FLFPPKPKDT LMISRTPEVT | 60 |
| | CVVVDVSHED PEVKFNWYVD GVEVHNAKTK PREEQYNSTY RVVSVLTVLH QDWLNGKEYK | 120 |
| | CKVSNKALPA PIEKTISKAK GQPREPQVYT LPPSREEMTK NQVSLTCLVK GFYPSDIAVE | 180 |
| | WESNGQPENN YKTTPPVLDS DGSFFLYSKL TVDKSRWQQG NVFSCSVMHE ALHNHYTQKS | 240 |
| | LSLSPG | 246 |
| SEQ ID NO: 43 linker | SGSGSGSGSG S | 11 |
| SEQ ID NO: 44 linker | SSSSSSGSGS GS | 12 |
| SEQ ID NO: 45 linker | SSSSSSGSGS GSGSGS | 16 |

In an embodiment, a 4-1BB agonist fusion protein according to structures I-A or I-B comprises one or more 4-1BB binding domains selected from the group consisting of a variable heavy chain and variable light chain of utomilumab, a variable heavy chain and variable light chain of urelumab, a variable heavy chain and variable light chain of utomilumab, a variable heavy chain and variable light chain selected from the variable heavy chains and variable light chains described in Table 4 or Table 5, any combination of a variable heavy chain and variable light chain of the foregoing, and fragments, derivatives, conjugates, variants, and biosimilars thereof.

In an embodiment, a 4-1BB agonist fusion protein according to structures I-A or I-B comprises one or more 4-1BB binding domains comprising a 4-1BBL sequence. In an embodiment, a 4-1BB agonist fusion protein according to one or more 4-1BB binding domains that is a scFv domain comprising $V_H$ and $V_L$ regions that are each at least 95% identical to the $V_H$ and $V_L$ sequences given in Table 8, wherein the $V_H$ and $V_L$ domains are connected by a linker.

TABLE 8

Additional polypeptide domains useful as 4-1BB binding domains in fusion proteins or as scFv 4-1BB agonist antibodies.

| Identifier | Sequence (One-Letter Amino Acid Symbols) |
|---|---|
| SEQ ID NO:46<br>4-1BBL | MEYASDASLD PEAPWPPAPR ARACRVLPWA LVAGLLLLLL LAAACAVFLA CPWAVSGARA 60<br>SPGSAASPRL REGPELSPDD PAGLLDLRQG MFAQLVAQNV LLIDGPLSWY SDPGLAGVSL 120<br>TGGLSYKEDT KELVVAKAGV YYVFFQLELR RVVAGEGSGS VSLALHLQPL RSAAGAAALA 180<br>LTVDLPPASS EARNSAFGFQ GRLLHLSAGQ RLGVHLHTEA RARHAWQLTQ GATVLGLFRV 240<br>TPEIPAGLPS PRSE 254 |
| SEQ ID NO: 47<br>4-1BBL soluble<br>domain | LRQGMFAQLV AQNVLLIDGP LSWYSDPGLA GVSLTGGLSY KEDTKELVVA KAGVYYVFFQ 60<br>LELRRVVAGE GSGSVSLALH LQPLRSAAGA AALALTVDLP PASSEARNSA FGFQGRLLHL 120<br>SAGQRLGVHL HTEARARHAW QLTQGATVLG LFRVTPEIPA GLPSPRSE 168 |
| SEQ ID NO: 48<br>variable heavy<br>chain for 4B4-1-<br>1 version 1 | QVQLQQPGAE LVKPGASVKL SCKASGYTFS SYWMHWVKQR PGQVLEWIGE INPGNGHTNY 60<br>NEKFKSKATL TVDKSSSTAY MQLSSLTSED SAVYYCARSF TTARGFAYWG QGTLVTVS 118 |
| SEQ ID NO: 49<br>variable light<br>chain for 4B4-1-<br>1 version 1 | DIVMTQSPAT QSVTPGDRVS LSCRASQTIS DYLHWYQQKS HESPRLLIKY ASQSISGIPS 60<br>RFSGSGSGSD FTLSINSVEP EDVGVYYCQD GHSFPPTFGG GTKLEIK 107 |
| SEQ ID NO: 50<br>variable heavy<br>chain for 4B4-1-<br>1 version 2 | QVQLQQPGAE LVKPGASVKL SCKASGYTFS SYWMHWVKQR PGQVLEWIGE INPGNGHTNY 60<br>NEKFKSKATL TVDKSSSTAY MQLSSLTSED SAVYYCARSF TTARGFAYWG QGTLVTVSA 119 |
| SEQ ID NO: 51<br>variable light<br>chain for 4B4-1-<br>1 version 2 | DIVMTQSPAT QSVTPGDRVS LSCRASQTIS DYLHWYQQKS HESPRLLIKY ASQSISGIPS 60<br>RFSGSGSGSD FTLSINSVEP EDVGVYYCQD GHSFPPTFGG GTKLEIKR 108 |
| SEQ ID NO: 52<br>variable heavy<br>chain for H39E3-<br>2 | MDWTWRILFL VAAATGAHSE VQLVESGGGL VQPGGSLRLS CAASGFTFSD YWMSWVRQAP 60<br>GKGLEWVADI KNDGSYTNYA PSLTNRFTIS RDNAKNSLYL QMNSLRAEDT AVYYCARELT 120 |
| SEQ ID NO: 53<br>variable light<br>chain for H39E3-<br>2 | MEAPAQLLFL LLLWLPDTTG DIVMTQSPDS LAVSLGERAT INCKSSQSLL SSGNQKNYL 60<br>WYQQKPGQPP KLLIYYASTR QSGVPDRFSG SGSGTDFTLT ISSLQAEDVA 110 | structures I-A or I-B comprises one or more 4-1BB binding domains comprising a sequence according to SEQ ID NO:46. In an embodiment, a 4-1BB agonist fusion protein according to structures I-A or I-B comprises one or more 4-1BB binding domains comprising a soluble 4-1BBL sequence. In an embodiment, a 4-1BB agonist fusion protein according to structures I-A or I-B comprises one or more 4-1BB binding domains comprising a sequence according to SEQ ID NO:47.

In an embodiment, a 4-1BB agonist fusion protein according to structures I-A or I-B comprises one or more 4-1BB binding domains that is a scFv domain comprising $V_H$ and $V_L$ regions that are each at least 95% identical to the sequences shown in SEQ ID NO:13 and SEQ ID NO:14, respectively, wherein the $V_H$ and $V_L$ domains are connected by a linker. In an embodiment, a 4-1BB agonist fusion protein according to structures I-A or I-B comprises one or more 4-1BB binding domains that is a scFv domain comprising $V_H$ and $V_L$ regions that are each at least 95% identical to the sequences shown in SEQ ID NO:23 and SEQ ID NO:24, respectively, wherein the $V_H$ and $V_L$ domains are connected by a linker. In an embodiment, a 4-1BB agonist fusion protein according to structures I-A or I-B comprises In an embodiment, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, and wherein the additional domain is a Fab or Fc fragment domain. In an embodiment, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, wherein the additional domain is a Fab or Fc fragment domain, wherein each of the soluble 4-1BB domains lacks a stalk region (which contributes to trimerisation and provides a certain distance to the cell membrane, but is not part of the 4-1BB binding domain) and the first and the second peptide linkers independently have a length of 3-8 amino acids.

In an embodiment, the 4-1BB agonist is a 4-1BB agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein each TNF superfamily cytokine domain is a 4-1BB binding domain.

In an embodiment, the 4-1BB agonist is a 4-1BB agonistic scFv antibody comprising any of the foregoing $V_H$ domains linked to any of the foregoing $V_L$ domains.

In an embodiment, the 4-1BB agonist is BPS Bioscience 4-1BB agonist antibody catalog no. 79097-2, commercially available from BPS Bioscience, San Diego, CA, USA. In an embodiment, the 4-1BB agonist is Creative Biolabs 4-1BB agonist antibody catalog no. MOM-18179, commercially available from Creative Biolabs, Shirley, NY, USA.

OX40 (CD134) Agonists as Optional Media Components

In an embodiment, the TNFRSF agonist is an OX40 (CD134) agonist. The OX40 agonist may be any OX40 binding molecule known in the art. The OX40 binding molecule may be a monoclonal antibody or fusion protein capable of binding to human or mammalian OX40. The OX40 agonists or OX40 binding molecules may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. The OX40 agonist or OX40 binding molecule may have both a heavy and a light chain. As used herein, the term binding molecule also includes antibodies (including full length antibodies), monoclonal antibodies (including full length monoclonal antibodies), polyclonal antibodies, multispecific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to OX40. In an embodiment, the OX40 agonist is an antigen binding protein that is a fully human antibody. In an embodiment, the OX40 agonist is an antigen binding protein that is a humanized antibody. In some embodiments, OX40 agonists for use in the presently disclosed methods and compositions include anti-OX40 antibodies, human anti-OX40 antibodies, mouse anti-OX40 antibodies, mammalian anti-OX40 antibodies, monoclonal anti-OX40 antibodies, polyclonal anti-OX40 antibodies, chimeric anti-OX40 antibodies, anti-OX40 adnectins, anti-OX40 domain antibodies, single chain anti-OX40 fragments, heavy chain anti-OX40 fragments, light chain anti-OX40 fragments, anti-OX40 fusion proteins, and fragments, derivatives, conjugates, variants, or biosimilars thereof. In a preferred embodiment, the OX40 agonist is an agonistic, anti-OX40 humanized or fully human monoclonal antibody (i.e., an antibody derived from a single cell line).

In a preferred embodiment, the OX40 agonist or OX40 binding molecule may also be a fusion protein. OX40 fusion proteins comprising an Fc domain fused to OX40L are described, for example, in Sadun, et al., *J. Immunother.*, 2009, 182, 1481-89. In a preferred embodiment, a multimeric OX40 agonist, such as a trimeric or hexameric OX40 agonist (with three or six ligand binding domains), may induce superior receptor (OX40L) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG1-Fc and optionally further linking two or more of these fusion proteins are described, for example, in Gieffers, et al., *Mol. Cancer Therapeutics*, 2013, 12, 2735-47.

Agonistic OX40 antibodies and fusion proteins are known to induce strong immune responses. Curti, et al., *Cancer Res.*, 2013, 73, 7189-98. In a preferred embodiment, the OX40 agonist is a monoclonal antibody or fusion protein that binds specifically to OX40 antigen in a manner sufficient to reduce toxicity. In some embodiments, the OX40 agonist is an agonistic OX40 monoclonal antibody or fusion protein that abrogates antibody-dependent cellular toxicity (ADCC), for example NK cell cytotoxicity. In some embodiments, the OX40 agonist is an agonistic OX40 monoclonal antibody or fusion protein that abrogates antibody-dependent cell phagocytosis (ADCP). In some embodiments, the OX40 agonist is an agonistic OX40 monoclonal antibody or fusion protein that abrogates complement-dependent cytotoxicity (CDC). In some embodiments, the OX40 agonist is an agonistic OX40 monoclonal antibody or fusion protein which abrogates Fc region functionality.

In some embodiments, the OX40 agonists are characterized by binding to human OX40 (SEQ ID NO:54) with high affinity and agonistic activity. In an embodiment, the OX40 agonist is a binding molecule that binds to human OX40 (SEQ ID NO:54). In an embodiment, the OX40 agonist is a binding molecule that binds to murine OX40 (SEQ ID NO:55). The amino acid sequences of OX40 antigen to which an OX40 agonist or binding molecule binds are summarized in Table 9.

TABLE 9

Amino acid sequences of OX40 antigens.

| Identifier | Sequence (One-Letter Amino Acid Symbols) | | | | | |
|---|---|---|---|---|---|---|
| SEQ ID NO: 54 human OX40 (Homo sapiens) | MCVGARRLGR | GPCAALLLLG | LGLSTVTGLH | CVGDTYPSND | RCCHECRPGN | GMVSRCSRSQ 60 |
| | NTVCRPCGPG | FYNDVVSSKP | CKPCTWCNLR | SGSERKQLCT | ATQDTVCRCR | AGTQPLDSYK 120 |
| | PGVDCAPCPP | GHFSPGDNQA | CKPWTNCTLA | GKHTLQPASN | SSDAICEDRD | PPATQPQETQ 180 |
| | GPPARPITVQ | PTEAWPRTSQ | GPSTRPVEVP | GGRAVAAILG | LGLVLGLLGP | LAILLALYLL 240 |
| | RRDQRLPPDA | HKPPGGGSFR | TPIQEEQADA | HSTLAKI | | 277 |
| SEQ ID NO: 55 murine OX40 (Mus musculus) | MYVWVQQPTA | LLLLGLTLGV | TARRLNCVKH | TYPSGHKCCR | ECQPGHGMVS | RCDHTRDTLC 60 |
| | HPCETGFYNE | AVNYDTCKQC | TQCNHRSGSE | LKQNCTPTQD | TVCRCRPGTQ | PRQDSGYKLG 120 |
| | VDCVPCPPGH | FSPGNNQACK | PWTNCTLSGK | QTRHPASDSL | DAVCEDRSLL | ATLLWETQRP 180 |
| | TFRPTTVQST | TVWPRTSELP | SPPTLVTPEG | PAFAVLLGLG | LGLLAPLTVL | LALYLLRKAW 240 |
| | RLPNTPKPCW | GNSFRTPIQE | EHTDAHFTLA | KI | | 272 |

In some embodiments, the compositions, processes and methods described include a OX40 agonist that binds human or murine OX40 with a KD of about 100 pM or lower, binds human or murine OX40 with a $K_D$ of about 90 pM or lower, binds human or murine OX40 with a KD of about 80 pM or lower, binds human or murine OX40 with a $K_D$ of about 70 pM or lower, binds human or murine OX40 with a $K_D$ of about 60 pM or lower, binds human or murine OX40 with a $K_D$ of about 50 pM or lower, binds human or murine OX40 with a $K_D$ of about 40 pM or lower, or binds human or murine OX40 with a $K_D$ of about 30 pM or lower.

In some embodiments, the compositions, processes and methods described include a OX40 agonist that binds to human or murine OX40 with a $k_{assoc}$ of about $7.5 \times 10^5$ 1/M·s or faster, binds to human or murine OX40 with a $k_{assoc}$ of about $7.5 \times 10^5$ 1/M·s or faster, binds to human or murine OX40 with a $k_{assoc}$ of about $8 \times 10^5$ 1/M·s or faster, binds to human or murine OX40 with a $k_{assoc}$ of about $8.5 \times 10^5$ 1/M·s or faster, binds to human or murine OX40 with a $k_{assoc}$ of about $9 \times 10^5$ 1/M·s or faster, binds to human or murine OX40 with a $k_{assoc}$ of about $9.5 \times 10^5$ 1/M·s or faster, or binds to human or murine OX40 with a $k_{assoc}$ of about $1 \times 10^6$ 1/M·s or faster.

In some embodiments, the compositions, processes and methods described include a OX40 agonist that binds to human or murine OX40 with a $k_{dissoc}$ of about $2 \times 10^{-5}$ 1/s or slower, binds to human or murine OX40 with a $k_{dissoc}$ of about $2.1 \times 10^{-5}$ 1/s or slower, binds to human or murine OX40 with a $k_{dissoc}$ of about $2.2 \times 10^{-5}$ 1/s or slower, binds to human or murine OX40 with a $k_{dissoc}$ of about $2.3 \times 10^{-5}$ 1/s or slower, binds to human or murine OX40 with a $k_{dissoc}$ of about $2.4 \times 10^{-5}$ 1/s or slower, binds to human or murine OX40 with a $k_{dissoc}$ of about $2.5 \times 10^{-5}$ 1/s or slower, binds to human or murine OX40 with a $k_{dissoc}$ of about $2.6 \times 10^{-5}$ 1/s or slower or binds to human or murine OX40 with a $k_{dissoc}$ of about $2.7 \times 10^{-5}$ 1/s or slower, binds to human or murine OX40 with a $k_{dissoc}$ of about $2.8 \times 10^{-5}$ 1/s or slower, binds to human or murine OX40 with a $k_{dissoc}$ of about $2.9 \times 10^{-5}$ 1/s or slower, or binds to human or murine OX40 with a $k_{dissoc}$ of about $3 \times 10^{-5}$ 1/s or slower.

In some embodiments, the compositions, processes and methods described include OX40 agonist that binds to human or murine OX40 with an $IC_{50}$ of about 10 nM or lower, binds to human or murine OX40 with an $IC_{50}$ of about 9 nM or lower, binds to human or murine OX40 with an $IC_{50}$ of about 8 nM or lower, binds to human or murine OX40 with an $IC_{50}$ of about 7 nM or lower, binds to human or murine OX40 with an $IC_{50}$ of about 6 nM or lower, binds to human or murine OX40 with an $IC_{50}$ of about 5 nM or lower, binds to human or murine OX40 with an $IC_{50}$ of about 4 nM or lower, binds to human or murine OX40 with an $IC_{50}$ of about 3 nM or lower, binds to human or murine OX40 with an $IC_{50}$ of about 2 nM or lower, or binds to human or murine OX40 with an $IC_{50}$ of about 1 nM or lower.

In some embodiments, the OX40 agonist is tavolixizumab, also known as MEDI0562 or MEDI-0562. Tavolixizumab is available from the MedImmune subsidiary of AstraZeneca, Inc. Tavolixizumab is immunoglobulin G1-kappa, anti-[*Homo sapiens* TNFRSF4 (tumor necrosis factor receptor (TNFR) superfamily member 4, OX40, CD134)], humanized and chimeric monoclonal antibody. The amino acid sequences of tavolixizumab are set forth in Table 10. Tavolixizumab comprises N-glycosylation sites at positions 301 and 301", with fucosylated complex bi-antennary CHO-type glycans; heavy chain intrachain disulfide bridges at positions 22-95 ($V_H$-$V_L$), 148-204 ($C_H$1-$C_L$), 265-325 ($C_H$2) and 371-429 ($C_H$3) (and at positions 22"-95", 148"-204", 265"-325", and 371"-429"); light chain intrachain disulfide bridges at positions 23'-88' ($V_H$-$V_L$) and 134'-194' ($C_H$1-$C_L$) (and at positions 23'''-88''' and 134'''-194'''); interchain heavy chain-heavy chain disulfide bridges at positions 230-230" and 233-233"; and interchain heavy chain-light chain disulfide bridges at 224-214' and 224"-214'''. Current clinical trials of tavolixizumab in a variety of solid tumor indications include U.S. National Institutes of Health clinicaltrials.gov identifiers NCT02318394 and NCT02705482.

In an embodiment, a OX40 agonist comprises a heavy chain given by SEQ ID NO:56 and a light chain given by SEQ ID NO:57. In an embodiment, a OX40 agonist comprises heavy and light chains having the sequences shown in SEQ ID NO:56 and SEQ ID NO:57, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:56 and SEQ ID NO:57, respectively. In an embodiment, a OX40 agonist comprises heavy and light chains that are each at least 98% identical to the sequences shown in SEQ ID NO:56 and SEQ ID NO:57, respectively. In an embodiment, a OX40 agonist comprises heavy and light chains that are each at least 97% identical to the sequences shown in SEQ ID NO:56 and SEQ ID NO:57, respectively. In an embodiment, a OX40 agonist comprises heavy and light chains that are each at least 96% identical to the sequences shown in SEQ ID NO:56 and SEQ ID NO:57, respectively. In an embodiment, a OX40 agonist comprises heavy and light chains that are each at least 95% identical to the sequences shown in SEQ ID NO:56 and SEQ ID NO:57, respectively.

In an embodiment, the OX40 agonist comprises the heavy and light chain CDRs or variable regions (VRs) of tavolixizumab. In an embodiment, the OX40 agonist heavy chain variable region ($V_H$) comprises the sequence shown in SEQ ID NO:58, and the OX40 agonist light chain variable region ($V_L$) comprises the sequence shown in SEQ ID NO:59, and conservative amino acid substitutions thereof. In an embodiment, a OX40 agonist comprises $V_H$ and $V_L$ regions that are each at least 99% identical to the sequences shown in SEQ ID NO:58 and SEQ ID NO:59, respectively. In an embodiment, a OX40 agonist comprises $V_H$ and $V_L$ regions that are each at least 98% identical to the sequences shown in SEQ ID NO:58 and SEQ ID NO:59, respectively. In an embodiment, a OX40 agonist comprises $V_H$ and $V_L$ regions that are each at least 97% identical to the sequences shown in SEQ ID NO:58 and SEQ ID NO:59, respectively. In an embodiment, a OX40 agonist comprises $V_H$ and $V_L$ regions that are each at least 96% identical to the sequences shown in SEQ ID NO:58 and SEQ ID NO:59, respectively. In an embodiment, a OX40 agonist comprises $V_H$ and $V_L$ regions that are each at least 95% identical to the sequences shown in SEQ ID NO:58 and SEQ ID NO:59, respectively. In an embodiment, an OX40 agonist comprises an scFv antibody comprising $V_H$ and $V_L$ regions that are each at least 99% identical to the sequences shown in SEQ ID NO:58 and SEQ ID NO:59.

In an embodiment, a OX40 agonist comprises heavy chain CDR1, CDR2 and CDR3 domains having the sequences set forth in SEQ ID NO:60, SEQ ID NO:61, and SEQ ID NO:62, respectively, and conservative amino acid substitutions thereof, and light chain CDR1, CDR2 and CDR3 domains having the sequences set forth in SEQ ID NO:63, SEQ ID NO:64, and SEQ ID NO:65, respectively, and conservative amino acid substitutions thereof.

In an embodiment, the OX40 agonist is a OX40 agonist biosimilar monoclonal antibody approved by drug regula tory authorities with reference to tavolixizumab. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is tavolixizumab. In some embodiments, the one or more post-translational modifications are selected from one or more of: glycosylation, oxidation, deamidation, and truncation. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tavolixizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tavolixizumab.

TABLE 10

Amino acid sequences for OX40 agonist antibodies related to tavolixizumab.

| Identifier | Sequence (One-Letter Amino Acid Symbols) |
|---|---|
| SEQ ID NO:56 heavy chain for tavolixizumab | QVQLQESGPG LVKPSQTLSL TCAVYGGSFS SGYWNWIRKH PGKGLEYIGY ISYNGITYHN 60<br>PSLKSRITIN RDTSKNQYSL QLNSVTPEDT AVYYCARYKY DYDGGHAMDY WGQGTLVTVS 120<br>SASTKGPSVF PLAPSSKSTS GGTAALGCLV KDYFPEPVTV SWNSGALTSG VHTFPAVLQS 180<br>SGLYSLSSVV TVPSSSLGTQ TYICNVNHKP SNTKVDKRVE PKSCDKTHTC PPCPAPELLG 240<br>GPSVFLFPPK PKDTLMISRT PEVTCVVVDV SHEDPEVKFN WYVDGVEVHN AKTKPREEQY 300<br>NSTYRVVSVL TVLHQDWLNG KEYKCKVSNK ALPAPIEKTI SKAKGQPREP QVYTLPPSRE 360<br>EMTKNQVSLT CLVKGFYPSD IAVEWESNGQ PENNYKTTPP VLDSDGSFFL YSKLTVDKSR 420<br>WQQGNVFSCS VMHEALHNHY TQKSLSLSPG K 451 |
| SEQ ID NO: 57 light chain for tavolixizumab | DIQMTQSPSS LSASVGDRVT ITCRASQDIS NYLNWYQQKP GKAPKLLIYY TSKLHSGVPS 60<br>RFSGSGSGTD YTLTISSLQP EDFATYGCQQ GSALPWTFGQ GTKVEIKRTV AAPSVFIFPP 120<br>SDEQLKSGTA SVVCLLNNFY PREAKVQWKV DNALQSGNSQ ESVTEQDSKD STYSLSSTLT 180<br>LSKADYEKHK VYACEVTHQG LSSPVTKSFN RGEC 214 |
| SEQ ID NO: 58 heavy chain variable region for tavolixizumab | QVQLQESGPG LVKPSQTLSL TCAVYGGSFS SGYWNWIRKH PGKGLEYIGY ISYNGITYHN 60<br>PSLKSRITIN RDTSKNQYSL QLNSVTPEDT AVYYCARYKY DYDGGHAMDY WGQGTLVT 118 |
| SEQ ID NO: 59 light chain variable region for tavolixizumab | DIQMTQSPSS LSASVGDRVT ITCRASQDIS NYLNWYQQKP GKAPKLLIYY TSKLHSGVPS 60<br>RFSGSGSGTD YTLTISSLQP EDFATYYCQQ GSALPWTFGQ GTKVEIKR 108 |
| SEQ ID NO: 60 heavy chain CDR1 for tavolixizumab | GSFSSGYWN 9 |
| SEQ ID NO: 61 heavy chain CDR2 for tavolixizumab | YIGYISYNGI TYH 13 |
| SEQ ID NO: 62 heavy chain CDR3 for tavolixizumab | RYKYDYDGGH AMDY 14 |
| SEQ ID NO: 63 light chain CDR1 for tavolixizumab | QDISNYLN 8 |
| SEQ ID NO: 64 light chain CDR2 for tavolixizumab | LLIYYTSKLH S 11 |
| SEQ ID NO: 65 light chain CDR3 for tavolixizumab | QQGSALPW 8 | some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is tavolixizumab. The OX40 agonist antibody may be authorized by a drug regulatory authority such as the U.S. FDA and/or the European Union's EMA. In some embodiments, the In some embodiments, the OX40 agonist is 11D4, which is a fully human antibody available from Pfizer, Inc. The preparation and properties of 11D4 are described in U.S. Pat. Nos. 7,960,515; 8,236,930; and 9,028,824, the disclosures of which are incorporated by reference herein. The amino acid sequences of 11D4 are set forth in Table 11.

In an embodiment, a OX40 agonist comprises a heavy chain given by SEQ ID NO:66 and a light chain given by SEQ ID NO:67. In an embodiment, a OX40 agonist comprises heavy and light chains having the sequences shown in SEQ ID NO:66 and SEQ ID NO:67, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:66 and SEQ ID NO:67, respectively. In an embodiment, a OX40 agonist comprises heavy and light chains that are each at least 98% identical to the sequences shown in SEQ ID NO:66 and SEQ ID NO:67, respectively. In an embodiment, a OX40 agonist comprises heavy and light chains that are each at least 97% identical to the sequences shown in SEQ ID NO:66 and SEQ ID NO:67, respectively. In an embodiment, a OX40 agonist comprises heavy and light chains that are each at least 96% identical to the sequences shown in SEQ ID NO:66 and SEQ ID NO:67, respectively. In an embodiment, a OX40 agonist comprises heavy and light chains that are each at least 95% identical to the sequences shown in SEQ ID NO:66 and SEQ ID NO:67, respectively.

In an embodiment, the OX40 agonist comprises the heavy and light chain CDRs or variable regions (VRs) of 11D4. In an embodiment, the OX40 agonist heavy chain variable region ($V_H$) comprises the sequence shown in SEQ ID NO:68, and the OX40 agonist light chain variable region ($V_L$) comprises the sequence shown in SEQ ID NO:69, and conservative amino acid substitutions thereof. In an embodiment, a OX40 agonist comprises $V_H$ and $V_L$ regions that are each at least 99% identical to the sequences shown in SEQ ID NO:68 and SEQ ID NO:69, respectively. In an embodiment, a OX40 agonist comprises $V_H$ and $V_L$ regions that are each at least 98% identical to the sequences shown in SEQ ID NO:68 and SEQ ID NO:69, respectively. In an embodiment, a OX40 agonist comprises $V_H$ and $V_L$ regions that are each at least 97% identical to the sequences shown in SEQ ID NO:68 and SEQ ID NO:69, respectively. In an embodiment, a OX40 agonist comprises $V_H$ and $V_L$ regions that are each at least 96% identical to the sequences shown in SEQ ID NO:68 and SEQ ID NO:69, respectively. In an embodiment, a OX40 agonist comprises $V_H$ and $V_L$ regions that are each at least 95% identical to the sequences shown in SEQ ID NO:68 and SEQ ID NO:69, respectively.

In an embodiment, a OX40 agonist comprises heavy chain CDR1, CDR2 and CDR3 domains having the sequences set forth in SEQ ID NO:70, SEQ ID NO:71, and SEQ ID NO:72, respectively, and conservative amino acid substitutions thereof, and light chain CDR1, CDR2 and CDR3 domains having the sequences set forth in SEQ ID NO:73, SEQ ID NO:74, and SEQ ID NO:75, respectively, and conservative amino acid substitutions thereof.

In an embodiment, the OX40 agonist is a OX40 agonist biosimilar monoclonal antibody approved by drug regulatory authorities with reference to 11D4. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is 11D4. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is 11D4. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 11D4. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 11D4.

TABLE 11

Amino acid sequences for OX40 agonist antibodies related to 11D4.

| Identifier | Sequence (One-Letter Amino Acid Symbols) | | | | | |
|---|---|---|---|---|---|---|
| SEQ ID NO: 66 heavy chain for 11D4 | EVQLVESGGG | LVQPGGSLRL | SCAASGFTFS | SYSMNWVRQA | PGKGLEWVSY | ISSSSSTIDY 60 |
| | ADSVKGRFTI | SRDNAKNSLY | LQMNSLRDED | TAVYYCARES | GWYLFDYWGQ | GTLVTVSSAS 120 |
| | TKGPSVFPLA | PCSRSTSEST | AALGCLVKDY | FPEPVTVSWN | SGALTSGVHT | FPAVLQSSGL 180 |
| | YSLSSVVTVP | SSNFGTQTYT | CNVDHKPSNT | KVDKTVERKC | CVECPPCPAP | PVAGPSVFLF 240 |
| | PPKPKDTLMI | SRTPEVTCVV | VDVSHEDPEV | QFNWYVDGVE | VHNAKTKPRE | EQFNSTFRVV 300 |
| | SVLTVVHQDW | LNGKEYKCKV | SNKGLPAPIE | KTISKTKGQP | REPQVYTLPP | SREEMTKNQV 360 |
| | SLTCLVKGFY | PSDIAVEWES | NGQPENNYKT | TPPMLDSDGS | FFLYSKLTVD | KSRWQQGNVF 420 |
| | SCSVMHEALH | NHYTQKSLSL | SPGK | | | 444 |
| SEQ ID NO: 67 light chain for 11D4 | DIQMTQSPSS | LSASVGDRVT | ITCRASQGIS | SWLAWYQQKP | EKAPKSLIYA | ASSLQSGVPS 60 |
| | RFSGSGSGTD | FTLTISSLQP | EDFATYYCQQ | YNSYPPTFGG | GTKVEIKRTV | AAPSVFIFPP 120 |
| | SDEQLKSGTA | SVVCLLNNFY | PREAKVQWKV | DNALQSGNSQ | ESVTEQDSKD | STYSLSSTLT 180 |
| | LSKADYEKHK | VYACEVTHQG | LSSPVTKSFN | RGEC | | 214 |
| SEQ ID NO: 68 heavy chain variable region for 11D4 | EVQLVESGGG | LVQPGGSLRL | SCAASGFTFS | SYSMNWVRQA | PGKGLEWVSY | ISSSSSTIDY 60 |
| | ADSVKGRFTI | SRDNAKNSLY | LQMNSLRDED | TAVYYCARES | GWYLFDYWGQ | GTLVTVSS 118 |

TABLE 11-continued

Amino acid sequences for OX40 agonist antibodies related to 11D4.

| Identifier | Sequence (One-Letter Amino Acid Symbols) | |
|---|---|---|
| SEQ ID NO: 69<br>light chain<br>variable region<br>for 11D4 | DIQMTQSPSS LSASVGDRVT ITCRASQGIS SWLAWYQQKP EKAPKSLIYA ASSLQSGVPS<br>RFSGSGSGTD FTLTISSLQP EDFATYYCQQ YNSYPPTFGG GTKVEIK | 60<br>107 |
| SEQ ID NO: 70<br>heavy chain CDR1<br>for 11D4 | SYSMN | 5 |
| SEQ ID NO: 71<br>heavy chain CDR2<br>for 11D4 | YISSSSSTID YADSVKG | 17 |
| SEQ ID NO: 72<br>heavy chain CDR3<br>for 11D4 | ESGWYLFDY | 9 |
| SEQ ID NO: 73<br>light chain CDR1<br>for 11D4 | RASQGISSWL A | 11 |
| SEQ ID NO: 74<br>light chain CDR2<br>for 11D4 | AASSLQS | 7 |
| SEQ ID NO: 75<br>light chain CDR3<br>for 11D4 | QQYNSYPPT | 9 |

In some embodiments, the OX40 agonist is 18D38, which is a fully human antibody available from Pfizer, Inc. The preparation and properties of 18D8 are described in U.S. Pat. Nos. 7,960,515; 8,236,930; and 9,028,824, the disclosures of which are incorporated by reference herein. The amino acid sequences of 18D8 are set forth in Table 12.

In an embodiment, a OX40 agonist comprises a heavy chain given by SEQ ID NO:76 and a light chain given by SEQ ID NO:77. In an embodiment, a OX40 agonist comprises heavy and light chains having the sequences shown in SEQ ID NO:76 and SEQ ID NO:77, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:76 and SEQ ID NO:77, respectively. In an embodiment, a OX40 agonist comprises heavy and light chains that are each at least 98% identical to the sequences shown in SEQ ID NO:76 and SEQ ID NO:77, respectively. In an embodiment, a OX40 agonist comprises heavy and light chains that are each at least 97% identical to the sequences shown in SEQ ID NO:76 and SEQ ID NO:77, respectively. In an embodiment, a OX40 agonist comprises heavy and light chains that are each at least 96% identical to the sequences shown in SEQ ID NO:76 and SEQ ID NO:77, respectively. In an embodiment, a OX40 agonist comprises heavy and light chains that are each at least 95% identical to the sequences shown in SEQ ID NO:76 and SEQ ID NO:77, respectively.

In an embodiment, the OX40 agonist comprises the heavy and light chain CDRs or variable regions (VRs) of 18D8. In an embodiment, the OX40 agonist heavy chain variable region ($V_H$) comprises the sequence shown in SEQ ID NO:78, and the OX40 agonist light chain variable region ($V_L$) comprises the sequence shown in SEQ ID NO:79, and conservative amino acid substitutions thereof. In an embodiment, a OX40 agonist comprises $V_H$ and $V_L$ regions that are each at least 99% identical to the sequences shown in SEQ ID NO:78 and SEQ ID NO:79, respectively. In an embodiment, a OX40 agonist comprises $V_H$ and $V_L$ regions that are each at least 98% identical to the sequences shown in SEQ ID NO:78 and SEQ ID NO:79, respectively. In an embodiment, a OX40 agonist comprises $V_H$ and $V_L$ regions that are each at least 97% identical to the sequences shown in SEQ ID NO:78 and SEQ ID NO:79, respectively. In an embodiment, a OX40 agonist comprises $V_H$ and $V_L$ regions that are each at least 96% identical to the sequences shown in SEQ ID NO:78 and SEQ ID NO:79, respectively. In an embodiment, a OX40 agonist comprises $V_H$ and $V_L$ regions that are each at least 95% identical to the sequences shown in SEQ ID NO:78 and SEQ ID NO:79, respectively.

In an embodiment, a OX40 agonist comprises heavy chain CDR1, CDR2 and CDR3 domains having the sequences set forth in SEQ ID NO:80, SEQ ID NO:81, and SEQ ID NO:82, respectively, and conservative amino acid substitutions thereof, and light chain CDR1, CDR2 and CDR3 domains having the sequences set forth in SEQ ID NO:83, SEQ ID NO:84, and SEQ ID NO:85, respectively, and conservative amino acid substitutions thereof.

In an embodiment, the OX40 agonist is a OX40 agonist biosimilar monoclonal antibody approved by drdigestregulatory authorities with reference to 18D8. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is 18D8. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is 18D8. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 18D8. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 18D8.

TABLE 12

Amino acid sequences for OX40 agonist antibodies related to 18D8.

| Identifier | Sequence (One-Letter Amino Acid Symbols) |
|---|---|
| SEQ ID NO: 76 heavy chain for 18D8 | EVQLVESGGG LVQPGRSLRL SCAASGFTFD DYAMHWVRQA PGKGLEWVSG ISWNSGSIGY 60<br>ADSVKGRFTI SRDNAKNSLY LQMNSLRAED TALYYCAKDQ STADYYFYYG MDVWGQGTTV 120<br>TVSSASTKGP SVFPLAPCSR STSESTAALG CLVKDYFPEP VTVSWNSGAL TSGVHTFPAV 180<br>LQSSGLYSLS SVVTVPSSNF GTQTYTCNVD HKPSNTKVDK TVERKCCVEC PPCPAPPVAG 240<br>PSVFLFPPKP KDTLMISRTP EVTCVVVDVS HEDPEVQFNW YVDGVEVHNA KTKPREEQFN 300<br>STFRVVSVLT VVHQDWLNGK EYKCKVSNKG LPAPIEKTIS KTKGQPREPQ VYTLPPSREE 360<br>MTKNQVSLTC LVKGFYPSDI AVEWESNGQP ENNYKTTPPM LDSDGSFFLY SKLTVDKSRW 420<br>QQGNVFSCSV MHEALHNHYT QKSLSLSPGK 450 |
| SEQ ID NO: 77 light chain for 18D8 | EIVVTQSPAT LSLSPGERAT LSCRASQSVS SYLAWYQQKP GQAPRLLIYD ASNRATGIPA 60<br>RFSGSGSGTD FTLTISSLEP EDFAVYYCQQ RSNWPTFGQG TKVEIKRTVA APSVFIFPPS 120<br>DEQLKSGTAS VVCLLNNFYP REAKVQWKVD NALQSGNSQE SVTEQDSKDS TYSLSSTLTL 180<br>SKADYEKHKV YACEVTHQGL SSPVTKSFNR GEC 213 |
| SEQ ID NO: 78 heavy chain variable region for 18D8 | EVQLVESGGG LVQPGRSLRL SCAASGFTFD DYAMHWVRQA PGKGLEWVSG ISWNSGSIGY 60<br>ADSVKGRFTI SRDNAKNSLY LQMNSLRAED TALYYCAKDQ STADYYFYYG MDVWGQGTTV 120<br>TVSS 124 |
| SEQ ID NO: 79 light chain variable region for 18D8 | EIVVTQSPAT LSLSPGERAT LSCRASQSVS SYLAWYQQKP GQAPRLLIYD ASNRATGIPA 60<br>RFSGSGSGTD FTLTISSLEP EDFAVYYCQQ RSNWPTFGQG TKVEIK 106 |
| SEQ ID NO: 80 heavy chain CDR1 for 18D8 | DYAMH 5 |
| SEQ ID NO: 81 heavy chain CDR2 for 18D8 | GISWNSGSIG YADSVKG 17 |
| SEQ ID NO: 82 heavy chain CDR3 for 18D8 | DQSTADYYFY YGMDV 15 |
| SEQ ID NO: 83 light chain CDR1 for 18D8 | RASQSVSSYL A 11 |
| SEQ ID NO: 84 light chain CDR2 for 18D8 | DASNRAT 7 |
| SEQ ID NO: 85 light chain CDR3 for 18D8 | QQRSNWPT 8 |

In some embodiments, the OX40 agonist is Hu119-122, which is a humanized antibody available from GlaxoSmithKline plc. The preparation and properties of Hu119-122 are described in U.S. Pat. Nos. 9,006,399 and 9,163,085, and in International Patent Publication No. WO 2012/027328, the disclosures of which are incorporated by reference herein. The amino acid sequences of Hu119-122 are set forth in Table 13.

In an embodiment, the OX40 agonist comprises the heavy and light chain CDRs or variable regions (VRs) of Hu119-122. In an embodiment, the OX40 agonist heavy chain variable region ($V_H$) comprises the sequence shown in SEQ ID NO:86, and the OX40 agonist light chain variable region ($V_L$) comprises the sequence shown in SEQ ID NO:87, and conservative amino acid substitutions thereof. In an embodiment, a OX40 agonist comprises $V_H$ and $V_L$ regions that are each at least 99% identical to the sequences shown in SEQ ID NO:86 and SEQ ID NO:87, respectively. In an embodiment, a OX40 agonist comprises $V_H$ and $V_L$ regions that are each at least 98% identical to the sequences shown in SEQ ID NO:86 and SEQ ID NO:87, respectively. In an embodiment, a OX40 agonist comprises $V_H$ and $V_L$ regions that are each at least 97% identical to the sequences shown in SEQ ID NO:86 and SEQ ID NO:87, respectively. In an embodiment, a OX40 agonist comprises $V_H$ and $V_L$ regions that are each at least 96% identical to the sequences shown in SEQ ID NO:86 and SEQ ID NO:87, respectively. In an embodiment, a OX40 agonist comprises $V_H$ and $V_L$ regions that are each at least 95% identical to the sequences shown in SEQ ID NO:86 and SEQ ID NO:87, respectively.

In an embodiment, a OX40 agonist comprises heavy chain CDR1, CDR2 and CDR3 domains having the sequences set forth in SEQ ID NO:88, SEQ ID NO:89, and SEQ ID NO:90, respectively, and conservative amino acid substitutions thereof, and light chain CDR1, CDR2 and CDR3 domains having the sequences set forth in SEQ ID NO:91, SEQ ID NO:92, and SEQ ID NO:93, respectively, and conservative amino acid substitutions thereof.

In an embodiment, the OX40 agonist is a OX40 agonist biosimilar monoclonal antibody approved by drug regulatory authorities with reference to Hu119-122. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is Hu119-122. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is Hu119-122. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu119-122. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu119-122.

TABLE 13

Amino acid sequences for OX40 agonist antibodies related to Hu119-122.

| Identifier | Sequence (One-Letter Amino Acid Symbols) | |
|---|---|---|
| SEQ ID NO: 86 heavy chain variable region for Hu119-122 | EVQLVESGGG LVQPGGSLRL SCAASEYEFP SHDMSWVRQA PGKGLELVAA INSDGGSTYY PDTMERRFTI SRDNAKNSLY LQMNSLRAED TAVYYCARHY DDYYAWFAYW GQGTMVTVSS | 60 120 |
| SEQ ID NO: 87 light chain variable region for Hu119-122 | EIVLTQSPAT LSLSPGERAT LSCRASKSVS TSGYSYMHWY QQKPGQAPRL LIYLASNLES GVPARFSGSG SGTDFTLTIS SLEPEDFAVY YCQHSRELPL TFGGGTKVEI K | 60 111 |
| SEQ ID NO: 88 heavy chain CDR1 for Hu119-122 | SHDMS | 5 |
| SEQ ID NO: 89 heavy chain CDR2 for Hu119-122 | AINSDGGSTY YPDTMER | 17 |
| SEQ ID NO: 90 heavy chain CDR3 for Hu119-122 | HYDDYYAWFA Y | 11 |
| SEQ ID NO: 91 light chain CDR1 for Hu119-122 | RASKSVSTSG YSYMH | 15 |
| SEQ ID NO: 92 light chain CDR2 for Hu119-122 | LASNLES | 7 |
| SEQ ID NO: 93 light chain CDR3 for Hu119-122 | QHSRELPLT | 9 |

In some embodiments, the OX40 agonist is Hu106-222, which is a humanized antibody available from GlaxoSmithKline plc. The preparation and properties of Hu1106-222 are described in U.S. Pat. Nos. 9,006,399 and 9,163,085, and in International Patent Publication No. WO 2012/027328, the disclosures of which are incorporated by reference herein. The amino acid sequences of Hu1106-222 are set forth in Table 14.

In an embodiment, the OX40 agonist comprises the heavy and light chain CDRs or variable regions (VRs) of Hu106-222. In an embodiment, the OX40 agonist heavy chain variable region ($V_H$) comprises the sequence shown in SEQ ID NO:94, and the OX40 agonist light chain variable region ($V_L$) comprises the sequence shown in SEQ ID NO:95, and conservative amino acid substitutions thereof. In an embodiment, a OX40 agonist comprises $V_H$ and $V_L$ regions that are each at least 99% identical to the sequences shown in SEQ ID NO:94 and SEQ ID NO:95, respectively. In an embodiment, a OX40 agonist comprises $V_H$ and $V_L$ regions that are each at least 98% identical to the sequences shown in SEQ ID NO:94 and SEQ ID NO:95, respectively. In an embodiment, a OX40 agonist comprises $V_H$ and $V_L$ regions that are each at least 97% identical to the sequences shown in SEQ ID NO:94 and SEQ ID NO:95, respectively. In an embodiment, a OX40 agonist comprises $V_H$ and $V_L$ regions that are each at least 96% identical to the sequences shown in SEQ ID NO:94 and SEQ ID NO:95, respectively. In an embodiment, a OX40 agonist comprises $V_H$ and $V_L$ regions that are each at least 95% identical to the sequences shown in SEQ ID NO:94 and SEQ ID NO:95, respectively.

In an embodiment, a OX40 agonist comprises heavy chain CDR1, CDR2 and CDR3 domains having the sequences set forth in SEQ ID NO:96, SEQ ID NO:97, and SEQ ID NO:98, respectively, and conservative amino acid substitutions thereof, and light chain CDR1, CDR2 and CDR3 domains having the sequences set forth in SEQ ID NO:99, SEQ ID NO:100, and SEQ ID NO:101, respectively, and conservative amino acid substitutions thereof.

In an embodiment, the OX40 agonist is a OX40 agonist biosimilar monoclonal antibody approved by drug regulatory authorities with reference to Hu106-222. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is Hu106-222. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is Hu106-222. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu106-222. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu126-222.

TABLE 14

Amino acid sequences for OX40 agonist antibodies related to Hu106-222.

| Identifier | Sequence (One-Letter Amino Acid Symbols) | | | | | | |
|---|---|---|---|---|---|---|---|
| SEQ ID NO: 94 heavy chain variable region for Hu106-222 | QVQLVQSGSE | LKKPGASVKV | SCKASGYTFT | DYSMHWVRQA | PGQGLKWMGW | INTETGEPTY | 60 |
| | ADDFKGRFVF | SLDTSVSTAY | LQISSLKAED | TAVYYCANPY | YDYVSYYAMD | YWGQGTTVTV | 120 |
| | SS | | | | | | 122 |
| SEQ ID NO: 95 light chain variable region for Hu106-222 | DIQMTQSPSS | LSASVGDRVT | ITCKASQDVS | TAVAWYQQKP | GKAPKLLIYS | ASYLYTGVPS | 60 |
| | RFSGSGSGTD | FTFTISSLQP | EDIATYYCQQ | HYSTPRTFGQ | GTKLEIK | | 107 |
| SEQ ID NO: 96 heavy chain CDR1 for Hu106-222 | DYSMH | | | | | | 5 |
| SEQ ID NO: 97 heavy chain CDR2 for Hu106-222 | WINTETGEPT YADDFKG | | | | | | 17 |
| SEQ ID NO: 98 heavy chain CDR3 for Hu106-222 | PYYDVSYYA MDY | | | | | | 13 |
| SEQ ID NO: 99 light chain CDR1 for Hu106-222 | KASQDVSTAV A | | | | | | 11 |
| SEQ ID NO: 100 light chain CDR2 for Hu106-222 | SASYLYT | | | | | | 7 |
| SEQ ID NO: 101 light chain CDR3 for Hu106-222 | QQHYSTPRT | | | | | | 9 |

In some embodiments, the OX40 agonist antibody is MEDI6469 (also referred to as 9B12). MEDI6469 is a murine monoclonal antibody. Weinberg, et al., *J. Immunother.*, 2006, 29, 575-585. In some embodiments the OX40 agonist is an antibody produced by the 9B12 hybridoma, deposited with Biovest Inc. (Malvern, MA, USA), as described in Weinberg, et al., *J. Immunother.*, 2006, 29, 575-585, the disclosure of which is hereby incorporated by reference in its entirety. In some embodiments, the antibody comprises the CDR sequences of MEDI6469. In some embodiments, the antibody comprises a heavy chain variable region sequence and/or a light chain variable region sequence of MEDI6469.

In an embodiment, the OX40 agonist is L106 BD (Pharmingen Product #340420). In some embodiments, the OX40 agonist comprises the CDRs of antibody L106 (BD Pharmingen Product #340420). In some embodiments, the OX40 agonist comprises a heavy chain variable region sequence and/or a light chain variable region sequence of antibody L106 (BD Pharmingen Product #340420). In an embodiment, the OX40 agonist is ACT35 (Santa Cruz Biotechnology, Catalog #20073). In some embodiments, the OX40 agonist comprises the CDRs of antibody ACT35 (Santa Cruz Biotechnology, Catalog #20073). In some embodiments, the OX40 agonist comprises a heavy chain variable region sequence and/or a light chain variable region sequence of antibody ACT35 (Santa Cruz Biotechnology, Catalog #20073). In an embodiment, the OX40 agonist is the murine monoclonal antibody anti-mCD134/mOX40 (clone OX86), commercially available from InVivoMAb, BioXcell Inc, West Lebanon, NH In an embodiment, the OX40 agonist is selected from the OX40 agonists described in International Patent Application Publication Nos. WO 95/12673, WO 95/21925, WO 2006/121810, WO 2012/027328, WO 2013/028231, WO 2013/038191, and WO 2014/148895; European Patent Application EP 0672141; U.S. Patent Application Publication Nos. US 2010/136030, US 2014/377284, US 2015/190506, and US 2015/132288 (including clones 20E5 and 12H3); and U.S. Pat. Nos. 7,504,101, 7,550,140, 7,622,444, 7,696,175, 7,960,515, 7,961,515, 8,133,983, 9,006,399, and 9,163,085, the disclosure of each of which is incorporated herein by reference in its entirety.

In an embodiment, the OX40 agonist is an OX40 agonistic fusion protein as depicted in Structure I-A (C-terminal Fc-antibody fragment fusion protein) or Structure I-B (N-terminal Fc-antibody fragment fusion protein), or a fragment, derivative, conjugate, variant, or biosimilar thereof. The properties of structures I-A and I-B are described above and in U.S. Pat. Nos. 9,359,420, 9,340,599, 8,921,519, and 8,450,460, the disclosures of which are incorporated by reference herein. Amino acid sequences for the polypeptide domains of structure I-A are given in Table 6. The Fc domain preferably comprises a complete constant domain (amino acids 17-230 of SEQ ID NO:31) the complete hinge domain (amino acids 1-16 of SEQ ID NO:31) or a portion of the hinge domain (e.g., amino acids 4-16 of SEQ ID NO:31). Preferred linkers for connecting a C-terminal Fc-antibody may be selected from the embodiments given in SEQ ID NO:32 to SEQ ID NO:41, including linkers suitable for fusion of additional polypeptides. Likewise, amino acid sequences for the polypeptide domains of structure I-B are given in Table 7. If an Fc antibody fragment is fused to the N-terminus of an TNRFSF fusion protein as in structure I-B, the sequence of the Fc module is preferably that shown in SEQ ID NO:42, and the linker sequences are preferably selected from those embodiments set forth in SED ID NO:43 to SEQ ID NO:45.

In an embodiment, an OX40 agonist fusion protein according to structures I-A or I-B comprises one or more OX40 binding domains selected from the group consisting of a variable heavy chain and variable light chain of tavolixizumab, a variable heavy chain and variable light chain of 11D4, a variable heavy chain and variable light chain of 18D8, a variable heavy chain and variable light chain of Hu119-122, a variable heavy chain and variable light chain of Hu106-222, a variable heavy chain and variable light chain selected from the variable heavy chains and variable light chains described in Table 19, any combination of a variable heavy chain and variable light chain of the foregoing, and fragments, derivatives, conjugates, variants, and biosimilars thereof.

In an embodiment, an OX40 agonist fusion protein according to structures I-A or I-B comprises one or more OX40 binding domains comprising an OX40L sequence. In an embodiment, an OX40 agonist fusion protein according to structures I-A or I-B comprises one or more OX40 binding domains comprising a sequence according to SEQ ID NO:102. In an embodiment, an OX40 agonist fusion protein according to structures I-A or I-B comprises one or more OX40 binding domains comprising a soluble OX40L sequence. In an embodiment, a OX40 agonist fusion protein according to structures I-A or I-B comprises one or more OX40 binding domains comprising a sequence according to SEQ ID NO:103. In an embodiment, a OX40 agonist fusion protein according to structures I-A or I-B comprises one or more OX40 binding domains comprising a sequence according to SEQ ID NO:104.

In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:58 and SEQ ID NO:59, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:68 and SEQ ID NO:69, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:78 and SEQ ID NO:79, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:86 and SEQ ID NO:87, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:94 and SEQ ID NO:95, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the $V_H$ and $V_L$ sequences given in Table 15, wherein the $V_H$ and $V_L$ domains are connected by a linker.

TABLE 15

Additional polypeptide domains useful as OX40 binding domains in fusion proteins (e.g., structures I-A and I-B) or as scFv OX40 agonist antibodies.

| Identifier | Sequence (One-Letter Amino Acid Symbols) | |
|---|---|---|
| SEQ ID NO: 102 OX40L | MERVQPLEEN VGNAARPRFE RNKLLLVASV IQGLGLLLCF TYICLHFSAL QVSHRYPRIQ | 60 |
| | SIKVQFTEYK KEKGFILTSQ KEDEIMKVQN NSVIINCDGF YLISLKGYFS QEVNISLHYQ | 120 |
| | KDEEPLFQLK KVRSVNSLMV ASLTYKDKVY LNVTTDNTSL DDFHVNGGEL ILIHQNPGEF | 180 |
| | CVL | 183 |
| SEQ ID NO: 103 OX40L soluble domain | SHRYPRIQSI KVQFTEYKKE KGFILTSQKE DEIMKVQNNS VIINCDGFYL ISLKGYFSQE | 60 |
| | VNISLHYQKD EEPLFQLKKV RSVNSLMVAS LTYKDKVYLN VTTDNTSLDD FHVNGGELIL | 120 |
| | IHQNPGEFCV L | 131 |
| SEQ ID NO: 104 OX40L soluble domain (alternative) | YPRIQSIKVQ FTEYKKEKGF ILTSQKEDEI MKVQNNSVII NCDGFYLISL KGYFSQEVNI | 60 |
| | SLHYQKDEEP LFQLKKVRSV NSLMVASLTY KDKVYLNVTT DNTSLDDFHV NGGELILIHQ | 120 |
| | NPGEFCVL | 128 |
| SEQ ID NO: 105 variable heavy chain for 008 | EVQLVESGGG LVQPGGSLRL SCAASGFTFS NYTMNWVRQA PGKGLEWVSA ISGSGGSTYY | 60 |
| | ADSVKGRFTI SRDNSKNTLY LQMNSLRAED TAVYYCAKDR YSQVHYALDY WGQGTLVTVS | 120 |
| SEQ ID NO: 106 variable light chain for 008 | DIVMTQSPDS LPVTPGEPAS ISCRSSQSLL HSNGYNYLDW YLQKAGQSPQ LLIYLGSNRA | 60 |
| | SGVPDRFSGS GSGTDFTLKI SRVEAEDVGV YYCQQYYNHP TTFGQGTK | 108 |
| SEQ ID NO: 107 variable heavy chain for 011 | EVQLVESGGG VVQPGRSLRL SCAASGFTFS DYTMNWVRQA PGKGLEWVSS ISGGSTYYAD | 60 |
| | SRKGRFTISR DNSKNTLYLQ MNNLRAEDTA VYYCARDRYF RQQNAFDYWG QGTLVTVSSA | 120 |
| SEQ ID NO: 108 variable light chain for 011 | DIVMTQSPDS LPVTPGEPAS ISCRSSQSLL HSNGYNYLDW YLQKAGQSPQ LLIYLGSNRA | 60 |
| | SGVPDRFSGS GSGTDFTLKI SRVEAEDVGV YYCQQYYNHP TTFGQGTK | 108 |
| SEQ ID NO: 109 variable heavy chain for 021 | EVQLVESGGG LVQPRGSLRL SCAASGFTFS SYAMNWVRQA PGKGLEWVAV ISYDGSNKYY | 60 |
| | ADSVKGRFTI SRDNSKNTLY LQMNSLRAED TAVYYCAKDR YITLPNALDY WGQGTLVTVS | 120 |
| SEQ ID NO: 110 variable light chain for 021 | DIQMTQSPVS LPVTPGEPAS ISCRSSQSLL HSNGYNYLDW YLQKPGQSPQ LLIYLGSNRA | 60 |
| | SGVPDRFSGS GSGTDFTLKI SRVEAEDVGV YYCQQYKSNP PTFGQGTK | 108 |
| SEQ ID NO: 111 variable heavy chain for 023 | EVQLVESGGG LVHPGGSLRL SCAGSGFTFS SYAMHWVRQA PGKGLEWVSA IGTGGGTYYA | 60 |
| | DSVMGRFTIS RDNSKNTLYL QMNSLRAEDT AVYYCARYDN VMGLYWFDYW GQGTLVTVSS | 120 |
| SEQ ID NO: 112 variable light chain for 023 | EIVLTQSPAT LSLSPGERAT LSCRASQSVS SYLAWYQQKP GQAPRLLIYD ASNRATGIPA | 60 |
| | RFSGSGSGTD FTLTISSLEP EDFAVYYCQQ RSNWPPAFGG GTKVEIKR | 108 |
| SEQ ID NO: 113 heavy chain variable region | EVQLQQSGPE LVKPGASVKM SCKASGYTFT SYVMHWVKQK PGQGLEWIGY INPYNDGTKY | 60 |
| | NEKFKGKATL TSDKSSSTAY MELSSLTSED SAVYYCANYY GSSLSMDYWG QGTSVTVSS | 119 |
| SEQ ID NO: 114 light chain variable region | DIQMTQTTSS LSASLGDRVT ISCRASQDIS NYLNWYQQKP DGTVKLLIYY TSRLHSGVPS | 60 |
| | RFSGSGSGTD YSLTISNLEQ EDIATYFCQQ GNTLPWTFGG GTKLEIKR | 108 |
| SEQ ID NO: 115 heavy chain variable region | EVQLQQSGPE LVKPGASVKI SCKTSGYTFK DYTMHWVKQS HGKSLEWIGG IYPNNGGSTY | 60 |
| | NQNFKDKATL TVDKSSSTAY MEFRSLTSED SAVYYCARMG YHGPHLDFDV WGAGTTVTVS | 120 |
| | P | 121 |
| SEQ ID NO: 116 light chain variable region | DIVMTQSHKF MSTSLGDRVS ITCKASQDVG AAVAWYQQKP GQSPKLLIYW ASTRHTGVPD | 60 |
| | RFTGGGSGTD FTLTISNVQS EDLTDYFCQQ YINYPLTFGG GTKLEIKR | 108 |
| SEQ ID NO: 117 heavy chain variable region of humanized antibody | QIQLVQSGPE LKKPGETVKI SCKASGYTFT DYSMHWVKQA PGKGLKWMGW INTETGEPTY | 60 |
| | ADDFKGRFAF SLETSASTAY LQINNLKNED TATYFCANPY YDYVSYYAMD YWGHGTSVTV | 120 |
| | SS | 122 |

TABLE 15-continued

Additional polypeptide domains useful as OX40 binding domains in fusion proteins (e.g., structures I-A and I-B) or as scFv OX40 agonist antibodies.

| Identifier | Sequence (One-Letter Amino Acid Symbols) | |
|---|---|---|
| SEQ ID NO: 118 heavy chain variable region of humanized antibody | QVQLVQSGSE LKKPGASVKV SCKASGYTFT DYSMHWVRQA PGQGLKWMGW INTETGEPTY<br>ADDFKGRFVF SLDTSVSTAY LQISSLKAED TAVYYCANPY YDYVSYYAMD YWGQGTTVTV<br>SS | 60<br>120<br>122 |
| SEQ ID NO: 119 light chain variable region of humanized antibody | DIVMTQSHKF MSTSVRDRVS ITCKASQDVS TAVAWYQQKP GQSPKLLIYS ASYLYTGVPD<br>RFTGSGSGTD FTFTISSVQA EDLAVYYCQQ HYSTPRTFGG GTKLEIK | 60<br>107 |
| SEQ ID NO: 120 light chain variable region of humanized antibody | DIVMTQSHKF MSTSVRDRVS ITCKASQDVS TAVAWYQQKP GQSPKLLIYS ASYLYTGVPD<br>RFTGSGSGTD FTFTISSVQA EDLAVYYCQQ HYSTPRTFGG GTKLEIK | 60<br>107 |
| SEQ ID NO: 121 heavy chain variable region of humanized antibody | EVQLVESGGG LVQPGESLKL SCESNEYEFP SHDMSWVRKT PEKRLELVAA INSDGGSTYY<br>PDTMERRFII SRDNTKKTLY LQMSSLRSED TALYYCARHY DDYYAWFAYW GQGTLVTVSA | 60<br>120 |
| SEQ ID NO: 122 heavy chain variable region of humanized antibody | EVQLVESGGG LVQPGGSLRL SCAASEYEFP SHDMSWVRQA PGKGLELVAA INSDGGSTYY<br>PDTMERRFTI SRDNAKNSLY LQMNSLRAED TAVYYCARHY DDYYAWFAYW GQGTMVTVSS | 60<br>120 |
| SEQ ID NO: 123 light chain variable region of humanized antibody | DIVLTQSPAS LAVSLGQRAT ISCRASKSVS TSGYSYMHWY QQKPGQPPKL LIYLASNLES<br>GVPARFSGSG SGTDFTLNIH PVEEEDAATY YCQHSRELPL TFGAGTKLEL K | 60<br>111 |
| SEQ ID NO: 124 light chain variable region of humanized antibody | EIVLTQSPAT LSLSPGERAT LSCRASKSVS TSGYSYMHWY QQKPGQAPRL LIYLASNLES<br>GVPARFSGSG SGTDFTLTIS SLEPEDFAVY YCQHSRELPL TFGGGTKVEI K | 60<br>111 |
| SEQ ID NO: 125 heavy chain variable region | MYLGLNYVFI VFLLNGVQSE VKLEESGGGL VQPGGSMKLS CAASGFTFSD AWMDWVRQSP<br>EKGLEWVAEI RSKANNHATY YAESVNGRFT ISRDDSKSSV YLQMNSLRAE DTGIYYCTWG<br>EVFYFDYWGQ GTTLTVSS | 60<br>120<br>138 |
| SEQ ID NO: 126 light chain variable region | MRPSIQFLGL LLFWLHGAQC DIQMTQSPSS LSASLGGKVT ITCKSSQDIN KYIAWYQHKP<br>GKGPRLLIHY TSTLQPGIPS RFSGSGSGRD YSFSISNLEP EDIATYYCLQ YDNLLTFGAG<br>TKLELK | 60<br>120<br>126 |

In an embodiment, the OX40 agonist is a OX40 agonistic single-chain fusion polypeptide comprising (i) a first soluble OX40 binding domain, (ii) a first peptide linker, (iii) a second soluble OX40 binding domain, (iv) a second peptide linker, and (v) a third soluble OX40 binding domain, further comprising an additional domain at the N-terminal and/or C-terminal end, and wherein the additional domain is a Fab or Fc fragment domain. In an embodiment, the OX40 agonist is a OX40 agonistic single-chain fusion polypeptide comprising (i) a first soluble OX40 binding domain, (ii) a first peptide linker, (iii) a second soluble OX40 binding domain, (iv) a second peptide linker, and (v) a third soluble OX40 binding domain, further comprising an additional domain at the N-terminal and/or C-terminal end, wherein the additional domain is a Fab or Fc fragment domain wherein each of the soluble OX40 binding domains lacks a stalk region (which contributes to trimerisation and provides a certain distance to the cell membrane, but is not part of the OX40 binding domain) and the first and the second peptide linkers independently have a length of 3-8 amino acids.

In an embodiment, the OX40 agonist is an OX40 agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein the TNF superfamily cytokine domain is an OX40 binding domain.

In some embodiments, the OX40 agonist is MEDI6383. MEDI6383 is an OX40 agonistic fusion protein and can be prepared as described in U.S. Pat. No. 6,312,700, the disclosure of which is incorporated by reference herein.

In an embodiment, the OX40 agonist is an OX40 agonistic scFv antibody comprising any of the foregoing $V_H$ domains linked to any of the foregoing $V_L$ domains.

In an embodiment, the OX40 agonist is Creative Biolabs OX40 agonist monoclonal antibody MOM-18455, commercially available from Creative Biolabs, Inc., Shirley, NY, USA.

In an embodiment, the OX40 agonist is OX40 agonistic antibody clone Ber-ACT35, commercially available from BioLegend, Inc., San Diego, CA, USA.

AKT Pathway Inhibitors as Adjunct to TIL Manufacturing

In some embodiments, an AKT pathway inhibitor is added to the first culture medium with the tumor fragments into a closed system. In some embodiments the AKT pathway inhibitor is an AKT inhibitor. In some embodiments, the AKT inhibitor is afuresertib, or a pharmaceutically acceptable salt, solvate, hydrate, cocrystal, or prodrug thereof, and is added at a sufficient concentration to attenuate AKT signaling. In another embodiment, the AKT inhibitor is uprosertib, or a pharmaceutically acceptable salt, solvate, hydrate, cocrystal, or prodrug thereof, and is added at a sufficient concentration to attenuate AKT signaling. In another embodiment, the AKT inhibitor is ipatasertib, or a pharmaceutically acceptable salt, solvate, hydrate, cocrystal, or prodrug thereof, and is added at a sufficient concentration to attenuate AKT signaling. In another embodiment, the AKT inhibitor is AT7867, or a pharmaceutically acceptable salt, solvate, hydrate, cocrystal, or prodrug thereof, and is added at a sufficient concentration to attenuate AKT signaling. In another embodiment, the AKT inhibitor is AT13148, or a pharmaceutically acceptable salt, solvate, hydrate, cocrystal, or prodrug thereof, and is added at a sufficient concentration to attenuate AKT signaling. In another embodiment, the AKT inhibitor is MK-2206, or a pharmaceutically acceptable salt, solvate, hydrate, cocrystal, or prodrug thereof, and is added at a sufficient concentration to attenuate AKT signaling.

In some embodiments, an AKT pathway inhibitor is added to the first priming expansion step. In some embodiments the AKT pathway inhibitor is an AKT inhibitor. In some embodiments, the AKT inhibitor is afuresertib, or a pharmaceutically acceptable salt, solvate, hydrate, cocrystal, or prodrug thereof, and is added at a sufficient concentration to attenuate AKT signaling. In another embodiment, the AKT inhibitor is uprosertib, or a pharmaceutically acceptable salt, solvate, hydrate, cocrystal, or prodrug thereof, and is added at a sufficient concentration to attenuate AKT signaling. In another embodiment, the AKT inhibitor is ipatasertib, or a pharmaceutically acceptable salt, solvate, hydrate, cocrystal, or prodrug thereof, and is added at a sufficient concentration to attenuate AKT signaling. In another embodiment, the AKT inhibitor is AT7867, or a pharmaceutically acceptable salt, solvate, hydrate, cocrystal, or prodrug thereof, and is added at a sufficient concentration to attenuate AKT signaling. In another embodiment, the AKT inhibitor is AT13148, or a pharmaceutically acceptable salt, solvate, hydrate, cocrystal, or prodrug thereof, and is added at a sufficient concentration to attenuate AKT signaling. In another embodiment, the AKT inhibitor is MK-2206, or a pharmaceutically acceptable salt, solvate, hydrate, cocrystal, or prodrug thereof, and is added at a sufficient concentration to attenuate AKT signaling.

In various embodiments, the AKT pathway inhibitor is a PI3K inhibitor. In an embodiment, the PI3K inhibitor is LY294002, or a pharmaceutically acceptable salt, solvate, hydrate, cocrystal, or prodrug thereof, and is added at a sufficient concentration to attenuate PI3K signaling.

In some embodiments, the AKT pathway inhibitor comprises one or more AKT pathway inhibitors selected from the group consisting of PI3K, AKT, PDK1, mTORC2, GSK3, FOXO, TSC2, mTORC1, PTEN, BAD, ASK1, MERIT40, MDM2, CHK1, IKKα, p21CIP1, p27KIP1, RAF1, PFKFB2, PDE3B, PRAS40, AMPK, ACLY, PIKfyve, eNOS, WNK1, Huntingtin, Palladin, and TBC1D4.

In an embodiment the AKT pathway inhibitor is added to the first culture medium at a concentration of between 0.01 µM and 1000 µM. In an embodiment the AKT pathway inhibitor is added to the first culture medium at a concentration of between 0.01 µM and 500 µM. In an embodiment the AKT pathway inhibitor is added to the first culture medium at a concentration of between 0.01 µM and 100 µM. In an embodiment AKT pathway inhibitor is added to the first culture medium at a concentration of between 0.01 µM and 50 µM. In an embodiment AKT pathway inhibitor is added to the first culture medium at a concentration of between 0.01 µM and 50 µM. In an embodiment AKT pathway inhibitor is added to the first culture medium at a concentration of between 0.01 µM and 25 µM.

In an embodiment the AKT pathway inhibitor is added to the first first priming expansion step at a concentration of between 0.01 µM and 1000 µM. In an embodiment the AKT pathway inhibitor is added to the first culture medium at a concentration of between 0.01 µM and 500 µM. In an embodiment the AKT pathway inhibitor is added to the first culture medium at a concentration of between 0.01 µM and 100 µM. In an embodiment AKT pathway inhibitor is added to the first culture medium at a concentration of between 0.01 µM and 50 µM. In an embodiment AKT pathway inhibitor is added to the first culture medium at a concentration of between 0.01 µM and 50 µM. In an embodiment AKT pathway inhibitor is added to the first culture medium at a concentration of between 0.01 µM and 25 µM.

In an embodiment the AKT pathway inhibitor is added to the first culture medium at a concentration wherein the targeted enzyme is at least 95% occupied at steady state. In an embodiment the AKT pathway inhibitor is added to the first culture medium at a concentration wherein the targeted enzyme is at least 85% occupied at steady state. In an embodiment the AKT pathway inhibitor is added to the first culture medium at a concentration wherein the targeted enzyme is at least 75% occupied at steady state. In an embodiment the AKT pathway inhibitor is added to the first culture medium at a concentration wherein the targeted enzyme is at least 50% occupied at steady state.

In an embodiment the AKT pathway inhibitor is added to the first priming expansion step at a concentration wherein the targeted enzyme is at least 95% occupied at steady state. In an embodiment the AKT pathway inhibitor is added to the first priming expansion step at a concentration wherein the targeted enzyme is at least 85% occupied at steady state. In an embodiment the AKT pathway inhibitor is added to the first priming expansion step at a concentration wherein the targeted enzyme is at least 75% occupied at steady state. In an embodiment the AKT pathway inhibitor is added to the first priming expansion step at a concentration wherein the targeted enzyme is at least 50% occupied at steady state.

In some embodiments the AKT pathway inhibitor is added to the first culture medium at a concentration per 100,000 cells selected from the group consisting of 10 nM, 20 nM, 25 nM, 30 nM, 50 nM, 60 nM, 75 nM, 80 nM, 90 nM, 100 nM, 125 nM, 150 nM, 175 nM, 200 nM, 225 nM, 250 nM, 275 nM, 300 nM, 325 nM, 375 nM, 400 nM, 450 nM, 500 nM, 550 nM, 600 nM, 625 nM, 650 nM, 675 nM, 700 nM, 725 nM, 750 nM, 775 nM, 800 nM, 825 nM, 850 nM, 875 nM, 900 nM, 925 nM, 950 nM, 975 nM, 1000 nM, 1100 nM, 1200 nM, 1300 nM, 1400 nM, 1500 nM, 1600 nM, 1700 nM, 1800 nM, 1900 nM, 2000 nM, 2.5 µM, 3 µM, 4 µM, 5 µM, 6 µM, 7 µM, 8 µM, 9 µM, 10 µM, 12.5 µM, 15 µM, 18 µM, 20 µM, and 25 µM.

In some embodiments the AKT pathway inhibitor is added to the first priming expansion step at a concentration per 100,000 cells selected from the group consisting of 10 nM, 20 nM, 25 nM, 30 nM, 50 nM, 60 nM, 75 nM, 80 nM, 90 nM, 100 nM, 125 nM, 150 nM, 175 nM, 200 nM, 225 nM, 250 nM, 275 nM, 300 nM, 325 nM, 375 nM, 400 nM, 450 nM, 500 nM, 550 nM, 600 nM, 625 nM, 650 nM, 675 nM, 700 nM, 725 nM, 750 nM, 775 nM, 800 nM, 825 nM, 850 nM, 875 nM, 900 nM, 925 nM, 950 nM, 975 nM, 1000 nM, 1100 nM, 1200 nM, 1300 nM, 1400 nM, 1500 nM, 1600 nM, 1700 nM, 1800 nM, 1900 nM, 2000 nM, 2.5 µM, 3 µM, 4 µM, 5 µM, 6 µM, 7 µM, 8 µM, 9 µM, 10 µM, 12.5 µM, 15 µM, 18 µM, 20 µM, and 25 µM.

In some embodiments, the first cell culture medium comprises at least two AKT pathway inhibitors. In a further embodiment, the first AKT pathway inhibitor is afuresertib, or a pharmaceutically acceptable salt, solvate, hydrate, cocrystal, or prodrug thereof.

In some embodiments, the first priming expansion step comprises at least two AKT pathway inhibitors. In a further embodiment, the first AKT pathway inhibitor is afuresertib, or a pharmaceutically acceptable salt, solvate, hydrate, cocrystal, or prodrug thereof.

In some embodiments, an AKT pathway inhibitor is added to the second culture medium with the tumor fragments into a closed system. In an embodiment the AKT pathway inhibitor is afuresertib, or a pharmaceutically acceptable salt, solvate, hydrate, cocrystal, or prodrug thereof, and is added at a sufficient concentration to attenuate AKT signaling. In another embodiment, the AKT pathway inhibitor is uprosertib, or a pharmaceutically acceptable salt, solvate, hydrate, cocrystal, or prodrug thereof, and is added at a sufficient concentration to attenuate AKT signaling. In another embodiment, the AKT pathway is ipatasertib, or a pharmaceutically acceptable salt, solvate, hydrate, cocrystal, or prodrug thereof, and is added at a sufficient concentration to block AKT signaling. In another embodiment, the AKT pathway inhibitor is AT7867, or a pharmaceutically acceptable salt, solvate, hydrate, cocrystal, or prodrug thereof, and is added at a sufficient concentration to block AKT signaling. In another embodiment, the AKT pathway inhibitor is AT13148, or a pharmaceutically acceptable salt, solvate, hydrate, cocrystal, or prodrug thereof, and is added at a sufficient concentration to block AKT signaling. In another embodiment, the AKT pathway inhibitor is MK-2206, or a pharmaceutically acceptable salt, solvate, hydrate, cocrystal, or prodrug thereof, family member and is added at a sufficient concentration to block AKT signaling. In an embodiment, the AKT pathway inhibitor is LY294002, or a pharmaceutically acceptable salt, solvate, hydrate, cocrystal, or prodrug thereof, family member and is added at a sufficient concentration to block AKT signaling.

In some embodiments, an AKT pathway inhibitor is added to the rapid second expansion step. In an embodiment the AKT pathway inhibitor is afuresertib, or a pharmaceutically acceptable salt, solvate, hydrate, cocrystal, or prodrug thereof, and is added at a sufficient concentration to attenuate AKT signaling. In another embodiment, the AKT pathway inhibitor is uprosertib, or a pharmaceutically acceptable salt, solvate, hydrate, cocrystal, or prodrug thereof, and is added at a sufficient concentration to attenuate AKT signaling. In another embodiment, the AKT pathway is ipatasertib, or a pharmaceutically acceptable salt, solvate, hydrate, cocrystal, or prodrug thereof, and is added at a sufficient concentration to block AKT signaling. In another embodiment, the AKT pathway inhibitor is AT7867, or a pharmaceutically acceptable salt, solvate, hydrate, cocrystal, or prodrug thereof, and is added at a sufficient concentration to block AKT signaling. In another embodiment, the AKT pathway inhibitor is AT13148, or a pharmaceutically acceptable salt, solvate, hydrate, cocrystal, or prodrug thereof, and is added at a sufficient concentration to block AKT signaling. In another embodiment, the AKT pathway inhibitor is MK-2206, or a pharmaceutically acceptable salt, solvate, hydrate, cocrystal, or prodrug thereof, family member and is added at a sufficient concentration to block AKT signaling. In an embodiment, the AKT pathway inhibitor is LY294002, or a pharmaceutically acceptable salt, solvate, hydrate, cocrystal, or prodrug thereof, family member and is added at a sufficient concentration to block AKT signaling.

In an embodiment the AKT pathway inhibitor is added to the second culture medium at a concentration of between 0.01 µM and 1000 µM. In an embodiment the AKT pathway inhibitor is added to the second culture medium at a concentration of between 0.01 µM and 500 µM. In an embodiment the AKT pathway inhibitor is added to the second culture medium at a concentration of between 0.01 µM and 100 µM. In an embodiment AKT pathway inhibitor is added to the second culture medium at a concentration of between 0.01 µM and 50 µM. In an embodiment AKT pathway inhibitor is added to the second culture medium at a concentration of between 0.01 µM and 50 µM. In an embodiment AKT pathway inhibitor is added to the second culture medium at a concentration of between 0.01 µM and 25 µM.

In an embodiment the AKT pathway inhibitor is added to the rapid second expansion step at a concentration of between 0.01 µM and 1000 µM. In an embodiment the AKT pathway inhibitor is added to the rapid second expansion step at a concentration of between 0.01 µM and 500 µM. In an embodiment the AKT pathway inhibitor is added to the rapid second expansion step at a concentration of between 0.01 µM and 100 µM. In an embodiment AKT pathway inhibitor is added to the rapid second expansion step at a concentration of between 0.01 µM and 50 µM. In an embodiment AKT pathway inhibitor is added to the rapid second expansion step at a concentration of between 0.01 µM and 50 µM. In an embodiment AKT pathway inhibitor is added to the rapid second expansion step at a concentration of between 0.01 µM and 25 µM.

In an embodiment the AKT pathway inhibitor is added to the second culture medium at a concentration wherein the targeted enzyme is at least 95% occupied at steady state. In an embodiment the AKT pathway inhibitor is added to the second culture medium at a concentration wherein the targeted enzyme is at least 85% occupied at steady state. In an embodiment the AKT pathway inhibitor is added to the second culture medium at a concentration wherein the targeted enzyme is at least 75% occupied at steady state. In an embodiment the AKT pathway inhibitor is added to the second culture medium at a concentration wherein the targeted enzyme is at least 50% occupied at steady state.

In an embodiment the AKT pathway inhibitor is added to the rapid second expansion step at a concentration wherein the targeted enzyme is at least 95% occupied at steady state. In an embodiment the AKT pathway inhibitor is added to the rapid second expansion step at a concentration wherein the targeted enzyme is at least 85% occupied at steady state. In an embodiment the AKT pathway inhibitor is added to the rapid second expansion step at a concentration wherein the targeted enzyme is at least 75% occupied at steady state. In an embodiment the AKT pathway inhibitor is added to the rapid second expansion step at a concentration wherein the targeted enzyme is at least 50% occupied at steady state.

In some embodiments the AKT pathway inhibitor is added to the second culture medium at a concentration per 100,000 cells selected from the group consisting of 10 nM, 20 nM, 25 nM, 30 nM, 50 nM, 60 nM, 75 nM, 80 nM, 90 nM, 100 nM, 125 nM, 150 nM, 175 nM, 200 nM, 225 nM, 250 nM, 275 nM, 300 nM, 325 nM, 375 nM, 400 nM, 450 nM, 500 nM, 550 nM, 600 nM, 625 nM, 650 nM, 675 nM, 700 nM, 725 nM, 750 nM, 775 nM, 800 nM, 825 nM, 850 nM, 875 nM, 900 nM, 925 nM, 950 nM, 975 nM, 1000 nM, 1100 nM, 1200 nM, 1300 nM, 1400 nM, 1500 nM, 1600 nM, 1700 nM, 1800 nM, 1900 nM, 2000 nM, 2.5 µM, 3 µM, 4 µM, 5 µM, 6 µM, 7 µM, 8 µM, 9 µM, 10 µM, 12.5 µM, 15 µM, 18 µM, 20 µM, and 25 µM.

In some embodiments the AKT pathway inhibitor is added to the rapid second expansion step at a concentration per 100,000 cells selected from the group consisting of 10 nM, 20 nM, 25 nM, 30 nM, 50 nM, 60 nM, 75 nM, 80 nM, 90 nM, 100 nM, 125 nM, 150 nM, 175 nM, 200 nM, 225 nM, 250 nM, 275 nM, 300 nM, 325 nM, 375 nM, 400 nM, 450 nM, 500 nM, 550 nM, 600 nM, 625 nM, 650 nM, 675 nM, 700 nM, 725 nM, 750 nM, 775 nM, 800 nM, 825 nM, 850 nM, 875 nM, 900 nM, 925 nM, 950 nM, 975 nM, 1000 nM, 1100 nM, 1200 nM, 1300 nM, 1400 nM, 1500 nM, 1600 nM, 1700 nM, 1800 nM, 1900 nM, 2000 nM, 2.5 µM, 3 µM, 4 µM, 5 µM, 6 µM, 7 µM, 8 µM, 9 µM, 10 µM, 12.5 µM, 15 µM, 18 µM, 20 µM, and 25 µM.

In one embodiment, an AKT pathway inhibitor is added to the first expansion culture medium. In a further embodiment an AKT pathway inhibitor is added to the first expansion culture medium and is present at a sufficient concentration to attenuate AKT pathway signaling. In an embodiment, the AKT pathway inhibitor is added to the first cell culture medium during the initial expansion at an interval selected from the group consisting of every day, every two days, every three days, every four days, every five days, every six days, every seven days, and every two weeks.

In another embodiment, an AKT pathway inhibitor is added to the second expansion culture medium. In a further embodiment an AKT pathway inhibitor is added to the second expansion culture medium and is present at a sufficient concentration to attenuate AKT signaling. In a further embodiment an AKT pathway inhibitor is added to the second expansion culture medium and is present at a sufficient concentration to attenuate AKT signaling.

It is understood that an AKT pathway inhibitor is suitable for use in the several TIL manufacturing methods known to the art. It is further understood that an AKT pathway inhibitor is suitable for use in the TIL manufacturing methods disclosed herein. For the avoidance of doubt, AKT pathway inhibitors may comprise the Gen 3 process step B culture medium. For the avoidance of doubt, AKT pathway inhibitors may comprise the Gen 3 process step D culture medium.

Option Cell Viability Analyses

Optionally, a cell viability assay can be performed after the first expansion (sometimes referred to as the initial bulk expansion), using standard assays known in the art. For example, a trypan blue exclusion assay can be done on a sample of the bulk TILs, which selectively labels dead cells and allows a viability assessment. Other assays for use in testing viability can include but are not limited to the Alamar blue assay; and the MTT assay.

Cell Counts, Viability, Flow Cytometry

In some embodiments, cell counts and/or viability are measured. The expression of markers such as but not limited CD3, CD4, CD8, and CD56, as well as any other disclosed or described herein, can be measured by flow cytometry with antibodies, for example but not limited to those commercially available from BD Bio-sciences (BD Biosciences, San Jose, CA) using a FACSCanto™ flow cytometer (BD Biosciences). The cells can be counted manually using a disposable c-chip hemocytometer (VWR, Batavia, IL) and viability can be assessed using any method known in the art, including but not limited to trypan blue staining. The cell viability can also be assayed based on U.S. application Ser. No. 15/863,634, "Processes for Production of Tumor Infiltrating Lymphocytes and Uses of Same in Immunotherapy," incorporated by reference herein in its entirety.

In some cases, the bulk TIL population can be cryopreserved immediately, using the protocols discussed below. Alternatively, the bulk TIL population can be subjected to REP and then cryopreserved as discussed below. Similarly, in the case where genetically modified TILs will be used in therapy, the bulk or REP TIL populations can be subjected to genetic modifications for suitable treatments.

According to the present disclosure, a method for assaying TILs for viability and/or further use in administration to a subject. In some embodiments, the method for assay tumor infiltrating lymphocytes (TILs) comprises:

(i) obtaining a first population of TILs;
(ii) performing a first expansion by culturing the first population of TILs in a cell culture medium comprising IL-2, and optionally OKT-3, to produce a second population of TILs; and
(iii) performing a second expansion by supplementing the cell culture medium of the second population of TILs with additional IL-2, OKT-3, and antigen presenting cells (APCs), to produce a third population of TILs, wherein the third population of TILs is at least 50-fold greater in number than the second population of TILs;
(iv) harvesting, washing, and cryopreserving the third population of TILs;
(v) storing the cryopreserved TILs at a cryogenic temperature;
(vi) thawing the third population of TILs to provide a thawed third population of TILs; and
(vii) performing an additional second expansion of a portion of the thawed third population of TILs by supplementing the cell culture medium of the third population with IL-2, OKT-3, and APCs for an additional expansion period (sometimes referred to as a reREP period) of at least 3 days, wherein the third expansion is performed to obtain a fourth population of TILs, wherein the number of TILs in the fourth population of TILs is compared to the number of TILs in the third population of TILs to obtain a ratio;
(viii) determining based on the ratio in step (vii) whether the thawed population of TILs is suitable for administration to a patient;
(ix) administering a therapeutically effective dosage of the thawed third population of TILs to the patient when the ratio of the number of TILs in the fourth population of TILs to the number of TILs in the third population of TILs is determined to be greater than 5:1 in step (viii).

In some embodiments, the TILs are assayed for viability after step (vii).

The present disclosure also provides further methods for assaying TILs. In some embodiments, the disclosure provides a method for assaying TILs comprising:

(i) obtaining a portion of a first population of cryopreserved TILs;

(ii) thawing the portion of the first population of cryopreserved TILs;

(iii) performing a first expansion by culturing the portion of the first population of TILs in a cell culture medium comprising IL-2, OKT-3, and antigen presenting cells (APCs) for an additional expansion period (sometimes referred to as a reREP period) of at least 3 days, to produce a second population of TILs, wherein the portion from the first population of TILs is compared to the second population of TILs to obtain a ratio of the number of TILs, wherein the ratio of the number of TILs in the second population of TILs to the number of TILs in the portion of the first population of TILs is greater than 5:1;

(iv) determining based on the ratio in step (iii) whether the first population of TILs is suitable for use in therapeutic administration to a patient;

(v) determining the first population of TILs is suitable for use in therapeutic administration when the ratio of the number of TILs in the second population of TILs to the number of TILs in the first population of TILs is determined to be greater than 5:1 in step (iv).

In some embodiments, the ratio of the number of TILs in the second population of TILs to the number of TILs in the portion of the first population of TILs is greater than 50:1.

In some embodiments, the method further comprises performing expansion of the entire first population of cryopreserved TILs from step (i) according to the methods as described in any of the embodiments provided herein.

In some embodiments, the method further comprises administering the entire first population of cryopreserved TILs from step (i) to the patient.

Cell Culture Media

In an embodiment, a method for expanding TILs, including those discussed above as well as exemplified in FIG. 1, may include using about 5,000 mL to about 25,000 mL of cell medium, about 5,000 mL to about 10,000 mL of cell medium, or about 5,800 mL to about 8,700 mL of cell medium. In some embodiments, the media is a serum free medium. In some embodiments, the media in the first expansion is serum free. In some embodiments, the media in the second expansion is serum free. In some embodiments, the media in the first expansion and the second are both serum free. In an embodiment, expanding the number of TILs uses no more than one type of cell culture medium. Any suitable cell culture medium may be used, e.g., AIM-V cell medium (L-glutamine, 50 µM streptomycin sulfate, and 10 µM gentamicin sulfate) cell culture medium (Invitrogen, Carlsbad CA). In this regard, the inventive methods advantageously reduce the amount of medium and the number of types of medium required to expand the number of TIL. In an embodiment, expanding the number of TIL may comprise feeding the cells no more frequently than every third or fourth day. Expanding the number of cells in a gas permeable container simplifies the procedures necessary to expand the number of cells by reducing the feeding frequency necessary to expand the cells.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME or PME; also known as 2-mercaptoethanol, CAS 60-24-2).

In an embodiment, the duration of the method comprising obtaining a tumor tissue sample from the mammal; culturing the tumor tissue sample in a first gas permeable container containing cell medium therein; obtaining TILs from the tumor tissue sample; expanding the number of TILs in a second gas permeable container containing cell medium for a duration of about 7 to 14 days, for example, about 11 days. In some embodiments pre-REP is about 7 to 14 days, for example, about 11 days. In some embodiments, REP is about 7 to 14 days, for example, about 11 days.

In an embodiment, TILs are expanded in gas-permeable containers. Gas-permeable containers have been used to expand TILs using PBMCs using methods, compositions, and devices known in the art, including those described in U.S. Patent Application Publication No. 2005/0106717 A1, the disclosures of which are incorporated herein by reference. In an embodiment, TILs are expanded in gas-permeable bags. In an embodiment, TILs are expanded using a cell expansion system that expands TILs in gas permeable bags, such as the Xuri Cell Expansion System W25 (GE Healthcare). In an embodiment, TILs are expanded using a cell expansion system that expands TILs in gas permeable bags, such as the WAVE Bioreactor System, also known as the Xuri Cell Expansion System W5 (GE Healthcare). In an embodiment, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, and about 10 L.

In an embodiment, TILs can be expanded in G-Rex flasks (commercially available from Wilson Wolf Manufacturing). Such embodiments allow for cell populations to expand from about $5\times10^5$ cells/cm$^2$ to between $10\times10^6$ and $30\times10^6$ cells/cm$^2$. In an embodiment this is without feeding. In an embodiment, this is without feeding so long as medium resides at a height of about 10 cm in the G-Rex flask. In an embodiment this is without feeding but with the addition of one or more cytokines. In an embodiment, the cytokine can be added as a bolus without any need to mix the cytokine with the medium. Such containers, devices, and methods are known in the art and have been used to expand TILs, and include those described in U.S. Patent Application Publication No. US 2014/0377739A1, International Publication No. WO 2014/210036 A1, U.S. Patent Application Publication No. us 2013/0115617 A1, International Publication No. WO 2013/188427 A1, U.S. Patent Application Publication No. US 2011/0136228 A1, U.S. Pat. No. 8,809,050 B2, International publication No. WO 2011/072088 A2, U.S. Patent Application Publication No. US 2016/0208216 A1, U.S. Patent Application Publication No. US 2012/0244133 A1, International Publication No. WO 2012/129201 A1, U.S. Patent Application Publication No. US 2013/0102075 A1, U.S. Pat. No. 8,956,860 B2, International Publication No. WO 2013/173835 A1, U.S. Patent Application Publication No. US 2015/0175966 A1, the disclosures of which are incorporated herein by reference. Such processes are also described in Jin et al., *J. Immunotherapy*, 2012, 35:283-292.

TIL Manufacturing Processes—Gen 3 Process

Without being limited to any particular theory, it is believed that the priming first expansion that primes an activation of T cells followed by the rapid second expansion that boosts the activation of T cells as described in the methods of the invention allows the preparation of expanded T cells that retain a "younger" phenotype, and as such the expanded T cells of the invention are expected to exhibit greater cytotoxicity against cancer cells than T cells expanded by other methods. In particular, it is believed that an activation of T cells that is primed by exposure to an anti-CD3 antibody (e.g. OKT-3), IL-2 and optionally antigen-presenting cells (APCs) and then boosted by subsequent exposure to additional anti-CD-3 antibody (e.g. OKT-3), IL-2 and APCs as taught by the methods of the invention limits or avoids the maturation of T cells in culture, yielding a population of T cells with a less mature phenotype, which T cells are less exhausted by expansion in culture and exhibit greater cytotoxicity against cancer cells.

The Gen 3 process is also described in U.S. 62/755,954, filed on Nov. 5, 2018, and is incorporated by reference herein in its entirety.

In some embodiments, the rapid second expansion is performed after the activation of T cells effected by the priming first expansion begins to decrease, abate, decay or subside.

In some embodiments, the rapid second expansion is performed after the activation of T cells effected by the priming first expansion has decreased by at or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

In some embodiments, the rapid second expansion is performed after the activation of T cells effected by the priming first expansion has decreased by a percentage in the range of at or about 1% to 100%.

In some embodiments, the rapid second expansion is performed after the activation of T cells effected by the priming first expansion has decreased by a percentage in the range of at or about 1% to 10%, 10% to 20%, 20% to 30%, 30% to 40%, 40% to 50%, 50% to 60%, 60% to 70%, 70% to 80%, 80% to 90%, or 90% to 100%.

In some embodiments, the rapid second expansion is performed after the activation of T cells effected by the priming first expansion has decreased by at least at or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%.

In some embodiments, the rapid second expansion is performed after the activation of T cells effected by the priming first expansion has decreased by up to at or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%.

In some embodiments, the decrease in the activation of T cells effected by the priming first expansion is determined by a reduction in the amount of interferon gamma released by the T cells in response to stimulation with antigen.

In some embodiments, the priming first expansion of T cells is performed during a period of up to at or about 7 days.

In some embodiments, the priming first expansion of T cells is performed during a period of up to at or about 1 day, 2 days, 3 days, 4 days, 5 days, 6 days, or 7 days.

In some embodiments, the priming first expansion of T cells is performed during a period of 1 day, 2 days, 3 days, 4 days, 5 days, 6 days, or 7 days.

In some embodiments, the rapid second expansion of T cells is performed during a period of up to at or about 11 days.

In some embodiments, the rapid second expansion of T cells is performed during a period of up to at or about 1 day, 2 days, 3 days, 4 days, 5 days, 6 days, 7 days, 8 days, 9 days, 10 days or 11 days.

In some embodiments, the rapid second expansion of T cells is performed during a period of 1 day, 2 days, 3 days, 4 days, 5 days, 6 days, 7 days, 8 days, 9 days, 10 days or 11 days.

In some embodiments, the priming first expansion of T cells is performed during a period of from at or about 1 day to at or about 7 days and the rapid second expansion of T cells is performed during a period of from at or about 1 day to at or about 11 days.

In some embodiments, the priming first expansion of T cells is performed during a period of up to at or about 1 day, 2 days, 3 days, 4 days, 5 days, 6 days, or 7 days and the rapid second expansion of T cells is performed during a period of up to at or about 1 day, 2 days, 3 days, 4 days, 5 days, 6 days, 7 days, 8 days, 9 days, 10 days or 11 days.

In some embodiments, the priming first expansion of T cells is performed during a period of from at or about 1 day to at or about 7 days and the rapid second expansion of T cells is performed during a period of from at or about 1 day to at or about 9 days.

In some embodiments, the priming first expansion of T cells is performed during a period of 7 days and the rapid second expansion of T cells is performed during a period of 9 days.

In some embodiments, the T cells are tumor infiltrating lymphocytes (TILs).

In some embodiments, the T cells are marrow infiltrating lymphocytes (MILs).

In some embodiments, the T cells are peripheral blood lymphocytes (PBLs).

In some embodiments, the T cells are obtained from a donor suffering from a cancer.

In some embodiments, the T cells are TILs obtained from a tumor excised from a patient suffering from a cancer.

In some embodiments, the T cells are MILs obtained from bone marrow of a patient suffering from a hematologic malignancy.

In some embodiments, the T cells are PBLs obtained from peripheral blood mononuclear cells (PBMCs) from a donor. In some embodiments, the donor is suffering from a cancer. In some embodiments, the donor is suffering from a hematologic malignancy.

In certain aspects of the present disclosure, immune effector cells, e.g., T cells, can be obtained from a unit of blood collected from a subject using any number of techniques known to the skilled artisan, such as FICOLL separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and, optionally, to place the cells in an appropriate buffer or media for subsequent processing steps. In one embodiment, the cells are washed with phosphate buffered saline (PBS). In an alternative embodiment, the wash solution lacks calcium and may lack magnesium or may lack many if not all divalent cations. In one aspect, T cells are isolated from peripheral blood lymphocytes by lysing the red blood cells and depleting the monocytes, for example, by centrifugation through a PERCOLL gradient or by counterflow centrifugal elutriation.

In some embodiments, the T cells are PBLs separated from whole blood or apheresis product enriched for lymphocytes from a donor. In some embodiments, the donor is suffering from a cancer. In some embodiments, the donor is suffering from a hematologic malignancy. In some embodiments, the PBLs are isolated from whole blood or apheresis product enriched for lymphocytes by using positive or negative selection methods, i.e., removing the PBLs using a marker(s), e.g., CD3+CD45+, for T cell phenotype, or removing non-T cell phenotype cells, leaving PBLs. In other embodiments, the PBLs are isolated by gradient centrifugation. Upon isolation of PBLs from donor tissue, the priming first expansion of PBLs can be initiated by seeding a suitable number of isolated PBLs (in some embodiments, approximately 1×107 PBLs) in the priming first expansion culture according to the priming first expansion step of any of the methods described herein.

Figure 38:
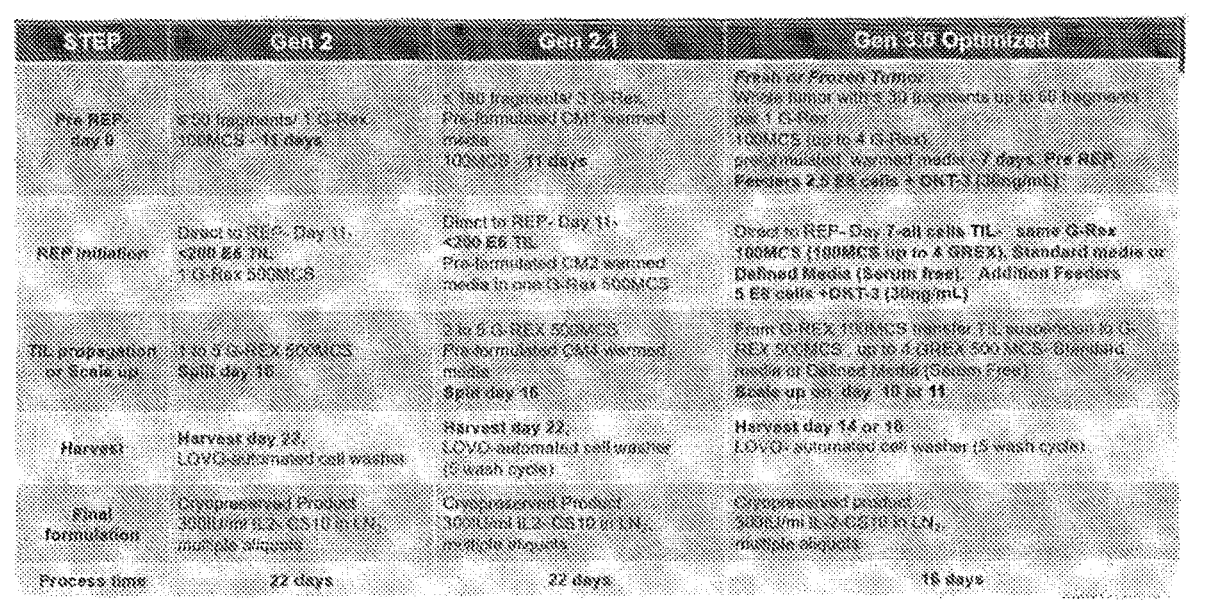

An exemplary TIL process known as process 3 (also referred to herein as "GEN3," "process 3," "Gen 3," or "Gen 3 Process") containing some of these features is depicted in FIG. 8 (in particular, e.g., FIG. 8B), and some of the advantages of this embodiment of the present invention over process 2A are described in FIGS. 8, 9, 38, and 39 (in particular, e.g., FIG. 8B). Two embodiments of process 3 are shown in FIGS. 8 and 38 (in particular, e.g., FIG. 8B). Process 2A or Gen 2 is also described in U.S. Patent Publication No. 2018/0280436, incorporated by reference herein in its entirety.

As discussed and generally outlined herein, TILs are taken from a patient sample and manipulated to expand their number prior to transplant into a patient using the TIL expansion process described herein and referred to as Gen 3. In some embodiments, the TILs may be optionally genetically manipulated as discussed below. In some embodiments, the TILs may be cryopreserved prior to or after expansion. Once thawed, they may also be restimulated to increase their metabolism prior to infusion into a patient.

In some embodiments, the priming first expansion (including processes referred herein as the pre-Rapid Expansion (Pre-REP), as well as processes shown in FIG. 8 (in particular, e.g., FIG. 8B) as Step B) is shortened to 1 to 7 days and the rapid second expansion (including processes referred to herein as Rapid Expansion Protocol (REP) as well as processes shown in FIG. 8 (in particular, e.g., FIG. 8B) as Step D) is shortened to 1 to 9 days, as discussed in detail below as well as in the examples and figures. In some embodiments, the priming first expansion (for example, an expansion described as Step B in FIG. 8 (in particular, e.g., FIG. 8B)) is shortened to 7 days and the rapid second expansion (for example, an expansion as described in Step D in FIG. 8 (in particular, e.g., FIG. 8B)) is 7 to 9 days. In some embodiments, the combination of the priming first expansion and rapid second expansion (for example, expansions described as Step B and Step D in FIG. 8 (in particular, e.g., FIG. 8B)) is 14-16 days, as discussed in detail below and in the examples and figures. Particularly, it is considered that certain embodiments of the present invention comprise a priming first expansion step in which TILs are activated by exposure to an anti-CD3 antibody, e.g., OKT-3 in the presence of IL-2 or exposure to an antigen in the presence of at least IL-2 and an anti-CD3 antibody e.g. OKT-3. In certain embodiments, the TILs which are activated in the priming first expansion step as described above are a first population of TILs i.e. which are a primary cell population.

The "Step" Designations A, B, C, etc., below are in reference to the non-limiting example in FIG. 8 (in particular, e.g., FIG. 8B) and in reference to certain non-limiting embodiments described herein. The ordering of the Steps below and in FIG. 8 (in particular, e.g., FIG. 8B) is exemplary and any combination or order of steps, as well as additional steps, repetition of steps, and/or omission of steps is contemplated by the present application and the methods disclosed herein.

Step A: Obtain Patient Tumor Sample

In general, TILs are initially obtained from a patient tumor sample ("primary TILs") or from circulating lymphocytes, such as peripheral blood lymphocytes, and then expanded into a larger population for further manipulation as described herein, optionally cryopreserved, and optionally evaluated for phenotype and metabolic parameters as an indication of TIL health.

A patient tumor sample may be obtained using methods known in the art, generally via surgical resection, needle biopsy or other means for obtaining a sample that contains a mixture of tumor and TIL cells. In general, the tumor sample may be from any solid tumor, including primary tumors, invasive tumors or metastatic tumors. The tumor sample may also be a liquid tumor, such as a tumor obtained from a hematological malignancy. The solid tumor may be of any cancer type, including, but not limited to, breast, pancreatic, prostate, colorectal, lung, brain, renal, stomach, and skin (including but not limited to squamous cell carcinoma, basal cell carcinoma, and melanoma). In some embodiments, the cancer is selected from cervical cancer, head and neck cancer (including, for example, head and neck squamous cell carcinoma (HNSCC)), glioblastoma (GBM), gastrointestinal cancer, ovarian cancer, sarcoma, pancreatic cancer, bladder cancer, breast cancer, triple negative breast cancer, and non-small cell lung carcinoma. In some embodiments, useful TILs are obtained from malignant melanoma tumors, as these have been reported to have particularly high levels of TILs.

Once obtained, the tumor sample is generally fragmented using sharp dissection into small pieces of between 1 to about 8 mm$^3$, with from about 2-3 mm$^3$ being particularly useful. The TILs are cultured from these fragments using enzymatic tumor digests. Such tumor digests may be produced by incubation in enzymatic media (e.g., Roswell Park Memorial Institute (RPMI) 1640 buffer, 2 mM glutamate, 10 μg/mL gentamicin, 30 units/mL of DNase and 1.0 mg/mL of collagenase) followed by mechanical dissociation (e.g., using a tissue dissociator). Tumor digests may be produced by placing the tumor in enzymatic media and mechanically dissociating the tumor for approximately 1 minute, followed by incubation for 30 minutes at 37° C. in 5% $CO_2$, followed by repeated cycles of mechanical dissociation and incubation under the foregoing conditions until only small tissue pieces are present. At the end of this process, if the cell suspension contains a large number of red blood cells or dead cells, a density gradient separation using FICOLL branched hydrophilic polysaccharide may be performed to remove these cells. Alternative methods known in the art may be used, such as those described in U.S. Patent Application Publication No. 2012/0244133 A1, the disclosure of which is incorporated by reference herein. Any of the foregoing methods may be used in any of the embodiments described herein for methods of expanding TILs or methods treating a cancer.

In general, the cell suspension obtained from the tumor is called a "primary cell population" or a "freshly obtained" or a "freshly isolated" cell population. In certain embodiments, the freshly obtained cell population of TILs is exposed to a cell culture medium comprising antigen presenting cells, IL-12 and OKT-3.

In some embodiments, fragmentation includes physical fragmentation, including, for example, dissection as well as digestion. In some embodiments, the fragmentation is physical fragmentation. In some embodiments, the fragmentation is dissection. In some embodiments, the fragmentation is by digestion. In some embodiments, TILs can be initially cultured from enzymatic tumor digests and tumor fragments obtained from patients. In an embodiment, TILs can be initially cultured from enzymatic tumor digests and tumor fragments obtained from patients.

In some embodiments, where the tumor is a solid tumor, the tumor undergoes physical fragmentation after the tumor sample is obtained in, for example, Step A (as provided in FIG. 8 (in particular, e.g., FIG. 8B)). In some embodiments, the fragmentation occurs before cryopreservation. In some embodiments, the fragmentation occurs after cryopreservation. In some embodiments, the fragmentation occurs after obtaining the tumor and in the absence of any cryopreservation. In some embodiments, the step of fragmentation is an in vitro or ex-vivo process. In some embodiments, the tumor is fragmented and 10, 20, 30, 40 or more fragments or pieces are placed in each container for the priming first expansion. In some embodiments, the tumor is fragmented and 30 or 40 fragments or pieces are placed in each container for the priming first expansion. In some embodiments, the tumor is fragmented and 40 fragments or pieces are placed in each container for the priming first expansion. In some embodiments, the multiple fragments comprise about 4 to about 50 fragments, wherein each fragment has a volume of about 27 $mm^3$. In some embodiments, the multiple fragments comprise about 30 to about 60 fragments with a total volume of about 1300 $mm^3$ to about 1500 $mm^3$. In some embodiments, the multiple fragments comprise about 50 fragments with a total volume of about 1350 $mm^3$. In some embodiments, the multiple fragments comprise about 50 fragments with a total mass of about 1 gram to about 1.5 grams. In some embodiments, the multiple fragments comprise about 4 fragments.

In some embodiments, the TILs are obtained from tumor fragments. In some embodiments, the tumor fragment is obtained by sharp dissection. In some embodiments, the tumor fragment is between about 1 $mm^3$ and 10 $mm^3$. In some embodiments, the tumor fragment is between about 1 $mm^3$ and 8 $mm^3$. In some embodiments, the tumor fragment is about 1 $mm^3$. In some embodiments, the tumor fragment is about 2 $mm^3$. In some embodiments, the tumor fragment is about 3 $mm^3$. In some embodiments, the tumor fragment is about 4 $mm^3$. In some embodiments, the tumor fragment is about 5 $mm^3$. In some embodiments, the tumor fragment is about 6 $mm^3$. In some embodiments, the tumor fragment is about 7 $mm^3$. In some embodiments, the tumor fragment is about 8 $mm^3$. In some embodiments, the tumor fragment is about 9 $mm^3$. In some embodiments, the tumor fragment is about 10 $mm^3$. In some embodiments, the tumor fragments are 1-4 mm×1-4 mm×1-4 mm. In some embodiments, the tumor fragments are 1 mm×1 mm×1 mm. In some embodiments, the tumor fragments are 2 mm×2 mm×2 mm. In some embodiments, the tumor fragments are 3 mm×3 mm×3 mm. In some embodiments, the tumor fragments are 4 mm×4 mm×4 mm.

In some embodiments, the tumors are fragmented in order to minimize the amount of hemorrhagic, necrotic, and/or fatty tissues on each piece. In some embodiments, the tumors are fragmented in order to minimize the amount of hemorrhagic tissue on each piece. In some embodiments, the tumors are fragmented in order to minimize the amount of necrotic tissue on each piece. In some embodiments, the tumors are fragmented in order to minimize the amount of fatty tissue on each piece. In certain embodiments, the step of fragmentation of the tumor is an in vitro or ex-vivo method.

In some embodiments, the tumor fragmentation is performed in order to maintain the tumor internal structure. In some embodiments, the tumor fragmentation is performed without preforming a sawing motion with a scalpel. In some embodiments, the TILs are obtained from tumor digests. In some embodiments, tumor digests were generated by incubation in enzyme media, for example but not limited to RPMI 1640, 2 mM GlutaMAX, 10 μg/mL gentamicin, 30 U/mL DNase, and 1.0 mg/mL collagenase, followed by mechanical dissociation (GentleMACS, Miltenyi Biotec, Auburn, CA). After placing the tumor in enzyme media, the tumor can be mechanically dissociated for approximately 1 minute. The solution can then be incubated for 30 minutes at 37° C. in 5% $CO_2$ and it then mechanically disrupted again for approximately 1 minute. After being incubated again for 30 minutes at 37° C. in 5% $CO_2$, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% $CO_2$. In some embodiments, at the end of the final incubation if the cell suspension contained a large number of red blood cells or dead cells, a density gradient separation using Ficoll can be performed to remove these cells.

In some embodiments, the cell suspension prior to the priming first expansion step is called a "primary cell population" or a "freshly obtained" or "freshly isolated" cell population.

In some embodiments, cells can be optionally frozen after sample isolation (e.g., after obtaining the tumor sample and/or after obtaining the cell suspension from the tumor sample) and stored frozen prior to entry into the expansion described in Step B, which is described in further detail below, as well as exemplified in FIG. 8 (in particular, e.g., FIG. 8B).

Methods of Expanding Peripheral Blood Lymphocytes (PBLs) from Peripheral Blood

PBL Method 1. In an embodiment of the invention, PBLs are expanded using the processes described herein. In an embodiment of the invention, the method comprises obtaining a PBMC sample from whole blood. In an embodiment, the method comprises enriching T-cells by isolating pure T-cells from PBMCs using negative selection of a non-CD19+ fraction. In an embodiment, the method comprises enriching T-cells by isolating pure T-cells from PBMCs using magnetic bead-based negative selection of a non-CD19+ fraction.

In an embodiment of the invention, PBL Method 1 is performed as follows: On Day 0, a cryopreserved PBMC sample is thawed and PBMCs are counted. T-cells are isolated using a Human Pan T-Cell Isolation Kit and LS columns (Miltenyi Biotec).

PBL Method 2. In an embodiment of the invention, PBLs are expanded using PBL Method 2, which comprises obtaining a PBMC sample from whole blood. The T-cells from the PBMCs are enriched by incubating the PBMCs for at least three hours at 37° C. and then isolating the non-adherent cells.

In an embodiment of the invention, PBL Method 2 is performed as follows: On Day 0, the cryopreserved PMBC sample is thawed and the PBMC cells are seeded at 6 million cells per well in a 6 well plate in CM-2 media and incubated for 3 hours at 37 degrees Celsius. After 3 hours, the non-adherent cells, which are the PBLs, are removed and counted.

PBL Method 3. In an embodiment of the invention, PBLs are expanded using PBL Method 3, which comprises obtaining a PBMC sample from peripheral blood. B-cells are isolated using a CD19+ selection and T-cells are selected using negative selection of the non-CD19+ fraction of the PBMC sample.

In an embodiment of the invention, PBL Method 3 is performed as follows: On Day 0, cryopreserved PBMCs derived from peripheral blood are thawed and counted. CD19+ B-cells are sorted using a CD19 Multisort Kit, Human (Miltenyi Biotec). Of the non-CD19+ cell fraction, T-cells are purified using the Human Pan T-cell Isolation Kit and LS Columns (Miltenyi Biotec).

In an embodiment, PBMCs are isolated from a whole blood sample. In an embodiment, the PBMC sample is used as the starting material to expand the PBLs. In an embodiment, the sample is cryopreserved prior to the expansion process. In another embodiment, a fresh sample is used as the starting material to expand the PBLs. In an embodiment of the invention, T-cells are isolated from PBMCs using methods known in the art. In an embodiment, the T-cells are isolated using a Human Pan T-cell isolation kit and LS columns. In an embodiment of the invention, T-cells are isolated from PBMCs using antibody selection methods known in the art, for example, CD19 negative selection.

In an embodiment of the invention, the PBMC sample is incubated for a period of time at a desired temperature effective to identify the non-adherent cells. In an embodiment of the invention, the incubation time is about 3 hours. In an embodiment of the invention, the temperature is about 370 Celsius. The non-adherent cells are then expanded using the process described above.

In some embodiments, the PBMC sample is from a subject or patient who has been optionally pre-treated with a regimen comprising a kinase inhibitor or an ITK inhibitor. In some embodiments, the tumor sample is from a subject or patient who has been pre-treated with a regimen comprising a kinase inhibitor or an ITK inhibitor. In some embodiments, the PBMC sample is from a subject or patient who has been pre-treated with a regimen comprising a kinase inhibitor or an ITK inhibitor, has undergone treatment for at least 1 month, at least 2 months, at least 3 months, at least 4 months, at least 5 months, at least 6 months, or 1 year or more. In another embodiment, the PBMCs are derived from a patient who is currently on an ITK inhibitor regimen, such as ibrutinib.

In some embodiments, the PBMC sample is from a subject or patient who has been pre-treated with a regimen comprising a kinase inhibitor or an ITK inhibitor and is refractory to treatment with a kinase inhibitor or an ITK inhibitor, such as ibrutinib.

In some embodiments, the PBMC sample is from a subject or patient who has been pre-treated with a regimen comprising a kinase inhibitor or an ITK inhibitor but is no longer undergoing treatment with a kinase inhibitor or an ITK inhibitor. In some embodiments, the PBMC sample is from a subject or patient who has been pre-treated with a regimen comprising a kinase inhibitor or an ITK inhibitor but is no longer undergoing treatment with a kinase inhibitor or an ITK inhibitor and has not undergone treatment for at least 1 month, at least 2 months, at least 3 months, at least 4 months, at least 5 months, at least 6 months, or at least 1 year or more. In another embodiment, the PBMCs are derived from a patient who has prior exposure to an ITK inhibitor, but has not been treated in at least 3 months, at least 6 months, at least 9 months, or at least 1 year.

In an embodiment of the invention, at Day 0, cells are selected for CD19+ and sorted accordingly. In an embodiment of the invention, the selection is made using antibody binding beads. In an embodiment of the invention, pure T-cells are isolated on Day 0 from the PBMCs.

In an embodiment of the invention, for patients that are not pre-treated with ibrutinib or other ITK inhibitor, 10-15 ml of Buffy Coat will yield about $5 \times 10^9$ PBMC, which, in turn, will yield about $5.5 \times 10^7$ PBLs.

In an embodiment of the invention, for patients that are pre-treated with ibrutinib or other ITK inhibitor, the expansion process will yield about $20 \times 10^9$ PBLs. In an embodiment of the invention, $40.3 \times 10^6$ PBMCs will yield about $4.7 \times 10^5$ PBLs.

In any of the foregoing embodiments, PBMCs may be derived from a whole blood sample, by apheresis, from the buffy coat, or from any other method known in the art for obtaining PBMCs.

Methods of Expanding Marrow Infiltrating Lymphocytes (MILs) from PBMCs Derived from Bone Marrow MIL Method 1. In an embodiment of the invention, a method for expanding MILs from PBMCs derived from bone marrow is described. In an embodiment of the invention, the method is performed over 14 days. In an embodiment, the method comprises obtaining bone marrow PBMCs and cryopreserving the PBMCs. On Day 0, the PBMCs are cultured with antiCD3/antiCD28 antibodies (DynaBeads®) in a 1:1 ratio (beads:cells) and IL-2 at 3000 IU/mL. On Day 4, additional IL-2 is added to the culture at 3000 IU/mL. On Day 7, the culture is again stimulated with antiCD3/antiCD28 antibodies (DynaBeads®) in a 1:1 ratio (beads:cells), and additional IL-2 at 3000 IU/mL is added to the culture. MILs are harvested on Day 14, beads are removed, and MILs are optionally counted and phenotyped.

In an embodiment of the invention, MIL Method 1 is performed as follows: On Day 0, a cryopreserved PBMC sample derived from bone marrow is thawed and the PBMCs are counted. The PBMCs are co-cultured in a GRex 24-well plate at $5 \times 10^5$ cells per well with anti-CD3/anti-CD28 antibodies (DynaBeads®) at a 1:1 ratio in about 8 ml per well of CM-2 cell culture medium (comprised of RPMI-1640, human AB serum, 1-glutamine, 2-mercaptoethanol, gentamicin sulfate, AIM-V media) in the presence of IL-2 at 3000 IU/mL. On Day 4, the cell culture media is exchanged with AIM-V supplemented with additional IL-2 at 3000 IU/mL. On Day 7, the expanded MILs are counted. $1 \times 10^6$ cells per well are transferred to a new GRex 24-well plate and cultured with anti-CD3/anti-CD28 antibodies (DynaBeads®) at a 1:1 ratio in about 8 ml per well of AIM-V media in the presence of IL-2 at 3000 IU/mL. On Day 11, the cell culture media is exchanged from AIM-V to CM-4 (comprised of AIM-V media, 2 mM Glutamax, and 3000 IU/mL IL2). On Day 14, the DynaBeads® are removed using a DynaMag Magnet (DynaMag™15) and the MILs are counted.

MIL Method 2. In an embodiment of the invention, the method is performed over 7 days. In an embodiment, the method comprises obtaining PMBCs derived from bone marrow and cryopreserving the PBMCs. On Day 0, the PBMCs are cultured with antiCD3/antiCD28 antibodies (DynaBeads®) in a 3:1 ratio (beads:cells) and IL-2 at 3000 IU/mL. MILs are harvested on Day 7, beads are removed, and MILs are optionally counted and phenotyped.

In an embodiment of the invention, MIL Method 2 is performed as follows: On Day 0, a cryopreserved PBMC sample is thawed and the PBMCs are counted. The PBMCs are co-cultured in a GRex 24-well plate at $5 \times 10^5$ cells per well with anti-CD3/anti-CD28 antibodies (DynaBeads®) at a 1:1 ratio in about 8 ml per well of CM-2 cell culture medium (comprised of RPMI-1640, human AB serum, 1-glutamine, 2-mercaptoethanol, gentamicin sulfate, AIM-V media) in the presence of IL-2 at 3000 IU/mL. On Day 7, the DynaBeads® are removed using a DynaMag Magnet (DynaMag™15) and the MILs are counted.

MIL Method 3. In an embodiment of the invention, the method comprises obtaining PBMCs from the bone marrow. On Day 0, the PBMCs are selected for CD3+/CD33+/CD20+/CD14+ and sorted, and the non-CD3+/CD33+/CD20+/CD14+ cell fraction is sonicated and a portion of the sonicated cell fraction is added back to the selected cell fraction. IL-2 is added to the cell culture at 3000 IU/mL. On Day 3, the PBMCs are cultured with antiCD3/antiCD28 antibodies (DynaBeads®) in a 1:1 ratio (beads:cells) and IL-2 at 3000 IU/mL. On Day 4, additional IL-2 is added to the culture at 3000 IU/mL. On Day 7, the culture is again stimulated with antiCD3/antiCD28 antibodies (DynaBeads®) in a 1:1 ratio (beads:cells), and additional IL-2 at 3000 IU/ml is added to the culture. On Day 11, IL-2 is added to the culture at 3000 IU/mL. MILs are harvested on Day 14, beads are removed, and MILs are optionally counted and phenotyped.

In an embodiment of the invention, MIL Method 3 is performed as follows: On Day 0, a cryopreserved sample of PBMCs is thawed and PBMCs are counted. The cells are stained with CD3, CD33, CD20, and CD14 antibodies and sorted using a S3e cell sorted (Bio-Rad). The cells are sorted into two fractions—an immune cell fraction (or the MIL fraction) (CD3+CD33+CD20+CD14+) and an AML blast cell fraction (non-CD3+CD33+CD20+CD14+). A number of cells from the AML blast cell fraction that is about equal to the number of cells from the immune cell fraction (or MIL fraction) to be seeded on a Grex 24-well plate is suspended in 100 ul of media and sonicated. In this example, about $2.8 \times 10^4$ to about $3.38 \times 10^5$ cells from the AML blast cell fraction is taken and suspended in 100 µl of CM2 media and then sonicated for 30 seconds. The 100 µl of sonicated AML blast cell fraction is added to the immune cell fraction in a Grex 24-well plate. The immune cells are present in an amount of about $2.8 \times 10^4$ to about $3.38 \times 10^5$ cells per well in about 8 mL per well of CM-2 cell culture medium in the presence of IL-2 at 6000 IU/mL and are cultured with the portion of AML blast cell fraction for about 3 days. On Day 3, anti-CD3/anti-CD28 antibodies (DynaBeads®) at a 1:1 ratio are added to the each well and cultured for about 1 day. On Day 4, the cell culture media is exchanged with AIM-V supplemented with additional IL-2 at 3000 IU/mL. On Day 7, the expanded MILs are counted. About $1.5 \times 10^5$ to $4 \times 10^5$ cells per well are transferred to a new GRex 24-well plate and cultured with anti-CD3/anti-CD28 antibodies (DynaBeads®) at a 1:1 ratio in about 8 ml per well of AIM-V medium in the presence of IL-2 at 3000 IU/mL. On Day 11, the cell culture media is exchanged from AIM-V to CM-4 (supplemented with IL-2 at 3000 IU/mL). On Day 14, the DynaBeads® are removed using a DynaMag Magnet (DynaMag™15) and the MILs are optionally counted.

In an embodiment of the invention, PBMCs are obtained from bone marrow. In an embodiment, the PBMCs are obtained from the bone marrow through apheresis, aspiration, needle biopsy, or other similar means known in the art. In an embodiment, the PBMCs are fresh. In another embodiment, the PBMCs are cryopreserved.

In an embodiment of the invention, the method is performed over about 7 days, about 8 days, about 9 days, about 10 days, about 11 days, about 12 days, about 13 days, or about 14 days. In another embodiment, the method is performed over about 7 days. In another embodiment, the method is performed over about 14 days.

In an embodiment of the invention, the PBMCs are cultured with antiCD3/antiCD28 antibodies. In an embodiment, any available antiCD3/antiCD28 product is useful in the present invention. In an embodiment of the invention, the commercially available product used are DynaBeads®. In an embodiment, the DynaBeads® are cultured with the PBMCs in a ratio of 1:1 (beads:cells). In another embodiment, the antibodies are DynaBeads® cultured with the PBMCs in a ratio of 1.5:1, 2:1, 2.5:1, 3:1, 3.5:1, 4:1, 4.5:1, or 5:1 (beads:cells). In any of the foregoing embodiments, magnetic bead-based selection of an immune cell fraction (or MIL fraction) (CD3+CD33+CD20+CD14+) or an AML blast cell fraction (non-CD3+CD33+CD20+CD14+) is used. In an embodiment of the invention, the antibody culturing steps and/or the step of restimulating cells with antibody is performed over a period of from about 2 to about 6 days, from about 3 to about 5 days, or for about 4 days. In an embodiment of the invention, the antibody culturing step is performed over a period of about 2 days, 3 days, 4 days, 5 days, or 6 days.

In an embodiment of the invention, the ratio of the number of cells from the AML blast cell fraction to the number of cells from the immune cell fraction (or MIL fraction) is about 0.1:1 to about 10:1. In another embodiment, the ratio is about 0.1:1 to about 5:1, about 0.1:1 to about 2:1, or about 1:1. In an embodiment of the invention, the AML blast cell fraction is optionally disrupted to break up cell aggregation. In an embodiment, the AML blast cell fraction is disrupted using sonication, homogenization, cell lysis, vortexing, or vibration. In another embodiment, the AML blast cell fraction is disrupted using sonication. In an embodiment of the invention, the non-CD3+, non-CD33+, non-CD20+, non-CD14+ cell fraction (AML blast fraction) is lysed using a suitable lysis method, including high temperature lysis, chemical lysis (such as organic alcohols), enzyme lysis, and other cell lysis methods known in the art.

In an embodiment of the invention, the cells from AML blast cell fraction are suspended at a concentration of from about $0.2 \times 10^5$ to about $2 \times 10^5$ cells per 100 µL and added to the cell culture with the immune cell fraction. In another embodiment, the concentration is from about $0.5 \times 10^5$ to about $2 \times 10^5$ cells per 100 µL, from about $0.7 \times 10^5$ to about $2 \times 10^5$ cells per 100 µL, from about $1 \times 10^5$ to about $2 \times 10^5$ cells per 100 µL, or from about $1.5 \times 10^5$ to about $2 \times 10^5$ cells per 100 µL.

In an embodiment, the PBMC sample is cultured with IL-2. In an embodiment of the invention, the cell culture medium used for expansion of the MILs comprises IL-2 at a concentration selected from the group consisting of about 100 IU/mL, about 200 IU/mL, about 300 IU/mL, about 400 IU/mL, about 100 IU/mL, about 100 IU/mL, about 100 IU/mL, about 100 IU/mL, about 100 IU/mL, about 500 IU/mL, about 600 IU/mL, about 700 IU/mL, about 800

IU/mL, about 900 IU/mL, about 1,000 IU/mL, about 1,100 IU/mL, about 1,200 IU/mL, about 1,300 IU/mL, about 1,400 IU/mL, about 1,500 IU/mL, about 1,600 IU/mL, about 1,700 IU/mL, about 1,800 IU/mL, about 1,900 IU/mL, about 2,000 IU/mL, about 2,100 IU/mL, about 2,200 IU/mL, about 2,300 IU/mL, about 2,400 IU/mL, about 2,500 IU/mL, about 2,600 IU/mL, about 2,700 IU/mL, about 2,800 IU/mL, about 2,900 IU/mL, about 3,000 IU/mL, about 3,100 IU/mL, about 3,200 IU/mL, about 3,300 IU/mL, about 3,400 IU/mL, about 3,500 IU/mL, about 3,600 IU/mL, about 3,700 IU/mL, about 3,800 IU/mL, about 3,900 IU/mL, about 4,000 IU/mL, about 4,100 IU/mL, about 4,200 IU/mL, about 4,300 IU/mL, about 4,400 IU/mL, about 4,500 IU/mL, about 4,600 IU/mL, about 4,700 IU/mL, about 4,800 IU/mL, about 4,900 IU/mL, about 5,000 IU/mL, about 5,100 IU/mL, about 5,200 IU/mL, about 5,300 IU/mL, about 5,400 IU/mL, about 5,500 IU/mL, about 5,600 IU/mL, about 5,700 IU/mL, about 5,800 IU/mL, about 5,900 IU/mL, about 6,000 IU/mL, about 6,500 IU/mL, about 7,000 IU/mL, about 7,500 IU/mL, about 8,000 IU/mL, about 8,500 IU/mL, about 9,000 IU/mL, about 9,500 IU/mL, and about 10,000 IU/mL.

In an embodiment of the invention, additional IL-2 may be added to the culture on one or more days throughout the method. In an embodiment of the invention, additional IL-2 is added on Day 4. In an embodiment of the invention, additional IL-2 is added on Day 7. In an embodiment of the invention, additional IL-2 is added on Day 11. In another embodiment, additional IL-2 is added on Day 4, Day 7, and/or Day 11. In an embodiment of the invention, the MILs are cultured with additional IL-2 for a period of 1 day, 2 days, 3 days, 4 days, 5 days, 6 days, 7 days, 8 days, 9 days, 10 days, 11 days, 12 days, 13 days, or 14 days. In an embodiment of the invention, MILs are cultured for a period of 3 days after each addition of IL-2.

In an embodiment, the cell culture medium is exchanged at least once time during the method. In an embodiment, the cell culture medium is exchanged at the same time that additional IL-2 is added. In another embodiment the cell culture medium is exchanged on at least one of Day 1, Day 2, Day 3, Day 4, Day 5, Day 6, Day 7, Day 8, Day 9, Day 10, Day 11, Day 12, Day 13, or Day 14. In an embodiment of the invention, the cell culture medium used throughout the method may be the same or different. In an embodiment of the invention, the cell culture medium is CM-2, CM-4, or AIM-V. In an embodiment of the invention, the cell culture medium exchange step on Day 11 is optional. In an embodiment of the invention, the starting cell number of PBMCs for the expansion process is from about 25,000 to about 1,000,000, from about 30,000 to about 900,000, from about 35,000 to about 850,000, from about 40,000 to about 800,000, from about 45,000 to about 800,000, from about 50,000 to about 750,000, from about 55,000 to about 700,000, from about 60,000 to about 650,000, from about 65,000 to about 600,000, from about 70,000 to about 550,000, preferably from about 75,000 to about 500,000, from about 80,000 to about 450,000, from about 85,000 to about 400,000, from about 90,000 to about 350,000, from about 95,000 to about 300,000, from about 100,000 to about 250,000, from about 105,000 to about 200,000, or from about 110,000 to about 150,000. In an embodiment of the invention, the starting cell number of PBMCs is about 138,000, 140,000, 145,000, or more. In another embodiment, the starting cell number of PBMCs is about 28,000. In another embodiment, the starting cell number of PBMCs is about 62,000. In another embodiment, the starting cell number of PBMCs is about 338,000. In another embodiment, the starting cell number of PBMCs is about 336,000.

In an embodiment of the invention, the fold expansion of MILs is from about 20% to about 100%, 25% to about 95%, 30% to about 90%, 35% to about 85%, 40% to about 80%, 45% to about 75%, 50% to about 100%, or 25% to about 75%. In an embodiment of the invention, the fold expansion is about 25%. In another embodiment of the invention, the fold expansion is about 50%. In another embodiment, the fold expansion is about 75%.

In an embodiment of the invention, MILs are expanded from 10-50 mL of bone marrow aspirate. In an embodiment of the invention, 10 mL of bone marrow aspirate is obtained from the patient. In another embodiment, 20 mL of bone marrow aspirate is obtained from the patient. In another embodiment, 30 mL of bone marrow aspirate is obtained from the patient. In another embodiment, 40 mL of bone marrow aspirate is obtained from the patient. In another embodiment, 50 mL of bone marrow aspirate is obtained from the patient.

In an embodiment of the invention, the number of PBMCs yielded from about 10-50 mL of bone marrow aspirate is about $5 \times 10^7$ to about $10 \times 10^7$ PBMCs. In another embodiment, the number of PMBCs yielded is about $7 \times 10^7$ PBMCs.

In an embodiment of the invention, about $5 \times 10^7$ to about $10 \times 10^7$ PBMCs, yields about $0.5 \times 10^6$ to about $1.5 \times 10^6$ expansion starting cell material. In an embodiment of the invention, about $1 \times 10^6$ expansion starting cell material is yielded.

In an embodiment of the invention, the total number of MILs harvested at the end of the expansion period is from about $0.01 \times 10^9$ to about $1 \times 10^9$, from about $0.05 \times 10^9$ to about $0.9 \times 10^9$, from about $0.1 \times 10^9$ to about $0.85 \times 10^9$, from about $0.15 \times 10^9$ to about $0.7 \times 10^9$, from about $0.2 \times 10^9$ to about $0.65 \times 10^9$, from about $0.25 \times 10^9$ to about $0.6 \times 10^9$, from about $0.3 \times 10^9$ to about $0.55 \times 10^9$, from about $0.35 \times 10^9$ to about $0.5 \times 10^9$, or from about $0.4 \times 10^9$ to about $0.45 \times 10^9$.

In an embodiment of the invention, $12 \times 10^6$ PBMC derived from bone marrow aspirate yields approximately $1.4 \times 10^5$ starting cell material, which yields about $1.1 \times 10^7$ MILs at the end of the expansion process.

In an embodiment of the invention, the MILs expanded from bone marrow PBMCs using MIL Method 3 described above comprise a high proportion of CD8+ cells and lower number of LAG3+ and PD1+ cells as compared with MILs expanded using MIL Method 1 or MIL Method 2. In an embodiment of the invention, PBLs expanded from blood PBMC using MIL Method 3 described above comprise a high proportion of CD8+ cells and increased levels of IFNγ production as compared with PBLs expanded using MIL Method 1 or MIL Method 2.

In an embodiment of the invention, the clinical dose of MILs useful for patients with acute myeloid leukemia (AML) is in the range of from about $4 \times 10^8$ to about $2.5 \times 10^9$ MILs. In another embodiment, the number of MILs provided in the pharmaceutical compositions of the invention is $9.5 \times 10^8$ MILs. In another embodiment, the number of MILs provided in the pharmaceutical compositions of the invention is $4.1 \times 10^8$. In another embodiment, the number of MILs provided in the pharmaceutical compositions of the invention is $2.2 \times 10^9$.

In any of the foregoing embodiments, PBMCs may be derived from a whole blood sample, from bone marrow, by apheresis, from the buffy coat, or from any other method known in the art for obtaining PBMCs.

Step B: Priming First Expansion

In some embodiments, the present methods provide for younger TILs, which may provide additional therapeutic benefits over older TILs (i.e., TILs which have further undergone more rounds of replication prior to administration to a subject/patient). Features of young TILs have been described in the literature, for example Donia, at al., *Scandinavian Journal of Immunology,* 75:157-167 (2012); Dudley et al., *Clin Cancer Res,* 16:6122-6131 (2010); Huang et al., *J Immunother,* 28(3):258-267 (2005); Besser et al., *Clin Cancer Res,* 19(17):OF1-OF9 (2013); Besser et al., *J Immunother* 32:415-423 (2009); Robbins, et al., *J Immunol* 2004; 173:7125-7130; Shen et al., *J Immunother,* 30:123-129 (2007); Zhou, et al., *J Immunother,* 28:53-62 (2005); and Tran, et al., *J Immunother,* 31:742-751 (2008), all of which are incorporated herein by reference in their entireties.

After dissection or digestion of tumor fragments and/or tumor fragments, for example such as described in Step A of FIG. 8 (in particular, e.g., FIG. 8B), the resulting cells are cultured in serum containing IL-2, OKT-3, and feeder cells (e.g., antigen-presenting feeder cells), under conditions that favor the growth of TILs over tumor and other cells. In some embodiments, the IL-2, OKT-3, and feeder cells are added at culture initiation along with the tumor digest and/or tumor fragments (e.g., at Day 0). In some embodiments, the tumor digests and/or tumor fragments are incubated in a container with up to 60 fragments per container and with 6000 IU/mL of IL-2. This primary cell population is cultured for a period of days, generally from 1 to 7 days, resulting in a bulk TIL population, generally about $1\times10^8$ bulk TIL cells. In some embodiments, priming first expansion occurs for a period of 1 to 7 days, resulting in a bulk TIL population, generally about $1\times10^8$ bulk TIL cells. In some embodiments, this priming first expansion occurs for a period of 5 to 7 days, resulting in a bulk TIL population, generally about $1\times10^8$ bulk TIL cells. In some embodiments, this priming first expansion occurs for a period of about 6 to 7 days, resulting in a bulk TIL population, generally about $1\times10^8$ bulk TIL cells. In some embodiments, this priming first expansion occurs for a period of about 7 days, resulting in a bulk TIL population, generally about $1\times10^8$ bulk TIL cells.

In a preferred embodiment, expansion of TILs may be performed using a priming first expansion step (for example such as those described in Step B of FIG. 8 (in particular, e.g., FIG. 8B), which can include processes referred to as pre-REP or priming REP and which contains feeder cells from Day 0 and/or from culture initiation) as described below and herein, followed by a rapid second expansion (Step D, including processes referred to as rapid expansion protocol (REP) steps) as described below under Step D and herein, followed by optional cryopreservation, and followed by a second Step D (including processes referred to as restimulation REP steps) as described below and herein. The TILs obtained from this process may be optionally characterized for phenotypic characteristics and metabolic parameters as described herein. In some embodiments, the tumor fragment is between about 1 mm$^3$ and 10 mm$^3$.

In some embodiments, the first expansion culture medium is referred to as "CM", an abbreviation for culture media. In some embodiments, CM for Step B consists of RPMI 1640 with GlutaMAX, supplemented with 10% human AB serum, 25 mM Hepes, and 10 µg/mL gentamicin.

In some embodiments, there are less than or equal to 240 tumor fragments. In some embodiments, there are less than or equal to 240 tumor fragments placed in less than or equal to 4 containers. In some embodiments, the containers are GREX100 MCS flasks. In some embodiments, less than or equal to 60 tumor fragments are placed in 1 container. In some embodiments, each container comprises less than or equal to 500 mL of media per container. In some embodiments, the media comprises IL-2. In some embodiments, the media comprises 6000 IU/mL of IL-2. In some embodiments, the media comprises antigen-presenting feeder cells (also referred to herein as "antigen-presenting cells"). In some embodiments, the media comprises $2.5\times10^8$ antigen-presenting feeder cells per container. In some embodiments, the media comprises OKT-3. In some embodiments, the media comprises 30 ng of OKT-3 per container. In some embodiments, the container is a GREX100 MCS flask. In some embodiments, the media comprises 6000 IU/mL of IL-2, 30 ng of OKT-3, and $2.5\times10^8$ antigen-presenting feeder cells. In some embodiments, the media comprises 6000 IU/mL of IL-2, 30 ng of OKT-3, and $2.5\times10^8$ antigen-presenting feeder cells per container.

After preparation of the tumor fragments, the resulting cells (i.e., fragments which is a primary cell population) are cultured in media containing IL-2, antigen-presenting feeder cells and OKT-3 under conditions that favor the growth of TILs over tumor and other cells and which allow for TIL priming and accelerated growth from initiation of the culture on Day 0. In some embodiments, the tumor digests and/or tumor fragments are incubated in with 6000 IU/mL of IL-2, as well as antigen-presenting feeder cells and OKT-3. This primary cell population is cultured for a period of days, generally from 1 to 7 days, resulting in a bulk TIL population, generally about $1\times10^8$ bulk TIL cells. In some embodiments, the growth media during the priming first expansion comprises IL-2 or a variant thereof, as well as antigen-presenting feeder cells and OKT-3. In some embodiments, the IL-2 is recombinant human IL-2 (rhIL-2). In some embodiments the IL-2 stock solution has a specific activity of 20-30$\times10^6$ IU/mg for a 1 mg vial. In some embodiments the IL-2 stock solution has a specific activity of 20$\times10^6$ IU/mg for a 1 mg vial. In some embodiments the IL-2 stock solution has a specific activity of 25$\times10^6$ IU/mg for a 1 mg vial. In some embodiments the IL-2 stock solution has a specific activity of 30$\times10^6$ IU/mg for a 1 mg vial. In some embodiments, the IL-2 stock solution has a final concentration of 4-8$\times10^6$ IU/mg of IL-2. In some embodiments, the IL-2 stock solution has a final concentration of 5-7$\times10^6$ IU/mg of IL-2. In some embodiments, the IL-2 stock solution has a final concentration of 6$\times10^6$ IU/mg of IL-2. In some embodiments, the IL-2 stock solution is prepare as described in Example 3. In some embodiments, the priming first expansion culture media comprises about 10,000 IU/mL of IL-2, about 9,000 IU/mL of IL-2, about 8,000 IU/mL of IL-2, about 7,000 IU/mL of IL-2, about 6000 IU/mL of IL-2 or about 5,000 IU/mL of IL-2. In some embodiments, the priming first expansion culture media comprises about 9,000 IU/mL of IL-2 to about 5,000 IU/mL of IL-2. In some embodiments, the priming first expansion culture media comprises about 8,000 IU/mL of IL-2 to about 6,000 IU/mL of IL-2. In some embodiments, the priming first expansion culture media comprises about 7,000 IU/mL of IL-2 to about 6,000 IU/mL of IL-2. In some embodiments, the priming first expansion culture media comprises about 6,000 IU/mL of IL-2. In an embodiment, the cell culture medium further comprises IL-2. In some embodiments, the priming first expansion cell culture medium comprises about 3000 IU/mL of IL-2. In an embodiment, the priming first expansion cell culture medium further comprises IL-2. In a preferred embodiment, the priming first expansion cell culture medium comprises about 3000 IU/mL of IL-2. In an embodiment, the priming first expansion cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500

IU/mL, about 7000 IU/mL, about 7500 IU/mL, or about 8000 IU/mL of IL-2. In an embodiment, the priming first expansion cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or about 8000 IU/mL of IL-2.

In some embodiments, priming first expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the priming first expansion culture media comprises about 500 IU/mL of IL-15 to about 100 IU/mL of IL-15. In some embodiments, the priming first expansion culture media comprises about 400 IU/mL of IL-15 to about 100 IU/mL of IL-15. In some embodiments, the priming first expansion culture media comprises about 300 IU/mL of IL-15 to about 100 IU/mL of IL-15. In some embodiments, the priming first expansion culture media comprises about 200 IU/mL of IL-15. In some embodiments, the priming first expansion cell culture medium comprises about 180 IU/mL of IL-15. In an embodiment, the priming first expansion cell culture medium further comprises IL-15. In a preferred embodiment, the priming first expansion cell culture medium comprises about 180 IU/mL of IL-15.

In some embodiments, priming first expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the priming first expansion culture media comprises about 20 IU/mL of IL-21 to about 0.5 IU/mL of IL-21. In some embodiments, the priming first expansion culture media comprises about 15 IU/mL of IL-21 to about 0.5 IU/mL of IL-21. In some embodiments, the priming first expansion culture media comprises about 12 IU/mL of IL-21 to about 0.5 IU/mL of IL-21. In some embodiments, the priming first expansion culture media comprises about 10 IU/mL of IL-21 to about 0.5 IU/mL of IL-21. In some embodiments, the priming first expansion culture media comprises about 5 IU/mL of IL-21 to about 1 IU/mL of IL-21. In some embodiments, the priming first expansion culture media comprises about 2 IU/mL of IL-21. In some embodiments, the priming first expansion cell culture medium comprises about 1 IU/mL of IL-21. In some embodiments, the priming first expansion cell culture medium comprises about 0.5 IU/mL of IL-21. In an embodiment, the cell culture medium further comprises IL-21. In a preferred embodiment, the priming first expansion cell culture medium comprises about 1 IU/mL of IL-21.

In an embodiment, the priming first expansion cell culture medium comprises OKT-3 antibody. In some embodiments, the priming first expansion cell culture medium comprises about 30 ng/mL of OKT-3 antibody. In an embodiment, the priming first expansion cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 μg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In an embodiment, the cell culture medium comprises between 15 ng/ml and 30 ng/mL of OKT-3 antibody. In an embodiment, the cell culture medium comprises 30 ng/mL of OKT-3 antibody. In some embodiments, the OKT-3 antibody is muromonab.

TABLE 16

Amino acid sequences of muromonab (exemplary OKT-3 antibody)

| Identifier | Sequence (One-Letter Amino Acid Symbols) | | | | |
|---|---|---|---|---|---|
| SEQ ID NO: 1 Muromonab heavy chain | QVQLQQSGAE | LARPGASVKM | SCKASGYTFT | RYTMHWVKQR | PGQGLEWIGY | INPSRGYTNY | 60 |
| | NQKFKDKATL | TTDKSSSTAY | MQLSSLTSED | SAVYYCARYY | DDHYCLDYWG | QGTTLTVSSA | 120 |
| | KTTAPSVYPL | APVCGGTTGS | SVTLGCLVKG | YFPEPVTLTW | NSGSLSSGVH | TFPAVLQSDL | 180 |
| | YTLSSSVTVT | SSTWPSQSIT | CNVAHPASST | KVDKKIEPRP | KSCDKTHTCP | PCPAPELLGG | 240 |
| | PSVFLFPPKP | KDTLMISRTP | EVTCVVVDVS | HEDPEVKFNW | YVDGVEVHNA | KTKPREEQYN | 300 |
| | STYRVVSVLT | VLHQDWLNGK | EYKCKVSNKA | LPAPIEKTIS | KAKGQPREPQ | VYTLPPSRDE | 360 |
| | LTKNQVSLTC | LVKGFYPSDI | AVEWESNGQP | ENNYKTTPPV | LDSDGSFFLY | SKLTVDKSRW | 420 |
| | QQGNVFSCSV | MHEALHNHYT | QKSLSLSPGK | | | | 450 |
| SEQ ID NO: 2 Muromonab light chain | QIVLTQSPAI | MSASPGEKVT | MTCSASSSVS | YMNWYQQKSG | TSPKRWIYDT | SKLASGVPAH | 60 |
| | FRGSGSGTSY | SLTISGMEAE | DAATYYCQQW | SSNPFTFGSG | TKLEINRADT | APTVSIFPPS | 120 |
| | SEQLTSGGAS | VVCFLNNFYP | KDINVKWKID | GSERQNGVLN | SWTDQDSKDS | TYSMSSTLTL | 180 |
| | TKDEYERHNS | YTCEATHKTS | TSPIVKSFNR | NEC | | | 213 |

In some embodiments, the priming first expansion cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 μg/mL and 100 μg/mL. In some embodiments, the TNFRSF agonist is added at a concentration sufficient to achieve a concentration in the cell culture medium of between 20 μg/mL and 40 μg/mL.

In some embodiments, in addition to one or more TNFRSF agonists, the priming first expansion cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist. In some embodiments, in addition to one or more TNFRSF agonists, the priming first expansion cell culture medium further comprises IL-2 at an initial concentration of about 6000 IU/mL and OKT-3 antibody at an initial concentration of about 30 ng/mL, and wherein the one or more TNFRSF agonists comprises a 4-1BB agonist.

In some embodiments, the priming first expansion culture medium is referred to as "CM", an abbreviation for culture media. In some embodiments, it is referred to as CM1 (culture medium 1). In some embodiments, CM consists of RPMI 1640 with GlutaMAX, supplemented with 10% human AB serum, 25 mM Hepes, and 10 µg/mL gentamicin. In some embodiments, the CM is the CM1 described in the Examples, see, Example 1. In some embodiments, the priming first expansion occurs in an initial cell culture medium or a first cell culture medium. In some embodiments, the priming first expansion culture medium or the initial cell culture medium or the first cell culture medium comprises IL-2, OKT-3 and antigen-presenting feeder cells (also referred to herein as feeder cells).

In some embodiments, the priming first expansion (including processes such as for example those described in Step B of FIG. 8 (in particular, e.g., FIG. 8B), which can include those sometimes referred to as the pre-REP or priming REP) process is 1 to 7 days, as discussed in the examples and figures. In some embodiments, the priming first expansion (including processes such as for example those described in Step B of FIG. 8 (in particular, e.g., FIG. 8B), which can include those sometimes referred to as the pre-REP or priming REP) process is 2 to 7 days. In some embodiments, the priming first expansion (including processes such as for example those described in Step B of FIG. 8 (in particular, e.g., FIG. 8B), which can include those sometimes referred to as the pre-REP or priming REP) process is 3 to 7 days. In some embodiments, the priming first expansion (including processes such as for example those described in Step B of FIG. 8 (in particular, e.g., FIG. 8B), which can include those sometimes referred to as the pre-REP or priming REP) process is 4 to 7 days. In some embodiments, the priming first expansion (including processes such as for example those described in Step B of FIG. 8 (in particular, e.g., FIG. 8B), which can include those sometimes referred to as the pre-REP or priming REP) process is 5 to 7 days. In some embodiments, the priming first expansion (including processes such as for example those described in Step B of FIG. 8 (in particular, e.g., FIG. 8B), which can include those sometimes referred to as the pre-REP or priming REP) process is 6 to 7 days. In some embodiments, the priming first expansion (including processes such as for example those provided in Step B of FIG. 8 (in particular, e.g., FIG. 8B), which can include those sometimes referred to as the pre-REP or priming REP) process is 7 days.

In some embodiments, the priming first TIL expansion can proceed for 1 days to 7 days from when fragmentation occurs and/or when the first priming expansion step is initiated. In some embodiments, the priming first TIL expansion can proceed for 2 days to 7 days from when fragmentation occurs and/or when the first priming expansion step is initiated. In some embodiments, the priming first TIL expansion can proceed for 3 days to 7 days from when fragmentation occurs and/or when the first priming expansion step is initiated. In some embodiments, the priming first TIL expansion can proceed for 4 days to 7 days from when fragmentation occurs and/or when the first priming expansion step is initiated. In some embodiments, the priming first TIL expansion can proceed for 5 days to 7 days from when fragmentation occurs and/or when the first priming expansion step is initiated. In some embodiments, the priming first TIL expansion can proceed for 6 days to 7 days from when fragmentation occurs and/or when the first priming expansion step is initiated. In some embodiments, the priming first TIL expansion can proceed for 7 days from when fragmentation occurs and/or when the first priming expansion step is initiated.

In some embodiments, the priming first expansion of the TILs can proceed for 1 day, 2 days, 3 days, 4 days, 5 days, 6 days, or 7 days. In some embodiments, the first TIL expansion can proceed for 1 day to 7 days. In some embodiments, the first TIL expansion can proceed for 2 days to 7 days. In some embodiments, the first TIL expansion can proceed for 3 days to 7 days. In some embodiments, the first TIL expansion can proceed for 4 days to 7 days. In some embodiments, the first TIL expansion can proceed for 5 days to 7 days. In some embodiments, the first TIL expansion can proceed for 6 days to 7 days. In some embodiments, the first TIL expansion can proceed for 7 days.

In some embodiments, a combination of IL-2, IL-7, IL-15, and/or IL-21 are employed as a combination during the priming first expansion. In some embodiments, IL-2, IL-7, IL-15, and/or IL-21 as well as any combinations thereof can be included during the priming first expansion, including, for example during Step B processes according to FIG. 8 (in particular, e.g., FIG. 8B), as well as described herein. In some embodiments, a combination of IL-2, IL-15, and IL-21 are employed as a combination during the priming first expansion. In some embodiments, IL-2, IL-15, and IL-21 as well as any combinations thereof can be included during Step B processes according to FIG. 8 (in particular, e.g., FIG. 8B) and as described herein.

In some embodiments, the priming first expansion, for example, Step B according to FIG. 8 (in particular, e.g., FIG. 8B), is performed in a closed system bioreactor. In some embodiments, a closed system is employed for the TIL expansion, as described herein. In some embodiments, a bioreactor is employed. In some embodiments, a bioreactor is employed as the container. In some embodiments, the bioreactor employed is for example a G-REX-10 or a G-REX-100. In some embodiments, the bioreactor employed is a G-REX-100. In some embodiments, the bioreactor employed is a G-REX-10.

Feeder Cells and Antigen Presenting Cells

In an embodiment, the priming first expansion procedures described herein (for example including expansion such as those described in Step B from FIG. 8 (in particular, e.g., FIG. 8B), as well as those referred to as pre-REP or priming REP) require feeder cells (also referred to herein as "antigen-presenting cells") at the initiation of the TIL expansion and during the priming first expansion. In many embodiments, the feeder cells are peripheral blood mononuclear cells (PBMCs) obtained from standard whole blood units from allogeneic healthy blood donors. The PBMCs are obtained using standard methods such as Ficoll-Paque gradient separation. In some embodiments, $2.5 \times 10^8$ feeder cells are used during the priming first expansion. In some embodiments, $2.5 \times 10^8$ feeder cells per container are used during the priming first expansion. In some embodiments, $2.5 \times 10^8$ feeder cells per GREX-10 are used during the priming first expansion. In some embodiments, $2.5 \times 10^8$ feeder cells per GREX-100 are used during the priming first expansion.

In general, the allogenic PBMCs are inactivated, either via irradiation or heat treatment, and used in the REP procedures, as described in the examples, which provides an exemplary protocol for evaluating the replication incompetence of irradiate allogeneic PBMCs.

In some embodiments, PBMCs are considered replication incompetent and acceptable for use in the TIL expansion procedures described herein if the total number of viable cells on day 14 is less than the initial viable cell number put into culture on day 0 of the priming first expansion.

In some embodiments, PBMCs are considered replication incompetent and acceptable for use in the TIL expansion procedures described herein if the total number of viable cells, cultured in the presence of OKT3 and IL-2, on day 7 have not increased from the initial viable cell number put into culture on day 0 of the priming first expansion. In some embodiments, the PBMCs are cultured in the presence of 30 ng/ml OKT3 antibody and 3000 IU/mL IL-2. In some embodiments, the PBMCs are cultured in the presence of 30 ng/ml OKT3 antibody and 6000 IU/mL IL-2.

In some embodiments, the media in the priming first expansion comprises IL-2. In some embodiments, the media in the priming first expansion comprises 6000 IU/mL of IL-2. In some embodiments, the media in the priming first expansion comprises antigen-presenting feeder cells. In some embodiments, the media in the priming first expansion comprises $2.5 \times 10^8$ antigen-presenting feeder cells per container. In some embodiments, the media in the priming first expansion comprises OKT-3. In some embodiments, the media comprises 30 ng of OKT-3 per container. In some embodiments, the container is a GREX100 MCS flask. In some embodiments, the media comprises 6000 IU/mL of IL-2, 30 ng/mL of OKT-3, and $2.5 \times 10^8$ antigen-presenting feeder cells. In some embodiments, the media comprises 6000 IU/mL of IL-2, 30 ng/mL of OKT-3, and $2.5 \times 10^8$ antigen-presenting feeder cells per container. In some embodiments, the media comprises 500 mL of culture medium and 15 μg of OKT-3 per $2.5 \times 10^8$ antigen-presenting feeder cells per container. In some embodiments, the media comprises 500 mL of culture medium and 15 μg of OKT-3 per container. In some embodiments, the container is a GREX100 MCS flask. In some embodiments, the media comprises 500 mL of culture medium and 6000 IU/mL of IL-2, 30 ng/mL ng of OKT-3, and $2.5 \times 10^8$ antigen-presenting feeder cells. In some embodiments, the media comprises 500 mL of culture medium and 6000 IU/mL of IL-2, 15 μg of OKT-3, and $2.5 \times 10^8$ antigen-presenting feeder cells per container. In some embodiments, the media comprises 500 mL of culture medium and 15 μg of OKT-3 per $2.5 \times 10^8$ antigen-presenting feeder cells per container.

In some embodiments, PBMCs are considered replication incompetent and acceptable for use in the TIL expansion procedures described herein if the total number of viable cells, cultured in the presence of OKT3 and IL-2, on day 7 have not increased from the initial viable cell number put into culture on day 0 of the priming first expansion. In some embodiments, the PBMCs are cultured in the presence of 5-60 ng/ml OKT3 antibody and 1000-6000 IU/mL IL-2. In some embodiments, the PBMCs are cultured in the presence of 10-50 ng/mL OKT3 antibody and 2000-5000 IU/mL IL-2. In some embodiments, the PBMCs are cultured in the presence of 20-40 ng/mL OKT3 antibody and 2000-4000 IU/mL IL-2. In some embodiments, the PBMCs are cultured in the presence of 25-35 ng/mL OKT3 antibody and 2500-3500 IU/mL IL-2. In some embodiments, the PBMCs are cultured in the presence of 30 ng/ml OKT3 antibody and 6000 IU/mL IL-2. In some embodiments, the PBMCs are cultured in the presence of 15 ng/mL OKT3 antibody and 3000 IU/mL IL-2. In some embodiments, the PBMCs are cultured in the presence of 15 ng/mL OKT3 antibody and 6000 IU/mL IL-2.

In some embodiments, the antigen-presenting feeder cells are PBMCs. In some embodiments, the antigen-presenting feeder cells are artificial antigen-presenting feeder cells. In an embodiment, the ratio of TILs to antigen-presenting feeder cells in the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to antigen-presenting feeder cells in the second expansion is between 1 to 50 and 1 to 300. In an embodiment, the ratio of TILs to antigen-presenting feeder cells in the second expansion is between 1 to 100 and 1 to 200.

In an embodiment, the priming first expansion procedures described herein require a ratio of about $2.5 \times 10^8$ feeder cells to about $100 \times 10^6$ TILs. In another embodiment, the priming first expansion procedures described herein require a ratio of about $2.5 \times 10^8$ feeder cells to about $50 \times 10^6$ TILs. In yet another embodiment, the priming first expansion described herein require about $2.5 \times 10^8$ feeder cells to about $25 \times 10^6$ TILs. In yet another embodiment, the priming first expansion described herein require about $2.5 \times 10^8$ feeder cells. In yet another embodiment, the priming first expansion requires one-fourth, one-third, five-twelfths, or one-half of the number of feeder cells used in the rapid second expansion.

In some embodiments, the media in the priming first expansion comprises IL-2. In some embodiments, the media in the priming first expansion comprises 6000 IU/mL of IL-2. In some embodiments, the media in the priming first expansion comprises antigen-presenting feeder cells. In some embodiments, the media in the priming first expansion comprises $2.5 \times 10^8$ antigen-presenting feeder cells per container. In some embodiments, the media in the priming first expansion comprises OKT-3. In some embodiments, the media comprises 30 ng of OKT-3 per container. In some embodiments, the container is a GREX100 MCS flask. In some embodiments, the media comprises 6000 IU/mL of IL-2, 30 ng of OKT-3, and $2.5 \times 10^8$ antigen-presenting feeder cells. In some embodiments, the media comprises 6000 IU/mL of IL-2, 30 ng of OKT-3, and $2.5 \times 10^8$ antigen-presenting feeder cells per container. In some embodiments, the media comprises 30 ng of OKT-3 per $2.5 \times 10^8$ antigen-presenting feeder cells per container. In some embodiments, the media comprises 15 ng of OKT-3 per container. In some embodiments, the container is a GREX100 MCS flask. In some embodiments, the media comprises 6000 IU/mL of IL-2, 15 ng of OKT-3, and $2.5 \times 10^8$ antigen-presenting feeder cells. In some embodiments, the media comprises 6000 IU/mL of IL-2, 15 ng of OKT-3, and $2.5 \times 10^8$ antigen-presenting feeder cells per container. In some embodiments, the media comprises 15 ng of OKT-3 per $2.5 \times 10^8$ antigen-presenting feeder cells per container.

In an embodiment, the priming first expansion procedures described herein require an excess of feeder cells over TILs during the second expansion. In many embodiments, the feeder cells are peripheral blood mononuclear cells (PBMCs) obtained from standard whole blood units from allogeneic healthy blood donors. The PBMCs are obtained using standard methods such as Ficoll-Paque gradient separation. In an embodiment, artificial antigen-presenting (aAPC) cells are used in place of PBMCs.

In general, the allogenic PBMCs are inactivated, either via irradiation or heat treatment, and used in the TIL expansion procedures described herein, including the exemplary procedures described in the figures and examples.

In an embodiment, artificial antigen presenting cells are used in the priming first expansion as a replacement for, or in combination with, PBMCs.

Cytokines

The expansion methods described herein generally use culture media with high doses of a cytokine, in particular IL-2, as is known in the art.

Alternatively, using combinations of cytokines for the priming first expansion of TILs is additionally possible, with combinations of two or more of IL-2, IL-15 and IL-21 as is generally outlined in International Publication No. WO 2015/189356 and WO 2015/189357, hereby expressly incorporated by reference in their entirety. Thus, possible combinations include IL-2 and IL-15, IL-2 and IL-21, IL-15 and IL-21, and IL-2, IL-15 and IL-21, with the latter finding particular use in many embodiments. The use of combinations of cytokines specifically favors the generation of lymphocytes, and in particular T-cells as described therein.

modifications for suitable treatments prior to the expansion step or after the priming first expansion and prior to the rapid second expansion.

In some embodiments, the TTLs obtained from the priming first expansion (for example, from Step B as indicated in FIG. 8 (in particular, e.g., FIG. 8B)) are stored until phenotyped for selection. In some embodiments, the TTLs obtained from the priming first expansion (for example, from Step B as indicated in FIG. 8 (in particular, e.g., FIG. 8B)) are not stored and proceed directly to the rapid second expansion. In some embodiments, the TTLs obtained from the priming first expansion are not cryopreserved after the priming first expansion and prior to the rapid second expansion. In some embodiments, the transition from the priming first expansion to the second expansion occurs at about 2 days, 3 days, 4, days, 5 days, 6 days, or 7 days, from when tumor fragmentation occurs and/or when the first priming expansion step is initiated. In some embodiments, the transition from the priming first expansion to the rapid second expansion occurs at about 3 days to 7 days from when fragmentation occurs and/or when the first priming expansion step is initiated. In some embodiments, the transition

TABLE 17

Amino acid sequences of interleukins.

| Identifier | Sequence (One-Letter Amino Acid Symbols) | |
|---|---|---|
| SEQ ID NO: 3 recombinant human IL-2 (rhIL-2) | MAPTSSSTKK TQLQLEHLLL DLQMILNGIN NYKNPKLTRM LTFKFYMPKK ATELKHLQCL EEELKPLEEV LNLAQSKNFH LRPRDLISNI NVIVLELKGS ETTFMCEYAD ETATIVEFLN RWITFCQSII STLT | 60 120 134 |
| SEQ ID NO: 4 Aldesleukin | PTSSSTKKTQ LQLEHLLLDL QMILNGINNY KNPKLTRMLT FKFYMPKKAT ELKHLQCLEE ELKPLEEVLN LAQSKNFHLR PRDLISNINV IVLELKGSET TFMCEYADET ATIVEFLNRW ITFSQSIIST LT | 60 120 132 |
| SEQ ID NO: 5 recombinant human IL-4 (rhIL-4) | MHKCDITLQE IIKTLNSLTE QKTLCTELTV TDIFAASKNT TEKETFCRAA TVLRQFYSHH EKDTRCLGAT AQQFHRHKQL IRFLKRLDRN LWGLAGLNSC PVKEANQSTL ENFLERLKTI MREKYSKCSS | 60 120 130 |
| SEQ ID NO: 6 recombinant human IL-7 (rhIL-7) | MDCDIEGKDG KQYESVLMVS IDQLLDSMKE IGSNCLNNEF NFFKRHICDA NKEGMFLFRA ARKLRQFLKM NSTGDFDLHL LKVSEGTTIL LNCTGQVKGR KPAALGEAQP TKSLEENKSL KEQKKLNDLC FLKRLLQEIK TCWNKILMGT KEH | 60 120 153 |
| SEQ ID NO: 7 recombinant human IL-15 (rhIL-15) | MNWVNVISDL KKIEDLIQSM HIDATLYTES DVHPSCKVTA MKCFLLELQV ISLESGDASI HDTVENLIIL ANNSLSSNGN VTESGCKECE ELEEKNIKEF LQSFVHIVQM FINTS | 60 115 |
| SEQ ID NO: 8 recombinant human IL-21 (rhIL-21) | MQDRHMIRMR QLIDIVDQLK NYVNDLVPEF LPAPEDVETN CEWSAFSCFQ KAQLKSANTG NNERIINVSI KKLKRKPPST NAGRRQKHRL TCPSCDSYEK KPPKEFLERF KSLLQKMIHQ HLSSRTHGSE DS | 60 120 132 |

Step C: Priming First Expansion to Rapid Second Expansion Transition

In some cases, the bulk TIL population obtained from the priming first expansion (which can include expansions sometimes referred to as pre-REP), including, for example the TIL population obtained from for example, Step B as indicated in FIG. 8 (in particular, e.g., FIG. 8B), can be subjected to a rapid second expansion (which can include expansions sometimes referred to as Rapid Expansion Protocol (REP)) and then cryopreserved as discussed below. Similarly, in the case where genetically modified TILs will be used in therapy, the expanded TIL population from the priming first expansion or the expanded TIL population from the rapid second expansion can be subjected to genetic from the priming first expansion to the second expansion occurs at about 4 days to 7 days from when fragmentation occurs and/or when the first priming expansion step is initiated. In some embodiments, the transition from the priming first expansion to the second expansion occurs at about 5 days to 7 days from when fragmentation occurs and/or when the first priming expansion step is initiated. In some embodiments, the transition from the priming first expansion to the second expansion occurs at about 6 days to 7 days from when fragmentation occurs and/or when the first priming expansion step is initiated. In some embodiments, the transition from the priming first expansion to the second expansion occurs at about 7 days from when fragmentation occurs and/or when the first priming expansion step is initiated.

In some embodiments, the transition from the priming first expansion to the rapid second expansion occurs at 1 day, 2 days, 3 days, 4 days, 5 days, 6 days, or 7 days, from when fragmentation occurs and/or when the first priming expansion step is initiated. In some embodiments, the transition from the priming first expansion to the rapid second expansion occurs 1 day to 7 days from when fragmentation occurs and/or when the first priming expansion step is initiated. In some embodiments, the transition from the priming first expansion to the second expansion occurs 2 days to 7 days from when fragmentation occurs and/or when the first priming expansion step is initiated. In some embodiments, the transition from the priming first expansion to the second expansion occurs 3 days to 7 days from when fragmentation occurs and/or when the first priming expansion step is initiated. In some embodiments, the transition from the priming first expansion to the rapid second expansion occurs 4 days to 7 days from when fragmentation occurs and/or when the first priming expansion step is initiated. In some embodiments, the transition from the priming first expansion to the rapid second expansion occurs 5 days to 7 days from when fragmentation occurs and/or when the first priming expansion step is initiated. In some embodiments, the transition from the priming first expansion to the rapid second expansion occurs 6 days to 7 days from when fragmentation occurs and/or when the first priming expansion step is initiated. In some embodiments, the transition from the priming first expansion to the rapid second expansion occurs 7 days from when fragmentation occurs and/or when the first priming expansion step is initiated.

In some embodiments, the TILs are not stored after the primary first expansion and prior to the rapid second expansion, and the TILs proceed directly to the rapid second expansion (for example, in some embodiments, there is no storage during the transition from Step B to Step D as shown in FIG. 8 (in particular, e.g., FIG. 8B)). In some embodiments, the transition occurs in closed system, as described herein. In some embodiments, the TILs from the priming first expansion, the second population of TILs, proceeds directly into the rapid second expansion with no transition period.

In some embodiments, the transition from the priming first expansion to the rapid second expansion, for example, Step C according to FIG. 8 (in particular, e.g., FIG. 8B), is performed in a closed system bioreactor. In some embodiments, a closed system is employed for the TIL expansion, as described herein. In some embodiments, a single bioreactor is employed. In some embodiments, the single bioreactor employed is for example a GREX-10 or a GREX-100. In some embodiments, the closed system bioreactor is a single bioreactor. In some embodiments, the transition from the priming first expansion to the rapid second expansion involves a scale-up in container size. In some embodiments, the priming first expansion is performed in a smaller container than the rapid second expansion. In some embodiments, the priming first expansion is performed in a GREX-100 and the rapid second expansion is performed in a GREX-500.

Step D: Rapid Second Expansion

In some embodiments, the TIL cell population is further expanded in number after harvest and the priming first expansion, after Step A and Step B, and the transition referred to as Step C, as indicated in FIG. 8 (in particular, e.g., FIG. 8B)). This further expansion is referred to herein as the rapid second expansion, which can include expansion processes generally referred to in the art as a rapid expansion process (Rapid Expansion Protocol or REP; as well as processes as indicated in Step D of FIG. 8 (in particular, e.g., FIG. 8B)). The rapid second expansion is generally accomplished using a culture media comprising a number of components, including feeder cells, a cytokine source, and an anti-CD3 antibody, in a gas-permeable container. In some embodiments, 1 day, 2 days, 3 days, or 4 days after initiation of the rapid second expansion (i.e., at days 8, 9, 10, or 11 of the overall Gen 3 process), the TILs are transferred to a larger volume container.

In some embodiments, the rapid second expansion (which can include expansions sometimes referred to as REP; as well as processes as indicated in Step D of FIG. 8 (in particular, e.g., FIG. 8B)) of TIL can be performed using any TIL flasks or containers known by those of skill in the art. In some embodiments, the second TIL expansion can proceed for 1 day, 2 days, 3 days, 4, days, 5 days, 6 days, 7 days, 8 days, or 9 days after initiation of the rapid second expansion. In some embodiments, the second TIL expansion can proceed for about 1 days to about 9 days after initiation of the rapid second expansion. In some embodiments, the second TIL expansion can proceed for about 2 days to about 9 days after initiation of the rapid second expansion. In some embodiments, the second TIL expansion can proceed for about 3 days to about 9 days after initiation of the rapid second expansion. In some embodiments, the second TIL expansion can proceed for about 4 days to about 9 days after initiation of the rapid second expansion. In some embodiments, the second TIL expansion can proceed for about 5 days to about 9 days after initiation of the rapid second expansion. In some embodiments, the second TIL expansion can proceed for about 6 days to about 9 days after initiation of the rapid second expansion. In some embodiments, the second TIL expansion can proceed for about 7 days to about 9 days after initiation of the rapid second expansion. In some embodiments, the second TIL expansion can proceed for about 1 day after initiation of the rapid second expansion. In some embodiments, the second TIL expansion can proceed for about 2 days after initiation of the rapid second expansion. In some embodiments, the second TIL expansion can proceed for about 3 days after initiation of the rapid second expansion. In some embodiments, the second TIL expansion can proceed for about 4 days after initiation of the rapid second expansion. In some embodiments, the second TIL expansion can proceed for about 5 days after initiation of the rapid second expansion. In some embodiments, the second TIL expansion can proceed for about 6 days after initiation of the rapid second expansion. In some embodiments, the second TIL expansion can proceed for about 7 days after initiation of the rapid second expansion. In some embodiments, the second TIL expansion can proceed for about 8 days after initiation of the rapid second expansion. In some embodiments, the second TIL expansion can proceed for about 9 days after initiation of the rapid second expansion.

In an embodiment, the rapid second expansion can be performed in a gas permeable container using the methods of the present disclosure (including, for example, expansions referred to as REP; as well as processes as indicated in Step D of FIG. 8 (in particular, e.g., FIG. 8B)). In some embodiments, the TILs are expanded in the rapid second expansion in the presence of IL-2, OKT-3, and feeder cells (also referred herein as "antigen-presenting cells"). In some embodiments, the TILs are expanded in the rapid second expansion in the presence of IL-2, OKT-3, and feeder cells, wherein the feeder cells are added to a final concentration that is twice, 2.4 times, 2.5 times, 3 times, 3.5 times or 4 times the concentration of feeder cells present in the priming first expansion. For example, TILs can be rapidly expanded using non-specific T-cell receptor stimulation in the presence of interleukin-2 (IL-2) or interleukin-15 (IL-15). The non-specific T-cell receptor stimulus can include, for example, an anti-CD3 antibody, such as about 30 ng/ml of OKT3, a mouse monoclonal anti-CD3 antibody (commercially available from Ortho-McNeil, Raritan, NJ or Miltenyi Biotech, Auburn, CA) or UHCT-1 (commercially available from BioLegend, San Diego, CA, USA). TILs can be expanded to induce further stimulation of the TILs in vitro by including one or more antigens during the second expansion, including antigenic portions thereof, such as epitope(s), of the cancer, which can be optionally expressed from a vector, such as a human leukocyte antigen A2 (HLA-A2) binding peptide, e.g., 0.3 µM MART-1:26-35 (27 L) or gpl 00:209-217 (210M), optionally in the presence of a T-cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. TIL may also be rapidly expanded by re-stimulation with the same antigen(s) of the cancer pulsed onto HLA-A2-expressing antigen-presenting cells. Alternatively, the TILs can be further re-stimulated with, e.g., example, irradiated, autologous lymphocytes or with irradiated HLA-A2+ allogeneic lymphocytes and IL-2. In some embodiments, the re-stimulation occurs as part of the second expansion. In some embodiments, the second expansion occurs in the presence of irradiated, autologous lymphocytes or with irradiated HLA-A2+ allogeneic lymphocytes and IL-2.

In an embodiment, the cell culture medium further comprises IL-2. In some embodiments, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In an embodiment, the cell culture medium comprises OKT-3 antibody. In some embodiments, the cell culture medium comprises about 30 ng/mL of OKT-3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 µg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In an embodiment, the cell culture medium comprises between 15 ng/ml and 30 ng/mL of OKT-3 antibody. In an embodiment, the cell culture medium comprises about 30 ng/mL OKT-3. In some embodiments, the OKT-3 antibody is muromonab.

In some embodiments, the media in the rapid second expansion comprises IL-2. In some embodiments, the media comprises 6000 IU/mL of IL-2. In some embodiments, the media in the rapid second expansion comprises antigen-presenting feeder cells. In some embodiments, the media in the rapid second expansion comprises $7.5 \times 10^8$ antigen-presenting feeder cells per container. In some embodiments, the media in the rapid second expansion comprises OKT-3. In some embodiments, the in the rapid second expansion media comprises 30 ng of OKT-3 per container. In some embodiments, the container is a GREX100 MCS flask. In some embodiments, the in the rapid second expansion media comprises 6000 IU/mL of IL-2, 30 ng of OKT-3, and $7.5 \times 10^8$ antigen-presenting feeder cells. In some embodiments, the media comprises 6000 IU/mL of IL-2, 30 ng of OKT-3, and $7.5 \times 10^8$ antigen-presenting feeder cells per container.

In some embodiments, the media in the rapid second expansion comprises IL-2. In some embodiments, the media comprises 6000 IU/mL of IL-2. In some embodiments, the media in the rapid second expansion comprises antigen-presenting feeder cells. In some embodiments, the media comprises between $5 \times 10^8$ and $7.5 \times 10^8$ antigen-presenting feeder cells per container. In some embodiments, the media in the rapid second expansion comprises OKT-3. In some embodiments, the media in the rapid second expansion comprises 30 ng of OKT-3 per container. In some embodiments, the container is a GREX100 MCS flask. In some embodiments, the media in the rapid second expansion comprises 6000 IU/mL of IL-2, 30 ng of OKT-3, and between $5 \times 10^8$ and $7.5 \times 10^8$ antigen-presenting feeder cells. In some embodiments, the media in the rapid second expansion comprises 6000 IU/mL of IL-2, 30 ng of OKT-3, and between $5 \times 10^8$ and $7.5 \times 10^8$ antigen-presenting feeder cells per container.

In some embodiments, the cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 µg/mL and 100 µg/mL. In some embodiments, the TNFRSF agonist is added at a concentration sufficient to achieve a concentration in the cell culture medium of between 20 µg/mL and 40 µg/mL.

In some embodiments, in addition to one or more TNFRSF agonists, the cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist.

In some embodiments, a combination of IL-2, IL-7, IL-15, and/or IL-21 are employed as a combination during the second expansion. In some embodiments, IL-2, IL-7, IL-15, and/or IL-21 as well as any combinations thereof can be included during the second expansion, including, for example during a Step D processes according to FIG. 8 (in particular, e.g., FIG. 8B), as well as described herein. In some embodiments, a combination of IL-2, IL-15, and IL-21 are employed as a combination during the second expansion. In some embodiments, IL-2, IL-15, and IL-21 as well as any combinations thereof can be included during Step D processes according to FIG. 8 (in particular, e.g., FIG. 8B) and as described herein.

In some embodiments, the second expansion can be conducted in a supplemented cell culture medium comprising IL-2, OKT-3, antigen-presenting feeder cells, and optionally a TNFRSF agonist. In some embodiments, the second expansion occurs in a supplemented cell culture medium. In some embodiments, the supplemented cell culture medium comprises IL-2, OKT-3, and antigen-presenting feeder cells. In some embodiments, the second cell culture medium comprises IL-2, OKT-3, and antigen-presenting cells (APCs; also referred to as antigen-presenting feeder cells). In some embodiments, the second expansion occurs in a cell culture medium comprising IL-2, OKT-3, and antigen-presenting feeder cells (i.e., antigen presenting cells).

In some embodiments, the second expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the second expansion culture media comprises about 500 IU/mL of IL-15 to about 100 IU/mL of IL-15. In some embodiments, the second expansion culture media comprises about 400 IU/mL of IL-15 to about 100 IU/mL of IL-15. In some embodiments, the second expansion culture media comprises about 300 IU/mL of IL-15 to about 100 IU/mL of IL-15. In some embodiments, the second expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, the second expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the second expansion culture media comprises about 20 IU/mL of IL-21 to about 0.5 IU/mL of IL-21. In some embodiments, the second expansion culture media comprises about 15 IU/mL of IL-21 to about 0.5 IU/mL of IL-21. In some embodiments, the second expansion culture media comprises about 12 IU/mL of IL-21 to about 0.5 IU/mL of IL-21. In some embodiments, the second expansion culture media comprises about 10 IU/mL of IL-21 to about 0.5 IU/mL of IL-21. In some embodiments, the second expansion culture media comprises about 5 IU/mL of IL-21 to about 1 IU/mL of IL-21. In some embodiments, the second expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In some embodiments the antigen-presenting feeder cells (APCs) are PBMCs. In an embodiment, the ratio of TILs to PBMCs and/or antigen-presenting cells in the rapid expansion and/or the second expansion is about 1 to 10, about 1 to 15, about 1 to 20, about 1 to 25, about 1 to 30, about 1 to 35, about 1 to 40, about 1 to 45, about 1 to 50, about 1 to 75, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to PBMCs in the rapid expansion and/or the second expansion is between 1 to 50 and 1 to 300. In an embodiment, the ratio of TILs to PBMCs in the rapid expansion and/or the second expansion is between 1 to 100 and 1 to 200.

In an embodiment, REP and/or the rapid second expansion is performed in flasks with the bulk TILs being mixed with a 100- or 200-fold excess of inactivated feeder cells, wherein the feeder cell concentration is at least 1.1 times (LIX), 1.2×, 1.3×, 1.4×, 1.5×, 1.6×, 1.7×, 1.8×, 1.8×, 2×, 2.1×2.2×, 2.3×, 2.4×, 2.5×, 2.6×, 2.7×, 2.8×, 2.9×, 3.0×, 3.1×, 3.2×, 3.3×, 3.4×, 3.5×, 3.6×, 3.7×, 3.8×, 3.9× or 4.0× the feeder cell concentration in the priming first expansion, 30 ng/mL OKT3 anti-CD3 antibody and 6000 IU/mL IL-2 in 150 ml media. Media replacement is done (generally ⅔ media replacement via aspiration of ⅔ of spent media and replacement with an equal volume of fresh media) until the cells are transferred to an alternative growth chamber. Alternative growth chambers include G-REX flasks and gas permeable containers as more fully discussed below.

In some embodiments, the rapid second expansion (which can include processes referred to as the REP process) is 7 to 9 days, as discussed in the examples and figures. In some embodiments, the second expansion is 7 days. In some embodiments, the second expansion is 8 days. In some embodiments, the second expansion is 9 days.

In an embodiment, the second expansion (which can include expansions referred to as REP, as well as those referred to in Step D of FIG. 8 (in particular, e.g., FIG. 8B)) may be performed in 500 mL capacity gas permeable flasks with 100 cm gas-permeable silicon bottoms (G-Rex 100, commercially available from Wilson Wolf Manufacturing Corporation, New Brighton, MN, USA), $5 \times 10^6$ or $10 \times 10^6$ TIL may be cultured with PBMCs in 400 mL of 50/50 medium, supplemented with 5% human AB serum, 3000 IU per mL of IL-2 and 30 ng per ml of anti-CD3 (OKT3). The G-Rex 100 flasks may be incubated at 37° C. in 5% $CO_2$. On day 5, 250 mL of supernatant may be removed and placed into centrifuge bottles and centrifuged at 1500 rpm (491×g) for 10 minutes. The TIL pellets may be re-suspended with 150 mL of fresh medium with 5% human AB serum, 6000 IU per mL of IL-2, and added back to the original GREX-100 flasks. When TIL are expanded serially in GREX-100 flasks, on day 10 or 11 the TILs can be moved to a larger flask, such as a GREX-500. The cells may be harvested on day 14 of culture. The cells may be harvested on day 15 of culture. The cells may be harvested on day 16 of culture. In some embodiments, media replacement is done until the cells are transferred to an alternative growth chamber. In some embodiments, ⅔ of the media is replaced by aspiration of spent media and replacement with an equal volume of fresh media. In some embodiments, alternative growth chambers include GREX flasks and gas permeable containers as more fully discussed below.

In an embodiment, the rapid second expansion (including expansions referred to as REP) is performed and further comprises a step wherein TILs are selected for superior tumor reactivity. Any selection method known in the art may be used. For example, the methods described in U.S. Patent Application Publication No. 2016/0010058 A1, the disclosures of which are incorporated herein by reference, may be used for selection of TILs for superior tumor reactivity.

Optionally, a cell viability assay can be performed after the rapid second expansion (including expansions referred to as the REP expansion), using standard assays known in the art. For example, a trypan blue exclusion assay can be done on a sample of the bulk TILs, which selectively labels dead cells and allows a viability assessment. In some embodiments, TIL samples can be counted and viability determined using a Cellometer K2 automated cell counter (Nexcelom Bioscience, Lawrence, MA). In some embodiments, viability is determined according to the standard Cellometer K2 Image Cytometer Automatic Cell Counter protocol.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained in the second expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCR$\alpha/\beta$).

In some embodiments, the rapid second expansion culture medium (e.g., sometimes referred to as CM2 or the second cell culture medium), comprises IL-2, OKT-3, as well as the antigen-presenting feeder cells (APCs), as discussed in more detail below. In some embodiments, the rapid second expansion culture medium (e.g., sometimes referred to as CM2 or the second cell culture medium), comprises 6000 IU/mL IL-2, 30 ng/flask OKT-3, as well as $7.5 \times 10^8$ antigen-presenting feeder cells (APCs), as discussed in more detail below. In some embodiments, the rapid second expansion culture medium (e.g., sometimes referred to as CM2 or the second cell culture medium), comprises IL-2, OKT-3, as well as the antigen-presenting feeder cells (APCs), as discussed in more detail below. In some embodiments, the rapid second expansion culture medium (e.g., sometimes referred to as CM2 or the second cell culture medium), comprises 6000 IU/mL IL-2, 30 ng/flask OKT-3, as well as $5 \times 10^8$ antigen-presenting feeder cells (APCs), as discussed in more detail below.

In some embodiments, the rapid second expansion, for example, Step D according to FIG. 8 (in particular, e.g., FIG. 8B), is performed in a closed system bioreactor. In some embodiments, a closed system is employed for the TIL expansion, as described herein. In some embodiments, a bioreactor is employed. In some embodiments, a bioreactor is employed as the container. In some embodiments, the bioreactor employed is for example a G-REX-100 or a G-REX-500. In some embodiments, the bioreactor employed is a G-REX-100. In some embodiments, the bioreactor employed is a G-REX-500.

Feeder Cells and Antigen Presenting Cells

In an embodiment, the rapid second expansion procedures described herein (for example including expansion such as those described in Step D from FIG. 8 (in particular, e.g., FIG. 8B), as well as those referred to as REP) require an excess of feeder cells during REP TIL expansion and/or during the rapid second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation.

In general, the allogenic PBMCs are inactivated, either via irradiation or heat treatment, and used in the REP procedures, as described in the examples, which provides an exemplary protocol for evaluating the replication incompetence of irradiate allogeneic PBMCs.

In some embodiments, PBMCs are considered replication incompetent and acceptable for use in the TIL expansion procedures described herein if the total number of viable cells on day 7 or 14 is less than the initial viable cell number put into culture on day 0 of the REP and/or day 0 of the second expansion (i.e., the start day of the second expansion).

In some embodiments, PBMCs are considered replication incompetent and acceptable for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 30 ng/mL OKT3 antibody and 3000 IU/mL IL-2. In some embodiments, the PBMCs are cultured in the presence of 30 ng/mL OKT3 antibody and 6000 IU/mL IL-2. In some embodiments, the PBMCs are cultured in the presence of 15 ng/mL OKT3 antibody and 3000 IU/mL IL-2. In some embodiments, the PBMCs are cultured in the presence of 15 ng/mL OKT3 antibody and 6000 IU/mL IL-2. In some embodiments, the PBMCs are cultured in the presence of 60 ng/mL OKT3 antibody and 6000 IU/mL IL-2. In some embodiments, the PBMCs are cultured in the presence of 60 ng/mL OKT3 antibody and 3000 IU/mL IL-2. In some embodiments, the PBMCs are cultured in the presence of 30 ng/mL OKT3 antibody and 6000 IU/mL IL-2.

In some embodiments, PBMCs are considered replication incompetent and acceptable for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 5-60 ng/ml OKT3 antibody and 1000-6000 IU/mL IL-2. In some embodiments, the PBMCs are cultured in the presence of 10-50 ng/ml OKT3 antibody and 2000-5000 IU/mL IL-2. In some embodiments, the PBMCs are cultured in the presence of 20-40 ng/mL OKT3 antibody and 2000-4000 IU/mL IL-2. In some embodiments, the PBMCs are cultured in the presence of 25-35 ng/mL OKT3 antibody and 2500-3500 IU/mL IL-2. In some embodiments, the PBMCs are cultured in the presence of 30 ng/ml OKT3 antibody and 6000 IU/mL IL-2.

In some embodiments, the antigen-presenting feeder cells are PBMCs. In some embodiments, the antigen-presenting feeder cells are artificial antigen-presenting feeder cells. In an embodiment, the ratio of TILs to antigen-presenting feeder cells in the second expansion is about 1 to 10, about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to antigen-presenting feeder cells in the second expansion is between 1 to 50 and 1 to 300. In an embodiment, the ratio of TILs to antigen-presenting feeder cells in the second expansion is between 1 to 100 and 1 to 200.

In an embodiment, the second expansion procedures described herein require a ratio of about $5 \times 10^8$ feeder cells to about $100 \times 10^6$ TILs. In an embodiment, the second expansion procedures described herein require a ratio of about $7.5 \times 10^8$ feeder cells to about $100 \times 10^6$ TILs. In another embodiment, the second expansion procedures described herein require a ratio of about $5 \times 10^8$ feeder cells to about $50 \times 10^6$ TILs. In another embodiment, the second expansion procedures described herein require a ratio of about $7.5 \times 10^8$ feeder cells to about $50 \times 10^6$ TILs. In yet another embodiment, the second expansion procedures described herein require about $5 \times 10^8$ feeder cells to about $25 \times 10^6$ TILs. In yet another embodiment, the second expansion procedures described herein require about $7.5 \times 10^8$ feeder cells to about $25 \times 10^6$ TILs. In yet another embodiment, the rapid second expansion requires twice the number of feeder cells as the rapid second expansion. In yet another embodiment, when the priming first expansion described herein requires about $2.5 \times 10^8$ feeder cells, the rapid second expansion requires about $5 \times 10^8$ feeder cells. In yet another embodiment, when the priming first expansion described herein requires about $2.5 \times 10^8$ feeder cells, the rapid second expansion requires about $7.5 \times 10^8$ feeder cells. In yet another embodiment, the rapid second expansion requires two times (2.0×), 2.5×, 3.0×, 3.5× or 4.0× the number of feeder cells as the priming first expansion.

In an embodiment, the rapid second expansion procedures described herein require an excess of feeder cells during the rapid second expansion. In many embodiments, the feeder cells are peripheral blood mononuclear cells (PBMCs) obtained from standard whole blood units from allogeneic healthy blood donors. The PBMCs are obtained using standard methods such as Ficoll-Paque gradient separation. In an embodiment, artificial antigen-presenting (aAPC) cells are used in place of PBMCs. In some embodiments, the PBMCs are added to the rapid second expansion at twice the concentration of PBMCs that were added to the priming first expansion.

In general, the allogenic PBMCs are inactivated, either via irradiation or heat treatment, and used in the TIL expansion procedures described herein, including the exemplary procedures described in the figures and examples.

In an embodiment, artificial antigen presenting cells are used in the rapid second expansion as a replacement for, or in combination with, PBMCs.

Cytokines

The rapid second expansion methods described herein generally use culture media with high doses of a cytokine, in particular IL-2, as is known in the art.

Alternatively, using combinations of cytokines for the rapid second expansion of TILs is additionally possible, with combinations of two or more of IL-2, IL-15 and IL-21 as is generally outlined in WO 2015/189356 and WO 2015/189357, hereby expressly incorporated by reference in their entirety. Thus, possible combinations include IL-2 and IL-15, IL-2 and IL-21, IL-15 and IL-21, and IL-2, IL-15 and IL-21, with the latter finding particular use in many embodiments. The use of combinations of cytokines specifically favors the generation of lymphocytes, and in particular T-cells as described therein.

Step E: Harvest TILs

After the rapid second expansion step, cells can be harvested. In some embodiments the TILs are harvested after one, two, three, four or more expansion steps, for example as provided in FIG. 8 (in particular, e.g., FIG. 8B). In some embodiments the TILs are harvested after two expansion steps, for example as provided in FIG. 8 (in particular, e.g., FIG. 8B). In some embodiments the TILs are harvested after two expansion steps, one priming first expansion and one rapid second expansion, for example as provided in FIG. 8 (in particular, e.g., FIG. 8B).

TILs can be harvested in any appropriate and sterile manner, including, for example by centrifugation. Methods for TIL harvesting are well known in the art and any such known methods can be employed with the present process. In some embodiments, TILs are harvested using an automated system.

Cell harvesters and/or cell processing systems are commercially available from a variety of sources, including, for example, Fresenius Kabi, Tomtec Life Science, Perkin Elmer, and Inotech Biosystems International, Inc. Any cell based harvester can be employed with the present methods. In some embodiments, the cell harvester and/or cell processing system is a membrane-based cell harvester. In some embodiments, cell harvesting is via a cell processing system, such as the LOVO system (manufactured by Fresenius Kabi). The term "LOVO cell processing system" also refers to any instrument or device manufactured by any vendor that can pump a solution comprising cells through a membrane or filter such as a spinning membrane or spinning filter in a sterile and/or closed system environment, allowing for continuous flow and cell processing to remove supernatant or cell culture media without pelletization. In some embodiments, the cell harvester and/or cell processing system can perform cell separation, washing, fluid-exchange, concentration, and/or other cell processing steps in a closed, sterile system.

In some embodiments, the rapid second expansion, for example, Step D according to FIG. 8 (in particular, e.g., FIG. 8B), is performed in a closed system bioreactor. In some embodiments, a closed system is employed for the TIL expansion, as described herein. In some embodiments, a bioreactor is employed. In some embodiments, a bioreactor is employed as the container. In some embodiments, the bioreactor employed is for example a G-REX-100 or a G-REX-500. In some embodiments, the bioreactor employed is a G-REX-100. In some embodiments, the bioreactor employed is a G-REX-500.

In some embodiments, Step E according to FIG. 8 (in particular, e.g., FIG. 8B), is performed according to the processes described herein. In some embodiments, the closed system is accessed via syringes under sterile conditions in order to maintain the sterility and closed nature of the system. In some embodiments, a closed system as described herein is employed.

In some embodiments, TTLs are harvested according to the methods described in herein. In some embodiments, TTLs between days 14 and 16 are harvested using the methods as described herein. In some embodiments, TILs are harvested at 14 days using the methods as described herein. In some embodiments, TILs are harvested at 15 days using the methods as described herein. In some embodiments, TILs are harvested at 16 days using the methods as described herein.

Step F: Final Formulation Transfer to Infusion Bag

After Steps A through E as provided in an exemplary order in FIG. 8 (in particular, e.g., FIG. 8B) and as outlined in detailed above and herein are complete, cells are transferred to a container for use in administration to a patient. In some embodiments, once a therapeutically sufficient number of TILs are obtained using the expansion methods described above, they are transferred to a container for use in administration to a patient.

In an embodiment, TILs expanded using the methods of the present disclosure are administered to a patient as a pharmaceutical composition. In an embodiment, the pharmaceutical composition is a suspension of TILs in a sterile buffer. TILs expanded as disclosed herein may be administered by any suitable route as known in the art. In some embodiments, the TILs are administered as a single intra-arterial or intravenous infusion, which preferably lasts approximately 30 to 60 minutes. Other suitable routes of administration include intraperitoneal, intrathecal, and intralymphatic.

PBMC Feeder Cell Ratios

In some embodiments, the culture media used in expansion methods described herein (see for example, FIG. 8 (in particular, e.g., FIG. 8B)) include an anti-CD3 antibody e.g. OKT-3. An anti-CD3 antibody in combination with IL-2 induces T cell activation and cell division in the TIL population. This effect can be seen with full length antibodies as well as Fab and F(ab')2 fragments, with the former being generally preferred; see, e.g., Tsoukas et al., *J. Immunol.* 1985, 135, 1719, hereby incorporated by reference in its entirety.

In an embodiment, the number of PBMC feeder layers is calculated as follows:

A. Volume of a T-cell (10 μm diameter): $V=(4/3)\pi r^3=523.6$ μm$^3$

B. Column of G-Rex 100 (M) with a 40 μm (4 cells) height: $V=(4/3)\pi r^3=4\times10^{12}$ μm$^3$ C. Number cell required to fill column B: $4\times10^{12}$ μm$^3$/523.6 μm$^3=7.6\times10^8$ μm$^3$*0.64=4.86$\times10^8$ D. Number cells that can be optimally activated in 4D space: $4.86\times10^8/24=20.25\times10^6$ E. Number of feeders and TIL extrapolated to G-Rex 500: TIL: $100\times10^6$ and Feeder: $2.5\times10^9$ In this calculation, an approximation of the number of mononuclear cells required to provide an icosahedral geometry for activation of TIL in a cylinder with a 100 cm$^2$ base is used. The calculation derives the experimental result of $\sim5\times10^8$ for threshold activation of T-cells which closely mirrors NCI experimental data.[1] (C) The multiplier (0.64) is the random packing density for equivalent spheres as calculated by Jaeger and Nagel in 1992[2]. (D) The divisor 24 is the number of equivalent spheres that could contact a similar object in 4 dimensional space "the Newton number."[3].

[1]Jin, Jianjian, et. al., Simplified Method of the Growth of Human Tumor Infiltrating Lymphocytes (TIL) in Gas-Permeable Flasks to Numbers Needed for Patient Treatment. J Immunother. 2012 April; 35(3): 283-292.

[2]Jaeger H M, Nagel S R. Physics of the granular state. Science. 1992 Mar. 20; 255(5051):1523-31.

[3]O. R. Musin (2003). "The problem of the twenty-five spheres". Russ. Math. Surv. 58 (4): 794-795.

In an embodiment, the number of antigen-presenting feeder cells exogenously supplied during the priming first expansion is approximately one-half the number of antigen-presenting feeder cells exogenously supplied during the rapid second expansion. In certain embodiments, the method comprises performing the priming first expansion in a cell culture medium which comprises approximately 50% fewer antigen presenting cells as compared to the cell culture medium of the rapid second expansion.

In another embodiment, the number of antigen-presenting feeder cells (APCs) exogenously supplied during the rapid second expansion is greater than the number of APCs exogenously supplied during the priming first expansion.

In another embodiment, the ratio of the number of APCs exogenously supplied during the rapid second expansion to the number of APCs exogenously supplied during the priming first expansion is selected from a range of from at or about 1.1:1 to at or about 20:1.

In another embodiment, the ratio of the number of APCs exogenously supplied during the rapid second expansion to the number of APCs exogenously supplied during the priming first expansion is selected from a range of from at or about 1.1:1 to at or about 10:1.

In another embodiment, the ratio of the number of APCs exogenously supplied during the rapid second expansion to the number of APCs exogenously supplied during the priming first expansion is selected from a range of from at or about 1.1:1 to at or about 9:1.

In another embodiment, the ratio of the number of APCs exogenously supplied during the rapid second expansion to the number of APCs exogenously supplied during the priming first expansion is selected from a range of from at or about 1.1:1 to at or about 8:1.

In another embodiment, the ratio of the number of APCs exogenously supplied during the rapid second expansion to the number of APCs exogenously supplied during the priming first expansion is selected from a range of from at or about 1.1:1 to at or about 7:1.

In another embodiment, the ratio of the number of APCs exogenously supplied during the rapid second expansion to the number of APCs exogenously supplied during the priming first expansion is selected from a range of from at or about 1.1:1 to at or about 6:1.

In another embodiment, the ratio of the number of APCs exogenously supplied during the rapid second expansion to the number of APCs exogenously supplied during the priming first expansion is selected from a range of from at or about 1.1:1 to at or about 5:1.

In another embodiment, the ratio of the number of APCs exogenously supplied during the rapid second expansion to the number of APCs exogenously supplied during the priming first expansion is selected from a range of from at or about 1.1:1 to at or about 4:1.

In another embodiment, the ratio of the number of APCs exogenously supplied during the rapid second expansion to the number of APCs exogenously supplied during the priming first expansion) is selected from a range of from at or about 1.1:1 to at or about 3:1.

In another embodiment, the ratio of the number of APCs exogenously supplied during the rapid second expansion to the number of APCs exogenously supplied during the priming first expansion is selected from a range of from at or about 1.1:1 to at or about 2.9:1.

In another embodiment, the ratio of the number of APCs exogenously supplied during the rapid second expansion to the number of APCs exogenously supplied during the priming first expansion is selected from a range of from at or about 1.1:1 to at or about 2.8:1.

In another embodiment, the ratio of the number of APCs exogenously supplied during the rapid second expansion to the number of APCs exogenously supplied during the priming first expansion is selected from a range of from at or about 1.1:1 to at or about 2.7:1.

In another embodiment, the ratio of the number of APCs exogenously supplied during the rapid second expansion to the number of APCs exogenously supplied during the priming first expansion is selected from a range of from at or about 1.1:1 to at or about 2.6:1.

In another embodiment, the ratio of the number of APCs exogenously supplied during the rapid second expansion to the number of APCs exogenously supplied during the priming first expansion is selected from a range of from at or about 1.1:1 to at or about 2.5:1.

In another embodiment, the ratio of the number of APCs exogenously supplied during the rapid second expansion to the number of APCs exogenously supplied during the priming first expansion is selected from a range of from at or about 1.1:1 to at or about 2.4:1.

In another embodiment, the ratio of the number of APCs exogenously supplied during the rapid second expansion to the number of APCs exogenously supplied during the priming first expansion is selected from a range of from at or about 1.1:1 to at or about 2.3:1.

In another embodiment, the ratio of the number of APCs exogenously supplied during the rapid second expansion to the number of APCs exogenously supplied during the priming first expansion is selected from a range of from at or about 1.1:1 to at or about 2.2:1.

In another embodiment, the ratio of the number of APCs exogenously supplied during the rapid second expansion to the number of APCs exogenously supplied during the priming first expansion is selected from a range of from at or about 1.1:1 to at or about 2.1:1.

In another embodiment, the ratio of the number of APCs exogenously supplied during the rapid second expansion to the number of APCs exogenously supplied during the priming first expansion is selected from a range of from at or about 1.1:1 to at or about 2:1.

In another embodiment, the ratio of the number of APCs exogenously supplied during the rapid second expansion to the number of APCs exogenously supplied during the priming first expansion is selected from a range of from at or about 2:1 to at or about 10:1.

In another embodiment, the ratio of the number of APCs exogenously supplied during the rapid second expansion to the number of APCs exogenously supplied during the priming first expansion is selected from a range of from at or about 2:1 to at or about 5:1.

In another embodiment, the ratio of the number of APCs exogenously supplied during the rapid second expansion to the number of APCs exogenously supplied during the priming first expansion is selected from a range of from at or about 2:1 to at or about 4:1.

In another embodiment, the ratio of the number of APCs exogenously supplied during the rapid second expansion to the number of APCs exogenously supplied during the priming first expansion is selected from a range of from at or about 2:1 to at or about 3:1.

In another embodiment, the ratio of the number of APCs exogenously supplied during the rapid second expansion to the number of APCs exogenously supplied during the priming first expansion is selected from a range of from at or about 2:1 to at or about 2.9:1.

In another embodiment, the ratio of the number of APCs exogenously supplied during the rapid second expansion to the number of APCs exogenously supplied during the priming first expansion is selected from a range of from at or about 2:1 to at or about 2.8:1.

In another embodiment, the ratio of the number of APCs exogenously supplied during the rapid second expansion to the number of APCs exogenously supplied during the priming first expansion is selected from a range of from at or about 2:1 to at or about 2.7:1.

In another embodiment, the ratio of the number of APCs exogenously supplied during the rapid second expansion to the number of APCs exogenously supplied during the priming first expansion is selected from a range of from at or about 2:1 to at or about 2.6:1.

In another embodiment, the ratio of the number of APCs exogenously supplied during the rapid second expansion to the number of APCs exogenously supplied during the priming first expansion is selected from a range of from at or about 2:1 to at or about 2.5:1.

In another embodiment, the ratio of the number of APCs exogenously supplied during the rapid second expansion to the number of APCs exogenously supplied during the priming first expansion is selected from a range of from at or about 2:1 to at or about 2.4:1.

In another embodiment, the ratio of the number of APCs exogenously supplied during the rapid second expansion to the number of APCs exogenously supplied during the priming first expansion is selected from a range of from at or about 2:1 to at or about 2.3:1.

In another embodiment, the ratio of the number of APCs exogenously supplied during the rapid second expansion to the number of APCs exogenously supplied during the priming first expansion is selected from a range of from at or about 2:1 to at or about 2.2:1.

In another embodiment, the ratio of the number of APCs exogenously supplied during the rapid second expansion to the number of APCs exogenously supplied during the priming first expansion is selected from a range of from at or about 2:1 to at or about 2.1:1.

In another embodiment, the ratio of the number of APCs exogenously supplied during the rapid second expansion to the number of APCs exogenously supplied during the priming first expansion is at or about 2:1.

In another embodiment, the ratio of the number of APCs exogenously supplied during the rapid second expansion to the number of APCs exogenously supplied during the priming first expansion is at or about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, or 5:1.

In another embodiment, the number of APCs exogenously supplied during the priming first expansion is at or about $1\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3\times10^8$, $3.1\times10^8$, $3.2\times10^8$, $33\times10^8$, $3.4\times10^8$ or $3.5\times10^8$ APCs, and the number of APCs exogenously supplied during the rapid second expansion is at or about $3.5\times10^8$, $3.6\times10^8$, $3.7\times10^8$, $3.8\times10^8$, $3.9\times10^8$, $4\times10^8$, $4.1\times10^8$, $4.2\times10^8$, $4.3\times10^8$, $4.4\times10^8$, $4.5\times10^8$, $4.6\times10^8$, $4.7\times10^8$, $4.8\times10^8$, $4.9\times10^8$, $5\times10^8$, $5.1\times10^8$, $5.2\times10^8$, $5.3\times10^8$, $5.4\times10^8$, $5.5\times10^8$, $5.6\times10^8$, $5.7\times10^8$, $5.8\times10^8$, $5.9\times10^8$, $6\times10^8$, $6.1\times10^8$, $6.2\times10^8$, $6.3\times10^8$, $6.4\times10^8$, $6.5\times10^8$, $6.6\times10^8$, $6.7\times10^8$, $6.8\times10^8$, $6.9\times10^8$, $7\times10^8$, $7.1\times10^8$, $7.2\times10^8$, $7.3\times10^8$, $7.4\times10^8$, $7.5\times10^8$, $7.6\times10^8$, $7.7\times10^8$, $7.8\times10^8$, $7.9\times10^8$, $8\times10^8$, $8.1\times10^8$, $8.2\times10^8$, $8.3\times10^8$, $8.4\times10^8$, $8.5\times10^8$, $8.6\times10^8$, $8.7\times10^8$, $8.8\times10^8$, $8.9\times10^8$, $9\times10^8$, $9.1\times10^8$, $9.2\times10^8$, $9.3\times10^8$, $9.4\times10^8$, $9.5\times10^8$, $9.6\times10^8$, $9.7\times10^8$, $9.8\times10^8$, $9.9\times10^8$ or $1\times10^9$ APCs.

In another embodiment, the number of APCs exogenously supplied during the priming first expansion is selected from the range of at or about $1.5\times10^8$ APCs to at or about $3\times10^8$ APCs, and the number of APCs exogenously supplied during the rapid second expansion is selected from the range of at or about $4 \times 10^8$ APCs to at or about $7.5 \times 10^8$ APCs.

In another embodiment, the number of APCs exogenously supplied during the priming first expansion is selected from the range of at or about $2 \times 10^8$ APCs to at or about $2.5 \times 10^8$ APCs, and the number of APCs exogenously supplied during the rapid second expansion is selected from the range of at or about $4.5 \times 10^8$ APCs to at or about $5.5 \times 10^8$ APCs.

In another embodiment, the number of APCs exogenously supplied during the priming first expansion is at or about $2.5 \times 10^8$ APCs, and the number of APCs exogenously supplied during the rapid second expansion is at or about $5 \times 10^8$ APCs.

In an embodiment, the number of APCs (including, for example, PBMCs) added at day 0 of the priming first expansion is approximately one-half of the number of PBMCs added at day 7 of the priming first expansion (e.g., day 7 of the method). In certain embodiments, the method comprises adding antigen presenting cells at day 0 of the priming first expansion to the first population of TILs and adding antigen presenting cells at day 7 to the second population of TILs, wherein the number of antigen presenting cells added at day 0 is approximately 50% of the number of antigen presenting cells added at day 7 of the priming first expansion (e.g., day 7 of the method).

In another embodiment, the number of APCs (including, for example, PBMCs) exogenously supplied at day 7 of the rapid second expansion is greater than the number of PBMCs exogenously supplied at day 0 of the priming first expansion.

In another embodiment, the ratio of the number of APCs (including, for example, PBMCs) exogenously supplied at day 7 of the rapid second expansion to the number of PBMCs exogenously supplied at day 0 of the priming first expansion is selected from a range of from at or about 1.1:1 to at or about 20:1.

In another embodiment, the ratio of the number of APCs (including, for example, PBMCs) exogenously supplied at day 7 of the rapid second expansion to the number of PBMCs exogenously supplied at day 0 of the priming first expansion is selected from a range of from at or about 1.1:1 to at or about 10:1.

In another embodiment, the ratio of the number of APCs (including, for example, PBMCs) exogenously supplied at day 7 of the rapid second expansion to the number of PBMCs exogenously supplied at day 0 of the priming first expansion is selected from a range of from at or about 1.1:1 to at or about 9:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 8:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 7:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 6:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 5:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 4:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 3:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.9:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.8:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.7:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.6:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.5:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.4:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.3:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.2:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.1:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 10:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 5:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 4:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 3:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.9:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.8:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.7:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.6:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.5:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.4:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.3:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.2:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.1:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is at or about 2:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is at or about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, or 5:1.

In another embodiment, the number of APCs (including, for example, PBMCs) exogenously supplied at day 0 of the priming first expansion is at or about $1 \times 10^8$, $1.1 \times 10^8$, $1.2 \times 10^8$, $1.3 \times 10^8$, $1.4 \times 10^8$, $1.5 \times 10^8$, $1.6 \times 10^8$, $1.7 \times 10^8$, $1.8 \times 10^8$, $1.9 \times 10^8$, $2 \times 10^8$, $2.1 \times 10^8$, $2.2 \times 10^8$, $2.3 \times 10^8$, $2.4 \times 10^8$, $2.5 \times 10^8$, $2.6 \times 10^8$, $2.7 \times 10^8$, $2.8 \times 10^8$, $2.9 \times 10^8$, $3 \times 10^8$, $3.1 \times 10^8$, $3.2 \times 10^8$, $3.3 \times 10^8$, $3.4 \times 10^8$ or $3.5 \times 10^8$ APCs (including, for example, PBMCs), and the number of APCs (including, for example, PBMCs) exogenously supplied at day 7 of the rapid second expansion is at or about $3.5 \times 10^8$, $3.6 \times 10^8$, $3.7 \times 10^8$, $3.8 \times 10^8$, $3.9 \times 10^8$, $4 \times 10^8$, $4.1 \times 10^8$, $4.2 \times 10^8$, $4.3 \times 10^8$, $4.4 \times 10^8$, $4.5 \times 10^8$, $4.6 \times 10^8$, $4.7 \times 10^8$, $4.8 \times 10^8$, $4.9 \times 10^8$, $5 \times 10^8$, $5.1 \times 10^8$, $5.2 \times 10^8$, $5.3 \times 10^8$, $5.4 \times 10^8$, $5.5 \times 10^8$, $5.6 \times 10^8$, $5.7 \times 10^8$, $5.8 \times 10^8$, $5.9 \times 10^8$, $6 \times 10^8$, $6.1 \times 10^8$, $6.2 \times 10^8$, $6.3 \times 10^8$, $6.4 \times 10^8$, $6.5 \times 10^8$, $6.6 \times 10^8$, $6.7 \times 10^8$, $6.8 \times 10^8$, $6.9 \times 10^8$, $7 \times 10^8$, $7.1 \times 10^8$, $7.2 \times 10^8$, $7.3 \times 10^8$, $7.4 \times 10^8$, $7.5 \times 10^8$, $7.6 \times 10^8$, $77 \times 10^8$, $7.8 \times 10^8$, $7.9 \times 10^8$, $8 \times 10^8$, $8.1 \times 10^8$, $8.2 \times 10^8$, $8.3 \times 10^8$, $8.4 \times 10^8$, $8.5 \times 10^8$, $8.6 \times 10^8$, $8.7 \times 10^8$, $8.8 \times 10^8$, $8.9 \times 10^8$, $9 \times 10^8$, $9.1 \times 10^8$, $9.2 \times 10^8$, $9.3 \times 10^8$, $9.4 \times 10^8$, $9.5 \times 10^8$, $9.6 \times 10^8$, $9.7 \times 10^8$, $9.8 \times 10^8$, $9.9 \times 10^8$ or $1 \times 10^9$ APCs (including, for example, PBMCs).

In another embodiment, the number of APCs (including, for example, PBMCs) exogenously supplied at day 0 of the priming first expansion is selected from the range of at or about $1 \times 10^8$ APCs (including, for example, PBMCs) to at or about $3.5 \times 10^8$ APCs (including, for example, PBMCs), and the number of APCs (including, for example, PBMCs) exogenously supplied at day 7 of the rapid second expansion is selected from the range of at or about $3.5 \times 10^8$ APCs (including, for example, PBMCs) to at or about 1×10⁹ APCs (including, for example, PBMCs).

In another embodiment, the number of APCs (including, for example, PBMCs) exogenously supplied at day 0 of the priming first expansion is selected from the range of at or about 1.5×10⁸ APCs to at or about 3×10⁸ APCs (including, for example, PBMCs), and the number of APCs (including, for example, PBMCs) exogenously supplied at day 7 of the rapid second expansion is selected from the range of at or about 4×10⁸ APCs (including, for example, PBMCs) to at or about 7.5×10⁸ APCs (including, for example, PBMCs).

In another embodiment, the number of APCs (including, for example, PBMCs) exogenously supplied at day 0 of the priming first expansion is selected from the range of at or about 2×10⁸ APCs (including, for example, PBMCs) to at or about 2.5×10⁸ APCs (including, for example, PBMCs), and the number of APCs (including, for example, PBMCs) exogenously supplied at day 7 of the rapid second expansion is selected from the range of at or about 4.5×10⁸ APCs (including, for example, PBMCs) to at or about 5.5×10⁸ APCs (including, for example, PBMCs).

In another embodiment, the number of APCs (including, for example, PBMCs) exogenously supplied at day 0 of the priming first expansion is at or about 2.5×10⁸ APCs (including, for example, PBMCs) and the number of APCs (including, for example, PBMCs) exogenously supplied at day 7 of the rapid second expansion is at or about 5×10⁸ APCs (including, for example, PBMCs).

In an embodiment, the number of layers of APCs (including, for example, PBMCs) added at day 0 of the priming first expansion is approximately one-half of the number of layers of APCs (including, for example, PBMCs) added at day 7 of the rapid second expansion. In certain embodiments, the method comprises adding antigen presenting cell layers at day 0 of the priming first expansion to the first population of TILs and adding antigen presenting cell layers at day 7 to the second population of TILs, wherein the number of antigen presenting cell layer added at day 0 is approximately 50% of the number of antigen presenting cell layers added at day 7.

In another embodiment, the number of layers of APCs (including, for example, PBMCs) exogenously supplied at day 7 of the rapid second expansion is greater than the number of layers of APCs (including, for example, PBMCs) exogenously supplied at day 0 of the priming first expansion.

In another embodiment, day 0 of the priming first expansion occurs in the presence of layered APCs (including, for example, PBMCs) with an average thickness of at or about 2 cell layers and day 7 of the rapid second expansion occurs in the presence of layered APCs (including, for example, PBMCs) with an average thickness of at or about 4 cell layers.

In another embodiment, day 0 of the priming first expansion occurs in the presence of layered APCs (including, for example, PBMCs) with an average thickness of at or about one cell layer and day 7 of the rapid second expansion occurs in the presence of layered APCs (including, for example, PBMCs) with an average thickness of at or about 3 cell layers.

In another embodiment, day 0 of the priming first expansion occurs in the presence of layered APCs (including, for example, PBMCs) with an average thickness of at or about 1.5 cell layers to at or about 2.5 cell layers and day 7 of the rapid second expansion occurs in the presence of layered APCs (including, for example, PBMCs) with an average thickness of at or about 3 cell layers.

In another embodiment, day 0 of the priming first expansion occurs in the presence of layered APCs (including, for example, PBMCs) with an average thickness of at or about one cell layer and day 7 of the rapid second expansion occurs in the presence of layered APCs (including, for example, PBMCs) with an average thickness of at or about 2 cell layers.

In another embodiment, day 0 of the priming first expansion occurs in the presence of layered APCs (including, for example, PBMCs) with an average thickness of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers and day 7 of the rapid second expansion occurs in the presence of layered APCs (including, for example, PBMCs) with an average thickness of at or about 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In another embodiment, day 0 of the priming first expansion occurs in the presence of layered APCs (including, for example, PBMCs) with an average thickness of at or about 1 cell layer to at or about 2 cell layers and day 7 of the rapid second expansion occurs in the presence of layered APCs (including, for example, PBMCs) with an average thickness of at or about 3 cell layers to at or about 10 cell layers.

In another embodiment, day 0 of the priming first expansion occurs in the presence of layered APCs (including, for example, PBMCs) with an average thickness of at or about 2 cell layers to at or about 3 cell layers and day 7 of the rapid second expansion occurs in the presence of layered APCs (including, for example, PBMCs) with an average thickness of at or about 4 cell layers to at or about 8 cell layers.

In another embodiment, day 0 of the priming first expansion occurs in the presence of layered APCs (including, for example, PBMCs) with an average thickness of at or about 2 cell layers and day 7 of the rapid second expansion occurs in the presence of layered APCs (including, for example, PBMCs) with an average thickness of at or about 4 cell layers to at or about 8 cell layers.

In another embodiment, day 0 of the priming first expansion occurs in the presence of layered APCs (including, for example, PBMCs) with an average thickness of at or about 1, 2 or 3 cell layers and day 7 of the rapid second expansion occurs in the presence of layered APCs (including, for example, PBMCs) with an average thickness of at or about 3, 4, 5, 6, 7, 8, 9 or 10 cell layers.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:10.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:8.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:7.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:6.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:5.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:4.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:3.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:2.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.2 to at or about 1:8.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.3 to at or about 1:7.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.4 to at or about 1:6.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.5 to at or about 1:5.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.6 to at or about 1:4.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.7 to at or about 1:3.5.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.8 to at or about 1:3.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.9 to at or about 1:2.5.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is at or about 1:2.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from at or about 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9, 1:6, 1:6.1, 1:6.2, 1:6.3, 1:6.4, 1:6.5, 1:6.6, 1:6.7, 1:6.8, 1:6.9, 1:7, 1:7.1, 1:7.2, 1:7.3, 1:7.4, 1:7.5, 1:7.6, 1:7.7, 1:7.8, 1:7.9, 1:8, 1:8.1, 1:8.2, 1:8.3, 1:8.4, 1:8.5, 1:8.6, 1:8.7, 1:8.8, 1:8.9, 1:9, 1:9.1, 1:9.2, 1:9.3, 1:9.4, 1:9.5, 1:9.6, 1:9.7, 1:9.8, 1:9.9 or 1:10.

In some embodiments, the number of APCs in the priming first expansion is selected from the range of about $1.0\times10^6$ APCs/cm$^2$ to about $4.5\times10^6$ APCs/cm$^2$, and the number of APCs in the rapid second expansion is selected from the range of about $2.5\times10^6$ APCs/cm$^2$ to about $7.5\times10^6$ APCs/cm$^2$.

In some embodiments, the number of APCs in the priming first expansion is selected from the range of about $1.5\times10^6$ APCs/cm$^2$ to about $3.5\times10^6$ APCs/cm$^2$, and the number of APCs in the rapid second expansion is selected from the range of about $3.5\times10^6$ APCs/cm$^2$ to about $6.0\times10^6$ APCs/cm$^2$.

In some embodiments, the number of APCs in the priming first expansion is selected from the range of about $2.0\times10^6$ APCs/cm$^2$ to about $3.0\times10^6$ APCs/cm$^2$, and the number of APCs in the rapid second expansion is selected from the range of about $4.0\times10^6$ APCs/cm$^2$ to about $5.5\times10^6$ APCs/cm$^2$.

Optional Cell Medium Components
Anti-CD3 Antibodies

In some embodiments, the culture media used in expansion methods described herein (see for example, FIG. 8 (in particular, e.g., FIG. 8B)) include an anti-CD3 antibody. An anti-CD3 antibody in combination with IL-2 induces T cell activation and cell division in the TIL population. This effect can be seen with full length antibodies as well as Fab and F(ab')2 fragments, with the former being generally preferred; see, e.g., Tsoukas et al., *J. Immunol.* 1985, 135, 1719, hereby incorporated by reference in its entirety.

As will be appreciated by those in the art, there are a number of suitable anti-human CD3 antibodies that find use in the invention, including anti-human CD3 polyclonal and monoclonal antibodies from various mammals, including, but not limited to, murine, human, primate, rat, and canine antibodies. In particular embodiments, the OKT3 anti-CD3 antibody is used (commercially available from Ortho-McNeil, Raritan, NJ or Miltenyi Biotech, Auburn, CA).

TABLE 18

Amino acid sequences of muromonab (exemplary OKT-3 antibody)

| Identifier | Sequence (One-Letter Amino Acid Symbols) | | | | | |
|---|---|---|---|---|---|---|
| SEQ ID NO: 1 Muromonab heavy chain | QVQLQQSGAE | LARPGASVKM | SCKASGYTFT | RYTMHWVKQR | PGQGLEWIGY | INPSRGYTNY 60 |
| | NQKFKDKATL | TTDKSSSTAY | MQLSSLTSED | SAVYYCARYY | DDHYCLDYWG | QGTTLTVSSA 120 |
| | KTTAPSVYPL | APVCGGTTGS | SVTLGCLVKG | YFPEPVTLTW | NSGSLSSGVH | TFPAVLQSDL 180 |
| | YTLSSSVTVT | SSTWPSQSIT | CNVAHPASST | KVDKKIEPRP | KSCDKTHTCP | PCPAPELLGG 240 |
| | PSVFLFPPKP | KDTLMISRTP | EVTCVVVDVS | HEDPEVKFNW | YVDGVEVHNA | KTKPREEQYN 300 |
| | STYRVVSVLT | VLHQDWLNGK | EYKCKVSNKA | LPAPIEKTIS | KAKGQPREPQ | VYTLPPSRDE 360 |
| | LTKNQVSLTC | LVKGFYPSDI | AVEWESNGQP | ENNYKTTPPV | LDSDGSFFLY | SKLTVDKSRW 420 |
| | QQGNVFSCSV | MHEALHNHYT | QKSLSLSPGK | | | 450 |

TABLE 18-continued

Amino acid sequences of muromonab (exemplary OKT-3 antibody)

| Identifier | Sequence (One-Letter Amino Acid Symbols) | |
|---|---|---|
| SEQ ID NO: 2 Muromonab light chain | QIVLTQSPAI MSASPGEKVT MTCSASSSVS YMNWYQQKSG TSPKRWIYDT SKLASGVPAH | 60 |
| | FRGSGSGTSY SLTISGMEAE DAATYYCQQW SSNPFTFGSG TKLEINRADT APTVSIFPPS | 120 |
| | SEQLTSGGAS VVCFLNNFYP KDINVKWKID GSERQNGVLN SWTDQDSKDS TYSMSSTLTL | 180 |
| | TKDEYERHNS YTCEATHKTS TSPIVKSFNR NEC | 213 |

4-1BB (CD137) Agonists

In an embodiment, the cell culture medium of the priming first expansion and/or the rapid second expansion comprises a TNFRSF agonist. In an embodiment, the TNFRSF agonist is a 4-1BB (CD137) agonist. The 4-1BB agonist may be any 4-1BB binding molecule known in the art. The 4-1BB binding molecule may be a monoclonal antibody or fusion protein capable of binding to human or mammalian 4-1BB. The 4-1BB agonists or 4-1BB binding molecules may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. The 4-1BB agonist or 4-1BB binding molecule may have both a heavy and a light chain. As used herein, the term binding molecule also includes antibodies (including full length antibodies), monoclonal antibodies (including full length monoclonal antibodies), polyclonal antibodies, multispecific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to 4-1BB. In an embodiment, the 4-1BB agonist is an antigen binding protein that is a fully human antibody. In an embodiment, the 4-1BB agonist is an antigen binding protein that is a humanized antibody. In some embodiments, 4-1 in agonists for use in the presently disclosed methods and compositions include anti-4-1BB antibodies, human anti-4-1 in antibodies, mouse anti-4-1 in antibodies, mammalian anti-4-1 in antibodies, monoclonal anti-4-1 in antibodies, polyclonal anti-4-1 in antibodies, chimeric anti-4-1 in antibodies, anti-4-1 in adnectins, anti-4-1 in domain antibodies, single chain anti-4-1 in fragments, heavy chain anti-4-1 in fragments, light chain anti-4-1 in fragments, anti-4-1 in fusion proteins, and fragments, derivatives, conjugates, variants, or biosimilars thereof. Agonistic anti-4-1 in antibodies are known to induce strong immune responses. Lee, et al., *PLOS One* 2013, 8, e69677. In a preferred embodiment, the 4-1 in agonist is an agonistic, anti-4-1 in humanized or fully human monoclonal antibody (i.e., an antibody derived from a single cell line). In an embodiment, the 4-1 in agonist is EU-101 (Eutilex Co. Ltd.), utomilumab, or urelumab, or a fragment, derivative, conjugate, variant, or biosimilar thereof. In a preferred embodiment, the 4-1BB agonist is utomilumab or urelumab, or a fragment, derivative, conjugate, variant, or biosimilar thereof.

In a preferred embodiment, the 4-1BB agonist or 4-1BB binding molecule may also be a fusion protein. In a preferred embodiment, a multimeric 4-1BB agonist, such as a trimeric or hexameric 4-1BB agonist (with three or six ligand binding domains), may induce superior receptor (4-1BBL) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG1-Fc and optionally further linking two or more of these fusion proteins are described, e.g., in Gieffers, et al., *Mol. Cancer Therapeutics* 2013, 12, 2735-47.

Agonistic 4-1BB antibodies and fusion proteins are known to induce strong immune responses. In a preferred embodiment, the 4-1BB agonist is a monoclonal antibody or fusion protein that binds specifically to 4-1BB antigen in a manner sufficient to reduce toxicity. In some embodiments, the 4-1BB agonist is an agonistic 4-1BB monoclonal antibody or fusion protein that abrogates antibody-dependent cellular toxicity (ADCC), for example NK cell cytotoxicity. In some embodiments, the 4-1BB agonist is an agonistic 4-1BB monoclonal antibody or fusion protein that abrogates antibody-dependent cell phagocytosis (ADCP). In some embodiments, the 4-1BB agonist is an agonistic 4-1BB monoclonal antibody or fusion protein that abrogates complement-dependent cytotoxicity (CDC). In some embodiments, the 4-1BB agonist is an agonistic 4-1BB monoclonal antibody or fusion protein which abrogates Fc region functionality.

In some embodiments, the 4-1BB agonists are characterized by binding to human 4-1BB (SEQ ID NO:9) with high affinity and agonistic activity. In an embodiment, the 4-1BB agonist is a binding molecule that binds to human 4-1BB (SEQ ID NO:9). In an embodiment, the 4-1BB agonist is a binding molecule that binds to murine 4-1BB (SEQ ID NO:10). The amino acid sequences of 4-1BB antigen to which a 4-1BB agonist or binding molecule binds are summarized in Table 19.

TABLE 19

Amino acid sequence of 4-1BB antigens.

| Identifier | Sequence (One-Letter Amino Acid Symbols) | |
|---|---|---|
| SEQ ID NO: 9 human 4-1BB, Tumor necrosis factor receptor superfamily, member 9 (*Homo sapiens*) | MGNSCYNIVA TLLLVLNFER TRSLQDPCSN CPAGTFCDNN RNQICSPCPP NSFSSAGGQR | 60 |
| | TCDICRQCKG VFRTRKECSS TSNAECDCTP GPHCLGAGCS MCEQDCKQGQ ELTKKGCKDC | 120 |
| | CFGTFNDQKR GICRPWTNCS LDGKSVLVNG TKERDVVCGP SPADLSPGAS SVTPPAPARE | 180 |
| | PGHSPQIISF FLALTSTALL FLLFFLTLRF SVVKRGRKKL LYIFKQPFMR PVQTTQEEDG | 240 |
| | CSCRFPEEEE GGCEL | 255 |

TABLE 19-continued

Amino acid sequence of 4-1BB antigens.

| Identifier | Sequence (One-Letter Amino Acid Symbols) | | | | | | |
|---|---|---|---|---|---|---|---|
| SEQ ID NO: 10 murine 4-1BB, Tumor necrosis factor receptor superfamily, member 9 (Mus musculus) | MGNNCYNVVV CNICRVCAGY LGTFNDQNGT GHSLQVLTLF CRCPQEEEGG | IVLLLVGCEK FRFKKFCSST GVCRPWTNCS LALTSALLLA GGGYEL | VGAVQNSCDN HNAECECIEG LDGRSVLKTG LIFITLLFSV | CQPGTFCRKY FHCLGPQCTR TTEKDVVCGP LKWIRKKFPH | NPVCKSCPPS CEKDCRPGQE PVVSFSPSTT IFKQPFKKTT | TFSSIGGQPN LTKQGCKTCS ISVTPEGGPG GAAQEEDACS | 60 120 180 240 256 |

In some embodiments, the compositions, processes and methods described include a 4-1BB agonist that binds human or murine 4-1BB with a $K_D$ of about 100 pM or lower, binds human or murine 4-1BB with a $K_D$ of about 90 pM or lower, binds human or murine 4-1BB with a $K_D$ of about 80 pM or lower, binds human or murine 4-1BB with a $K_D$ of about 70 pM or lower, binds human or murine 4-1BB with a $K_D$ of about 60 pM or lower, binds human or murine 4-1BB with a $K_D$ of about 50 pM or lower, binds human or murine 4-1BB with a $K_D$ of about 40 pM or lower, or binds human or murine 4-1BB with a $K_D$ of about 30 pM or lower.

In some embodiments, the compositions, processes and methods described include a 4-1BB agonist that binds to human or murine 4-1BB with a $k_{assoc}$ of about 7.5×10⁵ 1/M·s or faster, binds to human or murine 4-1 in with a $k_{dissoc}$ of about 7.5×10⁵ 1/M·s or faster, binds to human or murine 4-1BB with a $k_{assoc}$ of about 8×10⁵ 1/M·s or faster, binds to human or murine 4-1 in with a $k_{assoc}$ of about 8.5×10⁵ 1/M·s or faster, binds to human or murine 4-1BB with a $k_{assoc}$ of about 9×10⁵ 1/M·s or faster, binds to human or murine 4-1 in with a $k_{assoc}$ of about 9.5×10⁵ 1/M·s or faster, or binds to human or murine 4-1BB with a $k_{assoc}$ of about 1×10⁶ 1/M·s or faster.

In some embodiments, the compositions, processes and methods described include a 4-1BB agonist that binds to human or murine 4-1 in with a $k_{dissoc}$ of about 2×10⁻⁵ 1/s or slower, binds to human or murine 4-1 in with a $k_{dissoc}$ of about 2.1×10⁻⁵ 1/s or slower, binds to human or murine 4-1 in with a $k_{dissoc}$ of about 2.2×10⁻⁵ 1/s or slower, binds to human or murine 4-1 in with a $k_{dissoc}$ of about 2.3×10⁻⁵ 1/s or slower, binds to human or murine 4-1 in with a $k_{dissoc}$ of about 2.4×10⁻⁵ 1/s or slower, binds to human or murine 4-1 in with a $k_{dissoc}$ of about 2.5×10⁻⁵ 1/s or slower, binds to human or murine 4-1 in with a $k_{dissoc}$ of about 2.6×10⁻⁵ 1/s or slower or binds to human or murine 4-1BB with a $k_{dissoc}$ of about 2.7×10⁻⁵ 1/s or slower, binds to human or murine 4-1BB with a $k_{dissoc}$ of about 2.8×10⁻⁵ 1/s or slower, binds to human or murine 4-1BB with a $k_{dissoc}$ of about 2.9×10⁻⁵ 1/s or slower, or binds to human or murine 4-1BB with a $k_{dissoc}$ of about 3×10⁻⁵ 1/s or slower.

In some embodiments, the compositions, processes and methods described include a 4-1BB agonist that binds to human or murine 4-1BB with an $IC_{50}$ of about 10 nM or lower, binds to human or murine 4-1BB with an $IC_{50}$ of about 9 nM or lower, binds to human or murine 4-1BB with an $IC_{50}$ of about 8 nM or lower, binds to human or murine 4-1BB with an $IC_{50}$ of about 7 nM or lower, binds to human or murine 4-1 in with an $IC_{50}$ of about 6 nM or lower, binds to human or murine 4-1 in with an $IC_{50}$ of about 5 nM or lower, binds to human or murine 4-1 in with an $IC_{50}$ of about 4 nM or lower, binds to human or murine 4-1 in with an $IC_{50}$ of about 3 nM or lower, binds to human or murine 4-1BB with an $IC_{50}$ of about 2 nM or lower, or binds to human or murine 4-1BB with an $IC_{50}$ of about 1 nM or lower.

In a preferred embodiment, the 4-1 in agonist is utomilumab, also known as PF-05082566 or MOR-7480, or a fragment, derivative, variant, or biosimilar thereof. Utomilumab is available from Pfizer, Inc. Utomilumab is an immunoglobulin G2-lambda, anti-[*Homo sapiens* TNFRSF9 (tumor necrosis factor receptor (TNFR) superfamily member 9, 4-1 in, T cell antigen ILA, CD137)], *Homo sapiens* (fully human) monoclonal antibody. The amino acid sequences of utomilumab are set forth in Table 7. Utomilumab comprises glycosylation sites at Asn59 and Asn292; heavy chain intrachain disulfide bridges at positions 22-96 ($V_H$-$V_L$), 143-199 ($C_H1$-$C_L$), 256-316 ($C_H2$) and 362-420 ($C_H3$); light chain intrachain disulfide bridges at positions 22'-87' ($V_H$-$V_L$) and 136'-195' ($C_H1$-$C_L$); interchain heavy chain-heavy chain disulfide bridges at IgG2A isoform positions 218-218, 219-219, 222-222, and 225-225, at IgG2A/B isoform positions 218-130, 219-219, 222-222, and 225-225, and at IgG2n isoform positions 219-130 (2), 222-222, and 225-225; and interchain heavy chain-light chain disulfide bridges at IgG2A isoform positions 130-213' (2), IgG2A/B isoform positions 218-213' and 130-213', and at IgG2n isoform positions 218-213' (2). The preparation and properties of utomilumab and its variants and fragments are described in U.S. Pat. Nos. 8,821,867; 8,337,850; and 9,468, 678, and International Patent Application Publication No. WO 2012/032433 A1, the disclosures of each of which are incorporated by reference herein. Preclinical characteristics of utomilumab are described in Fisher, et al., *Cancer Immunolog. & Immunother.* 2012, 61, 1721-33. Current clinical trials of utomilumab in a variety of hematological and solid tumor indications include U.S. National Institutes of Health clinicaltrials.gov identifiers NCT02444793, NCT01307267, NCT02315066, and NCT02554812.

In an embodiment, a 4-1BB agonist comprises a heavy chain given by SEQ ID NO:11 and a light chain given by SEQ ID NO: 12. In an embodiment, a 4-1BB agonist comprises heavy and light chains having the sequences shown in SEQ ID NO:11 and SEQ ID NO:12, respectively, or antigen binding fragments, Fab fragments, single-chain variable fragments (scFv), variants, or conjugates thereof. In an embodiment, a 4-1BB agonist comprises heavy and light chains that are each at least 99% identical to the sequences shown in SEQ ID NO:11 and SEQ ID NO:12, respectively. In an embodiment, a 4-1BB agonist comprises heavy and light chains that are each at least 98% identical to the sequences shown in SEQ ID NO:11 and SEQ ID NO:12, respectively. In an embodiment, a 4-1BB agonist comprises heavy and light chains that are each at least 97% identical to the sequences shown in SEQ ID NO:11 and SEQ ID NO:12, respectively. In an embodiment, a 4-1BB agonist comprises heavy and light chains that are each at least 96% identical to the sequences shown in SEQ ID NO:11 and SEQ ID NO:12, respectively. In an embodiment, a 4-1BB agonist comprises heavy and light chains that are each at least 95% identical to the sequences shown in SEQ ID NO:11 and SEQ ID NO:12, respectively.

In an embodiment, the 4-1BB agonist comprises the heavy and light chain CDRs or variable regions (VRs) of utomilumab. In an embodiment, the 4-1BB agonist heavy chain variable region ($V_H$) comprises the sequence shown in SEQ ID NO:13, and the 4-1BB agonist light chain variable region ($V_L$) comprises the sequence shown in SEQ ID NO:14, and conservative amino acid substitutions thereof. In an embodiment, a 4-1BB agonist comprises $V_H$ and $V_L$ regions that are each at least 99% identical to the sequences shown in SEQ ID NO:13 and SEQ ID NO:14, respectively. In an embodiment, a 4-1BB agonist comprises $V_H$ and $V_L$ regions that are each at least 98% identical to the sequences shown in SEQ ID NO:13 and SEQ ID NO:14, respectively. In an embodiment, a 4-1BB agonist comprises $V_H$ and $V_L$ regions that are each at least 97% identical to the sequences shown in SEQ ID NO:13 and SEQ ID NO:14, respectively. In an embodiment, a 4-1BB agonist comprises $V_H$ and $V_L$ regions that are each at least 96% identical to the sequences shown in SEQ ID NO:13 and SEQ ID NO:14, respectively. In an embodiment, a 4-1BB agonist comprises $V_H$ and $V_L$ regions that are each at least 95% identical to the sequences shown in SEQ ID NO:13 and SEQ ID NO:14, respectively. In an embodiment, a 4-1BB agonist comprises an scFv antibody comprising $V_H$ and $V_L$ regions that are each at least 99% identical to the sequences shown in SEQ ID NO:13 and SEQ ID NO:14.

In an embodiment, a 4-1BB agonist comprises heavy chain CDR1, CDR2 and CDR3 domains having the sequences set forth in SEQ ID NO:15, SEQ ID NO:16, and SEQ ID NO:17, respectively, and conservative amino acid substitutions thereof, and light chain CDR1, CDR2 and CDR3 domains having the sequences set forth in SEQ ID NO:18, SEQ ID NO:19, and SEQ ID NO:20, respectively, and conservative amino acid substitutions thereof.

In an embodiment, the 4-1BB agonist is a 4-1BB agonist biosimilar monoclonal antibody approved by drug regulatory authorities with reference to utomilumab. In an embodiment, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is utomilumab. In some embodiments, the one or more post-translational modifications are selected from one or more of: glycosylation, oxidation, deamidation, and truncation. In some embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is utomilumab. The 4-1BB agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab.

TABLE 20

Amino acid sequences for 4-1BB agonist antibodies related to utomilumab.

| Identifier | Sequence (One-Letter Amino Acid Symbols) | | | | | |
|---|---|---|---|---|---|---|
| SEQ ID NO: 11 heavy chain for utomilumab | EVQLVQSGAE | VKKPGESLRI | SCKGSGYSFS | TYWISWVRQM | PGKGLEWMGK | IYPGDSYTNY 60 |
| | SPSFQGQVTI | SADKSISTAY | LQWSSLKASD | TAMYYCARGY | GIFDYWGQGT | LVTVSSASTK 120 |
| | GPSVFPLAPC | SRSTSESTAA | LGCLVKDYFP | EPVTVSWNSG | ALTSGVHTFP | AVLQSSGLYS 180 |
| | LSSVVTVPSS | NFGTQTYTCN | VDHKPSNTKV | DKTVERKCCV | ECPPCPAPPV | AGPSVFLFPP 240 |
| | KPKDTLMISR | TPEVTCVVVD | VSHEDPEVQF | NWYVDGVEVH | NAKTKPREEQ | FNSTFRVVSV 300 |
| | LTVVHQDWLN | GKEYKCKVSN | KGLPAPIEKT | ISKTKGQPRE | PQVYTLPPSR | EEMTKNQVSL 360 |
| | TCLVKGFYPS | DIAVEWESNG | QPENNYKTTP | PMLDSDGSFF | LYSKLTVDKS | RWQQGNVFSC 420 |
| | SVMHEALHNH | YTQKSLSLSP | G | | | 441 |
| SEQ ID NO: 12 light chain for utomilumab | SYELTQPPSV | SVSPGQTASI | TCSGDNIGDQ | YAHWYQQKPG | QSPVLVIYQD | KNRPSGIPER 60 |
| | FSGSNSGNTA | TLTISGTQAM | DEADYYCATY | TGFGSLAVFG | GGTKLTVLGQ | PKAAPSVTLF 120 |
| | PPSSEELQAN | KATLVCLISD | FYPGAVTVAW | KADSSPVKAG | VETTTPSKQS | NNKYAASSYL 180 |
| | SLTPEQWKSH | RSYSCQVTHE | GSTVEKTVAP | TECS | | 214 |
| SEQ ID NO: 13 heavy chain variable region for utomilumab | EVQLVQSGAE | VKKPGESLRI | SCKGSGYSFS | TYWISWVRQM | PGKGLEWMG | KIYPGDSYTN 60 |
| | YSPSFQGQVT | ISADKSISTA | YLQWSSLKAS | DTAMYYCARG | YGIFDYWGQ | GTLVTVSS 118 |
| SEQ ID NO: 14 light chain variable region for utomilumab | SYELTQPPSV | SVSPGQTASI | TCSGDNIGDQ | YAHWYQQKPG | QSPVLVIYQD | KNRPSGIPER 60 |
| | FSGSNSGNTA | TLTISGTQAM | DEADYYCATY | TGFGSLAVFG | GGTKLTVL | 108 |
| SEQ ID NO: 15 heavy chain CDR1 for utomilumab | STYWIS | | | | | 6 |

TABLE 20-continued

Amino acid sequences for 4-1BB agonist antibodies related to utomilumab.

| Identifier | Sequence (One-Letter Amino Acid Symbols) | |
|---|---|---|
| SEQ ID NO: 16 heavy chain CDR2 for utomilumab | KIYPGDSYTN YSPSFQG | 17 |
| SEQ ID NO: 17 heavy chain CDR3 for utomilumab | RGYGIFDY | 8 |
| SEQ ID NO: 18 light chain CDR1 for utomilumab | SGDNIGDQYA H | 11 |
| SEQ ID NO: 19 light chain CDR2 for utomilumab | QDKNRPS | 7 |
| SEQ ID NO: 20 light chain CDR3 for utomilumab | ATYTGFGSLA V | 11 |

In a preferred embodiment, the 4-1BB agonist is the monoclonal antibody urelumab, also known as BMS-663513 and 20H4.9.h4a, or a fragment, derivative, variant, or biosimilar thereof. Urelumab is available from Bristol-Myers Squibb, Inc., and Creative Biolabs, Inc. Urelumab is an immunoglobulin G4-kappa, anti-[*Homo sapiens* TNFRSF9 (tumor necrosis factor receptor superfamily member 9, 4-1BB, T cell antigen ILA, CD137)], *Homo sapiens* (fully human) monoclonal antibody. The amino acid sequences of urelumab are set forth in Table EE. Urelumab comprises N-glycosylation sites at positions 298 (and 298"); heavy chain intrachain disulfide bridges at positions 22-95 ($V_H$-$V_L$), 148-204 ($C_H$1-$C_L$), 262-322 ($C_H$2) and 368-426 ($C_H$3) (and at positions 22"-95", 148"-204", 262"-322", and 368"-426"); light chain intrachain disulfide bridges at positions 23'-88' ($V_H$-$V_L$) and 136'-196' ($C_H$1-$C_L$) (and at positions 23'''-88''' and 136'''-196'''); interchain heavy chain-heavy chain disulfide bridges at positions 227-227" and 230-230"; and interchain heavy chain-light chain disulfide bridges at 135-216' and 135"-216'". The preparation and properties of urelumab and its variants and fragments are described in U.S. Pat. Nos. 7,288,638 and 8,962,804, the disclosures of which are incorporated by reference herein. The preclinical and clinical characteristics of urelumab are described in Segal, et al., *Clin. Cancer Res.* 2016, available at http:/dx.doi.org/10.1158/1078-0432.CCR-16-1272. Current clinical trials of urelumab in a variety of hematological and solid tumor indications include U.S. National Institutes of Health clinicaltrials.gov identifiers NCT01775631, NCT02110082, NCT02253992, and NCT01471210.

In an embodiment, a 4-1BB agonist comprises a heavy chain given by SEQ ID NO:21 and a light chain given by SEQ ID NO:22. In an embodiment, a 4-1BB agonist comprises heavy and light chains having the sequences shown in SEQ ID NO:21 and SEQ ID NO:22, respectively, or antigen binding fragments, Fab fragments, single-chain variable fragments (scFv), variants, or conjugates thereof. In an embodiment, a 4-1BB agonist comprises heavy and light chains that are each at least 99% identical to the sequences shown in SEQ ID NO:21 and SEQ ID NO:22, respectively. In an embodiment, a 4-1BB agonist comprises heavy and light chains that are each at least 98% identical to the sequences shown in SEQ ID NO:21 and SEQ ID NO:22, respectively. In an embodiment, a 4-1BB agonist comprises heavy and light chains that are each at least 97% identical to the sequences shown in SEQ ID NO:21 and SEQ ID NO:22, respectively. In an embodiment, a 4-1BB agonist comprises heavy and light chains that are each at least 96% identical to the sequences shown in SEQ ID NO:21 and SEQ ID NO:22, respectively. In an embodiment, a 4-1BB agonist comprises heavy and light chains that are each at least 95% identical to the sequences shown in SEQ ID NO:21 and SEQ ID NO:22, respectively.

In an embodiment, the 4-1BB agonist comprises the heavy and light chain CDRs or variable regions (VRs) of urelumab. In an embodiment, the 4-1BB agonist heavy chain variable region ($V_H$) comprises the sequence shown in SEQ ID NO:23, and the 4-1BB agonist light chain variable region ($V_L$) comprises the sequence shown in SEQ ID NO:24, and conservative amino acid substitutions thereof. In an embodiment, a 4-1BB agonist comprises $V_H$ and $V_L$ regions that are each at least 99% identical to the sequences shown in SEQ ID NO:23 and SEQ ID NO:24, respectively. In an embodiment, a 4-1BB agonist comprises $V_H$ and $V_L$ regions that are each at least 98% identical to the sequences shown in SEQ ID NO:23 and SEQ ID NO:24, respectively. In an embodiment, a 4-1BB agonist comprises $V_H$ and $V_L$ regions that are each at least 97% identical to the sequences shown in SEQ ID NO:23 and SEQ ID NO:24, respectively. In an embodiment, a 4-1BB agonist comprises $V_H$ and $V_L$ regions that are each at least 96% identical to the sequences shown in SEQ ID NO:23 and SEQ ID NO:24, respectively. In an embodiment, a 4-1BB agonist comprises $V_H$ and $V_L$ regions that are each at least 95% identical to the sequences shown in SEQ ID NO:23 and SEQ ID NO:24, respectively. In an embodiment, a 4-1BB agonist comprises an scFv antibody comprising $V_H$ and $V_L$ regions that are each at least 99% identical to the sequences shown in SEQ ID NO:23 and SEQ ID NO:24.

In an embodiment, a 4-1BB agonist comprises heavy chain CDR1, CDR2 and CDR3 domains having the sequences set forth in SEQ ID NO:25, SEQ ID NO:26, and SEQ ID NO:27, respectively, and conservative amino acid substitutions thereof, and light chain CDR1, CDR2 and CDR3 domains having the sequences set forth in SEQ ID NO:28, SEQ ID NO:29, and SEQ ID NO:30, respectively, and conservative amino acid substitutions thereof.

In an embodiment, the 4-1BB agonist is a 4-1BB agonist biosimilar monoclonal antibody approved by drug regulatory authorities with reference to urelumab. In an embodiment, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is urelumab. In some embodiments, the one or more post-translational modifications are selected from one or more of: glycosylation, oxidation, deamidation, and truncation. In some embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is urelumab. The 4-1BB agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab.

TABLE 21

Amino acid sequences for 4-1BB agonist antibodies related to urelumab.

| Identifier | Sequence (One-Letter Amino Acid Symbols) | |
|---|---|---|
| SEQ ID NO: 21 heavy chain for urelumab | QVQLQQWGAG LLKPSETLSL TCAVYGGSFS GYYWSWIRQS PEKGLEWIGE INHGGYVTYN PSLESRVTIS VDTSKNQFSL KLSSVTAADT AVYYCARDYG PGNYDWYFDL WGRGTLVTVS SASTKGPSVF PLAPCSRSTS ESTAALGCLV KDYFPEPVTV SWNSGALTSG VHTFPAVLQS SGLYSLSSVV TVPSSSLGTK TYTCNVDHKP SNTKVDKRVE SKYGPPCPPC PAPEFLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK | 60 120 180 240 300 360 420 448 |
| SEQ ID NO: 22 light chain for urelumab | EIVLTQSPAT LSLSPGERAT LSCRASQSVS SYLAWYQQKP GQAPRLLIYD ASNRATGIPA RFSGSGSGTD FTLTISSLEP EDFAVYYCQQ RSNWPPALTF CGGTKVEIKR TVAAPSVFIF PPSDEQLKSG TASVVCLLNN FYPREAKVQW KVDNALQSGN SQESVTEQDS KDSTYSLSST LTLSKADYEK HKVYACEVTH QGLSSPVTKS FNRGEC | 60 120 180 216 |
| SEQ ID NO: 23 variable heavy chain for urelumab | MKHLWFFLLL VAAPRWVLSQ VQLQQWGAGL LKPSETLSLT CAVYGGSFSG YYWSWIRQSP EKGLEWIGEI NHGGYVTYNP SLESRVTISV DTSKNQFSLK LSSVTAADTA VYYCARDYGP | 60 120 |
| SEQ ID NO: 24 variable light chain for urelumab | MEAPAQLLFL LLLWLPDTTG EIVLTQSPAT LSLSPGERAT LSCRASQSVS SYLAWYQQKP GQAPRLLIYD ASNRATGIPA RFSGSGSGTD FTLTISSLEP EDFAVYYCQQ | 60 110 |
| SEQ ID NO: 25 heavy chain CDR1 for urelumab | GYYWS | 5 |
| SEQ ID NO: 26 heavy chain CDR2 for urelumab | EINHGGYVTY NPSLES | 16 |
| SEQ ID NO: 27 heavy chain CDR3 for urelumab | DYGPGNYDWY FDL | 13 |
| SEQ ID NO: 28 light chain CDR1 for urelumab | RASQSVSSYL A | 11 |
| SEQ ID NO: 29 light chain CDR2 for urelumab | DASNRAT | 7 |
| SEQ ID NO: 30 light chain CDR3 for urelumab | QQRSDWPPAL T | 11 |

In an embodiment, the 4-1BB agonist is selected from the group consisting of 1D8, 3Elor, 41B4 (BioLegend 309809), H4-1BB-M127 (BD Pharmingen 552532), BBK2 (Thermo Fisher MS621PABX), 145501 (Leinco Technologies B591), the antibody produced by cell line deposited as ATCC No. HB-11248 and disclosed in U.S. Pat. No. 6,974,863, 5F4 (BioLegend 31 1503), C65-485 (BD Pharmingen 559446), antibodies disclosed in U.S. Patent Application Publication No. US 2005/0095244, antibodies disclosed in U.S. Pat. No. 7,288,638 (such as 20H4.9-IgG1 (BMS-663031)), antibodies disclosed in U.S. Pat. No. 6,887,673 (such as 4E9 or BMS-554271), antibodies disclosed in U.S. Pat. No. 7,214,493, antibodies disclosed in U.S. Pat. No. 6,303,121, antibodies disclosed in U.S. Pat. No. 6,569,997, antibodies disclosed in U.S. Pat. No. 6,905,685 (such as 4E9 or BMS-554271), antibodies disclosed in U.S. Pat. No. 6,362,325 (such as 1D8 or BMS-469492; 3H3 or BMS-469497; or 3E1), antibodies disclosed in U.S. Pat. No. 6,974,863 (such as 53A2); antibodies disclosed in U.S. Pat. No. 6,210,669 (such as 1D8, 3B8, or 3E1), antibodies described in U.S. Pat. No. 5,928,893, antibodies disclosed in U.S. Pat. No. 6,303,121, antibodies disclosed in U.S. Pat. No. 6,569,997, antibodies disclosed in International Patent Application Publication Nos. WO 2012/177788, WO 2015/119923, and WO 2010/042433, and fragments, derivatives, conjugates, variants, or biosimilars thereof, wherein the disclosure of each of the foregoing patents or patent application publications is incorporated by reference here.

In an embodiment, the 4-1BB agonist is a 4-1BB agonistic fusion protein described in International Patent Application Publication Nos. WO 2008/025516 A1, WO 2009/007120 A1, WO 2010/003766 A1, WO 2010/010051 A1, and WO 2010/078066 A1; U.S. Patent Application Publication Nos. US 2011/0027218 A1, US 2015/0126709 A1, US 2011/0111494 A1, US 2015/0110734 A1, and US 2015/0126710 A1; and U.S. Pat. Nos. 9,359,420, 9,340,599, 8,921,519, and 8,450,460, the disclosures of which are incorporated by reference herein.

In an embodiment, the 4-1BB agonist is a 4-1BB agonistic fusion protein as depicted in Structure I-A (C-terminal Fc-antibody fragment fusion protein) or Structure I-B (N-terminal Fc-antibody fragment fusion protein) of FIG. 50, or a fragment, derivative, conjugate, variant, or biosimilar thereof. In structures I-A and I-B, the cylinders refer to individual polypeptide binding domains. Structures I-A and I-B comprise three linearly-linked TNFRSF binding domains derived from e.g., 4-1BBL or an antibody that binds 4-1BB, which fold to form a trivalent protein, which is then linked to a second trivalent protein through IgG1-Fc (including CH3 and CH2 domains) is then used to link two of the trivalent proteins together through disulfide bonds (small elongated ovals), stabilizing the structure and providing an agonists capable of bringing together the intracellular signaling domains of the six receptors and signaling proteins to form a signaling complex. The TNFRSF binding domains denoted as cylinders may be scFv domains comprising, e.g., a $V_H$ and a $V_L$ chain connected by a linker that may comprise hydrophilic residues and Gly and Ser sequences for flexibility, as well as Glu and Lys for solubility. Any scFv domain design may be used, such as those described in de Marco, Microbial Cell Factories, 2011, 10, 44; Ahmad, et al., Clin. & Dev. Immunol. 2012, 980250; Monnier, et al., Antibodies, 2013, 2, 193-208; or in references incorporated elsewhere herein. Fusion protein structures of this form are described in U.S. Pat. Nos. 9,359,420, 9,340,599, 8,921,519, and 8,450,460, the disclosures of which are incorporated by reference herein.

Amino acid sequences for the other polypeptide domains of structure I-A are given in Table 9. The Fc domain preferably comprises a complete constant domain (amino acids 17-230 of SEQ ID NO:31) the complete hinge domain (amino acids 1-16 of SEQ ID NO:31) or a portion of the hinge domain (e.g., amino acids 4-16 of SEQ ID NO:31). Preferred linkers for connecting a C-terminal Fc-antibody may be selected from the embodiments given in SEQ ID NO:32 to SEQ ID NO:41, including linkers suitable for fusion of additional polypeptides.

TABLE 22

Amino acid sequences for TNFRSF fusion proteins, including 4-1BB fusion proteins, with C-terminal Fc-antibody fragment fusion protein design (structure I-A).

| Identifier | Sequence (One-Letter Amino Acid Symbols) | |
|---|---|---|
| SEQ ID NO: 31 Fc domain | KSCDKTHTCP PCPAPELLGG PSVFLFPPKP KDTLMISRTP EVTCVVVDVS HEDPEVKFNW | 60 |
| | YVDGVEVHNA KTKPREEQYN STYRVVSVLT VLHQDWLNGK EYKCKVSNKA LPAPIEKTIS | 120 |
| | KAKGQPREPQ VYTLPPSREE MTKNQVSLTC LVKGFYPSDI AVEWESNGQP ENNYKTTPPV | 180 |
| | LDSDGSFFLY SKLTVDKSRW QQGNVFSCSV MHEALHNHYT QKSLSLSPGK | 230 |
| SEQ ID NO: 32 linker | GGPGSSKSCD KTHTCPPCPA PE | 22 |
| SEQ ID NO: 33 linker | GGSGSSKSCD KTHTCPPCPA PE | 22 |
| SEQ ID NO: 34 linker | GGPGSSSSSS SKSCDKTHTC PPCPAPE | 27 |
| SEQ ID NO: 35 linker | GGSGSSSSSS SKSCDKTHTC PPCPAPE | 27 |
| SEQ ID NO: 36 linker | GGPGSSSSSS SSSKSCDKTH TCPPCPAPE | 29 |
| SEQ ID NO: 37 linker | GGSGSSSSSS SSSKSCDKTH TCPPCPAPE | 29 |

TABLE 22-continued

Amino acid sequences for TNFRSF fusion proteins, including 4-1BB fusion proteins, with C-terminal Fc-antibody fragment fusion protein design (structure I-A).

| Identifier | Sequence (One-Letter Amino Acid Symbols) | |
|---|---|---|
| SEQ ID NO: 38 linker | GGPGSSGSGS SDKTHTCPPC PAPE | 24 |
| SEQ ID NO: 39 linker | GGPGSSGSGS DKTHTCPPCP APE | 23 |
| SEQ ID NO: 40 linker | GGPSSSGSDK THTCPPCPAP E | 21 |
| SEQ ID NO: 41 linker | GGSSSSSSSS GSDKTHTCPP CPAPE | 25 |

Amino acid sequences for the other polypeptide domains of structure I-B are given in Table 10. If an Fc antibody fragment is fused to the N-terminus of an TNRFSF fusion protein as in structure I-B, the sequence of the Fc module is preferably that shown in SEQ ID NO:42, and the linker sequences are preferably selected from those embodiments set forth in SED ID NO:43 to SEQ ID NO:45.

TABLE 23

Amino acid sequences for TNFRSF fusion proteins, including 4-1BB fusion proteins, with N-terminal Fc-antibody fragment fusion protein design (structure I-B).

| Identifier | Sequence (One-Letter Amino Acid Symbols) | |
|---|---|---|
| SEQ ID NO: 42 Fc domain | METDTLLLWV LLLWVPAGNG DKTHTCPPCP APELLGGPSV FLFPPKPKDT LMISRTPEVT | 60 |
| | CVVVDVSHED PEVKFNWYVD GVEVHNAKTK PREEQYNSTY RVVSVLTVLH QDWLNGKEYK | 120 |
| | CKVSNKALPA PIEKTISKAK GQPREPQVYT LPPSREEMTK NQVSLTCLVK GFYPSDIAVE | 180 |
| | WESNGQPENN YKTTPPVLDS DGSFFLYSKL TVDKSRWQQG NVFSCSVMHE ALHNHYTQKS | 240 |
| | LSLSPG | 246 |
| SEQ ID NO: 43 linker | SGSGSGSGSG S | 11 |
| SEQ ID NO: 44 linker | SSSSSSGSGS GS | 12 |
| SEQ ID NO: 45 linker | SSSSSSGSGS GSGSGS | 16 |

In an embodiment, a 4-1BB agonist fusion protein according to structures I-A or I-B comprises one or more 4-1BB binding domains selected from the group consisting of a variable heavy chain and variable light chain of utomilumab, a variable heavy chain and variable light chain of urelumab, a variable heavy chain and variable light chain of utomilumab, a variable heavy chain and variable light chain selected from the variable heavy chains and variable light chains described in Table 23, any combination of a variable heavy chain and variable light chain of the foregoing, and fragments, derivatives, conjugates, variants, and biosimilars thereof.

In an embodiment, a 4-1BB agonist fusion protein according to structures I-A or I-B comprises one or more 4-1BB binding domains comprising a 4-1BBL sequence. In an embodiment, a 4-1BB agonist fusion protein according to structures I-A or I-B comprises one or more 4-1BB binding domains comprising a sequence according to SEQ ID NO:46. In an embodiment, a 4-1BB agonist fusion protein according to structures I-A or I-B comprises one or more 4-1BB binding domains comprising a soluble 4-1BBL sequence. In an embodiment, a 4-inn agonist fusion protein according to structures I-A or I-B comprises one or more 4-1BB binding domains comprising a sequence according to SEQ ID NO:47.

In an embodiment, a 4-inn agonist fusion protein according to structures I-A or I-B comprises one or more 4-inn binding domains that is a scFv domain comprising $V_H$ and $V_L$ regions that are each at least 950 identical to the sequences shown in SEQ ID NO:13 and SEQ ID NO:14, respectively, wherein the $V_H$ and $V_L$ domains are connected by a linker. In an embodiment, a 4-inn agonist fusion protein according to structures I-A or I-B comprises one or more 4-inn binding domains that is a scFv domain comprising $V_H$ and $V_L$ regions that are each at least 95% identical to the sequences shown in SEQ ID NO:23 and SEQ ID NO:24, respectively, wherein the $V_H$ and $V_L$ domains are connected by a linker. In an embodiment, a 4-1BB agonist fusion protein according to structures I-A or I-B comprises one or more 4-inn binding domains that is a scFv domain comprising $V_H$ and $V_L$ regions that are each at least 9500 identical to the $V_H$ and $V_L$ sequences given in Table 24, wherein the $V_H$ and $V_L$ domains are connected by a linker.

TABLE 24

Additional polypeptide domains useful as 4-1BB binding domains in fusion proteins or as scFv 4-1BB agonist antibodies.

| Identifier | Sequence (One-Letter Amino Acid Symbols) | |
|---|---|---|
| SEQ ID NO: 46<br>4-1BBL | MEYASDASLD PEAPWPPAPR ARACRVLPWA LVAGLLLLLL LAAACAVFLA CPWAVSGARA<br>SPGSAASPRL REGPELSPDD PAGLLDLRQG MFAQLVAQNV LLIDGPLSWY SDPGLAGVSL<br>TGGLSYKEDT KELVVAKAGV YYVFFQLELR RVVAGEGSGS VSLALHLQPL RSAAGAAALA<br>LTVDLPPASS EARNSAFGFQ GRLLHLSAGQ RLGVHLHTEA RARHAWQLTQ GATVLGLFRV<br>TPEIPAGLPS PRSE | 60<br>120<br>180<br>240<br>254 |
| SEQ ID NO: 47<br>4-1BBL soluble<br>domain | LRQGMFAQLV AQNVLLIDGP LSWYSDPGLA GVSLTGGLSY KEDTKELVVA KAGVYYVFFQ<br>LELRRVVAGE GSGSVSLALH LQPLRSAAGA AALALTVDLP PASSEARNSA FGFQGRLLHL<br>SAGQRLGVHL HTEARARHAW QLTQGATVLG LFRVTPEIPA GLPSPRSE | 60<br>120<br>168 |
| SEQ ID NO: 48<br>variable heavy<br>chain for 4B4-1-<br>1 version 1 | QVQLQQPGAE LVKPGASVKL SCKASGYTFS SYWMHWVKQR PGQVLEWIGE INPGNGHTNY<br>NEKFKSKATL TVDKSSSTAY MQLSSLTSED SAVYYCARSF TTARGFAYWG QGTLVTVS | 60<br>118 |
| SEQ ID NO: 49<br>variable light<br>chain for 4B4-1-<br>1 version 1 | DIVMTQSPAT QSVTPGDRVS LSCRASQTIS DYLHWYQQKS HESPRLLIKY ASQSISGIPS<br>RFSGSGSGSD FTLSINSVEP EDVGVYYCQD GHSFPPTFGG GTKLEIK | 60<br>107 |
| SEQ ID NO: 50<br>variable heavy<br>chain for 4B4-1-<br>1 version 2 | QVQLQQPGAE LVKPGASVKL SCKASGYTFS SYWMHWVKQR PGQVLEWIGE INPGNGHTNY<br>NEKFKSKATL TVDKSSSTAY MQLSSLTSED SAVYYCARSF TTARGFAYWG QGTLVTVSA | 60<br>119 |
| SEQ ID NO: 51<br>variable light<br>chain for 4B4-1-<br>1 version 2 | DIVMTQSPAT QSVTPGDRVS LSCRASQTIS DYLHWYQQKS HESPRLLIKY ASQSISGIPS<br>RFSGSGSGSD FTLSINSVEP EDVGVYYCQD GHSFPPTFGG GTKLEIKR | 60<br>108 |
| SEQ ID NO: 52<br>variable heavy<br>chain for H39E3-<br>2 | MDWTWRILFL VAAATGAHSE VQLVESGGGL VQPGGSLRLS CAASGFTFSD YWMSWVRQAP<br>GKGLEWVADI KNDGSYTNYA PSLTNRFTIS RDNAKNSLYL QMNSLRAEDT AVYYCARELT | 60<br>120 |
| SEQ ID NO: 53<br>variable light<br>chain for H39E3-<br>2 | MEAPAQLLFL LLLWLPDTTG DIVMTQSPDS LAVSLGERAT INCKSSQSLL SSGNQKNYL<br>WYQQKPGQPP KLLIYYASTR QSGVPDRFSG SGSGTDFTLT ISSLQAEDVA | 60<br>110 |

In an embodiment, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, and wherein the additional domain is a Fab or Fc fragment domain. In an embodiment, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, wherein the additional domain is a Fab or Fc fragment domain, wherein each of the soluble 4-1BB domains lacks a stalk region (which contributes to trimerisation and provides a certain distance to the cell membrane, but is not part of the 4-1BB binding domain) and the first and the second peptide linkers independently have a length of 3-8 amino acids.

In an embodiment, the 4-1BB agonist is a 4-1BB agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein each TNF superfamily cytokine domain is a 4-1BB binding domain.

In an embodiment, the 4-1BB agonist is a 4-1BB agonistic scFv antibody comprising any of the foregoing $V_H$ domains linked to any of the foregoing $V_L$ domains.

In an embodiment, the 4-1BB agonist is BPS Bioscience 4-1BB agonist antibody catalog no. 79097-2, commercially available from BPS Bioscience, San Diego, CA, USA. In an embodiment, the 4-1BB agonist is Creative Biolabs 4-1BB agonist antibody catalog no. MOM-18179, commercially available from Creative Biolabs, Shirley, NY, USA.

OX40 (CD134) Agonists

In an embodiment, the TNFRSF agonist is an OX40 (CD134) agonist. The OX40 agonist may be any OX40 binding molecule known in the art. The OX40 binding molecule may be a monoclonal antibody or fusion protein capable of binding to human or mammalian OX40. The OX40 agonists or OX40 binding molecules may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. The OX40 agonist or OX40 binding molecule may have both a heavy and a light chain. As used herein, the term binding molecule also includes antibodies (including full length antibodies), monoclonal antibodies (including full length monoclonal antibodies), polyclonal antibodies, multispecific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to OX40. In an embodiment, the OX40 agonist is an antigen binding protein that is a fully human antibody. In an embodiment, the OX40 agonist is an antigen binding protein that is a humanized antibody. In some embodiments, OX40 agonists for use in the presently disclosed methods and compositions include anti-OX40 antibodies, human anti-OX40 antibodies, mouse anti-OX40 antibodies, mammalian anti-OX40 antibodies, monoclonal anti-OX40 antibodies, polyclonal anti-OX40 antibodies, chimeric anti-OX40 antibodies, anti-OX40 adnectins, anti-OX40 domain antibodies, single chain anti-OX40 fragments, heavy chain anti-OX40 fragments, light chain anti-OX40 fragments, anti-OX40 fusion proteins, and fragments, derivatives, conjugates, variants, or biosimilars thereof. In a preferred embodiment, the OX40 agonist is an agonistic, anti-OX40 humanized or fully human monoclonal antibody (i.e., an antibody derived from a single cell line).

In a preferred embodiment, the OX40 agonist or OX40 binding molecule may also be a fusion protein. OX40 fusion proteins comprising an Fc domain fused to OX40L are described, for example, in Sadun, et al., *J. Immunother.* 2009, 182, 1481-89. In a preferred embodiment, a multimeric OX40 agonist, such as a trimeric or hexameric OX40 agonist (with three or six ligand binding domains), may induce superior receptor (OX40L) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG1-Fc and optionally further linking two or more of these fusion proteins are described, e.g., in Gieffers, et al., *Mol. Cancer Therapeutics* 2013, 12, 2735-47.

Agonistic OX40 antibodies and fusion proteins are known to induce strong immune responses. Curti, et al., *Cancer Res.* 2013, 73, 7189-98. In a preferred embodiment, the OX40 agonist is a monoclonal antibody or fusion protein that binds specifically to OX40 antigen in a manner sufficient to reduce toxicity. In some embodiments, the OX40 agonist is an agonistic OX40 monoclonal antibody or fusion protein that abrogates antibody-dependent cellular toxicity (ADCC), for example NK cell cytotoxicity. In some embodiments, the OX40 agonist is an agonistic OX40 monoclonal antibody or fusion protein that abrogates antibody-dependent cell phagocytosis (ADCP). In some embodiments, the OX40 agonist is an agonistic OX40 monoclonal antibody or fusion protein that abrogates complement-dependent cytotoxicity (CDC). In some embodiments, the OX40 agonist is an agonistic OX40 monoclonal antibody or fusion protein which abrogates Fc region functionality.

In some embodiments, the OX40 agonists are characterized by binding to human OX40 (SEQ ID NO:54) with high affinity and agonistic activity. In an embodiment, the OX40 agonist is a binding molecule that binds to human OX40 (SEQ ID NO:54). In an embodiment, the OX40 agonist is a binding molecule that binds to murine OX40 (SEQ ID NO:55). The amino acid sequences of OX40 antigen to which an OX40 agonist or binding molecule binds are summarized in Table 25.

TABLE 25

Amino acid sequences of OX40 antigens.

| Identifier | Sequence (One-Letter Amino Acid Symbols) | | | | | |
|---|---|---|---|---|---|---|
| SEQ ID NO: 54 | MCVGARRLGR | GPCAALLLLG | LGLSTVTGLH | CVGDTYPSND | RCCHECRPGN | GMVSRCSRSQ | 60 |
| human OX40 | NTVCRPCGPG | FYNDVVSSKP | CKPCTWCNLR | SGSERKQLCT | ATQDTVCRCR | AGTQPLDSYK | 120 |
| (*Homo sapiens*) | PGVDCAPCPP | GHFSPGDNQA | CKPWTNCTLA | GKHTLQPASN | SSDAICEDRD | PPATQPQETQ | 180 |
| | GPPARPITVQ | PTEAWPRTSQ | GPSTRPVEVP | GGRAVAAILG | LGLVLGLLGP | LAILLALYLL | 240 |
| | RRDQRLPPDA | HKPPGGGSFR | TPIQEEQADA | HSTLAKI | | | 277 |
| | | | | | | | |
| SEQ ID NO: 55 | MYVWVQQPTA | LLLLGLTLGV | TARRLNCVKH | TYPSGHKCCR | ECQPGHGMVS | RCDHTRDTLC | 60 |
| murine OX40 | HPCETGFYNE | AVNYDTCKQC | TQCNHRSGSE | LKQNCTPTQD | TVCRCRPGTQ | PRQDSGYKLG | 120 |
| (*Mus musculus*) | VDCVPCPPGH | FSPGNNQACK | PWTNCTLSGK | QTRHPASDSL | DAVCEDRSLL | ATLLWETQRP | 180 |
| | TFRPTTVQST | TVWPRTSELP | SPPTLVTPEG | PAFAVLLGLG | LGLLAPLTVL | LALYLLRKAW | 240 |
| | RLPNTPKPCW | GNSFRTPIQE | EHTDAHFTLA | KI | | | 272 |

In some embodiments, the compositions, processes and methods described include a OX40 agonist that binds human or murine OX40 with a $K_D$ of about 100 pM or lower, binds human or murine OX40 with a $K_D$ of about 90 pM or lower, binds human or murine OX40 with a $K_D$ of about 80 pM or lower, binds human or murine OX40 with a $K_D$ of about 70 pM or lower, binds human or murine OX40 with a $K_D$ of about 60 pM or lower, binds human or murine OX40 with a $K_D$ of about 50 pM or lower, binds human or murine OX40 with a $K_D$ of about 40 pM or lower, or binds human or murine OX40 with a $K_D$ of about 30 pM or lower.

In some embodiments, the compositions, processes and methods described include a OX40 agonist that binds to human or murine OX40 with a $k_{assoc}$ of about $7.5 \times 10^5$ 1/M·s or faster, binds to human or murine OX40 with a $k_{assoc}$ of about $7.5 \times 10^5$ 1/M·s or faster, binds to human or murine OX40 with a $k_{assoc}$ of about $8 \times 10^5$ 1/M·s or faster, binds to human or murine OX40 with a $k_{assoc}$ of about $8.5 \times 10^5$ 1/M·s or faster, binds to human or murine OX40 with a $k_{assoc}$ of about $9 \times 10^5$ 1/M·s or faster, binds to human or murine OX40 with a $k_{assoc}$ of about $9.5 \times 10^5$ 1/M·s or faster, or binds to human or murine OX40 with a $k_{assoc}$ of about $1 \times 10^6$ 1/M·s or faster.

In some embodiments, the compositions, processes and methods described include a OX40 agonist that binds to human or murine OX40 with a $k_{dissoc}$ of about $2 \times 10^{-5}$ 1/s or slower, binds to human or murine OX40 with a $k_{dissoc}$ of about $2.1 \times 10^{-5}$ 1/s or slower, binds to human or murine OX40 with a $k_{dissoc}$ of about $2.2 \times 10^{-5}$ 1/s or slower, binds to human or murine OX40 with a $k_{dissoc}$ of about $2.3 \times 10^{-5}$ 1/s or slower, binds to human or murine OX40 with a $k_{dissoc}$ of about $2.4 \times 10^{-5}$ 1/s or slower, binds to human or murine OX40 with a $k_{dissoc}$ of about $2.5 \times 10^{-5}$ 1/s or slower, binds to human or murine OX40 with a $k_{dissoc}$ of about $2.6 \times 10^{-5}$ 1/s or slower or binds to human or murine OX40 with a $k_{dissoc}$ of about $2.7 \times 10^{-5}$ 1/s or slower, binds to human or murine OX40 with a $k_{dissoc}$ of about $2.8 \times 10^{-5}$ 1/s or slower, binds to human or murine OX40 with a $k_{dissoc}$ of about $2.9 \times 10^{-5}$ 1/s or slower, or binds to human or murine OX40 with a $k_{dissoc}$ of about $3 \times 10^{-5}$ 1/s or slower.

In some embodiments, the compositions, processes and methods described include OX40 agonist that binds to human or murine OX40 with an $IC_{50}$ of about 10 nM or lower, binds to human or murine OX40 with an $IC_{50}$ of about 9 nM or lower, binds to human or murine OX40 with an $IC_{50}$ of about 8 nM or lower, binds to human or murine OX40 with an $IC_{50}$ of about 7 nM or lower, binds to human or murine OX40 with an $IC_{50}$ of about 6 nM or lower, binds to human or murine OX40 with an $IC_{50}$ of about 5 nM or lower, binds to human or murine OX40 with an $IC_{50}$ of about 4 nM or lower, binds to human or murine OX40 with an $IC_{50}$ of about 3 nM or lower, binds to human or murine OX40 with an $IC_{50}$ of about 2 nM or lower, or binds to human or murine OX40 with an $IC_{50}$ of about 1 nM or lower.

In some embodiments, the OX40 agonist is tavolixizumab, also known as MEDI0562 or MEDI-0562. Tavolixizumab is available from the MedImmune subsidiary of AstraZeneca, Inc. Tavolixizumab is immunoglobulin G1-kappa, anti-[*Homo sapiens* TNFRSF4 (tumor necrosis factor receptor (TNFR) superfamily member 4, OX40, CD134)], humanized and chimeric monoclonal antibody. The amino acid sequences of tavolixizumab are set forth in Table 13. Tavolixizumab comprises N-glycosylation sites at positions 301 and 301", with fucosylated complex bi-antennary CHO-type glycans; heavy chain intrachain disulfide bridges at positions 22-95 ($V_H$-$V_L$), 148-204 ($C_H1$-$C_L$), 265-325 ($C_H2$) and 371-429 ($C_H3$) (and at positions 22"-95", 148"-204", 265"-325", and 371"-429"); light chain intrachain disulfide bridges at positions 23'-88' ($V_H$-$V_L$) and 134'-194' ($C_H1$-$C_L$) (and at positions 23'"-88'" and 134'"-194'"); interchain heavy chain-heavy chain disulfide bridges at positions 230-230" and 233-233"; and interchain heavy chain-light chain disulfide bridges at 224-214' and 224"-214'". Current clinical trials of tavolixizumab in a variety of solid tumor indications include U.S. National Institutes of Health clinicaltrials.gov identifiers NCT02318394 and NCT02705482.

In an embodiment, a OX40 agonist comprises a heavy chain given by SEQ ID NO:56 and a light chain given by SEQ ID NO:57. In an embodiment, a OX40 agonist comprises heavy and light chains having the sequences shown in SEQ ID NO:56 and SEQ ID NO:57, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:56 and SEQ ID NO:57, respectively. In an embodiment, a OX40 agonist comprises heavy and light chains that are each at least 98% identical to the sequences shown in SEQ ID NO:56 and SEQ ID NO:57, respectively. In an embodiment, a OX40 agonist comprises heavy and light chains that are each at least 97% identical to the sequences shown in SEQ ID NO:56 and SEQ ID NO:57, respectively. In an embodiment, a OX40 agonist comprises heavy and light chains that are each at least 96% identical to the sequences shown in SEQ ID NO:56 and SEQ ID NO:57, respectively. In an embodiment, a OX40 agonist comprises heavy and light chains that are each at least 95% identical to the sequences shown in SEQ ID NO:56 and SEQ ID NO:57, respectively.

In an embodiment, the OX40 agonist comprises the heavy and light chain CDRs or variable regions (VRs) of tavolixizumab. In an embodiment, the OX40 agonist heavy chain variable region ($V_H$) comprises the sequence shown in SEQ ID NO:58, and the OX40 agonist light chain variable region ($V_L$) comprises the sequence shown in SEQ ID NO:59, and conservative amino acid substitutions thereof. In an embodiment, a OX40 agonist comprises $V_H$ and $V_L$ regions that are each at least 99% identical to the sequences shown in SEQ ID NO:58 and SEQ ID NO:59, respectively. In an embodiment, a OX40 agonist comprises $V_H$ and $V_L$ regions that are each at least 98% identical to the sequences shown in SEQ ID NO:58 and SEQ ID NO:59, respectively. In an embodiment, a OX40 agonist comprises $V_H$ and $V_L$ regions that are each at least 97% identical to the sequences shown in SEQ ID NO:58 and SEQ ID NO:59, respectively. In an embodiment, a OX40 agonist comprises $V_H$ and $V_L$ regions that are each at least 96% identical to the sequences shown in SEQ ID NO:58 and SEQ ID NO:59, respectively. In an embodiment, a OX40 agonist comprises $V_H$ and $V_L$ regions that are each at least 95% identical to the sequences shown in SEQ ID NO:58 and SEQ ID NO:59, respectively. In an embodiment, an OX40 agonist comprises an scFv antibody comprising $V_H$ and $V_L$ regions that are each at least 99% identical to the sequences shown in SEQ ID NO:58 and SEQ ID NO:59.

In an embodiment, a OX40 agonist comprises heavy chain CDR1, CDR2 and CDR3 domains having the sequences set forth in SEQ ID NO:60, SEQ ID NO:61, and SEQ ID NO:62, respectively, and conservative amino acid substitutions thereof, and light chain CDR1, CDR2 and CDR3 domains having the sequences set forth in SEQ ID NO:63, SEQ ID NO:64, and SEQ ID NO:65, respectively, and conservative amino acid substitutions thereof.

In an embodiment, the OX40 agonist is a OX40 agonist biosimilar monoclonal antibody approved by drug regulatory authorities with reference to tavolixizumab. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is tavolixizumab. In some embodiments, the one or more post-translational modifications are selected from one or more of glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is tavolixizumab. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tavolixizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tavolixizumab.

TABLE 26

Amino acid sequences for OX40 agonist antibodies related to tavolixizumab.

| Identifier | Sequence (One-Letter Amino Acid Symbols) | |
|---|---|---|
| SEQ ID NO: 56 heavy chain for tavolixizumab | QVQLQESGPG LVKPSQTLSL TCAVYGGSFS SGYWNWIRKH PGKGLEYIGY ISYNGITYHN<br>PSLKSRITIN RDTSKNQYSL QLNSVTPEDT AVYYCARYKY DYDGGHAMDY WGQGTLVTVS<br>SASTKGPSVF PLAPSSKSTS GGTAALGCLV KDYFPEPVTV SWNSGALTSG VHTFPAVLQS<br>SGLYSLSSVV TVPSSSLGTQ TYICNVNHKP SNTKVDKRVE PKSCDKTHTC PPCPAPELLG<br>GPSVFLFPPK PKDTLMISRT PEVTCVVVDV SHEDPEVKFN WYVDGVEVHN AKTKPREEQY<br>NSTYRVVSVL TVLHQDWLNG KEYKCKVSNK ALPAPIEKTI SKAKGQPREP QVYTLPPSRE<br>EMTKNQVSLT CLVKGFYPSD IAVEWESNGQ PENNYKTTPP VLDSDGSFFL YSKLTVDKSR<br>WQQGNVFSCS VMHEALHNHY TQKSLSLSPG K | 60<br>120<br>180<br>240<br>300<br>360<br>420<br>451 |
| SEQ ID NO: 57 light chain for tavolixizumab | DIQMTQSPSS LSASVGDRVT ITCRASQDIS NYLNWYQQKP GKAPKLLIYY TSKLHSGVPS<br>RFSGSGSGTD YTLTISSLQP EDFATYYCQQ GSALPWTFGQ GTKVEIKRTV AAPSVFIFPP<br>SDEQLKSGTA SVVCLLNNFY PREAKVQWKV DNALQSGNSQ ESVTEQDSKD STYSLSSTLT<br>LSKADYEKHK VYACEVTHQG LSSPVTKSFN RGEC | 60<br>120<br>180<br>214 |
| SEQ ID NO: 58 heavy chain variable region for tavolixizumab | QVQLQESGPG LVKPSQTLSL TCAVYGGSFS SGYWNWIRKH PGKGLEYIGY ISYNGITYHN<br>PSLKSRITIN RDTSKNQYSL QLNSVTPEDT AVYYCARYKY DYDGGHAMDY WGQGTLVT | 60<br>118 |
| SEQ ID NO: 59 light chain variable region for tavolixizumab | DIQMTQSPSS LSASVGDRVT ITCRASQDIS NYLNWYQQKP GKAPKLLIYY TSKLHSGVPS<br>RFSGSGSGTD YTLTISSLQP EDFATYYCQQ GSALPWTFGQ GTKVEIKR | 60<br>108 |
| SEQ ID NO: 60 heavy chain CDR1 for tavolixizumab | GSFSSGYWN | 9 |
| SEQ ID NO: 61 heavy chain CDR2 for tavolixizumab | YIGYISYNGI TYH | 13 |
| SEQ ID NO: 62 heavy chain CDR3 for tavolixizumab | RYKYDYDGGH AMDY | 14 |
| SEQ ID NO: 63 light chain CDR1 for tavolixizumab | QDISNYLN | 8 |
| SEQ ID NO: 64 light chain CDR2 for tavolixizumab | LLIYYTSKLH S | 11 |
| SEQ ID NO: 65 light chain CDR3 for tavolixizumab | QQGSALPW | 8 |

In some embodiments, the OX40 agonist is 11D4, which is a fully human antibody available from Pfizer, Inc. The preparation and properties of 11D4 are described in U.S. Pat. Nos. 7,960,515; 8,236,930; and 9,028,824, the disclosures of which are incorporated by reference herein. The amino acid sequences of 11D4 are set forth in Table 26.

In an embodiment, a OX40 agonist comprises a heavy chain given by SEQ ID NO:66 and a light chain given by SEQ ID NO:67. In an embodiment, a OX40 agonist comprises heavy and light chains having the sequences shown in SEQ ID NO:66 and SEQ ID NO:67, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:66 and SEQ ID NO:67, respectively. In an embodiment, a OX40 agonist comprises heavy and light chains that are each at least 98% identical to the sequences shown in SEQ ID NO:66 and SEQ ID NO:67, respectively. In an embodiment, a OX40 agonist comprises heavy and light chains that are each at least 97% identical to the sequences shown in SEQ ID NO:66 and SEQ ID NO:67, respectively. In an embodiment, a OX40 agonist comprises heavy and light chains that are each at least 96% identical to the sequences shown in SEQ ID NO:66 and SEQ ID NO:67, respectively. In an embodiment, a OX40 agonist comprises heavy and light chains that are each at least 95% identical to the sequences shown in SEQ ID NO:66 and SEQ ID NO:67, respectively.

In an embodiment, the OX40 agonist comprises the heavy and light chain CDRs or variable regions (VRs) of 11D4. In an embodiment, the OX40 agonist heavy chain variable region ($V_H$) comprises the sequence shown in SEQ ID NO:68, and the OX40 agonist light chain variable region ($V_L$) comprises the sequence shown in SEQ ID NO:69, and conservative amino acid substitutions thereof. In an embodiment, a OX40 agonist comprises $V_H$ and $V_L$ regions that are each at least 99% identical to the sequences shown in SEQ ID NO:68 and SEQ ID NO:69, respectively. In an embodiment, a OX40 agonist comprises $V_H$ and $V_L$ regions that are each at least 98% identical to the sequences shown in SEQ ID NO:68 and SEQ ID NO:69, respectively. In an embodiment, a OX40 agonist comprises $V_H$ and $V_L$ regions that are each at least 97% identical to the sequences shown in SEQ ID NO:68 and SEQ ID NO:69, respectively. In an embodiment, a OX40 agonist comprises $V_H$ and $V_L$ regions that are each at least 96% identical to the sequences shown in SEQ ID NO:68 and SEQ ID NO:69, respectively. In an embodiment, a OX40 agonist comprises $V_H$ and $V_L$ regions that are each at least 95% identical to the sequences shown in SEQ ID NO:68 and SEQ ID NO:69, respectively.

In an embodiment, a OX40 agonist comprises heavy chain CDR1, CDR2 and CDR3 domains having the sequences set forth in SEQ ID NO:70, SEQ ID NO:71, and SEQ ID NO:72, respectively, and conservative amino acid substitutions thereof, and light chain CDR1, CDR2 and CDR3 domains having the sequences set forth in SEQ ID NO:73, SEQ ID NO:74, and SEQ ID NO:75, respectively, and conservative amino acid substitutions thereof.

In an embodiment, the OX40 agonist is a OX40 agonist biosimilar monoclonal antibody approved by drug regulatory authorities with reference to 11D4. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is 11D4. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is 11D4. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 11D4. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 11D4.

TABLE 27

Amino acid sequences for Ox40 agonist antibodies related to 11D4.

| Identifier | Sequence (One-Letter Amino Acid Symbols) | |
|---|---|---|
| SEQ ID NO: 66 heavy chain for 11D4 | EVQLVESGGG LVQPGGSLRL SCAASGFTFS SYSMNWVRQA PGKGLEWVSY ISSSSSTIDY<br>ADSVKGRFTI SRDNAKNSLY LQMNSLRDED TAVYYCARES GWYLFDYWGQ GTLVTVSSAS<br>TKGPSVFPLA PCSRSTSEST AALGCLVKDY FPEPVTVSWN SGALTSGVHT FPAVLQSSGL<br>YSLSSVVTVP SSNFGTQTYT CNVDHKPSNT KVDKTVERKC CVECPPCPAP PVAGPSVFLF<br>PPKPKDTLMI SRTPEVTCVV VDVSHEDPEV QFNWYVDGVE VHNAKTKPRE EQFNSTFRVV<br>SVLTVVHQDW LNGKEYKCKV SNKGLPAPIE KTISKTKGQP REPQVYTLPP SREEMTKNQV<br>SLTCLVKGFY PSDIAVEWES NGQPENNYKT TPPMLDSDGS FFLYSKLTVD KSRWQQGNVF<br>SCSVMHEALH NHYTQKSLSL SPGK | 60<br>120<br>180<br>240<br>300<br>360<br>420<br>444 |
| SEQ ID NO: 67 light chain for 11D4 | DIQMTQSPSS LSASVGDRVT ITCRASQGIS SWLAWYQQKP EKAPKSLIYA ASSLQSGVPS<br>RFSGSGSGTD FTLTISSLQP EDFATYYCQQ YNSYPPTFGG GTKVEIKRTV AAPSVFIFPP<br>SDEQLKSGTA SVVCLLNNFY PREAKVQWKV DNALQSGNSQ ESVTEQDSKD STYSLSSTLT<br>LSKADYEKHK VYACEVTHQG LSSPVTKSFN RGEC | 60<br>120<br>180<br>214 |
| SEQ ID NO: 68 heavy chain variable region for 11D4 | EVQLVESGGG LVQPGGSLRL SCAASGFTFS SYSMNWVRQA PGKGLEWVSY ISSSSSTIDY<br>ADSVKGRFTI SRDNAKNSLY LQMNSLRDED TAVYYCARES GWYLFDYWGQ GTLVTVSS | 60<br>118 |
| SEQ ID NO: 69 light chain variable region for 11D4 | DIQMTQSPSS LSASVGDRVT ITCRASQGIS SWLAWYQQKP EKAPKSLIYA ASSLQSGVPS<br>RFSGSGSGTD FTLTISSLQP EDFATYYCQQ YNSYPPTFGG GTKVEIK | 60<br>107 |
| SEQ ID NO: 70 heavy chain CDR1 for 11D4 | SYSMN | 5 |

TABLE 27-continued

Amino acid sequences for Ox40 agonist antibodies related to 11D4.

| Identifier | Sequence (One-Letter Amino Acid Symbols) | |
|---|---|---|
| SEQ ID NO: 71 heavy chain CDR2 for 11D4 | YISSSSSTID YADSVKG | 17 |
| SEQ ID NO: 72 heavy chain CDR3 for 11D4 | ESGWYLFDY | 9 |
| SEQ ID NO: 73 light chain CDR1 for 11D4 | RASQGISSWL A | 11 |
| SEQ ID NO: 74 light chain CDR2 for 11D4 | AASSLQS | 7 |
| SEQ ID NO: 75 light chain CDR3 for 11D4 | QQYNSYPPT | 9 |

In some embodiments, the OX40 agonist is 18D8, which is a fully human antibody available from Pfizer, Inc. The preparation and properties of 18D8 are described in U.S. Pat. Nos. 7,960,515; 8,236,930; and 9,028,824, the disclosures of which are incorporated by reference herein. The amino acid sequences of 18D8 are set forth in Table 28.

In an embodiment, a OX40 agonist comprises a heavy chain given by SEQ ID NO:76 and a light chain given by SEQ ID NO:77. In an embodiment, a OX40 agonist comprises heavy and light chains having the sequences shown in SEQ ID NO:76 and SEQ ID NO:77, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:76 and SEQ ID NO:77, respectively. In an embodiment, a OX40 agonist comprises heavy and light chains that are each at least 98% identical to the sequences shown in SEQ ID NO:76 and SEQ ID NO:77, respectively. In an embodiment, a OX40 agonist comprises heavy and light chains that are each at least 97% identical to the sequences shown in SEQ ID NO:76 and SEQ ID NO:77, respectively. In an embodiment, a OX40 agonist comprises heavy and light chains that are each at least 96% identical to the sequences shown in SEQ ID NO:76 and SEQ ID NO:77, respectively. In an embodiment, a OX40 agonist comprises heavy and light chains that are each at least 95% identical to the sequences shown in SEQ ID NO:76 and SEQ ID NO:77, respectively.

In an embodiment, the OX40 agonist comprises the heavy and light chain CDRs or variable regions (VRs) of 18D8. In an embodiment, the OX40 agonist heavy chain variable region ($V_H$) comprises the sequence shown in SEQ ID NO:78, and the OX40 agonist light chain variable region ($V_L$) comprises the sequence shown in SEQ ID NO:79, and conservative amino acid substitutions thereof. In an embodiment, a OX40 agonist comprises $V_H$ and $V_L$ regions that are each at least 99% identical to the sequences shown in SEQ ID NO:78 and SEQ ID NO:79, respectively. In an embodiment, a OX40 agonist comprises $V_H$ and $V_L$ regions that are each at least 98% identical to the sequences shown in SEQ ID NO:78 and SEQ ID NO:79, respectively. In an embodiment, a OX40 agonist comprises $V_H$ and $V_L$ regions that are each at least 97% identical to the sequences shown in SEQ ID NO:78 and SEQ ID NO:79, respectively. In an embodiment, a OX40 agonist comprises $V_H$ and $V_L$ regions that are each at least 96% identical to the sequences shown in SEQ ID NO:78 and SEQ ID NO:79, respectively. In an embodiment, a OX40 agonist comprises $V_H$ and $V_L$ regions that are each at least 95% identical to the sequences shown in SEQ ID NO:78 and SEQ ID NO:79, respectively.

In an embodiment, a OX40 agonist comprises heavy chain CDR1, CDR2 and CDR3 domains having the sequences set forth in SEQ ID NO:80, SEQ ID NO:81, and SEQ ID NO:82, respectively, and conservative amino acid substitutions thereof, and light chain CDR1, CDR2 and CDR3 domains having the sequences set forth in SEQ ID NO:83, SEQ ID NO:84, and SEQ ID NO:85, respectively, and conservative amino acid substitutions thereof.

In an embodiment, the OX40 agonist is a OX40 agonist biosimilar monoclonal antibody approved by drug regulatory authorities with reference to 18D8. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is 18D8. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is 18D8. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 18D8. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 18D8.

ID NO:86, and the OX40 agonist light chain variable region ($V_L$) comprises the sequence shown in SEQ ID NO:87, and conservative amino acid substitutions thereof. In an embodiment, a OX40 agonist comprises $V_H$ and $V_L$ regions that are each at least 99% identical to the sequences shown in SEQ ID NO:86 and SEQ ID NO:87, respectively. In an embodiment, a OX40 agonist comprises $V_H$ and $V_L$ regions that are each at least 98% identical to the sequences shown in SEQ ID NO:86 and SEQ ID NO:87, respectively. In an embodi-

TABLE 28

Amino acid sequences for OX40 agonist antibodies related to 18D8.

| Identifier | Sequence (One-Letter Amino Acid Symbols) | |
|---|---|---|
| SEQ ID NO: 76 heavy chain for 18D8 | EVQLVESGGG LVQPGRSLRL SCAASGFTFD DYAMHWVRQA PGKGLEWVSG ISWNSGSIGY<br>ADSVKGRFTI SRDNAKNSLY LQMNSLRAED TALYYCAKDQ STADYYFYYG MDVWGQGTTV<br>TVSSASTKGP SVFPLAPCSR STSESTAALG CLVKDYFPEP VTVSWNSGAL TSGVHTFPAV<br>LQSSGLYSLS SVVTVPSSNF GTQTYTCNVD HKPSNTKVDK TVERKCCVEC PPCPAPPVAG<br>PSVFLFPPKP KDTLMISRTP EVTCVVVDVS HEDPEVQFNW YVDGVEVHNA KTKPREEQFN<br>STFRVVSVLT VVHQDWLNGK EYKCKVSNKG LPAPIEKTIS KTKGQPREPQ VYTLPPSREE<br>MTKNQVSLTC LVKGFYPSDI AVEWESNGQP ENNYKTTPPM LDSDGSFFLY SKLTVDKSRW<br>QQGNVFSCSV MHEALHNHYT QKSLSLSPGK | 60<br>120<br>180<br>240<br>300<br>360<br>420<br>450 |
| SEQ ID NO: 77 light chain for 18D8 | EIVVTQSPAT LSLSPGERAT LSCRASQSVS SYLAWYQQKP GQAPRLLIYD ASNRATGIPA<br>RFSGSGSGTD FTLTISSLEP EDFAVYYCQQ RSNWPTFGQG TKVEIKRTVA APSVFIFPPS<br>DEQLKSGTAS VVCLLNNFYP REAKVQWKVD NALQSGNSQE SVTEQDSKDS TYSLSSTLTL<br>SKADYEKHKV YACEVTHQGL SSPVTKSFNR GEC | 60<br>120<br>180<br>213 |
| SEQ ID NO: 78 heavy chain variable region for 18D8 | EVQLVESGGG LVQPGRSLRL SCAASGFTFD DYAMHWVRQA PGKGLEWVSG ISWNSGSIGY<br>ADSVKGRFTI SRDNAKNSLY LQMNSLRAED TALYYCAKDQ STADYYFYYG MDVWGQGTTV<br>TVSS | 60<br>120<br>124 |
| SEQ ID NO: 79 light chain variable region for 18D8 | EIVVTQSPAT LSLSPGERAT LSCRASQSVS SYLAWYQQKP GQAPRLLIYD ASNRATGIPA<br>RFSGSGSGTD FTLTISSLEP EDFAVYYCQQ RSNWPTFGQG TKVEIK | 60<br>106 |
| SEQ ID NO: 80 heavy chain CDR1 for 18D8 | DYAMH | 5 |
| SEQ ID NO: 81 heavy chain CDR2 for 18D8 | GISWNSGSIG YADSVKG | 17 |
| SEQ ID NO: 82 heavy chain CDR3 for 18D8 | DQSTADYYFY YGMDV | 15 |
| SEQ ID NO: 83 light chain CDR1 for 18D8 | RASQSVSSYL A | 11 |
| SEQ ID NO: 84 light chain CDR2 for 18D8 | DASNRAT | 7 |
| SEQ ID NO: 85 light chain CDR3 for 18D8 | QQRSNWPT | 8 |

In some embodiments, the OX40 agonist is Hu119-122, which is a humanized antibody available from GlaxoSmithKline plc. The preparation and properties of Hu119-122 are described in U.S. Pat. Nos. 9,006,399 and 9,163,085, and in International Patent Publication No. WO 2012/027328, the disclosures of which are incorporated by reference herein. The amino acid sequences of Hu119-122 are set forth in Table 29.

In an embodiment, the OX40 agonist comprises the heavy and light chain CDRs or variable regions (VRs) of Hu119-122. In an embodiment, the OX40 agonist heavy chain variable region ($V_H$) comprises the sequence shown in SEQ ment, a OX40 agonist comprises $V_H$ and $V_L$ regions that are each at least 97% identical to the sequences shown in SEQ ID NO:86 and SEQ ID NO:87, respectively. In an embodiment, a OX40 agonist comprises $V_H$ and $V_L$ regions that are each at least 96% identical to the sequences shown in SEQ ID NO:86 and SEQ ID NO:87, respectively. In an embodiment, a OX40 agonist comprises $V_H$ and $V_L$ regions that are each at least 95% identical to the sequences shown in SEQ ID NO:86 and SEQ ID NO:87, respectively.

In an embodiment, a OX40 agonist comprises heavy chain CDR1, CDR2 and CDR3 domains having the sequences set forth in SEQ ID NO:88, SEQ ID NO:89, and SEQ ID NO:90, respectively, and conservative amino acid substitutions thereof, and light chain CDR1, CDR2 and CDR3 domains having the sequences set forth in SEQ ID NO:91, SEQ ID NO:92, and SEQ ID NO:93, respectively, and conservative amino acid substitutions thereof.

In an embodiment, the OX40 agonist is a OX40 agonist biosimilar monoclonal antibody approved by drug regulatory authorities with reference to Hu119-122. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is Hu119-122. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is Hu119-122. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu119-122. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu119-122.

TABLE 29

Amino acid sequences for OX40 agonist antibodies related to Hu119-122.

| Identifier | Sequence (One-Letter Amino Acid Symbols) | |
|---|---|---|
| SEQ ID NO: 86 heavy chain variable region for Hu119-122 | EVQLVESGGG LVQPGGSLRL SCAASEYEFP SHDMSWVRQA PGKGLELVAA INSDGGSTYY PDTMERRFTI SRDNAKNSLY LQMNSLRAED TAVYYCARHY DDYYAWFAYW GQGTMVTVSS | 60 120 |
| SEQ ID NO: 87 light chain variable region for Hu119-122 | EIVLTQSPAT LSLSPGERAT LSCRASKSVS TSGYSYMHWY QQKPGQAPRL LIYLASNLES GVPARFSGSG SGTDFTLTIS SLEPEDFAVY YCQHSRELPL TFGGGTKVEI K | 60 111 |
| SEQ ID NO: 88 heavy chain CDR1 for Hu119-122 | SHDMS | 5 |
| SEQ ID NO: 89 heavy chain CDR2 for Hu119-122 | AINSDGGSTY YPDTMER | 17 |
| SEQ ID NO: 90 heavy chain CDR3 for Hu119-122 | HYDDYYAWFA Y | 11 |
| SEQ ID NO: 91 light chain CDR1 for Hu119-122 | RASKSVSTSG YSYMH | 15 |
| SEQ ID NO: 92 light chain CDR2 for Hu119-122 | LASNLES | 7 |
| SEQ ID NO: 93 light chain CDR3 for Hu119-122 | QHSRELPLT | 9 |

In some embodiments, the OX40 agonist is Hu106-222, which is a humanized antibody available from GlaxoSmithKline plc. The preparation and properties of Hu106-222 are described in U.S. Pat. Nos. 9,006,399 and 9,163,085, and in International Patent Publication No. WO 2012/027328, the disclosures of which are incorporated by reference herein. The amino acid sequences of Hu106-222 are set forth in Table 30.

In an embodiment, the OX40 agonist comprises the heavy and light chain CDRs or variable regions (VRs) of Hu106-222. In an embodiment, the OX40 agonist heavy chain variable region ($V_H$) comprises the sequence shown in SEQ ID NO:94, and the OX40 agonist light chain variable region ($V_L$) comprises the sequence shown in SEQ ID NO:95, and conservative amino acid substitutions thereof. In an embodiment, a OX40 agonist comprises $V_H$ and $V_L$ regions that are each at least 99% identical to the sequences shown in SEQ ID NO:94 and SEQ ID NO:95, respectively. In an embodiment, a OX40 agonist comprises $V_H$ and $V_L$ regions that are each at least 98% identical to the sequences shown in SEQ ID NO:94 and SEQ ID NO:95, respectively. In an embodiment, a OX40 agonist comprises $V_H$ and $V_L$ regions that are each at least 97% identical to the sequences shown in SEQ ID NO:94 and SEQ ID NO:95, respectively. In an embodiment, a OX40 agonist comprises $V_H$ and $V_L$ regions that are each at least 96% identical to the sequences shown in SEQ ID NO:94 and SEQ ID NO:95, respectively. In an embodiment, a OX40 agonist comprises $V_H$ and $V_L$ regions that are each at least 95% identical to the sequences shown in SEQ ID NO:94 and SEQ ID NO:95, respectively.

In an embodiment, a OX40 agonist comprises heavy chain CDR1, CDR2 and CDR3 domains having the sequences set forth in SEQ ID NO:96, SEQ ID NO:97, and SEQ ID NO:98, respectively, and conservative amino acid substitutions thereof, and light chain CDR1, CDR2 and CDR3 domains having the sequences set forth in SEQ ID NO:99, SEQ ID NO:100, and SEQ ID NO:101, respectively, and conservative amino acid substitutions thereof.

In an embodiment, the OX40 agonist is a OX40 agonist biosimilar monoclonal antibody approved by drug regulatory authorities with reference to Hu106-222. In an embodiment, the biosimilar monoclonal antibody comprises an agonist antibody is provided in a formulation which differs from the formulations of a reference medicinal product or reference biological product, wherein the reference medicinal product or reference biological product is Hu106-222. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu106-222. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu6-222.

TABLE 30

Amino acid sequences for OX40 agonist antibodies related to Hu106-222.

| Identifier | Sequence (One-Letter Amino Acid Symbols) | |
|---|---|---|
| SEQ ID NO: 94<br>heavy chain<br>variable region<br>for Hu106-222 | QVQLVQSGSE LKKPGASVKV SCKASGYTFT DYSMHWVRQA PGQGLKWMGW INTETGEPTY<br>ADDFKGRFVF SLDTSVSTAY LQISSLKAED TAVYYCANPY YDYVSYYAMD YWGQGTTVTV<br>SS | 60<br>120<br>122 |
| SEQ ID NO: 95<br>light chain<br>variable region<br>for Hu106-222 | DIQMTQSPSS LSASVGDRVT ITCKASQDVS TAVAWYQQKP GKAPKLLIYS ASYLYTGVPS<br>RFSGSGSGTD FTFTISSLQP EDIATYYCQQ HYSTPRTFGQ GTKLEIK | 60<br>107 |
| SEQ ID NO: 96<br>heavy chain CDR1<br>for Hu106-222 | DYSMH | 5 |
| SEQ ID NO: 97<br>heavy chain CDR2<br>for Hu106-222 | WINTETGEPT YADDFKG | 17 |
| SEQ ID NO: 98<br>heavy chain CDR3<br>for Hu106-222 | PYYDYVSYYA MDY | 13 |
| SEQ ID NO: 99<br>light chain CDR1<br>for Hu106-222 | KASQDVSTAV A | 11 |
| SEQ ID NO: 100<br>light chain CDR2<br>for Hu106-222 | SASYLYT | 7 |
| SEQ ID NO: 101<br>light chain CDR3<br>for Hu106-222 | QQHYSTPRT | 9 |

OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is Hu106-222. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40

In some embodiments, the OX40 agonist antibody is MEDI6469 (also referred to as 9B12). MEDI6469 is a murine monoclonal antibody. Weinberg, et al., J. Immunother. 2006, 29, 575-585. In some embodiments the OX40 agonist is an antibody produced by the 9B12 hybridoma, deposited with Biovest Inc. (Malvern, MA, USA), as described in Weinberg, et al., J. Immunother. 2006, 29, 575-585, the disclosure of which is hereby incorporated by reference in its entirety. In some embodiments, the antibody comprises the CDR sequences of MEDI6469. In some embodiments, the antibody comprises a heavy chain variable region sequence and/or a light chain variable region sequence of MEDI6469.

In an embodiment, the OX40 agonist is L106 BD (Pharmingen Product #340420). In some embodiments, the OX40 agonist comprises the CDRs of antibody L106 (BD Pharmingen Product #340420). In some embodiments, the OX40 agonist comprises a heavy chain variable region sequence and/or a light chain variable region sequence of antibody L106 (BD Pharmingen Product #340420). In an embodiment, the OX40 agonist is ACT35 (Santa Cruz Biotechnology, Catalog #20073). In some embodiments, the OX40 agonist comprises the CDRs of antibody ACT35 (Santa Cruz Biotechnology, Catalog #20073). In some embodiments, the OX40 agonist comprises a heavy chain variable region sequence and/or a light chain variable region sequence of antibody ACT35 (Santa Cruz Biotechnology, Catalog #20073). In an embodiment, the OX40 agonist is the murine monoclonal antibody anti-mCD134/mOX40 (clone OX86), commercially available from InVivoMAb, BioXcell Inc, West Lebanon, NH In an embodiment, the OX40 agonist is selected from the OX40 agonists described in International Patent Application Publication Nos. WO 95/12673, WO 95/21925, WO 2006/121810, WO 2012/027328, WO 2013/028231, WO 2013/038191, and WO 2014/148895; European Patent Application EP 0672141; U.S. Patent Application Publication Nos. US 2010/136030, US 2014/377284, US 2015/190506, and US 2015/132288 (including clones 20E5 and 12H3); and U.S. Pat. Nos. 7,504,101, 7,550,140, 7,622,444, 7,696,175, 7,960,515, 7,961,515, 8,133,983, 9,006,399, and 9,163,085, the disclosure of each of which is incorporated herein by reference in its entirety.

In an embodiment, the OX40 agonist is an OX40 agonistic fusion protein as depicted in Structure I-A (C-terminal Fc-antibody fragment fusion protein) or Structure I-B (N-terminal Fc-antibody fragment fusion protein), or a fragment, derivative, conjugate, variant, or biosimilar thereof. The properties of structures I-A and I-B are described above and in U.S. Pat. Nos. 9,359,420, 9,340,599, 8,921,519, and 8,450,460, the disclosures of which are incorporated by reference herein. Amino acid sequences for the polypeptide domains of structure I-A are given in Table 9. The Fc domain preferably comprises a complete constant domain (amino acids 17-230 of SEQ ID NO:31) the complete hinge domain (amino acids 1-16 of SEQ ID NO:31) or a portion of the hinge domain (e.g., amino acids 4-16 of SEQ ID NO:31). Preferred linkers for connecting a C-terminal Fc-antibody may be selected from the embodiments given in SEQ ID NO:32 to SEQ ID NO:41, including linkers suitable for fusion of additional polypeptides. Likewise, amino acid sequences for the polypeptide domains of structure I-B are given in Table 10. If an Fc antibody fragment is fused to the N-terminus of an TNRFSF fusion protein as in structure I-B, the sequence of the Fc module is preferably that shown in SEQ ID NO:42, and the linker sequences are preferably selected from those embodiments set forth in SED ID NO:43 to SEQ ID NO:45.

In an embodiment, an OX40 agonist fusion protein according to structures I-A or I-B comprises one or more OX40 binding domains selected from the group consisting of a variable heavy chain and variable light chain of tavolixizumab, a variable heavy chain and variable light chain of 11D4, a variable heavy chain and variable light chain of 18D8, a variable heavy chain and variable light chain of Hu119-122, a variable heavy chain and variable light chain of Hu106-222, a variable heavy chain and variable light chain selected from the variable heavy chains and variable light chains described in Table 17, any combination of a variable heavy chain and variable light chain of the foregoing, and fragments, derivatives, conjugates, variants, and biosimilars thereof.

In an embodiment, an OX40 agonist fusion protein according to structures I-A or I-B comprises one or more OX40 binding domains comprising an OX40L sequence. In an embodiment, an OX40 agonist fusion protein according to structures I-A or I-B comprises one or more OX40 binding domains comprising a sequence according to SEQ ID NO:102. In an embodiment, an OX40 agonist fusion protein according to structures I-A or I-B comprises one or more OX40 binding domains comprising a soluble OX40L sequence. In an embodiment, a OX40 agonist fusion protein according to structures I-A or I-B comprises one or more OX40 binding domains comprising a sequence according to SEQ ID NO:103. In an embodiment, a OX40 agonist fusion protein according to structures I-A or I-B comprises one or more OX40 binding domains comprising a sequence according to SEQ ID NO:104.

In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:58 and SEQ ID NO:59, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:68 and SEQ ID NO:69, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:78 and SEQ ID NO:79, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:86 and SEQ ID NO:87, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:94 and SEQ ID NO:95, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the $V_H$ and $V_L$ sequences given in Table 14, wherein the $V_H$ and $V_L$ domains are connected by a linker.

TABLE 31

Additional polypeptide domains useful as OX40 binding domains in fusion proteins
(e.g., structures I-A and I-B) or as scFv OX40 agonist antibodies.

| Identifier | Sequence (One-Letter Amino Acid Symbols) | |
|---|---|---|
| SEQ ID NO: 102 OX40L | MERVQPLEEN VGNAARPRFE RNKLLLVASV IQGLGLLLCF TYICLHFSAL QVSHRYPRIQ | 60 |
| | SIKVQFTEYK KEKGFILTSQ KEDEIMKVQN NSVIINCDGF YLISLKGYFS QEVNISLHYQ | 120 |
| | KDEEPLFQLK KVRSVNSLMV ASLTYKDKVY LNVTTDNTSL DDFHVNGGEL ILIHQNPGEF | 180 |
| | CVL | 183 |
| SEQ ID NO: 103 OX40L soluble domain | SHRYPRIQSI KVQFTEYKKE KGFILTSQKE DEIMKVQNNS VIINCDGFYL ISLKGYFSQE | 60 |
| | VNISLHYQKD EEPLFQLKKV RSVNSLMVAS LTYKDKVYLN VTTDNTSLDD FHVNGGELIL | 120 |
| | IHQNPGEFCV L | 131 |
| SEQ ID NO: 104 OX40L soluble domain (alternative) | YPRIQSIKVQ FTEYKKEKGF ILTSQKEDEI MKVQNNSVII NCDGFYLISL KGYFSQEVNI | 60 |
| | SLHYQKDEEP LFQLKKVRSV NSLMVASLTY KDKVYLNVTT DNTSLDDFHV NGGELILIHQ | 120 |
| | NPGEFCVL | 128 |
| SEQ ID NO: 105 variable heavy chain for 008 | EVQLVESGGG LVQPGGSLRL SCAASGFTFS NYTMNWVRQA PGKGLEWVSA ISGSGGSTYY | 60 |
| | ADSVKGRFTI SRDNSKNTLY LQMNSLRAED TAVYYCAKDR YSQVHYALDY WGQGTLVTVS | 120 |
| SEQ ID NO: 106 variable light chain for 008 | DIVMTQSPDS LPVTPGEPAS ISCRSSQSLL HSNGYNYLDW YLQKAGQSPQ LLIYLGSNRA | 60 |
| | SGVPDRFSGS GSGTDFTLKI SRVEAEDVGV YYCQQYYNHP TTFGQGTK | 108 |
| SEQ ID NO: 107 variable heavy chain for 011 | EVQLVESGGG VVQPGRSLRL SCAASGFTFS DYTMNWVRQA PGKGLEWVSS ISGGSTYYAD | 60 |
| | SRKGRFTISR DNSKNTLYLQ MNNLRAEDTA VYYCARDRYF RQQNAFDYWG QGTLVTVSSA | 120 |
| SEQ ID NO: 108 variable light chain for 011 | DIVMTQSPDS LPVTPGEPAS ISCRSSQSLL HSNGYNYLDW YLQKAGQSPQ LLIYLGSNRA | 60 |
| | SGVPDRFSGS GSGTDFTLKI SRVEAEDVGV YYCQQYYNHP TTFGQGTK | 108 |
| SEQ ID NO: 109 variable heavy chain for 021 | EVQLVESGGG LVQPRGSLRL SCAASGFTFS SYAMNWVRQA PGKGLEWVAV ISYDGSNKYY | 60 |
| | ADSVKGRFTI SRDNSKNTLY LQMNSLRAED TAVYYCAKDR YITLPNALDY WGQGTLVTVS | 120 |
| SEQ ID NO: 110 variable light chain for 021 | DIQMTQSPVS LPVTPGEPAS ISCRSSQSLL HSNGYNYLDW YLQKPGQSPQ LLIYLGSNRA | 60 |
| | SGVPDRFSGS GSGTDFTLKI SRVEAEDVGV YYCQQYKSNP PTFGQGTK | 108 |
| SEQ ID NO: 111 variable heavy chain for 023 | EVQLVESGGG LVHPGGSLRL SCAGSGFTFS SYAMHWVRQA PGKGLEWVSA IGTGGGTYYA | 60 |
| | DSVMGRFTIS RDNSKNTLYL QMNSLRAEDT AVYYCARYDN VMGLYWFDYW GQGTLVTVSS | 120 |
| SEQ ID NO: 112 variable light chain for 023 | EIVLTQSPAT LSLSPGERAT LSCRASQSVS SYLAWYQQKP GQAPRLLIYD ASNRATGIPA | 60 |
| | RFSGSGSGTD FTLTISSLEP EDFAVYYCQQ RSNWPPAFGG GTKVEIKR | 108 |
| SEQ ID NO: 113 heavy chain variable region | EVQLQQSGPE LVKPGASVKM SCKASGYTFT SYVMHWVKQK PGQGLEWIGY INPYNDGTKY | 60 |
| | NEKFKGKATL TSDKSSSTAY MELSSLTSED SAVYYCANYY GSSLSMDYWG QGTSVTVSS | 119 |
| SEQ ID NO: 114 light chain variable region | DIQMTQTTSS LSASLGDRVT ISCRASQDIS NYLNWYQQKP DGTVKLLIYY TSRLHSGVPS | 60 |
| | RFSGSGSGTD YSLTISNLEQ EDIATYFCQQ GNTLPWTFGG GTKLEIKR | 108 |
| SEQ ID NO: 115 heavy chain variable region | EVQLQQSGPE LVKPGASVKI SCKTSGYTFK DYTMHWVKQS HGKSLEWIGG IYPNNGGSTY | 60 |
| | NQNFKDKATL TVDKSSSTAY MEFRSLTSED SAVYYCARMG YHGPHLDFDV WGAGTTVTVS | 120 |
| | P | 121 |
| SEQ ID NO: 116 light chain variable region | DIVMTQSHKF MSTSLGDRVS ITCKASQDVG AAVAWYQQKP GQSPKLLIYW ASTRHTGVPD | 60 |
| | RFTGGGSGTD FTLTISNVQS EDLTDYFCQQ YINYPLTFGG GTKLEIKR | 108 |
| SEQ ID NO: 117 heavy chain variable region of humanized antibody | QIQLVQSGPE LKKPGETVKI SCKASGYTFT DYSMHWVKQA PGKGLKWMGW INTETGEPTY | 60 |
| | ADDFKGRFAF SLETSASTAY LQINNLKNED TATYFCANPY YDYVSYYAMD YWGHGTSVTV | 120 |
| | SS | 122 |
| SEQ ID NO: 118 heavy chain variable region of humanized antibody | QVQLVQSGSE LKKPGASVKV SCKASGYTFT DYSMHWVRQA PGQGLKWMGW INTETGEPTY | 60 |
| | ADDFKGRFVF SLDTSVSTAY LQISSLKAED TAVYYCANPY YDYVSYYAMD YWGQGTTVTV | 120 |
| | SS | 122 |

TABLE 31-continued

Additional polypeptide domains useful as OX40 binding domains in fusion proteins (e.g., structures I-A and I-B) or as scFv OX40 agonist antibodies.

| Identifier | Sequence (One-Letter Amino Acid Symbols) | |
|---|---|---|
| SEQ ID NO: 119 light chain variable region of humanized antibody | DIVMTQSHKF MSTSVRDRVS ITCKASQDVS TAVAWYQQKP GQSPKLLIYS ASYLYTGVPD RFTGSGSGTD FTFTISSVQA EDLAVYYCQQ HYSTPRTFGG GTKLEIK | 60 107 |
| SEQ ID NO: 120 light chain variable region of humanized antibody | DIVMTQSHKF MSTSVRDRVS ITCKASQDVS TAVAWYQQKP GQSPKLLIYS ASYLYTGVPD RFTGSGSGTD FTFTISSVQA EDLAVYYCQQ HYSTPRTFGG GTKLEIK | 60 107 |
| SEQ ID NO: 121 heavy chain variable region of humanized antibody | EVQLVESGGG LVQPGESLKL SCESNEYEFP SHDMSWVRKT PEKRLELVAA INSDGGSTYY PDTMERRFII SRDNTKKTLY LQMSSLRSED TALYYCARHY DDYYAWFAYW GQGTLVTVSA | 60 120 |
| SEQ ID NO: 122 heavy chain variable region of humanized antibody | EVQLVESGGG LVQPGGSLRL SCAASEYEFP SHDMSWVRQA PGKGLELVAA INSDGGSTYY PDTMERRFTI SRDNAKNSLY LQMNSLRAED TAVYYCARHY DDYYAWFAYW GQGTMVTVSS | 60 120 |
| SEQ ID NO: 123 light chain variable region of humanized antibody | DIVLTQSPAS LAVSLGQRAT ISCRASKSVS TSGYSYMHWY QQKPGQPPKL LIYLASNLES GVPARFSGSG SGTDFTLNIH PVEEEDAATY YCQHSRELPL TFGAGTKLEL K | 60 111 |
| SEQ ID NO: 124 light chain variable region of humanized antibody | EIVLTQSPAT LSLSPGERAT LSCRASKSVS TSGYSYMHWY QQKPGQAPRL LIYLASNLES GVPARFSGSG SGTDFTLTIS SLEPEDFAVY YCQHSRELPL TFGGGTKVEI K | 60 111 |
| SEQ ID NO: 125 heavy chain variable region | MYLGLNYVFI VFLLNGVQSE VKLEESGGGL VQPGGSMKLS CAASGFTFSD AWMDWVRQSP EKGLEWVAEI RSKANNHATY YAESVNGRFT ISRDDSKSSV YLQMNSLRAE DTGIYYCTWG EVFYFDYWGQ GTTLTVSS | 60 120 138 |
| SEQ ID NO: 126 light chain variable region | MRPSIQFLGL LLFWLHGAQC DIQMTQSPSS LSASLGGKVT ITCKSSQDIN KYIAWYQHKP GKGPRLLIHY TSTLQPGIPS RFSGSGSGRD YSFSISNLEP EDIATYYCLQ YDNLLTFGAG TKLELK | 60 120 126 |

In an embodiment, the OX40 agonist is a OX40 agonistic single-chain fusion polypeptide comprising (i) a first soluble OX40 binding domain, (ii) a first peptide linker, (iii) a second soluble OX40 binding domain, (iv) a second peptide linker, and (v) a third soluble OX40 binding domain, further comprising an additional domain at the N-terminal and/or C-terminal end, and wherein the additional domain is a Fab or Fc fragment domain. In an embodiment, the OX40 agonist is a OX40 agonistic single-chain fusion polypeptide comprising (i) a first soluble OX40 binding domain, (ii) a first peptide linker, (iii) a second soluble OX40 binding domain, (iv) a second peptide linker, and (v) a third soluble OX40 binding domain, further comprising an additional domain at the N-terminal and/or C-terminal end, wherein the additional domain is a Fab or Fc fragment domain wherein each of the soluble OX40 binding domains lacks a stalk region (which contributes to trimerisation and provides a certain distance to the cell membrane, but is not part of the OX40 binding domain) and the first and the second peptide linkers independently have a length of 3-8 amino acids.

In an embodiment, the OX40 agonist is an OX40 agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein the TNF superfamily cytokine domain is an OX40 binding domain.

In some embodiments, the OX40 agonist is MEDI6383. MEDI6383 is an OX40 agonistic fusion protein and can be prepared as described in U.S. Pat. No. 6,312,700, the disclosure of which is incorporated by reference herein.

In an embodiment, the OX40 agonist is an OX40 agonistic scFv antibody comprising any of the foregoing $V_H$ domains linked to any of the foregoing $V_L$ domains.

In an embodiment, the OX40 agonist is Creative Biolabs OX40 agonist monoclonal antibody MOM-18455, commercially available from Creative Biolabs, Inc., Shirley, NY, USA.

In an embodiment, the OX40 agonist is OX40 agonistic antibody clone Ber-ACT35 commercially available from BioLegend, Inc., San Diego, CA, USA.

Optional Cell Viability Analyzes

Optionally, a cell viability assay can be performed after the priming first expansion (sometimes referred to as the initial bulk expansion), using standard assays known in the art. Thus, in certain embodiments, the method comprises performing a cell viability assay subsequent to the priming first expansion. For example, a trypan blue exclusion assay can be done on a sample of the bulk TILs, which selectively labels dead cells and allows a viability assessment. Other assays for use in testing viability can include but are not limited to the Alamar blue assay; and the MTT assay.

Cell Counts, Viability and Flow Cytometry

In some embodiments, cell counts and/or viability are measured. The expression of markers such as but not limited CD3, CD4, CD8, and CD56, as well as any other disclosed or described herein, can be measured by flow cytometry with antibodies, for example but not limited to those commercially available from BD Bio-sciences (BD Biosciences, San Jose, CA) using a FACSCanto™ flow cytometer (BD Biosciences). The cells can be counted manually using a disposable c-chip hemocytometer (VWR, Batavia, IL) and viability can be assessed using any method known in the art, including but not limited to trypan blue staining. The cell viability can also be assayed based on U.S. Ser. No. 15/863,634, incorporated by reference herein in its entirety. Cell viability can also be assayed based on U.S. Patent Publication No. 2018/0280436 or International Patent Publication No. WO/2018/081473, both of which are incorporate herein in their entireties for all purposes.

In some cases, the bulk TIL population can be cryopreserved immediately, using the protocols discussed below. Alternatively, the bulk TIL population can be subjected to REP and then cryopreserved as discussed below. Similarly, in the case where genetically modified TILs will be used in therapy, the bulk or REP TIL populations can be subjected to genetic modifications for suitable treatments.

Cell Cultures

In an embodiment, a method for expanding TILs, including those discussed above as well as exemplified in FIG. 1, in particular, e.g., FIG. 1B, may include using about 5,000 mL to about 25,000 mL of cell medium, about 5,000 mL to about 10,000 mL of cell medium, or about 5,800 mL to about 8,700 mL of cell medium. In some embodiments, the media is a serum free medium. In some embodiments, the media in the priming first expansion is serum free. In some embodiments, the media in the second expansion is serum free. In some embodiments, the media in the priming first expansion and the second expansion (also referred to as rapid second expansion) are both serum free. In an embodiment, expanding the number of TILs uses no more than one type of cell culture medium. Any suitable cell culture medium may be used, e.g., AIM-V cell medium (L-glutamine, 50 µM streptomycin sulfate, and 10 µM gentamicin sulfate) cell culture medium (Invitrogen, Carlsbad CA). In this regard, the inventive methods advantageously reduce the amount of medium and the number of types of medium required to expand the number of TIL. In an embodiment, expanding the number of TIL may comprise feeding the cells no more frequently than every third or fourth day. Expanding the number of cells in a gas permeable container simplifies the procedures necessary to expand the number of cells by reducing the feeding frequency necessary to expand the cells.

In an embodiment, the cell culture medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME).

In an embodiment, the duration of the method comprising obtaining a tumor tissue sample from the mammal; culturing the tumor tissue sample in a first gas permeable container containing cell medium including IL-2, 1× antigen-presenting feeder cells, and OKT-3 for a duration of about 1 to 7 days, e.g., about 7 days as a priming first expansion; transferring the TTLs to a second gas permeable container and expanding the number of TILs in the second gas permeable container containing cell medium including IL-2, 2× antigen-presenting feeder cells, and OKT-3 for a duration of about 7 to 9 days, e.g., about 7 days, about 8 days, or about 9 days.

In an embodiment, TILs are expanded in gas-permeable containers. Gas-permeable containers have been used to expand TILs using PBMCs using methods, compositions, and devices known in the art, including those described in U.S. Patent Application Publication No. 2005/0106717 A1, the disclosures of which are incorporated herein by reference. In an embodiment, TILs are expanded in gas-permeable bags. In an embodiment, TILs are expanded using a cell expansion system that expands TILs in gas permeable bags, such as the Xuri Cell Expansion System W25 (GE Healthcare). In an embodiment, TILs are expanded using a cell expansion system that expands TILs in gas permeable bags, such as the WAVE Bioreactor System, also known as the Xuri Cell Expansion System W5 (GE Healthcare). In an embodiment, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, and about 10 L.

In an embodiment, TILs can be expanded in G-Rex flasks (commercially available from Wilson Wolf Manufacturing). Such embodiments allow for cell populations to expand from about $5 \times 10^5$ cells/cm$^2$ to between $10 \times 10^6$ and $30 \times 10^6$ cells/cm$^2$. In an embodiment this is without feeding. In an embodiment, this is without feeding so long as medium resides at a height of about 10 cm in the G-Rex flask. In an embodiment this is without feeding but with the addition of one or more cytokines. In an embodiment, the cytokine can be added as a bolus without any need to mix the cytokine with the medium. Such containers, devices, and methods are known in the art and have been used to expand TILs, and include those described in U.S. Patent Application Publication No. US 2014/0377739A1, International Publication No. WO 2014/210036 A1, U.S. Patent Application Publication No. us 2013/0115617 A1, International Publication No. WO 2013/188427 A1, U.S. Patent Application Publication No. US 2011/0136228 A1, U.S. Pat. No. 8,809,050 B2, International publication No. WO 2011/072088 A2, U.S. Patent Application Publication No. US 2016/0208216 A1, U.S. Patent Application Publication No. US 2012/0244133 A1, International Publication No. WO 2012/129201 A1, U.S. Patent Application Publication No. US 2013/0102075 A1, U.S. Pat. No. 8,956,860 B2, International Publication No. WO 2013/173835 A1, U.S. Patent Application Publication No. US 2015/0175966 A1, the disclosures of which are incorporated herein by reference. Such processes are also described in Jin et al., J. Immunotherapy, 2012, 35:283-292.

Optional Genetic Engineering of TILs

In some embodiments, the expanded TILs of the present invention are further manipulated before, during, or after an expansion step, including during closed, sterile manufacturing processes, each as provided herein, in order to alter protein expression in a transient manner. In some embodiments, the transiently altered protein expression is due to transient gene editing. In some embodiments, the expanded TILs of the present invention are treated with transcription factors (TFs) and/or other molecules capable of transiently altering protein expression in the TILs. In some embodiments, the TFs and/or other molecules that are capable of transiently altering protein expression provide for altered expression of tumor antigens and/or an alteration in the number of tumor antigen-specific T cells in a population of TILs. It is understood that optional genetic engineering of TILs is applicable to TILs manufactured in process 1C, 2A, or Gen 3.

In certain embodiments, the method comprises genetically editing a population of TILs. In certain embodiments, the method comprises genetically editing the first population of TILs, the second population of TILs and/or the third population of TILs.

In some embodiments, the present invention includes genetic editing through nucleotide insertion, such as through ribonucleic acid (RNA) insertion, including insertion of messenger RNA (mRNA) or small (or short) interfering RNA (siRNA), into a population of TILs for promotion of the expression of one or more proteins or inhibition of the expression of one or more proteins, as well as simultaneous combinations of both promotion of one set of proteins with inhibition of another set of proteins.

In some embodiments, the expanded TILs of the present invention undergo transient alteration of protein expression. In some embodiments, the transient alteration of protein expression occurs in the bulk TIL population prior to first expansion, including, for example in the TIL population obtained from for example, Step A as indicated in FIG. 1 (particularly FIG. 1). In some embodiments, the transient alteration of protein expression occurs during the first expansion, including, for example in the TIL population expanded in for example, Step B as indicated in FIG. 1 (for example FIG. 1B). In some embodiments, the transient alteration of protein expression occurs after the first expansion, including, for example in the TIL population in transition between the first and second expansion (e.g. the second population of TILs as described herein), the TIL population obtained from for example, Step B and included in Step C as indicated in FIG. 1. In some embodiments, the transient alteration of protein expression occurs in the bulk TIL population prior to second expansion, including, for example in the TIL population obtained from for example, Step C and prior to its expansion in Step D as indicated in FIG. 1. In some embodiments, the transient alteration of protein expression occurs during the second expansion, including, for example in the TIL population expanded in for example, Step D as indicated in FIG. 1 (e.g. the third population of TILs). In some embodiments, the transient alteration of protein expression occurs after the second expansion, including, for example in the TIL population obtained from the expansion in for example, Step D as indicated in FIG. 1.

In some embodiments, the expanded TILs of the present invention undergo transient alteration of protein expression. In some embodiments, the transient alteration of protein expression occurs in the bulk TIL population prior to first expansion, including, for example in the TIL population obtained from for example, Step A as indicated in FIG. 8 (particularly FIG. 8B). In some embodiments, the transient alteration of protein expression occurs during the first expansion, including, for example in the TIL population expanded in for example, Step B as indicated in FIG. 8 (for example FIG. 8B). In some embodiments, the transient alteration of protein expression occurs after the first expansion, including, for example in the TIL population in transition between the first and second expansion (e.g. the second population of TILs as described herein), the TIL population obtained from for example, Step B and included in Step C as indicated in FIG. 8. In some embodiments, the transient alteration of protein expression occurs in the bulk TIL population prior to second expansion, including, for example in the TIL population obtained from for example, Step C and prior to its expansion in Step D as indicated in FIG. 8. In some embodiments, the transient alteration of protein expression occurs during the second expansion, including, for example in the TIL population expanded in for example, Step D as indicated in FIG. 1 (e.g. the third population of TILs). In some embodiments, the transient alteration of protein expression occurs after the second expansion, including, for example in the TIL population obtained from the expansion in for example, Step D as indicated in FIG. 8.

In an embodiment, a method of transiently altering protein expression in a population of TILs includes the step of electroporation. Electroporation methods are known in the art and are described, e.g., in Tsong, *Biophys. J.* 1991, 60, 297-306, and U.S. Patent Application Publication No. 2014/0227237 A1, the disclosures of each of which are incorporated by reference herein. In an embodiment, a method of transiently altering protein expression in population of TILs includes the step of calcium phosphate transfection. Calcium phosphate transfection methods (calcium phosphate DNA precipitation, cell surface coating, and endocytosis) are known in the art and are described in Graham and van der Eb, *Virology* 1973, 52, 456-467; Wigler, et al., *Proc. Natl. Acad. Sci.* 1979, 76, 1373-1376; and Chen and Okayarea, *Mol. Cell. Biol.* 1987, 7, 2745-2752; and in U.S. Pat. No. 5,593,875, the disclosures of each of which are incorporated by reference herein. In an embodiment, a method of transiently altering protein expression in a population of TILs includes the step of liposomal transfection. Liposomal transfection methods, such as methods that employ a 1:1 (w/w) liposome formulation of the cationic lipid N-[1-(2,3-dioleyloxy)propyl]-n,n,n-trimethylammonium chloride (DOTMA) and dioleoyl phophotidylethanolamine (DOPE) in filtered water, are known in the art and are described in Rose, et al., *Biotechniques* 1991, 10, 520-525 and Felgner, et al., *Proc. Natl. Acad. Sci. USA,* 1987, 84, 7413-7417 and in U.S. Pat. Nos. 5,279,833; 5,908,635; 6,056,938; 6,110,490; 6,534,484; and 7,687,070, the disclosures of each of which are incorporated by reference herein. In an embodiment, a method of transiently altering protein expression in a population of TTLs includes the step of transfection using methods described in U.S. Pat. Nos. 5,766,902; 6,025,337; 6,410,517; 6,475,994; and 7,189,705; the disclosures of each of which are incorporated by reference herein.

In some embodiments, transient alteration of protein expression results in an increase in Stem Memory T cells (TSCMs). TSCMs are early progenitors of antigen-experienced central memory T cells. TSCMs generally display the long-term survival, self-renewal, and multipotency abilities that define stem cells, and are generally desirable for the generation of effective TIL products. TSCM have shown enhanced anti-tumor activity compared with other T cell subsets in mouse models of adoptive cell transfer (Gattinoni et al. Nat Med 2009, 2011; Gattinoni, Nature Rev. Cancer, 2012; Cieri et al. Blood 2013). In some embodiments, transient alteration of protein expression results in a TIL population with a composition comprising a high proportion of TSCM. In some embodiments, transient alteration of protein expression results in an at least 5%, at least 10%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% increase in TSCM percentage. In some embodiments, transient alteration of protein expression results in an at least a 1-fold, 2-fold, 3-fold, 4-fold, 5-fold, or 10-fold increase in TSCMs in the TIL population. In some embodiments, transient alteration of protein expression results in a TIL population with at least at least 5%, at least 10%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% TSCMs. In some embodiments, transient alteration of protein expression results in a therapeutic TIL population with at least at least 5%, at least 10%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% TSCMs.

In some embodiments, transient alteration of protein expression results in rejuvenation of antigen-experienced T-cells. In some embodiments, rejuvenation includes, for example, increased proliferation, increased T-cell activation, and/or increased antigen recognition.

In some embodiments, transient alteration of protein expression alters the expression in a large fraction of the T-cells in order to preserve the tumor-derived TCR repertoire. In some embodiments, transient alteration of protein expression does not alter the tumor-derived TCR repertoire. In some embodiments, transient alteration of protein expression maintains the tumor-derived TCR repertoire.

In some embodiments, transient alteration of protein results in altered expression of a particular gene. In some embodiments, the transient alteration of protein expression targets a gene including but not limited to PD-1 (also referred to as PDCD1 or CC279), TGFBR2, CCR4/5, CBLB (CBL-B), CISH, CCRs (chimeric co-stimulatory receptors), IL-2, IL-12, IL-15, IL-21, NOTCH 1/2 ICD, TIM3, LAG3, TIGIT, TGFβ, CCR2, CCR4, CCR5, CXCR1, CXCR2, CSCR3, CCL2 (MCP-1), CCL3 (MIP-1α), CCL4 (MIP1-β), CCL5 (RANTES), CXCL1/CXCL8, CCL22, CCL17, CXCL1/CXCL8, VHL, CD44, PIK3CD, SOCS1, and/or cAMP protein kinase A (PKA). In some embodiments, the transient alteration of protein expression targets a gene selected from the group consisting of PD-1, TGFBR2, CCR4/5, CBLB (CBL-B), CISH, CCRs (chimeric co-stimulatory receptors), IL-2, IL-12, IL-15, IL-21, NOTCH 1/2 ICD, TIM3, LAG3, TIGIT, TGFβ, CCR2, CCR4, CCR5, CXCR1, CXCR2, CSCR3, CCL2 (MCP-1), CCL3 (MIP-1α), CCL4 (MIP1-β), CCL5 (RANTES), CXCL1/CXCL8, CCL22, CCL17, CXCL1/CXCL8, VHL, CD44, PIK3CD, SOCS1, and/or cAMP protein kinase A (PKA). In some embodiments, the transient alteration of protein expression targets PD-1. In some embodiments, the transient alteration of protein expression targets TGFBR2. In some embodiments, the transient alteration of protein expression targets CCR4/5. In some embodiments, the transient alteration of protein expression targets CBLB. In some embodiments, the transient alteration of protein expression targets CISH. In some embodiments, the transient alteration of protein expression targets CCRs (chimeric co-stimulatory receptors). In some embodiments, the transient alteration of protein expression targets IL-2. In some embodiments, the transient alteration of protein expression targets IL-12. In some embodiments, the transient alteration of protein expression targets IL-15. In some embodiments, the transient alteration of protein expression targets IL-21. In some embodiments, the transient alteration of protein expression targets NOTCH 1/2 ICD. In some embodiments, the transient alteration of protein expression targets TIM3. In some embodiments, the transient alteration of protein expression targets LAG3. In some embodiments, the transient alteration of protein expression targets TIGIT. In some embodiments, the transient alteration of protein expression targets TGFβ. In some embodiments, the transient alteration of protein expression targets CCR1. In some embodiments, the transient alteration of protein expression targets CCR2. In some embodiments, the transient alteration of protein expression targets CCR4. In some embodiments, the transient alteration of protein expression targets CCR5. In some embodiments, the transient alteration of protein expression targets CXCR1. In some embodiments, the transient alteration of protein expression targets CXCR2. In some embodiments, the transient alteration of protein expression targets CSCR3. In some embodiments, the transient alteration of protein expression targets CCL2 (MCP-1). In some embodiments, the transient alteration of protein expression targets CCL3 (MIP-1α). In some embodiments, the transient alteration of protein expression targets CCL4 (MIP1-β). In some embodiments, the transient alteration of protein expression targets CCL5 (RANTES). In some embodiments, the transient alteration of protein expression targets CXCL1. In some embodiments, the transient alteration of protein expression targets CXCL8. In some embodiments, the transient alteration of protein expression targets CCL22. In some embodiments, the transient alteration of protein expression targets CCL17. In some embodiments, the transient alteration of protein expression targets VHL. In some embodiments, the transient alteration of protein expression targets CD44. In some embodiments, the transient alteration of protein expression targets PIK3CD. In some embodiments, the transient alteration of protein expression targets SOCS1. In some embodiments, the transient alteration of protein expression targets cAMP protein kinase A (PKA).

In some embodiments, the transient alteration of protein expression results in increased and/or overexpression of a chemokine receptor. In some embodiments, the chemokine receptor that is overexpressed by transient protein expression includes a receptor with a ligand that includes but is not limited to CCL2 (MCP-1), CCL3 (MIP-1α), CCL4 (MIP1-β), CCL5 (RANTES), CXCL1, CXCL8, CCL22, and/or CCL17.

In some embodiments, the transient alteration of protein expression results in a decrease and/or reduced expression of PD-1, CTLA-4, TIM-3, LAG-3, TIGIT, TGFβR2, and/or TGFβ (including resulting in, for example, TGFβ pathway blockade). In some embodiments, the transient alteration of protein expression results in a decrease and/or reduced expression of CBLB (CBL-B). In some embodiments, the transient alteration of protein expression results in a decrease and/or reduced expression of CISH.

In some embodiments, the transient alteration of protein expression results in increased and/or overexpression of chemokine receptors in order to, for example, improve TIL trafficking or movement to the tumor site. In some embodiments, the transient alteration of protein expression results in increased and/or overexpression of a CCR (chimeric co-stimulatory receptor). In some embodiments, the transient alteration of protein expression results in increased and/or overexpression of a chemokine receptor selected from the group consisting of CCR1, CCR2, CCR4, CCR5, CXCR1, CXCR2, and/or CSCR3.

In some embodiments, the transient alteration of protein expression results in increased and/or overexpression of an interleukin. In some embodiments, the transient alteration of protein expression results in increased and/or overexpression of an interleukin selected from the group consisting of IL-2, IL-12, IL-15, and/or IL-21.

In some embodiments, the transient alteration of protein expression results in increased and/or overexpression of NOTCH 1/2 ICD. In some embodiments, the transient alteration of protein expression results in increased and/or overexpression of VHL. In some embodiments, the transient alteration of protein expression results in increased and/or overexpression of CD44. In some embodiments, the transient alteration of protein expression results in increased and/or overexpression of PIK3CD. In some embodiments, the transient alteration of protein expression results in increased and/or overexpression of SOCS1, In some embodiments, the transient alteration of protein expression results in decreased and/or reduced expression of cAMP protein kinase A (PKA).

In some embodiments, the transient alteration of protein expression results in decreased and/or reduced expression of a molecule selected from the group consisting of PD-1, LAG3, TIM3, CTLA-4, TIGIT, CISH, TGFβR2, PKA, CBLB, BAFF (BR3), and combinations thereof. In some embodiments, the transient alteration of protein expression results in decreased and/or reduced expression of two molecules selected from the group consisting of PD-1, LAG3, TIM3, CTLA-4, TIGIT, CISH, TGFβR2, PKA, CBLB, BAFF (BR3), and combinations thereof. In some embodiments, the transient alteration of protein expression results in decreased and/or reduced expression of PD-1 and one molecule selected from the group consisting of LAG3, TIM3, CTLA-4, TIGIT, CISH, TGFβR2, PKA, CBLB, BAFF (BR3), and combinations thereof. In some embodiments, the transient alteration of protein expression results in decreased and/or reduced expression of PD-1, LAG-3, CISH, CBLB, TIM3, and combinations thereof. In some embodiments, the transient alteration of protein expression results in decreased and/or reduced expression of PD-1 and one of LAG3, CISH, CBLB, TIM3, and combinations thereof. In some embodiments, the transient alteration of protein expression results in decreased and/or reduced expression of PD-1 and LAG3. In some embodiments, the transient alteration of protein expression results in decreased and/or reduced expression of PD-1 and CISH. In some embodiments, the transient alteration of protein expression results in decreased and/or reduced expression of PD-1 and CBLB. In some embodiments, the transient alteration of protein expression results in decreased and/or reduced expression of LAG3 and CISH. In some embodiments, the transient alteration of protein expression results in decreased and/or reduced expression of LAG3 and CBLB. In some embodiments, the transient alteration of protein expression results in decreased and/or reduced expression of CISH and CBLB. In some embodiments, the transient alteration of protein expression results in decreased and/or reduced expression of TIM3 and PD-1. In some embodiments, the transient alteration of protein expression results in decreased and/or reduced expression of TIM3 and LAG3. In some embodiments, the transient alteration of protein expression results in decreased and/or reduced expression of TIM3 and CISH. In some embodiments, the transient alteration of protein expression results in decreased and/or reduced expression of TIM3 and CBLB.

In some embodiments, an adhesion molecule selected from the group consisting of CCR2, CCR4, CCR5, CXCR2, CXCR3, CX3CR1, and combinations thereof, is inserted by a gammaretroviral or lentiviral method into the first population of TILs, second population of TILs, or harvested population of TILs (e.g., the expression of the adhesion molecule is increased).

In some embodiments, the transient alteration of protein expression results in decreased and/or reduced expression of a molecule selected from the group consisting of PD-1, LAG3, TIM3, CTLA-4, TIGIT, CISH, TGFβR2, PKA, CBLB, BAFF (BR3), and combinations thereof, and increased and/or enhanced expression of CCR2, CCR4, CCR5, CXCR2, CXCR3, CX3CR1, and combinations thereof. In some embodiments, the transient alteration of protein expression results in decreased and/or reduced expression of a molecule selected from the group consisting of PD-1, LAG3, TIM3, CISH, CBLB, and combinations thereof, and increased and/or enhanced expression of CCR2, CCR4, CCR5, CXCR2, CXCR3, CX3CR1, and combinations thereof.

In some embodiments, there is a reduction in expression of about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, there is a reduction in expression of at least about 65%, about 70%, about 75%, about 80%, about 85%, about 90%, or about 95%. In some embodiments, there is a reduction in expression of at least about 75%, about 80%, about 85%, about 90%, or about 95%. In some embodiments, there is a reduction in expression of at least about 80%, about 85%, about 90%, or about 95%. In some embodiments, there is a reduction in expression of at least about 85%, about 90%, or about 95%. In some embodiments, there is a reduction in expression of at least about 80%. In some embodiments, there is a reduction in expression of at least about 85%, In some embodiments, there is a reduction in expression of at least about 90%. In some embodiments, there is a reduction in expression of at least about 95%. In some embodiments, there is a reduction in expression of at least about 99%.

In some embodiments, there is an increase in expression of about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, there is an increase in expression of at least about 65%, about 70%, about 75%, about 80%, about 85%, about 90%, or about 95%. In some embodiments, there is an increase in expression of at least about 75%, about 80%, about 85%, about 90%, or about 95%. In some embodiments, there is an increase in expression of at least about 80%, about 85%, about 90%, or about 95%. In some embodiments, there is an increase in expression of at least about 85%, about 90%, or about 95%. In some embodiments, there is an increase in expression of at least about 80%. In some embodiments, there is an increase in expression of at least about 85%, In some embodiments, there is an increase in expression of at least about 90%. In some embodiments, there is an increase in expression of at least about 95%. In some embodiments, there is an increase in expression of at least about 99%.

In some embodiments, transient alteration of protein expression is induced by treatment of the TILs with transcription factors (TFs) and/or other molecules capable of transiently altering protein expression in the TILs. In some embodiments, the SQZ vector-free microfluidic platform is employed for intracellular delivery of the transcription factors (TFs) and/or other molecules capable of transiently altering protein expression. Such methods demonstrating the ability to deliver proteins, including transcription factors, to a variety of primary human cells, including T cells (Sharei et al. PNAS 2013, as well as Sharei et al. PLOS ONE 2015 and Greisbeck et al. J. Immunology vol. 195, 2015) have been described; see, for example, International Patent Publications WO 2013/059343A1, WO 2017/008063A1, and WO 2017/123663A1, all of which are incorporated by reference herein in their entireties. Such methods as described in International Patent Publications WO 2013/059343A1, WO 2017/008063A1, and WO 2017/123663A1 can be employed with the present invention in order to expose a population of TILs to transcription factors (TFs) and/or other molecules capable of inducing transient protein expression, wherein said TFs and/or other molecules capable of inducing transient protein expression provide for increased expression of tumor antigens and/or an increase in the number of tumor antigen-specific T cells in the population of TILs, thus resulting in reprogramming of the TIL population and an increase in therapeutic efficacy of the reprogrammed TIL population as compared to a non-reprogrammed TIL population. In some embodiments, the reprogramming results in an increased subpopulation of effector T cells and/or central memory T cells relative to the starting or prior population (i.e., prior to reprogramming) population of TILs, as described herein.

In some embodiments, the transcription factor (TF) includes but is not limited to TCF-1, NOTCH 1/2 ICD, and/or MYB. In some embodiments, the transcription factor (TF) is TCF-1. In some embodiments, the transcription factor (TF) is NOTCH 1/2 ICD. In some embodiments, the transcription factor (TF) is MYB. In some embodiments, the transcription factor (TF) is administered with induced pluripotent stem cell culture (iPSC), such as the commercially available KNOCKOUT Serum Replacement (Gibco/ThermoFisher), to induce additional TIL reprogramming. In some embodiments, the transcription factor (TF) is administered with an iPSC cocktail to induce additional TIL reprogramming. In some embodiments, the transcription factor (TF) is administered without an iPSC cocktail. In some embodiments, reprogramming results in an increase in the percentage of TSCMs. In some embodiments, reprogramming results in an increase in the percentage of TSCMs by about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95% TSCMs.

In some embodiments, a method of transient altering protein expression, as described above, may be combined with a method of genetically modifying a population of TILs includes the step of stable incorporation of genes for production of one or more proteins. In certain embodiments, the method comprises a step of genetically modifying a population of TILs. In certain embodiments, the method comprises genetically modifying the first population of TILs, the second population of TILs and/or the third population of TILs. In an embodiment, a method of genetically modifying a population of TILs includes the step of retroviral transduction. In an embodiment, a method of genetically modifying a population of TILs includes the step of lentiviral transduction. Lentiviral transduction systems are known in the art and are described, e.g., in Levine, et al., *Proc. Nat'l Acad. Sci.* 2006, 103, 17372-77; Zufferey, et al., *Nat. Biotechnol.* 1997, 15, 871-75; Dull, et al., *J. Virology* 1998, 72, 8463-71, and U.S. Pat. No. 6,627,442, the disclosures of each of which are incorporated by reference herein. In an embodiment, a method of genetically modifying a population of TILs includes the step of gamma-retroviral transduction. Gamma-retroviral transduction systems are known in the art and are described, e.g., Cepko and Pear, Cur. Prot. Mol. Biol. 1996, 9.9.1-9.9.16, the disclosure of which is incorporated by reference herein. In an embodiment, a method of genetically modifying a population of TILs includes the step of transposon-mediated gene transfer. Transposon-mediated gene transfer systems are known in the art and include systems wherein the transposase is provided as DNA expression vector or as an expressible RNA or a protein such that long-term expression of the transposase does not occur in the transgenic cells, for example, a transposase provided as an mRNA (e.g., an mRNA comprising a cap and poly-A tail). Suitable transposon-mediated gene transfer systems, including the salmonid-type Tel-like transposase (SB or Sleeping Beauty transposase), such as SB10, SB11, and SB100x, and engineered enzymes with increased enzymatic activity, are described in, e.g., Hackett, et al., *Mol. Therapy* 2010, 18, 674-83 and U.S. Pat. No. 6,489,458, the disclosures of each of which are incorporated by reference herein.

In some embodiments, transient alteration of protein expression is a reduction in expression induced by self-delivering RNA interference (sdRNA), which is a chemically-synthesized asymmetric siRNA duplex with a high percentage of 2'-OH substitutions (typically fluorine or —OCH$_3$) which comprises a 20-nucleotide antisense (guide) strand and a 13 to 15 base sense (passenger) strand conjugated to cholesterol at its 3' end using a tetraethylenglycol (TEG) linker. In some embodiments, the method comprises transient alteration of protein expression in a population of TILs, comprising the use of self-delivering RNA interference (sdRNA), which is a chemically-synthesized asymmetric siRNA duplex with a high percentage of 2'-OH substitutions (typically fluorine or —OCH$_3$) which comprises a 20-nucleotide antisense (guide) strand and a 13 to 15 base sense (passenger) strand conjugated to cholesterol at its 3' end using a tetraethyleneglycol (TEG) linker. Methods of using sdRNA have been described in Khvorova and Watts, *Nat. Biotechnol.* 2017, 35, 238-248; Byrne, et al., *J. Ocul. Pharmacol. Ther.* 2013, 29, 855-864; and Ligtenberg, et al., *Mol. Therapy*, 2018, in press, the disclosures of which are incorporated by reference herein. In an embodiment, delivery of sdRNA to a TIL population is accomplished without use of electroporation, SQZ, or other methods, instead using a 1 to 3 day period in which a TIL population is exposed to sdRNA at a concentration of 1 μM/10,000 TTLs in medium. In certain embodiments, the method comprises delivery sdRNA to a TTLs population comprising exposing the TTLs population to sdRNA at a concentration of 1 μM/10,000 TTLs in medium for a period of between 1 to 3 days. In an embodiment, delivery of sdRNA to a TIL population is accomplished using a 1 to 3 day period in which a TIL population is exposed to sdRNA at a concentration of 10 μM/10,000 TILs in medium. In an embodiment, delivery of sdRNA to a TIL population is accomplished using a 1 to 3 day period in which a TIL population is exposed to sdRNA at a concentration of 50 μM/10,000 TILs in medium. In an embodiment, delivery of sdRNA to a TIL population is accomplished using a 1 to 3 day period in which a TIL population is exposed to sdRNA at a concentration of between 0.1 μM/10,000 TILs and 50 μM/10,000 TILs in medium. In an embodiment, delivery of sdRNA to a TIL population is accomplished using a 1 to 3 day period in which a TIL population is exposed to sdRNA at a concentration of between 0.1 µM/10,000 TILs and 50 µM/10,000 TILs in medium, wherein the exposure to sdRNA is performed two, three, four, or five times by addition of fresh sdRNA to the media. Other suitable processes are described, for example, in U.S. Patent Application Publication No. US 2011/0039914 A1, US 2013/0131141 A1, and US 2013/0131142 A1, and U.S. Pat. No. 9,080,171, the disclosures of which are incorporated by reference herein.

In some embodiments, sdRNA is inserted into a population of TILs during manufacturing. In some embodiments, the sdRNA encodes RNA that interferes with NOTCH 1/2 ICD, PD-1, CTLA-4 TIM-3, LAG-3, TIGIT, TGFβ, TGFBR2, cAMP protein kinase A (PKA), BAFF BR3, CISH, and/or CBLB. In some embodiments, the reduction in expression is determined based on a percentage of gene silencing, for example, as assessed by flow cytometry and/or qPCR. In some embodiments, there is a reduction in expression of about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, there is a reduction in expression of at least about 65%, about 70%, about 75%, about 80%, about 85%, about 90%, or about 95%. In some embodiments, there is a reduction in expression of at least about 75%, about 80%, about 85%, about 90%, or about 95%. In some embodiments, there is a reduction in expression of at least about 80%, about 85%, about 90%, or about 95%. In some embodiments, there is a reduction in expression of at least about 85%, about 90%, or about 95%. In some embodiments, there is a reduction in expression of at least about 80%. In some embodiments, there is a reduction in expression of at least about 85%. In some embodiments, there is a reduction in expression of at least about 90%. In some embodiments, there is a reduction in expression of at least about 95%. In some embodiments, there is a reduction in expression of at least about 99%.

The self-deliverable RNAi technology based on the chemical modification of siRNAs can be employed with the methods of the present invention to successfully deliver the sdRNAs to the TILs as described herein. The combination of backbone modifications with asymmetric siRNA structure and a hydrophobic ligand (see, for example, Ligtenberg, et al., Mol. Therapy, 2018 and US20160304873) allow sdRNAs to penetrate cultured mammalian cells without additional formulations and methods by simple addition to the culture media, capitalizing on the nuclease stability of sdRNAs. This stability allows the support of constant levels of RNAi-mediated reduction of target gene activity simply by maintaining the active concentration of sdRNA in the media. While not being bound by theory, the backbone stabilization of sdRNA provides for extended reduction in gene expression effects which can last for months in non-dividing cells.

In some embodiments, over 95% transfection efficiency of TILs and a reduction in expression of the target by various specific sdRNA occurs. In some embodiments, sdRNAs containing several unmodified ribose residues were replaced with fully modified sequences to increase potency and/or the longevity of RNAi effect. In some embodiments, a reduction in expression effect is maintained for 12 hours, 24 hours, 36 hours, 48 hours, 5 days, 6 days, 7 days, or 8 days or more. In some embodiments, the reduction in expression effect decreases at 10 days or more post sdRNA treatment of the TILs. In some embodiments, more than 70% reduction in expression of the target expression is maintained. In some embodiments, more than 70% reduction in expression of the target expression is maintained TILs. In some embodiments, a reduction in expression in the PD-1/PD-L1 pathway allows for the TILs to exhibit a more potent in vivo effect, which is in some embodiments, due to the avoidance of the suppressive effects of the PD-1/PD-L1 pathway. In some embodiments, a reduction in expression of PD-1 by sdRNA results in an increase TIL proliferation.

Small interfering RNA (siRNA), sometimes known as short interfering RNA or silencing RNA, is a double stranded RNA molecule, generally 19-25 base pairs in length. siRNA is used in RNA interference (RNAi), where it interferes with expression of specific genes with complementary nucleotide sequences.

Double stranded DNA (dsRNA) can be generally used to define any molecule comprising a pair of complementary strands of RNA, generally a sense (passenger) and antisense (guide) strands, and may include single-stranded overhang regions. The term dsRNA, contrasted with siRNA, generally refers to a precursor molecule that includes the sequence of an siRNA molecule which is released from the larger dsRNA molecule by the action of cleavage enzyme systems, including Dicer.

sdRNA (self-deliverable RNA) are a new class of covalently modified RNAi compounds that do not require a delivery vehicle to enter cells and have improved pharmacology compared to traditional siRNAs. "Self-deliverable RNA" or "sdRNA" is a hydrophobically modified RNA interfering-antisense hybrid, demonstrated to be highly efficacious in vitro in primary cells and in vivo upon local administration. Robust uptake and/or silencing without toxicity has been demonstrated. sdRNAs are generally asymmetric chemically modified nucleic acid molecules with minimal double stranded regions. sdRNA molecules typically contain single stranded regions and double stranded regions, and can contain a variety of chemical modifications within both the single stranded and double stranded regions of the molecule. Additionally, the sdRNA molecules can be attached to a hydrophobic conjugate such as a conventional and advanced sterol-type molecule, as described herein. sdRNAs and associated methods for making such sdRNAs have also been described extensively in, for example, US20160304873, WO2010033246, WO2017070151, WO2009102427, WO2011119887, WO2010033247A2, WO2009045457, WO2011119852, all of which are incorporated by reference herein in their entireties for all purposes. To optimize sdRNA structure, chemistry, targeting position, sequence preferences, and the like, a proprietary algorithm has been developed and utilized for sdRNA potency prediction (see, for example, US 20160304873). Based on these analyses, functional sdRNA sequences have been generally defined as having over 70% reduction in expression at 1 µM concentration, with a probability over 40%.

In some embodiments, the sdRNA sequences used in the invention exhibit a 70% reduction in expression of the target gene. In some embodiments, the sdRNA sequences used in the invention exhibit a 75% reduction in expression of the target gene.

In some embodiments, the sdRNA sequences used in the invention exhibit an 80% reduction in expression of the target gene. In some embodiments, the sdRNA sequences used in the invention exhibit an 85% reduction in expression of the target gene. In some embodiments, the sdRNA sequences used in the invention exhibit a 90% reduction in expression of the target gene. In some embodiments, the sdRNA sequences used in the invention exhibit a 95% reduction in expression of the target gene. In some embodiments, the sdRNA sequences used in the invention exhibit a 99% reduction in expression of the target gene. In some embodiments, the sdRNA sequences used in the invention exhibit a reduction in expression of the target gene when delivered at a concentration of about 0.25 µM to about 4 µM. In some embodiments, the sdRNA sequences used in the invention exhibit a reduction in expression of the target gene when delivered at a concentration of about 0.25 µM. In some embodiments, the sdRNA sequences used in the invention exhibit a reduction in expression of the target gene when delivered at a concentration of about 0.5 µM. In some embodiments, the sdRNA sequences used in the invention exhibit a reduction in expression of the target gene when delivered at a concentration of about 0.75 µM. In some embodiments, the sdRNA sequences used in the invention exhibit a reduction in expression of the target gene when delivered at a concentration of about 1.0 µM. In some embodiments, the sdRNA sequences used in the invention exhibit a reduction in expression of the target gene when delivered at a concentration of about 1.25 µM. In some embodiments, the sdRNA sequences used in the invention exhibit a reduction in expression of the target gene when delivered at a concentration of about 1.5 µM. In some embodiments, the sdRNA sequences used in the invention exhibit a reduction in expression of the target gene when delivered at a concentration of about 1.75 µM. In some embodiments, the sdRNA sequences used in the invention exhibit a reduction in expression of the target gene when delivered at a concentration of about 2.0 µM. In some embodiments, the sdRNA sequences used in the invention exhibit a reduction in expression of the target gene when delivered at a concentration of about 2.25 µM. In some embodiments, the sdRNA sequences used in the invention exhibit a reduction in expression of the target gene when delivered at a concentration of about 2.5 µM. In some embodiments, the sdRNA sequences used in the invention exhibit a reduction in expression of the target gene when delivered at a concentration of about 2.75 µM. In some embodiments, the sdRNA sequences used in the invention exhibit a reduction in expression of the target gene when delivered at a concentration of about 3.0 µM. In some embodiments, the sdRNA sequences used in the invention exhibit a reduction in expression of the target gene when delivered at a concentration of about 3.25 µM. In some embodiments, the sdRNA sequences used in the invention exhibit a reduction in expression of the target gene when delivered at a concentration of about 3.5 µM. In some embodiments, the sdRNA sequences used in the invention exhibit a reduction in expression of the target gene when delivered at a concentration of about 3.75 µM. In some embodiments, the sdRNA sequences used in the invention exhibit a reduction in expression of the target gene when delivered at a concentration of about 4.0 µM.

In some embodiments, the oligonucleotide agents comprise one or more modification to increase stability and/or effectiveness of the therapeutic agent, and to effect efficient delivery of the oligonucleotide to the cells or tissue to be treated. Such modifications can include a 2'-O-methyl modification, a 2'-O-Fluoro modification, a diphosphorothioate modification, 2' F modified nucleotide, a 2'-O-methyl modified and/or a 2'-deoxy nucleotide. In some embodiments, the oligonucleotide is modified to include one or more hydrophobic modifications including, for example, sterol, cholesterol, vitamin D, naphtyl, isobutyl, benzyl, indol, tryptophane, and/or phenyl. In an additional particular embodiment, chemically modified nucleotides are combination of phosphorothioates, 2'-O-methyl, 2'-deoxy, hydrophobic modifications and phosphorothioates. In some embodiments, the sugars can be modified and modified sugars can include but are not limited to D-ribose, 2'-O-alkyl (including 2'-O-methyl and 2'-O-ethyl), i.e., 2'-alkoxy, 2'-amino, 2'-S-alkyl, 2'-halo (including 2'-fluoro), T-methoxyethoxy, 2'-allyloxy (—OCH$_2$CH=CH$_2$), 2'-propargyl, 2'-propyl, ethynyl, ethenyl, propenyl, and cyano and the like. In one embodiment, the sugar moiety can be a hexose and incorporated into an oligonucleotide as described (Augustyns, et al., Nucl. Acids. Res. 18:4711 (1992)).

In some embodiments, the double-stranded oligonucleotide of the invention is double-stranded over its entire length, i.e., with no overhanging single-stranded sequence at either end of the molecule, i.e., is blunt-ended. In some embodiments, the individual nucleic acid molecules can be of different lengths. In other words, a double-stranded oligonucleotide of the invention is not double-stranded over its entire length. For instance, when two separate nucleic acid molecules are used, one of the molecules, e.g., the first molecule comprising an antisense sequence, can be longer than the second molecule hybridizing thereto (leaving a portion of the molecule single-stranded). In some embodiments, when a single nucleic acid molecule is used a portion of the molecule at either end can remain single-stranded.

In some embodiments, a double-stranded oligonucleotide of the invention contains mismatches and/or loops or bulges, but is double-stranded over at least about 70% of the length of the oligonucleotide. In some embodiments, a double-stranded oligonucleotide of the invention is double-stranded over at least about 80% of the length of the oligonucleotide. In another embodiment, a double-stranded oligonucleotide of the invention is double-stranded over at least about 90%-95% of the length of the oligonucleotide. In some embodiments, a double-stranded oligonucleotide of the invention is double-stranded over at least about 96%-98% of the length of the oligonucleotide. In some embodiments, the double-stranded oligonucleotide of the invention contains at least or up to 1, 2, 3, 4, 5, 6, 7, 8, 9, 10, 11, 12, 13, 14, or 15 mismatches.

In some embodiments, the oligonucleotide can be substantially protected from nucleases e.g., by modifying the 3' or 5' linkages (e.g., U.S. Pat. No. 5,849,902 and WO 98/13526). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl (CH$_2$—CH$_2$—CH$_3$), glycol (—O—CH$_2$—CH$_2$—O—) phosphate (PO$_3^{2-}$), hydrogen phosphonate, or phosphoramidite). "Blocking groups" can also include "end blocking groups" or "exonuclease blocking groups" which protect the 5' and 3' termini of the oligonucleotide, including modified nucleotides and non-nucleotide exonuclease resistant structures.

In some embodiments, at least a portion of the contiguous polynucleotides within the sdRNA are linked by a substitute linkage, e.g., a phosphorothioate linkage.

In some embodiments, chemical modification can lead to at least a 1.5, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500 enhancements in cellular uptake. In some embodiments, at least one of the C or U residues includes a hydrophobic modification. In some embodiments, a plurality of Cs and Us contain a hydrophobic modification. In some embodiments, at least 10%, 15%, 20%, 30%, 40%, 50%, 55%, 60% 65%, 70%, 75%, 80%, 85%, 90% or at least 95% of the Cs and Us can contain a hydrophobic modification. In some embodiments, all of the Cs and Us contain a hydrophobic modification.

In some embodiments, the sdRNA or sd-rxRNAs exhibit enhanced endosomal release of sd-rxRNA molecules through the incorporation of protonatable amines. In some embodiments, protonatable amines are incorporated in the sense strand (in the part of the molecule which is discarded after RISC loading). In some embodiments, the sdRNA compounds of the invention comprise an asymmetric compound comprising a duplex region (required for efficient RISC entry of 10-15 bases long) and single stranded region of 4-12 nucleotides long; with a 13 nucleotide duplex. In some embodiments, a 6 nucleotide single stranded region is employed. In some embodiments, the single stranded region of the sdRNA comprises 2-12 phosphorothioate internucleotide linkages (referred to as phosphorothioate modifications). In some embodiments, 6-8 phosphorothioate internucleotide linkages are employed. In some embodiments, the sdRNA compounds of the invention also include a unique chemical modification pattern, which provides stability and is compatible with RISC entry.

The guide strand, for example, may also be modified by any chemical modification which confirms stability without interfering with RISC entry. In some embodiments, the chemical modification pattern in the guide strand includes the majority of C and U nucleotides being 2' F modified and the 5' end being phosphorylated.

In some embodiments, at least 30% of the nucleotides in the sdRNA or sd-rxRNA are modified. In some embodiments, at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the nucleotides in the sdRNA or sd-rxRNA are modified. In some embodiments, 100% of the nucleotides in the sdRNA or sd-rxRNA are modified.

In some embodiments, the sdRNA molecules have minimal double stranded regions. In some embodiments the region of the molecule that is double stranded ranges from 8-15 nucleotides long. In some embodiments, the region of the molecule that is double stranded is 8, 9, 10, 11, 12, 13, 14 or 15 nucleotides long. In some embodiments the double stranded region is 13 nucleotides long. There can be 100% complementarity between the guide and passenger strands, or there may be one or more mismatches between the guide and passenger strands. In some embodiments, on one end of the double stranded molecule, the molecule is either blunt-ended or has a one-nucleotide overhang. The single stranded region of the molecule is in some embodiments between 4-12 nucleotides long. In some embodiments, the single stranded region can be 4, 5, 6, 7, 8, 9, 10, 11 or 12 nucleotides long. In some embodiments, the single stranded region can also be less than 4 or greater than 12 nucleotides long. In certain embodiments, the single stranded region is 6 or 7 nucleotides long.

In some embodiments, the sdRNA molecules have increased stability. In some instances, a chemically modified sdRNA or sd-rxRNA molecule has a half-life in media that is longer than 1, 2, 3, 4, 5, 6, 7, 8, 9, 10, 11, 12, 13, 14, 15, 16, 17, 18, 19, 20, 21, 22, 23, 24 or more than 24 hours, including any intermediate values. In some embodiments, the sd-rxRNA has a half-life in media that is longer than 12 hours.

In some embodiments, the sdRNA is optimized for increased potency and/or reduced toxicity. In some embodiments, nucleotide length of the guide and/or passenger strand, and/or the number of phosphorothioate modifications in the guide and/or passenger strand, can in some aspects influence potency of the RNA molecule, while replacing 2'-fluoro (2'-F or 2'F) modifications with 2'-O-methyl (2'OMe) modifications can in some aspects influence toxicity of the molecule. In some embodiments, reduction in 2'F content of a molecule is predicted to reduce toxicity of the molecule. In some embodiments, the number of phosphorothioate modifications in an RNA molecule can influence the uptake of the molecule into a cell, for example the efficiency of passive uptake of the molecule into a cell. In some embodiments, the sdRNA has no 2'F modification and yet are characterized by equal efficacy in cellular uptake and tissue penetration.

In some embodiments, a guide strand is approximately 18-19 nucleotides in length and has approximately 2-14 phosphate modifications. For example, a guide strand can contain 2, 3, 4, 5, 6, 7, 8, 9, 10, 11, 12, 13, 14 or more than 14 nucleotides that are phosphate-modified. The guide strand may contain one or more modifications that confer increased stability without interfering with RISC entry. The phosphate modified nucleotides, such as phosphorothioate modified nucleotides, can be at the 3' end, 5' end or spread throughout the guide strand. In some embodiments, the 3' terminal 10 nucleotides of the guide strand contain 1, 2, 3, 4, 5, 6, 7, 8, 9 or 10 phosphorothioate modified nucleotides. The guide strand can also contain 2'F and/or 2'OMe modifications, which can be located throughout the molecule. In some embodiments, the nucleotide in position one of the guide strand (the nucleotide in the most 5' position of the guide strand) is 2'OMe modified and/or phosphorylated. C and U nucleotides within the guide strand can be 2'F modified. For example, C and U nucleotides in positions 2-10 of a 19 nt guide strand (or corresponding positions in a guide strand of a different length) can be 2'F modified. C and U nucleotides within the guide strand can also be 2'OMe modified. For example, C and U nucleotides in positions 11-18 of a 19 nt guide strand (or corresponding positions in a guide strand of a different length) can be 2'OMe modified. In some embodiments, the nucleotide at the most 3' end of the guide strand is unmodified. In certain embodiments, the majority of Cs and Us within the guide strand are 2'F modified and the 5' end of the guide strand is phosphorylated. In other embodiments, position 1 and the Cs or Us in positions 11-18 are 2'OMe modified and the 5' end of the guide strand is phosphorylated. In other embodiments, position 1 and the Cs or Us in positions 11-18 are 2'OMe modified, the 5' end of the guide strand is phosphorylated, and the Cs or Us in position 2-10 are 2'F modified.

The self-deliverable RNAi technology provides a method of directly transfecting cells with the RNAi agent, without the need for additional formulations or techniques. The ability to transfect hard-to-transfect cell lines, high in vivo activity, and simplicity of use, are characteristics of the compositions and methods that present significant functional advantages over traditional siRNA-based techniques, and as such, the sdRNA methods are employed in several embodiments related to the methods of reduction in expression of the target gene in the TILs of the present invention. The sdRNAi methods allows direct delivery of chemically synthesized compounds to a wide range of primary cells and tissues, both ex-vivo and in vivo. The sdRNAs described in some embodiments of the invention herein are commercially available from Advirna LLC, Worcester, MA, USA.

The sdRNA are formed as hydrophobically-modified siRNA-antisense oligonucleotide hybrid structures, and are disclosed, for example in Byrne et al., December 2013, J. Ocular Pharmacology and Therapeutics, 29(10): 855-864, incorporated by reference herein in its entirety.

In some embodiments, the sdRNA oligonucleotides can be delivered to the TILs described herein using sterile electroporation. In certain embodiments, the method comprises sterile electroporation of a population of TILs to deliver sdRNA oligonucleotides.

In some embodiments, the oligonucleotides can be delivered to the cells in combination with a transmembrane delivery system. In some embodiments, this transmembrane delivery system comprises lipids, viral vectors, and the like. In some embodiments, the oligonucleotide agent is a self-delivery RNAi agent, that does not require any delivery agents. In certain embodiments, the method comprises use of a transmembrane delivery system to deliver sdRNA oligonucleotides to a population of TILs.

Oligonucleotides and oligonucleotide compositions are contacted with (e.g., brought into contact with, also referred to herein as administered or delivered to) and taken up by TILs described herein, including through passive uptake by TILs. The sdRNA can be added to the TILs as described herein during the first expansion, for example Step B, after the first expansion, for example, during Step C, before or during the second expansion, for example before or during Step D, after Step D and before harvest in Step E, during or after harvest in Step F, before or during final formulation and/or transfer to infusion Bag in Step F, as well as before any optional cryopreservation step in Step F. Moreover, sdRNA can be added after thawing from any cryopreservation step in Step F. In an embodiment, one or more sdRNAs targeting genes as described herein, including PD-1, LAG-3, TIM-3, CISH, and CBLB, may be added to cell culture media comprising TILs and other agents at concentrations selected from the group consisting of 100 nM to 20 mM, 200 nM to 10 mM, 500 nm to 1 mM, 1 μM to 100 μM, and 1 μM to 100 μM. In an embodiment, one or more sdRNAs targeting genes as described herein, including PD-1, LAG-3, TIM-3, CISH, and CBLB, may be added to cell culture media comprising TILs and other agents at amounts selected from the group consisting of 0.1 μM sdRNA/10,000 TILs/100 μL media, 0.5 μM sdRNA/10,000 TILs/100 μL media, 0.75 μM sdRNA/10,000 TILs/100 μL media, 1 μM sdRNA/10,000 TILs/100 μL media, 1.25 μM sdRNA/10,000 TILs/100 μL media, 1.5 μM sdRNA/10,000 TILs/100 μL media, 2 μM sdRNA/10,000 TILs/100 μL media, 5 μM sdRNA/10,000 TILs/100 μL media, or 10 μM sdRNA/10,000 TILs/100 μL media. In an embodiment, one or more sdRNAs targeting genes as described herein, including PD-1, LAG-3, TIM-3, CISH, and CBLB, may be added to TIL cultures during the pre-REP or REP stages twice a day, once a day, every two days, every three days, every four days, every five days, every six days, or every seven days.

Oligonucleotide compositions of the invention, including sdRNA, can be contacted with TILs as described herein during the expansion process, for example by dissolving sdRNA at high concentrations in cell culture media and allowing sufficient time for passive uptake to occur. In certain embodiments, the method of the present invention comprises contacting a population of TILs with an oligonucleotide composition as described herein. In certain embodiments, the method comprises dissolving an oligonucleotide e.g. sdRNA in a cell culture media and contacting the cell culture media with a population of TILs. The TILs may be a first population, a second population and/or a third population as described herein.

In some embodiments, delivery of oligonucleotides into cells can be enhanced by suitable art recognized methods including calcium phosphate, DMSO, glycerol or dextran, electroporation, or by transfection, e.g., using cationic, anionic, or neutral lipid compositions or liposomes using methods known in the art (see, e.g., WO 90/14074; WO 91/16024; WO 91/17424; U.S. Pat. No. 4,897,355; Bergan et a 1993. Nucleic Acids Research. 21:3567).

In some embodiments, more than one sdRNA is used to reduce expression of a target gene. In some embodiments, one or more of PD-1, TIM-3, CBLB, LAG3 and/or CISH targeting sdRNAs are used together. In some embodiments, a PD-1 sdRNA is used with one or more of TIM-3, CBLB, LAG3 and/or CISH in order to reduce expression of more than one gene target. In some embodiments, a LAG3 sdRNA is used in combination with a CISH targeting sdRNA to reduce gene expression of both targets. In some embodiments, the sdRNAs targeting one or more of PD-1, TIM-3, CBLB, LAG3 and/or CISH herein are commercially available from Advirna LLC, Worcester, MA, USA.

In some embodiments, the sdRNA targets a gene selected from the group consisting of PD-1, LAG3, TIM3, CTLA-4, TIGIT, CISH, TGFβR2, PKA, CBLB, BAFF (BR3), and combinations thereof. In some embodiments, the sdRNA targets a gene selected from the group consisting of PD-1, LAG3, TIM3, CTLA-4, TIGIT, CISH, TGFβR2, PKA, CBLB, BAFF (BR3), and combinations thereof. In some embodiments, one sdRNA targets PD-1 and another sdRNA targets a gene selected from the group consisting of LAG3, TIM3, CTLA-4, TIGIT, CISH, TGFβR2, PKA, CBLB, BAFF (BR3), and combinations thereof. In some embodiments, the sdRNA targets a gene selected from PD-1, LAG-3, CISH, CBLB, TIM3, and combinations thereof. In some embodiments, the sdRNA targets a gene selected from PD-1 and one of LAG3, CISH, CBLB, TIM3, and combinations thereof. In some embodiments, one sdRNA targets PD-1 and one sdRNA targets LAG3. In some embodiments, one sdRNA targets PD-1 and one sdRNA targets CISH. In some embodiments, one sdRNA targets PD-1 and one sdRNA targets CBLB. In some embodiments, one sdRNA targets LAG3 and one sdRNA targets CISH. In some embodiments, one sdRNA targets LAG3 and one sdRNA targets CBLB. In some embodiments, one sdRNA targets CISH and one sdRNA targets CBLB. In some embodiments, one sdRNA targets TIM3 and one sdRNA targets PD-1. In some embodiments, one sdRNA targets TIM3 and one sdRNA targets LAG3. In some embodiments, one sdRNA targets TIM3 and one sdRNA targets CISH. In some embodiments, one sdRNA targets TIM3 and one sdRNA targets CBLB.

As discussed above, embodiments of the present invention provide tumor infiltrating lymphocytes (TILs) that have been genetically modified via gene-editing to enhance their therapeutic effect. Embodiments of the present invention embrace genetic editing through nucleotide insertion (RNA or DNA) into a population of TILs for both promotion of the expression of one or more proteins and inhibition of the expression of one or more proteins, as well as combinations thereof. Embodiments of the present invention also provide methods for expanding TILs into a therapeutic population, wherein the methods comprise gene-editing the TILs. There are several gene-editing technologies that may be used to genetically modify a population of TILs, which are suitable for use in accordance with the present invention.

In some embodiments, the method comprises a method of genetically modifying a population of TILs which include the step of stable incorporation of genes for production of one or more proteins. In an embodiment, a method of genetically modifying a population of TILs includes the step of retroviral transduction. In an embodiment, a method of genetically modifying a population of TILs includes the step of lentiviral transduction. Lentiviral transduction systems are known in the art and are described, e.g., in Levine, et al., *Proc. Nat'l Acad. Sci.* 2006, 103, 17372-77; Zufferey, et al., *Nat. Biotechnol.* 1997, 15, 871-75; Dull, et al., *J. Virology* 1998, 72, 8463-71, and U.S. Pat. No. 6,627,442, the disclosures of each of which are incorporated by reference herein. In an embodiment, a method of genetically modifying a population of TILs includes the step of gamma-retroviral transduction. Gamma-retroviral transduction systems are known in the art and are described, e.g., Cepko and Pear, *Cur. Prot. Mol. Biol.* 1996, 9.9.1-9.9.16, the disclosure of which is incorporated by reference herein. In an embodiment, a method of genetically modifying a population of TILs includes the step of transposon-mediated gene transfer. Transposon-mediated gene transfer systems are known in the art and include systems wherein the transposase is provided as DNA expression vector or as an expressible RNA or a protein such that long-term expression of the transposase does not occur in the transgenic cells, for example, a transposase provided as an mRNA (e.g., an mRNA comprising a cap and poly-A tail). Suitable transposon-mediated gene transfer systems, including the salmonid-type Tel-like transposase (SB or Sleeping Beauty transposase), such as SB10, SB11, and SB100×, and engineered enzymes with increased enzymatic activity, are described in, e.g., Hackett, et al., *Mol. Therapy* 2010, 18, 674-83 and U.S. Pat. No. 6,489,458, the disclosures of each of which are incorporated by reference herein.

In an embodiment, the method comprises a method of genetically modifying a population of TILs e.g. a first population, a second population and/or a third population as described herein. In an embodiment, a method of genetically modifying a population of TILs includes the step of stable incorporation of genes for production or inhibition (e.g., silencing) of one ore more proteins. In an embodiment, a method of genetically modifying a population of TILs includes the step of electroporation. Electroporation methods are known in the art and are described, e.g., in Tsong, *Biophys. J.* 1991, 60, 297-306, and U.S. Patent Application Publication No. 2014/0227237 A1, the disclosures of each of which are incorporated by reference herein. Other electroporation methods known in the art, such as those described in U.S. Pat. Nos. 5,019,034; 5,128,257; 5,137,817; 5,173,158; 5,232,856; 5,273,525; 5,304,120; 5,318,514; 6,010,613 and 6,078,490, the disclosures of which are incorporated by reference herein, may be used. In an embodiment, the electroporation method is a sterile electroporation method. In an embodiment, the electroporation method is a pulsed electroporation method. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein the sequence of at least three DC electrical pulses has one, two, or three of the following characteristics: (1) at least two of the at least three pulses differ from each other in pulse amplitude; (2) at least two of the at least three pulses differ from each other in pulse width; and (3) a first pulse interval for a first set of two of the at least three pulses is different from a second pulse interval for a second set of two of the at least three pulses. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein at least two of the at least three pulses differ from each other in pulse amplitude. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein at least two of the at least three pulses differ from each other in pulse width. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein a first pulse interval for a first set of two of the at least three pulses is different from a second pulse interval for a second set of two of the at least three pulses. In an embodiment, the electroporation method is a pulsed electroporation method comprising the steps of treating TILs with pulsed electrical fields to induce pore formation in the TILs, comprising the step of applying a sequence of at least three DC electrical pulses, having field strengths equal to or greater than 100 V/cm, to TILs, wherein the sequence of at least three DC electrical pulses has one, two, or three of the following characteristics: (1) at least two of the at least three pulses differ from each other in pulse amplitude; (2) at least two of the at least three pulses differ from each other in pulse width; and (3) a first pulse interval for a first set of two of the at least three pulses is different from a second pulse interval for a second set of two of the at least three pulses, such that induced pores are sustained for a relatively long period of time, and such that viability of the TILs is maintained. In an embodiment, a method of genetically modifying a population of TILs includes the step of calcium phosphate transfection. Calcium phosphate transfection methods (calcium phosphate DNA precipitation, cell surface coating, and endocytosis) are known in the art and are described in Graham and van der Eb, *Virology* 1973, 52, 456-467; Wigler, et al., *Proc. Natl. Acad. Sci.* 1979, 76, 1373-1376; and Chen and Okayarea, *Mol. Cell. Biol.* 1987, 7, 2745-2752; and in U.S. Pat. No. 5,593,875, the disclosures of each of which are incorporated by reference herein. In an embodiment, a method of genetically modifying a population of TILs includes the step of liposomal transfection. Liposomal transfection methods, such as methods that employ a 1:1 (w/w) liposome formulation of the cationic lipid N-[1-(2,3-dioleyloxy)propyl]-n,n,n-trimethylammonium chloride (DOTMA) and dioleoyl phophotidylethanolamine (DOPE) in filtered water, are known in the art and are described in Rose, et al., *Biotechniques* 1991, 10, 520-525 and Felgner, et al., *Proc. Natl. Acad. Sci. USA*, 1987, 84, 7413-7417 and in U.S. Pat. Nos. 5,279,833; 5,908,635; 6,056,938; 6,110,490; 6,534,484; and 7,687,070, the disclosures of each of which are incorporated by reference herein. In an embodiment, a method of genetically modifying a population of TTLs includes the step of transfection using methods described in U.S. Pat. Nos. 5,766,902; 6,025,337; 6,410,517; 6,475,994; and 7,189,705; the disclosures of each of which are incorporated by reference herein. The TILs may be a first population, a second population and/or a third population of TILs as described herein.

According to an embodiment, the gene-editing process may comprise the use of a programmable nuclease that mediates the generation of a double-strand or single-strand break at one or more immune checkpoint genes. Such programmable nucleases enable precise genome editing by introducing breaks at specific genomic loci, i.e., they rely on the recognition of a specific DNA sequence within the genome to target a nuclease domain to this location and mediate the generation of a double-strand break at the target sequence. A double-strand break in the DNA subsequently recruits endogenous repair machinery to the break site to mediate genome editing by either non-homologous end-joining (NHEJ) or homology-directed repair (HDR). Thus, the repair of the break can result in the introduction of insertion/deletion mutations that disrupt (e.g., silence, repress, or enhance) the target gene product.

Major classes of nucleases that have been developed to enable site-specific genomic editing include zinc finger nucleases (ZFNs), transcription activator-like nucleases (TALENs), and CRISPR-associated nucleases (e.g., CRISPR/Cas9). These nuclease systems can be broadly classified into two categories based on their mode of DNA recognition: ZFNs and TALENs achieve specific DNA binding via protein-DNA interactions, whereas CRISPR systems, such as Cas9, are targeted to specific DNA sequences by a short RNA guide molecule that base-pairs directly with the target DNA and by protein-DNA interactions. See, e.g., Cox et al., *Nature Medicine*, 2015, Vol. 21, No. 2.

Non-limiting examples of gene-editing methods that may be used in accordance with TIL expansion methods of the present invention include CRISPR methods, TALE methods, and ZFN methods, which are described in more detail below. According to an embodiment, a method for expanding TILs into a therapeutic population may be carried out in accordance with any embodiment of the methods described herein (e.g., GEN 3 process) or as described in PCT/US2017/058610, PCT/US2018/012605, or PCT/US2018/012633, wherein the method further comprises gene-editing at least a portion of the TILs by one or more of a CRISPR method, a TALE method or a ZFN method, in order to generate TILs that can provide an enhanced therapeutic effect. According to an embodiment, gene-edited TILs can be evaluated for an improved therapeutic effect by comparing them to non-modified TTLs in vitro, e.g., by evaluating in vitro effector function, cytokine profiles, etc. compared to unmodified TILs. In certain embodiments, the method comprises gene editing a population of TTLs using CRISPR, TALE and/or ZFN methods.

In some embodiments of the present invention, electroporation is used for delivery of a gene editing system, such as CRISPR, TALEN, and ZFN systems. In some embodiments of the present invention, the electroporation system is a flow electroporation system. An example of a suitable flow electroporation system suitable for use with some embodiments of the present invention is the commercially-available MaxCyte STX system. There are several alternative commercially-available electroporation instruments which may be suitable for use with the present invention, such as the AgilePulse system or ECM 830 available from BTX-Harvard Apparatus, Cellaxess Elektra (Cellectricon), Nucleofector (Lonza/Amaxa), GenePulser MXcell (BIORAD), iPorator-96 (Primax) or siPORTer96 (Ambion). In some embodiments of the present invention, the electroporation system forms a closed, sterile system with the remainder of the TIL expansion method. In some embodiments of the present invention, the electroporation system is a pulsed electroporation system as described herein, and forms a closed, sterile system with the remainder of the TIL expansion method.

A method for expanding TILs into a therapeutic population may be carried out in accordance with any embodiment of the methods described herein (e.g., process GEN 3) or as described in PCT/US2017/058610, PCT/US2018/012605, or PCT/US2018/012633, wherein the method further comprises gene-editing at least a portion of the TILs by a CRISPR method (e.g., CRISPR/Cas9 or CRISPR/Cpf1). According to particular embodiments, the use of a CRISPR method during the TIL expansion process causes expression of one or more immune checkpoint genes to be silenced or reduced in at least a portion of the therapeutic population of TILs. Alternatively, the use of a CRISPR method during the TIL expansion process causes expression of one or more immune checkpoint genes to be enhanced in at least a portion of the therapeutic population of TILs.

CRISPR stands for "Clustered Regularly Interspaced Short Palindromic Repeats." A method of using a CRISPR system for gene editing is also referred to herein as a CRISPR method. There are three types of CRISPR systems which incorporate RNAs and Cas proteins, and which may be used in accordance with the present invention: Types I, II, and III. The Type II CRISPR (exemplified by Cas9) is one of the most well-characterized systems.

CRISPR technology was adapted from the natural defense mechanisms of bacteria and archaea (the domain of single-celled microorganisms). These organisms use CRISPR-derived RNA and various Cas proteins, including Cas9, to foil attacks by viruses and other foreign bodies by chopping up and destroying the DNA of a foreign invader. A CRISPR is a specialized region of DNA with two distinct characteristics: the presence of nucleotide repeats and spacers. Repeated sequences of nucleotides are distributed throughout a CRISPR region with short segments of foreign DNA (spacers) interspersed among the repeated sequences. In the type II CRISPR/Cas system, spacers are integrated within the CRISPR genomic loci and transcribed and processed into short CRISPR RNA (crRNA). These crRNAs anneal to trans-activating crRNAs (tracrRNAs) and direct sequence-specific cleavage and silencing of pathogenic DNA by Cas proteins. Target recognition by the Cas9 protein requires a "seed" sequence within the crRNA and a conserved dinucleotide-containing protospacer adjacent motif (PAM) sequence upstream of the crRNA-binding region. The CRISPR/Cas system can thereby be retargeted to cleave virtually any DNA sequence by redesigning the crRNA. The crRNA and tracrRNA in the native system can be simplified into a single guide RNA (sgRNA) of approximately 100 nucleotides for use in genetic engineering. The CRISPR/Cas system is directly portable to human cells by co-delivery of plasmids expressing the Cas9 endo-nuclease and the necessary crRNA components. Different variants of Cas proteins may be used to reduce targeting limitations (e.g., orthologs of Cas9, such as Cpf1).

Non-limiting examples of genes that may be silenced or inhibited by permanently gene-editing TILs via a CRISPR method include PD-1, CTLA-4, LAG-3, HAVCR2 (TIM-3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

Non-limiting examples of genes that may be enhanced by permanently gene-editing TILs via a CRISPR method include CCR2, CCR4, CCR5, CXCR2, CXCR3, CX3CR1, IL-2, IL12, IL-15, and IL-21.

Examples of systems, methods, and compositions for altering the expression of a target gene sequence by a CRISPR method, and which may be used in accordance with embodiments of the present invention, are described in U.S. Pat. Nos. 8,697,359; 8,993,233; 8,795,965; 8,771,945; 8,889,356; 8,865,406; 8,999,641; 8,945,839; 8,932,814; 8,871,445; 8,906,616; and 8,895,308, which are incorporated by reference herein. Resources for carrying out CRISPR methods, such as plasmids for expressing CRISPR/Cas9 and CRISPR/Cpf1, are commercially available from companies such as GenScript.

In an embodiment, genetic modifications of populations of TILs, as described herein, may be performed using the CRISPR/Cpf1 system as described in U.S. Pat. No. 9,790,490, the disclosure of which is incorporated by reference herein.

A method for expanding TILs into a therapeutic population may be carried out in accordance with any embodiment of the methods described herein (e.g., process 2A, Gen 3 process) or as described in PCT/US2017/058610, PCT/US2018/012605, or PCT/US2018/012633, wherein the method further comprises gene-editing at least a portion of the TILs by a TALE method. According to particular embodiments, the use of a TALE method during the TIL expansion process causes expression of one or more immune checkpoint genes to be silenced or reduced in at least a portion of the therapeutic population of TILs. Alternatively, the use of a TALE method during the TIL expansion process causes expression of one or more immune checkpoint genes to be enhanced in at least a portion of the therapeutic population of TILs.

TALE stands for "Transcription Activator-Like Effector" proteins, which include TALENs ("Transcription Activator-Like Effector Nucleases"). A method of using a TALE system for gene editing may also be referred to herein as a TALE method. TALEs are naturally occurring proteins from the plant pathogenic bacteria genus *Xanthomonas*, and contain DNA-binding domains composed of a series of 33-35-amino-acid repeat domains that each recognizes a single base pair. TALE specificity is determined by two hypervariable amino acids that are known as the repeat-variable di-residues (RVDs). Modular TALE repeats are linked together to recognize contiguous DNA sequences. A specific RVD in the DNA-binding domain recognizes a base in the target locus, providing a structural feature to assemble predictable DNA-binding domains. The DNA binding domains of a TALE are fused to the catalytic domain of a type IIS FokI endonuclease to make a targetable TALE nuclease. To induce site-specific mutation, two individual TALEN arms, separated by a 14-20 base pair spacer region, bring FokI monomers in close proximity to dimerize and produce a targeted double-strand break.

Several large, systematic studies utilizing various assembly methods have indicated that TALE repeats can be combined to recognize virtually any user-defined sequence. Custom-designed TALE arrays are also commercially available through Cellectis Bioresearch (Paris, France), Transposagen Biopharmaceuticals (Lexington, KY, USA), and Life Technologies (Grand Island, NY, USA). TALE and TALEN methods suitable for use in the present invention are described in U.S. Patent Application Publication Nos. US 2011/0201118 A1; US 2013/0117869 A1; US 2013/0315884 A1; US 2015/0203871 A1 and US 2016/0120906 A1, the disclosures of which are incorporated by reference herein.

Non-limiting examples of genes that may be silenced or inhibited by permanently gene-editing TILs via a TALE method include PD-1, CTLA-4, LAG-3, HAVCR2 (TIM-3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

Non-limiting examples of genes that may be enhanced by permanently gene-editing TILs via a TALE method include CCR2, CCR4, CCR5, CXCR2, CXCR3, CX3CR1, IL-2, IL12, IL-15, and IL-21.

Examples of systems, methods, and compositions for altering the expression of a target gene sequence by a TALE method, and which may be used in accordance with embodiments of the present invention, are described in U.S. Pat. No. 8,586,526, which is incorporated by reference herein.

A method for expanding TILs into a therapeutic population may be carried out in accordance with any embodiment of the methods described herein (e.g., process GEN 3) or as described in PCT/US2017/058610, PCT/US2018/012605, or PCT/US2018/012633, wherein the method further comprises gene-editing at least a portion of the TILs by a zinc finger or zinc finger nuclease method. According to particular embodiments, the use of a zinc finger method during the TIL expansion process causes expression of one or more immune checkpoint genes to be silenced or reduced in at least a portion of the therapeutic population of TILs. Alternatively, the use of a zinc finger method during the TIL expansion process causes expression of one or more immune checkpoint genes to be enhanced in at least a portion of the therapeutic population of TILs.

An individual zinc finger contains approximately 30 amino acids in a conserved ββα configuration. Several amino acids on the surface of the α-helix typically contact 3 bp in the major groove of DNA, with varying levels of selectivity. Zinc fingers have two protein domains. The first domain is the DNA binding domain, which includes eukaryotic transcription factors and contain the zinc finger. The second domain is the nuclease domain, which includes the FokI restriction enzyme and is responsible for the catalytic cleavage of DNA.

The DNA-binding domains of individual ZFNs typically contain between three and six individual zinc finger repeats and can each recognize between 9 and 18 base pairs. If the zinc finger domains are specific for their intended target site then even a pair of 3-finger ZFNs that recognize a total of 18 base pairs can, in theory, target a single locus in a mammalian genome. One method to generate new zinc-finger arrays is to combine smaller zinc-finger "modules" of known specificity. The most common modular assembly process involves combining three separate zinc fingers that can each recognize a 3 base pair DNA sequence to generate a 3-finger array that can recognize a 9 base pair target site. Alternatively, selection-based approaches, such as oligomerized pool engineering (OPEN) can be used to select for new zinc-finger arrays from randomized libraries that take into consideration context-dependent interactions between neighboring fingers. Engineered zinc fingers are available commercially; Sangamo Biosciences (Richmond, CA, USA) has developed a propriety platform (CompoZr®) for zinc-finger construction in partnership with Sigma-Aldrich (St. Louis, MO, USA).

Non-limiting examples of genes that may be silenced or inhibited by permanently gene-editing TILs via a zinc finger method include PD-1, CTLA-4, LAG-3, HAVCR2 (TIM-3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

Non-limiting examples of genes that may be enhanced by permanently gene-editing TILs via a zinc finger method include CCR2, CCR4, CCR5, CXCR2, CXCR3, CX3CR1, IL-2, IL12, IL-15, and IL-21.

Examples of systems, methods, and compositions for altering the expression of a target gene sequence by a zinc finger method, which may be used in accordance with embodiments of the present invention, are described in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, which are incorporated by reference herein.

Other examples of systems, methods, and compositions for altering the expression of a target gene sequence by a zinc finger method, which may be used in accordance with embodiments of the present invention, are described in Beane, et al., *Mol. Therapy,* 2015, 23 1380-1390, the disclosure of which is incorporated by reference herein.

Closed Systems for TIL Manufacturing

The present invention provides for the use of closed systems during the TIL culturing process. Such closed systems allow for preventing and/or reducing microbial contamination, allow for the use of fewer flasks, and allow for cost reductions. In some embodiments, the closed system uses two containers.

Closed systems are known in the art and can be found, for example, at http.//www.fda.gov/cber/guidelines.htm and https.//www.fda.gov/BiologicsBloodVaccines/Guidance-ComplianceRegulatorylnformation/Guidances/Blood/ucm076779.htm.

Sterile connecting devices (STCDs) produce sterile welds between two pieces of compatible tubing. This procedure permits sterile connection of a variety of containers and tube diameters. In some embodiments, the closed systems include luer lock and heat sealed systems as described in for example, Example 4. In some embodiments, the closed system is accessed via syringes under sterile conditions in order to maintain the sterility and closed nature of the system. In some embodiments, a closed system as described in Example 6 is employed. In some embodiments, the TILs are formulated into a final product formulation container according to the method described in Example 4, section "Final Formulation and Fill".

In some embodiments, the closed system uses one container from the time the tumor fragments are obtained until the TILs are ready for administration to the patient or cryopreserving. In some embodiments when two containers are used, the first container is a closed G-container and the population of TILs is centrifuged and transferred to an infusion bag without opening the first closed G-container. In some embodiments, when two containers are used, the infusion bag is a HypoThermosol-containing infusion bag. A closed system or closed TIL cell culture system is characterized in that once the tumor sample and/or tumor fragments have been added, the system is tightly sealed from the outside to form a closed environment free from the invasion of bacteria, fungi, and/or any other microbial contamination.

In some embodiments, the reduction in microbial contamination is between about 5% and about 100%. In some embodiments, the reduction in microbial contamination is between about 5% and about 95%. In some embodiments, the reduction in microbial contamination is between about 5% and about 90%. In some embodiments, the reduction in microbial contamination is between about 10% and about 90%. In some embodiments, the reduction in microbial contamination is between about 15% and about 85%. In some embodiments, the reduction in microbial contamination is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 98%, about 99%, or about 100%.

The closed system allows for TIL growth in the absence and/or with a significant reduction in microbial contamination.

Moreover, pH, carbon dioxide partial pressure and oxygen partial pressure of the TIL cell culture environment each vary as the cells are cultured. Consequently, even though a medium appropriate for cell culture is circulated, the closed environment still needs to be constantly maintained as an optimal environment for TIL proliferation. To this end, it is desirable that the physical factors of pH, carbon dioxide partial pressure and oxygen partial pressure within the culture liquid of the closed environment be monitored by means of a sensor, the signal whereof is used to control a gas exchanger installed at the inlet of the culture environment, and the that gas partial pressure of the closed environment be adjusted in real time according to changes in the culture liquid so as to optimize the cell culture environment. In some embodiments, the present invention provides a closed cell culture system which incorporates at the inlet to the closed environment a gas exchanger equipped with a monitoring device which measures the pH, carbon dioxide partial pressure and oxygen partial pressure of the closed environment, and optimizes the cell culture environment by automatically adjusting gas concentrations based on signals from the monitoring device.

In some embodiments, the pressure within the closed environment is continuously or intermittently controlled. That is, the pressure in the closed environment can be varied by means of a pressure maintenance device for example, thus ensuring that the space is suitable for growth of TILs in a positive pressure state, or promoting exudation of fluid in a negative pressure state and thus promoting cell proliferation. By applying negative pressure intermittently, moreover, it is possible to uniformly and efficiently replace the circulating liquid in the closed environment by means of a temporary shrinkage in the volume of the closed environment.

In some embodiments, optimal culture components for proliferation of the TILs can be substituted or added, and including factors such as IL-2 and/or OKT3, as well as combination, can be added.

Optional Cryopreservation of TILs

As discussed above, and exemplified in Steps A through E as provided in FIG. 1, cryopreservation can occur at numerous points throughout the TIL expansion process, including at the final stage of the process after TIL harvesting for preservation of the therapeutic product. In some embodiments, the expanded population of TTLs after the second expansion (as provided for example, according to Step D of FIG. 1) can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See Sadeghi, et al., *Acta Oncologica*, 2013, 52, 978-986. In some embodiments, the TTLs are cryopreserved in 5% DMSO. In some embodiments, the TTLs are cryopreserved in cell culture media plus 5% DMSO. In some embodiments, the TTLs are cryopreserved according to the methods provided in Example 6.

Either the bulk TIL population (for example the second population of TILs) or the expanded population of TTLs (for example the third population of TILs) can be optionally cryopreserved. In some embodiments, cryopreservation occurs on the therapeutic TIL population. In some embodiments, cryopreservation occurs on the TTLs harvested after the second expansion. In some embodiments, cryopreservation occurs on the TTLs in exemplary Step F of FIG. 8 (in particular, e.g., FIG. 8B). In some embodiments, the TTLs are cryopreserved in the infusion bag. In some embodiments, the TILs are cryopreserved prior to placement in an infusion bag. In some embodiments, the TTLs are cryopreserved and not placed in an infusion bag. In some embodiments, cryopreservation is performed using a cryopreservation medium. In some embodiments, the cryopreservation media contains dimethylsulfoxide (DMSO). This is generally accomplished by putting the TIL population into a freezing solution, e.g. 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See Sadeghi, et al., *Acta Oncologica* 2013, 52, 978-986.

When appropriate, the cells are removed from the freezer and thawed in a 37° C. water bath until approximately ⅘ of the solution is thawed. The cells are generally resuspended in complete media and optionally washed one or more times. In some embodiments, the thawed TILs can be counted and assessed for viability as is known in the art.

Either the bulk TIL population or the expanded population of TILs can be optionally cryopreserved. In some embodiments, cryopreservation occurs on the therapeutic TIL population. In some embodiments, cryopreservation occurs on the TTLs harvested after the second expansion. In some embodiments, cryopreservation occurs on the TTLs in exemplary Step F of FIG. 1. In some embodiments, the TTLs are cryopreserved in the infusion bag. In some embodiments, the TTLs are cryopreserved prior to placement in an infusion bag. In some embodiments, the TTLs are cryopreserved and not placed in an infusion bag. In some embodiments, cryopreservation is performed using a cryopreservation medium. In some embodiments, the cryopreservation media contains dimethylsulfoxide (DMSO). This is generally accomplished by putting the TIL population into a freezing solution, e.g. 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See, Sadeghi, et al., *Acta Oncologica*, 2013, 52, 978-986.

When appropriate, the cells are removed from the freezer and thawed in a 37° C. water bath until approximately ⅘ of the solution is thawed. The cells are generally resuspended in complete media and optionally washed one or more times. In some embodiments, the thawed TTLs can be counted and assessed for viability as is known in the art.

In a preferred embodiment, a population of TILs is cryopreserved using CS10 cryopreservation media (CryoStor 10, BioLife Solutions). In a preferred embodiment, a population of TILs is cryopreserved using a cryopreservation media containing dimethylsulfoxide (DMSO). In a preferred embodiment, a population of TTLs is cryopreserved using a 1:1 (vol:vol) ratio of CS10 and cell culture media. In a preferred embodiment, a population of TILs is cryopreserved using about a 1:1 (vol:vol) ratio of CS10 and cell culture media, further comprising additional IL-2.

As discussed above in Steps A through E, cryopreservation can occur at numerous points throughout the TIL expansion process. In some embodiments, the bulk TIL population after the first expansion according to Step B or the expanded population of TTLs after the one or more second expansions according to Step D can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See Sadeghi, et al., *Acta Oncologica*, 2013, 52, 978-986.

When appropriate, the cells are removed from the freezer and thawed in a 37° C. water bath until approximately ⅘ of the solution is thawed. The cells are generally resuspended in complete media and optionally washed one or more times. In some embodiments, the thawed TILs can be counted and assessed for viability as is known in the art.

In some cases, the Step B TIL population can be cryopreserved immediately, using the protocols discussed below. Alternatively, the bulk TIL population can be subjected to Step C and Step D and then cryopreserved after Step D. Similarly, in the case where genetically modified TILs will be used in therapy, the Step B or Step D TIL populations can be subjected to genetic modifications for suitable treatments.

Phenotypic Characteristics of Expanded TILs

In some embodiments, the TILs are analyzed for expression of numerous phenotype markers after expansion, including those described herein and in the Examples. In an embodiment, expression of one or more phenotypic markers is examined. In some embodiments, the phenotypic characteristics of the TILs are analyzed after the first expansion in Step B, see, e.g. FIG. 1 and FIG. 8, particularly FIG. 8B. In some embodiments, the phenotypic characteristics of the TTLs are analyzed during the transition in Step C, see, e.g. FIG. 1 and FIG. 8, particularly FIG. 8B. In some embodiments, the phenotypic characteristics of the TILs are analyzed during the transition according to Step C and after cryopreservation. In some embodiments, the phenotypic characteristics of the TTLs are analyzed after the second expansion according to Step D, see, e.g. FIG. 1 and FIG. 8, particularly FIG. 8B. In some embodiments, the phenotypic characteristics of the TTLs are analyzed after two or more expansions according to Step D.

In some embodiments, the marker is selected from the group consisting of CD8 and CD28. In some embodiments, expression of CD8 is examined. In some embodiments, expression of CD28 is examined. In some embodiments, the expression of CD8 and/or CD28 is higher on TILs produced according the current invention process, as compared to other processes (e.g., the Gen 3 process as provided for example in FIG. 8 (in particular, e.g., FIG. 8B), as compared to the 2A process as provided for example in FIG. 1 and FIG. 8 (in particular, e.g., FIG. 8A)). In some embodiments, the expression of CD8 is higher on TILs produced according the current invention process, as compared to other processes (e.g., the Gen 3 process as provided for example in FIG. 8 (in particular, e.g., FIG. 8B), as compared to the 2A process as provided for example in FIG. 1 and FIG. 8 (in particular, e.g., FIG. 8A)). In some embodiments, the expression of CD28 is higher on TILs produced according the current invention process, as compared to other processes (e.g., the Gen 3 process as provided for example in FIG. 8 (in particular, e.g., FIG. 8B), as compared to the 2A process as provided for example in FIG. 1. In an embodiment, expression of one or more regulatory markers is measured.

In an embodiment, no selection of the first population of TILs, second population of TILs, third population of TILs, or harvested TIL population based on CD8 and/or CD28 expression is performed during any of the steps for the method for expanding tumor infiltrating lymphocytes (TILs) described herein.

In some embodiments, the percentage of central memory cells is higher on TILs produced according the current invention process, as compared to other processes (e.g., the Gen 3 process as provided for example in FIG. 8 (in particular, e.g., FIG. 8B), as compared to the 2A process as provided for example in FIG. 1 and in FIG. 8 (in particular, e.g., FIG. 8A)). In some embodiments the memory marker for central memory cells is selected from the group consisting of CCR7 and CD62L.

In an embodiment, restimulated TILs can also be evaluated for cytokine release, using cytokine release assays. In some embodiments, TILs can be evaluated for interferon-γ (IFN-γ) secretion. In some embodiments, the IFN-γ secretion is measured by an ELISA assay. In some embodiments, the IFN-γ secretion is measured by an ELISA assay after the rapid second expansion step, after Step D as provided in for example, FIG. 1 (in particular, e.g., FIG. 1). In some embodiments, TIL health is measured by IFN-gamma (IFN-γ) secretion. In some embodiments, IFN-γ secretion is indicative of active TILs. In some embodiments, a potency assay for IFN-γ production is employed. IFN-γ production is another measure of cytotoxic potential. IFN-γ production can be measured by determining the levels of the cytokine IFN-γ in the media of TIL stimulated with antibodies to CD3, CD28, and CD137/4-1BB. IFN-γ levels in media from these stimulated TIL can be determined using by measuring IFN-γ release. In some embodiments, an increase in IFN-γ production in for example Step D in the Gen 3 process as provided in FIG. 8 (in particular, e.g., FIG. 8B) TILs as compared to for example Step D in the 2A process as provided in FIG. 1 and FIG. 8 (in particular, e.g., FIG. 8A) is indicative of an increase in cytotoxic potential of the Step D TILs. In some embodiments, IFN-γ secretion is increased one-fold, two-fold, three-fold, four-fold, or five-fold or more. In some embodiments, IFN-γ secretion is increased one-fold. In some embodiments, IFN-γ secretion is increased two-fold. In some embodiments, IFN-γ secretion is increased three-fold. In some embodiments, IFN-γ secretion is increased four-fold. In some embodiments, IFN-γ secretion is increased five-fold. In some embodiments, IFN-γ is measured using a Quantikine ELISA kit. In some embodiments, IFN-γ is measured in TILs ex vivo. In some embodiments, IFN-γ is measured in TTLs ex vivo, including TTLs produced by the methods of the present invention, including, for example FIG. 8B methods.

Figure 12:
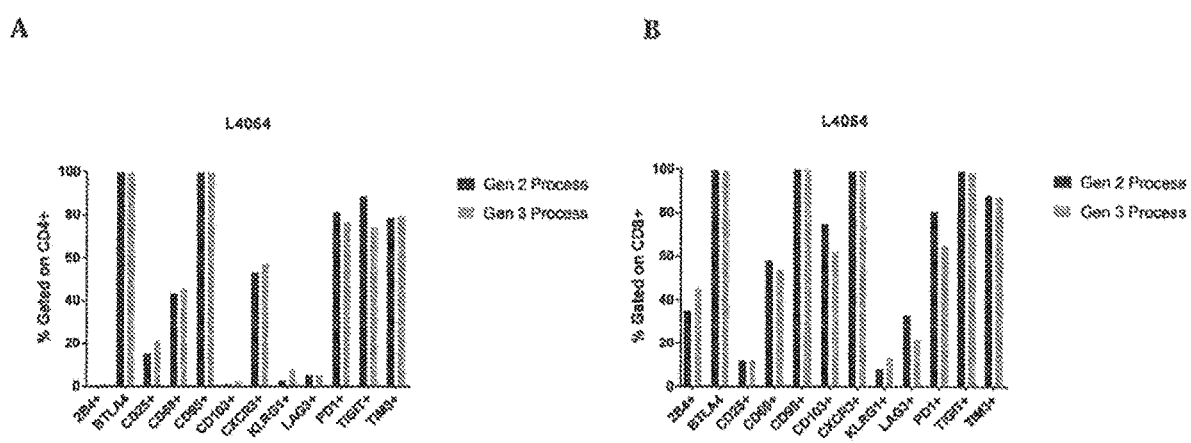
FIG. 12: L4054 Activation and exhaustion markers (A) Gated on CD4+, (B) Gated on CD8+.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TTLs obtained by the present method exhibit an increase in the T-cell repertoire diversity. In some embodiments, the TTLs obtained by the present method exhibit an increase in the T-cell repertoire diversity as compared to freshly harvested TTLs and/or TTLs prepared using other methods than those provide herein including, for example, methods other than those embodied in FIG. 8 (in particular, e.g., FIG. 8B). In some embodiments, the TTLs obtained by the present method exhibit an increase in the T-cell repertoire diversity as compared to freshly harvested TTLs and/or TTLs prepared using methods referred to as process 2A, as exemplified in FIG. 1 and FIG. 8 (in particular, e.g., FIG. 8A). In some embodiments, the TILs obtained in the first expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β). In some embodiments, the process as described herein (e.g., the Gen 3 process) shows higher clonal diversity as compared to other processes, for example the process referred to as the Gen 2 based on the number of unique peptide CDRs within the sample (see, for example FIGS. 12-14).

In some embodiments, the phenotypic characterization is examined after cryopreservation.

Additional Process Embodiments

In some embodiments, the invention provides a method for expanding tumor infiltrating lymphocytes (TILs) into a therapeutic population of TILs comprising: (a) obtaining a first population of TILs from a tumor resected from a subject by processing a tumor sample obtained from the subject into multiple tumor fragments; (b) performing a priming first expansion by culturing the first population of TILs in a cell culture medium comprising IL-2 and OKT-3, wherein the priming first expansion is performed for about 1 to 7 days to obtain the second population of TILs, wherein the second population of TTLs is greater in number than the first population of TILs; (c) performing a rapid second expansion by contacting the second population of TILs with a cell culture medium comprising IL-2, OKT-3 and exogenous antigen presenting cells (APCs) to produce a third population of TILs, wherein the rapid second expansion is performed for about 1 to 11 days to obtain the third population of TILs, wherein the third population of TTLs is a therapeutic population of TILs; and (d) harvesting the therapeutic population of TILs obtained from step (c). In some embodiments, the step of rapid second expansion is split into a plurality of steps to achieve a scaling up of the culture by: (1) performing the rapid second expansion by culturing the second population of TILs in a small scale culture in a first container, e.g., a G-REX 100MCS container, for a period of about 3 to 4 days, and then (2) effecting the transfer of the second population of TILs from the small scale culture to a second container larger than the first container, e.g., a G-REX 500MCS container, wherein in the second container the second population of TILs from the small scale culture is cultured in a larger scale culture for a period of about 4 to 7 days. In some embodiments, the step of rapid expansion is split into a plurality of steps to achieve a scaling out of the culture by: (1) performing the rapid second expansion by culturing the second population of TILs in a first small scale culture in a first container, e.g., a G-REX 100MCS container, for a period of about 3 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the second population of TILs from the first small scale culture transferred to such second container is cultured in a second small scale culture for a period of about 4 to 7 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100MCS container, for a period of about 3 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500MCS containers, wherein in each second container the portion of the second population of TILs transferred from the small scale culture to such second container is cultured in a larger scale culture for a period of about 4 to 7 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100MCS container, for a period of about 4 days, and then (2) effecting the transfer and apportioning of the second population of TILs from the first small scale culture into and amongst 2, 3 or 4 second containers that are larger in size than the first container, e.g., G-REX 500MCS containers, wherein in each second container the portion of the second population of TILs transferred from the small scale culture to such second container is cultured in a larger scale culture for a period of about 5 days.

In another embodiment, the invention provides the method described in any of the preceding paragraphs as applicable above modified such that in step (b) the primary first expansion is performed by contacting the first population of TILs with a culture medium which further comprises exogenous antigen-presenting cells (APCs), wherein the number of APCs in the culture medium in step (c) is greater than the number of APCs in the culture medium in step (b).

In another embodiment, the invention provides the method described in any of the preceding paragraphs as applicable above modified such that in step (c) the culture medium is supplemented with additional exogenous APCs.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 20:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 10:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 9:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 8:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 7:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 6:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 5:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 4:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 3:1.

In another embodiment, the invention provides the method described in any f the preceding paragraphs as applicable above modified such that the ratio of number of APCs added in the rapid second expansion to the number of APCs added in step (b) is selected from a range of from at or about 1.1:1 to at or about 2.9:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.8:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.7:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.6:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.5:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.4:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.3:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.2:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.1:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 10:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 5:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 4:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 3:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.9:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.8:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.7:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.6:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.5:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.4:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.3:1.

In another embodiment, the invention provides the method described in any of the preceding paragraph as applicable above modified such that the ratio of number of APCs added in the rapid second expansion to the number of APCs added in step (b) is selected from a range of from at or about 2:1 to at or about 2.2:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.1:1.

In another embodiment, the invention provides the method described in any of the preceding paragraphs as applicable above modified such that the ratio of number of APCs added in the rapid second expansion to the number of APCs added in step (b) is at or about 2:1.

In another embodiment, the invention provides the method described in any of the preceding paragraphs as applicable above modified such that the ratio of number of APCs added in the rapid second expansion to the number of APCs added in step (b) is at or about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, or 5:1.

In another embodiment, the invention provides the method described in any of the preceding paragraphs as applicable above modified such that the number of APCs added in the primary first expansion is at or about $1\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3\times10^8$, $3.1\times10^8$, $3.2\times10^8$, $3.3\times10^8$, $3.4\times10^8$ or $3.5\times10^8$ APCs, and such that the number of APCs added in the rapid second expansion is at or about $3.5\times10^8$, $3.6\times10^8$, $3.7\times10^8$, $3.8\times10^8$, $3.9\times10^8$, $4\times10^8$, $4.1\times10^8$, $4.2\times10^8$, $4.3\times10^8$, $4.4\times10^8$, $4.5\times10^8$, $4.6\times10^8$, $4.7\times10^8$, $4.8\times10^8$, $4.9\times10^8$, $5\times10^8$, $5.1\times10^8$, $5.2\times10^8$, $5.3\times10^8$, $5.4\times10^8$, $5.5\times10^8$, $5.6\times10^8$, $5.7\times10^8$, $5.8\times10^8$, $5.9\times10^8$, $6\times10^8$, $6.1\times10^8$, $6.2\times10^8$, $6.3\times10^8$, $6.4\times10^8$, $6.5\times10^8$, $6.6\times10^8$, $6.7\times10^8$, $6.8\times10^8$, $6.9\times10^8$, $7\times10^8$, $7.1\times10^8$, $7.2\times10^8$, $7.3\times10^8$, $7.4\times10^8$, $7.5\times10^8$, $7.6\times10^8$, $7.7\times10^8$, $7.8\times10^8$, $7.9\times10^8$, $8\times10^8$, $8.1\times10^8$, $8.2\times10^8$, $8.3\times10^8$, $8.4\times10^8$, $8.5\times10^8$, $8.6\times10^8$, $8.7\times10^8$, $8.8\times10^8$, $8.9\times10^8$, $9\times10^8$, $9.1\times10^8$, $9.2\times10^8$, $9.3\times10^8$, $9.4\times10^8$, $9.5\times10^8$, $9.6\times10^8$, $9.7\times10^8$, $9.8\times10^8$, $9.9\times10^8$ or $1\times10^9$ APCs.

In another embodiment, the invention provides the method described in any of the preceding paragraphs as applicable above modified such that the number of APCs added in the primary first expansion is selected from the range of at or about $1\times10^8$ APCs to at or about $3.5\times10^8$ APCs, and wherein the number of APCs added in the rapid second expansion is selected from the range of at or about $3.5\times10^8$ APCs to at or about $1\times10^9$ APCs.

In another embodiment, the invention provides the method described in any of the preceding paragraphs as applicable above modified such that the number of APCs added in the primary first expansion is selected from the range of at or about $1.5\times10^8$ APCs to at or about $3\times10^8$ APCs, and wherein the number of APCs added in the rapid second expansion is selected from the range of at or about $4\times10^8$ APCs to at or about $7.5\times10^8$ APCs.

In another embodiment, the invention provides the method described in any of the preceding paragraphs as applicable above modified such that the number of APCs added in the primary first expansion is selected from the range of at or about $2\times10^8$ APCs to at or about $2.5\times10^8$ APCs, and wherein the number of APCs added in the rapid second expansion is selected from the range of at or about $4.5\times10^8$ APCs to at or about $5.5\times10^8$ APCs.

In another embodiment, the invention provides the method described in any of the preceding paragraphs as applicable above modified such that at or about $2.5\times10^8$ APCs are added to the primary first expansion and at or about $5\times10^8$ APCs are added to the rapid second expansion.

In another embodiment, the invention provides the method described in any of the preceding paragraphs as applicable above modified such that the antigen-presenting cells are peripheral blood mononuclear cells (PBMCs).

In another embodiment, the invention provides the method described in any of the preceding paragraphs as applicable above modified such that the multiple tumor fragments are distributed into a plurality of separate containers, in each of which separate containers the first population of TILs is obtained in step (a), the second population of TILs is obtained in step (b), and the third population of TILs is obtained in step (c), and the therapeutic populations of TILs from the plurality of containers in step (c) are combined to yield the harvested TIL population from step (d).

In another embodiment, the invention provides the method described in any of the preceding paragraphs as applicable above modified such that the multiple tumors are evenly distributed into the plurality of separate containers.

In another embodiment, the invention provides the method described in any of the preceding paragraphs as applicable above modified such that the plurality of separate containers comprises at least two separate containers.

In another embodiment, the invention provides the method described in any of the preceding paragraphs as applicable above modified such that the plurality of separate containers comprises from two to twenty separate containers.

In another embodiment, the invention provides the method described in any of the preceding paragraphs as applicable above modified such that the plurality of separate containers comprises from two to fifteen separate containers.

In another embodiment, the invention provides the method described in any of the preceding paragraphs as applicable above modified such that the plurality of separate containers comprises from two to ten separate containers.

In another embodiment, the invention provides the method described in any of the preceding paragraphs as applicable above modified such that the plurality of separate containers comprises from two to five separate containers.

In another embodiment, the invention provides the method described in any of the preceding paragraphs as applicable above modified such that the plurality of separate containers comprises 2, 3, 4, 5, 6, 7, 8, 9, 10, 11, 12, 13, 14, 15, 16, 17, 18, 19, or 20 separate containers.

In another embodiment, the invention provides the method described in any of the preceding paragraphs as applicable above modified such that for each container in which the priming first expansion is performed on a first population of TILs in step (b) the rapid second expansion in step (c) is performed in the same container on the second population of TILs produced from such first population of TTLs.

In another embodiment, the invention provides the method described in any of the preceding paragraphs as applicable above modified such that each of the separate containers comprises a first gas-permeable surface area.

In another embodiment, the invention provides the method described in any of the preceding paragraphs as applicable above modified such that the multiple tumor fragments are distributed in a single container.

In another embodiment, the invention provides the method described in any of the preceding paragraphs as applicable above modified such that the single container comprises a first gas-permeable surface area.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein in step (b) the APCs are layered onto the first gas-permeable surface area at an average thickness of at or about one cell layer to at or about three cell layers.

In another embodiment, the invention provides the method described in any of the preceding paragraphs as applicable above modified such that in step (b) the APCs are layered onto the first gas-permeable surface area at an average thickness of at or about 1.5 cell layers to at or about 2.5 cell layers.

In another embodiment, the invention provides the method described in any of the preceding paragraphs as applicable above modified such that in step (b) the APCs are layered onto the first gas-permeable surface area at an average thickness of at or about 2 cell layers.

In another embodiment, the invention provides the method described in any of the preceding paragraphs as applicable above modified such that in step (b) the APCs are layered onto the first gas-permeable surface area at an average thickness of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers.

In another embodiment, the invention provides the method described in any of the preceding paragraphs as applicable above modified such that in step (c) the APCs are layered onto the first gas-permeable surface area at an average thickness of at or about 3 cell layers to at or about 10 cell layers.

In another embodiment, the invention provides the method described in any of the preceding paragraphs as applicable above modified such that in step (c) the APCs are layered onto the first gas-permeable surface area at an average thickness of at or about 4 cell layers to at or about 8 cell layers.

In another embodiment, the invention provides the method described in any of the preceding paragraphs as applicable above modified such that in step (c) the APCs are layered onto the first gas-permeable surface area at an average thickness of at or about 3, 4, 5, 6, 7, 8, 9 or 10 cell layers.

In another embodiment, the invention provides the method described in any of the preceding paragraphs as applicable above modified such that in step (c) the APCs are layered onto the first gas-permeable surface area at an average thickness of at or about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In another embodiment, the invention provides the method described in any of the preceding paragraphs as applicable above modified such that in step (b) the priming first expansion is performed in a first container comprising a first gas-permeable surface area and in step (c) the rapid second expansion is performed in a second container comprising a second gas-permeable surface area.

In another embodiment, the invention provides the method described in any of the preceding paragraphs as applicable above modified such that the second container is larger than the first container.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein in step (b) the APCs are layered onto the first gas-permeable surface area at an average thickness of at or about one cell layer to at or about three cell layers.

In another embodiment, the invention provides the method described in any of the preceding paragraphs as applicable above modified such that in step (b) the APCs are layered onto the first gas-permeable surface area at an average thickness of at or about 1.5 cell layers to at or about 2.5 cell layers.

In another embodiment, the invention provides the method described in any of the preceding paragraphs as applicable above modified such that in step (b) the APCs are layered onto the first gas-permeable surface area at an average thickness of at or about 2 cell layers.

In another embodiment, the invention provides the method described in any of the preceding paragraphs as applicable modified such that in step (b) the APCs are layered onto the first gas-permeable surface area at an average thickness of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers.

In another embodiment, the invention provides the method described in any of the preceding paragraphs as applicable above modified such that in step (c) the APCs are layered onto the second gas-permeable surface area at an average thickness of at or about 3 cell layers to at or about 10 cell layers.

In another embodiment, the invention provides the method described in any of the preceding paragraphs as applicable above modified such that in step (c) the APCs are layered onto the second gas-permeable surface area at an average thickness of at or about 4 cell layers to at or about 8 cell layers.

In another embodiment, the invention provides the method described in any of the preceding paragraphs as applicable above modified such that in step (c) the APCs are layered onto the second gas-permeable surface area at an average thickness of at or about 3, 4, 5, 6, 7, 8, 9 or 10 cell layers.

In another embodiment, the invention provides the method described in any of the preceding paragraphs as applicable above modified such that in step (c) the APCs are layered onto the second gas-permeable surface area at an average thickness of at or about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In another embodiment, the invention provides the method described in any of the preceding paragraphs as applicable above modified such that in step (b) the priming first expansion is performed in a first container comprising a first gas-permeable surface area and in step (c) the rapid second expansion is performed in the first container.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein in step (b) the APCs are layered onto the first gas-permeable surface area at an average thickness of at or about one cell layer to at or about three cell layers.

In another embodiment, the invention provides the method described in any of the preceding paragraphs as applicable above modified such that in step (b) the APCs are layered onto the first gas-permeable surface area at an average thickness of at or about 1.5 cell layers to at or about 2.5 cell layers.

In another embodiment, the invention provides the method described in any of the preceding paragraphs as applicable above modified such that in step (b) the APCs are layered onto the first gas-permeable surface area at an average thickness of at or about 2 cell layers.

In another embodiment, the invention provides the method described in any of the preceding paragraphs as applicable above modified such that in step (b) the APCs are layered onto the first gas-permeable surface area at an average thickness of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers.

In another embodiment, the invention provides the method described in any of the preceding paragraphs as applicable above modified such that in step (c) the APCs are layered onto the first gas-permeable surface area at an average thickness of at or about 3 cell layers to at or about 10 cell layers.

In another embodiment, the invention provides the method described in any of the preceding paragraphs as applicable above modified such that in step (c) the APCs are layered onto the first gas-permeable surface area at an average thickness of at or about 4 cell layers to at or about 8 cell layers.

In another embodiment, the invention provides the method described in any of the preceding paragraphs as applicable above modified such that in step (c) the APCs are layered onto the first gas-permeable surface area at an average thickness of at or about 3, 4, 5, 6, 7, 8, 9 or 10 cell layers.

In another embodiment, the invention provides the method described in any of the preceding paragraphs as applicable above modified such that in step (c) the APCs are layered onto the first gas-permeable surface area at an average thickness of at or about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:10.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:9.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:8.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:7.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:6.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:5.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:4.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:3.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:2.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.2 to at or about 1:8.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.3 to at or about 1:7.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.4 to at or about 1:6.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.5 to at or about 1:5.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.6 to at or about 1:4.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.7 to at or about 1:3.5.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.8 to at or about 1:3.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.9 to at or about 1:2.5.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:2.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from at or about 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9, 1:6, 1:6.1, 1:6.2, 1:6.3, 1:6.4, 1:6.5, 1:6.6, 1:6.7, 1:6.8, 1:6.9, 1:7, 1:7.1, 1:7.2, 1:7.3, 1:7.4, 1:7.5, 1:7.6, 1:7.7, 1:7.8, 1:7.9, 1:8, 1:8.1, 1:8.2, 1:8.3, 1:8.4, 1:8.5, 1:8.6, 1:8.7, 1:8.8, 1:8.9, 1:9, 1:9.1, 1:9.2, 1:9.3, 1:9.4, 1:9.5, 1:9.6, 1:9.7, 1:9.8, 1:9.9 or 1:10.

In another embodiment, the invention provides the method described in any of the preceding paragraphs as applicable above modified such that the ratio of the number of TILs in the second population of TILs to the number of TILs in the first population of TILs is at or about 1.5:1 to at or about 100:1.

In another embodiment, the invention provides the method described in any of the preceding paragraphs as applicable above modified such that the ratio of the number of TILs in the second population of TILs to the number of TILs in the first population of TILs is at or about 50:1.

In another embodiment, the invention provides the method described in any of the preceding paragraphs as applicable above modified such that the ratio of the number of TILs in the second population of TILs to the number of TILs in the first population of TILs is at or about 25:1.

In another embodiment, the invention provides the method described in any of the preceding paragraphs as applicable above modified such that the ratio of the number of TILs in the second population of TILs to the number of TILs in the first population of TILs is at or about 20:1.

In another embodiment, the invention provides the method described in any of the preceding paragraphs as applicable above modified such that the ratio of the number of TILs in the second population of TILs to the number of TILs in the first population of TILs is at or about 10:1.

In another embodiment, the invention provides the method described in any of the preceding paragraphs as applicable above modified such that the second population of TILs is at least at or about 50-fold greater in number than the first population of TILs.

In another embodiment, the invention provides the method described in any of the preceding paragraphs as applicable above modified such that the second population of TILs is at least at or about 1-, 2-, 3-, 4-, 5-, 6-, 7-, 8-, 9-, 10-, 11-, 12-, 13-, 14-, 15-, 16-, 17-, 18-, 19-, 20-, 21-, 22-, 23-, 24-, 25-, 26-, 27-, 28-, 29-, 30-, 31-, 32-, 33-, 34-, 35-, 36-, 37-, 38-, 39-, 40-, 41-, 42-, 43-, 44-, 45-, 46-, 47-, 48-, 49- or 50-fold greater in number than the first population of TTLs.

In another embodiment, the invention provides the method described in any of the preceding paragraphs as applicable above modified such that at or about 2 days or at or about 3 days after the commencement of the second period in step (c), the cell culture medium is supplemented with additional IL-2.

In another embodiment, the invention provides the method described in any of the preceding paragraphs as applicable above modified to further comprise the step of cryopreserving the harvested TIL population in step (d) using a cryopreservation process.

In another embodiment, the invention provides the method described in any of the preceding paragraphs as applicable above modified to comprise performing after step (d) the additional step of (e) transferring the harvested TIL population from step (d) to an infusion bag that optionally contains HypoThermosol.

In another embodiment, the invention provides the method described in any of the preceding paragraphs as applicable above modified to comprise the step of cryopreserving the infusion bag comprising the harvested TIL population in step (e) using a cryopreservation process.

In another embodiment, the invention provides the method described in any of the preceding paragraphs as applicable above modified such that the cryopreservation process is performed using a 1:1 ratio of harvested TIL population to cryopreservation media.

In another embodiment, the invention provides the method described in any of the preceding paragraphs as applicable above modified such that the antigen-presenting cells are peripheral blood mononuclear cells (PBMCs).

In another embodiment, the invention provides the method described in any of the preceding paragraphs as applicable above modified such that the PBMCs are irradiated and allogeneic.

In another embodiment, the invention provides the method described in any of the preceding paragraphs as applicable above modified such that the total number of APCs added to the cell culture in step (b) is $2.5 \times 10^8$.

In another embodiment, the invention provides the method described in any of the preceding paragraphs as applicable above modified such that the total number of APCs added to the cell culture in step (c) is $5 \times 10^8$.

In another embodiment, the invention provides the method described in any of the preceding paragraphs as applicable above modified such that the APCs are PBMCs.

In another embodiment, the invention provides the method described in any of the preceding paragraphs as applicable above modified such that the PBMCs are irradiated and allogeneic.

In another embodiment, the invention provides the method described in any of the preceding paragraphs as applicable above modified such that the antigen-presenting cells are artificial antigen-presenting cells.

In another embodiment, the invention provides the method described in any of the preceding paragraphs as applicable above modified such that the harvesting in step (d) is performed using a membrane-based cell processing system.

In another embodiment, the invention provides the method described in any of the preceding paragraphs as applicable above modified such that the harvesting in step (d) is performed using a LOVO cell processing system.

In another embodiment, the invention provides the method described in any of the preceding paragraphs as applicable above modified such that the multiple fragments comprise at or about 5 to at or about 60 fragments per container in step (b).

In another embodiment, the invention provides the method described in any of the preceding paragraphs as applicable above modified such that the multiple fragments comprise at or about 10 to at or about 60 fragments per container in step (b).

In another embodiment, the invention provides the method described in any of the preceding paragraphs as applicable above modified such that the multiple fragments comprise at or about 15 to at or about 60 fragments per container in step (b).

In another embodiment, the invention provides the method described in any of the preceding paragraphs as applicable above modified such that the multiple fragments comprise at or about 20 to at or about 60 fragments per container in step (b).

In another embodiment, the invention provides the method described in any of the preceding paragraphs as applicable above modified such that the multiple fragments comprise at or about 25 to at or about 60 fragments per container in step (b).

In another embodiment, the invention provides the method described in any of the preceding paragraphs as applicable above modified such that the multiple fragments comprise at or about 30 to at or about 60 fragments per container in step (b).

In another embodiment, the invention provides the method described in any of the preceding paragraphs as applicable above modified such that the multiple fragments comprise at or about 35 to at or about 60 fragments per container in step (b).

In another embodiment, the invention provides the method described in any of the preceding paragraphs as applicable above modified such that the multiple fragments comprise at or about 40 to at or about 60 fragments per container in step (b).

In another embodiment, the invention provides the method described in any of the preceding paragraphs as applicable above modified such that the multiple fragments comprise at or about 45 to at or about 60 fragments per container in step (b).

In another embodiment, the invention provides the method described in any of the preceding paragraphs as applicable above modified such that the multiple fragments comprise at or about 50 to at or about 60 fragments per container in step (b).

In another embodiment, the invention provides the method described in any of the preceding paragraphs as applicable above modified such that the multiple fragments comprise at or about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 fragment(s) per container in step (b).

In another embodiment, the invention provides the method described in any of the preceding paragraphs as applicable above modified such that each fragment has a volume of at or about 27 $mm^3$.

In another embodiment, the invention provides the method described in any of the preceding paragraphs as applicable above modified such that each fragment has a volume of at or about 20 $mm^3$ to at or about 50 $mm^3$.

In another embodiment, the invention provides the method described in any of the preceding paragraphs as applicable above modified such that each fragment has a volume of at or about 21 $mm^3$ to at or about 30 $mm^3$.

In another embodiment, the invention provides the method described in any of the preceding paragraphs as applicable above modified such that each fragment has a volume of at or about 22 $mm^3$ to at or about 29.5 $mm^3$.

In another embodiment, the invention provides the method described in any of the preceding paragraphs as applicable above modified such that each fragment has a volume of at or about 23 $mm^3$ to at or about 29 $mm^3$.

In another embodiment, the invention provides the method described in any of the preceding paragraphs as applicable above modified such that each fragment has a volume of at or about 24 $mm^3$ to at or about 28.5 $mm^3$.

In another embodiment, the invention provides the method described in any of the preceding paragraphs as applicable above modified such that each fragment has a volume of at or about 25 $mm^3$ to at or about 28 $mm^3$.

In another embodiment, the invention provides the method described in any of the preceding paragraphs as applicable above modified such that each fragment has a volume of at or about 26.5 $mm^3$ to at or about 27.5 $mm^3$.

In another embodiment, the invention provides the method described in any of the preceding paragraphs as applicable above modified such that each fragment has a volume of at or about 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 $mm^3$.

In another embodiment, the invention provides the method described in any of the preceding paragraphs as applicable above modified such that the multiple fragments comprise at or about 30 to at or about 60 fragments with a total volume of at or about 1300 $mm^3$ to at or about 1500 $mm^3$.

In another embodiment, the invention provides the method described in any of the preceding paragraphs as applicable above modified such that the multiple fragments comprise at or about 50 fragments with a total volume of at or about 1350 $mm^3$.

In another embodiment, the invention provides the method described in any of the preceding paragraphs as applicable above modified such that the multiple fragments comprise at or about 50 fragments with a total mass of at or about 1 gram to at or about 1.5 grams.

In another embodiment, the invention provides the method described in any of the preceding paragraphs as applicable above modified such that the cell culture medium is provided in a container that is a G-container or a Xuri cellbag.

In another embodiment, the invention provides the method described in any of the preceding paragraphs as applicable above modified such that the IL-2 concentration in the cell culture medium is about 10,000 IU/mL to about 5,000 IU/mL.

In another embodiment, the invention provides the method described in any of the preceding paragraphs as applicable above modified such that the IL-2 concentration in the cell culture medium is about 6,000 IU/mL.

In another embodiment, the invention provides the method described in any of the preceding paragraphs as applicable above modified such that the cryopreservation media comprises dimethylsulfoxide (DMSO).

In another embodiment, the invention provides the method described in any of the preceding paragraphs as applicable above modified such that the cryopreservation media comprises 7% to 10% DMSO.

In another embodiment, the invention provides the method described in any of the preceding paragraphs as applicable above modified such that the first period in step (b) is performed within a period of at or about 1 day, 2 days, 3 days, 4 days, 5 days, 6 days, or 7 days.

In another embodiment, the invention provides the method described in any of the preceding paragraphs as applicable above modified such that the second period in step (c) is performed within a period of at or about 1 day, 2 days, 3 days, 4 days, 5 days, 6 days, 7 days, 8 days, 9 days, 10 days or 11 days.

In another embodiment, the invention provides the method described in any of the preceding paragraphs as applicable above modified such that the first period in step (b) and the second period in step (c) are each individually performed within a period of at or about 1 day, 2 days, 3 days, 4 days, 5 days, 6 days, or 7 days.

In another embodiment, the invention provides the method described in any of the preceding paragraphs as applicable above modified such that the first period in step (b) and the second period in step (c) are each individually performed within a period of at or about 5 days, 6 days, or 7 days.

In another embodiment, the invention provides the method described in any of the preceding paragraphs as applicable above modified such that the first period in step (b) and the second period in step (c) are each individually performed within a period of at or about 7 days.

In another embodiment, the invention provides the method described in any of the preceding paragraphs as applicable above modified such that steps (a) through (d) are performed in a total of at or about 14 days to at or about 18 days.

In another embodiment, the invention provides the method described in any of the preceding paragraphs as applicable above modified such that steps (a) through (d) are performed in a total of at or about 15 days to at or about 18 days.

In another embodiment, the invention provides the method described in any of the preceding paragraphs as applicable above modified such that steps (a) through (d) are performed in a total of at or about 14 days.

In another embodiment, the invention provides the method described in any of the preceding paragraphs as applicable above modified such that steps (a) through (d) are performed in a total of at or about 15 days.

In another embodiment, the invention provides the method described in any of the preceding paragraphs as applicable above modified such that steps (a) through (d) are performed in a total of at or about 16 days.

In another embodiment, the invention provides the method described in any of the preceding paragraphs as applicable above modified such that steps (a) through (d) are performed in a total of at or about 17 days.

In another embodiment, the invention provides the method described in any of the preceding paragraphs as applicable above modified such that steps (a) through (d) are performed in a total of at or about 18 days.

In another embodiment, the invention provides the method described in any of the preceding paragraphs as applicable above modified such that steps (a) through (d) are performed in a total of at or about 16 days or less.

In another embodiment, the invention provides the method described in any of the preceding paragraphs as applicable above modified such that steps (a) through (d) are performed in a total of at or about 18 days or less.

In another embodiment, the invention provides the method described in any of the preceding paragraphs as applicable above modified such that the therapeutic population of TILs harvested in step (d) comprises sufficient TILs for a therapeutically effective dosage of the TILs.

In another embodiment, the invention provides the method described in any of the preceding paragraphs as applicable above modified such that the number of TILs sufficient for a therapeutically effective dosage is from at or about $2.3 \times 10^{10}$ to at or about $13.7 \times 10^{10}$.

In another embodiment, the invention provides the method described in any of the preceding paragraphs as applicable above modified such that the third population of TILs in step (c) provides for increased efficacy, increased interferon-gamma production, and/or increased polyclonality.

In another embodiment, the invention provides the method described in any of the preceding paragraphs as applicable above modified such that the third population of TILs in step (c) provides for at least a one-fold to five-fold or more interferon-gamma production as compared to TILs prepared by a process longer than 16 days.

In another embodiment, the invention provides the method described in any of the preceding paragraphs as applicable above modified such that the effector T cells and/or central memory T cells obtained from the third population of TILs step (c) exhibit increased CD8 and CD28 expression relative to effector T cells and/or central memory T cells obtained from the second population of cells step (b).

In another embodiment, the invention provides the method described in any of the preceding paragraphs as applicable above modified such that each container recited in the method is a closed container.

In another embodiment, the invention provides the method described in any of the preceding paragraphs as applicable above modified such that each container recited in the method is a G-container.

In another embodiment, the invention provides the method described in any of the preceding paragraphs as applicable above modified such that each container recited in the method is a GREX-10.

In another embodiment, the invention provides the method described in any of the preceding paragraphs as applicable above modified such that each container recited in the method is a GREX-100.

In another embodiment, the invention provides the method described in any of the preceding paragraphs as applicable above modified such that each container recited in the method is a GREX-500.

In another embodiment, the invention provides the therapeutic population of tumor infiltrating lymphocytes (TILs) made by the method described in any of the preceding paragraphs as applicable above.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed without any added antigen-presenting cells (APCs) or OKT3.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed without any added antigen-presenting cells (APCs).

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed without any added OKT3.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed with no added antigen-presenting cells (APCs) and no added OKT3.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process by a process longer than 16 days.

In another embodiment, the invention provides for the therapeutic population of TILs described in any of the preceding paragraphs as applicable above that provides for increased interferon-gamma production.

In another embodiment, the invention provides for the therapeutic population of TILs described in any of the preceding paragraphs as applicable above that provides for increased polyclonality.

In another embodiment, the invention provides for the therapeutic population of TILs described in any of the preceding paragraphs as applicable above that provides for increased efficacy.

In another embodiment, the invention provides for the therapeutic population of TILs described in any of the preceding paragraphs as applicable above modified such that the therapeutic population of TILs is capable of at least one-fold more interferon-gamma production as compared to TILs prepared by a process longer than 16 days.

In another embodiment, the invention provides for the therapeutic population of TILs described in any of the preceding paragraphs as applicable above modified such that the therapeutic population of TILs is capable of at least two-fold more interferon-gamma production as compared to TILs prepared by a process longer than 16 days.

In another embodiment, the invention provides for the therapeutic population of TILs described in any of the preceding paragraphs as applicable above modified such that the therapeutic population of TILs is capable of at least three-fold more interferon-gamma production as compared to TILs prepared by a process longer than 16 days.

In another embodiment, the invention provides for a therapeutic population of tumor infiltrating lymphocytes (TILs) that is capable of at least one-fold more interferon-gamma production as compared to TILs prepared by a process in which the first expansion of TILs is performed without any added antigen-presenting cells (APCs).

In another embodiment, the invention provides for a therapeutic population of tumor infiltrating lymphocytes (TILs) that is capable of at least one-fold more interferon-gamma production as compared to TILs prepared by a process in which the first expansion of TILs is performed without any added OKT3.

In another embodiment, the invention provides for a therapeutic population of TILs that is capable of at least two-fold more interferon-gamma production as compared to TILs prepared by a process in which the first expansion of TILs is performed without any added APCs.

In another embodiment, the invention provides for a therapeutic population of TILs that is capable of at least two-fold more interferon-gamma production as compared to TILs prepared by a process in which the first expansion of TILs is performed without any added OKT3.

In another embodiment, the invention provides for a therapeutic population of TILs that is capable of at least three-fold more interferon-gamma production as compared to TILs prepared by a process in which the first expansion of TILs is performed without any added APCs.

In another embodiment, the invention provides for a therapeutic population of TILs that is capable of at least three-fold more interferon-gamma production as compared to TILs prepared by a process in which the first expansion of TILs is performed without any added OKT3.

In another embodiment, the invention provides a method of expanding T cells comprising: (a) performing a priming first expansion of a first population of T cells obtained from a donor by culturing the first population of T cells to effect growth and to prime an activation of the first population of T cells; (b) after the activation of the first population of T cells primed in step (a) begins to decay, performing a rapid second expansion of the first population of T cells by culturing the first population of T cells to effect growth and to boost the activation of the first population of T cells to obtain a second population of T cells; and (c) harvesting the second population of T cells. In another embodiment, the step of rapid second expansion is split into a plurality of steps to achieve a scaling up of the culture by: (a) performing the rapid second expansion by culturing the first population of T cells in a small scale culture in a first container, e.g., a G-REX 100MCS container, for a period of about 3 to 4 days, and then (b) effecting the transfer of the first population of T cells from the small scale culture to a second container larger than the first container, e.g., a G-REX 500MCS container, and culturing the first population of T cells from the small scale culture in a larger scale culture in the second container for a period of about 4 to 7 days. In another embodiment, the step of rapid expansion is split into a plurality of steps to achieve a scaling out of the culture by: (a) performing the rapid second expansion by culturing the first population of T cells in a first small scale culture in a first container, e.g., a G-REX 100MCS container, for a period of about 3 to 4 days, and then (b) effecting the transfer and apportioning of the first population of T cells from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the first population of T cells from first small scale culture transferred to such second container is cultured in a second small scale culture for a period of about 4 to 7 days. In another embodiment, the step of rapid expansion is split into a plurality of steps to achieve a scaling out and scaling up of the culture by: (a) performing the rapid second expansion by culturing the first population of T cells in a small scale culture in a first container, e.g., a G-REX 100MCS container, for a period of about 3 to 4 days, and then (b) effecting the transfer and apportioning of the first population of T cells from the small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500MCS containers, wherein in each second container the portion of the first population of T cells from the small scale culture transferred to such second container is cultured in a larger scale culture for a period of about 4 to 7 days. In another embodiment, the step of rapid expansion is split into a plurality of steps to achieve a scaling out and scaling up of the culture by: (a) performing the rapid second expansion by culturing the first population of T cells in a small scale culture in a first container, e.g., a G-REX 100MCS container, for a period of about 4 days, and then (b) effecting the transfer and apportioning of the first population of T cells from the small scale culture into and amongst 2, 3 or 4 second containers that are larger in size than the first container, e.g., G-REX 500MCS containers, wherein in each second container the portion of the first population of T cells from the small scale culture transferred to such second container is cultured in a larger scale culture for a period of about 5 days.

In another embodiment, the invention provides the method described herein such that the priming first expansion of step (a) is performed during a period of up to 7 days.

In another embodiment, the invention provides the method described in any of the preceding paragraphs as applicable above modified such that the rapid second expansion of step (b) is performed during a period of up to 11 days.

In another embodiment, the invention provides the method described in any of the preceding paragraphs as applicable above modified such that the priming first expansion in step (a) is performed during a period of 7 days and the rapid second expansion of step (b) is performed during a period of up to 9 days.

In another embodiment, the invention provides the method described in any of the preceding paragraphs as applicable above modified such that in step (a) the first population of T cells is cultured in a first culture medium comprising OKT-3 and IL-2.

In another embodiment, the invention provides the method described in any of the preceding paragraphs as applicable above modified such that the first culture medium comprises OKT-3, IL-2 and antigen-presenting cells (APCs).

In another embodiment, the invention provides the method described in any of the preceding paragraphs as applicable above modified such that in step (b) the first population of T cells is cultured in a second culture medium comprising OKT-3, IL-2 and antigen-presenting cells (APCs).

In another embodiment, the invention provides the method described in any of the preceding paragraphs as applicable above modified such that in step (a) the first population of T cells is cultured in a first culture medium in a container comprising a first gas-permeable surface, wherein the first culture medium comprises OKT-3, IL-2 and a first population of antigen-presenting cells (APCs), wherein the first population of APCs is exogenous to the donor of the first population of T cells and the first population of APCs is layered onto the first gas-permeable surface, wherein in step (b) the first population of T cells is cultured in a second culture medium in the container, wherein the second culture medium comprises OKT-3, IL-2 and a second population of APCs, wherein the second population of APCs is exogenous to the donor of the first population of T cells and the second population of APCs is layered onto the first gas-permeable surface, and wherein the second population of APCs is greater than the first population of APCs.

In another embodiment, the invention provides the method described in any of the preceding paragraphs as applicable above modified such that the ratio of the number of APCs in the second population of APCs to the number of APCs in the first population of APCs is about 2:1.

In another embodiment, the invention provides the method described in any of the preceding paragraphs as applicable above modified such that the number of APCs in the first population of APCs is about $2.5 \times 10^8$ and the number of APCs in the second population of APCs is about $5 \times 10^8$.

In another embodiment, the invention provides the method described in any of the preceding paragraphs as applicable above modified such that in step (a) the first population of APCs is layered onto the first gas-permeable surface at an average thickness of 2 layers of APCs.

In another embodiment, the invention provides the method described in any of the preceding paragraphs as applicable above modified such that in step (b) the second population of APCs is layered onto the first gas-permeable surface at an average thickness selected from the range of 4 to 8 layers of APCs.

In another embodiment, the invention provides the method described in any of the preceding paragraphs as applicable above modified such that the ratio of the average number of layers of APCs layered onto the first gas-permeable surface in step (b) to the average number of layers of APCs layered onto the first gas-permeable surface in step (a) is 2:1.

In another embodiment, the invention provides the method described in any of the preceding paragraphs as applicable above modified such that in step (a) the first population of APCs is seeded on the first gas permeable surface at a density selected from the range of at or about $1.0 \times 10^6$ APCs/cm$^2$ to at or about $4.5 \times 10^6$ APCs/cm$^2$.

In another embodiment, the invention provides the method described in any of the preceding paragraphs as applicable above modified such that in step (a) the first population of APCs is seeded on the first gas permeable surface at a density selected from the range of at or about $1.5 \times 10^6$ APCs/cm$^2$ to at or about $3.5 \times 10^6$ APCs/cm$^2$.

In another embodiment, the invention provides the method described in any of the preceding paragraphs as applicable above modified such that in step (a) the first population of APCs is seeded on the first gas permeable surface at a density selected from the range of at or about $2.0 \times 10^6$ APCs/cm$^2$ to at or about $3.0 \times 10^6$ APCs/cm$^2$.

In another embodiment, the invention provides the method described in any of the preceding paragraphs as applicable above modified such that in step (a) the first population of APCs is seeded on the first gas permeable surface at a density of at or about $2.0 \times 10^6$ APCs/cm$^2$.

In another embodiment, the invention provides the method described in any of the preceding paragraphs as applicable above modified such that in step (b) the second population of APCs is seeded on the first gas permeable surface at a density selected from the range of at or about $2.5 \times 10^6$ APCs/cm$^2$ to at or about $7.5 \times 10^6$ APCs/cm$^2$.

In another embodiment, the invention provides the method described in any of the preceding paragraphs as applicable modified such that in step (b) the second population of APCs is seeded on the first gas permeable surface at a density selected from the range of at or about $3.5 \times 10^6$ APCs/cm$^2$ to at or about $6.0 \times 10^6$ APCs/cm$^2$.

In another embodiment, the invention provides the method described in any of the preceding paragraphs as applicable above modified such that in step (b) the second population of APCs is seeded on the first gas permeable surface at a density selected from the range of at or about $4.0 \times 10^6$ APCs/cm$^2$ to at or about $5.5 \times 10^6$ APCs/cm$^2$.

In another embodiment, the invention provides the method described in any of the preceding paragraphs as applicable above modified such that in step (b) the second population of APCs is seeded on the first gas permeable surface at a density of at or about $4.0 \times 10^6$ APCs/cm$^2$.

In another embodiment, the invention provides the method described in any of the preceding paragraphs as applicable above modified such that in step (a) the first population of APCs is seeded on the first gas permeable surface at a density selected from the range of at or about $1.0 \times 10^6$ APCs/cm$^2$ to at or about $4.5 \times 10^6$ APCs/cm$^2$ and in step (b) the second population of APCs is seeded on the first gas permeable surface at a density selected from the range of at or about $2.5 \times 10^6$ APCs/cm$^2$ to at or about $7.5 \times 10^6$ APCs/cm$^2$.

In another embodiment, the invention provides the method described in any of the preceding paragraphs as applicable modified such that in step (a) the first population of APCs is seeded on the first gas permeable surface at a density selected from the range of at or about $1.5 \times 10^6$ APCs/cm$^2$ to at or about $3.5 \times 10^6$ APCs/cm$^2$ and in step (b) the second population of APCs is seeded on the first gas permeable surface at a density selected from the range of at or about $3.5 \times 10^6$ APCs/cm$^2$ to at or about $6.0 \times 10^6$ APCs/cm$^2$.

In another embodiment, the invention provides the method described in any of the preceding paragraphs as applicable above modified such that in step (a) the first population of APCs is seeded on the first gas permeable surface at a density selected from the range of at or about $2.0 \times 10^6$ APCs/cm$^2$ to at or about $3.0 \times 10^6$ APCs/cm$^2$ and in step (b) the second population of APCs is seeded on the first gas permeable surface at a density selected from the range of at or about $4.0 \times 10^6$ APCs/cm$^2$ to at or about $5.5 \times 10^6$ APCs/cm$^2$.

In another embodiment, the invention provides the method described in any of the preceding paragraphs as applicable above modified such that in step (a) the first population of APCs is seeded on the first gas permeable surface at a density of at or about $2.0 \times 10^6$ APCs/cm$^2$ and in step (b) the second population of APCs is seeded on the first gas permeable surface at a density of at or about $4.0 \times 10^6$ APCs/cm$^2$ In another embodiment, the invention provides the method described in any of the preceding paragraphs as applicable above modified such that the APCs are peripheral blood mononuclear cells (PBMCs).

In another embodiment, the invention provides the method described in any of the preceding paragraphs as applicable above modified such that the PBMCs are irradiated and exogenous to the donor of the first population of T cells.

In another embodiment, the invention provides the method described in any of the preceding paragraphs as applicable above modified such that the T cells are tumor infiltrating lymphocytes (TILs).

In another embodiment, the invention provides the method described in any of the preceding paragraphs as applicable above modified such that the T cells are marrow infiltrating lymphocytes (MILs).

In another embodiment, the invention provides the method described in any of the preceding paragraphs as applicable above modified such that the T cells are peripheral blood lymphocytes (PBLs).

In another embodiment, the invention provides the method described in any of the preceding paragraphs as applicable above modified such that the first population of T cells is obtained by separation from the whole blood of the donor.

In another embodiment, the invention provides the method described in any of the preceding paragraphs as applicable above modified such that the first population of T cells is obtained by separation from the apheresis product of the donor.

In another embodiment, the invention provides the method described in any of the preceding paragraphs as applicable above modified such that the first population of T cells is separated from the whole blood or apheresis product of the donor by positive or negative selection of a T cell phenotype.

In another embodiment, the invention provides the method described in any of the preceding paragraphs as applicable above modified such that the T cell phenotype is CD3+ and CD45+.

In another embodiment, the invention provides the method described in any of the preceding paragraphs as applicable above modified such that at or about $1 \times 10^7$ T cells from the first population of T cells are seeded in a container to initiate the primary first expansion culture in such container.

In another embodiment, the invention provides the method described in any of the preceding paragraphs as applicable above modified such that the first population of T cells is distributed into a plurality of containers, and in each container at or about $1 \times 10^7$ T cells from the first population of T cells are seeded to initiate the primary first expansion culture in such container.

Expansion with AKT Pathway Inhibitors

TIL expansion in the presence of AKT pathway inhibitors comprises one solution to the problem of preserving an undifferentiated TIL phenotype during expansion. Less differentiated TILs are considered to be "young TILs" and are characterized by relatively long telomeres and high ratios of cells expressing, e.g., CD27, CD28, and CD62L. "Young TILs" share the same features of central memory T-Cells as described herein.

Unexpectedly, a first culture in the presence of an AKT pathway inhibitor enriches for therapeutically useful phenotypes (e.g. "young TIL" or central memory T-cells) and enhances the performance of process 2A and Gen 3 TIL manufacturing processes.

Pharmaceutical Compositions, Dosages, and Dosing Regimens

In an embodiment, TILs expanded using the methods of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic administration.

Any suitable dose of TILs can be administered. In some embodiments, from about $2.3 \times 10^{10}$ to about $13.7 \times 10^{10}$ TILs are administered, with an average of around $7.8 \times 10^{10}$ TILs, particularly if the cancer is melanoma. In an embodiment, about $1.2 \times 10^{10}$ to about $4.3 \times 10^{10}$ of TILs are administered. In some embodiments, about $3 \times 10^{10}$ to about $12 \times 10^{10}$ TILs are administered. In some embodiments, about $4 \times 10^{10}$ to about $10 \times 10^{10}$ TILs are administered. In some embodiments, about $5 \times 10^{10}$ to about $8 \times 10^{10}$ TILs are administered. In some embodiments, about $6 \times 10^{10}$ to about $8 \times 10^{10}$ TILs are administered. In some embodiments, about $7 \times 10^{10}$ to about $8 \times 10^{10}$ TILs are administered. In some embodiments, the therapeutically effective dosage is about $2.3 \times 10^{10}$ to about $13.7 \times 10^{10}$. In some embodiments, the therapeutically effective dosage is about $7.8 \times 10^{10}$ TILs, particularly of the cancer is melanoma. In some embodiments, the therapeutically effective dosage is about $1.2 \times 10^{10}$ to about $4.3 \times 10^{10}$ of TILs. In some embodiments, the therapeutically effective dosage is about $3 \times 10^{10}$ to about $12 \times 10^{10}$ TILs. In some embodiments, the therapeutically effective dosage is about $4 \times 10^{10}$ to about $10 \times 10^{10}$ TILs. In some embodiments, the therapeutically effective dosage is about $5 \times 10^{10}$ to about $8 \times 10^{10}$ TILs. In some embodiments, the therapeutically effective dosage is about $6 \times 10^{10}$ to about $8 \times 10^{10}$ TILs. In some embodiments, the therapeutically effective dosage is about $7 \times 10^{10}$ to about $8 \times 10^{10}$ TILs.

In some embodiments, the number of the TILs provided in the pharmaceutical compositions of the invention is about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8 4 \times 10^8$, $5 \times 10^8 6 \times 10^8$, $7 \times 10^8 8 \times 10^8$, $9 \times 10^8 1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10} 4 \times 10^{10} 5 \times 10^{10} 6 \times 10^{10}$, $7 \times 10^{10} 8 \times 10^{10}$, $9 \times 10^{10} 1 \times 10^{11}$, $2 \times 10^{11}$, $3 \times 10^{11}$, $4 \times 10^{11}$, $5 \times 10^{11}$, $6 \times 10^{11}$, $7 \times 10^1$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, and $9 \times 10^{13}$. In an embodiment, the number of the TILs provided in the pharmaceutical compositions of the invention is in the range of $1 \times 10^6$ to $5 \times 10^6$, $5 \times 10^6$ to $1 \times 10^7$, $1 \times 10^7$ to $5 \times 10^7$, $5 \times 10^7$ to $1 \times 10^8$, $1 \times 10^8$ to $5 \times 10^8$, $5 \times 10^8$ to $1 \times 10^9$, $1 \times 10^9$ to $5 \times 10^9$, $5 \times 10^9$ to $1 \times 10^1$, $1 \times 10^1$ to $5 \times 10^{10}$, $5 \times 10^{10}$ to $1 \times 10^{11}$, $5 \times 10^{11}$ to $1 \times 10^{12}$, $1 \times 10^{12}$ to $5 \times 10^{12}$, and $5 \times 10^{12}$ to $1 \times 10^{13}$.

In some embodiments, the concentration of the TILs provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of the TILs provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of the TILs provided in the pharmaceutical compositions of the invention is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the TILs provided in the pharmaceutical compositions of the invention is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the TILs provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the TILs provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The TILs provided in the pharmaceutical compositions of the invention are effective over a wide dosage range. The exact dosage will depend upon the route of administration, the form in which the compound is administered, the gender and age of the subject to be treated, the body weight of the subject to be treated, and the preference and experience of the attending physician. The clinically-established dosages of the TILs may also be used if appropriate. The amounts of the pharmaceutical compositions administered using the methods herein, such as the dosages of TILs, will be dependent on the human or mammal being treated, the severity of the disorder or condition, the rate of administration, the disposition of the active pharmaceutical ingredients and the discretion of the prescribing physician.

In some embodiments, TILs may be administered in a single dose. Such administration may be by injection, e.g., intravenous injection. In some embodiments, TILs may be administered in multiple doses. Dosing may be once, twice, three times, four times, five times, six times, or more than six times per year. Dosing may be once a month, once every two weeks, once a week, or once every other day. Administration of TILs may continue as long as necessary.

In some embodiments, an effective dosage of TILs is about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8 4 \times 10^8$, $5 \times 10^8$, $6 \times 10^8$, $7 \times 10^8 8 \times 10^8$, $9 \times 10^8 1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{11}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^2$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, and $9 \times 10^{13}$. In some embodiments, an effective dosage of TILs is in the range of $1 \times 10^6$ to $5 \times 10^6$, $5 \times 10^6$ to $1 \times 10^7$, $1 \times 10^7$ to $5 \times 10^7$, $5 \times 10^7$ to $1 \times 10^8$, $1 \times 10^8$ to $5 \times 10^8$, $5 \times 10^8$ to $1 \times 10^9$, $1 \times 10^9$ to $5 \times 10^9$, $5 \times 10^9$ to $1 \times 10^{10}$, $1 \times 10^{10}$ to $5 \times 10^{10}$, $5 \times 10^{10}$ to $1 \times 10^{11}$, $5 \times 10^{11}$ to $1 \times 10^{12}$, $1 \times 10^{12}$ to $5 \times 10^{12}$, and $5 \times 10^{12}$ to $1 \times 10^{13}$.

In some embodiments, an effective dosage of TILs is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of TILs is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg.

An effective amount of the TILs may be administered in either single or multiple doses by any of the accepted modes of administration of agents having similar utilities, including intranasal and transdermal routes, by intra-arterial injection, intravenously, intraperitoneally, parenterally, intramuscularly, subcutaneously, topically, by transplantation, or by inhalation.

Methods of Treating Patients

Methods of treatment begin with the initial TIL collection and culture of TILs. Such methods have been both described in the art by, for example, Jin et al., *J. Immunotherapy*, 2012, 35(3):283-292, incorporated by reference herein in its entirety. Embodiments of methods of treatment are described throughout the sections below, including the Examples.

The expanded TTLs produced according the methods described herein, including for example as described in Steps A through F above or according to Steps A through F above (also as shown, for example, in FIG. 1 and in FIG. 8, both FIG. 8A and FIG. 8B) find particular use in the treatment of patients with cancer (for example, as described in Goff, et al., *J. Clinical Oncology*, 2016, 34(20):2389-239, as well as the supplemental content; incorporated by reference herein in its entirety. In some embodiments, TIL were grown from resected deposits of metastatic melanoma as previously described (see, Dudley, et al., *J Immunother.*, 2003, 26:332-342; incorporated by reference herein in its entirety). Fresh tumor can be dissected under sterile conditions. A representative sample can be collected for formal pathologic analysis. Single fragments of 2 mm³ to 3 mm³ may be used. In some embodiments, 5, 10, 15, 20, 25 or 30 samples per patient are obtained. In some embodiments, 20, 25, or 30 samples per patient are obtained. In some embodiments, 20, 22, 24, 26, or 28 samples per patient are obtained. In some embodiments, 24 samples per patient are obtained. Samples can be placed in individual wells of a 24-well plate, maintained in growth media with high-dose IL-2 (6,000 IU/mL), and monitored for destruction of tumor and/or proliferation of TIL. Any tumor with viable cells remaining after processing can be enzymatically digested into a single cell suspension and cryopreserved, as described herein.

In some embodiments, successfully grown TIL can be sampled for phenotype analysis (CD3, CD4, CD8, and CD56) and tested against autologous tumor when available. TIL can be considered reactive if overnight coculture yielded interferon-gamma (IFN-γ) levels>200 pg/mL and twice background. (Goff, et al., *J Immunother.*, 2010, 33:840-847; incorporated by reference herein in its entirety). In some embodiments, cultures with evidence of autologous reactivity or sufficient growth patterns can be selected for a second expansion (for example, a second expansion as provided in according to Step D of FIG. 1), including second expansions that are sometimes referred to as rapid expansion (REP). In some embodiments, expanded TILs with high autologous reactivity (for example, high proliferation during a second expansion), are selected for an additional second expansion. In some embodiments, TTLs with high autologous reactivity (for example, high proliferation during second expansion as provided in Step D of FIG. 1), are selected for an additional second expansion according to Step D of FIG. 1 and in FIG. 8, both FIG. 8A and FIG. 8B.

In some embodiments, the patient is not moved directly to ACT (adoptive cell transfer), for example, in some embodiments, after tumor harvesting and/or a first expansion, the cells are not utilized immediately. In such embodiments, TILs can be cryopreserved and thawed 2 days before administration to a patient. In such embodiments, TILs can be cryopreserved and thawed 1 day before administration to a patient. In some embodiments, the TILs can be cryopreserved and thawed immediately before the administration to a patient.

Cell phenotypes of cryopreserved samples of infusion bag TIL can be analyzed by flow cytometry (e.g., FlowJo) for surface markers CD3, CD4, CD8, CCR7, and CD45RA (BD BioSciences), as well as by any of the methods described herein. Serum cytokines were measured by using standard enzyme-linked immunosorbent assay techniques. A rise in serum IFN-γ was defined as >100 pg/mL and greater than 3 to 4 times baseline levels.

In some embodiments, the TILs produced by the methods provided herein, for example those exemplified in FIG. 1, provide for a surprising improvement in clinical efficacy of the TILs. In some embodiments, the TILs produced by the methods provided herein, for example those exemplified in FIG. 1 and FIG. 8 (both FIG. 8A and FIG. 8B), exhibit increased clinical efficacy as compared to TILs produced by methods other than those described herein, including for example, methods other than those exemplified in FIG. 1. In some embodiments, the methods other than those described herein include methods referred to as process 1C and/or Generation 1 (Gen 1). In some embodiments, the increased efficacy is measured by DCR, ORR, and/or other clinical responses. In some embodiments, the TILs produced by the methods provided herein, for example those exemplified in FIG. 1, exhibit a similar time to response and safety profile compared to TILs produced by methods other than those described herein, including for example, methods other than those exemplified in FIG. 1, for example the Gen 1 process.

In some embodiments, IFN-gamma (IFN-γ) is indicative of treatment efficacy and/or increased clinical efficacy. In some embodiments, IFN-γ in the blood of subjects treated with TILs is indicative of active TILs. In some embodiments, a potency assay for IFN-γ production is employed. IFN-γ production is another measure of cytotoxic potential. IFN-γ production can be measured by determining the levels of the cytokine IFN-γ in the blood, serum, or TILs ex vivo of a subject treated with TILs prepared by the methods of the present invention, including those as described for example in FIG. 8. In some embodiments, an increase in IFN-γ is indicative of treatment efficacy in a patient treated with the TILs produced by the methods of the present invention. In some embodiments, IFN-γ is increased one-fold, two-fold, three-fold, four-fold, or five-fold or more as compared to an untreated patient and/or as compared to a patient treated with TILs prepared using other methods than those provide herein including for example, methods other than those embodied in FIG. 8. In some embodiments, IFN-γ secretion is increased one-fold as compared to an untreated patient and/or as compared to a patient treated with TILs prepared using other methods than those provide herein including for example, methods other than those embodied in FIG. 8. In some embodiments, IFN-γ secretion is increased two-fold as compared to an untreated patient and/or as compared to a patient treated with TILs prepared using other methods than those provide herein including for example, methods other than those embodied in FIG. 8. In some embodiments, IFN-γ secretion is increased three-fold as compared to an untreated patient and/or as compared to a patient treated with TILs prepared using other methods than those provide herein including for example, methods other than those embodied in FIG. 8. In some embodiments, IFN-γ secretion is increased four-fold as compared to an untreated patient and/or as compared to a patient treated with TILs prepared using other methods than those provide herein including for example, methods other than those embodied in FIG. 8. In some embodiments, IFN-γ secretion is increased five-fold as compared to an untreated patient and/or as compared to a patient treated with TILs prepared using other methods than those provide herein including for example, methods other than those embodied in FIG. 8. In some embodiments, IFN-γ is measured using a Quantikine ELISA kit. In some embodiments, IFN-γ is measured in TTLs ex vivo of a subject treated with TILs prepared by the methods of the present invention, including those as described for example in FIG. 8. In some embodiments, IFN-γ is measured in blood of a subject treated with TTLs prepared by the methods of the present invention, including those as described for example in FIG. 8. In some embodiments, IFN-γ is measured in TILs serum of a subject treated with TTLs prepared by the methods of the present invention, including those as described for example in FIG. 8.

In some embodiments, the TILs prepared by the methods of the present invention, including those as described for example in FIG. 8, exhibit increased polyclonality as compared to TILs produced by other methods, including those not exemplified in FIG. 8, such as for example, methods referred to as process 1C methods. In some embodiments, significantly improved polyclonality and/or increased polyclonality is indicative of treatment efficacy and/or increased clinical efficacy. In some embodiments, polyclonality refers to the T-cell repertoire diversity. In some embodiments, an increase in polyclonality can be indicative of treatment efficacy with regard to administration of the TILs produced by the methods of the present invention. In some embodiments, polyclonality is increased one-fold, two-fold, ten-fold, 100-fold, 500-fold, or 1000-fold as compared to TILs prepared using methods than those provide herein including for example, methods other than those embodied in FIG. 8. In some embodiments, polyclonality is increased one-fold as compared to an untreated patient and/or as compared to a patient treated with TILs prepared using other methods than those provide herein including for example, methods other than those embodied in FIG. 8. In some embodiments, polyclonality is increased two-fold as compared to an untreated patient and/or as compared to a patient treated with TILs prepared using other methods than those provide herein including for example, methods other than those embodied in FIG. 8. In some embodiments, polyclonality is increased ten-fold as compared to an untreated patient and/or as compared to a patient treated with TILs prepared using other methods than those provide herein including for example, methods other than those embodied in FIG. 8. In some embodiments, polyclonality is increased 100-fold as compared to an untreated patient and/or as compared to a patient treated with TILs prepared using other methods than those provide herein including for example, methods other than those embodied in FIG. 8. In some embodiments, polyclonality is increased 500-fold as compared to an untreated patient and/or as compared to a patient treated with TILs prepared using other methods than those provide herein including for example, methods other than those embodied in FIG. 8. In some embodiments, polyclonality is increased 1000-fold as compared to an untreated patient and/or as compared to a patient treated with TILs prepared using other methods than those provide herein including for example, methods other than those embodied in FIG. 8.

Measures of efficacy can include the disease control rate (DCR) as well as overall response rate (ORR), as known in the art as well as described herein.

Methods of Treating Cancer and Other Diseases

The compositions and methods described herein can be used in a method for treating diseases. In an embodiment, they are for use in treating hyperproliferative disorders. They may also be used in treating other disorders as described herein and in the following paragraphs.

In some embodiments, the hyperproliferative disorder is cancer. In some embodiments, the hyperproliferative disorder is a solid tumor cancer. In some embodiments, the solid tumor cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), renal cancer, and renal cell carcinoma. In some embodiments, the hyperproliferative disorder is a hematological malignancy. In some embodiments, the solid tumor cancer is selected from the group consisting of chronic lymphocytic leukemia, acute lymphoblastic leukemia, diffuse large B cell lymphoma, non-Hodgkin's lymphoma, Hodgkin's lymphoma, follicular lymphoma, and mantle cell lymphoma.

In an embodiment, the invention includes a method of treating a cancer with a population of TILs, wherein a patient is pre-treated with non-myeloablative chemotherapy prior to an infusion of TILs according to the present disclosure. In an embodiment, the non-myeloablative chemotherapy is cyclophosphamide 60 mg/kg/d for 2 days (days 27 and 26 prior to TIL infusion) and fludarabine 25 mg/m$^2$/d for 5 days (days 27 to 23 prior to TIL infusion). In an embodiment, after non-myeloablative chemotherapy and TIL infusion (at day 0) according to the present disclosure, the patient receives an intravenous infusion of IL-2 intravenously at 720,000 IU/kg every 8 hours to physiologic tolerance.

Efficacy of the compounds and combinations of compounds described herein in treating, preventing and/or managing the indicated diseases or disorders can be tested using various models known in the art, which provide guidance for treatment of human disease. For example, models for determining efficacy of treatments for ovarian cancer are described, e.g., in Mullany, et al., *Endocrinology* 2012, 153, 1585-92; and Fong, et al., *J. Ovarian Res.* 2009, 2, 12. Models for determining efficacy of treatments for pancreatic cancer are described in Herreros-Villanueva, et al., *World J. Gastroenterol.* 2012, 18, 1286-1294. Models for determining efficacy of treatments for breast cancer are described, e.g., in Fantozzi, *Breast Cancer Res.* 2006, 8, 212. Models for determining efficacy of treatments for melanoma are described, e.g., in Damsky, et al., *Pigment Cell & Melanoma Res.* 2010, 23, 853-859. Models for determining efficacy of treatments for lung cancer are described, e.g., in Meuwissen, et al., *Genes & Development,* 2005, 19, 643-664. Models for determining efficacy of treatments for lung cancer are described, e.g., in Kim, *Clin. Exp.* Otorhinolaryngol. 2009, 2, 55-60; and Sano, *Head Neck Oncol.* 2009, 1, 32.

In some embodiments, IFN-gamma (IFN-γ) is indicative of treatment efficacy for hyperproliferative disorder treatment. In some embodiments, IFN-γ in the blood of subjects treated with TILs is indicative of active TILs. In some embodiments, a potency assay for IFN-γ production is employed. IFN-γ production is another measure of cytotoxic potential. IFN-γ production can be measured by determining the levels of the cytokine IFN-γ in the blood of a subject treated with TILs prepared by the methods of the present invention, including those as described for example in FIG. 1. In some embodiments, the TILs obtained by the present method provide for increased IFN-γ in the blood of subjects treated with the TILs of the present method as compared subjects treated with TILs prepared using methods referred to as process 1C, as exemplified in FIG. 5 and/or FIG. 6. In some embodiments, an increase in IFN-γ is indicative of treatment efficacy in a patient treated with the TILs produced by the methods of the present invention. In some embodiments, IFN-γ is increased one-fold, two-fold, three-fold, four-fold, or five-fold or more as compared to an untreated patient and/or as compared to a patient treated with TILs prepared using other methods than those provide herein including for example, methods other than those embodied in FIG. 1. In some embodiments, IFN-γ secretion is increased one-fold as compared to an untreated patient and/or as compared to a patient treated with TILs prepared using other methods than those provide herein including for example, methods other than those embodied in FIG. 1. In some embodiments, IFN-γ secretion is increased two-fold as compared to an untreated patient and/or as compared to a patient treated with TILs prepared using other methods than those provide herein including for example, methods other than those embodied in FIG. 1. In some embodiments, IFN-γ secretion is increased three-fold as compared to an untreated patient and/or as compared to a patient treated with TILs prepared using other methods than those provide herein including for example, methods other than those embodied in FIG. 1. In some embodiments, IFN-γ secretion is increased four-fold as compared to an untreated patient and/or as compared to a patient treated with TILs prepared using other methods than those provide herein including for example, methods other than those embodied in FIG. 1. In some embodiments, IFN-γ secretion is increased five-fold as compared to an untreated patient and/or as compared to a patient treated with TILs prepared using other methods than those provide herein including for example, methods other than those embodied in FIG. 1. In some embodiments, IFN-γ is measured using a Quantikine ELISA kit. In some embodiments, IFN-γ is measured using a Quantikine ELISA kit. In some embodiments, IFN-γ is measured in TTLs ex vivo from a patient treated with the TTLs produced by the methods of the present invention. In some embodiments, IFN-γ is measured in blood in a patient treated with the TTLs produced by the methods of the present invention. In some embodiments, IFN-γ is measured in serum in a patient treated with the TTLs produced by the methods of the present invention.

In some embodiments, the TTLs prepared by the methods of the present invention, including those as described for example in FIG. 1, exhibit increased polyclonality as compared to TILs produced by other methods, including those not exemplified in FIG. 1, such as for example, methods referred to as process 1C methods. In some embodiments, significantly improved polyclonality and/or increased polyclonality is indicative of treatment efficacy and/or increased clinical efficacy for cancer treatment. In some embodiments, polyclonality refers to the T-cell repertoire diversity. In some embodiments, an increase in polyclonality can be indicative of treatment efficacy with regard to administration of the TTLs produced by the methods of the present invention. In some embodiments, polyclonality is increased one-fold, two-fold, ten-fold, 100-fold, 500-fold, or 1000-fold as compared to TTLs prepared using methods than those provide herein including for example, methods other than those embodied in FIG. 1. In some embodiments, polyclonality is increased one-fold as compared to an untreated patient and/or as compared to a patient treated with TILs prepared using other methods than those provide herein including for example, methods other than those embodied in FIG. 1. In some embodiments, polyclonality is increased two-fold as compared to an untreated patient and/or as compared to a patient treated with TTLs prepared using other methods than those provide herein including for example, methods other than those embodied in FIG. 1. In some embodiments, polyclonality is increased ten-fold as compared to an untreated patient and/or as compared to a patient treated with TTLs prepared using other methods than those provide herein including for example, methods other than those embodied in FIG. 1. In some embodiments, polyclonality is increased 100-fold as compared to an untreated patient and/or as compared to a patient treated with TILs prepared using other methods than those provide herein including for example, methods other than those embodied in FIG. 1. In some embodiments, polyclonality is increased 500-fold as compared to an untreated patient and/or as compared to a patient treated with TILs prepared using other methods than those provide herein including for example, methods other than those embodied in FIG. 1. In some embodiments, polyclonality is increased 1000-fold as compared to an untreated patient and/or as compared to a patient treated with TILs prepared using other methods than those provide herein including for example, methods other than those embodied in FIG. 1.

Additional Methods of Treatment

In another embodiment, the invention provides a method for treating a subject with cancer comprising administering to the subject a therapeutically effective dosage of the therapeutic TIL population described in any one of the preceding paragraphs as applicable above.

In another embodiment, the invention provides a method for treating a subject with cancer comprising administering to the subject a therapeutically effective dosage of the TIL composition described in any of the preceding paragraph as applicable above.

In another embodiment, the invention provides the method for treating a subject with cancer described in any of the preceding paragraphs as applicable above modified such that prior to administering the therapeutically effective dosage of the therapeutic TIL population described in any of the preceding paragraphs as applicable above or the therapeutically effective dosage of the TIL composition described in any of the preceding paragraphs as applicable above, a non-myeloablative lymphodepletion regimen has been administered to the subject.

In another embodiment, the invention provides the method for treating a subject with cancer described in any of the preceding paragraph as applicable above modified such that the non-myeloablative lymphodepletion regimen comprises the steps of administration of cyclophosphamide at a dose of 60 mg/m$^2$/day for two days followed by administration of fludarabine at a dose of 25 mg/m$^2$/day for five days.

In another embodiment, the invention provides the method for treating a subject with cancer described in any of the preceding paragraphs as applicable above modified to further comprise the step of treating the subject with a high-dose IL-2 regimen starting on the day after administration of the TIL cells to the subject.

In another embodiment, the invention provides the method for treating a subject with cancer described in any of the preceding paragraphs as applicable above modified such that the the high-dose IL-2 regimen comprises 600,000 or 720,000 IU/kg administered as a 15-minute bolus intravenous infusion every eight hours until tolerance.

In another embodiment, the invention provides the method for treating a subject with cancer described in any of the preceding paragraphs as applicable above modified such that the cancer is a solid tumor.

Methods of Co-Administration

In some embodiments, the TILs produced as described herein, including for example TILs derived from a method described in Steps A through F of FIG. 1, can be administered in combination with one or more immune checkpoint regulators, such as the antibodies described below. For example, antibodies that target PD-1 and which can be co-administered with the TILs of the present invention include, e.g., but are not limited to nivolumab (BMS-936558, Bristol-Myers Squibb; Opdivo®), pembrolizumab (lambrolizumab, MK03475 or MK-3475, Merck; Keytruda®), humanized anti-PD-1 antibody JS001 (Shang-Hai JunShi), monoclonal anti-PD-1 antibody TSR-042 (Tesaro, Inc.), Pidilizumab (anti-PD-1 mAb CT-011, Medivation), anti-PD-1 monoclonal Antibody BGB-A317 (BeiGene), and/or anti-PD-1 antibody SHR-1210 (ShangHai HengRui), human monoclonal antibody REGN2810 (Regeneron), human monoclonal antibody MDX-1106 (Bristol-Myers Squibb), and/or humanized anti-PD-1 IgG4 antibody PDR001 (Novartis). In some embodiments, the PD-1 antibody is from clone: RMP1-14 (rat IgG)—BioXcell cat #BP0146. Other suitable antibodies suitable for use in co-administration methods with TILs produced according to Steps A through F as described herein are anti-PD-1 antibodies disclosed in U.S. Pat. No. 8,008,449, herein incorporated by reference. In some embodiments, the antibody or antigen-binding portion thereof binds specifically to PD-L1 and inhibits its interaction with PD-1, thereby increasing immune activity. Any antibodies known in the art which bind to PD-L1 and disrupt the interaction between the PD-1 and PD-L1, and stimulates an anti-tumor immune response, are suitable for use in co-administration methods with TILs produced according to Steps A through F as described herein. For example, antibodies that target PD-L1 and are in clinical trials, include BMS-936559 (Bristol-Myers Squibb) and MPDL3280A (Genentech). Other suitable antibodies that target PD-L1 are disclosed in U.S. Pat. No. 7,943,743, herein incorporated by reference. It will be understood by one of ordinary skill that any antibody which binds to PD-1 or PD-L1, disrupts the PD-1/PD-L1 interaction, and stimulates an anti-tumor immune response, are suitable for use in co-administration methods with TILs produced according to Steps A through F as described herein. In some embodiments, the subject administered the combination of TILs produced according to Steps A through F is co administered with a and anti-PD-1 antibody when the patient has a cancer type that is refractory to administration of the anti-PD-1 antibody alone. In some embodiments, the patient is administered TILs in combination with and anti-PD-1 when the patient has refractory melanoma. In some embodiments, the patient is administered TILs in combination with and anti-PD-1 when the patient has non-small-cell lung carcinoma (NSCLC).

Optional Lymphodepletion Preconditioning of Patients

In an embodiment, the invention includes a method of treating a cancer with a population of TILs, wherein a patient is pre-treated with non-myeloablative chemotherapy prior to an infusion of TILs according to the present disclosure. In an embodiment, the invention includes a population of TILs for use in the treatment of cancer in a patient which has been pre-treated with non-myeloablative chemotherapy. In an embodiment, the population of TILs is for administration by infusion. In an embodiment, the non-myeloablative chemotherapy is cyclophosphamide 60 mg/kg/d for 2 days (days 27 and 26 prior to TIL infusion) and fludarabine 25 mg/m$^2$/d for 5 days (days 27 to 23 prior to TIL infusion). In an embodiment, after non-myeloablative chemotherapy and TIL infusion (at day 0) according to the present disclosure, the patient receives an intravenous infusion of IL-2 (aldesleukin, commercially available as PROLEUKIN) intravenously at 720,000 IU/kg every 8 hours to physiologic tolerance. In certain embodiments, the population of TILs is for use in treating cancer in combination with IL-2, wherein the IL-2 is administered after the population of TILs.

Experimental findings indicate that lymphodepletion prior to adoptive transfer of tumor-specific T lymphocytes plays a key role in enhancing treatment efficacy by eliminating regulatory T cells and competing elements of the immune system ('cytokine sinks'). Accordingly, some embodiments of the invention utilize a lymphodepletion step (sometimes also referred to as "immunosuppressive conditioning") on the patient prior to the introduction of the TILs of the invention.

In general, lymphodepletion is achieved using administration of fludarabine or cyclophosphamide (the active form being referred to as mafosfamide) and combinations thereof. Such methods are described in Gassner, et al., *Cancer Immunol. Immunother.* 2011, 60, 75-85, Muranski, et al., *Nat. Clin. Pract. Oncol.,* 2006, 3, 668-681, Dudley, et al., *J. Clin. Oncol.* 2008, 26, 5233-5239, and Dudley, et al., *J. Clin. Oncol.* 2005, 23, 2346-2357, all of which are incorporated by reference herein in their entireties.

In some embodiments, the fludarabine is administered at a concentration of 0.5 µg/mL-10 µg/mL fludarabine. In some embodiments, the fludarabine is administered at a concentration of 1 µg/mL fludarabine. In some embodiments, the fludarabine treatment is administered for 1 day, 2 days, 3 days, 4 days, 5 days, 6 days, or 7 days or more. In some embodiments, the fludarabine is administered at a dosage of 10 mg/kg/day, 15 mg/kg/day, 20 mg/kg/day, 25 mg/kg/day, 30 mg/kg/day, 35 mg/kg/day, 40 mg/kg/day, or 45 mg/kg/day. In some embodiments, the fludarabine treatment is administered for 2-7 days at 35 mg/kg/day. In some embodiments, the fludarabine treatment is administered for 4-5 days at 35 mg/kg/day. In some embodiments, the fludarabine treatment is administered for 4-5 days at 25 mg/kg/day.

In some embodiments, the mafosfamide, the active form of cyclophosphamide, is obtained at a concentration of 0.5 µg/mL-10 µg/mL by administration of cyclophosphamide. In some embodiments, mafosfamide, the active form of cyclophosphamide, is obtained at a concentration of 1 µg/mL by administration of cyclophosphamide. In some embodiments, the cyclophosphamide treatment is administered for 1 day, 2 days, 3 days, 4 days, 5 days, 6 days, or 7 days or more. In some embodiments, the cyclophosphamide is administered at a dosage of 100 mg/m$^2$/day, 150 mg/m$^2$/day, 175 mg/m$^2$/day, 200 mg/m$^2$/day, 225 mg/m$^2$/day, 250 mg/m$^2$/day, 275 mg/m$^2$/day, or 300 mg/m$^2$/day. In some embodiments, the cyclophosphamide is administered intravenously (i.v.) In some embodiments, the cyclophosphamide treatment is administered for 2-7 days at 35 mg/kg/day. In some embodiments, the cyclophosphamide treatment is administered for 4-5 days at 250 mg/m$^2$/day i.v. In some embodiments, the cyclophosphamide treatment is administered for 4 days at 250 mg/m$^2$/day i.v.

In some embodiments, lymphodepletion is performed by administering the fludarabine and the cyclophosphamide together to a patient. In some embodiments, fludarabine is administered at 25 mg/m$^2$/day i.v. and cyclophosphamide is administered at 250 mg/m$^2$/day i.v. over 4 days.

In an embodiment, the lymphodepletion is performed by administration of cyclophosphamide at a dose of 60 mg/m$^2$/day for two days followed by administration of fludarabine at a dose of 25 mg/m$^2$/day for five days.

IL-2 Regimens

In an embodiment, the IL-2 regimen comprises a high-dose IL-2 regimen, wherein the high-dose IL-2 regimen comprises aldesleukin, or a biosimilar or variant thereof, administered intravenously starting on the day after administering a therapeutically effective portion of the therapeutic population of TILs, wherein the aldesleukin or a biosimilar or variant thereof is administered at a dose of 0.037 mg/kg or 0.044 mg/kg IU/kg (patient body mass) using 15-minute bolus intravenous infusions every eight hours until tolerance, for a maximum of 14 doses. Following 9 days of rest, this schedule may be repeated for another 14 doses, for a maximum of 28 doses in total.

In an embodiment, the IL-2 regimen comprises a decrescendo IL-2 regimen. Decrescendo IL-2 regimens have been described in O'Day, et al., *J. Clin. Oncol.* 1999, 17, 2752-61 and Eton, et al., *Cancer* 2000, 88, 1703-9, the disclosures of which are incorporated herein by reference. In an embodiment, a decrescendo IL-2 regimen comprises 18×10$^6$ IU/n$^2$ administered intravenously over 6 hours, followed by 18×10$^6$ IU/m$^2$ administered intravenously over 12 hours, followed by 18×10$^6$ IU/m$^2$ administered intravenously over 24 hrs, followed by 4.5×10$^6$ IU/n$^2$ administered intravenously over 72 hours. This treatment cycle may be repeated every 28 days for a maximum of four cycles. In an embodiment, a decrescendo IL-2 regimen comprises 18,000,000 IU/m$^2$ on day 1, 9,000,000 IU/m$^2$ on day 2, and 4,500,000 IU/m$^2$ on days 3 and 4.

In an embodiment, the IL-2 regimen comprises administration of pegylated IL-2 every 1, 2, 4, 6, 7, 14 or 21 days at a dose of 0.10 mg/day to 50 mg/day.

Adoptive Cell Transfer

Adoptive cell transfer (ACT) is a very effective form of immunotherapy and involves the transfer of immune cells with antitumor activity into cancer patients. ACT is a treatment approach that involves the identification, in vitro, of lymphocytes with antitumor activity, the in vitro expansion of these cells to large numbers and their infusion into the cancer-bearing host. Lymphocytes used for adoptive transfer can be derived from the stroma of resected tumors (tumor infiltrating lymphocytes or TILs). TILs for ACT can be prepared as described in the TIL manufacturing process herein, including using a tumor cryopreservation and thawing step. In some embodiments, the TILs are prepared, for example, according to a method as described in FIG. 1. They can also be derived or from blood if they are genetically engineered to express antitumor T-cell receptors (TCRs) or chimeric antigen receptors (CARs), enriched with mixed lymphocyte tumor cell cultures (MLTCs), or cloned using autologous antigen presenting cells and tumor derived peptides. ACT in which the lymphocytes originate from the cancer-bearing host to be infused is termed autologous ACT. U.S. Publication No. 2011/0052530 relates to a method for performing adoptive cell therapy to promote cancer regression, primarily for treatment of patients suffering from metastatic melanoma, which is incorporated by reference in its entirety for these methods. In some embodiments, TILs can be administered as described herein. In some embodiments, TILs can be administered in a single dose. Such administration may be by injection, e.g., intravenous injection. In some embodiments, TILs and/or cytotoxic lymphocytes may be administered in multiple doses. Dosing may be once, twice, three times, four times, five times, six times, or more than six times per year. Dosing may be once a month, once every two weeks, once a week, or once every other day. Administration of TILs and/or cytotoxic lymphocytes may continue as long as necessary.

Combinations with PD-1 and PD-L1 Inhibitors

Programmed death 1 (PD-1) is a 288-amino acid transmembrane immunocheckpoint receptor protein expressed by T cells, B cells, natural killer (NK) T cells, activated monocytes, and dendritic cells. PD-1, which is also known as CD279, belongs to the CD28 family, and in humans is encoded by the Pdcd1 gene on chromosome 2. PD-1 consists of one immunoglobulin (Ig) superfamily domain, a transmembrane region, and an intracellular domain containing an immunoreceptor tyrosine-based inhibitory motif (ITIM) and an immunoreceptor tyrosine-based switch motif (ITSM). PD-1 and its ligands (PD-L1 and PD-L2) are known to play a key role in immune tolerance, as described in Keir, et al., *Annu. Rev. Immunol.* 2008, 26:677-704. PD-1 provides inhibitory signals that negatively regulate T cell immune responses. PD-L1 (also known as B7-H1 or CD274) and PD-L2 (also known as B7-DC or CD273) are expressed on tumor cells and stromal cells, which may be encountered by activated T cells expressing PD-1, leading to immunosuppression of the T cells. PD-L1 is a 290 amino acid transmembrane protein encoded by the Cd274 gene on human chromosome 9. Blocking the interaction between PD-1 and its ligands PD-L1 and PD-L2 by use of a PD-1 inhibitor, a PD-L1 inhibitor, and/or a PD-L2 inhibitor can overcome immune resistance, as demonstrated in recent clinical studies, such as that described in Topalian, et al., *N. Eng. J. Med.* 2012, 366:2443-54. PD-L1 is expressed on many tumor cell lines, while PD-L2 is expressed is expressed mostly on dendritic cells and a few tumor lines. In addition to T cells (which inducibly express PD-1 after activation), PD-1 is also expressed on B cells, natural killer cells, macrophages, activated monocytes, and dendritic cells.

The methods, compositions, and combinations of TILs and TNFRSF agonists described herein may also be further combined with programmed death-1 (PD-1), programmed death ligand 1 (PD-L1), and/or programmed death ligand 2 (PD-L2) binding antibodies, antagonists, or inhibitors (i.e., blockers). PD-1, PD-L1, and/or PD-L2 inhibitors may be used in cell culture in conjunction with the TNFRSF agonists described herein during the pre-REP or REP stages of TIL expansion. PD-1, PD-L1, and/or PD-L2 inhibitors may also be used in conjunction with TNFRSF agonists prior to surgical resection of tumor, or during or after infusion of TILs. For example, suitable methods of using PD-1/PD-L1 inhibitors in conjunction with agonistic GITR antibodies and compositions comprising PD-1/PD-L1 antagonists and GITR agonists are described in International Patent Application Publication No. WO 2015/026684 A1, the disclosures of which are incorporated by reference herein.

In an embodiment, the PD-1 inhibitor may be any PD-1 inhibitor or PD-1 blocker known in the art. In particular, it is one of the PD-1 inhibitors or blockers described in more detail in the following paragraphs. The terms "inhibitor," "antagonist," and "blocker" are used interchangeably herein in reference to PD-1 inhibitors. For avoidance of doubt, references herein to a PD-1 inhibitor that is an antibody may refer to a compound or antigen-binding fragments, variants, conjugates, or biosimilars thereof. For avoidance of doubt, references herein to a PD-1 inhibitor may also refer to a small molecule compound or a pharmaceutically acceptable salt, ester, solvate, hydrate, cocrystal, or prodrug thereof.

In some embodiments, the compositions and methods described herein include a PD-1 inhibitor. In some embodiments, the PD-1 inhibitor is a small molecule. In a preferred embodiment, the PD-1 inhibitor is an antibody (i.e., an anti-PD-1 antibody), a fragment thereof, including Fab fragments, or a single-chain variable fragment (scFv) thereof. In some embodiments the PD-1 inhibitor is a polyclonal antibody. In a preferred embodiment, the PD-1 inhibitor is a monoclonal antibody. In some embodiments, the PD-1 inhibitor competes for binding with PD-1, and/or binds to an epitope on PD-1. In an embodiment, the antibody competes for binding with PD-1, and/or binds to an epitope on PD-1.

In some embodiments, the compositions and methods described include a PD-1 inhibitor that binds human PD-1 with a $K_D$ of about 100 pM or lower, binds human PD-1 with a $K_D$ of about 90 pM or lower, binds human PD-1 with a $K_D$ of about 80 pM or lower, binds human PD-1 with a $K_D$ of about 70 pM or lower, binds human PD-1 with a $K_D$ of about 60 pM or lower, binds human PD-1 with a $K_D$ of about 50 pM or lower, binds human PD-1 with a $K_D$ of about 40 pM or lower, binds human PD-1 with a $K_D$ of about 30 pM or lower, binds human PD-1 with a $K_D$ of about 20 pM or lower, binds human PD-1 with a $K_D$ of about 10 pM or lower, or binds human PD-1 with a $K_D$ of about 1 pM or lower.

In some embodiments, the compositions and methods described include a PD-1 inhibitor that binds to human PD-1 with a $k_{assoc}$ of about $7.5 \times 10^5$ 1/M·s or faster, binds to human PD-1 with a $k_{assoc}$ of about $7.5 \times 10^5$ 1/M·s or faster, binds to human PD-1 with a $k_{assoc}$ of about $8 \times 10^5$ 1/M·s or faster, binds to human PD-1 with a $k_{assoc}$ of about $8.5 \times 10^5$ 1/M·s or faster, binds to human PD-1 with a $k_{assoc}$ of about $9 \times 10^5$ 1/M·s or faster, binds to human PD-1 with a $k_{assoc}$ of about $9.5 \times 10^5$ 1/M·s or faster, or binds to human PD-1 with a $k_{assoc}$ of about $1 \times 10^6$ 1/M·s or faster.

In some embodiments, the compositions and methods described include a PD-1 inhibitor that binds to human PD-1 with a $k_{dissoc}$ of about $2 \times 10^{-5}$ 1/s or slower, binds to human PD-1 with a $k_{dissoc}$ of about $2.1 \times 10^{-5}$ 1/s or slower, binds to human PD-1 with a $k_{dissoc}$ of about $2.2 \times 10^{-5}$ 1/s or slower, binds to human PD-1 with a $k_{dissoc}$ of about $2.3 \times 10^{-5}$ 1/s or slower, binds to human PD-1 with a $k_{dissoc}$ of about $2.4 \times 10^{-5}$ 1/s or slower, binds to human PD-1 with a $k_{dissoc}$ of about $2.5 \times 10^{-5}$ 1/s or slower, binds to human PD-1 with a $k_{dissoc}$ of about $2.6 \times 10^{-5}$ 1/s or slower or binds to human PD-1 with a $k_{dissoc}$ of about $2.7 \times 10^{-5}$ 1/s or slower, binds to human PD-1 with a $k_{dissoc}$ of about $2.8 \times 10^{-5}$ 1/s or slower, binds to human PD-1 with a $k_{dissoc}$ of about $2.9 \times 10^{-5}$ 1/s or slower, or binds to human PD-1 with a $k_{dissoc}$ of about $3 \times 10^{-5}$ 1/s or slower.

In some embodiments, the compositions and methods described include a PD-1 inhibitor that blocks or inhibits binding of human PD-L1 or human PD-L2 to human PD-1 with an $IC_{50}$ of about 10 nM or lower, blocks or inhibits binding of human PD-L1 or human PD-L2 to human PD-1 with an $IC_{50}$ of about 9 nM or lower, blocks or inhibits binding of human PD-L1 or human PD-L2 to human PD-1 with an $IC_{50}$ of about 8 nM or lower, blocks or inhibits binding of human PD-L1 or human PD-L2 to human PD-1 with an $IC_{50}$ of about 7 nM or lower, blocks or inhibits binding of human PD-L1 or human PD-L2 to human PD-1 with an $IC_{50}$ of about 6 nM or lower, blocks or inhibits binding of human PD-L1 or human PD-L2 to human PD-1 with an $IC_{50}$ of about 5 nM or lower, blocks or inhibits binding of human PD-L1 or human PD-L2 to human PD-1 with an $IC_{50}$ of about 4 nM or lower, blocks or inhibits binding of human PD-L1 or human PD-L2 to human PD-1 with an $IC_{50}$ of about 3 nM or lower, blocks or inhibits binding of human PD-L1 or human PD-L2 to human PD-1 with an $IC_{50}$ of about 2 nM or lower, or blocks or inhibits binding of human PD-L1 or human PD-L2 to human PD-1 with an $IC_{50}$ of about 1 nM or lower.

In an embodiment, the PD-1 inhibitor is nivolumab (commercially available as OPDIVO from Bristol-Myers Squibb Co.), or biosimilars, antigen-binding fragments, conjugates, or variants thereof. Nivolumab is a fully human IgG4 antibody blocking the PD-1 receptor. In an embodiment, the anti-PD-1 antibody is an immunoglobulin G4 kappa, anti-(human CD274) antibody. Nivolumab is assigned Chemical Abstracts Service (CAS) registry number 946414-94-4 and is also known as 5C4, BMS-936558, MDX-1106, and ONO-4538. The preparation and properties of nivolumab are described in U.S. Pat. No. 8,008,449 and International Patent Publication No. WO 2006/121168, the disclosures of which are incorporated by reference herein. The clinical safety and efficacy of nivolumab in various forms of cancer has been described in Wang, et al., *Cancer Immunol Res.* 2014, 2:846-56; Page, et al., *Ann. Rev. Med.,* 2014, 65, 185-202; and Weber, et al., *J. Clin. Oncology,* 2013, 31:4311-4318, the disclosures of which are incorporated by reference herein. The amino acid sequences of nivolumab are set forth in Table 16. Nivolumab has intra-heavy chain disulfide linkages at 22-96, 140-196, 254-314, 360-418, 22"-96", 140"-196", 254"-314", and 360"-418"; intra-light chain disulfide linkages at 23'-88', 134'-194', 23'''-88''', and 134'''-194'''; inter-heavy-light chain disulfide linkages at 127-214', 127"-214'''; inter-heavy-heavy chain disulfide linkages at 219-219" and 222-222"; and N-glycosylation sites (H CH$_2$ 84.4) at 290, 290".

In an embodiment, a PD-1 inhibitor comprises a heavy chain given by SEQ ID NO:127 and a light chain given by SEQ ID NO:128. In an embodiment, a PD-1 inhibitor comprises heavy and light chains having the sequences shown in SEQ ID NO:127 and SEQ ID NO:128, respectively, or antigen binding fragments, Fab fragments, single-chain variable fragments (scFv), variants, or conjugates thereof. In an embodiment, a PD-1 inhibitor comprises heavy and light chains that are each at least 99% identical to the sequences shown in SEQ ID NO:127 and SEQ ID NO:128, respectively. In an embodiment, a PD-1 inhibitor comprises heavy and light chains that are each at least 98% identical to the sequences shown in SEQ ID NO:127 and SEQ ID NO:128, respectively. In an embodiment, a PD-1 inhibitor comprises heavy and light chains that are each at least 97% identical to the sequences shown in SEQ ID NO:127 and SEQ ID NO:128, respectively. In an embodiment, a PD-1 inhibitor comprises heavy and light chains that are each at least 96% identical to the sequences shown in SEQ ID NO:127 and SEQ ID NO:128, respectively. In an embodiment, a PD-1 inhibitor comprises heavy and light chains that are each at least 95% identical to the sequences shown in SEQ ID NO:127 and SEQ ID NO:128, respectively.

In an embodiment, the PD-1 inhibitor comprises the heavy and light chain CDRs or variable regions (VRs) of nivolumab. In an embodiment, the PD-1 inhibitor heavy chain variable region ($V_H$) comprises the sequence shown in SEQ ID NO:129, and the PD-1 inhibitor light chain variable region ($V_L$) comprises the sequence shown in SEQ ID NO:130, and conservative amino acid substitutions thereof. In an embodiment, a PD-1 inhibitor comprises $V_H$ and $V_L$ regions that are each at least 99% identical to the sequences shown in SEQ ID NO:129 and SEQ ID NO:130, respectively. In an embodiment, a PD-1 inhibitor comprises $V_H$ and $V_L$ regions that are each at least 98% identical to the sequences shown in SEQ ID NO:129 and SEQ ID NO:130, respectively. In an embodiment, a PD-1 inhibitor comprises $V_H$ and $V_L$ regions that are each at least 97% identical to the sequences shown in SEQ ID NO:129 and SEQ ID NO:130, respectively. In an embodiment, a PD-1 inhibitor comprises $V_H$ and $V_L$ regions that are each at least 96% identical to the sequences shown in SEQ ID NO:129 and SEQ ID NO:130, respectively. In an embodiment, a PD-1 inhibitor comprises $V_H$ and $V_L$ regions that are each at least 95% identical to the sequences shown in SEQ ID NO:129 and SEQ ID NO:130, respectively.

In an embodiment, a PD-1 inhibitor comprises heavy chain CDR1, CDR2 and CDR3 domains having the sequences set forth in SEQ ID NO:131, SEQ ID NO:132, and SEQ ID NO:133, respectively, and conservative amino acid substitutions thereof, and light chain CDR1, CDR2 and CDR3 domains having the sequences set forth in SEQ ID NO:134, SEQ ID NO:135, and SEQ ID NO:136, respectively, and conservative amino acid substitutions thereof. In an embodiment, the antibody competes for binding with, and/or binds to the same epitope on PD-1 as any of the aforementioned antibodies.

In an embodiment, the PD-1 inhibitor is an anti-PD-1 biosimilar monoclonal antibody approved by drug regulatory authorities with reference to nivolumab. In an embodiment, the biosimilar comprises an anti-PD-1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is nivolumab. In some embodiments, the one or more post-translational modifications are selected from one or more of: glycosylation, oxidation, deamidation, and truncation. In some embodiments, the biosimilar is an anti-PD-1 antibody authorized or submitted for authorization, wherein the anti-PD-1 antibody is provided in a formulation which differs from the formulations of a reference medicinal product or reference biological product, wherein the reference medicinal product or reference biological product is nivolumab. The anti-PD-1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is nivolumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is nivolumab.

TABLE 32

Amino acid sequences for PD-1 inhibitors related to nivolumab.

| Identifier | Sequence (One-Letter Amino Acid Symbols) | | | | | | |
|---|---|---|---|---|---|---|---|
| SEQ ID NO: 127<br>nivolumab<br>heavy chain | QVQLVESGGG | VVQPGRSLRL | DCKASGITFS | NSGMHWVRQA | PGKGLEWVAV | IWYDGSKRYY | 60 |
| | ADSVKGRFTI | SRDNSKNTLF | LQMNSLRAED | TAVYYCATND | DYWGQGTLVT | VSSASTKGPS | 120 |
| | VFPLAPCSRS | TSESTAALGC | LVKDYFPEPV | TVSWNSGALT | SGVHTFPAVL | QSSGLYSLSS | 180 |
| | VVTVPSSSLG | TKTYTCNVDH | KPSNTKVDKR | VESKYGPPCP | PCPAPEFLGG | PSVFLFPPKP | 240 |
| | KDTLMISRTP | EVTCVVVDVS | QEDPEVQFNW | YVDGVEVHNA | KTKPREEQFN | STYRVVSVLT | 300 |
| | VLHQDWLNGK | EYKCKVSNKG | LPSSIEKTIS | KAKGQPREPQ | VYTLPPSQEE | MTKNQVSLTC | 360 |
| | LVKGFYPSDI | AVEWESNGQP | ENNYKTTPPV | LDSDGSFFLY | SRLTVDKSRW | QEGNVFSCSV | 420 |
| | MHEALHNHYT | QKSLSLSLGK | | | | | 440 |
| SEQ ID NO: 128<br>nivolumab<br>light chain | EIVLTQSPAT | LSLSPGERAT | LSCRASQSVS | SYLAWYQQKP | GQAPRLLIYD | ASNRATGIPA | 60 |
| | RFSGSGSGTD | FTLTISSLEP | EDFAVYYCQQ | SSNWPRTFGQ | GTKVEIKRTV | AAPSVFIFPP | 120 |
| | SDEQLKSGTA | SVVCLLNNFY | PREAKVQWKV | DNALQSGNSQ | ESVTEQDSKD | STYSLSSTLT | 180 |
| | LSKADYEKHK | VYACEVTHQG | LSSPVTKSFN | RGEC | | | 214 |
| SEQ ID NO: 129<br>nivolumab<br>variable heavy<br>chain | QVQLVESGGG | VVQPGRSLRL | DCKASGITFS | NSGMHWVRQA | PGKGLEWVAV | IWYDGSKRYY | 60 |
| | ADSVKGRFTI | SRDNSKNTLF | LQMNSLRAED | TAVYYCATND | DYWGQGTLVT | VSS | 113 |
| SEQ ID NO: 130<br>nivolumab<br>variable light<br>chain | EIVLTQSPAT | LSLSPGERAT | LSCRASQSVS | SYLAWYQQKP | GQAPRLLIYD | ASNRATGIPA | 60 |
| | RFSGSGSGTD | FTLTISSLEP | EDFAVYYCQQ | SSNWPRTFGQ | GTKVEIK | | 107 |
| SEQ ID NO: 131<br>nivolumab | NSGMH | | | | | | 5 |

TABLE 32-continued

Amino acid sequences for PD-1 inhibitors related to nivolumab.

| Identifier | Sequence (One-Letter Amino Acid Symbols) | |
|---|---|---|
| SEQ ID NO: 132 nivolumab heavy chain CDR1 | VIWYDGSKRY YADSVKG | 17 |
| SEQ ID NO: 133 nivolumab heavy chain CDR2 | NDDY | 4 |
| SEQ ID NO: 134 nivolumab heavy chain CDR3 | RASQSVSSYL A | 11 |
| SEQ ID NO: 135 nivolumab light chain CDR1 | DASNRAT | 7 |
| SEQ ID NO: 136 nivolumab light chain CDR2 | QQSSNWPRT | 9 |

In another embodiment, the PD-1 inhibitor comprises pembrolizumab (commercially available as KEYTRUDA from Merck & Co., Inc., Kenilworth, NJ, USA), or antigen-binding fragments, conjugates, or variants thereof. Pembrolizumab is assigned CAS registry number 1374853-91-4 and is also known as lambrolizumab, MK-3475, and SCH-900475. Pembrolizumab has an immunoglobulin G4, anti-(human protein PDCD1 (programmed cell death 1)) (human-Mus musculus monoclonal heavy chain), disulfide with human-Mus musculus monoclonal light chain, dimer structure. The structure of pembrolizumab may also be described as immunoglobulin G4, anti-(human programmed cell death 1); humanized mouse monoclonal [228-L-proline(H10-S>P)]δ4 heavy chain (134-218')-disulfide with humanized mouse monoclonal κ light chain dimer (226-226'':229-229'')-bisdisulfide. The properties, uses, and preparation of pembrolizumab are described in International Patent Publication No. WO 2008/156712 A1, U.S. Pat. No. 8,354,509 and U.S. Patent Application Publication Nos. US 2010/0266617 A1, US 2013/0108651 A1, and US 2013/0109843 A2, the disclosures of which are incorporated herein by reference. The clinical safety and efficacy of pembrolizumab in various forms of cancer is described in Fuerst, Oncology Times, 2014, 36:35-36; Robert, et al., Lancet, 2014, 384:1109-17; and Thomas, et al., Exp. Opin. Biol. Ther., 2014, 14:1061-1064. The amino acid sequences of pembrolizumab are set forth in Table 21. Pembrolizumab includes the following disulfide bridges: 22-96, 22''-96'', 23'-92', 23'''-92''', 134-218', 134''-218''', 138'-198', 138'''-198''', 147-203, 147-203'', 226-226'', 229-229'', 261-321, 261''-321'', 367-425, and 367''-425'', and the following glycosylation sites (N): Asn-297 and Asn-297''. Pembrolizumab is an IgG4/kappa isotype with a stabilizing S228P mutation in the Fc region; insertion of this mutation in the IgG4 hinge region prevents the formation of half molecules typically observed for IgG4 antibodies. Pembrolizumab is heterogeneously glycosylated at Asn297 within the Fc domain of each heavy chain, yielding a molecular weight of approximately 149 kDa for the intact antibody. The dominant glycoform of pembrolizumab is the fucosylated agalacto diantennary glycan form (GOF).

In an embodiment, a PD-1 inhibitor comprises a heavy chain given by SEQ ID NO:137 and a light chain given by SEQ ID NO:138. In an embodiment, a PD-1 inhibitor comprises heavy and light chains having the sequences shown in SEQ ID NO:137 and SEQ ID NO:138, respectively, or antigen binding fragments, Fab fragments, single-chain variable fragments (scFv), variants, or conjugates thereof. In an embodiment, a PD-1 inhibitor comprises heavy and light chains that are each at least 99% identical to the sequences shown in SEQ ID NO:137 and SEQ ID NO:138, respectively. In an embodiment, a PD-1 inhibitor comprises heavy and light chains that are each at least 98% identical to the sequences shown in SEQ ID NO:137 and SEQ ID NO:138, respectively. In an embodiment, a PD-1 inhibitor comprises heavy and light chains that are each at least 97% identical to the sequences shown in SEQ ID NO:137 and SEQ ID NO:138, respectively. In an embodiment, a PD-1 inhibitor comprises heavy and light chains that are each at least 96% identical to the sequences shown in SEQ ID NO:137 and SEQ ID NO:138, respectively. In an embodiment, a PD-1 inhibitor comprises heavy and light chains that are each at least 95% identical to the sequences shown in SEQ ID NO:137 and SEQ ID NO:138, respectively. Representative sequences are listed in Table 17.

In an embodiment, the PD-1 inhibitor comprises the heavy and light chain CDRs or variable regions (VRs) of pembrolizumab. In an embodiment, the PD-1 inhibitor heavy chain variable region ($V_H$) comprises the sequence shown in SEQ ID NO:139, and the PD-1 inhibitor light chain variable region ($V_L$) comprises the sequence shown in SEQ ID NO:140, and conservative amino acid substitutions thereof. In an embodiment, a PD-1 inhibitor comprises $V_H$ and $V_L$ regions that are each at least 99% identical to the sequences shown in SEQ ID NO:139 and SEQ ID NO:140, respectively. In an embodiment, a PD-1 inhibitor comprises $V_H$ and $V_L$ regions that are each at least 98% identical to the sequences shown in SEQ ID NO:139 and SEQ ID NO:140, respectively. In an embodiment, a PD-1 inhibitor comprises $V_H$ and $V_L$ regions that are each at least 97% identical to the sequences shown in SEQ ID NO:139 and SEQ ID NO:140, respectively. In an embodiment, a PD-1 inhibitor comprises $V_H$ and $V_L$ regions that are each at least 96% identical to the sequences shown in SEQ ID NO:139 and SEQ ID NO:140, respectively. In an embodiment, a PD-1 inhibitor comprises $V_H$ and $V_L$ regions that are each at least 95% identical to the sequences shown in SEQ ID NO:139 and SEQ ID NO:140, respectively.

In an embodiment, a PD-1 inhibitor comprises heavy chain CDR1, CDR2 and CDR3 domains having the sequences set forth in SEQ ID NO:141, SEQ ID NO:142, and SEQ ID NO:143, respectively, and conservative amino acid substitutions thereof, and light chain CDR1, CDR2 and CDR3 domains having the sequences set forth in SEQ ID NO:144, SEQ ID NO:145, and SEQ ID NO:146, respectively, and conservative amino acid substitutions thereof. In an embodiment, the antibody competes for binding with, and/or binds to the same epitope on PD-1 as any of the aforementioned antibodies.

In an embodiment, the PD-1 inhibitor is an anti-PD-1 biosimilar monoclonal antibody approved by drug regulatory authorities with reference to pembrolizumab. In an embodiment, the biosimilar comprises an anti-PD-1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is pembrolizumab. In some embodiments, the one or more post-translational modifications are selected from one or more of: glycosylation, oxidation, deamidation, and truncation. In some embodiments, the biosimilar is an anti-PD-1 antibody authorized or submitted for authorization, wherein the anti-PD-1 antibody is provided in a formulation which differs from the formulations of a reference medicinal product or reference biological product, wherein the reference medicinal product or reference biological product is pembrolizumab. The anti-PD-1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is pembrolizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is pembrolizumab.

TABLE 33

Amino acid sequences for PD-1 inhibitors related to pembrolizumab.

| Identifier | Sequence (One-Letter Amino Acid Symbols) | | | | | | |
|---|---|---|---|---|---|---|---|
| SEQ ID NO: 137 pembrolizumab heavy chain | QVQLVQSGVE | VKKPGASVKV | SCKASGYTFT | NYYMYWVRQA | PGQGLEWMGG | INPSNGGTNF | 60 |
| | NEKFKNRVTL | TTDSSTTTAY | MELKSLQFDD | TAVYYCARRD | YRFDMGFDYW | GQGTTVTVSS | 120 |
| | ASTKGPSVFP | LAPCSRSTSE | STAALGCLVK | DYFPEPVTVS | WNSGALTSGV | HTFPAVLQSS | 180 |
| | GLYSLSSVVT | VPSSSLGTKT | YTCNVDHKPS | NTKVDKRVES | KYGPPCPPCP | APEFLGGPSV | 240 |
| | FLFPPKPKDT | LMISRTPEVT | CVVVDVSQED | PEVQFNWYVD | GVEVHNAKTK | PREEQFNSTY | 300 |
| | RVVSVLTVLH | QDWLNGKEYK | CKVSNKGLPS | SIEKTISKAK | GQPREPQVYT | LPPSQEEMTK | 360 |
| | NQVSLTCLVK | GFYPSDIAVE | WESNGQPENN | YKTTPPVLDS | DGSFFLYSRL | TVDKSRWQEG | 420 |
| | NVFSCSVMHE | ALHNHYTQKS | LSLSLGK | | | | 447 |
| SEQ ID NO: 138 pembrolizumab light chain | EIVLTQSPAT | LSLSPGERAT | LSCRASKGVS | TSGYSYLHWY | QQKPGQAPRL | LIYLASYLES | 60 |
| | GVPARFSGSG | SGTDFTLTIS | SLEPEDFAVY | YCQHSRDLPL | TFGGGTKVEI | KRTVAAPSVF | 120 |
| | IFPPSDEQLK | SGTASVVCLL | NNFYPREAKV | QWKVDNALQS | GNSQESVTEQ | DSKDSTYSLS | 180 |
| | STLTLSKADY | EKHKVYACEV | THQGLSSPVT | KSFNRGEC | | | 218 |
| SEQ ID NO: 139 pembrolizumab variable heavy chain | QVQLVQSGVE | VKKPGASVKV | SCKASGYTFT | NYYMYWVRQA | PGQGLEWMGG | INPSNGGTNF | 60 |
| | NEKFKNRVTL | TTDSSTTTAY | MELKSLQFDD | TAVYYCARRD | YRFDMGFDYW | GQGTTVTVSS | 120 |
| SEQ ID NO: 140 pembrolizumab variable light chain | EIVLTQSPAT | LSLSPGERAT | LSCRASKGVS | TSGYSYLHWY | QQKPGQAPRL | LIYLASYLES | 60 |
| | GVPARFSGSG | SGTDFTLTIS | SLEPEDFAVY | YCQHSRDLPL | TFGGGTKVEI | K | 111 |
| SEQ ID NO: 141 pembrolizumab heavy chain CDR1 | NYYMY | | | | | | 5 |
| SEQ ID NO: 142 pembrolizumab heavy chain CDR2 | GINPSNGGTN FNEKFK | | | | | | 16 |
| SEQ ID NO: 143 pembrolizumab heavy chain CDR3 | RDYRFDMGFD Y | | | | | | 11 |

TABLE 33-continued

Amino acid sequences for PD-1 inhibitors related to pembrolizumab.

| Identifier | Sequence (One-Letter Amino Acid Symbols) | |
|---|---|---|
| SEQ ID NO: 144 pembrolizumab light chain CDR1 | RASKGVSTSG YSYLH | 15 |
| SEQ ID NO: 145 pembrolizumab light chain CDR2 | LASYLES | 7 |
| SEQ ID NO: 146 pembrolizumab light chain CDR3 | QHSRDLPLT | 9 |

In an embodiment, the PD-1 inhibitor is a commercially-available anti-PD-1 monoclonal antibody, such as anti-m-PD-1 clones J43 (Cat #BE0033-2) and RMP1-14 (Cat #BE0146) (Bio X Cell, Inc., West Lebanon, NH, USA). A number of commercially-available anti-PD-1 antibodies are known to one of ordinary skill in the art.

In an embodiment, the PD-1 inhibitor is an antibody disclosed in U.S. Pat. No. 8,354,509 or U.S. Patent Application Publication Nos. 2010/0266617 A1, 2013/0108651 A1, 2013/0109843 A2, the disclosures of which are incorporated by reference herein. In an embodiment, the PD-1 inhibitor is an anti-PD-1 antibody described in U.S. Pat. Nos. 8,287,856, 8,580,247, and 8,168,757 and U.S. Patent Application Publication Nos. 2009/0028857 A1, 2010/0285013 A1, 2013/0022600 A1, and 2011/0008369 A1, the teachings of which are hereby incorporated by reference. In another embodiment, the PD-1 inhibitor is an anti-PD-1 antibody disclosed in U.S. Pat. No. 8,735,553 B1, the disclosure of which is incorporated herein by reference. In an embodiment, the PD-1 inhibitor is pidilizumab, also known as CT-011, which is described in U.S. Pat. No. 8,686,119, the disclosure of which is incorporated by reference herein.

In an embodiment, the PD-1 inhibitor may be a small molecule or a peptide, or a peptide derivative, such as those described in U.S. Pat. Nos. 8,907,053; 9,096,642; and 9,044,442 and U.S. Patent Application Publication No. US 2015/0087581; 1,2,4-oxadiazole compounds and derivatives such as those described in U.S. Patent Application Publication No. 2015/0073024; cyclic peptidomimetic compounds and derivatives such as those described in U.S. Patent Application Publication No. US 2015/0073042; cyclic compounds and derivatives such as those described in U.S. Patent Application Publication No. US 2015/0125491; 1,3,4-oxadiazole and 1,3,4-thiadiazole compounds and derivatives such as those described in International Patent Application Publication No. WO 2015/033301; peptide-based compounds and derivatives such as those described in International Patent Application Publication Nos. WO 2015/036927 and WO 2015/04490, or a macrocyclic peptide-based compounds and derivatives such as those described in U.S. Patent Application Publication No. US 2014/0294898; the disclosures of each of which are hereby incorporated by reference in their entireties.

In an embodiment, the PD-L1 or PD-L2 inhibitor may be any PD-L1 or PD-L2 inhibitor, antagonist, or blocker known in the art. In particular, it is one of the PD-L1 or PD-L2 inhibitors, antagonist, or blockers described in more detail in the following paragraphs. The terms "inhibitor," "antagonist," and "blocker" are used interchangeably herein in reference to PD-L1 and PD-L2 inhibitors. For avoidance of doubt, references herein to a PD-L1 or PD-L2 inhibitor that is an antibody may refer to a compound or antigen-binding fragments, variants, conjugates, or biosimilars thereof. For avoidance of doubt, references herein to a PD-L1 or PD-L2 inhibitor may refer to a compound or a pharmaceutically acceptable salt, ester, solvate, hydrate, cocrystal, or prodrug thereof.

In some embodiments, the compositions, processes and methods described herein include a PD-L1 or PD-L2 inhibitor. In some embodiments, the PD-L1 or PD-L2 inhibitor is a small molecule. In a preferred embodiment, the PD-L1 or PD-L2 inhibitor is an antibody (i.e., an anti-PD-1 antibody), a fragment thereof, including Fab fragments, or a single-chain variable fragment (scFv) thereof. In some embodiments the PD-L1 or PD-L2 inhibitor is a polyclonal antibody. In a preferred embodiment, the PD-L1 or PD-L2 inhibitor is a monoclonal antibody. In some embodiments, the PD-L1 or PD-L2 inhibitor competes for binding with PD-L1 or PD-L2, and/or binds to an epitope on PD-L1 or PD-L2. In an embodiment, the antibody competes for binding with PD-L1 or PD-L2, and/or binds to an epitope on PD-L1 or PD-L2.

In some embodiments, the PD-L1 inhibitors provided herein are selective for PD-L1, in that the compounds bind or interact with PD-L1 at substantially lower concentrations than they bind or interact with other receptors, including the PD-L2 receptor. In certain embodiments, the compounds bind to the PD-L1 receptor at a binding constant that is at least about a 2-fold higher concentration, about a 3-fold higher concentration, about a 5-fold higher concentration, about a 10-fold higher concentration, about a 20-fold higher concentration, about a 30-fold higher concentration, about a 50-fold higher concentration, about a 100-fold higher concentration, about a 200-fold higher concentration, about a 300-fold higher concentration, or about a 500-fold higher concentration than to the PD-L2 receptor.

In some embodiments, the PD-L2 inhibitors provided herein are selective for PD-L2, in that the compounds bind or interact with PD-L2 at substantially lower concentrations than they bind or interact with other receptors, including the PD-L1 receptor. In certain embodiments, the compounds bind to the PD-L2 receptor at a binding constant that is at least about a 2-fold higher concentration, about a 3-fold higher concentration, about a 5-fold higher concentration, about a 10-fold higher concentration, about a 20-fold higher concentration, about a 30-fold higher concentration, about a 50-fold higher concentration, about a 100-fold higher concentration, about a 200-fold higher concentration, about a 300-fold higher concentration, or about a 500-fold higher concentration than to the PD-L1 receptor.

Without being bound by any theory, it is believed that tumor cells express PD-L1, and that T cells express PD-1. However, PD-L1 expression by tumor cells is not required for efficacy of PD-1 or PD-L1 inhibitors or blockers. In an embodiment, the tumor cells express PD-L1. In another embodiment, the tumor cells do not express PD-L1. In some embodiments, the methods and compositions described herein include a combination of a PD-1 and a PD-L1 antibody, such as those described herein, in combination with a TIL. The administration of a combination of a PD-1 and a PD-L1 antibody and a TIL may be simultaneous or sequential.

In some embodiments, the compositions and methods described include a PD-L1 and/or PD-L2 inhibitor that binds human PD-L1 and/or PD-L2 with a $K_D$ of about 100 pM or lower, binds human PD-L1 and/or PD-L2 with a $K_D$ of about 90 pM or lower, binds human PD-L1 and/or PD-L2 with a $K_D$ of about 80 pM or lower, binds human PD-L1 and/or PD-L2 with a $K_D$ of about 70 pM or lower, binds human PD-L1 and/or PD-L2 with a $K_D$ of about 60 pM or lower, a $K_D$ of about 50 pM or lower, binds human PD-L1 and/or PD-L2 with a $K_D$ of about 40 pM or lower, or binds human PD-L1 and/or PD-L2 with a KD of about 30 pM or lower, In some embodiments, the compositions and methods described include a PD-L1 and/or PD-L2 inhibitor that binds to human PD-L1 and/or PD-L2 with a $k_{dissoc}$ of about $7.5 \times 10^5$ 1/M·s or faster, binds to human PD-L1 and/or PD-L2 with a $k_{assoc}$ of about $8 \times 10^5$ 1/M·s or faster, binds to human PD-L1 and/or PD-L2 with a $k_{assoc}$ of about $8.5 \times 10^5$ 1/M·s or faster, binds to human PD-L1 and/or PD-L2 with a $k_{assoc}$ of about $9 \times 10^5$ 1/M·s or faster, binds to human PD-L1 and/or PD-L2 with a $k_{assoc}$ of about $9.5 \times 10^5$ 1/M·s and/or faster, or binds to human PD-L1 and/or PD-L2 with a $k_{assoc}$ of about $1 \times 10^6$ i/Ms or faster.

In some embodiments, the compositions and methods described include a PD-L1 and/or PD-L2 inhibitor that binds to human PD-L1 or PD-L2 with a $k_{dissoc}$ of about $2 \times 10^{-5}$ 1/s or slower, binds to human PD-1 with a $k_{dissoc}$ of about $2.1 \times 10^{-5}$ 1/s or slower, binds to human PD-1 with a $k_{dissoc}$ of about $2.2 \times 10^{-5}$ 1/s or slower, binds to human PD-1 with a $k_{dissoc}$ of about $2.3 \times 10^{-5}$ 1/s or slower, binds to human PD-1 with a $k_{dissoc}$ of about $2.4 \times 10^{-5}$ 1/s or slower, binds to human PD-1 with a $k_{dissoc}$ of about $2.5 \times 10^{-5}$ 1/s or slower, binds to human PD-1 with a $k_{dissoc}$ of about $2.6 \times 10^{-5}$ 1/s or slower, binds to human PD-L1 or PD-L2 with a $k_{dissoc}$ of about $2.7 \times 10^{-5}$ 1/s or slower, or binds to human PD-L1 or PD-L2 with a $k_{dissoc}$ of about $3 \times 10^{-5}$ 1/s or slower.

In some embodiments, the compositions and methods described include a PD-L1 and/or PD-L2 inhibitor that blocks or inhibits binding of human PD-L1 or human PD-L2 to human PD-1 with an $IC_{50}$ of about 10 nM or lower; blocks or inhibits binding of human PD-L1 or human PD-L2 to human PD-1 with an $IC_{50}$ of about 9 nM or lower; blocks or inhibits binding of human PD-L1 or human PD-L2 to human PD-1 with an $IC_{50}$ of about 8 nM or lower; blocks or inhibits binding of human PD-L1 or human PD-L2 to human PD-1 with an $IC_{50}$ of about 7 nM or lower; blocks or inhibits binding of human PD-L1 or human PD-L2 to human PD-1 with an $IC_{50}$ of about 6 nM or lower; blocks or inhibits binding of human PD-L1 or human PD-L2 to human PD-1 with an $IC_{50}$ of about 5 nM or lower; blocks or inhibits binding of human PD-L1 or human PD-L2 to human PD-1 with an $IC_{50}$ of about 4 nM or lower; blocks or inhibits binding of human PD-L1 or human PD-L2 to human PD-1 with an $IC_{50}$ of about 3 nM or lower; blocks or inhibits binding of human PD-L1 or human PD-L2 to human PD-1 with an $IC_{50}$ of about 2 nM or lower; or blocks human PD-1, or blocks binding of human PD-L1 or human PD-L2 to human PD-1 with an $IC_{50}$ of about 1 nM or lower.

In an embodiment, the PD-L1 inhibitor is durvalumab, also known as MEDI4736 (which is commercially available from Medimmune, LLC, Gaithersburg, Maryland, a subsidiary of AstraZeneca plc.), or antigen-binding fragments, conjugates, or variants thereof. In an embodiment, the PD-L1 inhibitor is an antibody disclosed in U.S. Pat. No. 8,779,108 or U.S. Patent Application Publication No. 2013/0034559, the disclosures of which are incorporated by reference herein. The clinical efficacy of durvalumab has been described in Page, et al., *Ann. Rev. Med.,* 2014, 65:185-202; Brahmer, et al., *J. Clin. Oncol.* 2014, 32:5s (supplement, abstract 8021); and McDermott, et al., *Cancer Treatment Rev.,* 2014, 40:1056-64. The preparation and properties of durvalumab are described in U.S. Pat. No. 8,779,108, the disclosure of which is incorporated by reference herein. The amino acid sequences of durvalumab are set forth in Table 18. The durvalumab monoclonal antibody includes disulfide linkages at 22-96, 22"-96", 23'-89', 23'''-89''', 135'-195', 135'''-195''', 148-204, 148"-204", 215'-224, 215'''-224", 230-230", 233-233", 265-325, 265"-325", 371-429, and 371"-429'; and N-glycosylation sites at Asn-301 and Asn-301".

In an embodiment, a PD-L1 inhibitor comprises a heavy chain given by SEQ ID NO:147 and a light chain given by SEQ ID NO:148. In an embodiment, a PD-L1 inhibitor comprises heavy and light chains having the sequences shown in SEQ ID NO:147 and SEQ ID NO:148, respectively, or antigen binding fragments, Fab fragments, single-chain variable fragments (scFv), variants, or conjugates thereof. In an embodiment, a PD-L1 inhibitor comprises heavy and light chains that are each at least 99% identical to the sequences shown in SEQ ID NO:147 and SEQ ID NO:148, respectively. In an embodiment, a PD-L1 inhibitor comprises heavy and light chains that are each at least 98% identical to the sequences shown in SEQ ID NO:147 and SEQ ID NO:148, respectively. In an embodiment, a PD-L1 inhibitor comprises heavy and light chains that are each at least 97% identical to the sequences shown in SEQ ID NO:147 and SEQ ID NO:148, respectively. In an embodiment, a PD-L1 inhibitor comprises heavy and light chains that are each at least 96% identical to the sequences shown in SEQ ID NO:147 and SEQ ID NO:148, respectively. In an embodiment, a PD-L1 inhibitor comprises heavy and light chains that are each at least 95% identical to the sequences shown in SEQ ID NO:147 and SEQ ID NO:148, respectively.

In an embodiment, the PD-L1 inhibitor comprises the heavy and light chain CDRs or variable regions (VRs) of durvalumab. In an embodiment, the PD-L1 inhibitor heavy chain variable region ($V_H$) comprises the sequence shown in SEQ ID NO:149, and the PD-L1 inhibitor light chain variable region ($V_L$) comprises the sequence shown in SEQ ID NO:150, and conservative amino acid substitutions thereof. In an embodiment, a PD-L1 inhibitor comprises $V_H$ and $V_L$ regions that are each at least 99% identical to the sequences shown in SEQ ID NO:149 and SEQ ID NO:150, respectively. In an embodiment, a PD-L1 inhibitor comprises $V_H$ and $V_L$ regions that are each at least 98% identical to the sequences shown in SEQ ID NO:149 and SEQ ID NO:150, respectively. In an embodiment, a PD-L1 inhibitor comprises $V_H$ and $V_L$ regions that are each at least 97% identical to the sequences shown in SEQ ID NO:149 and SEQ ID NO:150, respectively. In an embodiment, a PD-L1 inhibitor comprises $V_H$ and $V_L$ regions that are each at least 96% identical to the sequences shown in SEQ ID NO:149 and SEQ ID NO:150, respectively. In an embodiment, a PD-L1 inhibitor comprises $V_H$ and $V_L$ regions that are each at least 95% identical to the sequences shown in SEQ ID NO:149 and SEQ ID NO:150, respectively.

In an embodiment, a PD-L1 inhibitor comprises heavy chain CDR1, CDR2 and CDR3 domains having the sequences set forth in SEQ ID NO:151, SEQ ID NO:152, and SEQ ID NO:153, respectively, and conservative amino acid substitutions thereof, and light chain CDR1, CDR2 and CDR3 domains having the sequences set forth in SEQ ID NO:154, SEQ ID NO:155, and SEQ ID NO:156, respectively, and conservative amino acid substitutions thereof. In an embodiment, the antibody competes for binding with, and/or binds to the same epitope on PD-L1 as any of the aforementioned antibodies.

In an embodiment, the PD-L1 inhibitor is an anti-PD-L1 biosimilar monoclonal antibody approved by drug regulatory authorities with reference to durvalumab. In an embodiment, the biosimilar comprises an anti-PD-L1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is durvalumab. In some embodiments, the one or more post-translational modifications are selected from one or more of: glycosylation, oxidation, deamidation, and truncation. In some embodiments, the biosimilar is an anti-PD-L1 antibody authorized or submitted for authorization, wherein the anti-PD-L1 antibody is provided in a formulation which differs from the formulations of a reference medicinal product or reference biological product, wherein the reference medicinal product or reference biological product is durvalumab. The anti-PD-L1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is durvalumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is durvalumab.

TABLE 34

Amino acid sequences for PD-L1 inhibitors related to durvalumab.

| Identifier | Sequence (One-Letter Amino Acid Symbols) | |
|---|---|---|
| SEQ ID NO: 147 durvalumab heavy chain | EVQLVESGGG LVQPGGSLRL SCAASGFTFS RYWMSWVRQA PGKGLEWVAN IKQDGSEKYY | 60 |
| | VDSVKGRFTI SRDNAKNSLY LQMNSLRAED TAVYYCAREG GWFGELAFDY WGQGTLVTVS | 120 |
| | SASTKGPSVF PLAPSSKSTS GGTAALGCLV KDYFPEPVTV SWNSGALTSG VHTFPAVLQS | 180 |
| | SGLYSLSSVV TVPSSSLGTQ TYICNVNHKP SNTKVDKRVE PKSCDKTHTC PPCPAPEFEG | 240 |
| | GPSVFLFPPK PKDTLMISRT PEVTCVVVDV SHEDPEVKFN WYVDGVEVHN AKTKPREEQY | 300 |
| | NSTYRVVSVL TVLHQDWLNG KEYKCKVSNK ALPASIEKTI SKAKGQPREP QVYTLPPSRE | 360 |
| | EMTKNQVSLT CLVKGFYPSD IAVEWESNGQ PENNYKTTPP VLDSDGSFFL YSKLTVDKSR | 420 |
| | WQQGNVFSCS VMHEALHNHY TQKSLSLSPG K | 451 |
| SEQ ID NO: 148 durvalumab light chain | EVQLVESGGG LVQPGGSLRL SCAASGFTFS RYWMSWVRQA PGKGLEWVAN EIVLTQSPGT | 60 |
| | LSLSPGERAT LSCRASQRVS SSYLAWYQQK PGQAPRLLIY DASSRATGIP DRFSGSGSGT | 120 |
| | DFTLTISRLE PEDFAVYYCQ QYGSLPWTFG QGTKVEIKRT VAAPSVFIFP PSDEQLKSGT | 180 |
| | ASVVCLLNNF YPREAKVQWK VDNALQSGNS QESVTEQDSK DSTYSLSSTL TLSKADYEKH | 240 |
| | KVYACEVTHQ GLSSPVTKSF NRGEC | 265 |
| SEQ ID NO: 149 durvalumab variable heavy chain | EVQLVESGGG LVQPGGSLRL SCAASGFTFS RYWMSWVRQA PGKGLEWVAN IKQDGSEKYY | 60 |
| | VDSVKGRFTI SRDNAKNSLY LQMNSLRAED TAVYYCAREG GWFGELAFDY WGQGTLVTVS | 120 |
| | S | 121 |
| SEQ ID NO: 150 durvalumab variable light chain | EIVLTQSPGT LSLSPGERAT LSCRASQRVS SSYLAWYQQK PGQAPRLLIY DASSRATGIP | 60 |
| | PEDFAVYYCQ QYGSLPWTFG QGTKVEIK | 108 |
| SEQ ID NO: 151 durvalumab heavy chain CDR1 | RYWMS | 5 |
| SEQ ID NO: 152 durvalumab heavy chain CDR2 | NIKQDGSEKY YVDSVKG | 17 |
| SEQ ID NO: 153 durvalumab heavy chain CDR3 | EGGWFGELAF DY | 12 |

TABLE 34-continued

Amino acid sequences for PD-L1 inhibitors related to durvalumab.

| Identifier | Sequence (One-Letter Amino Acid Symbols) | |
|---|---|---|
| SEQ ID NO: 154 durvalumab light chain CDR1 | RASQRVSSSY LA | 12 |
| SEQ ID NO: 155 durvalumab light chain CDR2 | DASSRAT | 7 |
| SEQ ID NO: 156 durvalumab light chain CDR3 | QQYGSLPWT | 9 |

In an embodiment, the PD-L1 inhibitor is avelumab, also known as MSB0010718C (commercially available from Merck KGaA/EMD Serono), or antigen-binding fragments, conjugates, or variants thereof. The preparation and properties of avelumab are described in U.S. Patent Application Publication No. US 2014/0341917 A1, the disclosure of which is specifically incorporated by reference herein. The amino acid sequences of avelumab are set forth in Table 19. Avelumab has intra-heavy chain disulfide linkages (C23-C104) at 22-96, 147-203, 264-324, 370-428, 22"-96", 147-203", 264"-324", and 370"-428"; intra-light chain disulfide linkages (C23-C104) at 22'-90', 138'-197', 22'''-90''', and 138'''-197'''; intra-heavy-light chain disulfide linkages (h 5-CL 126) at 223-215' and 223"-215'''; intra-heavy-heavy chain disulfide linkages (h 11, h 14) at 229-229" and 232-232"; N-glycosylation sites (H $CH_2$ N84.4) at 300, 300"; fucosylated complex bi-antennary CHO-type glycans; and H CHS K2 C-terminal lysine clipping at 450 and 450'.

In an embodiment, a PD-L1 inhibitor comprises a heavy chain given by SEQ ID NO:157 and a light chain given by SEQ ID NO:158. In an embodiment, a PD-L1 inhibitor comprises heavy and light chains having the sequences shown in SEQ ID NO:157 and SEQ ID NO:158, respectively, or antigen binding fragments, Fab fragments, single-chain variable fragments (scFv), variants, or conjugates thereof. In an embodiment, a PD-L1 inhibitor comprises heavy and light chains that are each at least 99% identical to the sequences shown in SEQ ID NO:157 and SEQ ID NO:158, respectively. In an embodiment, a PD-L1 inhibitor comprises heavy and light chains that are each at least 98% identical to the sequences shown in SEQ ID NO:157 and SEQ ID NO:158, respectively. In an embodiment, a PD-L1 inhibitor comprises heavy and light chains that are each at least 97% identical to the sequences shown in SEQ ID NO:157 and SEQ ID NO:158, respectively. In an embodiment, a PD-L1 inhibitor comprises heavy and light chains that are each at least 96% identical to the sequences shown in SEQ ID NO:157 and SEQ ID NO:158, respectively. In an embodiment, a PD-L1 inhibitor comprises heavy and light chains that are each at least 95% identical to the sequences shown in SEQ ID NO:157 and SEQ ID NO:158, respectively.

In an embodiment, the PD-L1 inhibitor comprises the heavy and light chain CDRs or variable regions (VRs) of avelumab. In an embodiment, the PD-L1 inhibitor heavy chain variable region ($V_H$) comprises the sequence shown in SEQ ID NO:159, and the PD-L1 inhibitor light chain variable region ($V_L$) comprises the sequence shown in SEQ ID NO:160, and conservative amino acid substitutions thereof. In an embodiment, a PD-L1 inhibitor comprises $V_H$ and $V_L$ regions that are each at least 99% identical to the sequences shown in SEQ ID NO:159 and SEQ ID NO:160, respectively. In an embodiment, a PD-L1 inhibitor comprises $V_H$ and $V_L$ regions that are each at least 98% identical to the sequences shown in SEQ ID NO:160 and SEQ ID NO:160, respectively. In an embodiment, a PD-L1 inhibitor comprises $V_H$ and $V_L$ regions that are each at least 97% identical to the sequences shown in SEQ ID NO:159 and SEQ ID NO:160, respectively. In an embodiment, a PD-L1 inhibitor comprises $V_H$ and $V_L$ regions that are each at least 96% identical to the sequences shown in SEQ ID NO:159 and SEQ ID NO:160, respectively. In an embodiment, a PD-L1 inhibitor comprises $V_H$ and $V_L$ regions that are each at least 95% identical to the sequences shown in SEQ ID NO:159 and SEQ ID NO:160, respectively.

In an embodiment, a PD-L1 inhibitor comprises heavy chain CDR1, CDR2 and CDR3 domains having the sequences set forth in SEQ ID NO:161, SEQ ID NO:162, and SEQ ID NO:163, respectively, and conservative amino acid substitutions thereof, and light chain CDR1, CDR2 and CDR3 domains having the sequences set forth in SEQ ID NO:164, SEQ ID NO:165, and SEQ ID NO:166, respectively, and conservative amino acid substitutions thereof. In an embodiment, the antibody competes for binding with, and/or binds to the same epitope on PD-L1 as any of the aforementioned antibodies.

In an embodiment, the PD-L1 inhibitor is an anti-PD-L1 biosimilar monoclonal antibody approved by drug regulatory authorities with reference to avelumab. In an embodiment, the biosimilar comprises an anti-PD-L1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is avelumab. In some embodiments, the one or more post-translational modifications are selected from one or more of: glycosylation, oxidation, deamidation, and truncation. In some embodiments, the biosimilar is an anti-PD-L1 antibody authorized or submitted for authorization, wherein the anti-PD-L1 antibody is provided in a formulation which differs from the formulations of a reference medicinal product or reference biological product, wherein the reference medicinal product or reference biological product is avelumab. The anti-PD-L1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is avelumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is avelumab.

TABLE 35

Amino acid sequences for PD-L1 inhibitors related to avelumab.

| Identifier | Sequence (One-Letter Amino Acid Symbols) | |
|---|---|---|
| SEQ ID NO: 157 avelumab heavy chain | EVQLLESGGG LVQPGGSLRL SCAASGFTFS SYIMMWVRQA PGKGLEWVSS IYPSGGITFY<br>ADTVKGRFTI SRDNSKNTLY LQMNSLRAED TAVYYCARIK LGTVTTVDYW GQGTLVTVSS<br>ASTKGPSVFP LAPSSKSTSG GTAALGCLVK DYFPEPVTVS WNSGALTSGV HTFPAVLQSS<br>GLYSLSSVVT VPSSSLGTQT YICNVNHKPS NTKVDKKVEP KSCDKTHTCP PCPAPELLGG<br>PSVFLFPPKP KDTLMISRTP EVTCVVVDVS HEDPEVKFNW YVDGVEVHNA KTKPREEQYN<br>STYRVVSVLT VLHQDWLNGK EYKCKVSNKA LPAPIEKTIS KAKGQPREPQ VYTLPPSRDE<br>LTKNQVSLTC LVKGFYPSDI AVEWESNGQP ENNYKTTPPV LDSDGSFFLY SKLTVDKSRW<br>QQGNVFSCSV MHEALHNHYT QKSLSLSPGK | 60<br>120<br>180<br>240<br>300<br>360<br>420<br>450 |
| SEQ ID NO: 158 avelumab light chain | QSALTQPASV SGSPGQSITI SCTGTSSDVG GYNYVSWYQQ HPGKAPKLMI YDVSNRPSGV<br>SNRFSGSKSG NTASLTISGL QAEDEADYYC SSYTSSSTRV FGTGTKVTVL GQPKANPTVT<br>LFPPSSEELQ ANKATLVCLI SDFYPGAVTV AWKADGSPVK AGVETTKPSK QSNNKYAASS<br>YLSLTPEQWK SHRSYSCQVT HEGSTVEKTV APTECS | 60<br>120<br>180<br>216 |
| SEQ ID NO: 159 avelumab variable heavy chain | EVQLLESGGG LVQPGGSLRL SCAASGFTFS SYIMMWVRQA PGKGLEWVSS IYPSGGITFY<br>ADTVKGRFTI SRDNSKNTLY LQMNSLRAED TAVYYCARIK LGTVTTVDYW GQGTLVTVSS | 60<br>120 |
| SEQ ID NO: 160 avelumab variable light chain | QSALTQPASV SGSPGQSITI SCTGTSSDVG GYNYVSWYQQ HPGKAPKLMI YDVSNRPSGV<br>SNRFSGSKSG NTASLTISGL QAEDEADYYC SSYTSSSTRV FGTGTKVTVL | 60<br>110 |
| SEQ ID NO: 161 avelumab heavy chain CDR1 | SYIMM | 5 |
| SEQ ID NO: 162 avelumab heavy chain CDR2 | SIYPSGGITF YADTVKG | 17 |
| SEQ ID NO: 163 avelumab heavy chain CDR3 | IKLGTVTTVD Y | 11 |
| SEQ ID NO: 164 avelumab light chain CDR1 | TGTSSDVGGY NYVS | 14 |
| SEQ ID NO: 165 avelumab light chain CDR2 | DVSNRPS | 7 |
| SEQ ID NO: 166 avelumab light chain CDR3 | SSYTSSSTRV | 10 |

In an embodiment, the PD-L1 inhibitor is atezolizumab, also known as MPDL3280A or RG7446 (commercially available as TECENTRIQ from Genentech, Inc., a subsidiary of Roche Holding AG, Basel, Switzerland), or antigen-binding fragments, conjugates, or variants thereof. In an embodiment, the PD-L1 inhibitor is an antibody disclosed in U.S. Pat. No. 8,217,149, the disclosure of which is specifically incorporated by reference herein. In an embodiment, the PD-L1 inhibitor is an antibody disclosed in U.S. Patent Application Publication Nos. 2010/0203056 A1, 2013/0045200 A1, 2013/0045201 A1, 2013/0045202 A1, or 2014/0065135 A1, the disclosures of which are specifically incorporated by reference herein. The preparation and properties of atezolizumab are described in U.S. Pat. No. 8,217,149, the disclosure of which is incorporated by reference herein. The amino acid sequences of atezolizumab are set forth in Table 20. Atezolizumab has intra-heavy chain disulfide linkages (C23-C104) at 22-96, 145-201, 262-322, 368-426, 22"-96", 145"-201", 262"-322", and 368"-426"; intra-light chain disulfide linkages (C23-C104) at 23'-88', 134'-194', 23'"-88'", and 134'"-194'"; intra-heavy-light chain disulfide linkages (h 5-CL 126) at 221-214' and 221"-214'"; intra-heavy-heavy chain disulfide linkages (h 11, h 14) at 227-227" and 230-230"; and N-glycosylation sites (H CH$_2$ N84.4>A) at 298 and 298'.

In an embodiment, a PD-L1 inhibitor comprises a heavy chain given by SEQ ID NO:167 and a light chain given by SEQ ID NO:168. In an embodiment, a PD-L1 inhibitor comprises heavy and light chains having the sequences shown in SEQ ID NO:167 and SEQ ID NO:168, respectively, or antigen binding fragments, Fab fragments, single-chain variable fragments (scFv), variants, or conjugates thereof. In an embodiment, a PD-L1 inhibitor comprises heavy and light chains that are each at least 99% identical to the sequences shown in SEQ ID NO:167 and SEQ ID NO:168, respectively. In an embodiment, a PD-L1 inhibitor comprises heavy and light chains that are each at least 98% identical to the sequences shown in SEQ ID NO:167 and SEQ ID NO:168, respectively. In an embodiment, a PD-L1 inhibitor comprises heavy and light chains that are each at least 97% identical to the sequences shown in SEQ ID NO:167 and SEQ ID NO:168, respectively. In an embodiment, a PD-L1 inhibitor comprises heavy and light chains that are each at least 96% identical to the sequences shown in SEQ ID NO:167 and SEQ ID NO:168, respectively. In an embodiment, a PD-L1 inhibitor comprises heavy and light chains that are each at least 95% identical to the sequences shown in SEQ ID NO:167 and SEQ ID NO:168, respectively.

In an embodiment, the PD-L1 inhibitor comprises the heavy and light chain CDRs or variable regions (VRs) of atezolizumab. In an embodiment, the PD-L1 inhibitor heavy chain variable region (V$_H$) comprises the sequence shown in SEQ ID NO:169, and the PD-L1 inhibitor light chain variable region (V$_L$) comprises the sequence shown in SEQ ID NO:170, and conservative amino acid substitutions thereof. In an embodiment, a PD-L1 inhibitor comprises V$_H$ and V$_L$ regions that are each at least 99% identical to the sequences shown in SEQ ID NO:169 and SEQ ID NO:170, respectively. In an embodiment, a PD-L1 inhibitor comprises V$_H$ and V$_L$ regions that are each at least 98% identical to the sequences shown in SEQ ID NO:169 and SEQ ID NO:170, respectively. In an embodiment, a PD-L1 inhibitor comprises V$_H$ and V$_L$ regions that are each at least 97% identical to the sequences shown in SEQ ID NO:169 and SEQ ID NO:170, respectively. In an embodiment, a PD-L1 inhibitor comprises V$_H$ and V$_L$ regions that are each at least 96% identical to the sequences shown in SEQ ID NO:169 and SEQ ID NO:170, respectively. In an embodiment, a PD-L1 inhibitor comprises V$_H$ and V$_L$ regions that are each at least 95% identical to the sequences shown in SEQ ID NO:169 and SEQ ID NO:170, respectively.

In an embodiment, a PD-L1 inhibitor comprises heavy chain CDR1, CDR2 and CDR3 domains having the sequences set forth in SEQ ID NO:171, SEQ ID NO:172, and SEQ ID NO:173, respectively, and conservative amino acid substitutions thereof, and light chain CDR1, CDR2 and CDR3 domains having the sequences set forth in SEQ ID NO:174, SEQ ID NO:175, and SEQ ID NO:176, respectively, and conservative amino acid substitutions thereof. In an embodiment, the antibody competes for binding with, and/or binds to the same epitope on PD-L1 as any of the aforementioned antibodies.

In an embodiment, the anti-PD-L1 antibody is an anti-PD-L1 biosimilar monoclonal antibody approved by drug regulatory authorities with reference to atezolizumab. In an embodiment, the biosimilar comprises an anti-PD-L1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is atezolizumab. In some embodiments, the one or more post-translational modifications are selected from one or more of: glycosylation, oxidation, deamidation, and truncation. In some embodiments, the biosimilar is an anti-PD-L1 antibody authorized or submitted for authorization, wherein the anti-PD-L1 antibody is provided in a formulation which differs from the formulations of a reference medicinal product or reference biological product, wherein the reference medicinal product or reference biological product is atezolizumab. The anti-PD-L1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is atezolizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is atezolizumab.

TABLE 36

Amino acid sequences for PD-L1 inhibitors related to atezolizumab.

| Identifier | Sequence (One-Letter Amino Acid Symbols) | | | | | | |
|---|---|---|---|---|---|---|---|
| SEQ ID NO: 167 atezolizumab heavy chain | EVQLVESGGG | LVQPGGSLRL | SCAASGFTFS | DSWIHWVRQA | PGKGLEWVAW | ISPYGGSTYY | 60 |
| | ADSVKGRFTI | SADTSKNTAY | LQMNSLRAED | TAVYYCARRH | WPGGFDYWGQ | GTLVTVSSAS | 120 |
| | TKGPSVFPLA | PSSKSTSGGT | AALGCLVKDY | FPEPVTVSWN | SGALTSGVHT | FPAVLQSSGL | 180 |
| | YSLSSVVTVP | SSSLGTQTYI | CNVNHKPSNT | KVDKKVEPKS | CDKTHTCPPC | PAPELLGGPS | 240 |
| | VFLFPPKPKD | TLMISRTPEV | TCVVVDVSHE | DPEVKFNWYV | DGVEVHNAKT | KPREEQYAST | 300 |
| | YRVVSVLTVL | HQDWLNGKEY | KCKVSNKALP | APIEKTISKA | KGQPREPQVY | TLPPSREEMT | 360 |
| | KNQVSLTCLV | KGFYPSDIAV | EWESNGQPEN | NYKTTPPVLD | SDGSFFLYSK | LTVDKSRWQQ | 420 |
| | GNVFSCSVMH | EALHNHYTQK | SLSLSPGK | | | | 448 |
| SEQ ID NO: 168 atezolizumab | DIQMTQSPSS | LSASVGDRVT | ITCRASQDVS | TAVAWYQQKP | GKAPKLLIYS | ASFLYSGVPS | 60 |
| | RFSGSGSGTD | FTLTISSLQP | EDFATYYCQQ | YLYHPATFGQ | GTKVEIKRTV | AAPSVFIFPP | 120 |

TABLE 36-continued

Amino acid sequences for PD-L1 inhibitors related to atezolizumab.

| Identifier | Sequence (One-Letter Amino Acid Symbols) | |
|---|---|---|
| light chain | SDEQLKSGTA SVVCLLNNFY PREAKVQWKV DNALQSGNSQ ESVTEQDSKD STYSLSSTLT<br>LSKADYEKHK VYACEVTHQG LSSPVTKSFN RGEC | 180<br>214 |
| SEQ ID NO: 169<br>atezolizumab<br>variable<br>heavy chain | EVQLVESGGG LVQPGGSLRL SCAASGFTFS DSWIHWVRQA PGKGLEWVAW ISPYGGSTYY<br>ADSVKGRFTI SADTSKNTAY LQMNSLRAED TAVYYCARRH WPGGFDYWGQ GTLVTVSA | 60<br>118 |
| SEQ ID NO: 170<br>atezolizumab<br>variable<br>light chain | DIQMTQSPSS LSASVGDRVT ITCRASQDVS TAVAWYQQKP GKAPKLLIYS ASFLYSGVPS<br>RFSGSGSGTD FTLTISSLQP EDFATYYCQQ YLYHPATFGQ GTKVEIKR | 60<br>108 |
| SEQ ID NO: 171<br>atezolizumab<br>heavy chain<br>CDR1 | GFTFSDSWIH | 10 |
| SEQ ID NO: 172<br>atezolizumab<br>heavy chain<br>CDR2 | AWISPYGGST YYADSVKG | 18 |
| SEQ ID NO: 173<br>atezolizumab<br>heavy chain<br>CDR3 | RHWPGGFDY | 9 |
| SEQ ID NO: 174<br>atezolizumab<br>light chain<br>CDR1 | RASQDVSTAV A | 11 |
| SEQ ID NO: 175<br>atezolizumab<br>light chain<br>CDR2 | SASFLYS | 7 |
| SEQ ID NO: 176<br>atezolizumab<br>light chain<br>CDR3 | QQYLYHPAT | 9 |

While preferred embodiments of the invention are shown and described herein, such embodiments are provided by way of example only and are not intended to otherwise limit the scope of the invention. Various alternatives to the described embodiments of the invention may be employed in practicing the invention. Therefore, the spirit and scope of the appended claims should not be limited to the description of the preferred versions contained herein.

The reader's attention is directed to all papers and documents which are filed concurrently with this specification and which are open to public inspection with this specification, and the contents of all such papers and documents incorporated herein by reference. All the features disclosed in the specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1. Preparation of Media for Pre-REP and REP Processes

This Example describes the procedure for the preparation of tissue culture media for use in protocols involving the culture of tumor infiltrating lymphocytes (TIL) derived from various tumor types including, but not limited to, metastatic melanoma, head and neck squamous cell carcinoma (HN-SCC), ovarian carcinoma, triple-negative breast carcinoma, and lung adenocarcinoma. This media can be used for preparation of any of the TILs described in the present application and Examples.

Preparation of CM1

Removed the following reagents from cold storage and warmed them in a 37° C. water bath: (RPMI1640, Human AB serum, 200 mM L-glutamine). Prepared CM1 medium according to Table 37 below by adding each of the ingredients into the top section of a 0.2 μm filter unit appropriate to the volume to be filtered. Store at 4° C.

TABLE 37

Preparation of CM1

| Ingredient | Final Concentration | Final Volume 500 ml | Final Volume 1 L |
|---|---|---|---|
| RPMI1640 | NA | 450 mL | 900 mL |
| Human AB serum, heat-inactivated 10% | 50 mL | 100 mL | |
| 200 mM L-glutamine | 2 mM | 5 mL | 10 mL |
| 55 mM BME | 55 µM | 0.5 mL | 1 mL |
| 50 mg/mL gentamicin sulfate | 50 µg/mL | 0.5 mL | 1 mL |

On the day of use, prewarmed required amount of CM1 in 37° C. water bath and add 6000 IU/mL IL-2.

Additional supplementation as needed according to Table 38.

TABLE 38

Additional supplementation of CM1, as needed.

| Supplement | Stock concentration | Dilution | Final concentration |
|---|---|---|---|
| GlutaMAX ™ | 200 mM | 1:100 | 2 mM |
| Penicillin/streptomycin | 10,000 U/mL penicillin 10,000 µg/mL streptomycin | 1:100 | 100 U/mL penicillin 100 µg/mL streptomycin |
| Amphotericin B | 250 µg/mL | 1:100 | 2.5 µg/mL |

Preparation of CM2

Removed prepared CM1 from refrigerator or prepare fresh CM1 as above. Removed AIM-V® from refrigerator and prepared the amount of CM2 needed by mixing prepared CM1 with an equal volume of AIM-V® in a sterile media bottle. Added 3000 IU/mL IL-2 to CM2 medium on the day of usage. Made sufficient amount of CM2 with 3000 IU/mL IL-2 on the day of usage. Labeled the CM2 media bottle with its name, the initials of the preparer, the date it was filtered/prepared, the two-week expiration date and store at 4° C. until needed for tissue culture.

Preparation of CM3

Prepared CM3 on the day it was required for use. CM3 was the same as AIM-V®, medium, supplemented with 3000 IU/mL IL-2 on the day of use. Prepared an amount of CM3 sufficient to experimental needs by adding IL-2 stock solution directly to the bottle or bag of AIM-V. Mixed well by gentle shaking. Label bottle with "3000 IU/mL IL-2" immediately after adding to the AIM-V. If there was excess CM3, stored it in bottles at 4° C. labeled with the media name, the initials of the preparer, the date the media was prepared, and its expiration date (7 days after preparation). Discarded media supplemented with IL-2 after 7 days of storage at 4° C.

Preparation of CM4

CM4 was the same as CM3, with the additional supplement of 2 mM GlutaMAX™ (final concentration). For every 1 L of CM3, added 10 ml of 200 mM GlutaMAX™. Prepared an amount of CM4 sufficient to experimental needs by adding IL-2 stock solution and GlutaMAX™ stock solution directly to the bottle or bag of AIM-V. Mixed well by gentle shaking. Labeled bottle with "3000 IL/mL IL-2 and GlutaMAX" immediately after adding to the AIM-V. If there was excess CM4, stored it in bottles at 4° C. labeled with the media name, "GlutaMAX", and its expiration date (7 days after preparation). Discarded media supplemented with IL-2 after 7-days of storage at 4° C.

Example 2. Use of IL-2, IL-15, and IL-21 Cytokine Cocktail

This example describes the use of IL-2, IL-15, and IL-21 cytokines, which serve as additional T cell growth factors, in combination with the TIL process of any of the examples or embodiments herein, including examples and embodiments that encompass cryopreservation of tumor tissue or tumor fragments.

Using the processes described herein, TILs were grown from colorectal, melanoma, cervical, triple negative breast, lung and renal tumors in presence of IL-2 in one arm of the experiment and, in place of IL-2, a combination of IL-2, IL-15, and IL-21 in another arm at the initiation of culture. At the completion of the pre-REP, cultures were assessed for expansion, phenotype, function (CD107a$^+$ and IFN-γ) and TCR Vβ repertoire. IL-15 and IL-21 are described elsewhere herein and in Gruijl, et al., IL-21 promotes the expansion of CD27$^+$CD28$^+$ tumor infiltrating lymphocytes with high cytotoxic potential and low collateral expansion of regulatory T cells, Santegoets, S. J., *J. Transl Med.*, 11:37 (2013) available at https://www.ncbi.nlm.nih.gov/pmc/articles/PMC3626797/.

The results showed that enhanced TIL expansion (>20%), in both CD4$^+$ and CD8$^+$ cells in the IL-2, IL-15, and IL-21 treated conditions were observed in multiple histologies relative to the IL-2 only conditions. There was a skewing towards a predominantly CD8$^+$ population with a skewed TCR Vβ repertoire in the TILs obtained from the IL-2, IL-15, and IL-21 treated cultures relative to the IL-2 only cultures. IFN-γ and CD107a were elevated in the IL-2, IL-15, and IL-21 treated TILs, in comparison to TILs treated only IL-2.

Example 3. Preparation of IL-2 Stock Solution

This Example describes the process of dissolving purified, lyophilized recombinant human interleukin-2 into stock samples suitable for use in further tissue culture protocols, including all of those described in the present application and Examples, including those that involve using rhIL-2.

Procedure

Prepared 0.2% Acetic Acid solution (HAc). Transferred 29 mL sterile water to a 50 mL conical tube. Added 1 mL 1N (1 normal) acetic acid to the 50 mL conical tube. Mixed well by inverting tube 2-3 times. Sterilized the HAc solution by filtration using a Steriflip filter Prepare 1% HSA in PBS. Added 4 mL of 25% HSA stock solution to 96 mL PBS in a 150 mL sterile filter unit. Filtered solution. Stored at 4° C. For each vial of rhIL-2 prepared, fill out forms.

Prepared rhIL-2 stock solution (6×10$^6$ IU/mL final concentration). Each lot of rhIL-2 was different and required information found in the manufacturer's Certificate of Analysis (COA), such as: 1) Mass of rhIL-2 per vial (mg), 2) Specific activity of rhIL-2 (IU/mg) and 3) Recommended 0.2% HAc reconstitution volume (mL).

Calculated the volume of 1% HSA required for rhIL-2 lot by using the equation below:

$$\left( \frac{\text{Vial Mass (mg)} \times \text{Biological Activity}\left(\frac{IU}{mg}\right)}{6 \times 10^6 \frac{IU}{mL}} \right) - HAc\ vol\ (mL) = 1\%\ HSA\ vol\ (mL)$$

For example, according to CellGenix's rhIL-2 lot 10200121 COA, the specific activity for the 1 mg vial is $25 \times 10^6$ IU/mg. It recommends reconstituting the rhIL-2 in 2 mL 0.2% HAc.

$$\left( \frac{1\ mg \times 25 \times 10^6 \frac{IU}{mg}}{6 \times 10^6 \frac{IU}{mL}} \right) - 2\ mL = 2.167\ mL\ HSA$$

Wiped rubber stopper of IL-2 vial with alcohol wipe. Using a 16 G needle attached to a 3 mL syringe, injected recommended volume of 0.2% HAc into vial. Took care to not dislodge the stopper as the needle is withdrawn. Inverted vial 3 times and swirled until all powder is dissolved. Carefully removed the stopper and set aside on an alcohol wipe. Added the calculated volume of 1% HSA to the vial.

Storage of rhIL-2 solution. For short-term storage (<72 hrs), stored vial at 4° C. For long-term storage (>72 hrs), aliquoted vial into smaller volumes and stored in cryovials at −20° C. until ready to use. Avoided freeze/thaw cycles. Expired 6 months after date of preparation. Rh-IL-2 labels included vendor and catalog number, lot number, expiration date, operator initials, concentration and volume of aliquot.

Example 4. TIL Cryopreservation Processes

This example describes the cryopreservation process method for TILs prepared with the abbreviated, closed procedure described in Example 5 using the CryoMed Controlled Rate Freezer, Model 7454 (Thermo Scientific).

The equipment used was as follows: aluminum cassette holder rack (compatible with CS750 freezer bags), cryostorage cassettes for 750 mL bags, low pressure (22 psi) liquid nitrogen tank, refrigerator, thermocouple sensor (ribbon type for bags), and CryoStore CS750 Freezing bags (OriGen Scientific).

The freezing process provides for a 0.5° C. rate from nucleation to −20° C. and 1° C. per minute cooling rate to −80° C. end temperature. The program parameters are as follows: Step 1—wait at 4° C.; Step 2: 1.0° C./min (sample temperature) to −4° C.; Step 3: 20.0° C./min (chamber temperature) to −45° C.; Step 4: 10.0° C./min (chamber temperature) to −10.0° C.; Step 5: 0.5° C./min (chamber temperature) to −20° C.; and Step 6: 1.0° C./min (sample temperature) to −80° C.

Example 5. Production of a Process 2A Cryopreserved TIL Cell Therapy Using a Closed System This example describes the procedure for cGMP manufacture of TIL cell therapy process in gas permeable containers, such as G-Rex Flasks (Wilson Wolf Manufacturing Corp., New Brighton, MN, USA), according to current Good Tissue Practices and current Good Manufacturing Practices. This material will be manufactured under US FDA Good Manufacturing Practices Regulations (21 CFR Part 210, 211, 1270, and 1271), and applicable ICH Q7 standards for Phase I through Commercial Material. This method may be combined with the tumor cryopreservation and thawing processes described herein.

The process summary is provided in Table 39 below.

TABLE 39

Process Summary.

| Estimated Day (post-seed) | Activity | Target Criteria | Anticipated Vessels | Estimated Total Volume (mL) |
|---|---|---|---|---|
| 0 | Tumor Dissection | ≤50 desirable tumor fragments per G-Rex100MCS | G-Rex100MCS 1 flask | ≤1000 |
| 11 | REP Seed | 5-200 × $10^6$ viable cells per G-Rex500MCS | G-Rex500MCS 1 flasks | ≤5000 |
| 16 | REP Split | 1 × $10^9$ viable cells per G-Rex500MCS | G-Rex500MCS ≤5 flasks | ≤25000 |
| 22 | Harvest | Total available cells | 3-4 CS-750 bags | ≤530 |

Throughout this Example, it is assumed that 1.0 mL/L=1.0 g/kg, unless otherwise specified. Once opened, the following expiries apply at 2° C.-8° C.: Human Serum, type AB (HI) Gemini, 1 month; 2-mercaptoethanol, 1 month. Gentamicin Sulfate, 50 mg/mL stock may be kept at room temperature for 1 month. Bags containing 10 L of AIM-V media may be warmed at room temperature once only for up to 24 hours prior to use. During the Day 22 harvest two Gatherex™ pumps may be used to harvest the TIL from the G-Rex500MCS flasks.

Day 0—CM1 Media Preparation

Prepare RPMI 1640 Media. In the BSC, using an appropriately sized pipette, remove 100.0 mL from 1000 mL RPMI 1640 Media and place into an appropriately sized container labeled "Waste."

In the BSC, add reagents to RPMI 1640 Media bottle. Add the following reagents to the RPMI 1640 Media bottle as shown in Table 26. Record volumes added. Amount added per bottle: Heat Inactivated Human AB Serum (100.0 mL); GlutaMax (10.0 mL); Gentamicin sulfate, 50 mg/mL (1.0 mL); 2-mercaptoethanol (1.0 mL)

Cap RPMI 1640 Media bottle and swirl bottle to ensure reagents were mixed thoroughly. Filter RPMI 1640 Media through 1 L 0.22-micron filter unit. Label filtered media. Aseptically cap the filtered media and label.

Thaw one 1.1 mL IL-2 aliquot ($6 \times 10^6$ IU/mL) (BR71424) until all ice had melted. Transfer IL-2 stock solution to media. In the BSC, transfer 1.0 mL of IL-2 stock solution to the CM1 Day 0 Media Bottle prepared above. Add CM1 Day 0 Media 1 bottle and IL-2 (6×10⁶ IU/mL) 1.0 mL. Cap and swirl the bottle to mix media containing IL-2. Relabeled as "Complete CM1 Day 0 Media".

Remove 20.0 mL of media using an appropriately sized pipette and dispensed into a 50 mL conical tube. In BSC, transfer 25.0 mL of "Complete CM1 Day 0 Media" to a 50 mL conical tube. Label the tube as "Tissue Pieces". Aseptically pass G-Rex100MCS (W3013130) into the BSC. In the BSC, closed all clamps on the G-Rex100MCS, leaving vent filter clamp open. Connect the red line of G-Rex100MCS flask to the larger diameter end of the repeater pump fluid transfer set (W3009497) via luer connection. Stage Baxa pump next to BSC. Remove pump tubing section of repeater pump fluid transfer set from BSC and install in repeater pump. Within the BSC, remove the syringe from Pumpmatic Liquid-Dispensing System (PLDS) (W3012720) and discard.

Connect PLDS pipette to the smaller diameter end of repeater pump fluid transfer set via luer connection and placed pipette tip in "Complete CM1 Day 0 Media" for aspiration. Open all clamps between media and G-Rex100MCS. Pump Complete CM1 media into G-Rex100MCS flask. Set the pump speed to "High" and "9" and pumped all Complete CM1 Day 0 Media into G-Rex100MCS flask. Once all media is transferred, clear the line and stop pump.

Disconnect pump from flask. Ensure all clamps were closed on the flask, except vent filter. Remove the repeater pump fluid transfer set from the red media line, and place a red cap (W3012845) on the red media line. Remove G-Rex100MCS flask from BSC, heat seal off the red cap from the red line near the terminal luer. Incubator parameters: 37.0±2.0° C.; $CO_2$ Percentage: 5.0±1.5% $CO_2$.

Place the 50 mL conical tube" in incubator for ≥30 minutes of warming.

Day 0—Tumor Wash Media Preparation

Add gentamicin to HBSS. In the BSC, add 5.0 mL gentamicin (W3009832 or W3012735) to 1×500 mL HBSS Media (W3013128) bottle. Record volumes. Add per bottle: HBSS (500.0 mL); Gentamicin sulfate, 50 mg/ml (5.0 mL). Mix reagents thoroughly. Filter HBSS containing gentamicin through a 1 L 0.22-micron (0.22 μm) filter unit (W1218810). Aseptically cap the filtered media and labeled with the following information.

Day 0—Tumor Processing

Obtain tumor specimen (from cryopreserved tumor) and transfer into suite at 2° C.-8° C. immediately for processing and recorded tumor information.

Wash tumor specimens three times at 2° C.-8° C., with gentle agitation for at least 3 minutes for each wash. The wash solution is removed and replaced with fresh solution after each wash.

Using a transfer pipette, place 4 individual drops of Tumor Wash Media from the conical into each of the 6 circles on the upturned lids of the 6-well plates (2 lids). Place an extra drop on two circles for a total of 50 drops.

Tumor Wash 3: Using forceps, remove the tumor from the "Wash 2" dish and transferred to the "Wash 3" dish. Using forceps, wash tumor specimen by gently agitating and allow it to sit for ≥3 minutes. Record time.

Place a ruler under 150 mm dish lid. Using forceps, aseptically transferred tumor specimen to the 150 mm dissection dish lid. Arrange all pieces of tumor specimen end to end and recorded the approximate overall length and number of fragments. Assess the tumor for necrotic/fatty tissue. Assess whether >30% of entire tumor area observed to be necrotic and/or fatty tissue; if yes, ensure tumor was of appropriate size if so proceed. Assess whether <30% of entire tumor area were observed to be necrotic or fatty tissue; if yes, proceed.

Clean-Up Dissection. If tumor was large and >30% of tissue exterior was observed to be necrotic/fatty, performed "clean up dissection" by removing necrotic/fatty tissue while preserving tumor inner structure using a combination of scalpel and/or forceps. To maintain tumor internal structure, use only vertical cutting pressure. Did not cut in a sawing motion with scalpel.

Using a combination of scalpel and/or forceps, cut the tumor specimen into even, appropriately sized fragments (up to 6 intermediate fragments). To maintain tumor internal structure, use only vertical cutting pressure. Again, do not cut in a sawing motion with scalpel. Keep non-dissected intermediate fragments completely submerged in "Tumor Wash Media". Transfer each intermediate fragment to the "holding" dish.

Manipulate one intermediate fragment at a time, dissected the tumor intermediate fragment in the dissection dish into pieces approximately 3×3×3 mm in size, minimizing the amount of hemorrhagic, necrotic, and/or fatty tissues on each piece. To maintain tumor internal structure, use only vertical cutting pressure. Again, do not cut in a sawing motion with scalpel.

Select up to eight (8) tumor pieces without hemorrhagic, necrotic, and/or fatty tissue. Used the ruler for reference. Continue dissection until 8 favorable pieces have been obtained, or the entire intermediate fragment has been dissected. Transfer each selected piece to one of the drops of "Tumor Wash Media".

After selecting up to eight (8) pieces from the intermediate fragment, place remnants of intermediate fragment into a new single well of "favorable intermediate fragments" 6-well plate.

If desirable tissue remains, selected additional Favorable Tumor Pieces from the "favorable intermediate fragments" 6-well plate to fill the drops for a maximum of 50 pieces. Recorded the total number of dissected pieces created.

Remove the "Tissue Pieces" 50 mL conical tube from the incubator. Ensured conical tube was warmed for ≥30 min. Pass "Tissue Pieces" 50 mL conical into the BSC, ensuring not to compromise the sterility of open processing surfaces.

Using a transfer pipette, scalpel, forceps or combination, transfer the selected 50 best tumor fragments from favorable dish lids to the "Tissue Pieces" 50 mL conical tube. If a tumor piece was dropped during transfer and desirable tissue remains, additional pieces from the favorable tumor intermediate fragment wells were added. Recorded numbers of pieces.

Remove G-Rex100MCS containing media from incubator. Aseptically passed G-Rex100MCS flask into the BSC. When transferring the flask, do not hold from the lid or the bottom of the vessel. Transfer the vessel by handling the sides. In the BSC, lift G-Rex100MCS flask cap, ensuring that sterility of internal tubing was maintained. Swirl conical tube with tumor pieces to suspend and quickly pour the contents into the G-Rex100MCS flask. Ensure that the tumor pieces are evenly distributed across the membrane of the flask. Gently tilted the flask back and forth if necessary to evenly distribute the tumor pieces. Record number of tumor fragments on bottom membrane of vessel and number of observed to be floating in vessel. NOTE: If the number of fragments seeded were NOT equivalent to number of collected, contacted Area Management, and documented in Section 10.0.

Incubate G-Rex100MCS at the following parameters: Incubate G-Rex flask: Temperature LED Display: 37.0±2.0° C.; $CO_2$ Percentage: 5.0±1.5% $CO_2$. Perform calculations to determine the proper time to remove G-Rex100MCS incubator on Day 11. Calculations: Time of incubation; lower limit=time of incubation+252 hours; upper limit=time of incubation+276 hours.

Day 11—Media Preparation

Monitor Incubator. Incubator parameters: Temperature LED Display: 37.0±2.0° C.; $CO_2$ Percentage: 5.0±1.5% $CO_2$. Warm 3×1000 mL RPMI 1640 Media (W3013112) bottles and 3×1000 mL AIM-V (W3009501) bottles in an incubator for ≥30 minutes. Recorded time. Media: RPMI 1640 and AIM-V. Placed an additional 1×1000 mL bottle of AIM-V Media (W3009501) at room temperature for further use.

Remove the RPMI 1640 Media when time was reached. Record end incubation time in previous step. Ensure media is warmed for ≥30 min. In the BSC, removed 100.0 mL from each of the three pre-warmed 1000 mL RPMI 1640 Media bottles and place into an appropriately sized container labeled "Waste". In the BSC, add the following reagents to each of the three RPMI 1640 Media bottles and recorded volumes added to each bottle. GemCell Human serum, Heat Inactivated Type AB (100.0 mL), GlutaMax (10.0 mL), Gentamicin sulfate, 50 µg/mL (1.0 mL), 2-mercaptoethanol (1.0 mL).

Cap bottles and swirl do ensure reagents were mixed thoroughly. Filtered each bottle of media through a separate 1 L 0.22-micron filter unit. Aseptically cap the filtered media and label each bottle with CM1 Day 11 Media. Thawed 3×1.1 mL aliquots of IL-2 ($6×10^6$ IU/mL) (BR71424) until all ice had melted Recorded IL 2 lot # and expiration date/time.

Remove the three bottles of AIM-V Media from the incubator. Record end incubation time. Ensure media had been warmed for ≥30 minutes. Using a micropipette, add 3.0 mL of thawed IL-2 into one 1 L bottle of pre-warmed AIM-V media. Rinse micropipette tip with media after dispensing IL-2. Use a new sterile micropipette tip for each aliquot. Record the total volume added. Label bottle as "AIM-V Containing IL-2". Aseptically transfer a 10 L Labtainer Bag and a repeater pump transfer set into the BSC. Closed all lines on a 10 L Labtainer bag. Attach the larger diameter tubing end of a repeater pump transfer set to the middle female port of the 10 L Labtainer Bag via luer lock connection.

Stage the Baxa pump next to the BSC. Feed the transfer set tubing through the Baxa pump. Set the Baxa Pump to "High" and "9". Remove syringe from Pumpmatic Liquid-Dispensing System (PLDS) and discarded. Do not compromise the sterility of the PLDS pipette.

Connect the PLDS pipette to smaller diameter end of repeater pump fluid transfer set via luer connection and place pipette tip in AIM-V media containing IL-2 bottle for aspiration. Opened all clamps between media bottle and 10 L Labtainer.

Using the PLDS, transfer pre-warmed AIM-V media containing IL-2 prepared, as well as two additional AIM-V bottles into the 10 L Labtainer bag. Add the three bottles of filtered CM1 Day 11 Media. After addition of final bottle, clear the line to the bag. Stop the pump between addition of each bottle of media. Remove PLDS from the transfer set and place a red cap on the luer of the line in the BSC. Gently massage the bag to mix. Label the media bag with the following information. Expiration date is 24 hours from the preparation date.

Attach a 60 mL syringe to the available female port of the "Complete CM2 Day 11 Media" bag. Remove 20.0 mL of media and place in a 50 mL conical tube. Place a red cap on the female port of the "Complete CM2 Day 11 Media" Bag. Label and stored Media Retain Sample at 2° C.-8° C. until submitted for testing. Heat seal off the red cap on the transfer set line, close to red cap. Keep the transfer set on the bag.

In the BSC, add 4.5 mL of AIM-V Media that had been labelled with "For Cell Count Dilutions" and lot number to four 15 mL conical tubes. Label the tubes with the lot number and tube number (1-4). Labeled 4 cryovials "Feeder" and vial number (1-4). Transfer any remaining 2-mercaptoethanol, GlutaMax, and human serum from the BSC to 2° C. to 8° C.

Outside of the BSC, weld a 1 L Transfer Pack to the transfer set attached to the "Complete CM2 Day 11 Media" bag prepared. Labeled transfer pack as "Feeder Cell CM2 Media" and lot number. Make a mark on the tubing of the 1 L Transfer Pack tubing a few inches away from the bag. Place the empty Transfer Pack onto the scale so that the tubing was on the scale to the point of the mark. Tare the scale and leave the empty Transfer Pack on the scale.

Set the Baxa pump to "Medium" and "4." Pump 500.0±5.0 mL of "Complete CM2 Day 11" media into Cell CM2 Media" transfer pack. Measure by weight and record the volume of Complete CM2 media added to the Transfer Pack.

Once filled, heat seal the line. Separate CM2 Day 11 media bag with transfer set from feeder cell media transfer pack, kept weld toward 1 L transfer pack. Place "Complete CM2 Day 11 Media" prepared in incubator until use.

Day 11—TIL Harvest

Incubator parameters: Temperature LED Display: 37.0±2.0° C.; $CO_2$ Percentage: 5.0±1.5% $CO_2$. Performed check to ensure incubation parameters are met before removing G-Rex100MCS from incubator. Lower limits are the same as described above.

Record time of removal from incubator. Carefully remove G-Rex100MCS from incubator and ensured all clamps were closed except large filter line. Record processing start time.

Label a 300 mL Transfer pack as "TIL Suspension". Sterile weld the TIL Suspension transfer (single line) of a Gravity Blood Filter. Place the 300 mL Transfer Pack on a scale and record dry weight. Labeled 1 L Transfer Pack as "Supernatant".

Sterile weld the red media removal line from the G-Rex100MCS to the "Supernatant" transfer pack. Sterile weld the clear cell removal line from the G-Rex100MCS to one of the two spike lines on the top of the blood filter connected to the "TIL Suspension" transfer pack. Place G-Rex100MCS on the left side of the GatheRex and the "Supernatant" and "TIL Suspension" transfer packs to the right side.

Install the red media removal line from the G Rex100MCS to the top clamp (marked with a red line) and tubing guides on the GatheRex. Install the clear harvest line from the G-Rex100MCS to the bottom clamp (marked with a blue line) and tubing guides on the GatheRex. Attach the gas line from the GatheRex to the sterile filter of the G-Rex100MCS flask. Before removing the supernatant from the G-Rex100MCS flask, ensure all clamps on the cell removal lines were closed. Transfer ~900 mL of culture supernatant from the G-Rex100MCS to the 1 L Transfer Pack. Visually inspect G-Rex100MCS flask to ensure flask is level and media has been reduced to the end of the aspirating dip tube.

After removal of the supernatant, close all clamps to the red line.

Vigorously tap flask and swirl media to release cells. Perform an inspection of the flask to ensure all cells have detached. Tilt flask away from collection tubing and allow tumor pieces to settle along edge. Slowly tip flask toward collection tubing so pieces remained on the opposite side of the flask. If the cell collection straw is not at the junction of the wall and bottom membrane, rap the flask while tilted at a 450 angle is usually sufficient to properly position the straw.

Release all clamps leading to the TIL Suspension transfer pack. Using the GatheRex, transfer the cell suspension through the blood filter into the 300 mL transfer pack. Maintain the tilted edge until all cells and media are collected. Inspect membrane for adherent cells. Rinse the bottom of the G-Rex100MCS. Cover ~¼ of gas exchange membrane with rinse media. Ensure all clamps are closed. Heat seal the TIL suspension transfer pack as close to the weld as possible so that the overall tubing length remains approximately the same. Heat sealed the "Supernatant" transfer pack. Maintain enough line to weld. Record weight of TIL Suspension transfer pack and calculate the volume of cell suspension.

Weld a 4-inch (4") plasma transfer set to "supernatant" transfer pack, retaining the luer connection on the 4-inch plasma transfer set, and transfer into the BSC. Weld a 4-inch plasma transfer set to 300 mL "TIL Suspension" transfer pack, retain the luer connection on the 4-inch plasma transfer set, and transfer into the BSC.

Draw up approximately 20.0 mL of supernatant from the 1 L "Supernatant" transfer pack and dispense into a sterile 50 mL conical tube labeled "Bac-T." Remove a 1.0 mL sample from the 50 mL conical labeled BacT using an appropriately sized syringe and inoculate the anaerobic bottle.

Label 4 cryovials with vial number (1-4). Using separate 3 mL syringes, pull 4×1.0 mL cell count samples from TIL Suspension Transfer Pack using the luer connection, and place in respective cryovials. Placed a red cap (W3012845) on the line. Place TIL Transfer Pack in incubator until needed. Perform cell counts and calculations. Perform initial cell counts undiluted. If no dilution needed, "Sample [μL]"=200, "Dilution [μL]"=0.

Record cell counts and TIL numbers. If Total Viable TIL Cells is <5×10$^6$ cells, proceeded to "Day 11 G-Rex Fill and Seed". If Total Viable TIL Cells is >5×10$^6$, proceed to "Calculation for flow cytometry".

If the Total Viable TIL Cell count was ≥4.0×10$^7$, calculated the volume to obtain 1.0×10$^7$ cells for the flow cytometry sample. Total viable cells required for flow cytometry: 1.0×10$^7$ cells. Volume of cells required for flow cytometry: Viable cell concentration divided by 1.0×10$^7$ cells.

If Applicable: Recalculate Total Viable Cells and Volume flow. Calculate the remaining Total Viable Cells and remaining volume after the removal of cytometry sample below.

If applicable: Calculate volume for cryopreservation. Calculate the volume of cells required to obtain 1×10$^7$ cells for cryopreservation.

TABLE 40

TIL Cryopreservation Calculation.

| Total Viable TIL required for cryopreservation | Viable Cell Concentration | Volume of Cells required for cryopreservation C = A ÷ B |
|---|---|---|
| A. 1 × 10$^7$ cells | B. cells/mL | C. mL |

If applicable: Remove sample for Cryopreservation. Remove the calculated volume from the TIL Suspension transfer pack. Place in appropriately sized conical tube and label as "Cryopreservation Sample 1×10$^7$ cells," dated, and lot number. Place a red cap (W3012845) on the TIL Suspension transfer pack.

Centrifuge the "Cryopreservation Sample 1×10$^7$ cells" according to the following parameters: Speed: 350×g, Time: 10:00 minutes, Temperature: Ambient, Brake: Full (9); Acceleration: Full (9).

Add CS-10. In BSC, aseptically aspirate supernatant. Gently tap bottom of tube to resuspend cells in remaining fluid. Added CS-10. Slowly added 0.5 mL of CS10. Record volume added. Cryopreservation Sample Vials Filled at ~0.5 mL.

Day 11—Feeder Cells

Obtain 3 bags of feeder cells with at least two different lot numbers from LN$_2$ freezer. Keep cells on dry ice until ready to thaw. Record feeder cell information. Confirm that at least two different lots of feeder cells were obtained. Place the Feeder Cell bags into individual zip top bags, based on Lot number, and thawed 37.0±2.0° C. water bath or cytotherm for ~3-5 minutes or until ice has just disappeared.

Feeder cell harness preparation. Weld 4S-4M60 to a CC2 Cell Connect (W3012820), replacing a single spike of the Cell Connect apparatus with the 4-spike end of the 4S-4M60 manifold. Weld as needed.

Attach media transfer pack: Weld the "Feeder Cell CM2 Media" transfer pack to a CC2 luer. The bag will be attached to the side of the harness with the needless injection port. Transferred the assembly containing the Complete CM2 Day 11 Media into the BSC.

Pool thawed feeder cells. Within the BSC, pull 10 mL of air into a 100 mL syringe. Used this to replace the 60 mL syringe on the CC2. Wipe each port on the feeder cell bags with an alcohol pad prior to removing the cover. Spike the three feeder bags using three of the spikes of the CC2. Maintain constant pressure while turning the spike in one direction. Do not puncture the side of the port. Opened the stopcock so that the line from the feeder cell bags is open and the line to the needless injection port is closed. Draw up the contents of the feeder cell bags into the syringe. All three bags drained at once. Once feeder cell bags had been drained, while maintaining pressure on the syringe, clamp off the line to the feeder cell bags. Do not detach syringe below. the syringe from the harness. Record the total volume of feeder cells in the syringe.

Add feeder cells to transfer pack. Turn the stopcock so the line to the feeder cell bag was closed and the line to the media Transfer Pack was open. Ensure the line to media transfer pack is unclamped. Dispense the feeder cells from the syringe into the "Feeder Cell CM2 Media" transfer pack. Clamp off the line to the transfer pack containing the feeder cells and leave the syringe attached to the harness. Massage bag to mix the pooled feeder cells in the transfer pack. Labeled bag as "Feeder Cell Suspension".

Calculated the total volume of feeder cell suspension. Remove cell count samples. Using a separate 3 mL syringe for each sample, pulled 4×1.0 mL cell count samples from Feeder Cell Suspension Transfer Pack using the needless injection port. Aliquot each sample into labeled cryovials.

Perform cell counts and calculations utilizing NC-200 and Process Note 5.14. Dilute cell count samples by adding 0.5 mL of cell suspension into 4.5 mL of AIM-V media labelled with the lot number and "For Cell Count Dilutions". This will give a 1:10 dilution.

Record Cell Count and Sample volumes. If Total Viable Cells are $<5\times10^9$, proceed. If Total Viable Cells are $\geq 5\times10^9$, proceed as above for higher cells counts. Obtain additional feeder cells as needed and added to transfer pack as discussed above. Calculate the volume of feeder cell suspension that was required to obtain $5\times10^9$ viable feeder cells. Calculate the volume of excess feeder cells to remove. Round down to nearest whole number.

Remove excess feeder cells. In a new 100 mL syringe, pull up 10 mL of air and attached the syringe to the harness. Open the line to the "Feeder Cell Suspension" transfer pack. Using the syringe, draw up the volume of feeder cells calculated plus an additional 10.0 mL from the Transfer Pack into a 100 mL syringe. Close the line to the Feeder Cell Suspension transfer pack once the volume of feeder cells is removed. Do not remove final syringe. Once a syringe has been filled, replace it with a new syringe. Multiple syringes could be used to remove total volume. With each new syringe, pull in 10 mL of air. Record the total volume (including the additional 10 mL) of feeder cells removed.

Added OKT3. In the BSC, using a 1.0 mL syringe and 16 gauge (16 G or 16 Ga) needle, draw up 0.15 mL of OKT3. Aseptically remove the needle from the syringe and attach the syringe to the needless injection port. Injected the OKT3. Open the stopcock to the "Feeder Cell Suspension" transfer pack and add 10 mL of feeder cells removed previously to flush OKT3 through the line. Turn the syringe upside down and push air through to clear the line to the Feeder Cell Suspension transfer pack. Leave the remaining feeder cell suspension in the syringe. Close all clamps and remove the harness from the BSC. Heat seal the Feeder Cell Suspension transfer pack, leaving enough tubing to weld.

Day 11—G-Rex Fill and Seed

Set up G-Rex500MCS. Remove a G-Rex500MCS from packaging and inspected the flask for any cracks or kinks in the tubing. Ensure all luer connections and closures were tight. Closed all clamps on the G-Rex500MCS lines except for the vent filter line. Using a marker draw a line at the 4.5 L gradation. Removed the "Complete CM2 Day 11 Media", from the incubator.

Prepare to pump media. Weld the red line of the G-Rex500MCS to the repeater pump transfer set attached to the complete CM2 Day 11 Media. Hang the "Complete CM2 Day 11 Media" bag on an IV pole. Fed the pump tubing through the Baxa pump. Pump media into G-Rex500MCS. Set the Baxa pump to "High" and "9". Pump 4.5 L of media into the G-Rex500MCS, filling to the line marked on the flask at the 4.5 L gradation. Heat seal the red line of the G-Rex500MCS near the weld. Label the flask with the "Day 11" label. Weld the Feeder Cell: Suspension transfer pack to the flask. Sterile weld the red line of the G-Rex500MCS to the "Feeder Cell Suspension" transfer pack.

Add Feeder Cells to G-Rex500MCS. Open all clamps between Feeder Cell Suspension and G-Rex500MCS and added Feeder Cell Suspension to flask by gravity feed. Heat seal the red line near the weld. Welded the TIL Suspension transfer pack to the flask. Sterile weld the red line of the G-Rex500MCS to the "TIL Suspension" transfer pack.

Add TIL to G-Rex500MCS. Open all clamps between TIL Suspension and G-Rex500MCS and added TIL Suspension to flask by gravity feed. Heat seal the red line near the weld to remove the TIL suspension bag.

Incubate G-Rex500MCS. Check that all clamps on the G-Rex500MCS were closed except the large filter line and place in the incubator. Incubator parameters: Temperature LED Display: 37.0±2.0° C., $CO_2$ Percentage: 5.0±1.5% $CO_2$.

Calculate incubation window. Perform calculations to determine the proper time to remove G-Rex500MCS from incubator on Day 16. Lower limit: Time of incubation+108 hours. Upper limit: Time of incubation+132 hours.

Day 11—Excess TIL Cryopreservation

Freeze Excess TIL Vials. Record and verify the total number of vials placed into the Control Rate Freezer (CRF). Upon completion of freeze, transfer vials from CRF to the appropriate storage container.

Day 16—Media Preparation

Pre-warm AIM-V Media. Remove three CTS AIM V 10 L media bags from 2° C. to 8° C. at least 12 hours prior to use and place at room temperature protected from light. Label each bag. Record warming start time and date. Ensure all bags have been warmed for a duration between 12 and 24 hours.

Attach the larger diameter end of a fluid pump transfer set to one of the female ports of a 10 L Labtainer bag using the Luer connectors. Setup 10 L Labtainer for Supernatant. Label as "Supernatant". Setup 10 L Labtainer for Supernatant. Ensure all clamps were closed prior to removing from the BSC.

Thaw 5×1.1 mL aliquots of IL-2 ($6\times10^6$ IU/mL) (BR71424) per bag of CTS AIM V media until all ice had melted. Aliquot 100.0 mL of Glutamax into an appropriately sized receiver. Record the volume added to each receiver and labeled each receiver as "GlutaMax."

Add IL-2 to GlutaMax. Using a micropipette, add 5.0 mL of IL-2 to each GlutaMax receiver. Rinse the tip per process and use a new pipette tip for each mL added. Record volume added to each Glutamax receiver and labeled each receiver as "GlutaMax+IL-2" and receiver number.

Prepare CTS AIM V media bag for formulation. Ensure CTS AIM V 10 L media bag (W3012717) was warmed at room temperature and protected from light for 12-24 hours prior to use. Record end incubation time. In the BSC, close clamp on a 4" plasma transfer set, then connected to the bag using the spike ports. Maintain constant pressure while turning the spike in one direction. Ensure to not puncture the side of the port. Connect the larger diameter end of a repeater pump fluid transfer set to the 4" plasma transfer set via luer.

Stage Baxa pump next to BSC. Remove pump tubing section of repeater pump fluid transfer set from BSC and installed in repeater pump.

Prepare to formulate media. In BSC, remove syringe from Pumpmatic Liquid-Dispensing System (PLDS) and discarded. Ensure to not compromise the sterility of the PLDS pipette. Connect PLDS pipette to smaller diameter end of repeater pump fluid transfer set via luer connection and placed pipette tip in "GlutaMax+IL-2" prepared above for aspiration. Open all clamps between receiver and 10 L bag.

Pump GlutaMax+IL-2 into bag. Set the pump speed to "Medium" and "3" and pump all "GlutaMax+IL-2" into 10 L CTS AIM V media bag. Once no solution remains, clear line and stop pump. Record the volume of GlutaMax containing IL-2 added to each Aim V bag below.

Remove PLDS. Ensure all clamps are closed, and removed the PLDS pipette from the repeater pump fluid transfer set. Remove repeater pump fluid transfer set and red cap the 4" plasma transfer set.

Label each bag of "Complete CM4 Day 16 media" prepared.

Remove Media Retain per Sample Plan. Using a 30 mL syringe, remove 20.0 mL of "Complete CM4 Day 16 media" by attaching syringe to the 4" plasma transfer set and dispensed sample into a 50 mL conical tube. Ensure 4" plasma transfer set was either clamped or red capped after removal of syringe.

Attach new repeater pump fluid transfer set. Attach the larger diameter end of a new fluid pump transfer set onto the 4" plasma transfer set that was connected to the "Complete CM4 Day 16 media" bag. Label with sample plan inventory label and stored media retain sample at 2-8° C. until submitted for testing.

Monitored Incubator. If applicable, monitor for additional bags prepared. Incubator parameters: Temperature LED Display: 37.0±2.0° C., $CO_2$ Percentage: 5.0±1.5% $CO_2$.

Warmed Complete CM4 Day 16 Media. Warm the first bag of Complete CM4 Day 16 Media in incubator for ≥30 minutes until ready for use. If applicable, warm additional bags.

Prepared Dilutions. In the BSC, added 4.5 mL of AIM-V Media that had been labelled with "For Cell Count Dilutions" to each 4 each, 15 mL conical tube. Label the conical tubes. Labeled 4 cryovials.

Day 16—REP Spilt

Monitor Incubator. Incubator parameters: Temperature LED Display: 37.0±2.0° C., $CO_2$ Percentage: 5.0±1.5% $CO_2$.

Remove G-Rex500MCS from Incubator. Perform check below to ensure incubation parameters are met before removing G-Rex500MCS from incubator: upper limit, lower limit, time of removal. Remove G-Rex500MCS from the incubator.

Heat seal a 1 L transfer pack (W3006645), leaving ~12 inches of line. Label 1 L transfer pack as TIL Suspension. Place 1 L transfer pack, including the entire line, on a scale and record dry weight.

GatheRex Setup. Sterile weld the red media removal line from the G-Rex500MCS to the repeater pump transfer set on the 10 L labtainer bag "Supernatant" prepared above. Sterile weld the clear cell removal line from the G-Rex500MCS to the TIL Suspension transfer pack prepared above. Place G-Rex500MCS flask on the left side of the GatheRex. Place the supernatant labtainer bag and TIL suspension transfer pack to the right side. Install the red media removal line from the G-Rex500MCS to the top clamp (marked with a red line) and tubing guides on the GatheRex. Install the clear harvest line from the G-Rex500MCS to the bottom clamp (marked with a blue line) and tubing guides on the GatheRex. Attach the gas line from the GatheRex to the sterile filter of the G-Rex500 MCS. Before removing the supernatant from the G-Rex500MCS, ensure all clamps on the cell removal lines were closed.

Volume Reduction of G-Rex500MCS. Transfer ~4.5 L of culture supernatant from the G-Rex500MCS to the 10 L Labtainer per SOP-01777. Visually inspect G-Rex500MCS to ensure flask as level and media had been reduced to the end of the aspirating dip tube.

Prepare flask for TIL Harvest. After removal of the supernatant, close all clamps to the red line.

Initiation of TIL Harvest. Record the start time of the TIL harvest. Vigorously tap flask and swirl media to release cells. Perform an inspection of the flask to ensure all cells have detached. Tilt the flask to ensure hose is at the edge of the flask. If the cell collection straw is not at the junction of the wall and bottom membrane, rapping the flask while tilted at a 450 angle is usually sufficient to properly position the straw.

TIL Harvest. Release all clamps leading to the TIL suspension transfer pack. Using the GatheRex, transfer the cell suspension into the TIL Suspension transfer pack. Be sure to maintain the tilted edge until all cells and media are collected. Inspect membrane for adherent cells.

Rinsed flask membrane. Rinsed the bottom of the G-Rex500MCS. Cover ~¼ of gas exchange membrane with rinse media. Closed clamps on G-Rex500MCS. Ensured all clamps were closed on the G-Rex500MCS.

Heat seal the Transfer Pack containing the TIL as close to the weld as possible so that the overall tubing length remained approximately the same. Heat seal the 10 L Labtainer containing the supernatant and passed into the BSC for sample collection.

Record weight of Transfer Pack with cell suspension and calculate the volume suspension. Prepare transfer pack for sample removal. Weld a 4" plasma transfer set to the TIL Suspension transfer pack from above, leaving the female luer end attached as close to the bag as possible.

Remove testing samples from cell supernatant. In the BSC, remove 10.0 mL of supernatant from 10 L labtainer using female luer port and appropriately sized syringe. Place into a 15 mL conical tube and label as "BacT" and Retain the tube for BacT sample. Using a separate syringe, removed 10.0 mL of supernatant and placed into a 15 mL conical tube. Retained the tube for *Mycoplasma* sample for testing. Label tube as "*Mycoplasma* diluent". Closed supernatant bag. Place a red cap on the luer port to close the bag, and pass out of BSC.

Remove Cell Count Samples. In the BSC, using separate 3 mL syringes for each sample, removed 4×1.0 mL cell count samples from "TIL Suspension" transfer pack using the luer connection. Place samples in cryovials prepared above.

Remove *Mycoplasma* Samples. Using a 3 mL syringe, removed 1.0 mL from TIL Suspension transfer pack and place into 15 mL conical labeled "*Mycoplasma* diluent" prepared above. Label and stored *Mycoplasma* sample at 2-8° C. until submitted for testing.

Prepare Transfer Pack for Seeding. In the BSC, attach the large diameter tubing end of a Repeater Pump Fluid Transfer Set to the Luer adapter on the transfer pack containing the TIL. Clamp the line close to the transfer pack using a hemostat. Place a red cap onto the end of the transfer set.

Place TIL in incubator. Remove cell suspension from the BSC and place in incubator until needed. Record time.

Perform cell counts and calculations utilizing NC-200. Diluted cell count samples initially by adding 0.5 mL of cell suspension into 4.5 mL of AIM-V media prepared above. This gave a 1:10 dilution.

Calculate flasks for subculture. Calculate the total number of flasks to seed. Rounded the number of G-Rex500MCS flasks to seed up to the neared whole number.

Example 6. Identifying AKT Pathway Inhibitors Useful for TIL Expansion

An exemplary screening strategy for identifying AKT pathway compounds useful for TIL expansion. Fresh tumors samples are obtained and disaggregated into fresh tumor digests, which comprise primary tumor infiltrating lymphocytes. Exemplary methods of obtaining such TILs are described by Quatromoni et al., "An optimized disaggregation method for human lung tumors that preservers phenotype and function of immune cells," *J. Leukoc. Biol.* 97:201-209 (2015). These disaggregated cells are aliquoted into 24-well plates.

Negative control wells have culture medium with no added small molecule library compound. Positive control wells have an effective amount of afuresertib added, for example 500 nM per 100,000 cells. Small molecule compounds, comprising a library, designed e.g. according to methods described by Harris et al., "The Design and Application of Target-Focused Libraries", *Comb. Chem. High Throughput Screen.* 14:521-531 (2011), are added, one per well. The cultures are maintained for seven days following addition of the library compounds. On the seventh day, the cells are collected and washed then characterized using flow cytometry to characterized the expression of cell surface proteins indicating central memory T-cell phenotype, e.g. CD62L and CCR7. Cells are also characterized for gene expression of genes associated with various T-cell subsets, e.g. $CD8^+$, $CD4^+$, MHC Class I, MHC Class II, etc. "Hits" are wells whose T-cells show enrichment for the "young TIL" phenotype, e.g. enriched for CD8 expression, CD27 expression, and relatively longer telomeres.

Example 7. Gen3 Exemplary Process

The example provides a comparison between the Gen 2 and Gen 3 processes. This example describes the development of a robust TIL expansion platform. The modifications to the Gen 2 process reduce risk and streamline the manufacturing process by reducing the number of operator interventions, reduce the overall time of manufacturing, optimize the use of reagents, and facilitate a flexible semi-closed and semi-automated cell production process amenable to high-throughput manufacturing on a commercial scale.

Process Gen 2 and Gen 3 are composed of autologous TIL derived from an individual patient through surgical resection of a tumor that is expanded ex vivo. The expansion process is a cell culture in the presence of interleukin-2 (IL-2) and the monoclonal antibody OKT3, which targets the T-cell co-receptor CD3 on a scaffold of irradiated peripheral blood mononuclear cells (PBMCs).

The manufacture of Gen 2 TIL products consists of two phases: 1) pre-Rapid Expansion (Pre-REP) and 2) Rapid Expansion Protocol (REP). During the Pre-REP resected tumors are cut up into ≤50 fragments 2-3 mm in each dimension which are cultured with serum-containing culture medium and 6,000 IU/mL of Interleukin-2 (IL-2) for a period of 11 days. On day 11 TIL are harvested and introduced into the large-scale secondary REP expansion. The REP consists of activation of the T cells in a co-culture of irradiated allogeneic PBMCs feeder cells loaded with monoclonal anti-CD3 antibody (OKT3) and culture in the presence of 3000 IU/mL of rhIL-2. On day 16 cells are split into multiple G-REX-500 flasks at $≥1×10^9$ viable lymphocytes/flask. The REP is harvested on day 22, washed, formulated, and cryo-preserved prior to shipping at −150° C. to the clinical site for infusion.

The manufacture of Gen 3 TIL products consisted of two phases: 1) pre-Rapid Expansion Protocol (Pre-REP) and 2) Subculture Split. During the pre-REP TIL propagation resected tumor are cut up into ≤120 fragments 2-3 mm in each dimension which are cultured in up to 3, 100 M vessel with serum-containing culture medium and 6,000 IU/mL of Interleukin-2 (IL-2) for a period of 7 days. On day 7, a feeder cell layer is incorporated into the tumor fragmented culture phase to generate numbers of pre-REP TIL sufficient for entry into the REP phase. The REP initiation was enhanced by activating the entire pre-REP culture in the same vessel using closed system fluid transfer of OKT3 loaded feeder cells into the 1OOM vessel. For Gen 3, the TI, scale up or split involves process steps where the whole cell culture was scaled to a larger vessel through closed system fluid transfer and was transferred (from 100 M flask to a 500 M flask) and additional CM4 media added. The REP cells were harvested on day 16, washed, formulated, and cryo-preserved prior to shipping at −150° C. to the clinical site for infusion.

Overall, the Gen 3 process is a shorter, more scalable, and easily modifiable expansion platform that will accommodate to fit robust manufacturing and process comparability.

TABLE 41

Comparison of Exemplary Gen 2 and Exemplary Gen 3 manufacturing process.

| Step | Process (Gen 2) | Process (Gen 3) |
|---|---|---|
| Pre REP-day 0 | Up to 50 fragments/1-G-Rex 100MCS - 11 days In 1 L of CM1 media + IL-2 (6000 IU/mL) | Whole tumor up to 120 fragments divided evenly among up to 3 flasks. 1 flask: 1-60 fragments 2 flasks: 61-89 fragments 3 flasks 90-120 fragments 7 days in 500 mL of CM1 media + IL-2 (6000 IU/mL) $2.5 × 10^8$ feeder cells/flask 15 µg OKT-3/flask |
| REP Initiation | Direct to REP- Day 11-<$200e^6$ TIL (1) G-Rex 500MCS in 5 L CM2 media IL-2 (3000 IU/mL) $5 × 10^9$ feeder cells 150 µg OKT-3 | Direct to REP- Day 7-all cells TIL- same G-Rex 100MCS Add 500 mL CM2 media IL-2 (6000 IU/mL) $5 × 10^8$ feeder cells/flask 30 µg OKT-3/flask |
| TIL propagation or Scale up | Volume reduce and split cell fraction in up to 5 G-REX 500MCS 4.5 L CM4 media + IL-2 (3000 IU/mL) $≥1 × 10^9$ TVC/flask Split day 16 | Each G-REX 100MCS(1 L) transfers to 1 G-REX 500MCS Add 4 L CM4 media + IL-2 (3000 IU/mL) Scale up on day 9 to 11 |
| Harvest | Harvest day 22, LOVO-automated cell washer | Harvest day 16 LOVO-automated cell washer |
| Final formulation | Cryopreserved Product 300 IU/mL IL2- CS10 in $LN_2$, multiple aliquots | Cryopreserved product 300 IU/mL IL-2-CS10 in $LN_2$, multiple aliquots |
| Process time | 22 days | 16 days |

On day 0, for both processes, the tumor was washed 3 times and the fragments were randomized and divided into two pools; one pool per process. For the Gen 2 Process, the fragments were transferred to one GREX 100MCS flask with 1 L of CM1 media containing 6,000 IU/mL rhIL-2. For the Gen 3 Process, fragments were transferred to one GREX100MCS flask with 200 mL of CM1 containing 6,000 IU/mL rhIL-2.

Seeding of TIL for Rep initiation day occurred on different days according to each process, for the Gen 2 Process, in which the G-REX 100MCS flask was 90% volume reduced, collected cell suspension was transferred to a new G-REX 500MCS to start REP initiation on day 11, then cells were expanded and split on day 16 into multiple GREX 500 MCS flask and then harvested on day 22. For the Gen 3 process, the REP initiation occurred on day 7, in which the same G-REX 100MCS was used for REP initiation, then the cells were scaled up on day 9-11 where the cells from the G-REX 100MCS were transferred to a new single G-REX 500MCS, then the TIL were harvested on day 16.

Three different tumors were included in the comparison, two lung tumors (L4054 and L4055) and one melanoma tumor (M1085T).

CM1 (culture media 1), CM2 (culture media 2), and CM4 (culture media 4) media were prepared in advance and held at 4° C. for L4054 and L4055. CM1 and CM2 media were prepared without filtration to compare cell growth with and without filtration of media.

Media was warmed at 37° C. up to 24 hours in advance for L4055 tumor on REP initiation and scale-up.

Results Summary

Gen 3 will fall within 30% of Gen 2 for total viable cells achieved. Gen 3 final product is will have higher production of INF-γ after restimulation. Gen 3 final product is will have an increased clonal diversity as measured by total unique CDR3 sequences present. Gen 3 final product will have a longer mean telomere length.

Results Achieved

Cell count and % viability: Pre REP and REP expansion on Gen 2 and Gen 3 processes followed details described above.

Table 42: Pre-REP cell counts. For each tumor, the two pools contained equal number of fragments. Due to the small size of tumors, the maximum number of fragments per flask was not achieved. Total pre-Rep cells (TVC) were harvested and counted at day 11 for the Gen 2 process and at day 7 for the Gen 3 process. To compare the two pre-REP arms, the cell count was divided over the number of fragments provided in the culture in order to calculate an average of viable cells per fragment. As indicated in the table below, the Gen 2 process consistently grew more cells per fragment compared to the Gen 3 Process. An extrapolated calculation of the number of TVC expected for Gen 3 process at day 11, which was calculated dividing the pre-REP TVC by 7 and then multiply by 11.

TABLE 42 pre-REP cell counts

| | Tumor ID | | | | | |
|---|---|---|---|---|---|---|
| | L4054 | | L4055* | | M1085T | |
| Process | Gen 2 | Gen 3 | Gen 2 | Gen 3 | Gen 2 | Gen 3 |
| pre-REP TVC | 1.42E+08 | 4.32E+07 | 2.68E+07 | 1.38E+07 | 1.23E+07 | 3.50E+06 |
| Number of fragments | 21 | 21 | 24 | 24 | 16 | 16 |
| Average TVC per fragment at pre-REP | 6.65E+06 | 2.06E+06 | 1.12E+06 | 5.75E+05 | 7.66E+05 | 2.18E+05 |
| Gen 3 extrapolated value at pre REP day 11 | N/A | 6.79E+07 | N/A | 2.17E+07 | N/A | 5.49E+06 |

(*L4055, unfiltered media)

Table 43: Total viable cell count and fold expansion on TIL final product: For the Gen 2 and Gen 3 processes, TVC was counted per process condition and percent viable cells was generated for each day of the process. On harvest, day 22 (Gen 2) and day 16 (Gen 3) cells were collected and the TVC count was established. The TVC was then divided by the number of fragments provided on day 0, to calculate an average of viable cells per fragment. Fold expansion was calculated by dividing harvest TVC by over the REP initiation TVC. As exhibited in the table, comparing Gen 2 and the Gen 3, fold expansions were similar for L4054; in the case of L4055, the fold expansion was higher for the Gen 2 process. Specifically, in this case, the media was warmed up 24 in advance of REP initiation day. A higher fold expansion was also observed in Gen 3 for M1085T. An extrapolated calculation of the number of TVC expected for Gen 3 process at day 22, which was calculated dividing the REP TVC by 16 and then multiply by 22.

TABLE 43

Total viable cell count and fold expansion on TIL final product

| | Tumor ID | | | | | |
|---|---|---|---|---|---|---|
| | L4054 | | L4055* | | M1085T | |
| Process | Gen 2 | Gen 3 | Gen 2 | Gen 3 | Gen 2 | Gen 3 |
| # Fragments | 21 | 21 | 24 | 24 | 16 | 16 |
| TVC/fragment (at Harvest) | 3.18E+09 | 8.77E+08 | 2.30E+09 | 3.65E+08 | 7.09E+08 | 4.80E+08 |
| REP initiation | 1.42E+08 | 4.32E+07 | 2.68E+07 | 1.38E+07 | 1.23E+07 | 3.50E+06 |
| Scale up | 3.36E+09 | 9.35E+08 | 3.49E+09 | 8.44E+08 | 1.99E+09 | 3.25E+08 |
| Harvest | 6.67E+10 | 1.84E+10 | 5.52E+10 | 8.76E+09 | 1.13E+10 | 7.68E+09 |

TABLE 43-continued

Total viable cell count and fold expansion on TIL final product

| | Tumor ID | | | | | |
| --- | --- | --- | --- | --- | --- | --- |
| | L4054 | | L4055* | | M1085T | |
| Process | Gen 2 | Gen 3 | Gen 2 | Gen 3 | Gen 2 | Gen 3 |
| Fold Expansion Harvest/ REP initiation | 468.4 | 425.9 | 2056.8 | 634.6 | 925.0 | 2197.2 |
| Gen 3 extrapolated value at REP harvest day 22 | N/A | 2.53E+10 | N/A | 1.20E+10 | N/A | 1.06E+10 |

((*L4055, unfiltered media)

Table 44: Percent Viability of TIL final product: Upon harvest, the final TIL, REP products were compared against release criteria for 0% viability. All of the conditions for the Gen 2 and Gen 3 processes process surpassed the 70% viability criterion and were comparable across processes and tumors.

TABLE 44

| Percent Viability of REP | | | | | | |
| --- | --- | --- | --- | --- | --- | --- |
| | Tumor ID | | | | | |
| | L4054 | | L4055 | | M1085T | |
| Process | Gen 2 | Gen 3 | Gen 2 | Gen 3 | Gen 2 | Gen 3 |
| REP initiation | 98.23% | 97.97% | 97.43% | 92.03% | 81.85% | 68.27% |
| Scale up | 94.00% | 93.57% | 90.50% | 95.93% | 78.55% | 71.15% |
| Harvest | 87.95% | 89.85% | 87.50% | 86.70% | 86.10% | 87.45% |

Table 45: Estimate cell count per additional flask for Gen 3 process. Due to the number of fragments per flask was not the maximum required number, an estimate cell count at harvest day was calculated for each tumor. The estimation was based on the expectation that clinical tumors were large enough to seed 2 or 3 flasks on day 0.

TABLE 45

| Extrapolated estimate cell count calculation to full scale 2 and 3 flask on Gen 3 Process | | | | | | |
| --- | --- | --- | --- | --- | --- | --- |
| | Tumor ID | | | | | |
| | L4054 | | L4055 | | M1085T | |
| Gen 3 Process | 2 flasks | 3 Flasks | 2 flasks | 3 Flasks | 2 flasks | 3 Flasks |
| Estimate Harvest | 3.68E+10 | 5.52E+10 | 1.75E+10 | 2.63E+10 | 1.54E+10 | 2.30E+10 |

Immunotyping

Three tumors L4054, L4055, and M1085T underwent TIL expansion in both the Gen 2 and Gen 3 processes. Upon harvest, the REP TIL final products were subjected to flow cytometry analysis to test purity, differentiation, and memory markers. For all the conditions the percentage of TCR a/b+ cells were over 90%.

Figure 10:
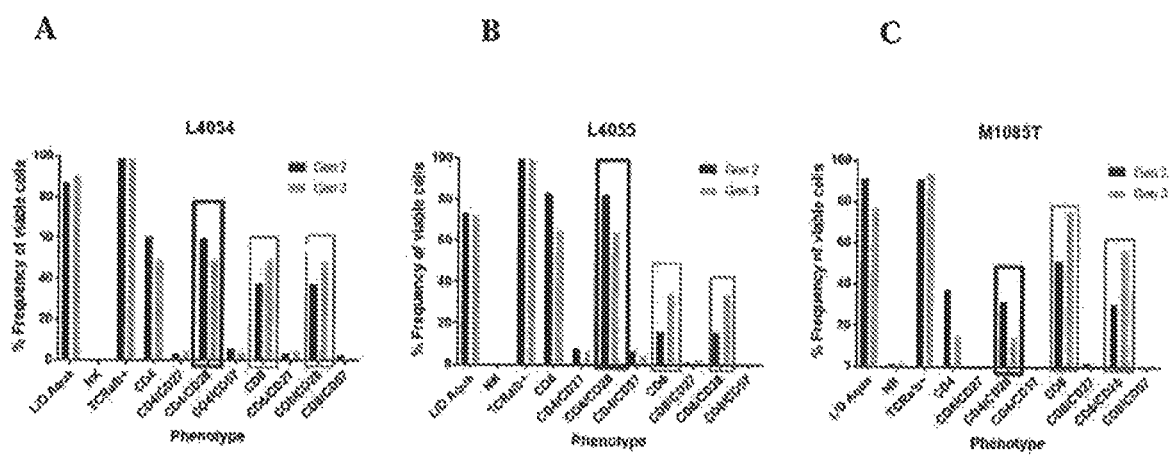
FIG. 10.

TIL harvested from the Gen 3 process showed a higher expression of CD8 and CD28 compared to TIL harvested from the Gen 2 process. The Gen 2 process showed a higher percentage of CD4+. See FIG. 10 (ABC).

Memory Markers Comparison on TIL Final Product

Figure 11:
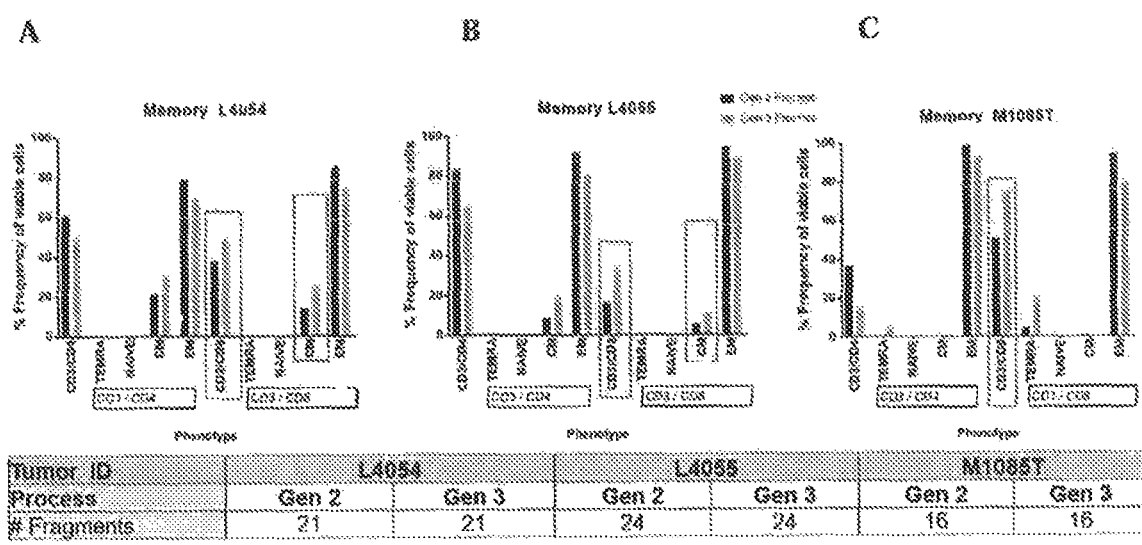
FIG. 11.

TIL harvested from the Gen 3 process showed a higher expression on central memory compartments compared to TIL from the Gen 2 process. See, FIG. 11 (A, B, C).

Activation and Exhaustion Markers Comparison on TIL Final Product

Figure 13:
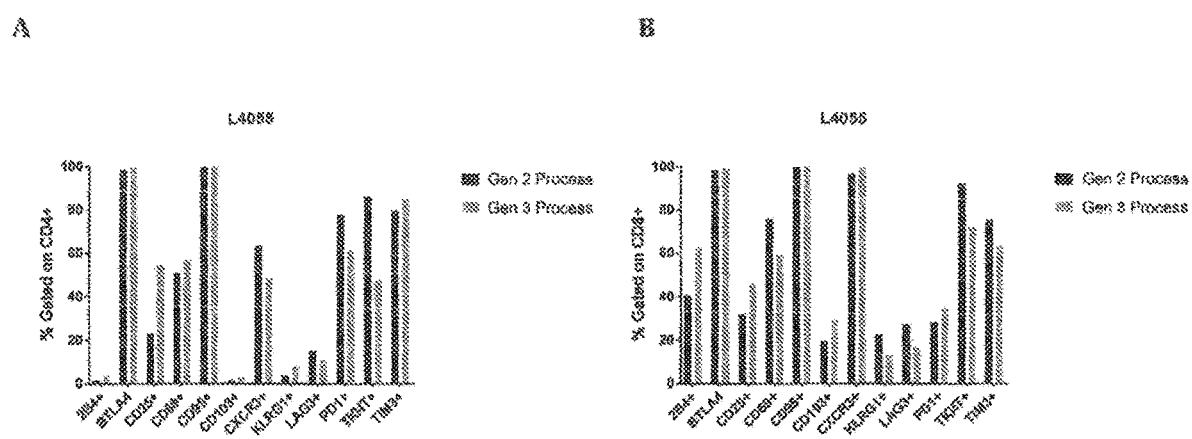
FIG. 13: L4055 Activation and exhaustion markers (A) Gated on CD4+, (B) Gated on CD8+.
Figure 14:
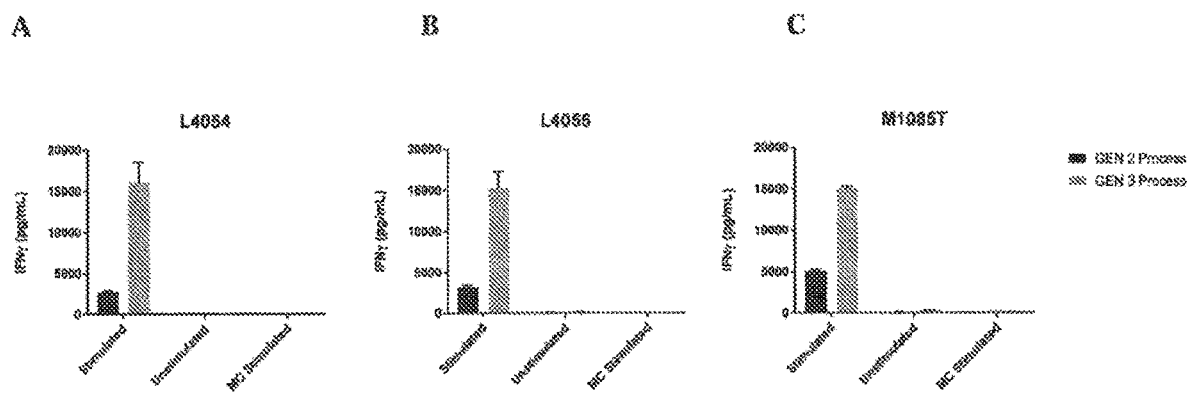
FIG. 14: IFNγ production (pg/mL): (A) L4054, (B) L4055, and (C) M1085T for the Gen 2 and Gen 3 processes: Each bar represented here is mean+SEM for IFNγ levels of stimulated, unstimulated, and media control. Optical density measured at 450 nm.
Figure 15:
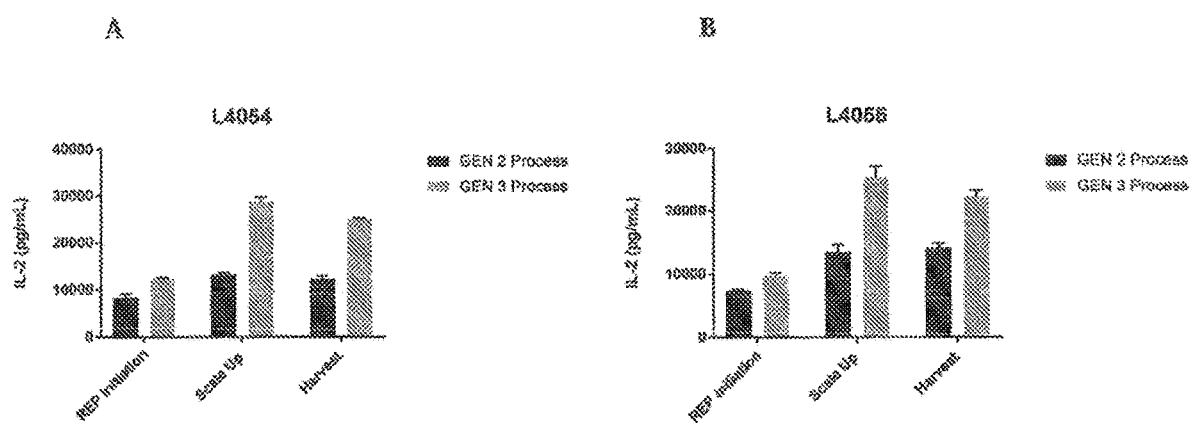
FIG. 15: ELISA analysis of IL-2 concentration in cell culture supernatant: (A) L4054 and (B) L4055. Each bar represented here is mean+SEM for IL-2 levels on spent media. Optical density measured at 450 nm.

Activation and exhaustion marker were analyzed in TIL from two, tumors L4054 and L4055 to compare the final TIL product by from the Gen 2 and Gen 3 TIL expansion processes. Activation and exhaustion markers were comparable between the Gen 2 and Gen 3 processes. See, FIG. 12 (A, B); FIG. 13 (A, B).

Interferon Gamma Secretion Upon Restimulation

On harvest day, 22 for Gen 2 and day 16 for Gen 3, TIL underwent an overnight restimulation with coated anti-CD3 plates for L4054 and L4055. The restimulation on M1085T was using anti-CD3, CD28, and CD137 beads. Supernatant was collected after 24 hours of the restimulation in all conditions and the supernatant was frozen. IFNγ analysis by ELISA was assessed on the supernatant from both processes at the same time using the same ELISA plate. Higher production of IFNγ from the Gen 3 process was observed. See, FIG. 14 (A, B, C).

Measurement of IL-2 Levels in Culture Media

Figure 16:
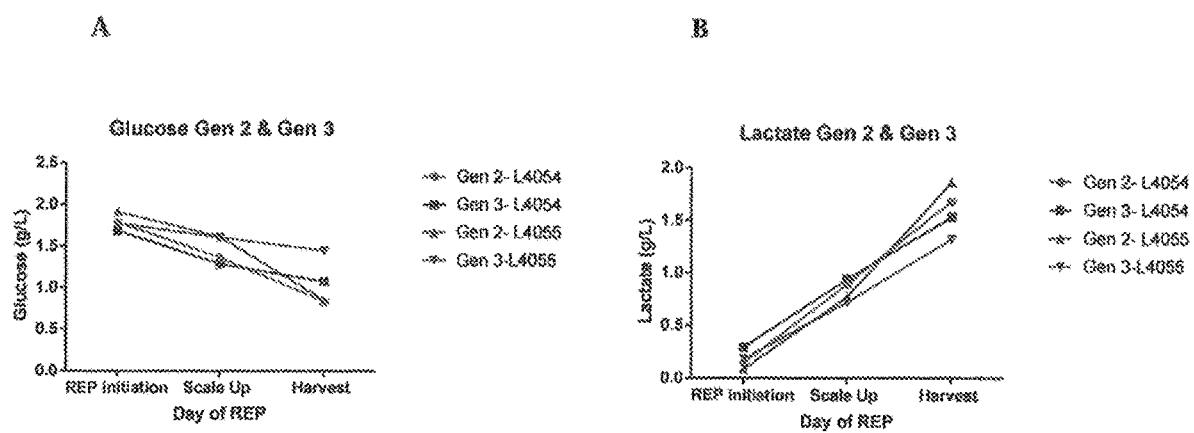
FIG. 16: Quantification of glucose and lactate (g/L) in spent media: (A) Glucose and (B) Lactate: In the two tumor lines, and in both processes, a decrease in glucose was observed throughout the REP expansion. Conversely, as expected, an increase in lactate was observed. Both the decrease in glucose and the increase in lactate were comparable between the Gen 2 and Gen 3 processes.

To compare the IL-2 consumption between Gen 2 and Gen 3 process, cell supernatant was collected on REP initiation, scale up, and harvest day, on tumor L4054 and L4055. The quantity of IL-2 in cell culture supernatant was measured by Quantitate ELISA Kit from R&D. The general trend indicates that the IL-2 concentration remains higher in the Gen 3 process when compared to the Gen 2 process. This is likely due to the higher concentration of IL-2 on REP initiation (6000 IU/mL) for Gen 3 coupled with the carry-over of the media throughout the process. See, FIG. 16 (A, B).

Metabolic Substrate and Metabolite Analysis

The levels of metabolic substrates such as D-glucose and L-glutamine were measured as surrogates of overall media consumption. Their reciprocal metabolites, such lactic acid and ammonia, were measured. Glucose is a simple sugar in media that is utilized by mitochondria to produce energy in the form of ATP. When glucose is oxidized, lactic acid is produced (lactate is an ester of lactic acid). Lactate is strongly produced during the cells exponential growth phase. High levels of lactate have a negative impact on cell culture processes. See, FIG. 16 (A, B).

Spent media for L4054 and L4055 was collected at REP initiation, scale up, and harvest days for both process Gen 2 and Gen 3. Supernatant was analyzed on a CEDEX Bioanalyzer for concentrations of glucose, lactic acid, glutamine, glutamax, and ammonia.

Figure 17:
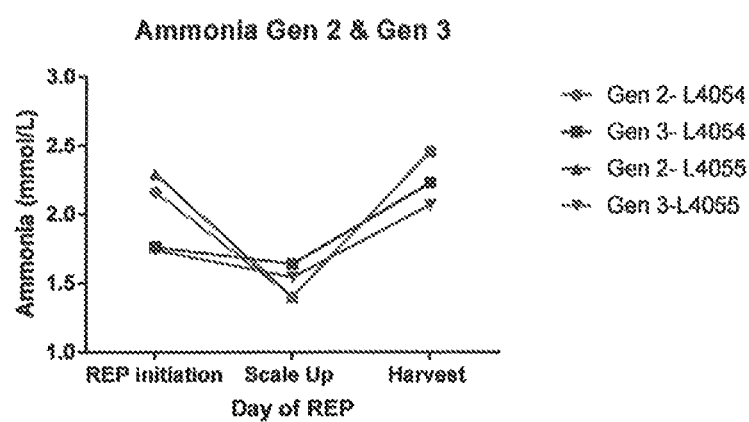
FIG. 17: A) Quantification of L-glutamine in spent media for L4054 and L4055. B) Quantification of Glutamax in spent media for L4054 and L4055. C) Quantification of ammonia in spent media for L4054 and L4055.
Figure 18:
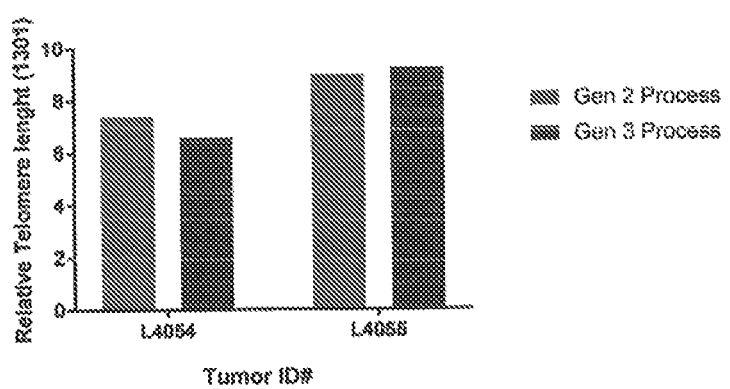
FIG. 18: Telomere length analysis: The relative telomere length (RTL) value indicates that the average telomere fluorescence per chromosome/genome in Gen 2 and Gen 3 process of the telomere fluorescence per chromosome/genome in the control cells line (1301 Leukemia cell line) using DAKO kit.
Figure 19:
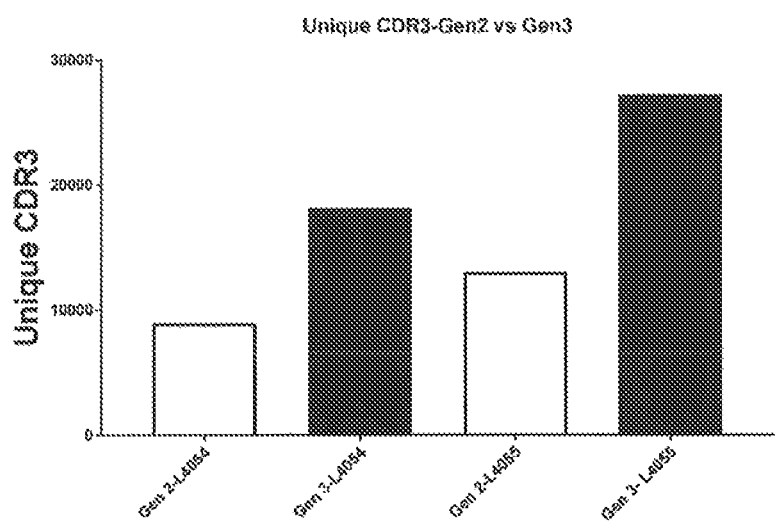
FIG. 19: Unique CDR3 sequence analysis for TIL final product on L4054 and L4055 under Gen 2 and Gen 3 process. Columns show the number of unique TCR B clonotypes identified from 1×106 cells collected on Harvest Day Gen 2 (e.g., day 22) and Gen 3 process (e.g., day 14-16). Gen 3 shows higher clonal diversity compared to Gen 2 based on the number of unique peptide CDRs within the sample.
Figure 20:
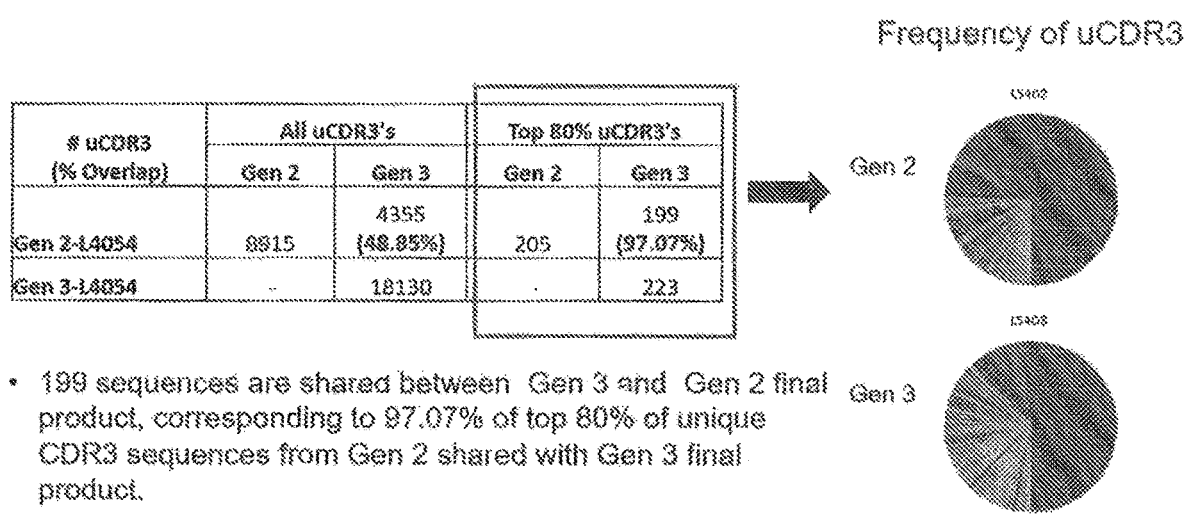
FIG. 20: Frequency of unique CDR3 sequences on L4054 IL harvested final cell product (Gen 2 (e.g., day 22) and Gen 3 process (e.g., day 14-16)).
Figure 21:
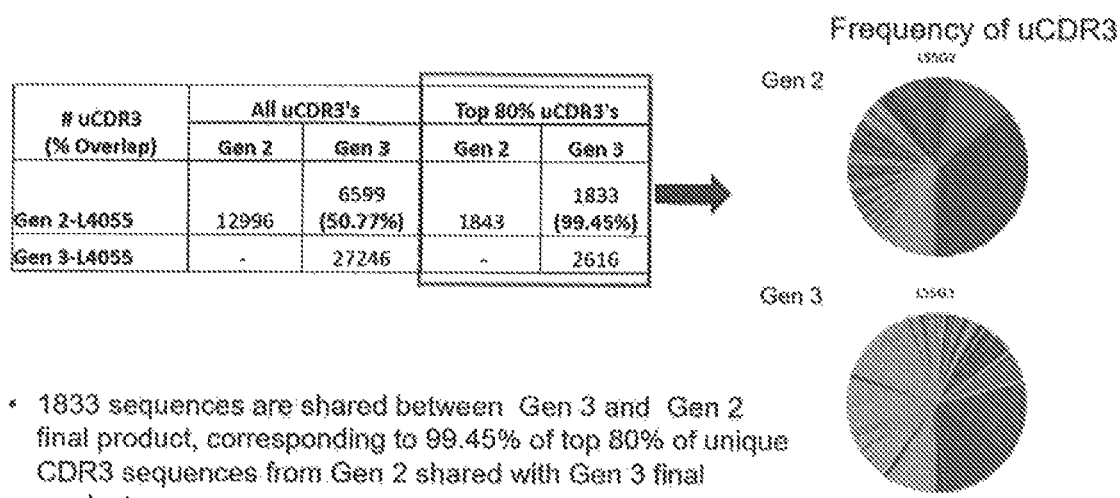
FIG. 21: Frequency of unique CDR3 sequences on L4055 TIL harvested final cell product (Gen 2 (e.g., day 22) and Gen 3 process (e.g., day 14-16)).
Figure 22:
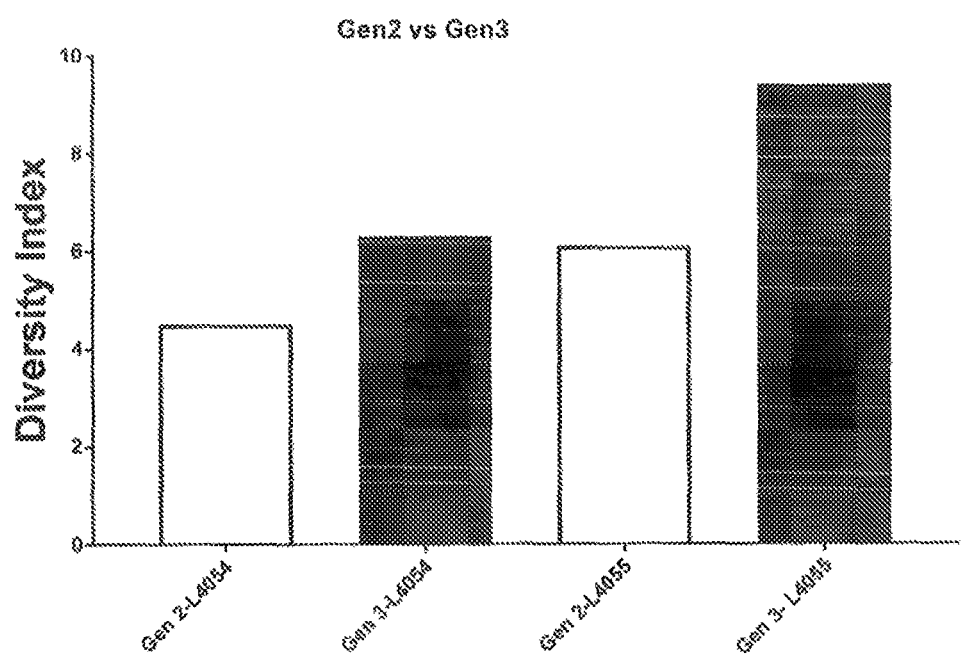
FIG. 22: Diversity Index for TIL final product on L4054 and L4055 under Gen 2 and Gen 3 process. Shanon entropy diversity index is a more reliable and common metric for comparison. Gen 3 L4054 and L4055 showed a slightly higher diversity than Gen 2.
Figure 27:
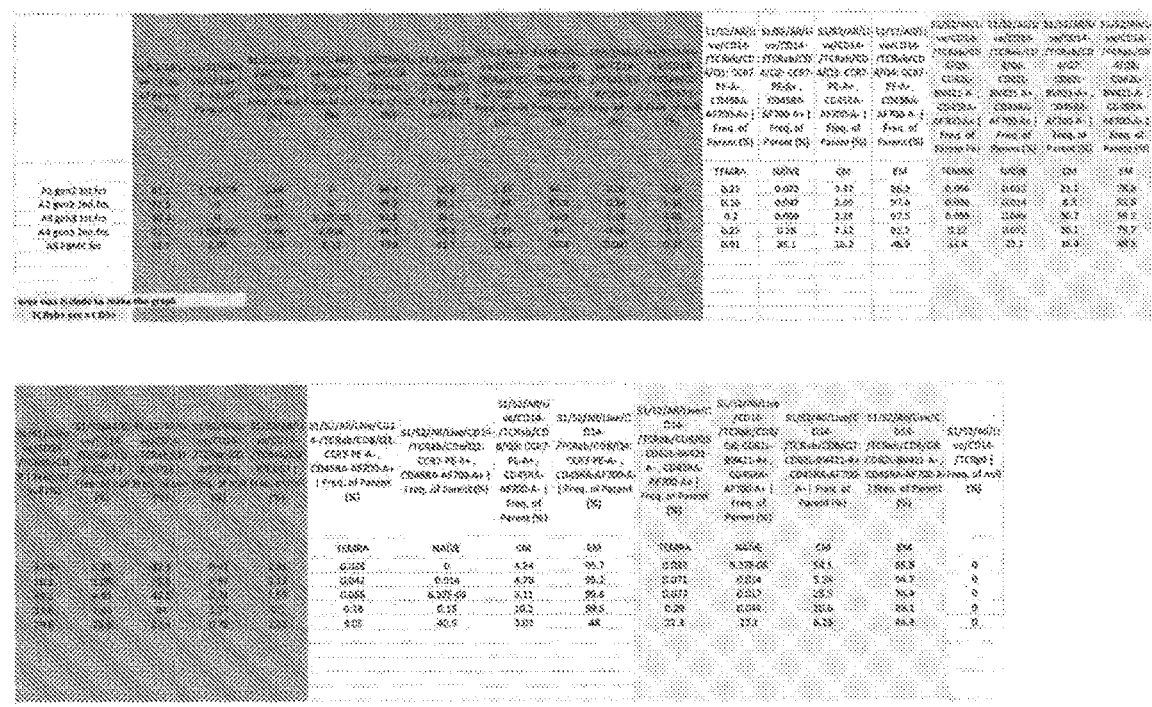
FIG. 27: Raw data for flow cytometry results depicted in FIGS. 10A, 11A, and 11B.
Figure 30:
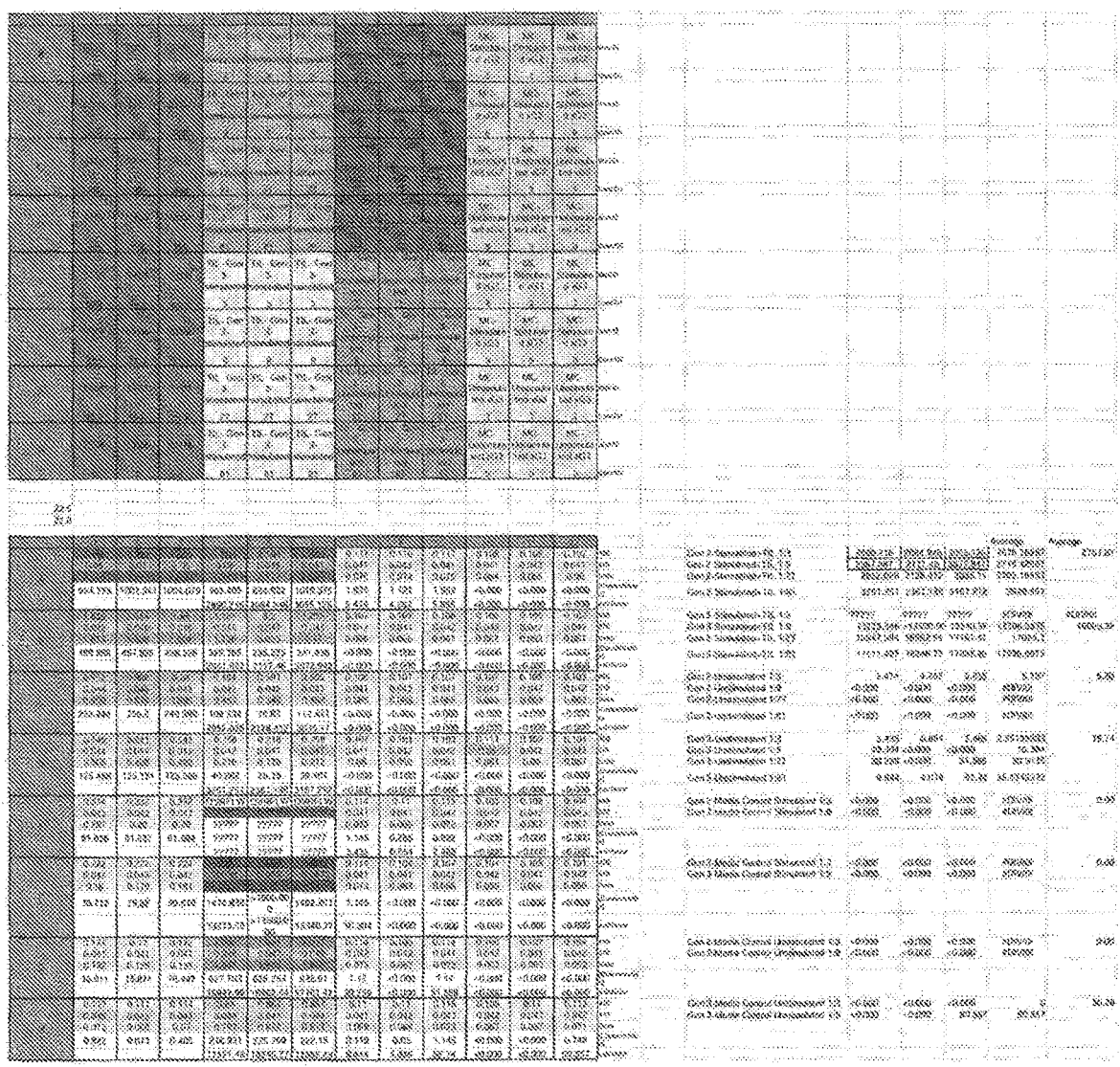
FIG. 30: Raw data for IFNγ production assay results for L4054 samples depicted in FIG. 7.
Figure 32:
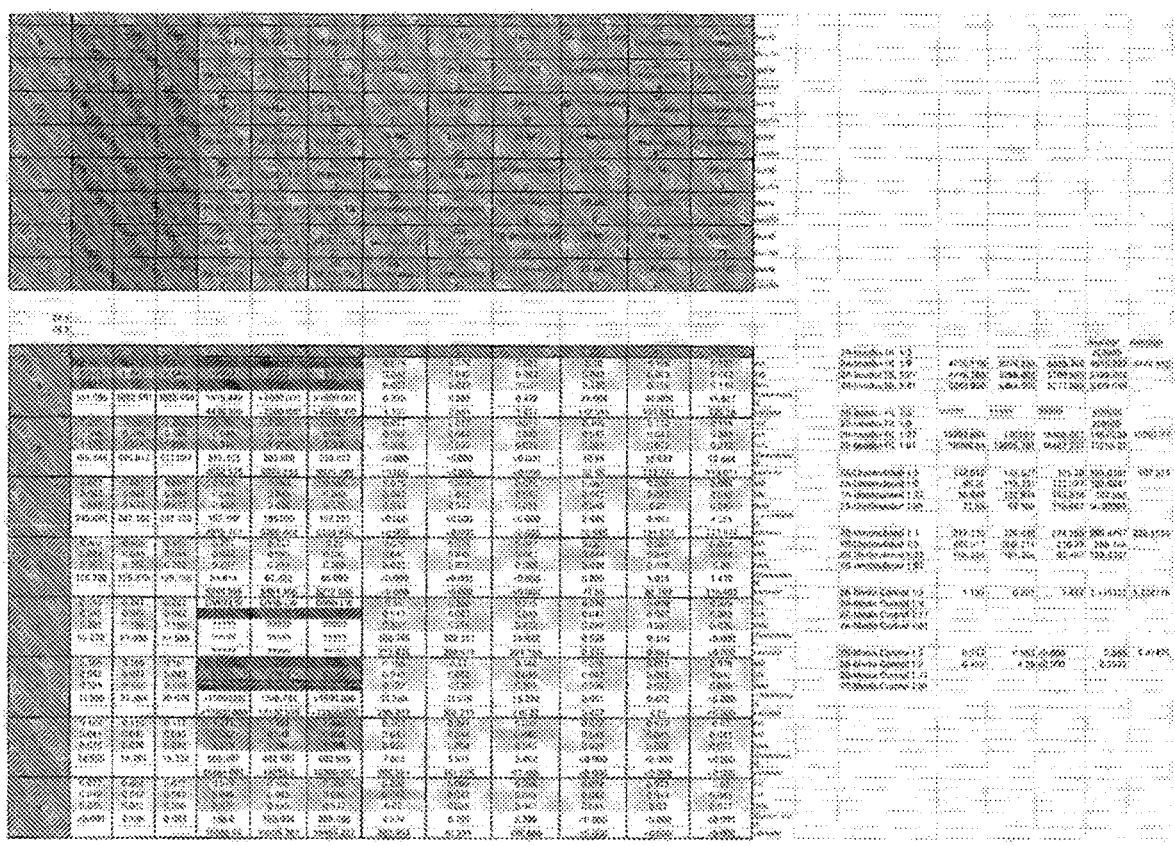
FIG. 32: Raw data for IFNγ production assay results for M1085T samples depicted in FIG. 7.
Figure 37:
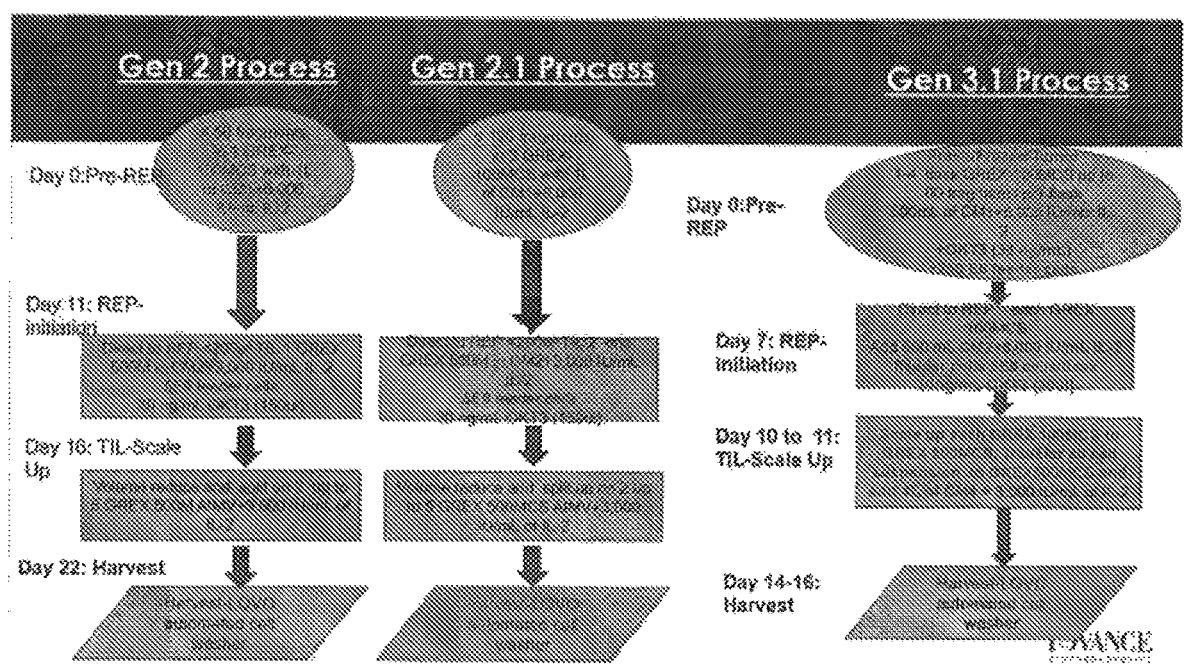
FIG. 37: Shows a comparison between various Gen 2 (2A process) and the Gen 3.1 process embodiment.
Figure 43:
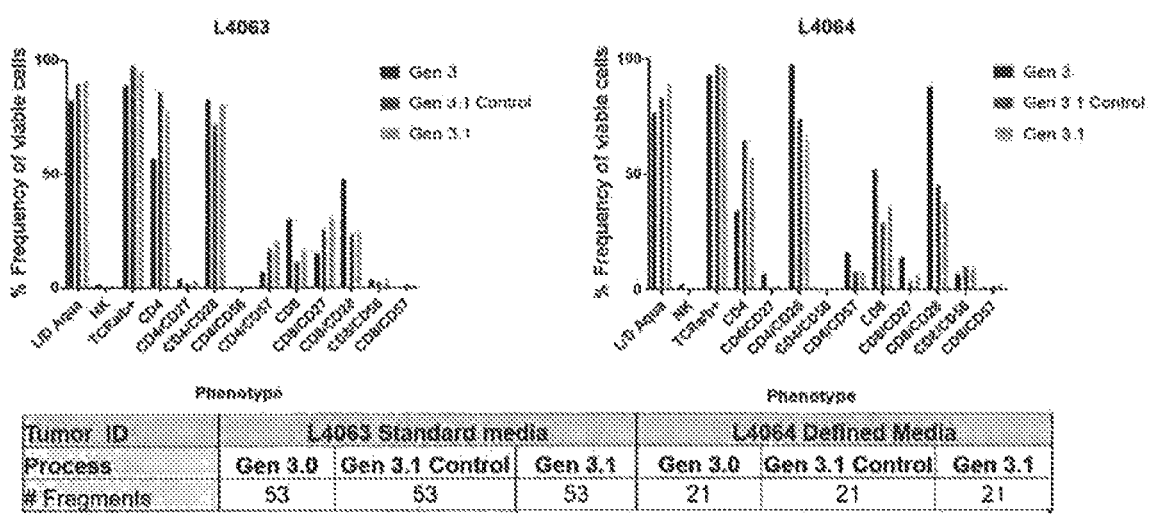
FIG. 43: Phenotype comparison: Gen 3.0 and Gen 3.1 embodiments of the process showed comparable CD28, CD27 and CD57 expression.
Figure 44:
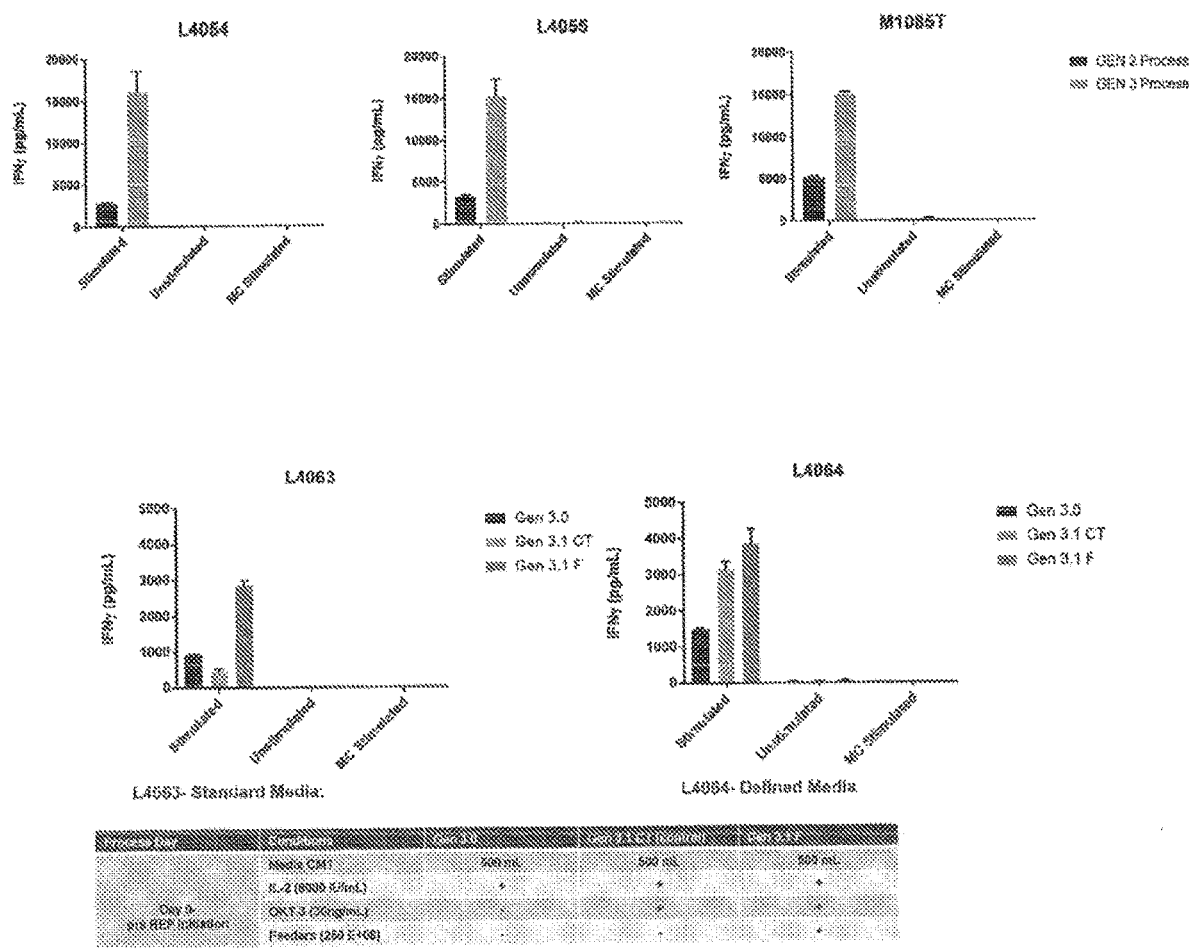
FIG. 44: Higher production of IFNγ on Gen 3 final product. IFNγ analysis (by ELISA) was assessed in the culture frozen supernatant to compared both processes. For each tumor overnight stimulation with coated anti-CD3 plate, using fresh TIL product on each Gen 2 (e.g., day 22) and Gen 3 process (e.g., day 16). Each bar represents here are IFNγ levels of stimulated, unstimulated and media control.
Figure 46:
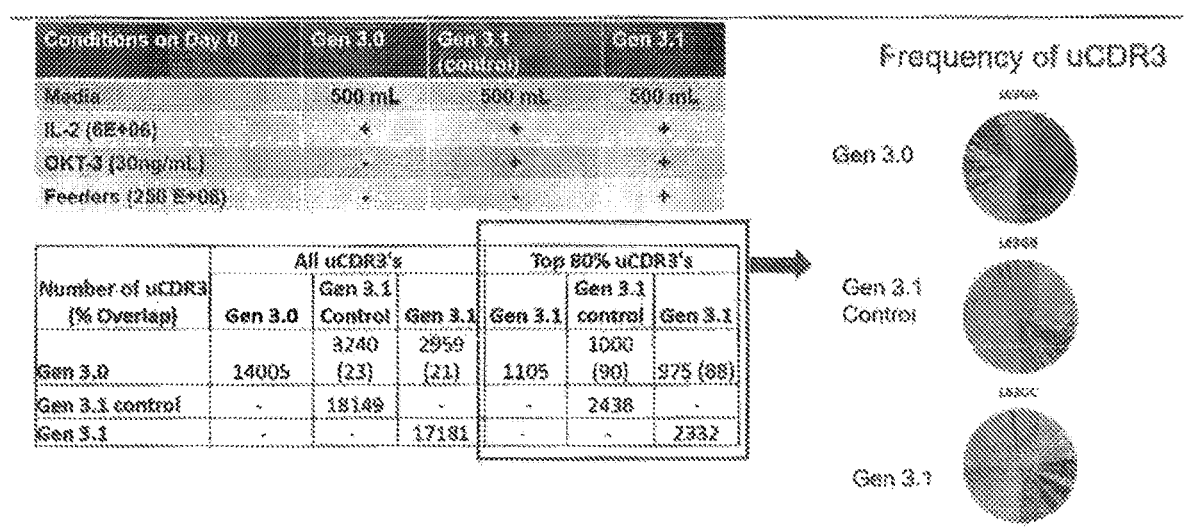
FIG. 46: 199 sequences are shared between Gen 3 and Gen 2 final product, corresponding to 97.07% of top 80% of unique CDR3 sequences from Gen 2 shared with Gen 3 final product.
Figure 47:
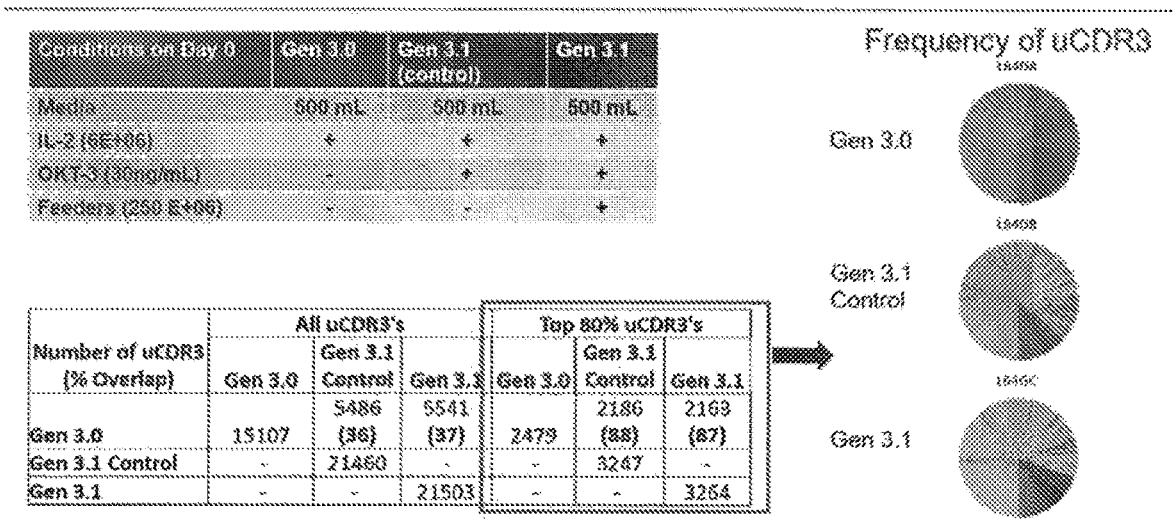
FIG. 47: 1833 sequences are shared between Gen 3 and Gen 2 final product, corresponding to 99.45% of top 80% of unique CDR3 sequences from Gen 2 shared with Gen 3 final product.
Figure 48:
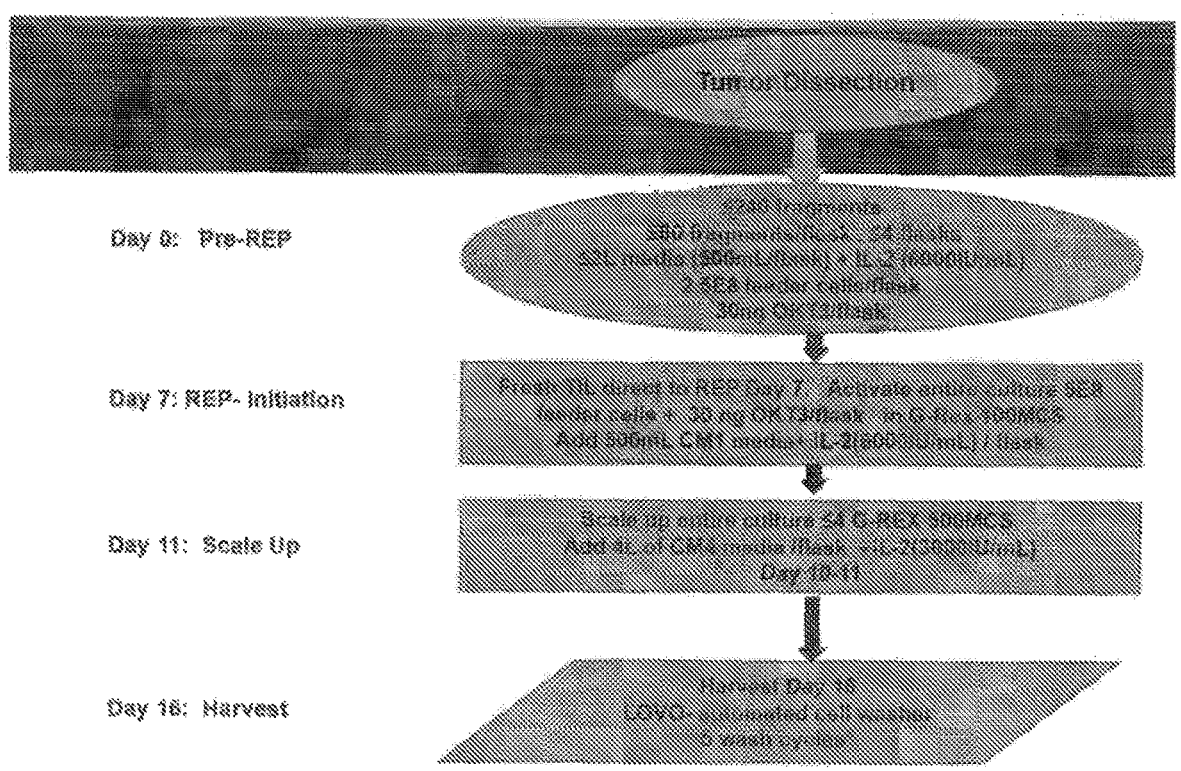
FIG. 48: Schematic of an exemplary embodiment of the Gen 3 process (a 16-day process).
Figure 49:
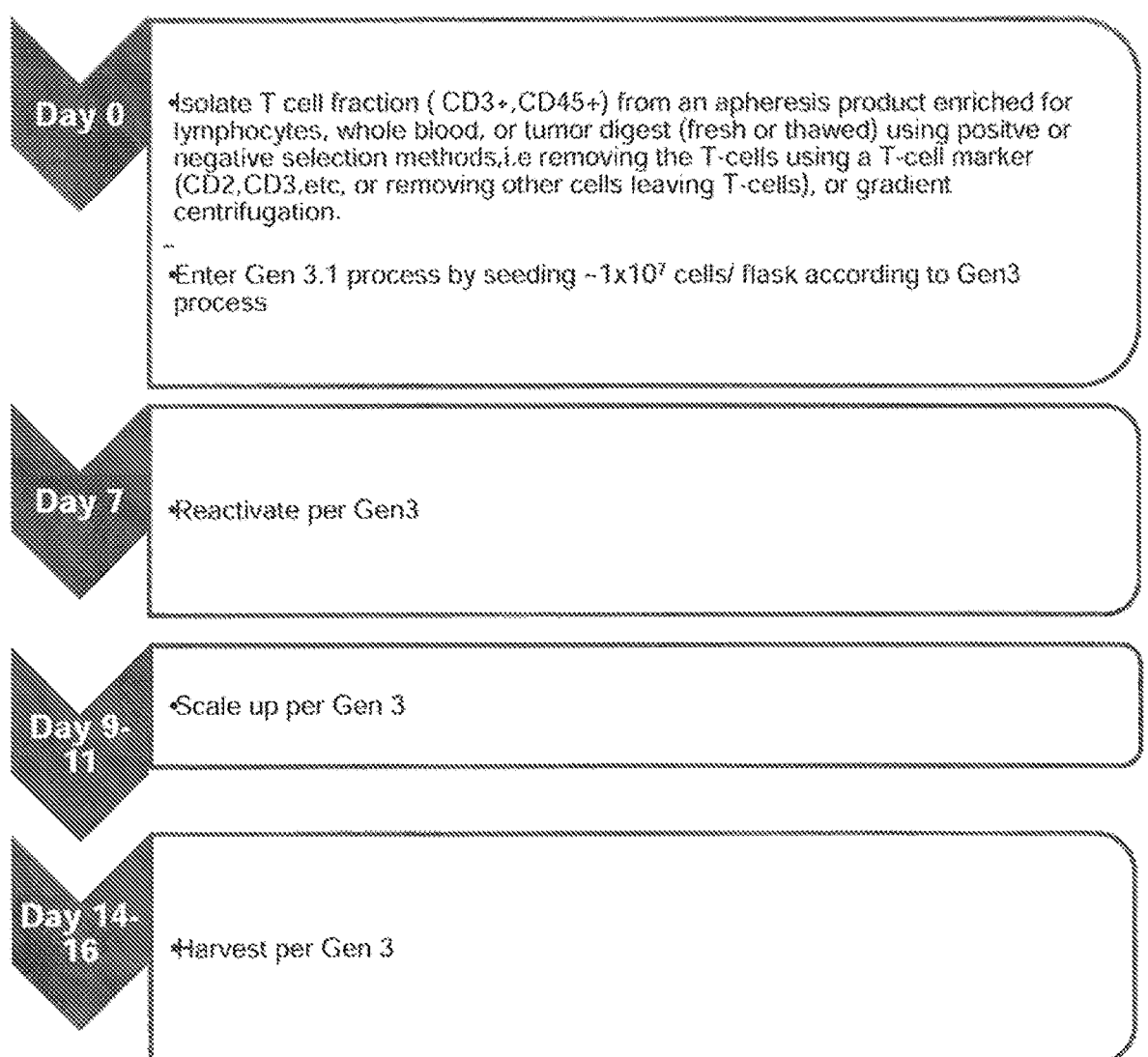
FIG. 49: Schematic of an exemplary embodiment for expanding TILs from hematopoietic malignancies using the Gen 3 process. At Day 0, a T cell fraction (CD3+, CD45+) is isolated from an apheresis product enriched for lymphocytes, whole blood, or tumor digest (fresh or thawed) using positive or negative selection methods, i.e removing the T-cells using a T-cell marker (CD2, CD3, etc, or removing other cells leaving T-cells), or gradient centrifugation.

L-glutamine is an unstable essential amino acid required in cell culture media formulations. Glutamine contains an amine, and this amide structural group can transport and deliver nitrogen to cells. When L-glutamine oxidizes, a toxic ammonia by-product is produced by the cell. To counteract the degradation of L-glutamine the media for the Gen 2 and Gen 3 processes was supplemented with Glutamax, which is more stable in aqueous solutions and does not spontaneously degrade. In the two tumor lines, the Gen 3 arm showed a decrease in L-glutamine and Glutamax during the process and an increase in ammonia throughout the REP. In the Gen 2 arm a constant concentration of L-glutamine and Glutamax, and a slight increase in the ammonia production was observed. The Gen 2 and Gen 3 processes were comparable at harvest day for ammonia and showed a slight difference in L-glutamine degradation. See, FIG. 17 (A, B, C).

Telomere Repeats by Flow Fish

Flow-FISH technology was used to measure the average length of the telomere repeat on L4054 and L4055 under Gen 2 and Gen 3 process. The determination of a relative telomere length (RTL) was calculated using Telomere PNA kit/FITC for flow cytometry analysis from DAKO. Gen 3 showed comparable telomere length to Gen 2.

CD3 Analysis

To determine the clonal diversity of the cell products generated in each process, TIL final product harvested for L4054 and L4055, were sampled and assayed for clonal diversity analysis through sequencing of the CDR3 portion of the T-cell receptors.

Table 46: Comparison of Gen 2 and Gen3 of percentage shared unique CDR3 sequences on L4054 on TIL harvested cell product. 199 sequences are shared between Gen 3 and Gen 2 final product, corresponding to 97.07% of top 80% of unique CDR3 sequences from Gen 2 shared with Gen 3 final product.

TABLE 46

Comparison of shared uCDR3 sequences between Gen 2 and Gen 3 processes on L4054.

| # uCDR3 | All uCDR3's | | Top 80% uCDR3's | |
|---|---|---|---|---|
| (% Overlap) | Gen 2 | Gen 3 | Gen 2 | Gen 3 |
| Gen 2-L4054 | 8915 | 4355 (48.85%) | 205 | 199 (97.07%) |
| Gen 3-L4054 | — | 18130 | — | 223 |

Table 47: Comparison of Gen 2 and Gen3 of percentage shared unique CDR3 sequences on L4055 on TIL harvested cell product. 1833 sequences are shared between Gen 3 and Gen 2 final product, corresponding to 99.45% of top 80% of unique CDR3 sequences from Gen 2 shared with Gen 3 final product.

TABLE 47

Comparison of shared uCDR3 sequences between Gen 2 and Gen 3 processes on L4055.

| # uCDR3 | All uCDR3's | | Top 80% uCDR3's | |
|---|---|---|---|---|
| (% Overlap) | Gen 2 | Gen 3 | Gen 2 | Gen 3 |
| Gen 2-L4055 | 12996 | 6599 (50.77%) | 1843 | 1833 (99.45%) |
| Gen 3-L4055 | — | 27246 | — | 2616 |

CM1 and CM2 media was prepared in advanced without filtration and held at 4° C. until use for tumor L4055 to use on Gen 2 and Gen 3 process.

Media was warmed up at 37° C. for 24 hours in advance for tumor L4055 on REP initiation day for Gen 2 and Gen 3 process.

LDH was not measured in the supernatants collected on the processes.

M1085T TIL cell count was executed with K2 cellometer cell counter.

On tumor M1085T, samples were not available such as supernatant for metabolic analysis, TIL product for activation and exhaustion markers analysis, telomere length and CD3-TCR vb Analysis.

Conclusions

This example compares 3 independent donor tumors tissue in terms of functional quality attributes, plus extended phenotypic characterization and media consumption among Gen 2 and Gen 3 processes.

Gen 2 and Gen 3 pre-REP and REP expansion comparison were evaluated in terms of total viable cells generated and viability of the total nucleated cell population. TVC cell doses at harvest day was not comparable between Gen 2 (22 days) and Gen 3 (16 days). Gen 3 cell doses were lower than Gen 2 at around 40% of total viable cells collected at harvest.

An extrapolated cell number was calculated for Gen 3 process assuming the pre-REP harvest occurred at day 11 instead day 7 and REP Harvest at Day 22 instead day 16. In both cases shows closer number on TVC compared to Gen 2 process, indicating that the early activation could allow an overall better performance on TIL growth. Table 4 and 5 bottom row.

In the case of extrapolated value for extra flasks (2 or 3) on Gen 3 process assuming a bigger size of tumor processed, and reaching the maximum number of fragments required per process as described. Is observed a similar dose can be reachable on TVC at Day 16 Harvest for Gen 3 process compared to Gen 2 process at Day 22. This observation is important and indicates an early activation of the culture can allow better performance of TIL in less processing time Gen 2 and Gen 3 pre-REP and REP expansion comparison were evaluated in terms of total viable cells generated and viability of the total nucleated cell population. TVC cell doses at harvest day was not comparable between Gen 2 (22 days) and Gen 3 (16 days). Gen 3 cell doses were lower than Gen 2 at around 40% of total viable cells collected at harvest.

In terms of phenotypic characterization, a higher CD8+ and CD28+ expression was observed on three tumors on Gen 3 process compared to Gen 2 process. This data indicates the Gen 3 process has improved attributes of final TIL product compared to Gen 2.

Gen 3 process showed slightly higher central memory compartments compared to Gen 2 process.

Gen 2 and Gen 3 process showed comparable activation and exhaustion markers.

IFN gamma (IFNγ) production was 3 times higher on Gen 3 final product compared to Gen 2 in the three tumors analyzed. This data indicates the Gen 3 process generated a more potent TIL product as compared to the Gen 2 process, possibly due to the higher expression of CD8 and CD28 expression on Gen 3.

Telomere length on TIL final product between Gen 2 and Gen 3 were comparable.

Glucose and Lactate levels were comparable between Gen 2 and Gen 3 final product, suggesting the levels of nutrients on the media of Gen 3 process were not affected due to the not execution of volume reduction removal in each day of the process and less volume media overall the process, compared to Gen 2.

Overall Gen 3 process showed a reduction almost two times of the processing time compared to Gen 2 process, and a substantial reduction on the COGs.

IL-2 consumption indicates a general trend of IL-2 consumption on Gen 2 process, and in Gen 3 process IL-2 was higher due to the unremoval of the old media.

The Gen 3 process showed a higher clonal diversity measured by CDR3 TCRab sequence analysis.

The addition of feeders and OKT3 on day 0 of the pre-REP, allowed an early activation of TWL and overall a better growth TWL performance using the Gen 3 process. Table 48 describes various embodiments and outcomes for the Gen 3 process as compared to the current Gen 2 process.

TABLE 48

Exemplary Gen 3 process

| Step | Process Gen 2 | Process Gen 3 |
|---|---|---|
| Pre REP-day 0 | ≤50 fragments<br>1X G-Rex 100MCS<br>1 L media +<br>IL-2 (6000 IU/mL)<br>11 days | ≤240 fragments<br>≤60 fragments/flask<br>≤4 flasks<br>≤2 L media (500 mL/flask) +<br>IL-2 (6000 IU/mL)<br>$2.5 \times 10^8$ feeder cells/flask<br>30 ng OKT3/flask |
| REP Initiation | Fresh TIL direct to REP<br>Day 11<br>≤200e$^6$ viable cells<br>$5 \times 10^9$ feeder cells<br>G-Rex 500MCS<br>5 L media<br>30 ng/OKT3 | Fresh TIL direct to REP<br>Day 7<br>Activate entire culture<br>$5 \times 10^8$ feeder cells<br>30 ng OKT3/flask<br>G-Rex 100MCS<br>500 mL media +<br>IL-2(6000 IU/mL) |
| TIL propagation or Scale up | ≤5 G-REX 500MCS<br>≤1 × 10 viable cells/flask<br>5 L/flask<br>Day 16 | ≤4 G-REX 500MCS<br>Scale up entire culture<br>4 L/flask<br>Day 10-11 |
| Harvest | Harvest Day 22, LOVO-automated cell washer<br>2 wash cycles | Harvest Day 16 LOVO-automated cell washer<br>5 wash cycles* |
| Final formulation | Cryopreserved Product<br>300 IU/ml IL2- CS10 in LN$_2$, multiple aliquots | Cryopreserved product<br>300 IU/mL IL-2-CS10 in LN$_2$, multiple aliquots |
| Process time | 22 days | 16 days |

Example 8. Evaluating a Range of Allogenic Feeder Cell:TIL Ratios from 100:1 to 25:1

This study tested the proliferation of TIL at 25:1 and 50:1 against the control of 100:1 allogeneic feeder cells to TIL currently utilized in Process 1C.

Studies published by the Surgery Branch at the National Cancer Institute have shown the threshold for optimal activation of TIL in the G-Rex 100 flask at $5 \times 10^6$ allogeneic feeder cells per cm$^2$ at the initiation of the REP[1]. This has been verified through mathematical modeling, and, with the same model, predicted that with a feeder layer optimized for cell:cell contact per unit area the proportion of allogeneic feeder cells relative to TIL may be decreased to 25:1 with minimal effect on TIL activation and expansion.

This study established an optimal density of feeder cells per unit area at REP onset, and validated the effective range of allogeneic feeder ratios at REP initiation needed to decrease and normalize the amount of feeder cells used per clinical lot. The study also validated the initiation of the REP with less than $200 \times 10^6$ TIL co-cultured with a fixed number of feeder cells.

A. Volume of a T-cell (10 μm diameter): $V=(4/3)\pi r^3 = 523.6$ μm$^3$

B. Column of G-Rex 100 (M) with a 40 μm (4 cells) height: $V=(4/3)\pi r^3 = 4 \times 10^{12}$ μm$^3$ C. Number cell required to fill column B: $4 \times 10^{12}$ m$^3$/523.6 μm$^3$ = $7.6 \times 10^8$ m$^3$ * $0.64 = 4.86 \times 10^8$ D. Number cells that can be optimally activated in 4D space: $4.86 \times 10^8/24 = 20.25 \times 10^6$ E. Number of feeders and TIL extrapolated to G-Rex 500: TIL: $100 \times 10^6$ and Feeder: $2.5 \times 10^9$ Equation 1. Approximation of the number of mononuclear cells required to provide an icosahedral geometry for activation of TIL in a cylinder with a 100 cm$^2$ base. The calculation derives the experimental result of $5 \times 10^8$ for threshold activation of T-cells which closely mirrors NCI experimental data.[1] (C) The multiplier (0.64) is the random packing density for equivalent spheres as calculated by Jaeger and Nagel in 1992[2]. (D) The divisor 24 is the number of equivalent spheres that could contact a similar object in 4 dimensional space "the Newton number."[3].

REFERENCES

[1] Jin, Jianjian, et. al., Simplified Method of the Growth of Human Tumor Infiltrating Lymphocytes (TIL) in Gas-Permeable Flasks to Numbers Needed for Patient Treatment. J Immunother. 2012 April; 35(3): 283-292.

[2] Jaeger H M, Nagel S R. Physics of the granular state. Science. 1992 Mar. 20; 255(5051):1523-31.

[3] O. R. Musin (2003). "The problem of the twenty-five spheres". Russ. Math. Surv. 58 (4): 794-795.

Example 9. An Exemplary Embodiment Od Selecting and Expanding PBLs from PBMCs in CLL Patients PBMCs are collected from patients and either frozen for later use, or used fresh. Enough volume of peripheral blood is collected to yield at least about 400,000,000 ($400 \times 10^6$) PBMCs for starting material in the method of the present invention. On Day 0 of the method, IL-2 at $6 \times 10^6$ IU/mL is either prepared fresh or thawed, and stored at 4° C. or on ice until ready to use. 200 mL of CM2 medium is prepared by combining 100 mL of CM1 medium (containing Gluta-MAX®), then diluting it with 100 mL (1:1) with AIM-V to make CM2. The CM2 is protected from light, and sealed tightly when not in use.

All of the following steps are performed under sterile cell culture conditions. An aliquot of CM2 is warmed in a 50 mL conical tube in a 37° C. water bath for use in thawing and/or washing a frozen PBMC sample. If a frozen PBMC sample is used, the sample is removed from freezer storage and kept on dry ice until ready to thaw. When ready to thaw the PBMC cryovial, 5 mL of CM2 medium is placed in a sterile 50 mL conical tube. The PBMC sample cryovial is placed in a 37° C. water bath until only a few ice crystals remain. Warmed CM2 medium is added, dropwise, to the sample vial in a 1:1 volume ratio of sample:medium (about 1 mL). The entire contents is removed from the cryovial and transferred to the remaining CM2 medium in the 50 mL conical tube. An additional 1-2 mL of CM2 medium is used to rinse the cryovial and the entire contents of the cryovial is removed and transferred to the 50 mL conical tube. The volume in the conical tube is then adjusted with additional CM2 medium to 15 mL, and swirled gently to rinse the cells. The conical tube is then centrifuged at 400 g for 5 minutes at room temperature in order to collect the cell pellet.

The supernatant is removed from the pellet, the conical tube is capped, and then the cell pellet is disrupted by, for example, scraping the tube along a rough surface. About 1 mL of CM2 medium is added to the cell pellet, and the pellet and medium are aspirated up and down 5-10 times with a pipette to break up the cell pellet. An additional 3-5 mL of CM2 medium is added to the tube and mixed via pipette to suspend the cells. At this point, the volume of the cell suspension is recorded. Remove 100 µL of the cell suspension from the tube for cell counting with an automatic cell counter, for example, a Nexcelom Cellometer K2. Determine the number of live cells in the sample and record.

Reserve a minimum of $5 \times 10^6$ cells for phenotyping and other characterization experiments. Spin the reserved cells at 400 g for 5 minutes at room temperature to collect the cell pellet. Resuspend the cell pellet in freezing medium (sterile, heat-inactivated FBS containing 20% DMSO). Freeze one or two aliquots of the reserved cells in freezing medium, and slow-freeze the aliquots in a cell freezer (Mr. Frosty™) in a −80° C. freezer. Transfer to liquid nitrogen storage after a minimum of 24 hours at −80° C.

For the following steps, use pre-cooled solutions, work quickly, and keep the cells cold. The next step is to purify the T-cell fraction of the PBMC sample. This is completed using a Pan T-cell Isolation Kit (Miltenyi, catalog #130-096-535). Prepare the cells for purification by washing the cells with a sterile-filtered wash buffer containing PBS, 0.5% BSA, and 2 mM EDTA at pH 7.2. The PBMC sample is centrifuged at 400 g for 5 minutes to collect the cell pellet. The supernatant is aspirated off and the cell pellet is resuspended in 40 µL of wash buffer for every $10^7$ cells. Add 10 µL of Pan T Cell Biotin-Antibody Cocktail for every $10^7$ cells. Mix well and incubate for 5 minutes in refrigerator or on ice. Add 30 µL of wash buffer for every $10^7$ cells. Add 20 µL of Pan T-cell MicroBead Cocktail for every $10^7$ cells. Mix well and incubate for 10 minutes in refrigerator or on ice. Prepare an LS column and magnetically separate cells from the microbeads. The LS column is placed in the QuadroMACS magnetic field. The LS column is washed with 3 mL of cold wash buffer, and the wash is collected and discarded. The cell suspension is applied to the column and the flow-through (unlabeled cells) is collected. This flow-through is the enriched T-cell fraction (PBLs). Wash the column with 3 mL of wash buffer and collect the flow-through in the same tube as the initial flow-through. Cap the tube and place on ice. This is the T-cell fraction, or PBLs. Remove the LS column from the magnetic field, wash the column with 5 mL of wash buffer, and collect the non-T-cell fraction (magnetically labeled cells) into another tube. Centrifuge both fractions at 400 g for 5 minutes to collect the cell pellets. Supernatants are aspirated from both samples, disrupt the pellet, and resuspend the cells in 1 mL of CM2 medium supplemented with 3000 IU/mL IL-2 to each pellet, and pipette up and down 5-10 times to break up the pellets. Add 1-2 mL of CM2 to each sample, and mix each sample well, and store in tissue culture incubator for next steps. Remove about a 50 µL aliquot from each sample, count cells, and record count and viability.

The T-cells (PBLs) are then cultured with Dunabeads™ Human T-Expander CD3/CD28. A stock vial of Dynabeads is vortexed for 30 seconds at medium speed. A required aliquot of beads is removed from the stock vial into a sterile 1.5 mL microtube. The beads are washed with bead wash solution by adding 1 mL of bead wash to the 1.5 mL microtube containing the beads. Mix gently. Place the tube onto the DynaMag™-2 magnet and let sit for 30 minutes while beads draw toward the magnet. Aspirate the wash solution off the beads and remove tube from the magnet. 1 mL of CM2 medium supplemented with 3000 IU/mL IL-2 is added to the beads. The entire contents of the microtube is transferred to a 15 or 50 mL conical tube. Bring the beads to a final concentration of about 500,000/mL using CM2 medium with IL-2.

The T-cells (PBLs) and beads are cultured together as follows. On day 0: In a G-Rex 24 well plate, in a total of 7 mL per well, add 500,000 T-cells, 500,000 CD3/CD28 Dynabeads, and CM2 supplemented with IL-2. The G-Rex plate is placed into a humidified 37° C., 5% $CO_2$ incubator until the next step in the process (on Day 4). Remaining cells are frozen in CS10 cryopreservation medium using a Mr. Frosty™ cell freezer. The non-T-cell fraction of cells are frozen in CS10 cryopreservation medium using a Mr. Frosty™ cell freezer. On day 4, medium is exchanged. Half of the medium (about 3.5 mL) is removed from each well of the G-rex plate. A sufficient volume (about 3.5 mL) of CM4 medium supplemented with 3000 IU/mL IL-2 warmed to 37° C. is added to replace the medium removed from each sample well. The G-rex plate is returned to the incubator.

On day 7, cells are prepared for expansion by REP. The G-rex plate is removed from the incubator and half of medium is removed from each well and discarded. The cells are resuspended in the remaining medium and transferred to a 15 mL conical tube. The wells are washed with 1 mL each of CM4 supplemented with 3000 IU/mL IL-2 warmed to 37° C. and the wash medium is transferred to the same 15 mL tube with the cells. A representative sample of cells is removed and counted using an automated cell counter. If there are less than $1 \times 10^6$ live cells, the Dynabead expansion process at Day 0 is repeated. The remainder of the cells are frozen for back-up expansion or for phenotyping and other characterization studies. If there are $1 \times 10^6$ live cells or more, the REP expansion is set up in replicate according to the protocol from Day 0. Alternatively, with enough cells, the expansion may be set up in a G-rex 10M culture flask using $10\text{-}15 \times 10^6$ PBLs per flask and a 1:1 ratio of Dynabeads: PBLs in a final volume of 100 mL/well of CM4 medium supplemented with 3000 IU/mL IL-2. The plate and/or flask is returned to the incubator. Excess PBLs may be aliquoted and slow-frozen in a Mr. Frosty™ cell freezer in a −80° C. freezer, and the transferred to liquid nitrogen storage after a minimum of 24 hours at −80° C. These PBLs may be used as back-up samples for expansion or for phenotyping or other characterization studies.

On Day 11, the medium is exchanged. Half of the medium is removed from either each well of the G-rex plate or the flask and replaced with the same amount of fresh CM4 medium supplemented with 3000 IU/mL IL-2 at 37° C.

On Day 14, the PBLs are harvested. If the G-rex plate is used, about half of the medium is removed from each well of the plate and discarded. The PBLs and beads are suspended in the remaining medium and transferred to a sterile 15 mL conical tube (Tube 1). The wells are washed with 1-2 mL of fresh AIM-V medium warmed to 37° C., and the wash is transferred to Tube 1. Tube 1 is capped and placed in the DynaMag™-15 Magnet for 1 minute to allow the beads to be drawn to the magnet. The cell suspension is transferred into a new 15 mL tube (Tube 2), and the beads are washed with 2 mL of fresh AIM-V at 37° C. Tube 1 is placed back in the magnet for an additional 1 minute, and the wash medium is then transferred to Tube 2. The wells may be combined if desired, after the final washing step. Remove a representative sample of cells and count, record count and viability. Tubes may be placed in the incubator while counting. Additional AIM-V medium may be added to the Tube 2 if cells appear very dense. If a flask is used, the volume in the flask should be reduced to about 10 mL. The contents of the flask is mixed and transferred to a 15 mL conical tube (Tube A). The flask is washed with 2 mL of the AIM-V medium as described above and the wash medium is also transferred to Tube A. Tube A is capped and placed in the DynaMag™-15 Magnet for 1 minute to allow the beads to be drawn to the magnet. The cell suspension is transferred into a new 15 mL tube (Tube B), and the beads are washed with 2 mL of fresh AIM-V at 37° C. Tube A is placed back in the magnet for an additional 1 minute, and the wash medium is then transferred to Tube B. The wells may be combined if desired, after the final washing step. Remove a representative sample of cells and count, record count and viability. Tubes may be placed in the incubator while counting. Additional AIM-V medium may be added to the Tube B if cells appear very dense. Cells may be used fresh or frozen in CS10 preservation medium at desired concentrations.

Example 10. An Exemplary Embodiment of Expanding TILs from Hematopoeitic Malignancies Using Gen 3 Expansion Platform At Day 0, a T cell fraction (CD3+,CD45+) was isolated from an apheresis product enriched for lymphocytes, whole blood, or tumor digest (fresh or thawed) using positive or negative selection methods, i.e removing the T-cells using a T-cell marker (CD2, CD3, etc, or removing other cells leaving T-cells), or gradient centrifugation.

Entered the Gen 3.1 process by seeding ~$1 \times 10^7$ cells/flask according to Gen3 process described herein.

At Day 7, the cells were reactivated per the Gen 3.1 process.

At Day 9-11, the cells were scaled up per the Gen 3.1 process.

At Day 14-16, the cells were harvested per the Gen 3.1 process.

FIG. 42 provides a schematic diagram of an exemplary embodiment for expanding TILs from hematopoietic malignancies using the Gen 3 process.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

We claim:
1. A method for preparing tumor infiltrating lymphocytes (TILs) for adoptive T-cell therapy, the method comprising a two-step process comprising:
(a) a pre-rapid expansion (pre-REP) stage by treating a tumor fragment with a first cell culture medium comprising interleukin 2 (IL-2), OKT-3 antibody, and one or more AKT pathway inhibitor (AKTi) comprising an AKT kinase inhibitor, an mTOR inhibitor, and/or an PI3K inhibitor to provide TILs;
(b) a rapid expansion (REP) stage by expanding the TILs from step (a) with a second cell culture medium comprising cell culture media, irradiated feeder cells, OKT-3 antibody, and IL-2 to provide an expanded number of TILs; and,
(c) optionally cryopreserving the expanded number of TILs.
2. The method of claim 1, wherein the AKT kinase inhibitor is selected from the group consisting of afuresertib, uprosertib, ipatasertib, AT7867, AT13148, and pharmaceutically acceptable salts, solvates, hydrates, cocrystals, or prodrugs thereof.
3. The method of claim 1, wherein the mTOR inhibitor is AZD8055 or pharmaceutically acceptable salts, solvates, hydrates, cocrystals, or prodrugs thereof.
4. The method of claim 1, wherein the PI3K inhibitor is LY294002 or pharmaceutically acceptable salts, solvates, hydrates, cocrystals, or prodrugs thereof.
5. The method of claim 1, wherein the one or more AKT pathway inhibitor comprises two AKT pathway inhibitors each targeting different AKT pathway components.
6. The method of claim 5, wherein one AKT pathway inhibitor targets AKT and a second AKT pathway inhibitor targets PI3K.
7. The method of claim 5, wherein one AKT pathway inhibitor targets AKT and a second AKT pathway inhibitor targets mTOR.
8. The method of claim 5, wherein one AKT pathway inhibitor targets AKT and a second AKT pathway inhibitor targets PDK1.
9. The method of claim 5, wherein one AKT pathway inhibitor targets AKT and a second AKT pathway inhibitor targets CHK1.
10. The method of claim 5, wherein one AKT pathway inhibitor targets AKT and a second AKT pathway inhibitor targets Raf1.
11. The method of claim 5, wherein one AKT pathway inhibitor targets AKT and a second AKT pathway inhibitor targets one or more of FOXO1, FOXO3A, and FOX04.
12. The method of claim 5, wherein one AKT pathway inhibitor targets AKT and a second AKT pathway inhibitor targets GSK3.
13. The method of claim 1, wherein the tumor infiltrating lymphocytes (TILs) for adoptive T-cell therapy are enriched for TILs expressing one or more selected from the group consisting of CD8, CD27, CD 28, IL7R, CCR9, SELL (L-selectin or CD62L), FCER1G, SATB1, LEF1, and KLF2.
14. The method of claim 1, wherein the tumor infiltrating lymphocytes (TILs) for adoptive T-cell therapy are enriched for TILs expressing memory subset T-cell surface markers.
15. The method of claim 1, wherein the wherein the tumor infiltrating lymphocytes (TILs) for adoptive T-cell therapy are enriched for TILs expressing young TIL phenotype.
16. The method of claim 1, wherein the wherein the tumor infiltrating lymphocytes (TILs) for adoptive T-cell therapy are enriched for TILs with long telomeres as compared to TILs expanded without AKT pathway inhibitors.
17. The method of claim 1, wherein in step (a) the tumor fragment is cryopreserved.
18. A method for treating a subject with cancer, the method comprising administering expanded tumor infiltrating lymphocytes (TILs) comprising:
(a) performing a first pre-rapid expansion (pre-REP) by culturing the first population of TILs obtained from a tumor from the subject in a cell culture medium comprising IL-2 and one or more AKT pathway inhibitor comprising an AKT kinase inhibitor, an mTOR inhibitor, and/or an PI3K inhibitor to produce a second population of TILs, wherein the first expansion is performed in a closed system comprising a closed container providing a first gas-permeable surface area, wherein the first expansion is performed for about 3-14 days to obtain the second population of TILs, wherein the second population of TILs is at least 50-fold greater in number than the first population of TILs;
(b) performing a second rapid expansion (REP) by supplementing the cell culture medium of the second population of TILs with additional IL-2, OKT-3, and antigen presenting cells (APCs) and culturing to produce a third population of TILs, wherein the second expansion is performed for about 7-14 days to obtain the third population of TILs, wherein the third population of TILs is a therapeutic population of TILs which comprises an increased subpopulation of effector T cells and/or central memory T cells relative to the second population of TILs, wherein the second expansion is performed in the closed system in a second closed container providing a second gas-permeable surface area, and wherein the transition from step (a) to step (b) occurs without opening the system;
(c) harvesting the therapeutic population of TILs obtained from step (b), wherein the transition from step (b) to step (c) occurs without opening the system;
(d) administering a therapeutically effective dosage of the harvested therapeutic population of TILs from step (c) to the subject.
19. The method of claim 18, wherein after step (c) and before step (d) the method further comprises the step of transferring the harvested therapeutic population of TILs from step (c) to an infusion bag, wherein the transfer occurs without opening the system, and wherein step (d) is performed by administering a therapeutically effective dosage of the harvested therapeutic population of TILs from the infusion bag to the subject.
20. The method of claim 18, wherein after the step of transferring the harvested TIL population from step (c) to an infusion bag the method further comprises the step of cryopreserving the infusion bag comprising the harvested therapeutic population of TILs using a cryopreservation process.
21. The method of claim 18, further comprising administering to the subject, a therapeutically effective dosage of aldesleukin or a biosimilar thereof concomitantly with or after the administration of the therapeutically effective dosage of the harvested therapeutic population of TILs.
22. The method of claim 18, further comprising administering to the subject, a therapeutically effective dosage of a PD-1/PD-L1 inhibitor concomitantly with, before or after the administration of the therapeutically effective dosage of the harvested therapeutic population of TILs.
23. The method of claim 22, wherein the PD-1/PD-L1 inhibitor is selected from the group consisting of pembrolizumab, nivolumab, avelumab, durvalumab, atezolizumab, and biosimilars thereof.

24. The method of claim 18, wherein the cancer is selected from the group consisting of melanoma, cervical cancer, head and neck squamous cell cancer, non-small cell lung cancer, bladder cancer, ovarian cancer, pancreatic cancer, and sarcoma.

25. The method of claim 18, wherein the culture medium of step (c) further comprises one or more AKT pathway inhibitor comprising AKT kinase inhibitor, an mTOR inhibitor, and/or an PI3K inhibitor.

26. The method of claim 25, wherein the AKT pathway inhibitor is selected from the group consisting of afuresertib, uprosertib, ipatasertib, AT7867, AT13148, AZD8055, MK-2206, LY294002, and pharmaceutically acceptable salts, solvates, hydrates, cocrystals, or prodrugs thereof.

27. A method for expanding tumor infiltrating lymphocytes (TILs) into a therapeutic population of TILs comprising:
(a) obtaining a first population of TILs from a tumor resected from a subject by processing a tumor sample obtained from the subject into multiple tumor fragments;
(b) performing a priming first expansion by culturing the first population of TILs in a cell culture medium comprising IL-2, OKT-3, one or more AKT pathway inhibitor (AKTi) comprising an AKT kinase inhibitor, an mTOR inhibitor, and/or an PI3K inhibitor, and antigen presenting cells (APCs) to produce a second population of TILs, wherein the priming first expansion is performed in a container comprising a first gas-permeable surface area, wherein the priming first expansion is performed for first period of about 1 to 7 days to obtain the second population of TILs, wherein the second population of TILs is greater in number than the first population of TILs;
(c) performing a rapid second expansion by supplementing the cell culture medium of the second population of TILs with additional IL-2, OKT-3, and APCs, to produce a third population of TILs, wherein the number of APCs added in the rapid second expansion is at least twice the number of APCs added in step (b), wherein the rapid second expansion is performed for a second period of about 1 to 11 days to obtain the third population of TILs, wherein the third population of TILs is a therapeutic population of TILs, wherein the rapid second expansion is performed in a container comprising a second gas-permeable surface area;
(d) harvesting the therapeutic population of TILs obtained from step (c); and
(e) transferring the harvested TIL population from step (d) to an infusion bag.

28. The method of claim 27, wherein the culture medium of step (c) is further supplemented with one or more AKT pathway inhibitor (AKTi) comprising AKT kinase inhibitor, an mTOR inhibitor, and/or an PI3K inhibitor.

* * * * *

SEQUENCE LISTING

```
<160> NUMBER OF SEQ ID NOS: 176

<210> SEQ ID NO 1
<211> LENGTH: 450
<212> TYPE: PRT
<213> ORGANISM: Artificial Sequence
<220> FEATURE:
<223> OTHER INFORMATION: Muromonab heavy chain

<400> SEQUENCE: 1

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60
```

Lys Asp Lys Ala Thr Leu Thr Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Lys Thr Thr Ala Pro Ser Val Tyr
        115                 120                 125

Pro Leu Ala Pro Val Cys Gly Gly Thr Thr Gly Ser Ser Val Thr Leu
130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
450

<210> SEQ ID NO 2
<211> LENGTH: 213

-continued

```
<212> TYPE: PRT
<213> ORGANISM: Artificial Sequence
<220> FEATURE:
<223> OTHER INFORMATION: Muromonab light chain

<400> SEQUENCE: 2
```

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Ala Asp Thr Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

```
<210> SEQ ID NO 3
<211> LENGTH: 134
<212> TYPE: PRT
<213> ORGANISM: Artificial Sequence
<220> FEATURE:
<223> OTHER INFORMATION: recombinant human IL-2 (rhIL-2)

<400> SEQUENCE: 3
```

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

```
Ala Thr Ile Val Glu Phe Leu Asn Arg Trp Ile Thr Phe Cys Gln Ser
            115                 120                 125

Ile Ile Ser Thr Leu Thr
            130

<210> SEQ ID NO 4
<211> LENGTH: 132
<212> TYPE: PRT
<213> ORGANISM: Artificial Sequence
<220> FEATURE:
<223> OTHER INFORMATION: Aldesleukin

<400> SEQUENCE: 4

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
            130

<210> SEQ ID NO 5
<211> LENGTH: 130
<212> TYPE: PRT
<213> ORGANISM: Artificial Sequence
<220> FEATURE:
<223> OTHER INFORMATION: recombinant human IL-4 (rhIL-4)

<400> SEQUENCE: 5

Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
            20                  25                  30

Ile Phe Ala Ala Ser Lys Asn Thr Thr Glu Lys Glu Thr Phe Cys Arg
            35                  40                  45

Ala Ala Thr Val Leu Arg Gln Phe Tyr Ser His His Glu Lys Asp Thr
        50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110
```

```
Phe Leu Glu Arg Leu Lys Thr Ile Met Arg Glu Lys Tyr Ser Lys Cys
        115                 120                 125

Ser Ser
    130

<210> SEQ ID NO 6
<211> LENGTH: 153
<212> TYPE: PRT
<213> ORGANISM: Artificial Sequence
<220> FEATURE:
<223> OTHER INFORMATION: recombinant human IL-7 (rhIL-7)

<400> SEQUENCE: 6

Met Asp Cys Asp Ile Glu Gly Lys Asp Gly Lys Gln Tyr Glu Ser Val
1               5                   10                  15

Leu Met Val Ser Ile Asp Gln Leu Leu Asp Ser Met Lys Glu Ile Gly
            20                  25                  30

Ser Asn Cys Leu Asn Asn Glu Phe Asn Phe Lys Arg His Ile Cys
        35                  40                  45

Asp Ala Asn Lys Glu Gly Met Phe Leu Phe Arg Ala Arg Lys Leu
    50                  55                  60

Arg Gln Phe Leu Lys Met Asn Ser Thr Gly Asp Phe Asp Leu His Leu
65                  70                  75                  80

Leu Lys Val Ser Glu Gly Thr Thr Ile Leu Leu Asn Cys Thr Gly Gln
                85                  90                  95

Val Lys Gly Arg Lys Pro Ala Ala Leu Gly Glu Ala Gln Pro Thr Lys
            100                 105                 110

Ser Leu Glu Glu Asn Lys Ser Leu Lys Glu Gln Lys Lys Leu Asn Asp
        115                 120                 125

Leu Cys Phe Leu Lys Arg Leu Leu Gln Glu Ile Lys Thr Cys Trp Asn
    130                 135                 140

Lys Ile Leu Met Gly Thr Lys Glu His
145                 150

<210> SEQ ID NO 7
<211> LENGTH: 115
<212> TYPE: PRT
<213> ORGANISM: Artificial Sequence
<220> FEATURE:
<223> OTHER INFORMATION: recombinant human IL-15 (rhIL-15)

<400> SEQUENCE: 7

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95
```

Ile Lys Glu Phe Leu Gln Ser Phe Val His Ile Val Gln Met Phe Ile
                100                 105                 110

Asn Thr Ser
        115

<210> SEQ ID NO 8
<211> LENGTH: 132
<212> TYPE: PRT
<213> ORGANISM: Artificial Sequence
<220> FEATURE:
<223> OTHER INFORMATION: recombinant human IL-21 (rhIL-21)

<400> SEQUENCE: 8

Met Gln Asp Arg His Met Ile Arg Met Arg Gln Leu Ile Asp Ile Val
1               5                   10                  15

Asp Gln Leu Lys Asn Tyr Val Asn Asp Leu Val Pro Glu Phe Leu Pro
            20                  25                  30

Ala Pro Glu Asp Val Glu Thr Asn Cys Glu Trp Ser Ala Phe Ser Cys
        35                  40                  45

Phe Gln Lys Ala Gln Leu Lys Ser Ala Asn Thr Gly Asn Asn Glu Arg
    50                  55                  60

Ile Ile Asn Val Ser Ile Lys Lys Leu Lys Arg Lys Pro Pro Ser Thr
65                  70                  75                  80

Asn Ala Gly Arg Arg Gln Lys His Arg Leu Thr Cys Pro Ser Cys Asp
                85                  90                  95

Ser Tyr Glu Lys Lys Pro Pro Lys Glu Phe Leu Glu Arg Phe Lys Ser
            100                 105                 110

Leu Leu Gln Lys Met Ile His Gln His Leu Ser Ser Arg Thr His Gly
        115                 120                 125

Ser Glu Asp Ser
    130

<210> SEQ ID NO 9
<211> LENGTH: 255
<212> TYPE: PRT
<213> ORGANISM: Artificial Sequence
<220> FEATURE:
<223> OTHER INFORMATION: human 4-1BB, Tumor necrosis factor receptor
      superfamily, member 9 (Homo sapiens)

<400> SEQUENCE: 9

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

```
Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255
```

<210> SEQ ID NO 10
<211> LENGTH: 256
<212> TYPE: PRT
<213> ORGANISM: Artificial Sequence
<220> FEATURE:
<223> OTHER INFORMATION: murine 4-1BB, Tumor necrosis factor receptor
      superfamily, member 9 (Mus musculus)

<400> SEQUENCE: 10

```
Met Gly Asn Asn Cys Tyr Asn Val Val Ile Val Leu Leu Leu Val
1               5                   10                  15

Gly Cys Glu Lys Val Gly Ala Val Gln Asn Ser Cys Asp Asn Cys Gln
                20                  25                  30

Pro Gly Thr Phe Cys Arg Lys Tyr Asn Pro Val Cys Lys Ser Cys Pro
            35                  40                  45

Pro Ser Thr Phe Ser Ser Ile Gly Gly Gln Pro Asn Cys Asn Ile Cys
50                  55                  60

Arg Val Cys Ala Gly Tyr Phe Arg Phe Lys Lys Phe Cys Ser Ser Thr
65                  70                  75                  80

His Asn Ala Glu Cys Glu Cys Ile Glu Gly Phe His Cys Leu Gly Pro
                85                  90                  95

Gln Cys Thr Arg Cys Glu Lys Asp Cys Arg Pro Gly Gln Glu Leu Thr
            100                 105                 110

Lys Gln Gly Cys Lys Thr Cys Ser Leu Gly Thr Phe Asn Asp Gln Asn
        115                 120                 125

Gly Thr Gly Val Cys Arg Pro Trp Thr Asn Cys Ser Leu Asp Gly Arg
    130                 135                 140

Ser Val Leu Lys Thr Gly Thr Thr Glu Lys Asp Val Val Cys Gly Pro
145                 150                 155                 160

Pro Val Val Ser Phe Ser Pro Ser Thr Thr Ile Ser Val Thr Pro Glu
                165                 170                 175

Gly Gly Pro Gly Gly His Ser Leu Gln Val Leu Thr Leu Phe Leu Ala
            180                 185                 190

Leu Thr Ser Ala Leu Leu Leu Ala Leu Ile Phe Ile Thr Leu Leu Phe
        195                 200                 205

Ser Val Leu Lys Trp Ile Arg Lys Lys Phe Pro His Ile Phe Lys Gln
    210                 215                 220

Pro Phe Lys Lys Thr Thr Gly Ala Ala Gln Glu Glu Asp Ala Cys Ser
225                 230                 235                 240
```

```
Cys Arg Cys Pro Gln Glu Glu Gly Gly Gly Gly Tyr Glu Leu
            245                 250                 255

<210> SEQ ID NO 11
<211> LENGTH: 441
<212> TYPE: PRT
<213> ORGANISM: Artificial Sequence
<220> FEATURE:
<223> OTHER INFORMATION: heavy chain for utomilumab

<400> SEQUENCE: 11

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350
```

```
Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly
        435                 440

<210> SEQ ID NO 12
<211> LENGTH: 214
<212> TYPE: PRT
<213> ORGANISM: Artificial Sequence
<220> FEATURE:
<223> OTHER INFORMATION: light chain for utomilumab

<400> SEQUENCE: 12

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 13
<211> LENGTH: 116
<212> TYPE: PRT
<213> ORGANISM: Artificial Sequence
<220> FEATURE:
<223> OTHER INFORMATION: heavy chain variable region for utomilumab
```

<400> SEQUENCE: 13

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser
            115

<210> SEQ ID NO 14
<211> LENGTH: 108
<212> TYPE: PRT
<213> ORGANISM: Artificial Sequence
<220> FEATURE:
<223> OTHER INFORMATION: light chain variable region for utomilumab

<400> SEQUENCE: 14

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu
            100                 105

<210> SEQ ID NO 15
<211> LENGTH: 6
<212> TYPE: PRT
<213> ORGANISM: Artificial Sequence
<220> FEATURE:
<223> OTHER INFORMATION: heavy chain CDR1 for utomilumab

<400> SEQUENCE: 15

Ser Thr Tyr Trp Ile Ser
1               5

<210> SEQ ID NO 16
<211> LENGTH: 17
<212> TYPE: PRT
<213> ORGANISM: Artificial Sequence
<220> FEATURE:
<223> OTHER INFORMATION: heavy chain CDR2 for utomilumab -continued

```
<400> SEQUENCE: 16

Lys Ile Tyr Pro Gly Asp Ser Tyr Thr Asn Tyr Ser Pro Ser Phe Gln
1               5                   10                  15

Gly

<210> SEQ ID NO 17
<211> LENGTH: 8
<212> TYPE: PRT
<213> ORGANISM: Artificial Sequence
<220> FEATURE:
<223> OTHER INFORMATION: heavy chain CDR3 for utomilumab

<400> SEQUENCE: 17

Arg Gly Tyr Gly Ile Phe Asp Tyr
1               5

<210> SEQ ID NO 18
<211> LENGTH: 11
<212> TYPE: PRT
<213> ORGANISM: Artificial Sequence
<220> FEATURE:
<223> OTHER INFORMATION: light chain CDR1 for utomilumab

<400> SEQUENCE: 18

Ser Gly Asp Asn Ile Gly Asp Gln Tyr Ala His
1               5                   10

<210> SEQ ID NO 19
<211> LENGTH: 7
<212> TYPE: PRT
<213> ORGANISM: Artificial Sequence
<220> FEATURE:
<223> OTHER INFORMATION: light chain CDR2 for utomilumab

<400> SEQUENCE: 19

Gln Asp Lys Asn Arg Pro Ser
1               5

<210> SEQ ID NO 20
<211> LENGTH: 11
<212> TYPE: PRT
<213> ORGANISM: Artificial Sequence
<220> FEATURE:
<223> OTHER INFORMATION: light chain CDR3 for utomilumab

<400> SEQUENCE: 20

Ala Thr Tyr Thr Gly Phe Gly Ser Leu Ala Val
1               5                   10

<210> SEQ ID NO 21
<211> LENGTH: 448
<212> TYPE: PRT
<213> ORGANISM: Artificial Sequence
<220> FEATURE:
<223> OTHER INFORMATION: heavy chain for urelumab

<400> SEQUENCE: 21

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Ser Pro Glu Lys Gly Leu Glu Trp Ile
            35                  40                  45
```

Gly Glu Ile Asn His Gly Gly Tyr Val Thr Tyr Asn Pro Ser Leu Glu
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Tyr Gly Pro Gly Asn Tyr Asp Trp Tyr Phe Asp Leu Trp Gly
             100                 105                 110

Arg Gly Thr Leu Val Thr Val Ser Ala Ser Thr Lys Gly Pro Ser
         115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 22
<211> LENGTH: 216
<212> TYPE: PRT

<213> ORGANISM: Artificial Sequence
<220> FEATURE:
<223> OTHER INFORMATION: light chain for urelumab

<400> SEQUENCE: 22

| | | | | | | | | | | | | | | |
|---|---|---|---|---|---|---|---|---|---|---|---|---|---|---|
| Glu | Ile | Val | Leu | Thr | Gln | Ser | Pro | Ala | Thr | Leu | Ser | Leu | Ser | Pro | Gly |
| 1 | | | | 5 | | | | | 10 | | | | | 15 | |
| Glu | Arg | Ala | Thr | Leu | Ser | Cys | Arg | Ala | Ser | Gln | Ser | Val | Ser | Ser | Tyr |
| | | | 20 | | | | | 25 | | | | | 30 | | |
| Leu | Ala | Trp | Tyr | Gln | Gln | Lys | Pro | Gly | Gln | Ala | Pro | Arg | Leu | Leu | Ile |
| | | | 35 | | | | | 40 | | | | | 45 | | |
| Tyr | Asp | Ala | Ser | Asn | Arg | Ala | Thr | Gly | Ile | Pro | Ala | Arg | Phe | Ser | Gly |
| | 50 | | | | | 55 | | | | | 60 | | | | |
| Ser | Gly | Ser | Gly | Thr | Asp | Phe | Thr | Leu | Thr | Ile | Ser | Ser | Leu | Glu | Pro |
| 65 | | | | | 70 | | | | | 75 | | | | | 80 |
| Glu | Asp | Phe | Ala | Val | Tyr | Tyr | Cys | Gln | Gln | Arg | Ser | Asn | Trp | Pro | Pro |
| | | | | 85 | | | | | 90 | | | | | 95 | |
| Ala | Leu | Thr | Phe | Cys | Gly | Gly | Thr | Lys | Val | Glu | Ile | Lys | Arg | Thr | Val |
| | | | 100 | | | | | 105 | | | | | 110 | | |
| Ala | Ala | Pro | Ser | Val | Phe | Ile | Phe | Pro | Pro | Ser | Asp | Glu | Gln | Leu | Lys |
| | | | 115 | | | | | 120 | | | | | 125 | | |
| Ser | Gly | Thr | Ala | Ser | Val | Val | Cys | Leu | Leu | Asn | Asn | Phe | Tyr | Pro | Arg |
| | 130 | | | | | 135 | | | | | 140 | | | | |
| Glu | Ala | Lys | Val | Gln | Trp | Lys | Val | Asp | Asn | Ala | Leu | Gln | Ser | Gly | Asn |
| 145 | | | | | 150 | | | | | 155 | | | | | 160 |
| Ser | Gln | Glu | Ser | Val | Thr | Glu | Gln | Asp | Ser | Lys | Asp | Ser | Thr | Tyr | Ser |
| | | | | 165 | | | | | 170 | | | | | 175 | |
| Leu | Ser | Ser | Thr | Leu | Thr | Leu | Ser | Lys | Ala | Asp | Tyr | Glu | Lys | His | Lys |
| | | | 180 | | | | | 185 | | | | | 190 | | |
| Val | Tyr | Ala | Cys | Glu | Val | Thr | His | Gln | Gly | Leu | Ser | Ser | Pro | Val | Thr |
| | | 195 | | | | | 200 | | | | | 205 | | | |
| Lys | Ser | Phe | Asn | Arg | Gly | Glu | Cys | | | | | | | | |
| | 210 | | | | | 215 | | | | | | | | | |

<210> SEQ ID NO 23
<211> LENGTH: 120
<212> TYPE: PRT
<213> ORGANISM: Artificial Sequence
<220> FEATURE:
<223> OTHER INFORMATION: variable heavy chain for urelumab

<400> SEQUENCE: 23

| | | | | | | | | | | | | | | | |
|---|---|---|---|---|---|---|---|---|---|---|---|---|---|---|---|
| Met | Lys | His | Leu | Trp | Phe | Phe | Leu | Leu | Leu | Val | Ala | Ala | Pro | Arg | Trp |
| 1 | | | | 5 | | | | | 10 | | | | | 15 | |
| Val | Leu | Ser | Gln | Val | Gln | Leu | Gln | Gln | Trp | Gly | Ala | Gly | Leu | Leu | Lys |
| | | | 20 | | | | | 25 | | | | | 30 | | |
| Pro | Ser | Glu | Thr | Leu | Ser | Leu | Thr | Cys | Ala | Val | Tyr | Gly | Gly | Ser | Phe |
| | | | 35 | | | | | 40 | | | | | 45 | | |
| Ser | Gly | Tyr | Tyr | Trp | Ser | Trp | Ile | Arg | Gln | Ser | Pro | Glu | Lys | Gly | Leu |
| | 50 | | | | | 55 | | | | | 60 | | | | |
| Glu | Trp | Ile | Gly | Glu | Ile | Asn | His | Gly | Gly | Tyr | Val | Thr | Tyr | Asn | Pro |
| 65 | | | | | 70 | | | | | 75 | | | | | 80 |
| Ser | Leu | Glu | Ser | Arg | Val | Thr | Ile | Ser | Val | Asp | Thr | Ser | Lys | Asn | Gln |
| | | | | 85 | | | | | 90 | | | | | 95 | |
| Phe | Ser | Leu | Lys | Leu | Ser | Ser | Val | Thr | Ala | Ala | Asp | Thr | Ala | Val | Tyr |
| | | | 100 | | | | | 105 | | | | | 110 | | |

```
Tyr Cys Ala Arg Asp Tyr Gly Pro
        115                 120

<210> SEQ ID NO 24
<211> LENGTH: 110
<212> TYPE: PRT
<213> ORGANISM: Artificial Sequence
<220> FEATURE:
<223> OTHER INFORMATION: variable light chain for urelumab

<400> SEQUENCE: 24

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln
            100                 105                 110

<210> SEQ ID NO 25
<211> LENGTH: 5
<212> TYPE: PRT
<213> ORGANISM: Artificial Sequence
<220> FEATURE:
<223> OTHER INFORMATION: heavy chain CDR1 for urelumab

<400> SEQUENCE: 25

Gly Tyr Tyr Trp Ser
1               5

<210> SEQ ID NO 26
<211> LENGTH: 16
<212> TYPE: PRT
<213> ORGANISM: Artificial Sequence
<220> FEATURE:
<223> OTHER INFORMATION: heavy chain CDR2 for urelumab

<400> SEQUENCE: 26

Glu Ile Asn His Gly Gly Tyr Val Thr Tyr Asn Pro Ser Leu Glu Ser
1               5                   10                  15

<210> SEQ ID NO 27
<211> LENGTH: 13
<212> TYPE: PRT
<213> ORGANISM: Artificial Sequence
<220> FEATURE:
<223> OTHER INFORMATION: heavy chain CDR3 for urelumab

<400> SEQUENCE: 27

Asp Tyr Gly Pro Gly Asn Tyr Asp Trp Tyr Phe Asp Leu
1               5                   10

<210> SEQ ID NO 28
<211> LENGTH: 11
<212> TYPE: PRT
<213> ORGANISM: Artificial Sequence
<220> FEATURE:
```

-continued

<223> OTHER INFORMATION: light chain CDR1 for urelumab

<400> SEQUENCE: 28

Arg Ala Ser Gln Ser Val Ser Ser Tyr Leu Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: light chain CDR2 for urelumab

<400> SEQUENCE: 29

Asp Ala Ser Asn Arg Ala Thr
1               5

<210> SEQ ID NO 30
<211> LENGTH: 11
<212> TYPE: PRT
<213> ORGANISM: Artificial Sequence
<220> FEATURE:
<223> OTHER INFORMATION: light chain CDR3 for urelumab

<400> SEQUENCE: 30

Gln Gln Arg Ser Asp Trp Pro Pro Ala Leu Thr
1               5                   10

<210> SEQ ID NO 31
<211> LENGTH: 230
<212> TYPE: PRT
<213> ORGANISM: Artificial Sequence
<220> FEATURE:
<223> OTHER INFORMATION: Fc domain

<400> SEQUENCE: 31

Lys Ser Cys Asp Lys Thr His Thr Cys Pro Pro Cys Pro Ala Pro Glu
1               5                   10                  15

Leu Leu Gly Gly Pro Ser Val Phe Leu Phe Pro Pro Lys Pro Lys Asp
                20                  25                  30

Thr Leu Met Ile Ser Arg Thr Pro Glu Val Thr Cys Val Val Val Asp
            35                  40                  45

Val Ser His Glu Asp Pro Glu Val Lys Phe Asn Trp Tyr Val Asp Gly
        50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
            195                 200                 205

Ser Val Met His Glu Ala Leu His Asn His Tyr Thr Gln Lys Ser Leu
        210                 215                 220

Ser Leu Ser Pro Gly Lys
225                 230

<210> SEQ ID NO 32
<211> LENGTH: 22
<212> TYPE: PRT
<213> ORGANISM: Artificial Sequence
<220> FEATURE:
<223> OTHER INFORMATION: linker

<400> SEQUENCE: 32

Gly Gly Pro Gly Ser Ser Lys Ser Cys Asp Lys Thr His Thr Cys Pro
1               5                   10                  15

Pro Cys Pro Ala Pro Glu
            20

<210> SEQ ID NO 33
<211> LENGTH: 22
<212> TYPE: PRT
<213> ORGANISM: Artificial Sequence
<220> FEATURE:
<223> OTHER INFORMATION: linker

<400> SEQUENCE: 33

Gly Gly Ser Gly Ser Ser Lys Ser Cys Asp Lys Thr His Thr Cys Pro
1               5                   10                  15

Pro Cys Pro Ala Pro Glu
            20

<210> SEQ ID NO 34
<211> LENGTH: 27
<212> TYPE: PRT
<213> ORGANISM: Artificial Sequence
<220> FEATURE:
<223> OTHER INFORMATION: linker

<400> SEQUENCE: 34

Gly Gly Pro Gly Ser Ser Ser Ser Ser Ser Lys Ser Cys Asp Lys
1               5                   10                  15

Thr His Thr Cys Pro Pro Cys Pro Ala Pro Glu
            20                  25

<210> SEQ ID NO 35
<211> LENGTH: 27
<212> TYPE: PRT
<213> ORGANISM: Artificial Sequence
<220> FEATURE:
<223> OTHER INFORMATION: linker

<400> SEQUENCE: 35

Gly Gly Ser Gly Ser Ser Ser Ser Ser Ser Lys Ser Cys Asp Lys
1               5                   10                  15

Thr His Thr Cys Pro Pro Cys Pro Ala Pro Glu
            20                  25

<210> SEQ ID NO 36
<211> LENGTH: 29
<212> TYPE: PRT
<213> ORGANISM: Artificial Sequence
<220> FEATURE:

<223> OTHER INFORMATION: linker

<400> SEQUENCE: 36

Gly Gly Pro Gly Ser Ser Ser Ser Ser Ser Ser Lys Ser Cys
1               5                   10                  15

Asp Lys Thr His Thr Cys Pro Pro Cys Pro Ala Pro Glu
            20                  25

<210> SEQ ID NO 37
<211> LENGTH: 29
<212> TYPE: PRT
<213> ORGANISM: Artificial Sequence
<220> FEATURE:
<223> OTHER INFORMATION: linker

<400> SEQUENCE: 37

Gly Gly Ser Gly Ser Ser Ser Ser Ser Ser Ser Lys Ser Cys
1               5                   10                  15

Asp Lys Thr His Thr Cys Pro Pro Cys Pro Ala Pro Glu
            20                  25

<210> SEQ ID NO 38
<211> LENGTH: 24
<212> TYPE: PRT
<213> ORGANISM: Artificial Sequence
<220> FEATURE:
<223> OTHER INFORMATION: linker

<400> SEQUENCE: 38

Gly Gly Pro Gly Ser Ser Gly Ser Gly Ser Asp Lys Thr His Thr
1               5                   10                  15

Cys Pro Pro Cys Pro Ala Pro Glu
            20

<210> SEQ ID NO 39
<211> LENGTH: 23
<212> TYPE: PRT
<213> ORGANISM: Artificial Sequence
<220> FEATURE:
<223> OTHER INFORMATION: linker

<400> SEQUENCE: 39

Gly Gly Pro Gly Ser Ser Gly Ser Gly Ser Asp Lys Thr His Thr Cys
1               5                   10                  15

Pro Pro Cys Pro Ala Pro Glu
            20

<210> SEQ ID NO 40
<211> LENGTH: 21
<212> TYPE: PRT
<213> ORGANISM: Artificial Sequence
<220> FEATURE:
<223> OTHER INFORMATION: linker

<400> SEQUENCE: 40

Gly Gly Pro Ser Ser Ser Gly Ser Asp Lys Thr His Thr Cys Pro Pro
1               5                   10                  15

Cys Pro Ala Pro Glu
            20

<210> SEQ ID NO 41
<211> LENGTH: 25
<212> TYPE: PRT
<213> ORGANISM: Artificial Sequence

```
<220> FEATURE:
<223> OTHER INFORMATION: linker

<400> SEQUENCE: 41

Gly Gly Ser Ser Ser Ser Ser Ser Gly Ser Asp Lys Thr His
1               5                   10                  15

Thr Cys Pro Pro Cys Pro Ala Pro Glu
            20                  25

<210> SEQ ID NO 42
<211> LENGTH: 246
<212> TYPE: PRT
<213> ORGANISM: Artificial Sequence
<220> FEATURE:
<223> OTHER INFORMATION: Fc domain

<400> SEQUENCE: 42

Met Glu Thr Asp Thr Leu Leu Leu Trp Val Leu Leu Leu Trp Val Pro
1               5                   10                  15

Ala Gly Asn Gly Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly
                245

<210> SEQ ID NO 43
<211> LENGTH: 11
<212> TYPE: PRT
<213> ORGANISM: Artificial Sequence
<220> FEATURE:
<223> OTHER INFORMATION: linker
```

```
<400> SEQUENCE: 43

Ser Gly Ser Gly Ser Gly Ser Gly Ser Gly Ser
1               5                   10

<210> SEQ ID NO 44
<211> LENGTH: 12
<212> TYPE: PRT
<213> ORGANISM: Artificial Sequence
<220> FEATURE:
<223> OTHER INFORMATION: linker

<400> SEQUENCE: 44

Ser Ser Ser Ser Ser Ser Gly Ser Gly Ser Gly Ser
1               5                   10

<210> SEQ ID NO 45
<211> LENGTH: 16
<212> TYPE: PRT
<213> ORGANISM: Artificial Sequence
<220> FEATURE:
<223> OTHER INFORMATION: linker

<400> SEQUENCE: 45

Ser Ser Ser Ser Ser Ser Gly Ser Gly Ser Gly Ser Gly Ser Gly Ser
1               5                   10                  15

<210> SEQ ID NO 46
<211> LENGTH: 254
<212> TYPE: PRT
<213> ORGANISM: Artificial Sequence
<220> FEATURE:
<223> OTHER INFORMATION: 4-1BBL

<400> SEQUENCE: 46

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
                20                  25                  30

Ala Gly Leu Leu Leu Leu Leu Leu Leu Ala Ala Cys Ala Val Phe
            35                  40                  45

Leu Ala Cys Pro Trp Ala Val Ser Gly Ala Arg Ala Ser Pro Gly Ser
        50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
                100                 105                 110

Pro Gly Leu Ala Gly Val Ser Leu Thr Gly Gly Leu Ser Tyr Lys Glu
            115                 120                 125

Asp Thr Lys Glu Leu Val Val Ala Lys Ala Gly Val Tyr Tyr Val Phe
        130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
                180                 185                 190
```

-continued

```
Arg Asn Ser Ala Phe Gly Phe Gln Gly Arg Leu Leu His Leu Ser Ala
            195                 200                 205

Gly Gln Arg Leu Gly Val His Leu His Thr Glu Ala Arg Ala Arg His
        210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 47
<211> LENGTH: 168
<212> TYPE: PRT
<213> ORGANISM: Artificial Sequence
<220> FEATURE:
<223> OTHER INFORMATION: 4-1BBL soluble domain

<400> SEQUENCE: 47

Leu Arg Gln Gly Met Phe Ala Gln Leu Val Ala Gln Asn Val Leu Leu
1               5                   10                  15

Ile Asp Gly Pro Leu Ser Trp Tyr Ser Asp Pro Gly Leu Ala Gly Val
            20                  25                  30

Ser Leu Thr Gly Gly Leu Ser Tyr Lys Glu Asp Thr Lys Glu Leu Val
        35                  40                  45

Val Ala Lys Ala Gly Val Tyr Tyr Val Phe Phe Gln Leu Glu Leu Arg
    50                  55                  60

Arg Val Val Ala Gly Glu Gly Ser Gly Ser Val Ser Leu Ala Leu His
65                  70                  75                  80

Leu Gln Pro Leu Arg Ser Ala Ala Gly Ala Ala Ala Leu Ala Leu Thr
                85                  90                  95

Val Asp Leu Pro Pro Ala Ser Ser Glu Ala Arg Asn Ser Ala Phe Gly
            100                 105                 110

Phe Gln Gly Arg Leu Leu His Leu Ser Ala Gly Gln Arg Leu Gly Val
        115                 120                 125

His Leu His Thr Glu Ala Arg Ala Arg His Ala Trp Gln Leu Thr Gln
    130                 135                 140

Gly Ala Thr Val Leu Gly Leu Phe Arg Val Thr Pro Glu Ile Pro Ala
145                 150                 155                 160

Gly Leu Pro Ser Pro Arg Ser Glu
                165

<210> SEQ ID NO 48
<211> LENGTH: 118
<212> TYPE: PRT
<213> ORGANISM: Artificial Sequence
<220> FEATURE:
<223> OTHER INFORMATION: variable heavy chain for 4B4-1-1 version 1

<400> SEQUENCE: 48

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Lys Gln Arg Pro Gly Gln Val Leu Glu Trp Ile
        35                  40                  45

Gly Glu Ile Asn Pro Gly Asn Gly His Thr Asn Tyr Asn Glu Lys Phe
    50                  55                  60
```

```
Lys Ser Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser Phe Thr Thr Ala Arg Gly Phe Ala Tyr Trp Gly Gln Gly
            100                 105                 110

Thr Leu Val Thr Val Ser
        115

<210> SEQ ID NO 49
<211> LENGTH: 107
<212> TYPE: PRT
<213> ORGANISM: Artificial Sequence
<220> FEATURE:
<223> OTHER INFORMATION: variable light chain for 4B4-1-1 version 1

<400> SEQUENCE: 49

Asp Ile Val Met Thr Gln Ser Pro Ala Thr Gln Ser Val Thr Pro Gly
 1               5                  10                  15

Asp Arg Val Ser Leu Ser Cys Arg Ala Ser Gln Thr Ile Ser Asp Tyr
             20                  25                  30

Leu His Trp Tyr Gln Gln Lys Ser His Glu Ser Pro Arg Leu Leu Ile
         35                  40                  45

Lys Tyr Ala Ser Gln Ser Ile Ser Gly Ile Pro Ser Arg Phe Ser Gly
 50                  55                  60

Ser Gly Ser Gly Ser Asp Phe Thr Leu Ser Ile Asn Ser Val Glu Pro
 65                  70                  75                  80

Glu Asp Val Gly Val Tyr Tyr Cys Gln Asp Gly His Ser Phe Pro Pro
                 85                  90                  95

Thr Phe Gly Gly Gly Thr Lys Leu Glu Ile Lys
            100                 105

<210> SEQ ID NO 50
<211> LENGTH: 119
<212> TYPE: PRT
<213> ORGANISM: Artificial Sequence
<220> FEATURE:
<223> OTHER INFORMATION: variable heavy chain for 4B4-1-1 version 2

<400> SEQUENCE: 50

Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Ser Ser Tyr
             20                  25                  30

Trp Met His Trp Val Lys Gln Arg Pro Gly Gln Val Leu Glu Trp Ile
         35                  40                  45

Gly Glu Ile Asn Pro Gly Asn Gly His Thr Asn Tyr Asn Glu Lys Phe
 50                  55                  60

Lys Ser Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser Phe Thr Thr Ala Arg Gly Phe Ala Tyr Trp Gly Gln Gly
            100                 105                 110

Thr Leu Val Thr Val Ser Ala
        115
```

<210> SEQ ID NO 51
<211> LENGTH: 108
<212> TYPE: PRT
<213> ORGANISM: Artificial Sequence
<220> FEATURE:
<223> OTHER INFORMATION: variable light chain for 4B4-1-1 version 2

<400> SEQUENCE: 51

```
Asp Ile Val Met Thr Gln Ser Pro Ala Thr Gln Ser Val Thr Pro Gly
1               5                   10                  15

Asp Arg Val Ser Leu Ser Cys Arg Ala Ser Gln Thr Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asp Gly His Ser Phe Pro Pro
                85                  90                  95

Thr Phe Gly Gly Gly Thr Lys Leu Glu Ile Lys Arg
            100                 105
```

<210> SEQ ID NO 52
<211> LENGTH: 120
<212> TYPE: PRT
<213> ORGANISM: Artificial Sequence
<220> FEATURE:
<223> OTHER INFORMATION: variable heavy chain for H39E3-2

<400> SEQUENCE: 52

```
Met Asp Trp Thr Trp Arg Ile Leu Phe Leu Val Ala Ala Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asp Tyr Trp Met Ser Trp Val Arg Gln Ala Pro Gly Lys Gly Leu
50                  55                  60

Glu Trp Val Ala Asp Ile Lys Asn Asp Gly Ser Tyr Thr Asn Tyr Ala
65                  70                  75                  80

Pro Ser Leu Thr Asn Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Glu Leu Thr
        115                 120
```

<210> SEQ ID NO 53
<211> LENGTH: 109
<212> TYPE: PRT
<213> ORGANISM: Artificial Sequence
<220> FEATURE:
<223> OTHER INFORMATION: variable light chain for H39E3-2

<400> SEQUENCE: 53

```
Met Glu Ala Pro Ala Gln Leu Leu Phe Leu Leu Leu Leu Trp Leu Pro
1               5                   10                  15

Asp Thr Thr Gly Asp Ile Val Met Thr Gln Ser Pro Asp Ser Leu Ala
            20                  25                  30
```

```
Val Ser Leu Gly Glu Arg Ala Thr Ile Asn Cys Lys Ser Ser Gln Ser
        35                  40                  45

Leu Leu Ser Ser Gly Asn Gln Lys Asn Tyr Leu Trp Tyr Gln Gln Lys
 50                  55                  60

Pro Gly Gln Pro Pro Lys Leu Leu Ile Tyr Tyr Ala Ser Thr Arg Gln
 65                  70                  75                  80

Ser Gly Val Pro Asp Arg Phe Ser Gly Ser Gly Ser Gly Thr Asp Phe
                 85                  90                  95

Thr Leu Thr Ile Ser Ser Leu Gln Ala Glu Asp Val Ala
                100                 105

<210> SEQ ID NO 54
<211> LENGTH: 277
<212> TYPE: PRT
<213> ORGANISM: Artificial Sequence
<220> FEATURE:
<223> OTHER INFORMATION: human OX40 (Homo sapiens)

<400> SEQUENCE: 54

Met Cys Val Gly Ala Arg Arg Leu Gly Arg Gly Pro Cys Ala Ala Leu
 1               5                  10                  15

Leu Leu Leu Gly Leu Gly Leu Ser Thr Val Thr Gly Leu His Cys Val
                20                  25                  30

Gly Asp Thr Tyr Pro Ser Asn Asp Arg Cys Cys His Glu Cys Arg Pro
             35                  40                  45

Gly Asn Gly Met Val Ser Arg Cys Ser Arg Ser Gln Asn Thr Val Cys
 50                  55                  60

Arg Pro Cys Gly Pro Gly Phe Tyr Asn Asp Val Val Ser Ser Lys Pro
 65                  70                  75                  80

Cys Lys Pro Cys Thr Trp Cys Asn Leu Arg Ser Gly Ser Glu Arg Lys
                 85                  90                  95

Gln Leu Cys Thr Ala Thr Gln Asp Thr Val Cys Arg Cys Arg Ala Gly
                100                 105                 110

Thr Gln Pro Leu Asp Ser Tyr Lys Pro Gly Val Asp Cys Ala Pro Cys
             115                 120                 125

Pro Pro Gly His Phe Ser Pro Gly Asp Asn Gln Ala Cys Lys Pro Trp
130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275
```

<210> SEQ ID NO 55
<211> LENGTH: 272
<212> TYPE: PRT
<213> ORGANISM: Artificial Sequence
<220> FEATURE:
<223> OTHER INFORMATION: murine OX40 (Mus musculus)

<400> SEQUENCE: 55

Met Tyr Val Trp Val Gln Gln Pro Thr Ala Leu Leu Leu Gly Leu
1               5                   10                  15

Thr Leu Gly Val Thr Ala Arg Arg Leu Asn Cys Val Lys His Thr Tyr
            20                  25                  30

Pro Ser Gly His Lys Cys Cys Arg Glu Cys Gln Pro Gly His Gly Met
        35                  40                  45

Val Ser Arg Cys Asp His Thr Arg Asp Thr Leu Cys His Pro Cys Glu
    50                  55                  60

Thr Gly Phe Tyr Asn Glu Ala Val Asn Tyr Asp Thr Cys Lys Gln Cys
65                  70                  75                  80

Thr Gln Cys Asn His Arg Ser Gly Ser Glu Leu Lys Gln Asn Cys Thr
                85                  90                  95

Pro Thr Gln Asp Thr Val Cys Arg Cys Arg Pro Gly Thr Gln Pro Arg
            100                 105                 110

Gln Asp Ser Gly Tyr Lys Leu Gly Val Asp Cys Val Pro Cys Pro Pro
        115                 120                 125

Gly His Phe Ser Pro Gly Asn Asn Gln Ala Cys Lys Pro Trp Thr Asn
    130                 135                 140

Cys Thr Leu Ser Gly Lys Gln Thr Arg His Pro Ala Ser Asp Ser Leu
145                 150                 155                 160

Asp Ala Val Cys Glu Asp Arg Ser Leu Leu Ala Thr Leu Leu Trp Glu
                165                 170                 175

Thr Gln Arg Pro Thr Phe Arg Pro Thr Thr Val Gln Ser Thr Thr Val
            180                 185                 190

Trp Pro Arg Thr Ser Glu Leu Pro Ser Pro Thr Leu Val Thr Pro
        195                 200                 205

Glu Gly Pro Ala Phe Ala Val Leu Leu Gly Leu Gly Leu Gly Leu Leu
    210                 215                 220

Ala Pro Leu Thr Val Leu Leu Ala Leu Tyr Leu Leu Arg Lys Ala Trp
225                 230                 235                 240

Arg Leu Pro Asn Thr Pro Lys Pro Cys Trp Gly Asn Ser Phe Arg Thr
                245                 250                 255

Pro Ile Gln Glu Glu His Thr Asp Ala His Phe Thr Leu Ala Lys Ile
            260                 265                 270

<210> SEQ ID NO 56
<211> LENGTH: 451
<212> TYPE: PRT
<213> ORGANISM: Artificial Sequence
<220> FEATURE:
<223> OTHER INFORMATION: heavy chain for tavolixizumab

<400> SEQUENCE: 56

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

```
Tyr Trp Asn Trp Ile Arg Lys His Pro Gly Lys Gly Leu Glu Tyr Ile
         35                  40                  45

Gly Tyr Ile Ser Tyr Asn Gly Ile Thr Tyr His Asn Pro Ser Leu Lys
 50                  55                  60

Ser Arg Ile Thr Ile Asn Arg Asp Thr Ser Lys Asn Gln Tyr Ser Leu
 65                  70                  75                  80

Gln Leu Asn Ser Val Thr Pro Glu Asp Thr Ala Val Tyr Tyr Cys Ala
                 85                  90                  95

Arg Tyr Lys Tyr Asp Tyr Asp Gly Gly His Ala Met Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445
```

Pro Gly Lys
    450

<210> SEQ ID NO 57
<211> LENGTH: 214
<212> TYPE: PRT
<213> ORGANISM: Artificial Sequence
<220> FEATURE:
<223> OTHER INFORMATION: light chain for tavolixizumab

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Ser Ala Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 58
<211> LENGTH: 118
<212> TYPE: PRT
<213> ORGANISM: Artificial Sequence
<220> FEATURE:
<223> OTHER INFORMATION: heavy chain variable region for tavolixizumab

<400> SEQUENCE: 58

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Gly Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

```
Gln Leu Asn Ser Val Thr Pro Glu Asp Thr Ala Val Tyr Tyr Cys Ala
                85                  90                  95

Arg Tyr Lys Tyr Asp Tyr Asp Gly Gly His Ala Met Asp Tyr Trp Gly
            100                 105                 110

Gln Gly Thr Leu Val Thr
        115

<210> SEQ ID NO 59
<211> LENGTH: 108
<212> TYPE: PRT
<213> ORGANISM: Artificial Sequence
<220> FEATURE:
<223> OTHER INFORMATION: light chain variable region for tavolixizumab

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Ser Ala Leu Pro Trp
                85                  90                  95

Thr Phe Gly Gln Gly Thr Lys Val Glu Ile Lys Arg
            100                 105

<210> SEQ ID NO 60
<211> LENGTH: 9
<212> TYPE: PRT
<213> ORGANISM: Artificial Sequence
<220> FEATURE:
<223> OTHER INFORMATION: heavy chain CDR1 for tavolixizumab

<400> SEQUENCE: 60

Gly Ser Phe Ser Ser Gly Tyr Trp Asn
1               5

<210> SEQ ID NO 61
<211> LENGTH: 13
<212> TYPE: PRT
<213> ORGANISM: Artificial Sequence
<220> FEATURE:
<223> OTHER INFORMATION: heavy chain CDR2 for tavolixizumab

<400> SEQUENCE: 61

Tyr Ile Gly Tyr Ile Ser Tyr Asn Gly Ile Thr Tyr His
1               5                   10

<210> SEQ ID NO 62
<211> LENGTH: 14
<212> TYPE: PRT
<213> ORGANISM: Artificial Sequence
<220> FEATURE:
<223> OTHER INFORMATION: heavy chain CDR3 for tavolixizumab

<400> SEQUENCE: 62

Arg Tyr Lys Tyr Asp Tyr Asp Gly Gly His Ala Met Asp Tyr
1               5                   10
```

```
<210> SEQ ID NO 63
<211> LENGTH: 8
<212> TYPE: PRT
<213> ORGANISM: Artificial Sequence
<220> FEATURE:
<223> OTHER INFORMATION: light chain CDR1 for tavolixizumab

<400> SEQUENCE: 63

Gln Asp Ile Ser Asn Tyr Leu Asn
1               5

<210> SEQ ID NO 64
<211> LENGTH: 11
<212> TYPE: PRT
<213> ORGANISM: Artificial Sequence
<220> FEATURE:
<223> OTHER INFORMATION: light chain CDR2 for tavolixizumab

<400> SEQUENCE: 64

Leu Leu Ile Tyr Tyr Thr Ser Lys Leu His Ser
1               5                   10

<210> SEQ ID NO 65
<211> LENGTH: 8
<212> TYPE: PRT
<213> ORGANISM: Artificial Sequence
<220> FEATURE:
<223> OTHER INFORMATION: light chain CDR3 for tavolixizumab

<400> SEQUENCE: 65

Gln Gln Gly Ser Ala Leu Pro Trp
1               5

<210> SEQ ID NO 66
<211> LENGTH: 444
<212> TYPE: PRT
<213> ORGANISM: Artificial Sequence
<220> FEATURE:
<223> OTHER INFORMATION: heavy chain for 11D4

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Ser Gly Trp Tyr Leu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160
```

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 67
<211> LENGTH: 214
<212> TYPE: PRT
<213> ORGANISM: Artificial Sequence
<220> FEATURE:
<223> OTHER INFORMATION: light chain for 11D4

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 68
<211> LENGTH: 118
<212> TYPE: PRT
<213> ORGANISM: Artificial Sequence
<220> FEATURE:
<223> OTHER INFORMATION: heavy chain variable region for 11D4

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Ser Gly Trp Tyr Leu Phe Asp Tyr Trp Gly Gln Gly Thr
            100                 105                 110

Leu Val Thr Val Ser Ser
        115

<210> SEQ ID NO 69
<211> LENGTH: 107
<212> TYPE: PRT
<213> ORGANISM: Artificial Sequence
<220> FEATURE:
<223> OTHER INFORMATION: light chain variable region for 11D4

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30
```

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys
            100                 105

<210> SEQ ID NO 70
<211> LENGTH: 5
<212> TYPE: PRT
<213> ORGANISM: Artificial Sequence
<220> FEATURE:
<223> OTHER INFORMATION: heavy chain CDR1 for 11D4

<400> SEQUENCE: 70

Ser Tyr Ser Met Asn
1               5

<210> SEQ ID NO 71
<211> LENGTH: 17
<212> TYPE: PRT
<213> ORGANISM: Artificial Sequence
<220> FEATURE:
<223> OTHER INFORMATION: heavy chain CDR2 for 11D4

<400> SEQUENCE: 71

Tyr Ile Ser Ser Ser Ser Ser Thr Ile Asp Tyr Ala Asp Ser Val Lys
1               5                   10                  15

Gly

<210> SEQ ID NO 72
<211> LENGTH: 9
<212> TYPE: PRT
<213> ORGANISM: Artificial Sequence
<220> FEATURE:
<223> OTHER INFORMATION: heavy chain CDR3 for 11D4

<400> SEQUENCE: 72

Glu Ser Gly Trp Tyr Leu Phe Asp Tyr
1               5

<210> SEQ ID NO 73
<211> LENGTH: 11
<212> TYPE: PRT
<213> ORGANISM: Artificial Sequence
<220> FEATURE:
<223> OTHER INFORMATION: light chain CDR1 for 11D4

<400> SEQUENCE: 73

Arg Ala Ser Gln Gly Ile Ser Ser Trp Leu Ala
1               5                   10

<210> SEQ ID NO 74
<211> LENGTH: 7
<212> TYPE: PRT
<213> ORGANISM: Artificial Sequence
<220> FEATURE:
<223> OTHER INFORMATION: light chain CDR2 for 11D4

<400> SEQUENCE: 74

Ala Ala Ser Ser Leu Gln Ser
1               5

<210> SEQ ID NO 75
<211> LENGTH: 9
<212> TYPE: PRT
<213> ORGANISM: Artificial Sequence
<220> FEATURE:
<223> OTHER INFORMATION: light chain CDR3 for 11D4

<400> SEQUENCE: 75

Gln Gln Tyr Asn Ser Tyr Pro Pro Thr
1               5

<210> SEQ ID NO 76
<211> LENGTH: 450
<212> TYPE: PRT
<213> ORGANISM: Artificial Sequence
<220> FEATURE:
<223> OTHER INFORMATION: heavy chain for 18D8

<400> SEQUENCE: 76

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gln Ser Thr Ala Asp Tyr Tyr Phe Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

```
Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300

Val Val Ser Val Leu Thr Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 77
<211> LENGTH: 213
<212> TYPE: PRT
<213> ORGANISM: Artificial Sequence
<220> FEATURE:
<223> OTHER INFORMATION: light chain for 18D8

<400> SEQUENCE: 77

Glu Ile Val Val Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175
```

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 78
<211> LENGTH: 124
<212> TYPE: PRT
<213> ORGANISM: Artificial Sequence
<220> FEATURE:
<223> OTHER INFORMATION: heavy chain variable region for 18D8

<400> SEQUENCE: 78

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gln Ser Thr Ala Asp Tyr Tyr Pro Phe Tyr Tyr Gly Met Asp
            100                 105                 110

Val Trp Gly Gln Gly Thr Val Thr Val Ser Ser
        115                 120

<210> SEQ ID NO 79
<211> LENGTH: 106
<212> TYPE: PRT
<213> ORGANISM: Artificial Sequence
<220> FEATURE:
<223> OTHER INFORMATION: light chain variable region for 18D8

<400> SEQUENCE: 79

Glu Ile Val Val Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 80
<211> LENGTH: 5
<212> TYPE: PRT

```
<213> ORGANISM: Artificial Sequence
<220> FEATURE:
<223> OTHER INFORMATION: heavy chain CDR1 for 18D8

<400> SEQUENCE: 80

Asp Tyr Ala Met His
1               5

<210> SEQ ID NO 81
<211> LENGTH: 17
<212> TYPE: PRT
<213> ORGANISM: Artificial Sequence
<220> FEATURE:
<223> OTHER INFORMATION: heavy chain CDR2 for 18D8

<400> SEQUENCE: 81

Gly Ile Ser Trp Asn Ser Gly Ser Ile Gly Tyr Ala Asp Ser Val Lys
1               5                   10                  15

Gly

<210> SEQ ID NO 82
<211> LENGTH: 15
<212> TYPE: PRT
<213> ORGANISM: Artificial Sequence
<220> FEATURE:
<223> OTHER INFORMATION: heavy chain CDR3 for 18D8

<400> SEQUENCE: 82

Asp Gln Ser Thr Ala Asp Tyr Tyr Phe Tyr Tyr Gly Met Asp Val
1               5                   10                  15

<210> SEQ ID NO 83
<211> LENGTH: 11
<212> TYPE: PRT
<213> ORGANISM: Artificial Sequence
<220> FEATURE:
<223> OTHER INFORMATION: light chain CDR1 for 18D8

<400> SEQUENCE: 83

Arg Ala Ser Gln Ser Val Ser Ser Tyr Leu Ala
1               5                   10

<210> SEQ ID NO 84
<211> LENGTH: 7
<212> TYPE: PRT
<213> ORGANISM: Artificial Sequence
<220> FEATURE:
<223> OTHER INFORMATION: light chain CDR2 for 18D8

<400> SEQUENCE: 84

Asp Ala Ser Asn Arg Ala Thr
1               5

<210> SEQ ID NO 85
<211> LENGTH: 8
<212> TYPE: PRT
<213> ORGANISM: Artificial Sequence
<220> FEATURE:
<223> OTHER INFORMATION: light chain CDR3 for 18D8

<400> SEQUENCE: 85

Gln Gln Arg Ser Asn Trp Pro Thr
1               5

<210> SEQ ID NO 86
<211> LENGTH: 120
```

```
<212> TYPE: PRT
<213> ORGANISM: Artificial Sequence
<220> FEATURE:
<223> OTHER INFORMATION: heavy chain variable region for Hu119-122

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Glu Tyr Glu Phe Pro Ser His
            20                  25                  30

Asp Met Ser Trp Val Arg Gln Ala Pro Gly Lys Gly Leu Glu Leu Val
        35                  40                  45

Ala Ala Ile Asn Ser Asp Gly Gly Ser Thr Tyr Tyr Pro Asp Thr Met
    50                  55                  60

Glu Arg Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Tyr Asp Asp Tyr Tyr Ala Trp Phe Ala Tyr Trp Gly Gln
            100                 105                 110

Gly Thr Met Val Thr Val Ser Ser
        115                 120

<210> SEQ ID NO 87
<211> LENGTH: 111
<212> TYPE: PRT
<213> ORGANISM: Artificial Sequence
<220> FEATURE:
<223> OTHER INFORMATION: light chain variable region for Hu119-122

<400> SEQUENCE: 87

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Glu Leu Pro Leu Thr Phe Gly Gly Gly Thr Lys Val Glu Ile Lys
            100                 105                 110

<210> SEQ ID NO 88
<211> LENGTH: 5
<212> TYPE: PRT
<213> ORGANISM: Artificial Sequence
<220> FEATURE:
<223> OTHER INFORMATION: heavy chain CDR1 for Hu119-122

<400> SEQUENCE: 88

Ser His Asp Met Ser
1               5

<210> SEQ ID NO 89
<211> LENGTH: 17
<212> TYPE: PRT
```

-continued

```
<213> ORGANISM: Artificial Sequence
<220> FEATURE:
<223> OTHER INFORMATION: heavy chain CDR2 for Hu119-122

<400> SEQUENCE: 89

Ala Ile Asn Ser Asp Gly Gly Ser Thr Tyr Tyr Pro Asp Thr Met Glu
1               5                   10                  15
Arg

<210> SEQ ID NO 90
<211> LENGTH: 11
<212> TYPE: PRT
<213> ORGANISM: Artificial Sequence
<220> FEATURE:
<223> OTHER INFORMATION: heavy chain CDR3 for Hu119-122

<400> SEQUENCE: 90

His Tyr Asp Asp Tyr Tyr Ala Trp Phe Ala Tyr
1               5                   10

<210> SEQ ID NO 91
<211> LENGTH: 15
<212> TYPE: PRT
<213> ORGANISM: Artificial Sequence
<220> FEATURE:
<223> OTHER INFORMATION: light chain CDR1 for Hu119-122

<400> SEQUENCE: 91

Arg Ala Ser Lys Ser Val Ser Thr Ser Gly Tyr Ser Tyr Met His
1               5                   10                  15

<210> SEQ ID NO 92
<211> LENGTH: 7
<212> TYPE: PRT
<213> ORGANISM: Artificial Sequence
<220> FEATURE:
<223> OTHER INFORMATION: light chain CDR2 for Hu119-122

<400> SEQUENCE: 92

Leu Ala Ser Asn Leu Glu Ser
1               5

<210> SEQ ID NO 93
<211> LENGTH: 9
<212> TYPE: PRT
<213> ORGANISM: Artificial Sequence
<220> FEATURE:
<223> OTHER INFORMATION: light chain CDR3 for Hu119-122

<400> SEQUENCE: 93

Gln His Ser Arg Glu Leu Pro Leu Thr
1               5

<210> SEQ ID NO 94
<211> LENGTH: 122
<212> TYPE: PRT
<213> ORGANISM: Artificial Sequence
<220> FEATURE:
<223> OTHER INFORMATION: heavy chain variable region for Hu106-222

<400> SEQUENCE: 94

Gln Val Gln Leu Val Gln Ser Gly Ser Glu Leu Lys Lys Pro Gly Ala
1               5                   10                  15
Ser Val Lys Val Ser Cys Lys Ala Ser Gly Tyr Thr Phe Thr Asp Tyr
                20                  25                  30
```

```
Ser Met His Trp Val Arg Gln Ala Pro Gly Gln Gly Leu Lys Trp Met
            35                  40                  45

Gly Trp Ile Asn Thr Glu Thr Gly Glu Pro Thr Tyr Ala Asp Asp Phe
 50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Asn Pro Tyr Tyr Asp Tyr Val Ser Tyr Tyr Ala Met Asp Tyr Trp
            100                 105                 110

Gly Gln Gly Thr Thr Val Thr Val Ser Ser
        115                 120
```

<210> SEQ ID NO 95
<211> LENGTH: 107
<212> TYPE: PRT
<213> ORGANISM: Artificial Sequence
<220> FEATURE:
<223> OTHER INFORMATION: light chain variable region for Hu106-222

<400> SEQUENCE: 95

```
Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Leu Tyr Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln His Tyr Ser Thr Pro Arg
                 85                  90                  95

Thr Phe Gly Gln Gly Thr Lys Leu Glu Ile Lys
            100                 105
```

<210> SEQ ID NO 96
<211> LENGTH: 5
<212> TYPE: PRT
<213> ORGANISM: Artificial Sequence
<220> FEATURE:
<223> OTHER INFORMATION: heavy chain CDR1 for Hu106-222

<400> SEQUENCE: 96

```
Asp Tyr Ser Met His
 1               5
```

<210> SEQ ID NO 97
<211> LENGTH: 17
<212> TYPE: PRT
<213> ORGANISM: Artificial Sequence
<220> FEATURE:
<223> OTHER INFORMATION: heavy chain CDR2 for Hu106-222

<400> SEQUENCE: 97

```
Trp Ile Asn Thr Glu Thr Gly Glu Pro Thr Tyr Ala Asp Asp Phe Lys
 1               5                  10                  15

Gly
```

<210> SEQ ID NO 98

-continued

```
<211> LENGTH: 13
<212> TYPE: PRT
<213> ORGANISM: Artificial Sequence
<220> FEATURE:
<223> OTHER INFORMATION: heavy chain CDR3 for Hu106-222

<400> SEQUENCE: 98

Pro Tyr Tyr Asp Tyr Val Ser Tyr Tyr Ala Met Asp Tyr
1               5                   10

<210> SEQ ID NO 99
<211> LENGTH: 11
<212> TYPE: PRT
<213> ORGANISM: Artificial Sequence
<220> FEATURE:
<223> OTHER INFORMATION: light chain CDR1 for Hu106-222

<400> SEQUENCE: 99

Lys Ala Ser Gln Asp Val Ser Thr Ala Val Ala
1               5                   10

<210> SEQ ID NO 100
<211> LENGTH: 7
<212> TYPE: PRT
<213> ORGANISM: Artificial Sequence
<220> FEATURE:
<223> OTHER INFORMATION: light chain CDR2 for Hu106-222

<400> SEQUENCE: 100

Ser Ala Ser Tyr Leu Tyr Thr
1               5

<210> SEQ ID NO 101
<211> LENGTH: 9
<212> TYPE: PRT
<213> ORGANISM: Artificial Sequence
<220> FEATURE:
<223> OTHER INFORMATION: light chain CDR3 for Hu106-222

<400> SEQUENCE: 101

Gln Gln His Tyr Ser Thr Pro Arg Thr
1               5

<210> SEQ ID NO 102
<211> LENGTH: 183
<212> TYPE: PRT
<213> ORGANISM: Artificial Sequence
<220> FEATURE:
<223> OTHER INFORMATION: OX40L

<400> SEQUENCE: 102

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
                20                  25                  30

Gly Leu Gly Leu Leu Leu Cys Phe Thr Tyr Ile Cys Leu His Phe Ser
            35                  40                  45

Ala Leu Gln Val Ser His Arg Tyr Pro Arg Ile Gln Ser Ile Lys Val
        50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95
```

-continued

```
Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 103
<211> LENGTH: 131
<212> TYPE: PRT
<213> ORGANISM: Artificial Sequence
<220> FEATURE:
<223> OTHER INFORMATION: OX40L soluble domain

<400> SEQUENCE: 103

Ser His Arg Tyr Pro Arg Ile Gln Ser Ile Lys Val Gln Phe Thr Glu
1               5                   10                  15

Tyr Lys Lys Glu Lys Gly Phe Ile Leu Thr Ser Gln Lys Glu Asp Glu
            20                  25                  30

Ile Met Lys Val Gln Asn Asn Ser Val Ile Ile Asn Cys Asp Gly Phe
        35                  40                  45

Tyr Leu Ile Ser Leu Lys Gly Tyr Phe Ser Gln Glu Val Asn Ile Ser
    50                  55                  60

Leu His Tyr Gln Lys Asp Glu Glu Pro Leu Phe Gln Leu Lys Lys Val
65                  70                  75                  80

Arg Ser Val Asn Ser Leu Met Val Ala Ser Leu Thr Tyr Lys Asp Lys
                85                  90                  95

Val Tyr Leu Asn Val Thr Thr Asp Asn Thr Ser Leu Asp Asp Phe His
            100                 105                 110

Val Asn Gly Gly Glu Leu Ile Leu Ile His Gln Asn Pro Gly Glu Phe
        115                 120                 125

Cys Val Leu
    130

<210> SEQ ID NO 104
<211> LENGTH: 128
<212> TYPE: PRT
<213> ORGANISM: Artificial Sequence
<220> FEATURE:
<223> OTHER INFORMATION: OX40L soluble domain (alternative)

<400> SEQUENCE: 104

Tyr Pro Arg Ile Gln Ser Ile Lys Val Gln Phe Thr Glu Tyr Lys Lys
1               5                   10                  15

Glu Lys Gly Phe Ile Leu Thr Ser Gln Lys Glu Asp Glu Ile Met Lys
            20                  25                  30

Val Gln Asn Asn Ser Val Ile Ile Asn Cys Asp Gly Phe Tyr Leu Ile
        35                  40                  45

Ser Leu Lys Gly Tyr Phe Ser Gln Glu Val Asn Ile Ser Leu His Tyr
    50                  55                  60
```

-continued

Gln Lys Asp Glu Glu Pro Leu Phe Gln Leu Lys Lys Val Arg Ser Val
65                  70                  75                  80

Asn Ser Leu Met Val Ala Ser Leu Thr Tyr Lys Asp Lys Val Tyr Leu
                85                  90                  95

Asn Val Thr Thr Asp Asn Thr Ser Leu Asp Asp Phe His Val Asn Gly
            100                 105                 110

Gly Glu Leu Ile Leu Ile His Gln Asn Pro Gly Glu Phe Cys Val Leu
        115                 120                 125

<210> SEQ ID NO 105
<211> LENGTH: 120
<212> TYPE: PRT
<213> ORGANISM: Artificial Sequence
<220> FEATURE:
<223> OTHER INFORMATION: variable heavy chain for 008

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Thr Met Asn Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Ser Gln Val His Tyr Ala Leu Asp Tyr Trp Gly
            100                 105                 110

Gln Gly Thr Leu Val Thr Val Ser
        115                 120

<210> SEQ ID NO 106
<211> LENGTH: 108
<212> TYPE: PRT
<213> ORGANISM: Artificial Sequence
<220> FEATURE:
<223> OTHER INFORMATION: variable light chain for 008

<400> SEQUENCE: 106

Asp Ile Val Met Thr Gln Ser Pro Asp Ser Leu Pro Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Ala Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Tyr Asn His Pro Thr Thr Phe Gly Gln Gly Thr Lys
            100                 105

```
<210> SEQ ID NO 107
<211> LENGTH: 120
<212> TYPE: PRT
<213> ORGANISM: Artificial Sequence
<220> FEATURE:
<223> OTHER INFORMATION: variable heavy chain for 011

<400> SEQUENCE: 107
```

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Thr Met Asn Trp Val Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Lys Asn Thr Leu Tyr Leu Gln
65                  70                  75                  80

Met Asn Asn Leu Arg Ala Glu Asp Thr Ala Val Tyr Tyr Cys Ala Arg
                85                  90                  95

Asp Arg Tyr Phe Arg Gln Gln Asn Ala Phe Asp Tyr Trp Gly Gln Gly
            100                 105                 110

Thr Leu Val Thr Val Ser Ser Ala
        115                 120

```
<210> SEQ ID NO 108
<211> LENGTH: 108
<212> TYPE: PRT
<213> ORGANISM: Artificial Sequence
<220> FEATURE:
<223> OTHER INFORMATION: variable light chain for 011

<400> SEQUENCE: 108
```

Asp Ile Val Met Thr Gln Ser Pro Asp Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Ala Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Tyr Asn His Pro Thr Thr Phe Gly Gln Gly Thr Lys
            100                 105

```
<210> SEQ ID NO 109
<211> LENGTH: 120
<212> TYPE: PRT
<213> ORGANISM: Artificial Sequence
<220> FEATURE:
<223> OTHER INFORMATION: variable heavy chain for 021

<400> SEQUENCE: 109
```

Glu Val Gln Leu Val Glu Ser Gly Gly Gly Leu Val Gln Pro Arg Gly
1               5                   10                  15

Ser Leu Arg Leu Ser Cys Ala Ala Ser Gly Phe Thr Phe Ser Ser Tyr
            20                  25                  30

```
Ala Met Asn Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Ile Thr Leu Pro Asn Ala Leu Asp Tyr Trp Gly
            100                 105                 110

Gln Gly Thr Leu Val Thr Val Ser
        115                 120

<210> SEQ ID NO 110
<211> LENGTH: 108
<212> TYPE: PRT
<213> ORGANISM: Artificial Sequence
<220> FEATURE:
<223> OTHER INFORMATION: variable light chain for 021

<400> SEQUENCE: 110

Asp Ile Gln Met Thr Gln Ser Pro Val Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Lys Ser Asn Pro Pro Thr Phe Gly Gln Gly Thr Lys
            100                 105

<210> SEQ ID NO 111
<211> LENGTH: 120
<212> TYPE: PRT
<213> ORGANISM: Artificial Sequence
<220> FEATURE:
<223> OTHER INFORMATION: variable heavy chain for 023

<400> SEQUENCE: 111

Glu Val Gln Leu Val Glu Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Thr Tyr Tyr Ala Asp Ser Val Met
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

```
Arg Tyr Asp Asn Val Met Gly Leu Tyr Trp Phe Asp Tyr Trp Gly Gln
            100                 105                 110

Gly Thr Leu Val Thr Val Ser Ser
        115                 120

<210> SEQ ID NO 112
<211> LENGTH: 108
<212> TYPE: PRT
<213> ORGANISM: Artificial Sequence
<220> FEATURE:
<223> OTHER INFORMATION: variable light chain for 023

<400> SEQUENCE: 112

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Phe Gly Gly Gly Thr Lys Val Glu Ile Lys Arg
            100                 105

<210> SEQ ID NO 113
<211> LENGTH: 119
<212> TYPE: PRT
<213> ORGANISM: Artificial Sequence
<220> FEATURE:
<223> OTHER INFORMATION: heavy chain variable region

<400> SEQUENCE: 113

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Ser Val Thr Val Ser Ser
        115

<210> SEQ ID NO 114
<211> LENGTH: 108
<212> TYPE: PRT
<213> ORGANISM: Artificial Sequence
<220> FEATURE:
<223> OTHER INFORMATION: light chain variable region
```

<400> SEQUENCE: 114

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys Arg
            100                 105

<210> SEQ ID NO 115
<211> LENGTH: 121
<212> TYPE: PRT
<213> ORGANISM: Artificial Sequence
<220> FEATURE:
<223> OTHER INFORMATION: heavy chain variable region

<400> SEQUENCE: 115

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Lys Asp Tyr
            20                  25                  30

Thr Met His Trp Val Lys Gln Ser His Gly Lys Ser Leu Glu Trp Ile
        35                  40                  45

Gly Gly Ile Tyr Pro Asn Asn Gly Gly Ser Thr Tyr Asn Gln Asn Phe
50                  55                  60

Lys Asp Lys Ala Thr Leu Thr Val Asp Lys Ser Ser Ser Thr Ala Tyr
65                  70                  75                  80

Met Glu Phe Arg Ser Leu Thr Ser Glu Asp Ser Ala Val Tyr Tyr Cys
                85                  90                  95

Ala Arg Met Gly Tyr His Gly Pro His Leu Asp Phe Asp Val Trp Gly
            100                 105                 110

Ala Gly Thr Thr Val Thr Val Ser Pro
        115                 120

<210> SEQ ID NO 116
<211> LENGTH: 108
<212> TYPE: PRT
<213> ORGANISM: Artificial Sequence
<220> FEATURE:
<223> OTHER INFORMATION: light chain variable region

<400> SEQUENCE: 116

Asp Ile Val Met Thr Gln Ser His Lys Phe Met Ser Thr Ser Leu Gly
1               5                   10                  15

Asp Arg Val Ser Ile Thr Cys Lys Ala Ser Gln Asp Val Gly Ala Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

```
Gly Gly Ser Gly Thr Asp Phe Thr Leu Thr Ile Ser Asn Val Gln Ser
65                  70                  75                  80

Glu Asp Leu Thr Asp Tyr Phe Cys Gln Gln Tyr Ile Asn Tyr Pro Leu
                85                  90                  95

Thr Phe Gly Gly Gly Thr Lys Leu Glu Ile Lys Arg
            100                 105
```

<210> SEQ ID NO 117
<211> LENGTH: 122
<212> TYPE: PRT
<213> ORGANISM: Artificial Sequence
<220> FEATURE:
<223> OTHER INFORMATION: heavy chain variable region of humanized
      antibody

<400> SEQUENCE: 117

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Asn Pro Tyr Tyr Asp Tyr Val Ser Tyr Tyr Ala Met Asp Tyr Trp
            100                 105                 110

Gly His Gly Thr Ser Val Thr Val Ser Ser
        115                 120
```

<210> SEQ ID NO 118
<211> LENGTH: 122
<212> TYPE: PRT
<213> ORGANISM: Artificial Sequence
<220> FEATURE:
<223> OTHER INFORMATION: heavy chain variable region of humanized
      antibody

<400> SEQUENCE: 118

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Pro Tyr Tyr Asp Tyr Val Ser Tyr Tyr Ala Met Asp Tyr Trp
            100                 105                 110

Gly Gln Gly Thr Thr Val Thr Val Ser Ser
        115                 120
```

<210> SEQ ID NO 119
<211> LENGTH: 107
<212> TYPE: PRT
<213> ORGANISM: Artificial Sequence
<220> FEATURE:
<223> OTHER INFORMATION: light chain variable region of humanized
      antibody

<400> SEQUENCE: 119

Asp Ile Val Met Thr Gln Ser His Lys Phe Met Ser Thr Ser Val Arg
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Leu Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Arg
                85                  90                  95

Thr Phe Gly Gly Gly Thr Lys Leu Glu Ile Lys
            100                 105

<210> SEQ ID NO 120
<211> LENGTH: 107
<212> TYPE: PRT
<213> ORGANISM: Artificial Sequence
<220> FEATURE:
<223> OTHER INFORMATION: light chain variable region of humanized
      antibody

<400> SEQUENCE: 120

Asp Ile Val Met Thr Gln Ser His Lys Phe Met Ser Thr Ser Val Arg
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Leu Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Arg
                85                  90                  95

Thr Phe Gly Gly Gly Thr Lys Leu Glu Ile Lys
            100                 105

<210> SEQ ID NO 121
<211> LENGTH: 120
<212> TYPE: PRT
<213> ORGANISM: Artificial Sequence
<220> FEATURE:
<223> OTHER INFORMATION: heavy chain variable region of humanized
      antibody

<400> SEQUENCE: 121

Glu Val Gln Leu Val Glu Ser Gly Gly Gly Leu Val Gln Pro Gly Glu
1               5                   10                  15

Ser Leu Lys Leu Ser Cys Glu Ser Asn Glu Tyr Glu Phe Pro Ser His
         20                  25                  30

Asp Met Ser Trp Val Arg Lys Thr Pro Glu Lys Arg Leu Glu Leu Val
             35                  40                  45

Ala Ala Ile Asn Ser Asp Gly Gly Ser Thr Tyr Tyr Pro Asp Thr Met
 50                  55                  60

Glu Arg Arg Phe Ile Ile Ser Arg Asp Asn Thr Lys Lys Thr Leu Tyr
 65                  70                  75                  80

Leu Gln Met Ser Ser Leu Arg Ser Glu Asp Thr Ala Leu Tyr Tyr Cys
             85                  90                  95

Ala Arg His Tyr Asp Asp Tyr Tyr Ala Trp Phe Ala Tyr Trp Gly Gln
            100                 105                 110

Gly Thr Leu Val Thr Val Ser Ala
        115                 120

<210> SEQ ID NO 122
<211> LENGTH: 120
<212> TYPE: PRT
<213> ORGANISM: Artificial Sequence
<220> FEATURE:
<223> OTHER INFORMATION: heavy chain variable region of humanized
      antibody

<400> SEQUENCE: 122

Glu Val Gln Leu Val Glu Ser Gly Gly Gly Leu Val Gln Pro Gly Gly
 1               5                  10                  15

Ser Leu Arg Leu Ser Cys Ala Ala Ser Glu Tyr Glu Phe Pro Ser His
             20                  25                  30

Asp Met Ser Trp Val Arg Gln Ala Pro Gly Lys Gly Leu Glu Leu Val
             35                  40                  45

Ala Ala Ile Asn Ser Asp Gly Gly Ser Thr Tyr Tyr Pro Asp Thr Met
 50                  55                  60

Glu Arg Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg His Tyr Asp Asp Tyr Tyr Ala Trp Phe Ala Tyr Trp Gly Gln
            100                 105                 110

Gly Thr Met Val Thr Val Ser Ser
        115                 120

<210> SEQ ID NO 123
<211> LENGTH: 111
<212> TYPE: PRT
<213> ORGANISM: Artificial Sequence
<220> FEATURE:
<223> OTHER INFORMATION: light chain variable region of humanized
      antibody

<400> SEQUENCE: 123

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Lys Ser Val Ser Thr Ser
             20                  25                  30

Gly Tyr Ser Tyr Met His Trp Tyr Gln Gln Lys Pro Gly Gln Pro Pro
             35                  40                  45

Lys Leu Leu Ile Tyr Leu Ala Ser Asn Leu Glu Ser Gly Val Pro Ala
 50                  55                  60

```
Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Arg
                 85                  90                  95

Glu Leu Pro Leu Thr Phe Gly Ala Gly Thr Lys Leu Glu Leu Lys
                100                 105                 110

<210> SEQ ID NO 124
<211> LENGTH: 111
<212> TYPE: PRT
<213> ORGANISM: Artificial Sequence
<220> FEATURE:
<223> OTHER INFORMATION: light chain variable region of humanized
      antibody

<400> SEQUENCE: 124

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Lys Ser Val Ser Thr Ser
                 20                  25                  30

Gly Tyr Ser Tyr Met His Trp Tyr Gln Gln Lys Pro Gly Gln Ala Pro
             35                  40                  45

Arg Leu Leu Ile Tyr Leu Ala Ser Asn Leu Glu Ser Gly Val Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                 85                  90                  95

Glu Leu Pro Leu Thr Phe Gly Gly Gly Thr Lys Val Glu Ile Lys
                100                 105                 110

<210> SEQ ID NO 125
<211> LENGTH: 138
<212> TYPE: PRT
<213> ORGANISM: Artificial Sequence
<220> FEATURE:
<223> OTHER INFORMATION: heavy chain variable region

<400> SEQUENCE: 125

Met Tyr Leu Gly Leu Asn Tyr Val Phe Ile Val Phe Leu Leu Asn Gly
  1               5                  10                  15

Val Gln Ser Glu Val Lys Leu Glu Glu Ser Gly Gly Gly Leu Val Gln
                 20                  25                  30

Pro Gly Gly Ser Met Lys Leu Ser Cys Ala Ala Ser Gly Phe Thr Phe
             35                  40                  45

Ser Asp Ala Trp Met Asp Trp Val Arg Gln Ser Pro Glu Lys Gly Leu
 50                  55                  60

Glu Trp Val Ala Glu Ile Arg Ser Lys Ala Asn Asn His Ala Thr Tyr
 65                  70                  75                  80

Tyr Ala Glu Ser Val Asn Gly Arg Phe Thr Ile Ser Arg Asp Asp Ser
                 85                  90                  95

Lys Ser Ser Val Tyr Leu Gln Met Asn Ser Leu Arg Ala Glu Asp Thr
                100                 105                 110

Gly Ile Tyr Tyr Cys Thr Trp Gly Glu Val Phe Tyr Phe Asp Tyr Trp
            115                 120                 125

Gly Gln Gly Thr Thr Leu Thr Val Ser Ser
            130                 135
```

```
<210> SEQ ID NO 126
<211> LENGTH: 126
<212> TYPE: PRT
<213> ORGANISM: Artificial Sequence
<220> FEATURE:
<223> OTHER INFORMATION: light chain variable region

<400> SEQUENCE: 126

Met Arg Pro Ser Ile Gln Phe Leu Gly Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Leu Gly Gly Lys Val Thr Ile Thr Cys Lys Ser Ser Gln Asp
        35                  40                  45

Ile Asn Lys Tyr Ile Ala Trp Tyr Gln His Lys Pro Gly Lys Gly Pro
    50                  55                  60

Arg Leu Leu Ile His Tyr Thr Ser Thr Leu Gln Pro Gly Ile Pro Ser
65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Ala Thr Tyr Tyr Cys Leu Gln Tyr Asp
            100                 105                 110

Asn Leu Leu Thr Phe Gly Ala Gly Thr Lys Leu Glu Leu Lys
        115                 120                 125

<210> SEQ ID NO 127
<211> LENGTH: 380
<212> TYPE: PRT
<213> ORGANISM: Artificial Sequence
<220> FEATURE:
<223> OTHER INFORMATION: nivolumab heavy chain

<400> SEQUENCE: 127

Ala Asp Ser Val Lys Gly Arg Phe Thr Ile Ser Arg Asp Asn Ser Lys
1               5                   10                  15

Asn Thr Leu Phe Leu Gln Met Asn Ser Leu Arg Ala Glu Asp Thr Ala
            20                  25                  30

Val Tyr Tyr Cys Ala Thr Asn Asp Asp Tyr Trp Gly Gln Gly Thr Leu
        35                  40                  45

Val Thr Val Ser Ser Ala Ser Thr Lys Gly Pro Ser Val Phe Pro Leu
    50                  55                  60

Ala Pro Cys Ser Arg Ser Thr Ser Glu Ser Thr Ala Ala Leu Gly Cys
65                  70                  75                  80

Leu Val Lys Asp Tyr Phe Pro Glu Pro Val Thr Val Ser Trp Asn Ser
                85                  90                  95

Gly Ala Leu Thr Ser Gly Val His Thr Phe Pro Ala Val Leu Gln Ser
            100                 105                 110

Ser Gly Leu Tyr Ser Leu Ser Ser Val Val Thr Val Pro Ser Ser Ser
        115                 120                 125

Leu Gly Thr Lys Thr Tyr Thr Cys Asn Val Asp His Lys Pro Ser Asn
    130                 135                 140

Thr Lys Val Asp Lys Arg Val Glu Ser Lys Tyr Gly Pro Pro Cys Pro
145                 150                 155                 160

Pro Cys Pro Ala Pro Glu Phe Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190
```

```
Thr Cys Val Val Val Asp Val Ser Gln Glu Asp Pro Glu Val Gln Phe
            195                 200                 205

Asn Trp Tyr Val Asp Gly Val Glu Val His Asn Ala Lys Thr Lys Pro
210                 215                 220

Arg Glu Glu Gln Phe Asn Ser Thr Tyr Arg Val Val Ser Val Leu Thr
225                 230                 235                 240

Val Leu His Gln Asp Trp Leu Asn Gly Lys Glu Tyr Lys Cys Lys Val
            245                 250                 255

Ser Asn Lys Gly Leu Pro Ser Ser Ile Glu Lys Thr Ile Ser Lys Ala
            260                 265                 270

Lys Gly Gln Pro Arg Glu Pro Gln Val Tyr Thr Leu Pro Pro Ser Gln
            275                 280                 285

Glu Glu Met Thr Lys Asn Gln Val Ser Leu Thr Cys Leu Val Lys Gly
            290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
            325                 330                 335

Phe Phe Leu Tyr Ser Arg Leu Thr Val Asp Lys Ser Arg Trp Gln Glu
            340                 345                 350

Gly Asn Val Phe Ser Cys Ser Val Met His Glu Ala Leu His Asn His
            355                 360                 365

Tyr Thr Gln Lys Ser Leu Ser Leu Ser Leu Gly Lys
            370                 375                 380

<210> SEQ ID NO 128
<211> LENGTH: 214
<212> TYPE: PRT
<213> ORGANISM: Artificial Sequence
<220> FEATURE:
<223> OTHER INFORMATION: nivolumab light chain

<400> SEQUENCE: 128

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

-continued

```
Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 129
<211> LENGTH: 113
<212> TYPE: PRT
<213> ORGANISM: Artificial Sequence
<220> FEATURE:
<223> OTHER INFORMATION: nivolumab variable heavy chain

<400> SEQUENCE: 129

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 130
<211> LENGTH: 107
<212> TYPE: PRT
<213> ORGANISM: Artificial Sequence
<220> FEATURE:
<223> OTHER INFORMATION: nivolumab variable light chain

<400> SEQUENCE: 130

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 131
<211> LENGTH: 5
<212> TYPE: PRT
<213> ORGANISM: Artificial Sequence
<220> FEATURE:
```

```
<223> OTHER INFORMATION: nivolumab heavy chain CDR1

<400> SEQUENCE: 131

Asn Ser Gly Met His
1               5

<210> SEQ ID NO 132
<211> LENGTH: 17
<212> TYPE: PRT
<213> ORGANISM: Artificial Sequence
<220> FEATURE:
<223> OTHER INFORMATION: nivolumab heavy chain CDR2

<400> SEQUENCE: 132

Val Ile Trp Tyr Asp Gly Ser Lys Arg Tyr Tyr Ala Asp Ser Val Lys
1               5                   10                  15

Gly

<210> SEQ ID NO 133
<211> LENGTH: 4
<212> TYPE: PRT
<213> ORGANISM: Artificial Sequence
<220> FEATURE:
<223> OTHER INFORMATION: nivolumab heavy chain CDR3

<400> SEQUENCE: 133

Asn Asp Asp Tyr
1

<210> SEQ ID NO 134
<211> LENGTH: 11
<212> TYPE: PRT
<213> ORGANISM: Artificial Sequence
<220> FEATURE:
<223> OTHER INFORMATION: nivolumab light chain CDR1

<400> SEQUENCE: 134

Arg Ala Ser Gln Ser Val Ser Ser Tyr Leu Ala
1               5                   10

<210> SEQ ID NO 135
<211> LENGTH: 7
<212> TYPE: PRT
<213> ORGANISM: Artificial Sequence
<220> FEATURE:
<223> OTHER INFORMATION: nivolumab light chain CDR2

<400> SEQUENCE: 135

Asp Ala Ser Asn Arg Ala Thr
1               5

<210> SEQ ID NO 136
<211> LENGTH: 9
<212> TYPE: PRT
<213> ORGANISM: Artificial Sequence
<220> FEATURE:
<223> OTHER INFORMATION: nivolumab light chain CDR3

<400> SEQUENCE: 136

Gln Gln Ser Ser Asn Trp Pro Arg Thr
1               5

<210> SEQ ID NO 137
<211> LENGTH: 447
<212> TYPE: PRT
<213> ORGANISM: Artificial Sequence
```

<220> FEATURE:
<223> OTHER INFORMATION: pembrolizumab heavy chain

<400> SEQUENCE: 137

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

-continued

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 138
<211> LENGTH: 218
<212> TYPE: PRT
<213> ORGANISM: Artificial Sequence
<220> FEATURE:
<223> OTHER INFORMATION: pembrolizumab light chain

<400> SEQUENCE: 138

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 139
<211> LENGTH: 120
<212> TYPE: PRT
<213> ORGANISM: Artificial Sequence
<220> FEATURE:
<223> OTHER INFORMATION: pembrolizumab variable heavy chain

<400> SEQUENCE: 139

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
 50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
            115                 120

<210> SEQ ID NO 140
<211> LENGTH: 111
<212> TYPE: PRT
<213> ORGANISM: Artificial Sequence
<220> FEATURE:
<223> OTHER INFORMATION: pembrolizumab variable light chain

<400> SEQUENCE: 140

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 141
<211> LENGTH: 5
<212> TYPE: PRT
<213> ORGANISM: Artificial Sequence
<220> FEATURE:
<223> OTHER INFORMATION: pembrolizumab heavy chain CDR1

<400> SEQUENCE: 141

Asn Tyr Tyr Met Tyr
 1               5

<210> SEQ ID NO 142
<211> LENGTH: 16
<212> TYPE: PRT
<213> ORGANISM: Artificial Sequence
<220> FEATURE:
<223> OTHER INFORMATION: pembrolizumab heavy chain CDR2

<400> SEQUENCE: 142

Gly Ile Asn Pro Ser Asn Gly Gly Thr Asn Phe Asn Glu Lys Phe Lys
 1               5                  10                  15

<210> SEQ ID NO 143
<211> LENGTH: 11

```
<212> TYPE: PRT
<213> ORGANISM: Artificial Sequence
<220> FEATURE:
<223> OTHER INFORMATION: pembrolizumab heavy chain CDR3

<400> SEQUENCE: 143

Arg Asp Tyr Arg Phe Asp Met Gly Phe Asp Tyr
1               5                   10

<210> SEQ ID NO 144
<211> LENGTH: 15
<212> TYPE: PRT
<213> ORGANISM: Artificial Sequence
<220> FEATURE:
<223> OTHER INFORMATION: pembrolizumab light chain CDR1

<400> SEQUENCE: 144

Arg Ala Ser Lys Gly Val Ser Thr Ser Gly Tyr Ser Tyr Leu His
1               5                   10                  15

<210> SEQ ID NO 145
<211> LENGTH: 7
<212> TYPE: PRT
<213> ORGANISM: Artificial Sequence
<220> FEATURE:
<223> OTHER INFORMATION: pembrolizumab light chain CDR2

<400> SEQUENCE: 145

Leu Ala Ser Tyr Leu Glu Ser
1               5

<210> SEQ ID NO 146
<211> LENGTH: 9
<212> TYPE: PRT
<213> ORGANISM: Artificial Sequence
<220> FEATURE:
<223> OTHER INFORMATION: pembrolizumab light chain CDR3

<400> SEQUENCE: 146

Gln His Ser Arg Asp Leu Pro Leu Thr
1               5

<210> SEQ ID NO 147
<211> LENGTH: 451
<212> TYPE: PRT
<213> ORGANISM: Artificial Sequence
<220> FEATURE:
<223> OTHER INFORMATION: durvalumab heavy chain

<400> SEQUENCE: 147

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110
```

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 148
<211> LENGTH: 265
<212> TYPE: PRT
<213> ORGANISM: Artificial Sequence
<220> FEATURE:
<223> OTHER INFORMATION: durvalumab light chain

<400> SEQUENCE: 148

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Glu Ile Val Leu Thr Gln Ser Pro Gly Thr Leu Ser Leu Ser
50                  55                  60

Pro Gly Glu Arg Ala Thr Leu Ser Cys Arg Ala Ser Gln Arg Val Ser
65                  70                  75                  80

Ser Ser Tyr Leu Ala Trp Tyr Gln Gln Lys Pro Gly Gln Ala Pro Arg
                85                  90                  95

Leu Leu Ile Tyr Asp Ala Ser Ser Arg Ala Thr Gly Ile Pro Asp Arg
            100                 105                 110

Phe Ser Gly Ser Gly Ser Gly Thr Asp Phe Thr Leu Thr Ile Ser Arg
        115                 120                 125

Leu Glu Pro Glu Asp Phe Ala Val Tyr Tyr Cys Gln Gln Tyr Gly Ser
130                 135                 140

Leu Pro Trp Thr Phe Gly Gln Gly Thr Lys Val Glu Ile Lys Arg Thr
145                 150                 155                 160

Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
            180                 185                 190

Arg Glu Ala Lys Val Gln Trp Lys Val Asp Asn Ala Leu Gln Ser Gly
        195                 200                 205

Asn Ser Gln Glu Ser Val Thr Glu Gln Asp Ser Lys Asp Ser Thr Tyr
210                 215                 220

Ser Leu Ser Ser Thr Leu Thr Leu Ser Lys Ala Asp Tyr Glu Lys His
225                 230                 235                 240

Lys Val Tyr Ala Cys Glu Val Thr His Gln Gly Leu Ser Ser Pro Val
                245                 250                 255

Thr Lys Ser Phe Asn Arg Gly Glu Cys
            260                 265

<210> SEQ ID NO 149
<211> LENGTH: 121
<212> TYPE: PRT
<213> ORGANISM: Artificial Sequence
<220> FEATURE:
<223> OTHER INFORMATION: durvalumab variable heavy chain

<400> SEQUENCE: 149

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110
```

```
Gln Gly Thr Leu Val Thr Val Ser Ser
        115                 120

<210> SEQ ID NO 150
<211> LENGTH: 108
<212> TYPE: PRT
<213> ORGANISM: Artificial Sequence
<220> FEATURE:
<223> OTHER INFORMATION: durvalumab variable light chain

<400> SEQUENCE: 150

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 151
<211> LENGTH: 5
<212> TYPE: PRT
<213> ORGANISM: Artificial Sequence
<220> FEATURE:
<223> OTHER INFORMATION: durvalumab heavy chain CDR1

<400> SEQUENCE: 151

Arg Tyr Trp Met Ser
1               5

<210> SEQ ID NO 152
<211> LENGTH: 17
<212> TYPE: PRT
<213> ORGANISM: Artificial Sequence
<220> FEATURE:
<223> OTHER INFORMATION: durvalumab heavy chain CDR2

<400> SEQUENCE: 152

Asn Ile Lys Gln Asp Gly Ser Glu Lys Tyr Tyr Val Asp Ser Val Lys
1               5                   10                  15

Gly

<210> SEQ ID NO 153
<211> LENGTH: 12
<212> TYPE: PRT
<213> ORGANISM: Artificial Sequence
<220> FEATURE:
<223> OTHER INFORMATION: durvalumab heavy chain CDR3

<400> SEQUENCE: 153

Glu Gly Gly Trp Phe Gly Glu Leu Ala Phe Asp Tyr
1               5                   10

<210> SEQ ID NO 154
<211> LENGTH: 12
```

-continued

```
<212> TYPE: PRT
<213> ORGANISM: Artificial Sequence
<220> FEATURE:
<223> OTHER INFORMATION: durvalumab light chain CDR1

<400> SEQUENCE: 154

Arg Ala Ser Gln Arg Val Ser Ser Ser Tyr Leu Ala
1               5                   10

<210> SEQ ID NO 155
<211> LENGTH: 7
<212> TYPE: PRT
<213> ORGANISM: Artificial Sequence
<220> FEATURE:
<223> OTHER INFORMATION: durvalumab light chain CDR2

<400> SEQUENCE: 155

Asp Ala Ser Ser Arg Ala Thr
1               5

<210> SEQ ID NO 156
<211> LENGTH: 9
<212> TYPE: PRT
<213> ORGANISM: Artificial Sequence
<220> FEATURE:
<223> OTHER INFORMATION: durvalumab light chain CDR3

<400> SEQUENCE: 156

Gln Gln Tyr Gly Ser Leu Pro Trp Thr
1               5

<210> SEQ ID NO 157
<211> LENGTH: 450
<212> TYPE: PRT
<213> ORGANISM: Artificial Sequence
<220> FEATURE:
<223> OTHER INFORMATION: avelumab heavy chain

<400> SEQUENCE: 157

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 158
<211> LENGTH: 216
<212> TYPE: PRT
<213> ORGANISM: Artificial Sequence
<220> FEATURE:
<223> OTHER INFORMATION: avelumab light chain

<400> SEQUENCE: 158

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80
```

```
Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 159
<211> LENGTH: 120
<212> TYPE: PRT
<213> ORGANISM: Artificial Sequence
<220> FEATURE:
<223> OTHER INFORMATION: avelumab variable heavy chain

<400> SEQUENCE: 159

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser
        115                 120

<210> SEQ ID NO 160
<211> LENGTH: 110
<212> TYPE: PRT
<213> ORGANISM: Artificial Sequence
<220> FEATURE:
<223> OTHER INFORMATION: avelumab variable light chain

<400> SEQUENCE: 160

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45
```

```
Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110

<210> SEQ ID NO 161
<211> LENGTH: 5
<212> TYPE: PRT
<213> ORGANISM: Artificial Sequence
<220> FEATURE:
<223> OTHER INFORMATION: avelumab heavy chain CDR1

<400> SEQUENCE: 161

Ser Tyr Ile Met Met
1               5

<210> SEQ ID NO 162
<211> LENGTH: 17
<212> TYPE: PRT
<213> ORGANISM: Artificial Sequence
<220> FEATURE:
<223> OTHER INFORMATION: avelumab heavy chain CDR2

<400> SEQUENCE: 162

Ser Ile Tyr Pro Ser Gly Gly Ile Thr Phe Tyr Ala Asp Thr Val Lys
1               5                   10                  15

Gly

<210> SEQ ID NO 163
<211> LENGTH: 11
<212> TYPE: PRT
<213> ORGANISM: Artificial Sequence
<220> FEATURE:
<223> OTHER INFORMATION: avelumab heavy chain CDR3

<400> SEQUENCE: 163

Ile Lys Leu Gly Thr Val Thr Thr Val Asp Tyr
1               5                   10

<210> SEQ ID NO 164
<211> LENGTH: 14
<212> TYPE: PRT
<213> ORGANISM: Artificial Sequence
<220> FEATURE:
<223> OTHER INFORMATION: avelumab light chain CDR1

<400> SEQUENCE: 164

Thr Gly Thr Ser Ser Asp Val Gly Gly Tyr Asn Tyr Val Ser
1               5                   10

<210> SEQ ID NO 165
<211> LENGTH: 7
<212> TYPE: PRT
<213> ORGANISM: Artificial Sequence
<220> FEATURE:
<223> OTHER INFORMATION: avelumab light chain CDR2

<400> SEQUENCE: 165

Asp Val Ser Asn Arg Pro Ser
1               5
```

<210> SEQ ID NO 166
<211> LENGTH: 10
<212> TYPE: PRT
<213> ORGANISM: Artificial Sequence
<220> FEATURE:
<223> OTHER INFORMATION: avelumab light chain CDR3

<400> SEQUENCE: 166

```
Ser Ser Tyr Thr Ser Ser Ser Thr Arg Val
1               5                   10
```

<210> SEQ ID NO 167
<211> LENGTH: 448
<212> TYPE: PRT
<213> ORGANISM: Artificial Sequence
<220> FEATURE:
<223> OTHER INFORMATION: atezolizumab heavy chain

<400> SEQUENCE: 167

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285
```

```
Lys Thr Lys Pro Arg Glu Glu Gln Tyr Ala Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 168
<211> LENGTH: 214
<212> TYPE: PRT
<213> ORGANISM: Artificial Sequence
<220> FEATURE:
<223> OTHER INFORMATION: atezolizumab light chain

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210

<210> SEQ ID NO 169
<211> LENGTH: 118
<212> TYPE: PRT
<213> ORGANISM: Artificial Sequence
<220> FEATURE:
<223> OTHER INFORMATION: atezolizumab variable heavy chain

<400> SEQUENCE: 169

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 170
<211> LENGTH: 108
<212> TYPE: PRT
<213> ORGANISM: Artificial Sequence
<220> FEATURE:
<223> OTHER INFORMATION: atezolizumab variable light chain

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 171
<211> LENGTH: 10
<212> TYPE: PRT
<213> ORGANISM: Artificial Sequence
<220> FEATURE:
<223> OTHER INFORMATION: atezolizumab heavy chain CDR1
```

```
<400> SEQUENCE: 171

Gly Phe Thr Phe Ser Asp Ser Trp Ile His
1               5                   10

<210> SEQ ID NO 172
<211> LENGTH: 18
<212> TYPE: PRT
<213> ORGANISM: Artificial Sequence
<220> FEATURE:
<223> OTHER INFORMATION: atezolizumabheavy chain CDR2

<400> SEQUENCE: 172

Ala Trp Ile Ser Pro Tyr Gly Gly Ser Thr Tyr Tyr Ala Asp Ser Val
1               5                   10                  15

Lys Gly

<210> SEQ ID NO 173
<211> LENGTH: 9
<212> TYPE: PRT
<213> ORGANISM: Artificial Sequence
<220> FEATURE:
<223> OTHER INFORMATION: atezolizumab heavy chain CDR3

<400> SEQUENCE: 173

Arg His Trp Pro Gly Gly Phe Asp Tyr
1               5

<210> SEQ ID NO 174
<211> LENGTH: 11
<212> TYPE: PRT
<213> ORGANISM: Artificial Sequence
<220> FEATURE:
<223> OTHER INFORMATION: atezolizumab light chain CDR1

<400> SEQUENCE: 174

Arg Ala Ser Gln Asp Val Ser Thr Ala Val Ala
1               5                   10

<210> SEQ ID NO 175
<211> LENGTH: 7
<212> TYPE: PRT
<213> ORGANISM: Artificial Sequence
<220> FEATURE:
<223> OTHER INFORMATION: atezolizumab light chain CDR2

<400> SEQUENCE: 175

Ser Ala Ser Phe Leu Tyr Ser
1               5

<210> SEQ ID NO 176
<211> LENGTH: 9
<212> TYPE: PRT
<213> ORGANISM: Artificial Sequence
<220> FEATURE:
<223> OTHER INFORMATION: atezolizumab light chain CDR3

<400> SEQUENCE: 176

Gln Gln Tyr Leu Tyr His Pro Ala Thr
1               5
```